(12) United States Patent
Pitts et al.

(10) Patent No.: US 6,489,333 B2
(45) Date of Patent: Dec. 3, 2002

(54) INTEGRIN ANTAGONISTS

(75) Inventors: William J. Pitts, Newtown, PA (US); Prabhakar K. Jadhav, Wilmington, DE (US)

(73) Assignee: Bristol - Meyers Squibb Pharma Company, Princeton, NJ (US)

( * ) Notice: Subject to any disclaimer, the term of this patent is extended or adjusted under 35 U.S.C. 154(b) by 54 days.

(21) Appl. No.: 09/828,751

(22) Filed: Apr. 9, 2001

(65) Prior Publication Data

US 2001/0044535 A1 Nov. 22, 2001

Related U.S. Application Data

(62) Division of application No. 09/282,496, filed on Mar. 31, 1999, now abandoned.
(60) Provisional application No. 60/080,242, filed on Apr. 1, 1998.

(51) Int. Cl.$^7$ .................. C07D 403/02; C07D 403/12; C07D 403/06; A61K 31/416
(52) U.S. Cl. .................. 514/272; 514/63; 514/241; 514/245; 514/246; 514/252.14; 514/252.16; 514/252.17; 514/254.06; 514/259.1; 514/259.3; 514/259.31; 514/259.5; 514/261.1; 514/263.2; 514/264.11; 514/265.1; 514/266.23; 514/275; 544/195; 544/209; 544/212; 544/243; 544/244; 544/256; 544/265; 544/281; 544/319; 544/320; 544/321
(58) Field of Search .................. 544/320, 321, 544/195, 209, 212, 243, 244, 256, 265, 319, 281; 514/272, 275, 241, 245, 246, 252.14, 252.16, 252.17, 254.06

(56) References Cited

U.S. PATENT DOCUMENTS

| 5,084,466 A | 1/1992 | Alig et al. .................. 514/353 |
| 5,187,157 A | 2/1993 | Kettner et al. .................. 514/18 |
| 5,256,812 A | 10/1993 | Alig et al. .................. 560/35 |
| 5,399,585 A | 3/1995 | Alig et al. .................. 514/438 |
| 5,489,693 A | 2/1996 | Linz et al. .................. 548/550 |
| 5,541,343 A | 7/1996 | Himmelsbach et al. ..... 514/424 |
| 5,563,158 A | 10/1996 | DeGrado et al. .......... 514/340 |
| 5,591,769 A | 1/1997 | Himmelsbach et al. ..... 514/423 |
| 6,214,834 B1 * | 4/2001 | Jadhav et al. ............... 514/275 |

FOREIGN PATENT DOCUMENTS

| EP | 0471651 | 2/1992 |
| EP | 0478328 | 4/1992 |
| EP | 0478363 | 4/1992 |
| EP | 0529858 | 3/1993 |
| EP | 0537980 | 4/1993 |
| EP | 0539343 | 4/1993 |
| EP | 0542363 | 5/1993 |
| EP | 0635492 | 1/1995 |
| WO | 9207869 | 5/1992 |
| WO | 9300095 | 1/1993 |
| WO | 9308174 | 4/1993 |
| WO | 9408577 | 4/1994 |
| WO | 9408962 | 4/1994 |
| WO | 9412181 | 6/1994 |
| WO | 9504057 | 2/1995 |
| WO | 9532710 | 12/1995 |
| WO | 9600730 | 1/1996 |
| WO | WO 97/23480 * | 7/1997 |
| WO | 9726250 | 7/1997 |

OTHER PUBLICATIONS

Simone, Oncology: Introduction, Cecil Textbook of Medicine, 20th Edition, vol. 1, pp. 1004–1010, 1996.*

* cited by examiner

Primary Examiner—Deepak R. Rao
(74) Attorney, Agent, or Firm—Scott K. Larsen; Jing S. Belfield

(57) ABSTRACT

This invention relates to novel heterocycles which are useful as antagonists of the $\alpha_v\beta_3$ integrin, the $\alpha_{2b}\beta_3$ integrin, and related cell surface adhesive protein receptors, to pharmaceutical compositions containing such compounds, processes for preparing such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

15 Claims, No Drawings

INTEGRIN ANTAGONISTS

This application is a divisional application of U.S. application Ser. No. 09/282,496 filed Mar. 31, 1999, now abandoned, which claims the benefit of U.S. Provisional Application No. 60/080,242 filed Apr. 1, 1998, the contents of which are hereby incorporated by reference.

FIELD OF THE INVENTION

This invention relates to novel heterocycles which are useful as antagonists of the $\alpha_v\beta_3$ integrin, the $\alpha_{2b}\beta_3$ integrin, and related cell surface adhesive protein receptors, to pharmaceutical compositions containing such compounds, processes for preparing such compounds, and to methods of using these compounds, alone or in combination with other therapeutic agents, for the inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

BACKGROUND OF THE INVENTION

Angiogenesis or neovascularization is critical for normal physiological processes such as embryonic development and wound repair (Folkman and Shing, J. Biol. Chem. 1992, 267:10931–10934; D'Amore and Thompson, Ann. Rev. Physiol. 1987, 49:453–464). However, angiogenesis also occurs pathologically, for example, in ocular neovascularization (leading to diabetic retinopathy, neovascular glaucoma, retinal vein occlusion and blindness), in rheumatoid arthritis and in solid tumors (Folkman and Shing, J. Biol. Chem., 1992, 267:10931–10934; Blood and Zetter, Biochim. Biophys. Acta., 1990, 1032:118–128).

Tumor dissemination, or metastasis, involves several distinct and complementary components, including the penetration and transversion of tumor cells through basement membranes and the establishment of self-sustaining tumor foci in diverse organ systems. To this end, the development and proliferation of new blood vessels, or angiogenesis, is critical to tumor survival. Without neovascularization, tumor cells lack the nourishment to divide and will not be able to leave the primary tumor site (Folkman and Shing, J. Biol. Chem., 1992, 267:10931–10934).

Inhibition of angiogenesis in animal models of cancer has been shown to result in tumor growth suppression and prevention of metastatic growth (Herblin et al., Exp. Opin. Ther. Patents, 1994, 1–14). Many angiogenic inhibitors have been directed toward blocking initial cytokine-dependent induction of new vessel growth, e.g. antibodies to endothelial cell growth factors. However, these approaches are problematic because tumor and inflammatory cells can secrete multiple activators of angiogenesis (Brooks et al., Cell, 1994, 79:1157–1164). Therefore, a more general approach that would allow inhibition of angiogenesis due to a variety of stimuli would be of benefit.

The integrin $\alpha_v\beta_3$ is preferentially expressed on angiogenic blood vessels in chick and man (Brooks et al., Science, 1994, 264:569–571; Enenstein and Kramer, J. Invest. Dermatol., 1994, 103:381–386). Integrin $\alpha_v\beta_3$ is the most promiscuous member of the integrin family, allowing endothelial cells to interact with a wide variety of extracellular matrix components (Hynes, Cell, 1992, 69:11–25). These adhesive interactions are considered to be critical for angiogenesis since vascular cells must ultimately be capable of invading virtually all tissues.

While integrin $\alpha_v\beta_3$ promotes adhesive events important for angiogenesis, this receptor also transmits signals from the extracellular environment to the intracellular compartment (Leavesley et al., J. Cell Biol., 1993, 121:163–170, 1993). For example, the interaction between the $\alpha_v\beta_3$ integrin and extracellular matrix components promotes a calcium signal required for cell motility.

During endothelium injury, the basement membrane zones of blood vessels express several adhesive proteins, including but not limited to von Willebrand factor, fibronectin, and fibrin. Additionally, several members of the integrin family of adhesion receptors are expressed on the surface of endothelial, smooth muscle and on other circulating cells. Among these integrins is $\alpha_v\beta_3$, the endothelial cell, fibroblast, and smooth muscle cell receptor for adhesive proteins including von Willebrand factor, fibrinogen (fibrin), vitronectin, thrombospondin, and osteopontin. These integrins initiate a calcium-dependent signaling pathway that can lead to endothelial cell, smooth muscle cell migration and, therefore, may play a fundamental role in vascular cell biology.

Recently, an antibody to the $\alpha_v\beta_3$ integrin has been developed that inhibits the interaction of this integrin with agonists such as vitronectin (Brooks et al., Science, 1994, 264:569–571). Application of this antibody has been shown to disrupt ongoing angiogenesis on the chick chorioallantoic membrane (CAM), leading to rapid regression of histologically distinct human tumor transplanted onto the CAM (Brooks et al., Cell, 1994, 79:1157–1164). In this model, antagonists of the $\alpha_v\beta_3$ integrin induced apoptosis of the proliferating angiogenic vascular cells, leaving pre-existing quiescent blood vessels unaffected. Thus, $\alpha_v\beta_3$ integrin antagonists have been shown to inhibit angiogenesis and are recognized as being useful as therapeutic agents for the treatment of human diseases such as cancer, restenosis, thromoembolic disorders, rheumatoid arthritis and ocular vasculopathies (Folkman and Shing, J. Biol. Chem., 1992, 267:10931–10934).

Increasing numbers of other cell surface receptors have been identified which bind to extracellular matrix ligands or other cell adhesion ligands thereby mediating cell-cell and cell-matrix adhesion processes. These receptors belong to a gene superfamily called integrins and are composed of heterodimeric transmembrane glycoproteins containing α- and β-subunits. Integrin subfamilies contain a common β-subunit combined with different α-subunits to form adhesion receptors with unique specificity. The genes for eight distinct β-subunits have been cloned and sequenced to date.

The $\alpha_v\beta_3$ heterodimer is a member of the $\beta_3$ integrin subfamily and has been described on platelets, endothelial cells, melanoma, smooth muscle cells, and osteoclasts (Horton and Davies, J. Bone Min. Res. 1989, 4:803–808; Davies et al., J. Cell. Biol. 1989, 109:1817–1826; Horton, Int. J. Exp. Pathol., 1990, 71:741–759). Like GPIIb/IIIa, the vitronectin receptor binds a variety of RGD-containing adhesive proteins such as vitronectin, fibronectin, VWF, fibrinogen, osteopontin, bone sialo protein II and thrombospondin in a manner mediated by the RGD sequence. A key event in bone resorption is the adhesion of osteoclasts to the matrix of bone. Studies with monoclonal antibodies have implicated the $\alpha_v\beta_3$ receptor in this process and suggest that a selective $\alpha_v\beta_3$ antagonist would have utility in blocking bone resorption (Horton et al., J. Bone Miner. Res., 1993, 8:239–247; Helfrich et al., J. Bone Miner. Res., 1992, 7:335–343).

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. The platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with a variety of pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are activated by a wide variety of agonists resulting in platelet shape change, secretion of granular contents and aggregation. Aggregation of platelets serves to further focus clot formation by concentrating activated clotting factors at the site of injury. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane $A_2$ synthetase inhibitors or receptor antagonists, which act against thromboxane $A_2$; and hirudin, which acts against thrombin.

Recently, a common pathway for all known agonists has been identified, namely platelet glycoprotein IIb/IIIa complex (GPIIb/IIIa), which is the membrane protein mediating platelet aggregation. GPIIb/IIIa is a member of the integrin family, and is also referred to as the fibrinogen receptor or the $\alpha_{2b}\beta_3$ integrin. A recent review of GPIIb/IIIa is provided by Phillips et al. Cell (1991) 65:359–362. The development of a GPIIb/IIIa antagonist represents a promising new approach for antiplatelet therapy.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the RGD recognition sequence which is common to the adhesive proteins that bind GPIIb/IIIa.

Degrado, et al. in U.S. Pat. No. 5,563,158, disclose aromatic compounds containing basic and acidic termini of a general formula shown below:

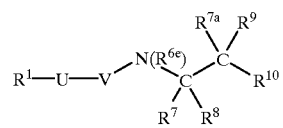

useful as fibrinogen receptor antagonists

PCT Patent Application Publication Number WO95/14683, published Jun. 1, 1995 discloses isoxazoline and isoxazole fibrinogen receptor antagonists of general formula shown below:

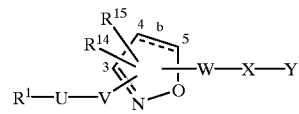

Copending, commonly assigned U.S. patent application Ser. No. 08/455,768 filed May 31, 1995 discloses integrin inhibitors of the general formula shown below:

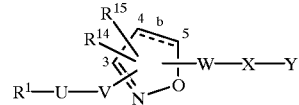

PCT Patent Application Publication Number WO95/32710, published Dec. 7, 1995 discloses compounds for inhibition of osteoclast-mediated bone resorption of general formula: X-Y-Z-Aryl-A-B ; wherein Aryl is a 6-membered aromatic ring system. Similarly, PCT Patent Application Publication Number WO94/08577, published Apr. 28, 1994, and PCT Patent Application Publication Number WO94/12181, published Jun. 9, 1994 disclose compounds as fibrinogen receptor antagonists of general formula: X-Y-Z-Aryl-A-B wherein Aryl is a 5 or 6-membered aromatic ring system such as phenyl, pyridyl, isoxozolyl, thiophenyl, and imidazolyl.

PCT Patent Application Publication Number WO96/00730, published Jan. 11, 1996 discloses relevant compounds as vitronectin receptor antagonists of general formulae shown below:

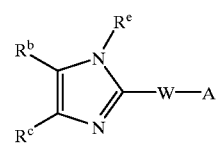

wherein W is a bridging group and A is a fibrinogen receptor antagonist template.

None of the above references discloses or suggests the pyrimidine/pyrimidone and triazine/triazinone compounds of the present invention which are described in detail below.

SUMMARY OF THE INVENTION

The present invention provides novel nonpeptide compounds which bind to integrin receptors thereby altering cell-matrix and cell-cell adhesion processes. The compounds of the present invention are useful for the inhibition of cell adhesion and the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis.

One aspect of this invention provides novel compounds of Formula (IA) (described below) which are useful as antagonists of the $\alpha_v\beta_3$ integrin, which is also referred to as the vitronectin receptor. The compounds of the present invention inhibit the binding of vitronectin or other RGD-containing ligands to $\alpha_v\beta_3$ and inhibit cell adhesion. The present invention also includes pharmaceutical compositions containing such compounds of Formula (IA), and methods of using such compounds for the inhibition of angiogenesis, and/or for the treatment of disorders mediated by angiogenesis.

Another aspect of the present invention comprises agents that inhibit the binding of vitronectin to the $\alpha_v\beta_3$ receptor for the treatment (including prevention) of thrombosis which do not significantly alter hemostatic balance and do not significantly inhibit platelet aggregation and do not significantly inhibit coagulation. Also the compounds of the current invention can be used for the treatment or prevention of restenosis.

The present invention also provides novel compounds, pharmaceutical compositions and methods which may be used in the treatment or prevention of other diseases which involve cell adhesion processes, including, but not limited to, rheumatoid arthritis, asthma, allergies, adult respiratory distress syndrome, graft versus host disease, organ transplantation, septic shock, psoriasis, eczema, contact dermatitis, osteoporosis, osteoarthritis, atherosclerosis, metastasis, wound healing, diabetic retinopathy, ocular vasculopathies, thrombosis, inflammatory bowel disease and other autoimmune diseases.

Also included in the present invention are pharmaceutical kits comprising one or more containers containing pharmaceutical dosage units comprising a compound of Formula (IA), for the therapeutic inhibition of cell adhesion, the treatment of angiogenic disorders, inflammation, bone degradation, cancer metastasis, diabetic retinopathy, thrombosis, restenosis, macular degeneration, and other conditions mediated by cell adhesion and/or cell migration and/or angiogenesis.

Another aspect of the present invention comprises pharmaceutical compositions containing compounds of Formula (IA), and methods of using such compounds for the treatment (including prevention) of cardiovascular disease, thrombosis or harmful platelet aggregation, reocclusion following thrombolysis, reperfusion injury, or restenosis by administering a compound of Formula (IA) alone or in combination with one or more additional therapeutic agents selected from: anti-coagulants such as warfarin or heparin; anti-platelet agents such as aspirin, piroxicam or ticlopidine; thrombin inhibitors such as boroarginine derivatives, hirudin or argatroban; or thrombolytic agents such as tissue plasminogen activator, anistreplase, urokinase or streptokinase; or combinations thereof.

DETAILED DESCRIPTION OF THE INVENTION

The present invention provides novel nonpeptide compounds of Formula (IA) (described below) which bind to integrin receptors thereby altering cell-matrix and cell-cell adhesion processes. The compounds of the present invention are useful for the inhibition of cell adhesion and the treatment of angiogenic disorders, inflammation, bone degradation, cancer metastases, diabetic retinopathy, thrombosis, restenosis, macular degeneration, and other conditions mediated by cell adhesion and/or cell migration and/or angiogenesis, in a mammal.

One aspect of this invention provides novel compounds of Formula (IA) which are useful as antagonists of the $\alpha_v\beta_3$ integrin or GPIIb/IIIa. The compounds of the present invention inhibit the binding of vitronectin and other RGD-containing ligands to the $\alpha_v\beta_3$ integrin or GPIIb/IIIa and inhibit cell adhesion. The present invention also includes pharmaceutical compositions containing such compounds of Formula (IA) and methods of using such compounds for the inhibition of angiogenesis, and/or for the treatment of angiogenic disorders, and/or for the inhibition or prevention of thrombosis, and/or for the treatment of thromboembolic disorders, and/or for the treatment of inflammation, bone degradation, cancer metastasis, diabetic retinopathy, restenosis, macular degeneration, and other conditions mediated by cell adhesion and/or cell migration and/or angiogenesis.

As use herein the term "integrin antagonist template" means the core structure of an integrin receptor antagonist, said core including an acidic group. An integrin receptor antagonist is an agent which binds to integrin receptors thereby altering cell-matrix and cell-cell adhesion processes. The present invention provides for an integrin receptor antagonist are preferably RGD peptidomimetic compounds comprising a guanidine mimic linked to an integrin antagonist template. Such integrin receptor antagonists preferably bind to the integrin receptors of the $\alpha_v\beta_3$ integrin, the $\alpha_2\beta_3$ integrin, the integrin receptor GPIIb-IIIa, and related cell surface adhesive protein receptors.

[1] The present invention comprises compounds of Formula (I):

$$G-T \tag{I}$$

including stereoisomeric forms thereof, tautomeric forms thereof, pharmaceutically acceptable salt forms thereof or prodrug forms thereof, wherein:

T is an integrin antagonist template; and

G is a guanidine mimic selected from:

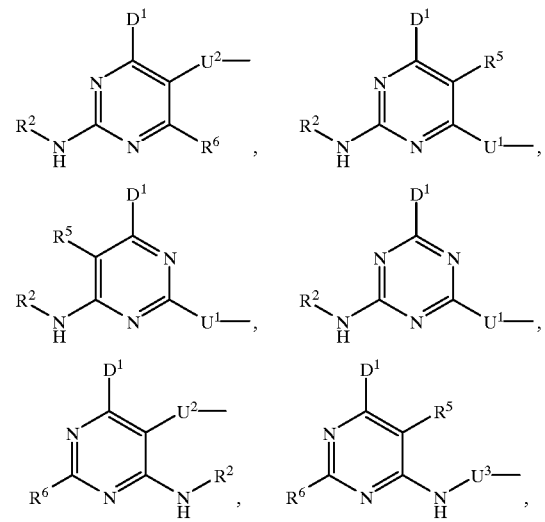

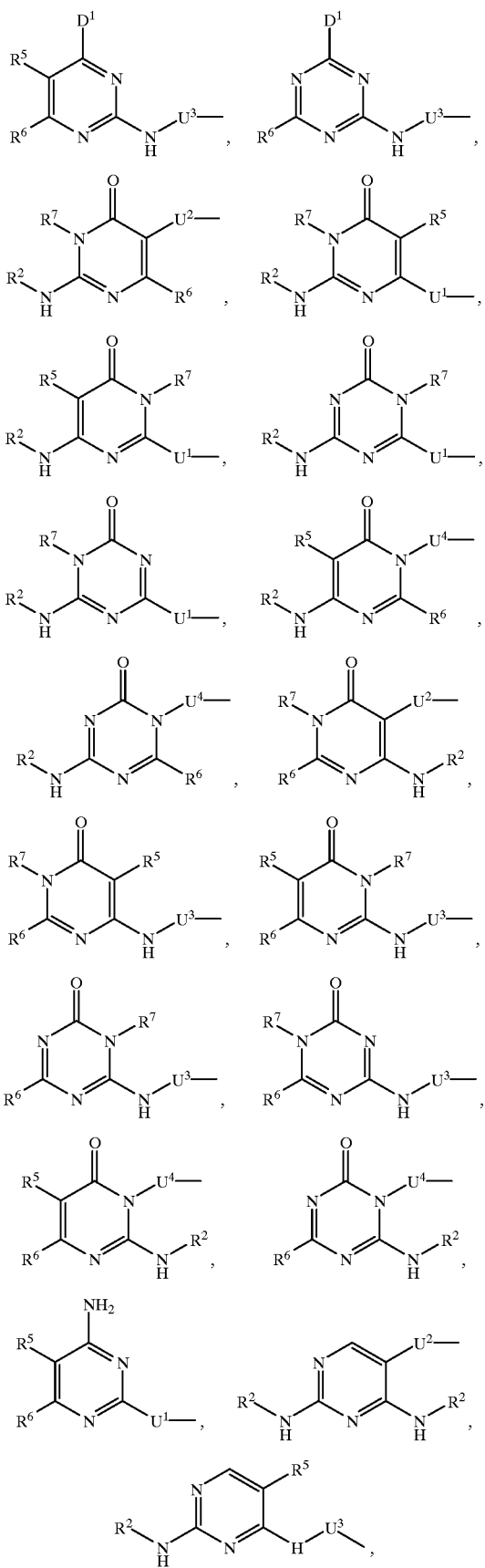
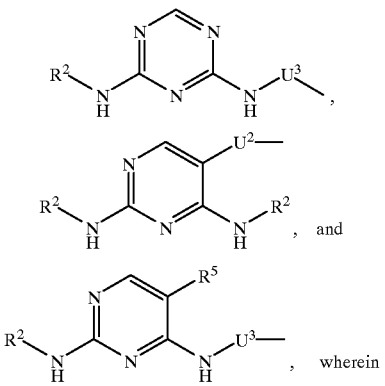

wherein $D^1$ is selected from:

H, $NR^2R^4$, $OR^3$, $SR^3$, F, Cl, Br, $CF_3$, and $C_1$–$C_4$ alkyl;

$R^2$ at each occurrence is independently selected from:

H, $OR^3$, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl($C_0$–$C_4$ alkyl)carbonyl, $C_3$–$C_7$ cycloalkyl ($C_0$–$C_4$ alkoxy)carbonyl, aryl($C_0$–$C_6$ alkyl), heteroaryl ($C_0$–$C_6$ alkyl), aryl($C_0$–$C_6$alkyl)carbonyl, heteroaryl ($C_0$–$C_6$ alkyl)carbonyl, $C_1$–$C_6$ alkylsulfonyl, aryl ($C_0$–$C_6$ alkyl)sulfonyl, heteroaryl($C_0$–$C_6$ alkyl) sulfonyl, aryl($C_1$–$C_6$ alkoxy)carbonyl, and heteroaryl ($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^3$ at each occurrence is independently selected from:

H, $C_1$–$C_6$ alkyl, ($C_1$–$C_6$ alkyl)carbonyl, ($C_1$–$C_6$ alkoxy) carbonyl, ($C_0$–$C_6$ alkyl)aminocarbonyl, $C_3$–$C_6$ alkenyl, $C_3$–$C_7$ cycloalkyl ($C_0$–$C_4$ alkyl), $C_3$–$C_7$ cycloalkyl ($C_0$–$C_4$ alkyl)carbonyl, cycloalkyl($C_0$–$C_4$ alkoxy) carbonyl, aryl($C_0$–$C_6$ alkyl), heteroaryl($C_0$–$C_6$ alkyl), aryl($C_0$–$C_6$ alkyl)carbonyl, heteroaryl($C_0$–$C_6$ alkyl) carbonyl, aryl($C_1$–$C_6$ alkoxy)carbonyl, and heteroaryl ($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^4$ is selected from:

H, $C_1$–$C_6$ alkyl, $C_1$–$C_6$ alkylcarbonyl, $C_1$–$C_6$ alkoxycarbonyl, $C_3$–$C_7$ cycloalkyl($C_0$–$C_4$ alkyl), $C_3$–$C_7$ cycloalkyl($C_0$–$C_4$ alkyl)carbonyl, cycloalkyl ($C_0$–$C_4$ alkoxy)carbonyl, aryl($C_0$–$C_6$ alkyl), heteroaryl ($C_0$–$C_6$ alkyl), aryl($C_0$–$C_6$ alkyl)carbonyl, heteroaryl ($C_0$–$C_6$ alkyl)carbonyl, aryl($C_1$–$C_6$ alkoxy)carbonyl, and heteroaryl($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^2$ and $R^4$ when both substituents on the same nitrogen atom as in (—$NR^2R^4$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$–$C_6$ alkyl, $C_3$–$C_7$ cycloalkyl($C_0$–$C_4$ alkyl), $C_1$–$C_6$ alkylcarbonyl, $C_3$–$C_7$ cycloalkyl ($C_0$–$C_5$ alkyl)carbonyl, Cl-$C_6$ alkoxycarbonyl, $C_3$–$C_7$ cycloalkyl ($C_0$–$C_5$ alkoxy)carbonyl, aryl($C_0$–$C_5$ alkyl), heteroaryl ($C_0$–$C_5$ alkyl), aryl($C_1$–$C_5$ alkoxy)carbonyl, heteroaryl ($C_1$–$C_5$ alkoxy)carbonyl, $C_1$–$C_6$ alkylsulfonyl, arylsulfonyl, and heteroarylsulfonyl;

$R^5$ is selected from:

H, $NR^2R^4$, $OR^3$, $NO_2$, NO, $C_1$–$C_6$ alkyl, $C_3$–$C_7$ cycloalkyl($C_0$–$C_4$ alkyl), aryl($C_0$–$C_6$ alkyl), or heteroaryl($C_0$–$C_6$ alkyl), wherein said aryl and heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$; alternatively, —$NHR^2$ and $R^5$, when substituents on adjacent carbon atoms, are taken together with the carbon atoms to which they are attached to form a 5–7 membered heterocyclic ring containing 1, 2 or 3 nitrogen atoms, said heterocyclic ring being aromatic or nonaromatic, said heterocyclic ring being substituted with 0–2 substituents independently selected from the group consisting of $C_1$–$C_4$ alkyl, $C_1$–$C_4$ alkoxy, F, Cl, Br, $CF_3$, $NO_2$, and aryl, wherein said aryl group is substituted with 0–2 substituents independently selected from the group consisting of $C_1$–$C_4$ alkyl, $C_1$–$C_4$ alkoxy, F, Cl, Br, $CF_3$, and $NO_2$;

$R^6$ is selected from:

H, $NR^2R^4$, $OR^3$, $C_1$–$C_6$ alkyl, aryl($C_0$–$C_5$ alkyl), heteroaryl($C_0$–$C_5$ alkyl), $CF_3$, F, Cl, and Br, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^5$ and $R^6$, when substituents on adjacent carbon atoms, are taken together with the carbon atoms to which they are attached to form a 5–7 membered heterocyclic ring containing 1, 2 or 3 nitrogen atoms or a 5–7 membered carbocyclic ring, said carbocyclic or heterocyclic ring being aromatic or nonaromatic, said carbocyclic or heterocyclic ring being substituted with 0–2 substituents independently selected from the group consisting of $C_1$–$C_4$ alkyl, $C_1$–$C_4$ alkoxy, F, Cl, Br, $CF_3$, $NO_2$ and aryl, wherein said aryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^7$ is selected from:

H, $C_1$–$C_4$ alkyl, $C_3$–$C_6$ alkenyl, $C_3$–$C_6$ alkynyl, aryl ($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$NHR^2$ and $R^7$, when substituents on adjacent atoms, are taken together with the atoms to which they are attached to form a 5–7 membered heterocyclic ring containing 2 or 3 nitrogen atoms, said heterocyclic ring being aromatic or nonaromatic, said heterocyclic ring being substituted with 0–2 substituents independently selected from the group consisting of $C_1$–$C_4$ alkyl, $C_1$–$C_4$ alkoxy, F, Cl, Br, $CF_3$, $NO_2$, and aryl, wherein said aryl groups are substituted with 0–2 substituents independently selected from the group consisting of $C_1$–$C_4$ alkyl, $C_1$–$C_4$ alkoxy, F, Cl, Br, $CF_3$, and $NO_2$;

$U^1$ is selected from:

—$(CH_2)_n$-,
—$Q^1$-$(CH_2)_m$-,
—$(CH_2)_m$-$Q^2$—,
—$(CH_2)_t$-$Q^2$-$CH_2$—,
—$CH_2$-$Q^2$-$(CH_2)_t$-,
—$(CH_2)_t$-N($R^3$)—C(=O)—,
—$(CH_2)_t$-N($R^3$)—S(=O)$_2$—,
—$(CH_2)_t$-C(=O)—N($R^3$)—,
—$(CH_2)_t$-S(=O)$_2$—N($R^3$)—,
—C(=O)—N($R^4$)—$(CH_2)_t$-,
—N($R^4$)—,
—N($R^4$)—$(CH_2)_q$-$Q^2$-,
—N($R^4$)—C(=O)—$(CH_2)_r$-, and
—N($R^4$)—$(CH_2)_r$-C(=O)—;

$U^2$ is selected from:

—$(CH_2)_h$-,
—$Q^1$-$(CH_2)_r$-,
—$(CH_2)_r$-$Q^2$-,
—$(CH_2)_i$-N($R^3$)—C(=O)—,
—$(CH_2)_i$-N($R^3$)—S(=O)$_2$—,
—$(CH_2)_i$-C(=O)—N($R^3$)—,
—$(CH_2)_i$-S(=O)$_2$—N($R^3$)—,
—$(CH_2)_i$-$Q^2$—$CH_2$—,
—$CH_2$-$Q^2$-$(CH_2)_i$-, —C(=O)—N($R^4$)—$(CH_2)_i$-,
—N($R^4$)—,
—N($R^4$)—$(CH_2)_2$-$Q^2$-,
—N($R^4$)—C(=O)—$(CH_2)_i$-, and
—N($R^4$)—$(CH_2)_r$-C(=O)—;

$U^3$ is selected from:

—$(CH_2)_h$-,
—$(CH_2)_q$-$Q^2$-,
—$(CH_2)_q$-N($R^3$)—C(=O)—,
—$(CH_2)_r$-C(=O)—($R^3$)—,
—$(CH_2)_q$-S(O)$_2$—N($R^3$),
—$(CH_2)_q$-N($R^3$)-S(O)$_2$—,
—$(CH_2)_q$-N($R^3$)—$CH_2$—,
—$(CH_2)_q$-O-$CH_2$—,
—$(CH_2)_h$-C(=O)—,
—C(=O)—$(CH_2)_r$-, and
—C(=O)—N($R^4$)-$(CH_2)_p$;

$U^4$ is selected from:

—$(CH_2)_h$-,
—$(CH_2)_2$-$Q^2$,
—$(CH_2)_2$—O—$CH_2$—,
—$(CH_2)_r$-C(=O)—,
—C(=O)—$(CH_2)_r$-, and
—C(=O)—N($R^4$)—$(CH_2)_r$;

$Q^1$ is —O—, —S—, or N($R^4$);
$Q^2$ is —O—, —S—, —S(=O)—, —S(=O)$_2$—, or N($R^3$);
h is 0–4;
i is 0–2;
m is 1–4;
n is 0–5;
q is 2–3;
r is 0–3;
t is 1–3; and
p is 0–2.

provided that when $R^6$ is hydrogen then $D^1$ is not hydrogen.

[2] The present invention preferably comprises compounds of Formula (IA), (IB), (IC), (ID), (IE), (IG) or (IH):

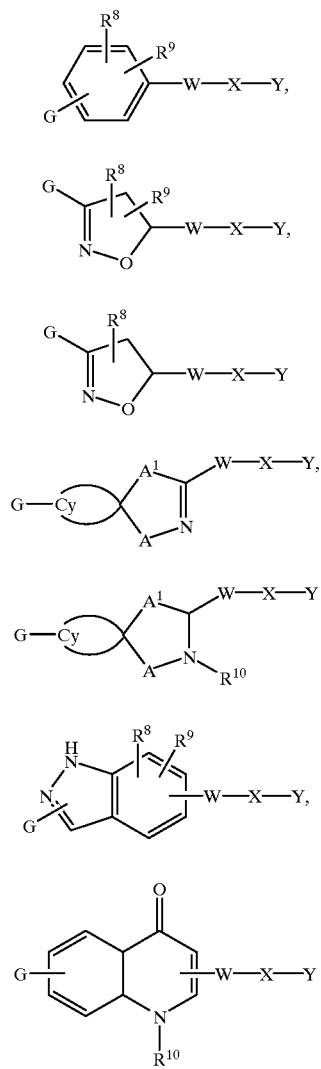
including stereoisomeric forms thereof, tautomeric forms thereof, pharmaceutically acceptable salt forms thereof or prodrug forms thereof, wherein:
G is a meta or para substituent with respect to W and is selected from:
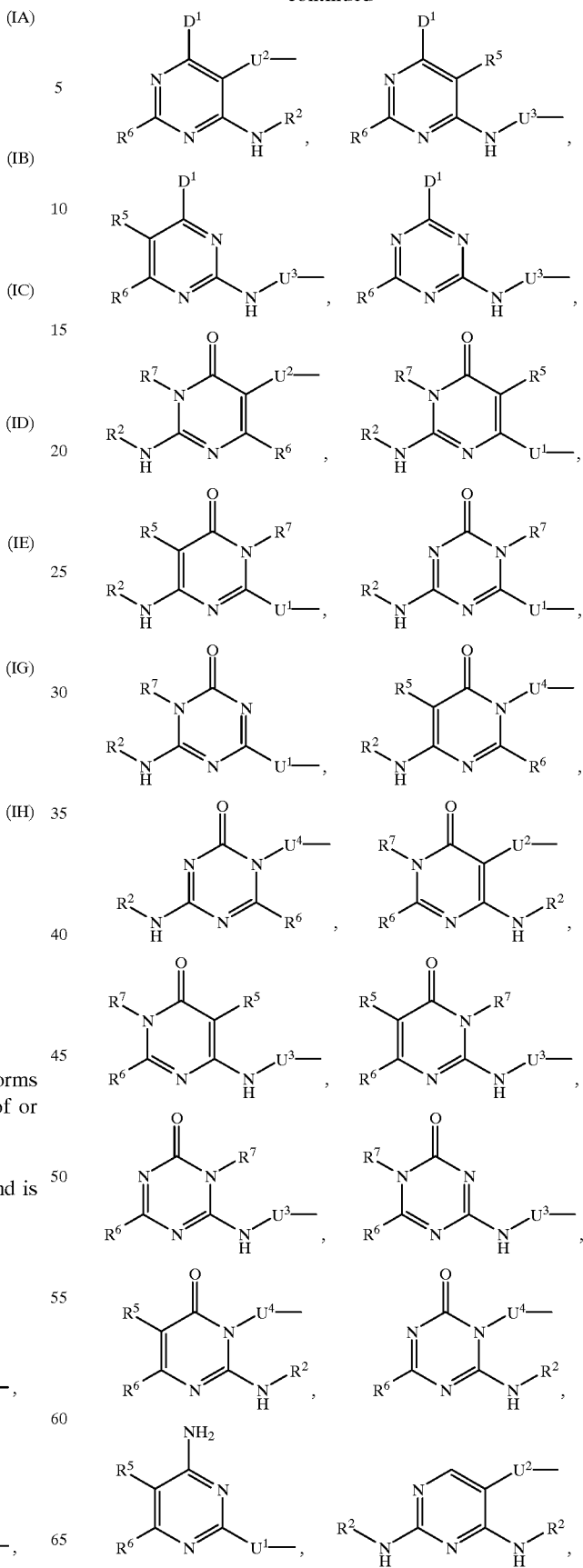

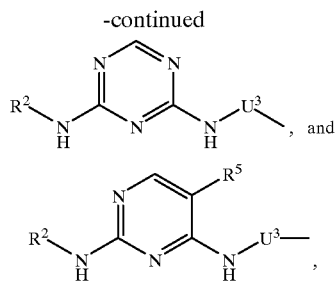, and

A¹ is selected from —NH—, —CH— or —O—;
A is selected from —O— or —NH—;
Cy is a spiro-fused 4–7 membered ring, including the spiro atom, containing 0–2 heteroatoms selected from O, S, or N, said ring system optionally being substituted on carbon with keto, or being substituted on carbon or nitrogen independently with 0–2 $R^8$;
$D^1$ is selected from:
  $NR^2R^4$, $OR^3$, $SR^3$, F, Cl, Br, $CF_3$, and $C_1$–$C_4$ alkyl;
$R^2$ at each occurrence is independently selected from:
  H, $OR^3$, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl($C_0$–$C_4$ alkyl)carbonyl, $C_3$–$C_7$ cycloalkyl($C_0$–$C_4$ alkoxy)carbonyl, aryl($C_0$–$C_6$ alkyl), heteroaryl($C_0$–$C_6$ alkyl), aryl($C_0$–$C_6$ alkyl)carbonyl, heteroaryl($C_0$–$C_6$ alkyl)carbonyl, $C_1$–$C_6$ alkylsulfonyl, aryl($C_0$–$C_6$ alkyl)sulfonyl, heteroaryl($C_0$–$C_6$ alkyl)sulfonyl, aryl($C_1$–$C_6$ alkoxy)carbonyl, and heteroaryl($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;
$R^3$ at each occurrence is independently selected from:
  H, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl($C_0$–$C_4$ alkyl)carbonyl, cycloalkyl($C_0$–$C_4$ alkoxy)carbonyl, aryl($C_0$–$C_6$ alkyl), heteroaryl($C_0$–$C_6$ alkyl), aryl($C_0$–$C_6$ alkyl)carbonyl, heteroaryl($C_0$–$C_6$ alkyl)carbonyl, aryl($C_1$–$C_6$ alkoxy)carbonyl, and heteroaryl($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;
$R^4$ is selected from:
  H, $C_1$–$C_6$ alkyl, $C_1$–$C_6$ alkylcarbonyl, $C_1$–$C_6$ alkoxycarbonyl, $C_3$–$C_7$ cycloalkyl($C_0$–$C_4$ alkyl), $C_3$–$C_7$ cycloalkyl($C_0$–$C_4$ alkyl)carbonyl, cycloalkyl($C_0$–$C_4$ alkoxy)carbonyl, aryl($C_0$–$C_6$ alkyl), heteroaryl($C_0$–$C_6$ alkyl), aryl($C_0$–$C_6$ alkyl)carbonyl, heteroaryl($C_0$–$C_6$ alkyl)carbonyl, aryl($C_1$–$C_6$ alkoxy)carbonyl, and heteroaryl($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;
alternatively, $R^2$ and $R^4$ when both substituents on the same nitrogen atom as in (—$NR^2R^4$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$–$C_6$ alkyl, $C_3$–$C_7$ cycloalkyl($C_0$–$C_4$ alkyl), $C_1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heteroaryl($C_0$–$C_5$ alkyl), aryl($C_1$–$C_5$ alkoxy)carbonyl, heteroaryl($C_1$–$C_5$ alkoxy)carbonyl, $C_1$–$C_6$ alkylsulfonyl, arylsulfonyl, and heteroarylsulfonyl;
$R^5$ is selected from:
  H, $NR^2R^4$, $OR^3$, $NO_2$, NO, $C_1$–$C_6$ alkyl, $C_3$–$C_7$ cycloalkyl($C_0$–$C_4$ alkyl), aryl($C_0$–$C_6$ alkyl), or heteroaryl($C_0$–$C_6$ alkyl), wherein said aryl and heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;
alternatively, —$NHR^2$ and $R^5$, when substituents on adjacent carbon atoms, are taken together with the carbon atoms to which they are attached to form a 5–7 membered heterocyclic ring containing 1, 2 or 3 nitrogen atoms, said heterocyclic ring being aromatic or nonaromatic, said heterocyclic ring being substituted with 0–2 substituents independently selected from the group consisting of $C_1$–$C_4$ alkyl, $C_1$–$C_4$ alkoxy, F, Cl, Br, $CF_3$, $NO_2$, and aryl, wherein said aryl group is substituted with 0–2 substituents independently selected from the group consisting of $C_1$–$C_4$ alkyl, $C_1$–$C_4$ alkoxy, F, Cl, Br, $CF_3$, and $NO_2$;
$R^6$ is selected from:
  H, $NR^2R^4$, $OR^3$, $C_1$–$C_6$ alkyl, aryl($C_0$–$C_5$ alkyl), heteroaryl($C_0$–$C_5$ alkyl), $CF_3$, F, Cl, and Br, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;
alternatively, $R^5$ and $R^6$, when substituents on adjacent carbon atoms, are taken together with the carbon atoms to which they are attached to form a 5–7 membered heterocyclic ring containing 1, 2 or 3 nitrogen atoms or a 5–7 membered carbocyclic ring, said carbocyclic or heterocyclic ring being aromatic or nonaromatic, said carbocyclic or heterocyclic ring being substituted with 0–2 substituents independently selected from the group consisting of $C_1$–$C_4$ alkyl, $C_1$–$C_4$ alkoxy, F, Cl, Br, $CF_3$, $NO_2$ and aryl, wherein said aryl groups are substituted with 0–2 substituents independently selected from the group consisting of $C_1$–$C_4$ alkyl, $C_1$–$C_4$ alkoxy, F, Cl, Br, $CF_3$, and $NO_2$;
$R^7$ is selected from:
  H, $C_1$–$C_4$ alkyl, $C_3$–$C_6$ alkenyl, $C_3$–$C_6$ alkynyl, aryl($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;
alternatively, —$NHR^2$ and $R^7$, when substituents on adjacent atoms, are taken together with the atoms to which they are attached to form a 5–7 membered heterocyclic ring containing 2 or 3 nitrogen atoms, said heterocyclic ring being aromatic or nonaromatic, said heterocyclic ring being substituted with 0–2 substituents independently selected from the group consisting of $C_1$–$C_4$ alkyl, $C_1$–$C_4$ alkoxy, F, Cl, Br, $CF_3$, $NO_2$, and aryl, wherein said aryl groups are substituted with 0–2 substituents independently selected from the group consisting of $C_1$–$C_4$ alkyl, $C_1$–$C_4$ alkoxy, F, Cl, Br, $CF_3$, and $NO_2$;
$U^1$ is selected from:
  —$(CH_2)_n$-,
  —$Q^1$-$(CH_2)_m$-,
  —$(CH_2)_m$-$Q^2$—, —$(CH_2)_r$-$Q^2$-$CH_2$—,
—$CH_2$-$Q^2$-$(CH_2)_r$-,
—$(CH_2)_r$-$N(R^3)$—$C(=O)$—,
—$(CH_2)_r$-$N(R^3)$—$S(=O)_2$—,
—$(CH_2)_r$-$C(=O)$—$N(R^3)$—,
—$(CH_2)_r$-$S(=O)_2$—$N(R^3)$—,
—$C(=O)$—$N(R^4)$—$(CH_2)_r$-,
—$N(R^4)$—,
—$N(R^4)$—$(CH_2)_q$-$Q^2$-,
—$N(R^4)$—$C(=O)$—$(CH_2)_r$-, and
—$N(R^4)$—$(CH_2)_r$-$C(=O)$—;
$U^2$ is selected from:
—$(CH_2)_h$-,
—$Q^1$-$(CH_2)_r$-,
—$(CH_2)_r$-$Q^2$-,
—$(CH_2)_r$-$N(R^3)$—$C(=O)$—,
—$(CH_2)_r$-$N(R^3)$—$S(=O)_2$—,
—$(CH_2)_r$-$C(=O)$—$N(R^3)$—,
—$(CH_2)_r$-$S(=O)_2$—$N(R^3)$—,
—$(CH_2)_r$-$Q^2$—$CH_2$—,
—$CH_2$-$Q^2$-$(CH_2)_r$-, —$C(=O)$—$N(R^4)$—$(CH_2)_r$-,
—$N(R^4)$—,
—$N(R^4)$—$(CH_2)_2$-$Q^2$-,
—$N(R^4)$—$C(=O)$—$(CH_2)_r$-, and
—$N(R^4)$—$(CH_2)_r$-$C(=O)$—;
$U^3$ is selected from:
—$(CH_2)_h$-,
—$(CH_2)_q$-$Q^2$-,
—$(CH_2)_q$-$N(R^3)$—$C(=O)$—,
—$(CH_2)_r$-$C(=O)$—$(R^3)$—,
—$(CH_2)_q$-$S(O)_2$—$N(R^3)$,
—$(CH_2)_q$-$N(R^3)$-$S(O)_2$—,
—$(CH_2)_q$-$N(R^3)$—$CH_2$—,
—$(CH_2)_q$-$O$-$CH_2$—,
—$(CH_2)_h$-$C(=O)$—,
—$C(=O)$—$(CH_2)_r$-, and
—$C(=O)$—$N(R^4)$-$(CH_2)_p$;
$U^4$ is selected from:
—$(CH_2)_h$-,
—$(CH_2)_2$-$Q^2$,
—$(CH_2)_2$—$O$—$CH_2$—,
—$(CH_2)_r$-$C(=O)$—,
—$C(=O)$—$(CH_2)_r$-, and
—$C(=O)$—$N(R^4)$—$(CH_2)_r$;
$Q^1$ is —$O$—, —$S$—, or $N(R^4)$;
$Q^2$ is —$O$—, —$S$—, —$S(=O)$—, —$S(=O)_2$—, or $N(R^3)$;
$R^8$ and $R^9$ are independently selected from:
H, $C_1$-$C_{10}$ alkyl, $NO_2$, $CF_3$, F, Cl, Br, $C_1$-$C_{10}$ alkylcarbonyl, —$NR^2R^4$, $OC(=O)R^{10}$, $OC(=O)$ $OR^{10}$, $OR^{10}$, $OC(=O)NR^{10}R^{11}$, $OCH_2CO_2R^{10}$, $CO_2CH_2CO_2R^{10}$, $CO_2R^{10}$, $C(=O)R^{11}$, $NR^{10}C(=O)$ $R^{11}$, $NR^7C(=O)OR^{10}$, $NR^7C(=O)NR^{10}R^{11}$, $NR^7SO_2NR^{10}R^{11}$, $NR^7SO_2R^{10}$, $SR^{10}$, $S(=O)R^{10}$, $SO_2R^{10}$, $SO_2NR^{10}R^{11}$, $SiMe_3$, $R^{10}OOC(C_1$-$C_6$ alkyl), $R^2R^4N(C_2$-$C_6$ alkyl), $R^{10}OOC(C_1$-$C_6$ alkoxy), $R^2R^4N$ ($C_2$-$C_6$ alkoxy), $C_2$-$C_6$ alkenyl, $C_3$-$C_{10}$ cycloalkyl, $C_3$-$C_{10}$ cycloalkylmethyl, aryl, and aryl($C_1$-$C_5$ alkyl)-, wherein said aryl groups are substituted with 0–2 substituents independently selected from a group consisting of $C_1$-$C_4$ alkyl, $C_1$-$C_4$ alkoxy, F, Cl, Br, $CF_3$, and $NO_2$;

$R^{10}$ and $R^{11}$ are independently selected from:
H, $C_1$-$C_8$ alkyl, $C_3$-$C_6$ alkenyl, $C_3$-$C_{10}$ cycloalkyl($C_0$-$C_4$ alkyl), aryl($C_0$-$C_4$ alkyl), and heteroaryl($C_0$-$C_4$ alkyl), wherein said aryl or heteroaryl groups are substituted with 0–2 substituents independently selected from the group consisting of $C_1$-$C_4$ alkyl, $C_1$-$C_4$ alkoxy, F, Cl, Br, $CF_3$, and $NO_2$;
alternatively, $R^{10}$ and $R^{11}$ when both substituents on the same nitrogen atom as in (—$NR^{10}R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$-$C_6$ alkyl, $C_3$-$C_7$ cycloalkyl($C_0$-$C_4$ alkyl), $C_1$-$C_6$ alkylcarbonyl, $C_3$-$C_7$ cycloalkyl($C_0$-$C_5$ alkyl) carbonyl, $C_1$-$C_6$ alkoxycarbonyl, $C_3$-$C_7$ cycloalkyl($C_0$-$C_5$ alkoxy)carbonyl, aryl($C_0$-$C_5$ alkyl), heteroaryl($C_0$-$C_5$ alkyl), aryl ($C_1$-$C_5$ alkoxy) carbonyl, heteroaryl ($C_1$-$C_5$ alkoxy)carbonyl, $C_1$-$C_6$ alkylsulfonyl arylsulfonyl and heteroarylsulfonyl;
W is selected from:
$C_1$-$C_4$ alkylene,
—$(C(R^{12})_2)_pO(C(R^{12})_2)_p$-,
—$(C(R^{12})_2)_pC(=O) (C(R^{12})_2)_p$-,
—$(C(R^{12})_2)_pC(=))N(R^{13})$-, and
—$(=O)$—$N(R^{13})$-$(C(R^{12})_2)_p$-;
X is —$(C(R^{12})_2)_pC(R^{12}) (R^{14})$—$C(R^{12})_2$— or
—$(C(R^{12})_2)_p$-$C(R^{12}) (R^{15})$-;
alternatively, W and X can be taken together to be

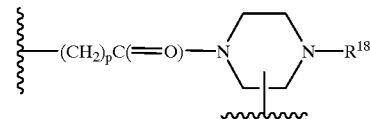

$R^{12}$ at each occurrence is independently selected from:
H, $C_1$-$C_6$ alkyl, $C_2$-$C_6$ alkenyl, $C_2$-$C_6$ alkynyl, $C_3$-$C_7$ cycloalkyl($C_0$-$C_4$ alkyl)-, ($C_1$-$C_4$ alkyl)carbonyl, aryl ($C_0$-$C_6$ alkyl), and heteroaryl($C_0$-$C_6$ alkyl), wherein said aryl or heteroaryl groups are substituted with 0–2 substituents independently selected from the group consisting of $C_1$-$C_4$ alkyl, $C_1$-$C_4$ alkoxy, F, Cl, Br, $CF_3$, and $NO_2$;
$R^{13}$ is selected from:
H, $C_1$-$C_6$ alkyl, $C_3$-$C_7$ cycloalkyl($C_0$-$C_6$ alkyl) , aryl ($C_0$-$C_6$ alkyl), or heteroaryl($C_0$-$C_6$ alkyl), wherein said aryl and heteroaryl groups are substituted with 0–2 substituents independently selected from the group consisting of $C_1$-$C_4$ alkyl, $C_1$-$C_4$ alkoxy, F, Cl, Br, $CF_3$, and $NO_2$;
$R^{14}$ is selected from:
H, $C_1$-$C_{10}$ alkyl, $C_2$-$C_{10}$ alkenyl, $C_2$-$C_{10}$ alkynyl, $C_3$-$C_{10}$ cycloalkyl, $C_1$-$C_6$ hydroxyalkyl, $C_1$-$C_6$ alkoxy ($C_1$-$C_6$ alkyl), aryl($C_0$-$C_6$ alkoxy $C_1$-$C_6$ alkyl), $C_1$-$C_6$ alkylthio($C_1$-$C_6$ alkyl), $C_1$-$C_6$ alkylsulfonyl($C_1$-$C_6$ alkyl), aryl($C_0$-$C_6$ alkylthio $C_1$-$C_6$ alkyl), aryl($C_0$-$C_6$ alkylsulfonyl $C_1$-$C_6$ alkyl), $C_3$-$C_{10}$ cycloalkyl($C_0$-$C_6$ alkyl), aryl($C_0$-$C_6$ alkyl), heteroaryl($C_0$-$C_6$ alkyl), $R^{17}R^{20}NC(=O) (C_1$-$C_4$ alkyl), $R^{10}OC(=O)(C_1$-$C_4$ alkyl), and $R^{17}R^{20}N(C_1$-$C_4$ alkyl), provided that any of the above alkyl, cycloalkyl, aryl or heteroaryl groups may optionally be substituted independently with 0–1 $R^{16}$ or 0–2 $R^8$;

$R^{15}$ is selected from:

H, $R^{16}$, $C_1$–$C_{10}$ alkyl, $C_2$–$C_{10}$ alkenyl, $C_2$–$C_{10}$ alkynyl, $C_3$–$C_{10}$ cycloalkyl ($C_0$–$C_6$ alkyl), $C_1$–$C_6$ alkoxy($C_1$–$C_6$ alkyl), $C_1$–$C_6$ alkylamino($C_1$–$C_6$ alkyl), $C_2$–$C_{10}$ dialkylamino($C_1$–$C_6$ alkyl), ($C_1$–$C_{10}$ alkyl)carbonyl, aryl($C_0$–$C_6$ alkyl) carbonyl, heteroaryl ($C_0$–$C_6$ alkyl) carbonyl, aryl($C_0$–$C_6$ alkyl), heteroaryl($C_0$–$C_6$ alkyl), $CO_2R^{17}$, $C(=O)R^{17}$, $CONR^{17}R^2O$, $SO_2R^{17}$, and $SO_2NR^{17}R^{20}$, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

Y is selected from $-C(=O)R^{19}$, $-SO_3H$, and $-PO_3H$;

$R^{16}$ is selected from:

—N($R^{20}$)—C(=O)—O—$R^{17}$,

—N($R^{20}$)—C(=O)—$R^{17}$,

—N($R^{20}$)—C(=O)—NH—$R^{17}$,

—N($R^{20}$)SO$_2$—$R^{17}$, and

—N($R^{20}$)SO$_2$—NR$^{20}$R$^{17}$;

$R^{17}$ is selected from:

$C_1$–$C_{10}$ alkyl, $C_3$–$C_{10}$ cycloalkyl, aryl($C_0$–$C_6$ alkyl), heteroaryl($C_0$–$C_6$ alkyl), arylaryl($C_0$–$C_6$ alkyl), heteroarylaryl ($C_0$–$C_6$ alkyl), arylheteroaryl ($C_0$–$C_6$ alkyl), and heteroarylheteroaryl ($C_0$–$C_6$ alkyl), wherein said aryl or heteroaryl groups are optionally substituted with 0–3 substituents independently selected from the group consisting of: $C_1$–$C_4$ alkyl, $C_1$–$C_4$ alkoxy, aryl, F, Cl, Br, CN, $NH_2$, $CF_3$, and $NO_2$;

$R^{18}$ is selected from:

H,

—C(=O)OR$^{17}$,

—C(=O)R$^{17}$,

—C(=O)NHR$^{17}$,

—SO$_2$R$^{17}$,

—SO$_2$NR$^{20}$R$^{17}$, $C_1$–$C_{10}$ alkyl, $C_3$–$C_{10}$ cycloalkyl ($C_0$–$C_6$ alkyl), aryl($C_0$–$C_6$ alkyl), and heteroaryl ($C_0$–$C_6$ alkyl), wherein said aryl group is optionally substituted with 0–3 substituents independently selected from the group consisting of: $C_1$–$C_4$ alkyl, $C_1$–$C_4$ alkoxy, aryl, F, Cl, Br, —CN, —NH$_2$, —CF$_3$, and —NO$_2$;

$R^{19}$ is selected from:

hydroxy, $C_1$–$C_{10}$ alkyloxy, $C_3$–$C_{10}$ cycloalkyloxy, aryloxy, aryl($C_1$–$C_6$ alkoxy), $C_2$–$C_{10}$ alkylcarbonyloxy($C_1$–$C_2$ alkyl)oxy, $C_2$–$C_{10}$ alkoxycarbonyloxy($C_1$–$C_2$ alkyl)oxy, $C_2$–$C_{10}$ alkoxycarbonyl($C_1$–$C_2$ alkyl)oxy, $C_3$–$C_{10}$ cycloalkylcarbonyloxy($C_1$–$C_2$ alkyl)oxy, $C_3$–$C_{10}$ cycloalkoxycarbonyloxy($C_1$–$C_2$ alkyl)oxy, $C_3$–$C_{10}$ cycloalkoxycarbonyl($C_1$–$C_2$ alkyl)oxy, aryloxycarbonyl($C_1$–$C_2$ alkyl)oxy, aryloxycarbonyloxy($C_1$–$C_2$ alkyl)oxy, arylcarbonyloxy($C_1$–$C_2$ alkyl)oxy, $C_1$–$C_5$ alkoxy($C_1$–$C_5$ alkyl)carbonyloxy($C_1$–$C_2$ alkyl)oxy, (5-($C_1$–$C_5$ alkyl)-1,3-dioxa-cyclopenten-2-one-yl)methyloxy, (5-aryl-1,3-dioxa-cyclopenten-2-one-yl)methyloxy, ($R^{10}$)($R^{11}$)N-($C_1$–$C_{10}$ alkoxy) and —O(CH$_2$)$_k$N$^+$(R$^{21}$) (R$^{22}$) (R$^{23}$) Z$^-$;

$R^{20}$ is selected from:

H, $C_1$–$C_6$ alkyl, $C_3$–$C_7$ cycloalkyl($C_0$–$C_6$ alkyl)-, aryl, aryl($C_0$–$C_6$ alkyl)-, and heteroaryl($C_0$–$C_6$ alkyl), wherein said aryl or heteroaryl groups are optionally substituted with 0–3 substituents independently selected from the group consisting of: $C_1$–$C_4$ alkyl, $C_1$–$C_4$ alkoxy, F, Cl, Br, $CF_3$, and $NO_2$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{21}$, $R^{22}$ and $R^{23}$ are independently selected from:

H, $C_1$–$C_9$ alkyl, $C_3$–$C_7$ cycloalkyl($C_0$–$C_4$ alkyl), aryl ($C_0$–$C_6$ alkyl), heteroaryl, and heteroaryl($C_0$–$C_6$ alkyl), wherein said alkyl or aryl groups are substituted with 0–2 substituents selected from the group consisting of $C_1$–$C_4$ alkyl, $C_1$–$C_4$ alkoxy, OH, F, Cl, Br, $CF_3$, and $NO_2$;

alternatively $R^{21}$ and $R^{22}$ can be taken together to form a 5–7 membered heterocyclic aromatic or non-aromatic ring system containing 1–3 heteroatoms selected from N, O and S and $R^{23}$ is defined as above or $R^{21}$, $R^{22}$, and $R^{23}$ can be taken together to form a heterobicyclic ring system containing 1–3 heteroatoms selected from N, O and S, wherein said heterocyclic or heterobicyclic ring being substituted with 0–2 groups selected from $C_1$–$C_4$ alkyl, $C_1$–$C_4$ alkoxy, halo, —CN, —NH$_2$, —CF$_3$, and —NO$_2$;

h is 0–4;

i is 0–2;

k is 2–6;

m is 1–4;

n is 0–5;

q is 2–3;

r is 0–3;

t is 1–3; and p is 0–2;

provided that h, i, m, n, q, r, t, and p at each occurrence, are chosen such that the number of in-chain atoms between Y and the pyrimidine, pyrimidone, triazine or triazinone of G is in the range of 8–12.

[3] Preferred compounds of the invention as described above are compounds of Formula (IA):

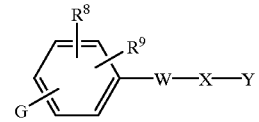

(IA)

including stereoisomeric forms thereof, tautomeric forms thereof, pharmaceutically acceptable salt forms thereof or prodrug forms thereof, wherein:

G is a meta or para substituent with respect to W and is selected from:

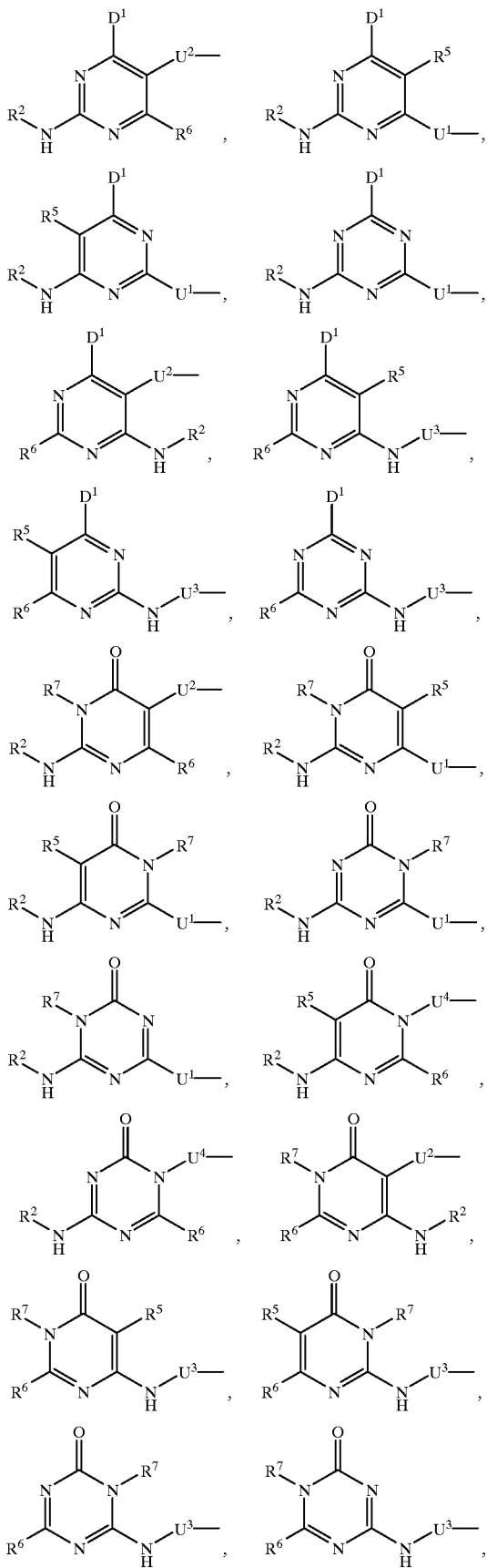

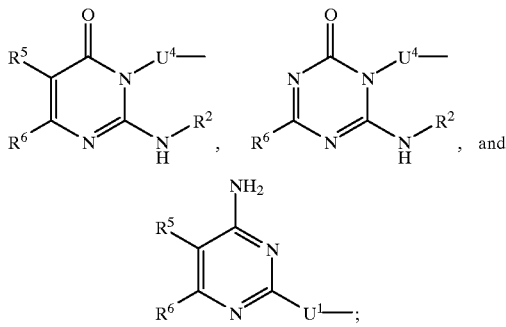

$D^1$ is selected from: $NR^2R^4$, $OR^3$, $SR^3$, F, Cl, Br, $CF_3$, methyl, ethyl, propyl, and butyl;

$R^2$ at each occurrence is independently selected from:
H, $OR^3$, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl($C_0$–$C_4$ alkyl)carbonyl, $C_3$–$C_7$ cycloalkyl ($C_0$–$C_4$ alkoxy)carbonyl, aryl($C_0$–$C_6$ alkyl), heteroaryl ($C_0$–$C_6$ alkyl), aryl($C_0$–$C_6$alkyl)carbonyl, heteroaryl ($C_0$–$C_6$ alkyl)carbonyl, $C_1$–$C_6$ alkylsulfonyl, aryl ($C_0$–$C_6$ alkyl)sulfonyl, heteroaryl($C_0$–$C_6$ alkyl) sulfonyl, aryl($C_1$–$C_6$ alkoxy)carbonyl, and heteroaryl ($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^3$ at each occurrence is independently selected from:
H, $C_1$–$C_6$ alkyl, ($C_1$–$C_6$ alkyl)carbonyl, ($C_1$–$C_6$ alkoxy) carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl ($C_0$–$C_4$ alkyl)carbonyl, cycloalkyl($C_0$–$C_4$ alkoxy) carbonyl, aryl($C_0$–$C_6$ alkyl), heteroaryl($C_0$–$C_6$ alkyl), aryl($C_0$–$C_6$ alkyl)carbonyl, heteroaryl($C_0$–$C_6$ alkyl) carbonyl, aryl($C_1$–$C_6$ alkoxy)carbonyl, and heteroaryl ($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^4$ is selected from:
H, $C_1$–$C_6$ alkyl, $C_1$–$C_6$ alkylcarbonyl, $C_1$–$C_6$ alkoxycarbonyl, $C_3$–$C_7$ cycloalkyl($C_0$–$C_4$ alkyl), $C_3$–$C_7$ cycloalkyl($C_0$–$C_4$ alkyl)carbonyl, cycloalkyl ($C_0$–$C_4$ alkoxy)carbonyl, aryl($C_0$–$C_6$ alkyl), heteroaryl ($C_0$–$C_6$ alkyl), aryl ($C_0$–$C_6$ alkyl) carbonyl, heteroaryl ($C_0$–$C_6$ alkyl)carbonyl, aryl($C_1$–$C_6$ alkoxy)carbonyl, and heteroaryl($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^2$ and $R^4$ when both substituents on the same nitrogen atom as in ($—NR^2R^4$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$–$C_6$ alkyl, $C_3$–$C_7$ cycloalkyl($C_0$–$C_4$ alkyl), $C_1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heteroaryl($C_0$–$C_5$ alkyl), aryl($C_1$–$C_5$ alkoxy)carbonyl, heteroaryl($C_1$–$C_5$ alkoxy)carbonyl, $C_1$–$C_6$ alkylsulfonyl, arylsulfonyl, and heteroarylsulfonyl;

$R^5$ is selected from:

H, $NR^2R^4$, $OR^3$, $NO_2$, NO, $C_1$–$C_6$ alkyl, $C_3$–$C_7$ cycloalkyl($C_0$–$C_4$ alkyl), aryl($C_0$–$C_6$ alkyl), or heteroaryl($C_0$–$C_6$ alkyl), wherein said aryl and heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$NHR^2$ and $R^5$, when substituents on adjacent carbon atoms, are taken together with the carbon atoms to which they are attached to form a 5–7 membered heterocyclic ring containing 1, 2 or 3 nitrogen atoms, said heterocyclic ring being aromatic or nonaromatic, said heterocyclic ring being substituted with 0–2 substituents independently selected from the group consisting of $C_1$–$C_4$ alkyl, $C_1$–$C_4$ alkoxy, F, Cl, Br, $CF_3$, $NO_2$, and phenyl, wherein said phenyl group is substituted with 0–2 substituents independently selected from the group consisting of $C_1$–$C_4$ alkyl, $C_1$–$C_4$ alkoxy, F, Cl, Br, $CF_3$, and $NO_2$;

$R^6$ is selected from:

H, $NR^2R^4$, $OR^3$, $C_1$–$C_6$ alkyl, aryl($C_0$–$C_5$ alkyl), heteroaryl($C_0$–$C_5$ alkyl), $CF_3$, F, Cl, and Br, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^5$ and $R^6$, when substituents on adjacent carbon atoms, are taken together with the carbon atoms to which they are attached to form a 5–7 membered heterocyclic ring containing 1, 2 or 3 nitrogen atoms or a 5–7 membered carbocyclic ring, said carbocyclic or heterocyclic ring being aromatic or nonaromatic, said carbocyclic or heterocyclic ring being substituted with 0–2 substituents independently selected from the group consisting of $C_1$–$C_4$ alkyl, $C_1$–$C_4$ alkoxy, F, Cl, Br, $CF_3$, $NO_2$ and phenyl, wherein said phenyl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^7$ is selected from:

H, $C_1$–$C_4$ alkyl, $C_3$–$C_6$ alkenyl, $C_3$–$C_6$ alkynyl, aryl ($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$NHR^2$ and $R^7$, when substituents on adjacent atoms, are taken together with the atoms to which they are attached to form a 5–7 membered heterocyclic ring containing 2 or 3 nitrogen atoms, said heterocyclic ring being aromatic or nonaromatic, said heterocyclic ring being substituted with 0–2 substituents independently selected from the group consisting of $C_1$–$C_4$ alkyl, $C_1$–$C_4$ alkoxy, F, Cl, Br, $CF_3$, $NO_2$, and phenyl, wherein said phenyl groups are substituted with 0–2 substituents independently selected from the group consisting of $C_1$–$C_4$ alkyl, $C_1$–$C_4$ alkoxy, F, Cl, Br, $CF_3$, and $NO_2$;

$U^1$ is selected from:

—$(CH_2)_n$-,
—O—$(CH_2)_m$-,
—$(CH_2)_m$-O—,
—$(CH_2)_m$-N($R^3$)—,
—S—$(CH_2)_m$-,
—$(CH_2)_m$-S—,
—$(CH_2)_m$-S(=O)—,
—$(CH_2)_m$-S(=O)$_2$—,
—$(CH_2)_r$-N($R^3$)—$CH_2$—,
—$(CH_2)_r$-N($R^3$)—C(=O)—,
—$(CH_2)_r$-N($R^3$)—S(=O)$_2$—,
—$(CH_2)_r$-C(=O)—N($R^3$)—,
—$(CH_2)_r$-S(=O)$_2$—N($R^3$)—,
—$(CH_2)_r$-O—$CH_2$—,
—$(CH_2)_r$-S—$CH_2$—,
—$(CH_2)_r$-S—(=O)—$CH_2$—,
—$(CH_2)_r$-S(=O)$_2$—$CH_2$—,
—$CH_2$—O—$(CH_2)_r$-,
—$CH_2$—S—$(CH_2)_r$-,
—$CH_2$—S(=O)—$(CH_2)_r$-,
—$CH_2$—S(=O)$_2$—$(CH_2)_r$-,
—$CH_2$—N($R^3$)—$(CH_2)_r$-,
—C(=O)—N($R^4$)—$(CH_2)_r$-,
—N($R^4$)—,
—N($R^4$)—$(CH_2)_m$-,
—N($R^4$)—$(CH_2)_q$-N($R^3$)—,
—N($R^4$)—$(CH_2)_q$-O—,
—N($R^4$)—$(CH_2)_q$-S—,
—N($R^4$)—$(CH_2)_q$-S(O)—,
—N($R^4$)—$(CH_2)_q$-S(O)$_2$—,
—N($R^4$)—C(=O)—$(CH_2)_r$-, and
—N($R^4$)—$(CH_2)_r$-C(=O)—;

$U^2$ is selected from:

—$(CH_2)_h$-,
—O—$(CH_2)_r$-,
—$(CH_2)_r$-O—,
—$(CH_2)_r$-N($R^3$)—,
—S—$(CH_2)_r$-,
($CH_2)_r$-S—,
—$(CH_2)_r$-S(=O)—,
—$(CH_2)_r$-S(=O)$_2$—,
—$(CH_2)_i$-N($R^3$)—$CH_2$—,
—$(CH_2)_i$-N($R^3$)—C(=O)—,
—$(CH_2)_i$-N($R^3$)—S(=O)$_2$—,
—$(CH_2)_i$-C(=O)—N($R^3$)—,
—$(CH_2)_i$-S (=O)$_2$—N($R^3$)—,
—$(CH_2)_i$-O—$CH_2$—,
—$(CH_2)_i$-S—$CH_2$—,
—$(CH_2)_i$-S(=O)—$CH_2$—,
—$(CH_2)_i$-S(=O)$_2$—$CH_2$—,
—$CH_2$—O—$(CH_2)_i$-,
—$CH_2$—S—$(CH_2)_i$-,
—$CH_2$—S(=O)—$(CH_2)_i$-,
—$CH_2$—S(=O)$_2$-$(CH_2)_i$-,
—$CH_2$—N($R^3$)—$(CH_2)_i$,
—C(=O)—N($R^4$)—$(CH_2)_i$-,
—N($R^4$)—,
—N($R^4$)—$(CH_2)_r$-,
—N($R^4$)—$(CH_2)_2$—N($R^3$)—,
—N($R^4$)—$(CH_2)_2$—O—,
—N($R^4$)—$(CH_2)_2$—S—,
—N($R^4$)—$(CH_2)_2$—S(O)—,
—N($R^4$)—$(CH_2)_2$—S(O)$_2$—,
—N($R^4$)—C(=O)—$(CH_2)_i$-, and —N($R^4$)—($CH_2$)$_r$-C(=O)—;

$U^3$ is selected from:
—($CH_2$)$_h$-,
—($CH_2$)$_q$-O—,
—($CH_2$)$_q$N($R^3$)—,
—($CH_2$)$_q$-N($R^3$)—C(=O)—,
—($CH_2$)$_r$-C(=O)—N($R^3$)—,
—($CH_2$)$_q$-S—,
—($CH_2$)$_q$-S(O)—,
—($CH_2$)$_q$-S(O)$_2$—
—($CH_2$)$_q$-S(O)$_2$—N($R^3$),
—($CH_2$)$_q$-N($R^3$)—S(O)$_2$—,
—($CH_2$)$_q$-N($R^3$)—$CH_2$—,
—($CH_2$)$_q$-O-13 $CH_2$—,
—($CH_2$)$_h$-C(=O)—,
—C(=O)—($CH_2$)$_r$-, and
—C(=O)—N($R^4$)—($CH_2$)$_p$;

$U^4$ is selected from:
—($CH_2$)$_h$-,
—($CH_2$)$_2$—O—,
—($CH_2$)$_2$—N($R^3$)—,
—($CH_2$)$_2$—S—,
—($CH_2$)$_2$—S(O)—,
—($CH_2$)$_2$—S(O)$_2$—,
—($CH_2$)$_2$—O—$CH_2$—,
—($CH_2$)$_r$-C(=O)—,
—C(=O)—($CH_2$)$_r$, and
—C(=O)—N($R^4$)—($CH_2$)$_r$;

$R^8$ and $R^9$ are independently selected from: H, $C_1$–$C_4$ alkyl, $CF_3$, F, Cl, Br, and $OR^{10}$;

$R^{10}$ and $R^{11}$ are independently selected from:
H, $C_1$–$C_8$ alkyl, $C_3$–$C_6$ alkenyl, $C_3$–$C_{10}$ cycloalkyl($C_0$–$C_4$ alkyl), aryl($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^{10}$ and $R^{11}$ when both substituents on the same nitrogen atom as in (—$NR^{10}R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$–$C_6$ alkyl, $C_3$–$C_7$ cycloalkyl($C_0$–$C_4$ alkyl), $C_1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heteroaryl($C_0$–$C_5$ alkyl), aryl($C_1$–$C_5$ alkoxy)carbonyl, heteroaryl($C_1$–$C_5$ alkoxy)carbonyl, $C_1$–$C_6$ alkylsulfonyl arylsulfonyl and heteroarylsulfonyl;

W is —($CHR^{12}$)$_p$C(=O)N($R^{13}$)— or —C(=O)—N($R^{13}$)—($CHR^{12}$)$_p$-;

X is —CH($R^{14}$)—$CHR^{12}$— or —$CHR^{12}$—CH($R^{15}$)—;

$R^{12}$ at each occurrence is independently selected from: H, or $C_1$–$C_6$ alkyl;

$R^{13}$ is selected from:
H, $C_1$–$C_6$ alkyl, $C_3$–$C_7$ cycloalkyl($C_0$–$C_6$ alkyl), aryl ($C_0$–$C_6$ alkyl), or heteroaryl($C_0$–$C_6$ alkyl), wherein said aryl and heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^{14}$ is selected from:
H, $C_1$–$C_{10}$ alkyl, $C_2$–$C_{10}$ alkenyl, $C_2$–$C_{10}$ alkynyl, $C_3$–$C_{10}$ cycloalkyl, $C_1$–$C_6$ hydroxyalkyl, $C_1$–$C_6$ alkoxy ($C_1$–$C_6$ alkyl), aryl($C_0$–$C_6$ alkoxy $C_1$–$C_6$ alkyl), $C_1$–$C_6$ alkylthio($C_1$–$C_6$ alkyl), $C_1$–$C_6$ alkylsulfonyl($C_1$–$C_6$ alkyl), aryl($C_0$–$C_6$ alkylthio $C_1$–$C_6$ alkyl), aryl($C_0$–$C_6$ alkylsulfonyl $C_1$–$C_6$ alkyl),$C_3$–$C_{10}$ cycloalkyl($C_0$–$C_6$ alkyl), aryl ($C_0$–$C_6$ alkyl), heteroaryl ($C_0$–$C_6$ alkyl), $R^{17}R^{20}$NC(=O)($C_1$–$C_4$ alkyl), $R^{10}$OC(=O)($C_1$–$C_4$ alkyl), and $R^{17}R^{20}$N($C_1$–$C_4$ alkyl), provided that any of the above alkyl, cycloalkyl, aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^{15}$ is selected from:
—NH—C(=O)—O—$R^{17}$,
—NH—C(=O)—$R^{17}$,
—NH—C(=O)—NH—$R^{17}$,
—$NHSO_2$—$R^{17}$, and
—$NHSO_2$—$NR^{20}R^{17}$;

Y is —C(=O)$R^{19}$;

$R^{17}$ is selected from:
$C_1$–$C_{10}$ alkyl, $C_3$–$C_{10}$ cycloalkyl, aryl($C_0$–$C_6$ alkyl), heteroaryl($C_0$–$C_6$ alkyl), arylaryl($C_0$–$C_6$ alkyl), heteroarylaryl($C_0$–$C_6$ alkyl), arylheteroaryl($C_0$–$C_6$ alkyl), and heteroarylheteroaryl ($C_0$–$C_6$ alkyl), wherein said aryl or heteroaryl groups are optionally substituted with 0–3 substituents independently selected from the group consisting of: $C_1$–$C_4$ alkyl, $C_1$–$C_4$ alkoxy, aryl, F, Cl, Br, CN, $NH_2$, $CF_3$, and $NO_2$;

$R^{19}$ is selected from:
hydroxy,
$C_1$–$C_{10}$ alkyloxy,
$C_3$–$C_{10}$ cycloalkyloxy,
aryloxy,
aryl ($C_1$–$C_6$ alkoxy)
$C_2$–$C_{10}$ alkylcarbonyloxy($C_1$–$C_2$ alkyl)oxy-,
$C_2$–$C_{10}$ alkoxycarbonyloxy($C_1$–$C_2$ alkyl)oxy-,
$C_2$–$C_{10}$ alkoxycarbonyl ($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl) oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl) oxy-,
(5-($C_1$–$C_5$ alkyl)-1,3-dioxa-cyclopenten-2-one-yl) methyloxy,
(5-aryl-1,3-dioxa-cyclopenten-2-one-yl)methyloxy,
($R^{10}$) ($R^{11}$)N-($C_1$–$C_{10}$ alkoxy)- and
—O($CH_2$)$_k$$N^+$($R^{21}$) ($R^{22}$) ($R^{23}$)$Z^-$;

$R^{20}$ is selected from H, methyl, ethyl, propyl, and butyl;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{21}$, $R^{22}$ and $R^{23}$ are independently selected from:
H, $C_1$–$C_6$ alkyl, $C_3$–$C_7$ cycloalkyl($C_0$–$C_4$ alkyl)-, aryl, aryl($C_1$–$C_6$ alkyl)-, heteroaryl, and heteroaryl($C_1$–$C_6$ alkyl)- wherein said alkyl or aryl groups are substituted with 0–2 substituents selected from the group consisting of $C_1$–$C_4$ alkyl, $C_1$–$C_4$ alkoxy, OH, F, Cl, Br, $CF_3$, and $NO_2$;

alternatively $R^{21}$ and $R^{22}$ can be taken together to form a 5–7 membered heterocyclic aromatic or non-aromatic ring system containing 1–3 heteroatoms selected from N, O and S and $R^{23}$ is defined as above or $R^{21}$, $R^{22}$, and $R^{23}$ can be taken together to form a heterobicyclic ring system containing 1–3 heteroatoms selected from N, O and S, wherein said heterocyclic or heterobicyclic ring being substituted with 0–2 groups selected from $C_1$–$C_4$ alkyl, $C_1$–$C_4$ alkoxy, halo, —CN, —$NH_2$, —$CF_3$, and —$NO_2$;

h is 0–4;
i is 0–2;
k is 2–6;
m is 1–4;
n is 0–5;
q is 2–3;
r is 0–3;
t is 1–3; and
p is 0–2;

provided that h, i, m, n, q, r, t, and p at each occurrence, are chosen such that the number of in-chain atoms between Y and the pyrimidine, pyrimidone, triazine or triazinone of G is in the range of 8–12.

[4] Further preferred compounds of the invention as described above are compounds of the Formula (IA):

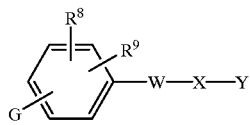

(IA)

including stereoisomeric forms thereof, tautomeric forms thereof, pharmaceutically acceptable salt forms thereof or prodrug forms thereof, wherein:

G is a meta or para substituent with respect to W and is selected from:

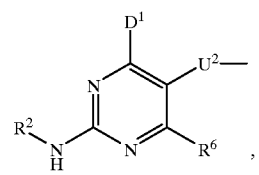
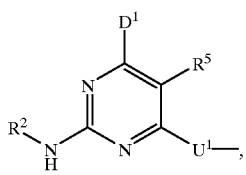
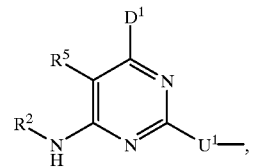
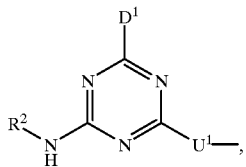
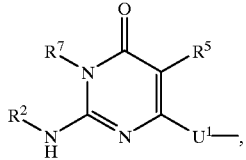

-continued

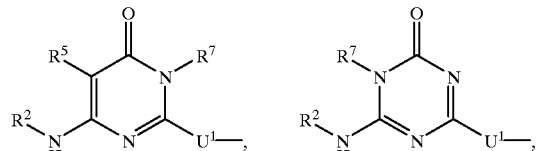

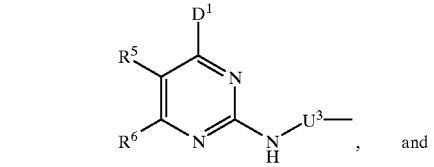
, and

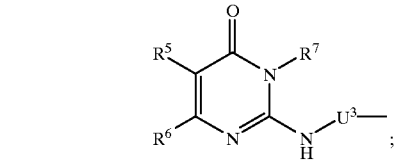
;

$D^1$ is $NR^2R^4$ or $OR^3$;

$R^2$ at each occurrence is independently selected from:
H, methyl, ethyl, propyl, butyl, ($C_1$–$C_4$ alkyl)carbonyl, ($C_1$–$C_4$ alkoxy) carbonyl, $C_3$–$C_7$ cycloalkyl ($C_0$–$C_4$ alkyl), $C_3$–$C_7$ cycloalkyl($C_0$–$C_4$ alkyl)carbonyl, and $C_3$–$C_7$ cycloalkyl ($C_0$–$C_4$ alkoxy) carbonyl;

$R^3$ is selected from: H, methyl, ethyl, propyl, and butyl;

$R^4$ is selected from: H, methyl, ethyl, propyl, butyl cyclopropyl, and cyclopropylmethyl;

$R^5$ is selected from H, $NR^2R^4$, methyl, ethyl, propyl, butyl, pentyl, and hexyl;

alternatively, —$NHR^2$ and $R^5$, when substituents on adjacent carbon atoms, are taken together with the carbon atoms to which they are attached to form a 5–6 membered heterocyclic ring containing 1, 2 or 3 nitrogen atoms, wherein —$NHR^2$—$R^5$- taken together are selected from the group —NH—CH=N—, —NH—N=N—, —NH—N=C—, —NH—CH=CH—, —NH—$CH_2$—$CH_2$—, —NH—$CH_2$—$CH_2$—$CH_2$—, and —NH—$CH_2$—$CH_2$—NH—, $R^6$ is selected from:
H, $NR^2R^4$, $OR^3$, methyl, ethyl, propyl, butyl, pentyl, hexyl, aryl($C_0$–$C_5$ alkyl), heteroaryl($C_0$–$C_5$ alkyl), $CF_3$, F, Cl, and Br, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$R^5$ and —$R^6$, when substituents on adjacent carbon atoms, are taken together with the carbon atoms to which they are attached to form a 6 membered heterocyclic ring containing 1 or 2 nitrogen atoms or a 5–6 membered carbocyclic ring, wherein —$R^5$—$R^6$— taken together are selected from the group —$CH_2$—$CH_2$—$CH_2$—, —$CH_2$—$CH_2$—$CH_2$—$CH_2$—, —CH=CH—CH=CH—, —N=CH—CH=CH—, —N=CH—CH=N—, —N=CH—N=CH—, and —N=N—CH=CH—;

$R^7$ is selected from:
H, methyl, ethyl, propyl, butyl, $C_3$–$C_6$ alkenyl, $C_3$–$C_6$ alkynyl, aryl($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$NHR^2$ and $R^7$, when substituents on adjacent atoms, are taken together with the atoms to which they are attached to form a 5–6 membered heterocyclic ring containing 2 or 3 nitrogen atoms, wherein —NHR$^2$—R$^7$— taken together are selected from the group —NH—CH=N—, —NH—N=N—, —NH—N=C—, —NH—CH=CH—, —NH—CH$_2$—CH$_2$—, —NH—CH$_2$—CH$_2$—CH$_2$—, —NH—CH$_2$—CH$_2$—NH—, —N=CH—CH=CH—, —N=CH—CH=N—, —N=CH—N=CH—, and —N=N—CH=CH—;

U$^1$ is selected from:
—(CH$_2$)$_n$-,
—O(CH$_2$)$_m$-,
—(CH$_2$)$_m$-O—,
—(CH$_2$)$_m$-N(R$^3$)—,
—(CH$_2$)$_r$-N(R$^3$)—CH$_2$—,
—(CH$_2$)$_r$-O—CH$_2$—,
—CH$_2$—O—(CH$_2$)$_r$-,
—CH$_2$—N(R$^3$)—(CH$_2$)$_r$-, and
—N(R$^4$)—(CH$_2$)$_m$-;

U$^2$ is selected from:
—(CH$_2$)$_h$-,
—O—(CH$_2$)$_i$-,
—(CH$_2$)$_i$-O—,
—(CH$_2$)$_i$-N(R$^3$)—,
—(CH$_2$)$_i$-N(R$^3$)—CH$_2$—,
—(CH$_2$)$_i$-O—CH$_2$—,
—CH$_2$—O—(CH$_2$)$_i$-,
—CH$_2$—N(R$^3$)—(CH$_2$)$_i$-, and
—N(R$^4$)—(CH$_2$)$_i$-;

U$^3$ is selected from:
—(CH$_2$)$_h$-,
—(CH$_2$)$_q$O—,
—(CH$_2$)$_q$-N(R$^3$)—,
—(CH$_2$)$_q$-N(R$^3$)—CH$_2$—, and
—(CH$_2$)$_q$-O—CH$_2$—;

R$^8$ and R$^9$ are independently selected from: H, methyl, ethyl, propyl, butyl, CF$_3$, F, Cl, Br, and OR$^{10}$;

R$^{10}$ and R$^{11}$ are independently selected from:
H, C$_1$–C$_8$ alkyl, C$_3$–C$_6$ alkenyl, C$_3$–C$_{10}$ cycloalkyl(C$_0$–C$_4$ alkyl), aryl(C$_0$–C$_4$ alkyl), and heteroaryl(C$_0$–C$_4$ alkyl), wherein said aryl or heteroaryl groups are substituted with 0–2 substituents independently selected from the group consisting of C$_1$–C$_4$ alkyl, C$_1$–C$_4$ alkoxy, F, Cl, Br, CF$_3$, and NO$_2$;

alternatively, R$^{10}$ and R$^{11}$ when both substituents on the same nitrogen atom as in (—NR$^{10}$R$^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from oxo, C$_1$–C$_6$ alkyl, C$_3$–C$_7$ cycloalkyl(C$_0$–C$_4$ alkyl), C$_1$–C$_6$ alkylcarbonyl, C$_3$–C$_7$ cycloalkyl(C$_0$–C$_5$ alkyl) carbonyl, C$_1$–C$_6$ alkoxycarbonyl, C$_3$–C$_7$ cycloalkyl(C$_0$–C$_5$ alkoxy)carbonyl, aryl(C$_0$–C$_5$ alkyl), heteroaryl(C$_0$–C$_5$ alkyl), aryl(C$_1$–C$_5$ alkoxy)carbonyl, heteroaryl(C$_1$–C$_5$ alkoxy)carbonyl, C$_1$–C$_6$ alkylsulfonyl arylsulfonyl and heteroarylsulfonyl;

W is —CH$_2$C(=O)N(R$^{13}$)—, —CH$_2$CH$_2$C(=O)N(R$^{13}$)—, or —C(=O)N(R$^{13}$)—;

X is —CH(R$^{14}$)—CH$_2$— or —CH$_2$—CH(R$^{15}$)—;

R$^{13}$ is H or methyl;

R$^{14}$ is selected from:
H, C$_1$–C$_{10}$ alkyl, C$_2$–C$_{10}$ alkenyl, C$_2$–C$_{10}$ alkynyl, C$_3$–C$_{10}$ cycloalkyl, C$_1$–C$_6$ hydroxyalkyl, C$_1$–C$_6$ alkoxy (C$_1$–C$_6$ alkyl), aryl(C$_0$–C$_6$ alkoxy C$_1$–C$_6$ alkyl), C$_1$–C$_6$ alkylthio(C$_1$–C$_6$ alkyl), C$_1$–C$_6$ alkylsulfonyl(C$_1$–C$_6$ alkyl), aryl(C$_0$–C$_6$ alkylthio C$_1$–C$_6$ alkyl), aryl(C$_0$–C$_6$ alkylsulfonyl C$_1$–C$_6$ alkyl),C$_3$–C$_{10}$ cycloalkyl (C$_0$–C$_6$ alkyl), aryl(C$_0$–C$_6$ alkyl), heteroaryl(C$_0$–C$_6$ alkyl), R$^{17}$HNC(=O) (C$_1$–C$_4$ alkyl), R$^{10}$OC(=O) (C$_1$–C$_4$ alkyl), and R$^{17}$HN(C$_1$–C$_4$ alkyl), provided that any of the above alkyl, cycloalkyl, aryl or heteroaryl groups are substituted with 0–2 substituents independently selected from the group consisting of C$_1$–C$_4$ alkyl, C$_1$–C$_4$ alkoxy, F, Cl, Br, CF$_3$, and NO$_2$;

R$^{15}$ is selected from:
—NH—C(=O)—O—R$^{17}$,
—NH—C(=O)—R$^{17}$,
—NH—C(=O)—NH—R$^{17}$,
—NHSO$_2$—R$^{17}$, and
—NHSO$_2$—NHR$^{17}$;

Y is —C(=O)R$^{19}$;

R$^{17}$ is selected from:
C$_1$–C$_{10}$ alkyl, C$_3$–C$_{10}$ cycloalkyl, aryl(C$_0$–C$_6$ alkyl), heteroaryl(C$_0$–C$_6$ alkyl), arylaryl(C$_0$–C$_6$ alkyl), heteroarylaryl(C$_0$–C$_6$ alkyl), arylheteroaryl(C$_0$–C$_6$ alkyl), and heteroarylheteroaryl (C$_0$–C$_6$ alkyl), wherein said aryl or heteroaryl groups are optionally substituted with 0–3 substituents independently selected from the group consisting of: C$_1$–C$_4$ alkyl, C$_1$–C$_4$ alkoxy, aryl, F, Cl, Br, CN, NH$_2$, CF$_3$, and NO$_2$;

R$^{19}$ is selected from:
hydroxy,
C$_1$–C$_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5- (t-butyl) -1, 3-dioxacyclopenten-2-on-4-yl)methoxy-,
(1,3-dioxa-5-phenyl-cyclopenten-2-on-4-yl)methoxy-,
1-(2-(2-methoxypropyl)carbonyloxy)ethoxy-,
(R$^{10}$)(R$^{11}$)N-(C$_1$–C$_{10}$ alkoxy)-, and
—O (CH$_2$)$_k$N$^+$(R$^{21}$) (R$^{22}$) (R$^{23}$) Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{21}$ R$^{22}$ and R$^{23}$ are independently selected from:
H, methyl, ethyl, propyl, butyl, C$_3$–C$_7$ cycloalkyl (C$_0$–C$_4$ alkyl), phenyl, benzyl, wherein said phenyl group is substituted with 0–2 substituents selected from the group consisting of C$_1$–C$_4$ alkyl, C$_1$–C$_4$ alkoxy, OH, F, Cl, Br, CF$_3$, and NO$_2$;

alternatively $R^{21}$ and $R^{22}$ can be taken together to form a 5–7 membered heterocyclic aromatic or non-aromatic ring system containing 1–2 heteroatoms selected from N, O and S and $R^{23}$ is defined as above or $R^{21}$, $R^{22}$, and $R^{23}$ can be taken together to form a heterobicyclic ring system containing 1–2 heteroatoms selected from N, O and S;

h is 0–4;

i is 0–2;

k is 2–6;

m is 1–4;

n is 0–5;

q is 2–3;

r is 0–3; and t is 1–3;

provided that h, i, m, n, q, r, and t, at each occurrence, are chosen such that the number of in-chain atoms between Y and the pyrimidine, pyrimidone, triazine or triazinone of G is in the range of 8–12.

[5] Still further preferred compounds of the above invention as described above are compounds of the Formula (IA):

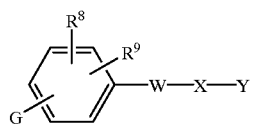

(IA)

including stereoisomeric forms thereof, tautomeric forms thereof, pharmaceutically acceptable salt forms thereof or prodrug forms thereof, wherein:

G is a meta or para substituent with respect to W and is selected from:

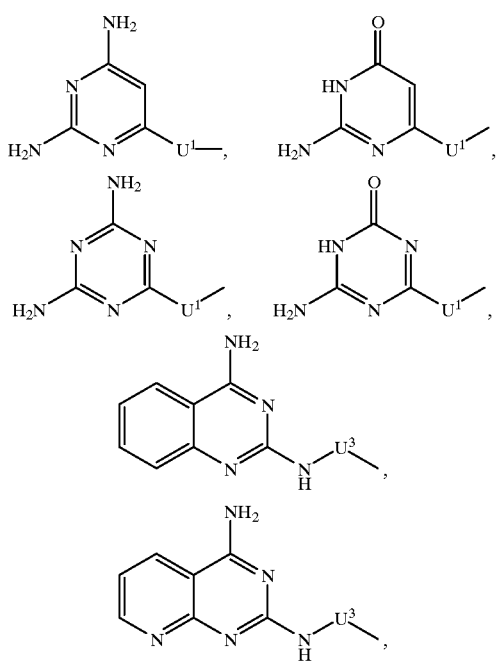

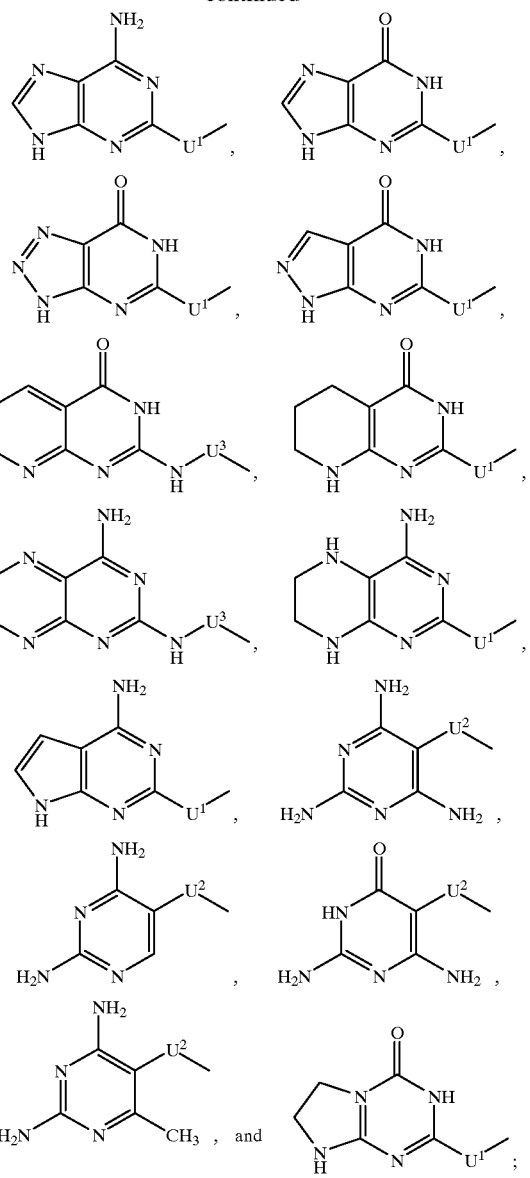

$U^1$ is selected from: —$CH_2CH_2$—, —$CH_2CH_2CH_2$—, —NH—$CH_2$—, and —NH—$CH_2CH_2$—;

$U^2$ is selected from: —$CH_2CH_2$—, —$CH_2CH_2$—, —NH—$CH_2$—, and —NH—$CH_2CH_2$—;

$U^3$ is —$CH_2$—, —$CH_2CH_2$— or —$CH_2CH_2CH_2$—;

$R^8$ is selected from: H, methyl, ethyl, propyl, butyl, —OH, methoxy, ethoxy, F, Cl, Br, and $CF_3$;

$R^9$ is H, $R^{10}$ and $R^{11}$ are independently selected from:

H, methyl, ethyl, propyl, butyl, $C_3$–$C_6$ alkenyl, $C_3$–$C_4$ cycloalkyl($C_0$–$C_4$ alkyl), aryl($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$; alternatively, $R^{10}$ and $R^{11}$ when both substituents on the same nitrogen atom as in (—$NR^{10}R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl;

W is —CH$_2$C(=O)N(R$^{13}$)—, —CH$_2$CH$_2$C(=O)N(R$^{13}$)—, or —C(=O)N(R$^{13}$)—;

X is —CH(R$^{14}$)—CH$_2$— or —CH$_2$—CH(R$^{15}$)—;

R$^{13}$ is H, methyl, ethyl, propyl, butyl, pentyl, or hexyl;

R$^{14}$ is selected from:

C$_2$–C$_8$ alkenyl, C$_2$–C$_8$ alkynyl, C$_3$–C$_8$ cycloalkyl, C$_1$–C$_6$ hydroxyalkyl, C$_3$–C$_8$ cycloalkyl(C$_0$–C$_6$ alkyl), aryl (C$_0$–C$_6$ alkyl), heteroaryl (C$_0$–C$_6$ alkyl), R$^{17}$HNC(=O) (C$_1$–C$_4$ alkyl), and R$^{17}$HN(C$_1$–C$_4$ alkyl), provided that any of the above alkyl, cycloalkyl, aryl or heteroaryl groups are substituted with 0–2 substituents independently selected from the group consisting of methyl, ethyl, propyl, butyl, methoxy, ethoxy, propoxy, butoxy, F, Cl, Br, CF$_3$, and NO$_2$;

R$^{15}$ is selected from:

—NH—C(=O)—O—R$^{17}$,

—NHSO$_2$—R$^{17}$ and

—NHSO$_2$—NHR$^{17}$;

Y is —C(=O)R$^{19}$;

R$^{17}$ is selected from:

methyl, ethyl, propyl, butyl, pentyl, hexyl, cyclopropyl, cyclobutyl, cyclopentyl, cyclohexyl, phenylmethyl, phenylethyl, phenylpropyl, phenylbutyl, heteroaryl (C$_1$–C$_3$ alkyl)-, arylaryl(C$_1$–C$_3$ alkyl)-, heteroarylaryl (C$_1$–C$_3$ alkyl)-, arylheteroaryl(C$_1$–C$_3$ alkyl)-, heteroarylheteroaryl(C$_1$–C$_3$ alkyl)-, heteroaryl, and aryl, wherein said aryl or heteroaryl groups are optionally substituted with 0–3 substituents independently selected from the group consisting of: methyl, ethyl, propyl, butyl, methoxy, ethoxy, propoxy, butoxy, phenyl, F, Cl, Br, —CN, —NH$_2$, —CF$_3$, and —NO$_2$;

R$^{19}$ is selected from:

hydroxy, methoxy, ethoxy, propoxy, butoxy, methylcarbonyloxymethoxy-, ethylcarbonyloxymethoxy-, t-butylcarbonyloxymethoxy-, cyclohexylcarbonyloxymethoxy-, 1-(methylcarbonyloxy)ethoxy-, 1-(ethylcarbonyloxy)ethoxy-, 1-(t-butylcarbonyloxy)ethoxy-, 1-(cyclohexylcarbonyloxy)ethoxy-, i-propyloxycarbonyloxymethoxy-, t-butyloxycarbonyloxymethoxy-, 1-(i-propyloxycarbonyloxy)ethoxy-, 1-(cyclohexyloxycarbonyloxy)ethoxy-, 1-(t-butyloxycarbonyloxy)ethoxy-, dimethylaminoethoxy-, diethylaminoethoxy-, (5-methyl-1,3-dioxacyclopenten-2-on-4-yl)methoxy-, (5-(t-butyl)-1,3-dioxacyclopenten-2-on-4-yl)methoxy-, (1,3-dioxa-5-phenyl-cyclopenten-2-on-4-yl)methoxy-, 1-(2-(2-methoxypropyl)carbonyloxy)ethoxy-, (R$^1$O) (R$^{11}$)N-(C$_1$–C$_{10}$ alkoxy)-, and —O(CH$_2$)$_k$N$^+$(R$^{21}$) (R$^{22}$) (R$^{23}$)Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{21}$, R$^{22}$ and R$^{23}$ are independently selected from: H, methyl, ethyl, propyl and butyl;

alternatively R$^{21}$ and R$^{22}$ can be taken together to form a 5–7 membered heterocyclic ring system containing 1–2 heteroatoms selected from N, O and S and R$^{23}$ is defined as above;

h is 0–4;

i is 0–2;

k is 2–6;

m is 1–4;

n is 0–5;

q is 2–3;

r is 0–3; and t is 1–3;

provided that h, i, m, n, q, r, and t, at each occurrence, are chosen such that the number of in-chain atoms between Y and the pyrimidine, pyrimidone, triazine or triazinone of G is in the range of 8–12.

[6] Specifically preferred compounds of the above invention are compounds including enantiomeric or 2-[(S)-((2,4,6-Trimethylphenyl)sulfonyl)amino]-3-[4-(2-(2-aminopyrimid-4-one-6-yl)ethylphenylcarbonyl]-aminopropionic acid sodium salt, 2-[(S)-Phenylsulfonylamino]-3-[4-(2-(2-aminopyrimid-4-one-6-yl)ethylphenylcarbonyl]aminopropionic acid sodium salt, 2-[(S)-i-Butylsulfonylamino]-3-[4-(2-(2-aminopyrimid-4-one-6-yl)ethylphenylcarbonyl]aminopropionic acid sodium salt, 2-[(S)-n-Butylsulfonylamino]-3-[4-(2-(2-aminopyrimid-4-one-6-yl)ethylphenylcarbonyl]aminopropionic acid sodium salt, 2-[ (S)-(i-Butyloxycarbonyl)amino]-3-[4-(2-(2-aminopyrimid-4-one-6-yl) ethylphenylcarbonyl] aminopropionic acid sodium salt, 2-[(S)-(n-Butyloxycarbonyl)amino]-3-[4-(2-(2-aminopyrimid-4-one-6-yl)ethylphenylcarbonyl] aminopropionic acid sodium salt, 2-[(S)-Benzyloxycarbonylamino]-3-[4-(2-(2-aminopyrimid-4-one-6-yl)ethylphenylcarbonyl] aminopropionic acid sodium salt, 2-[(S)-((2,4,6-Trimethylphenyl)sulfonyl)amino]-3-[4-(2-(2,4-diaminopyrimidin-6-yl) ethylphenylcarbonyl]-aminopropionic acid trifluoroacetate salt, 2-[(S)-Phenylsulfonylamino]-3-[4-(2-(2,4-diaminopyrimidin-6-yl)ethylphenylcarbonyl] aminopropionic acid trifluoroacetate salt, 2-[(S)-i-Butylsulfonylamino]-3-[4-(2-(2,4-diaminopyrimidin-6-yl)ethylphenylcarbonyl] aminopropionic acid trifluoroacetate salt, 2-[(S)-n-Butylsulfonylamino]-3-[4-(2-(2,4-diaminopyrimidin-6-yl)ethylphenylcarbonyl] aminopropionic acid trifluoroacetate salt, 2-[(S)-i-Butyloxycarbonylamino]-3-[4-(2-(2,4-diaminopyrimidin-6-yl)ethylphenylcarbonyl]-aminopropionic acid trifluoroacetate salt, 2-[(S)-n-Butyloxycarbonylamino]-3-[4-(2-(2,4-diaminopyrimidin-6-yl)ethylphenylcarbonyl]-aminopropionic acid trifluoroacetate salt, 2-[(S)-Benzyloxycarbonylamino]-3-[4-(2-(2,4-diaminopyrimidin-6-yl)ethylphenylcarbonyl]-aminopropionic acid trifluoroacetate salt, 2-[(S)-((2,4,6-Trimethylphenyl)sulfonyl)amino]-3-[4-(2-(2,4-diaminotriazin-6-yl)ethylphenylcarbonyl]-aminopropionic acid, 2-[(S)-((2,4,6-Trimethylphenyl)sulfonyl)amino]-3-[4-(2-(4-aminoquinazolin-2-yl) aminomethylphenylcarbonyl]-aminopropionic acid, 2-[(S)-Phenylsulfonylamino]-3-[4-(2-(4-aminoquinazolin-2-yl)aminomethylphenylcarbonyl] aminopropionic acid, 2-[(S)-i-Butylsulfonylamino]-3-[4-(2-(4-aminoquinazolin-2-yl)aminomethylphenylcarbonyl] aminopropionic acid, 2-[(S)-n-Butylsulfonylamino]-3-[4-(2-(4-aminoquinazolin-2-yl)aminomethylphenylcarbonyl] aminopropionic acid, 2-[(S)-i-Butyloxycarbonylamino]-3-[4-(2-(4-aminoquinazolin-2-yl)aminomethylphenylcarbonyl]-aminopropionic acid, 2-[(S)-n-Butyloxycarbonylamino]-3-[4-(2-(4-aminoquinazolin-2-yl)aminomethylphenylcarbonyl]-aminopropionic acid, 2-[(S)-Benzyloxycarbonylamino]-3-[4-(2-(4-aminoquinazolin-2-yl)aminomethylphenylcarbonyl] aminopropionic acid, and ester forms thereof, said ester being selected from the group consisting of:

methyl,
ethyl,
isopropyl,
n-butyl,
isobutyl,
benzyl,
methylcarbonyloxymethyl,
ethylcarbonyloxymethyl,
tert-butylcarbonyloxyrmethyl,
cyclohexylcarbonyloxymethyl,
tert-butyloxycarbonyloxymethyl,
dimethylaminoethyl,
diethylaminoethyl,
morpholinoethyl,
pyrrolidinoethyl,
trimethylammonioethyl, and 2-(1-methylmorpholinium-1-yl)ethyl.

[7] In a second emodiment preferred compounds of the invention as described above are compounds of the Formula (IA):

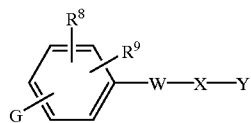

(IA)

including stereoisomeric forms thereof, tautomeric forms thereof, pharmaceutically acceptable salt forms thereof or prodrug forms thereof, wherein:

G is a meta or para substituent with respect to W and is selected from:

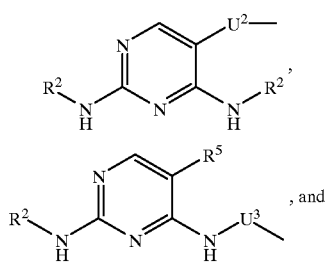

, and

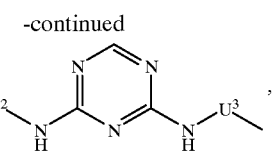

$R^2$ at each occurrence is independently selected from:
H, methyl, ethyl, propyl, butyl, ($C_1$–$C_4$ alkyl)carbonyl, ($C_1$–$C_4$ alkoxy)carbonyl, $C_3$–$c_7$ cycloalkyl($C_0$–$C_4$ alkyl), $C_3$–$C_7$ cycloalkyl($C_0$–$C_4$ alkyl)carbonyl, and $C_3$–$C_7$ cycloalkyl($C_0$–$C_4$ alkoxy)carbonyl;

$R^4$ is selected from: H, methyl, ethyl, propyl, butyl cyclopropyl, and cyclopropylmethyl;

$R^5$ is selected from H, $NR^2R^4$, methyl, ethyl, propyl, butyl, pentyl, and hexyl;

$U^2$ is selected from:
—$(CH_2)_h$-,
—O—$(CH_2)_r$-,
—$(CH_2)_r$-O—,
—$(CH_2)_r$-N($R^3$)—,
—$(CH_2)_i$-N($R^3$)—$CH_2$—,
—$(CH_2)_i$-O—$CH_2$—,
—$CH_2$—O—$(CH_2)_i$-,
—$CH_2$—N($R^3$)—$(CH_2)_i$-, and
—N($R^4$)—$(CH_2)_r$-;

$U^3$ is selected from:
—$(CH_2)_h$-,
—$(CH_2)_q$-O—,
—$(CH_2)_q$-N($R^3$)—,
—$(CH_2)_q$-N($R^3$)—$CH_2$—, and
—$(CH_2)_q$-O—$CH_2$—;

$R^8$ and $R^9$ are independently selected from: H, methyl, ethyl, propyl, butyl, $CF_3$, F, Cl, Br, and $OR^{10}$;

$R^{10}$ and $R^1$1 are independently selected from:
H, $C_1$–$C_8$ alkyl, $C_3$–$C_6$ alkenyl, $C_3$–$C_{10}$ cycloalkyl($C_0$–$C_4$ alkyl), aryl($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^{10}$ and $R^1$1 when both substituents on the same nitrogen atom as in (—$NR^{10}R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from oxo, $C_1$–$C_6$ alkyl, $C_3$–$C_7$ cycloalkyl(C –$C_4$ alkyl), $C_1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl($C_0$–$C_5$ alkoxy)carbonyl, aryl($C_0$–$C_5$ alkyl), heteroaryl($C_0$–$C_5$ alkyl), aryl($C_1$–$C_5$ alkoxy)carbonyl, heteroaryl($C_1$–$C_5$ alkoxy)carbonyl, $C_1$–$C_6$ alkylsulfonyl arylsulfonyl and heteroarylsulfonyl;

W is —$CH_2C$(=O)N($R^{13}$)—, —$CH_2CH_2C$(=O)N($R^{13}$)—, or —C(=O)N($R^{13}$)—;

X is —CH($R^{14}$)—$CH_2$— or —$CH_2$—CH($R^{15}$)—;

$R^{13}$ is H or methyl;

$R^{14}$ is selected from:
H, $C_1$–$C_{10}$ alkyl, $C_2$–$C_{10}$ alkenyl, $C_2$–$C_{10}$ alkynyl, $C_3$–$C_{10}$ cycloalkyl, $C_1$–$C_6$ hydroxyalkyl, $C_1$–$C_6$ alkoxy ($C_1$–$C_6$ alkyl), aryl($C_0$–$C_6$ alkoxy $C_1$–$C_6$ alkyl), $C_1$–$C_6$ alkylthio ($C_1$–$C_6$ alkyl), $C_1$–$C_6$ alkylsulfonyl ($C_1$–$C_6$ alkyl), aryl($C_0$–$C_6$ alkylthio $C_1$–$C_6$ alkyl), aryl($C_0$–$C_6$ alkylsulfonyl $C_1$–$C_6$ alkyl),$C_3$–$C_{10}$ cycloalkyl ($C_0$–$C_6$ alkyl), aryl($C_0$–$C_6$ alkyl), heteroaryl($C_0$–$C_6$ alkyl), $R^{17}HNC(=O)(C_1$–$C_4$ alkyl), $R^{10}OC(=O)(C_1$–$C_4$ alkyl), and $R^{17}HN(C_1$–$C_4$ alkyl), provided that any of the above alkyl, cycloalkyl, aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^{15}$ is selected from:
—NH—C (=O)—O—$R^{17}$,
—NH—C (=O)—$R^{17}$,
—NH—C(=O)—NH—$R^{17}$,
—$NHSO_2$—$R^{17}$, and
—$NHSO_2$—$NHR^{17}$;

Y is —C(=O)$R^{19}$;

$R^{17}$ is selected from:
$C_1$–$C_{10}$ alkyl, $C_3$–$C_{10}$ cycloalkyl, aryl($C_0$–$C_6$ alkyl), heteroaryl ($C_0$–$C_6$ alkyl), arylaryl ($C_0$–$C_6$ alkyl), heteroarylaryl ($C_0$–$C_6$ alkyl), arylheteroaryl ($C_0$–$C_6$ alkyl), and heteroarylheteroaryl ($C_0$–$C_6$ alkyl), wherein said aryl or heteroaryl groups are optionally substituted with 0–3 substituents independently selected from the group consisting of: $C_1$–$C_4$ alkyl, $C_1$–$C_4$ alkoxy, aryl, F, Cl, Br, CN, $NH_2$, $CF_3$, and $NO_2$;

$R^{19}$ is selected from:
hydroxy,
$C_1$–$C_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
1-(2-(2-methoxypropyl)carbonyloxy)ethoxy-,
($R^{10}$) ($R^{11}$)N-($C_1$–$C_{10}$ alkoxy)-, and
—O($CH_2$)$_k$$N^+$($R^{21}$) ($R^{22}$) ($R^{23}$)$Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{21}$, $R^{22}$ and $R^{23}$ are independently selected from:
H, methyl, ethyl, propyl, butyl, $C_3$–$C_7$ cycloalkyl($C_0$–$C_4$ alkyl), phenyl, benzyl, wherein said phenyl group is substituted with 0–2 substituents selected from the group consisting of $C_1$–$C_4$ alkyl, $C_1$–$C_4$ alkoxy, OH, F, Cl, Br, $CF_3$, and $NO_2$;

alternatively $R^{21}$ and $R^{22}$ can be taken together to form a 5–7 membered heterocyclic aromatic or non-aromatic ring system containing 1–2 heteroatoms selected from N, O and S and $R^{23}$ is defined as above or $R^{21}$, $R^{22}$, and $R^{23}$ can be taken together to form a heterobicyclic ring system containing 1–2 heteroatoms selected from N, O and S;

h is 0–4;
i is 0–2;
k is 2–6;
m is 1–4;
n is 0–5;
q is 2–3;
r is 0–3; and
t is 1–3;

provided that h, i, m, n, q, r, and t, at each occurrence, are chosen such that the number of in-chain atoms between Y and the pyrimidine or triazine of G is in the range of 8–12.

[8] Further preferred compounds of the above invention as described above are compounds of the Formula (IA):

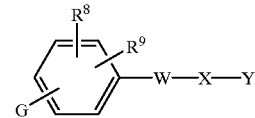

(IA)

including stereoisomeric forms thereof, tautomeric forms thereof, pharmaceutically acceptable salt forms thereof or prodrug forms thereof, wherein:

G is a meta or para substituent with respect to W and is selected from:

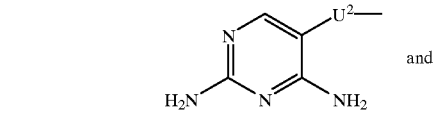

and

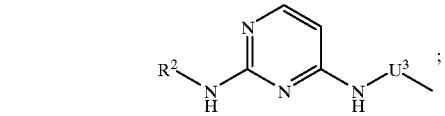

;

$U^2$ is selected from: —$CH_2CH_2$—, —$CH_2CH_2CH_2$—, —NH—$CH_2$—, and —NH—$CH_2CH_2$—;
$U^3$ is —$CH_2$—, —$CH_2CH_2$— or —$CH_2CH_2CH_2$—;
$R^8$ is selected from: H, methyl, ethyl, propyl, butyl, —OH, methoxy, ethoxy, F, Cl, Br, and $CF_3$;
$R^9$ is H,
$R^{10}$ and $R^{11}$ are independently selected from:
H, methyl, ethyl, propyl, butyl, $C_3$–$C_6$ alkenyl, $C_3$–$C_4$ cycloalkyl($C_0$–$C_4$ alkyl), aryl($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;
alternatively, $R^{10}$ and $R^{11}$ when both substituents on the same nitrogen atom as in (-$NR^{10}R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl;

W is —$CH_2C(=O)N(R^{13})$—, —$CH_2CH_2C(=O)N(R^{13})$—, or —C(=O)N($R^{13}$)—;

X is —CH($R^{14}$)—$CH_2$— or —$CH_2$—CH($R^{15}$)—;

$R^{13}$ is H, methyl, ethyl, propyl, pentyl, or hexyl;

$R^{14}$ is selected from:

C$_2$–C$_8$ alkenyl, C$_2$–C$_8$ alkynyl, C$_3$–C$_8$ cycloalkyl, C$_1$–C$_6$ hydroxyalkyl, C$_3$–C$_8$ cycloalkyl(C$_0$–C$_6$ alkyl), aryl (C$_0$–C$_6$ alkyl), heteroaryl (C$_0$–C$_6$ alkyl), R$^{17}$HNC(=O) (C$_1$–C$_4$ alkyl), and R$^{17}$HN(C$_1$–C$_4$ alkyl), provided that any of the above alkyl, cycloalkyl, aryl or heteroaryl groups are substituted with 0–2 substituents independently selected from the group consisting of methyl, ethyl, propyl, butyl, methoxy, ethoxy, propoxy, butoxy, F, Cl, Br, CF$_3$, and NO$_2$;

R$^{15}$ is selected from:
—NH—C(=O)—O—R$^{17}$,
—NHSO$_2$—R$^{17}$ and
—NHSO$_2$—NHR$^{17}$;
Y is —C(=O)R$^{19}$;
R$^{17}$ is selected from:

methyl, ethyl, propyl, butyl, pentyl, hexyl, cyclopropyl, cyclobutyl, cyclopentyl, cyclohexyl, phenylmethyl, phenylethyl, phenylpropyl, phenylbutyl, heteroaryl (C$_1$–C$_3$ alkyl)-, arylaryl (C$_1$–C$_3$ alkyl)-, heteroarylaryl (C$_1$–C$_3$ alkyl)-, arylheteroaryl (C$_1$–C$_3$ alkyl)-, heteroarylheteroaryl (C$_1$–C$_3$ alkyl)-, heteroaryl, and aryl, wherein said aryl or heteroaryl groups are optionally substituted with 0–3 substituents independently selected from the group consisting of: methyl, ethyl, propyl, butyl, methoxy, ethoxy, propoxy, butoxy, phenyl, F, Cl, Br, —CN, —NH$_2$, —CF$_3$, and —NO$_2$;

R$^{19}$ is selected from:
hydroxy, methoxy, ethoxy, propoxy, butoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5-(t-butyl)-1,3-dioxacyclopenten-2-on-4-yl)methoxy-,
(1,3-dioxa-5-phenyl-cyclopenten-2-on-4-yl)methoxy-,
1-(2-(2-methoxypropyl)carbonyloxy)ethoxy-,
(R$^{10}$) (R$^{11}$)N-(C$_1$–C$_{10}$ alkoxy)-, and
—O(CH$_2$)$_k$N$^+$ (R$^{21}$) (R$^{22}$) (R$^{23}$)Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{21}$, R$^{22}$ and R$^{23}$ are independently selected from: H, methyl, ethyl, propyl and butyl;
alternatively R$^{21}$ and R$^{22}$ can be taken together to form a 5–7 membered heterocyclic ring system containing 1–2 heteroatoms selected from N, O and S and R$^{23}$ is defined as above;

h is 0–4;
i is 0–2;
k is 2–6;
m is 1–4;
n is 0–5;
q is 2–3;
r is 0–3; and
t is 1–3;
provided that h, i, m, n, q, r, and t, at each occurrence, are chosen such that the number of in-chain atoms between Y and the pyrimidine, pyrimidone, triazine or triazinone of G is in the range of 8–12.

[9] Specifically preferred compounds of the above invention are compounds including enantiomeric forms, diasteriomeric forms or mixtures of enantiomeric or diasteriomeric forms thereof, and pharmaceutically acceptable salt forms thereof, selected from:

2-[(S)-((2,4,6-Trimethylphenyl)sulfonyl)amino]-3-[4-(2-(2-aminopyrimidin-4-yl)aminomethyl)phenylcarbonyl]-aminopropionic acid, 2-[(S)-i-Butyloxycarbonylamino]-3-[4-(2-(2-aminopyrimidin-4-yl)aminomethyl)phenylcarbonyl]aminopropionic acid trifluoroacetate salt, 2-[(S)-n-Butyloxycarbonylamino]-3-[4-(2-(2-aminopyrimidin-4-yl)aminomethyl)phenylcarbonyl]aminopropionic acid trifluoroacetate salt, 2-[(S)-Benzyloxycarbonylamino]-3-[4-(2-(2-aminopyrimidin-4-yl)aminomethyl)phenylcarbonyl]aminopropionic acid trifluoroacetate salt, and 2-[(S)-Phenylsulfonylamino]-3-[4-(2-(2-aminopyrimidin-4-yl)aminomethyl)phenylcarbonyl]aminopropionic acid trifluoroacetate salt.

2-[(S)-i-Butylsulfonylamino]-3-[4-(2-(2-aminopyrimidin-4-yl)aminomethyl)phenylcarbonyl]aminopropionic acid trifluoroacetate salt.

2-[(S)-n-Butylsulfonylamino]-3-[4-(2-(2-aminopyrimidin-4-yl)aminomethyl)phenylcarbonyl]aminopropionic acid trifluoroacetate salt.

Generally, the compounds of this invention are comprised of a guanidine mimic "G" and an integrin antagonist template "T". The guanidine mimic comprises a substituted or unsubstituted pyrimidine, pyrimidone, triazinine or trizanone ring, optionally fused, and a linking group U. Preferably, the integrin antagonist template "T" is

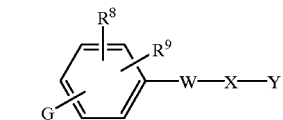

(IA)

as defined in the present invention. However, other integrin antagonist templates disclosed herein as T$_1$ through T$_{14}$ are included within the scope of the present invention and summarized below.

Template T$_1$, disclosed in Bondinell, et al., WO 93/00095, published Jan. 7, 1993, is of the sub-formula (T$_1$):

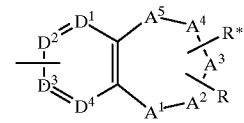

wherein, A$^1$ to A$^5$ form an accessible substituted seven-membered ring, which may be saturated or unsaturated, optionally containing up to two heteroatoms chosen from the group of O, S and N wherein S and N may be optionally oxidized; $D^1$ to $D^4$ form an accessible substituted six membered ring, optionally containing up to two nitrogen atoms; R, R*, and all substituents thereform are as defined in the Bondinell specification. Suitably, with reference to formula $(T_1)$; $A^1$ is $CR^1R^1$, $CR^1$, $NR^1$, N, O or $S(O)_x$; $A^2$ is $CR^2R^{2'}$, $CR^2$, $NR^2$; $A^3$ is $CR^3R^{3'}$, $CR^3$, $NR^3$, N. O or $S(O)_x$; $A^4$ is $CR^4R^4$, $CR^4$, $NR^4$, or N; $A^5$ is $CR^5R^{5'}$, $CR^5$, $NR^5$, N, O or $S(O)_x$; and $D^1$-$D^4$ are $CR^{11}$, $CR^6$ or N.

A preferred integrin antagonist template of sub-formula $(T_1)$ is defined by Bondinell wherein $A^1$ equals $N-R^1$, $A^2$ equals $CHCH_2CO_2H$, $A^3$ equals C=O, $A^4$ equals $N-R^4$, $A^5$ equals $CH_2$, and $D^1$ to $D^4$ are carbon.

Another embodiment of a preferred integrin antagonist template of sub-formula $(T_1)$ is represented by the 1,4-benzodiazepine 2,5-dione of sub-formula $(T_2)$;

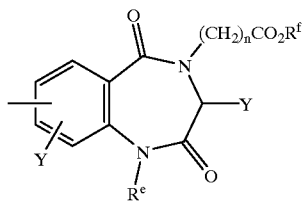

The preparation and the use of this sub-structure in preparing integrin antagonists of this sub-formula is detailed in Bondinell, et al., WO 93/00095 published Jan. 7, 1993 and Blackburn, et al., WO 93/08174, published Apr. 29, 1993.

Template $T_3$, of sub-formulae:

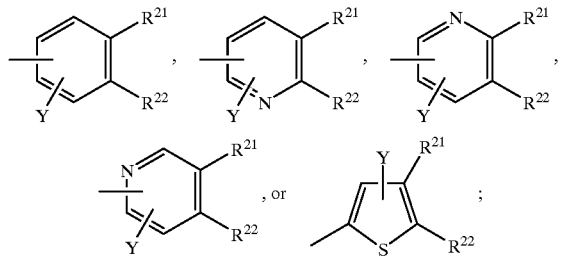

is disclosed in Alig, et al., EP 0 381 033, published Aug. 8, 1990, wherein $R^{21}$ or $R^{22}$ provide for the acid terminus.

Template $T_4$, of sub-formula:

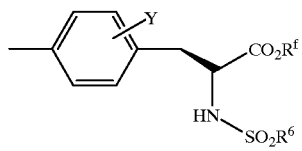

is disclosed in Egbertson, et al., EP 0 478 328, published Apr. 1, 1992.

Template $T_5$, of sub-formula:

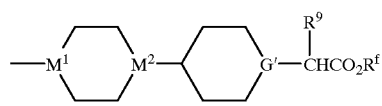

is disclosed in Eldred, et al., EP 0542 363, published May 19, 1993.

Template $T_6$, of sub-formula:

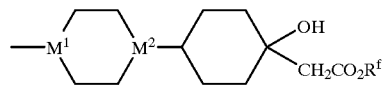

is disclosed in Porter, et al., EP 0537 980, published Apr. 21, 1993.

Template $T_7$, of sub-formula:

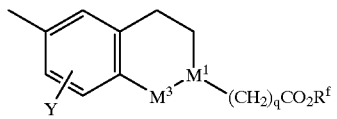

is disclosed in Klinnick, et al., EP 0 635,492, published Jan. 25, 1995.

Template $T_8$, of sub-formula:

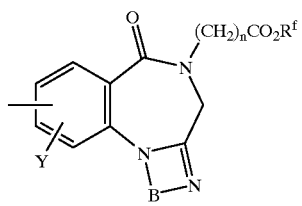

is disclosed in Blackburn, et al., WO 95/04057, published Feb. 9, 1995.

Template $T_9$, of sub-formula:

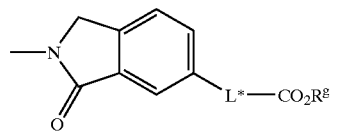

is disclosed in Hartman, et al., EP 0 540 331, published May 5, 1993.

Template $T_{10}$, of sub-formula:

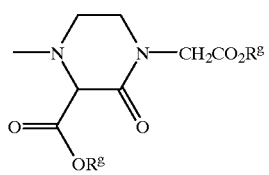

is disclosed in Sugihara, et al., EP 0 529, 858, published Mar. 3, 1993.

Template $T_{11}$, of sub-formula:

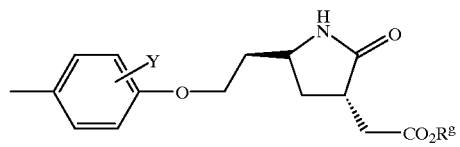

is disclosed in Himmelsbach, et al., EP 0 483 667, published May 6, 1992.

Template T$_{12}$, of sub-formula:

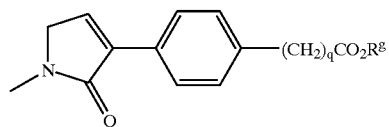

is disclosed in Linz, et al, EP 0 567 968, published Nov. 3, 1993.

Template T$_{13}$, of sub-formula:

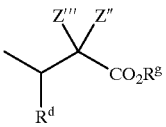

is disclosed in Bovy, et al., EP 0 539 343, published Apr. 28, 1993.

Template T$_{14}$, of sub-formula:

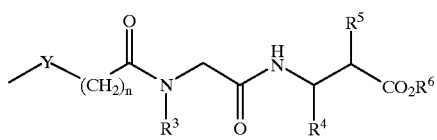

is disclosed in Hartman, et al., WO97/26250, published Jul. 24, 1997.

The above description of integrin antagonist templates for use in the present invention were taken from pending published patent applications. Reference should be made to such patent applications for their full disclosures, including the methods of preparing said templates and specific compounds using said templates, the entire disclosure of such patent applications being incorporated herein by reference.

In the present invention it has been discovered that the compounds of Formula (IA) above are useful as inhibitors of cell-matrix and cell-cell adhesion processes. The present invention includes novel compounds of Formula (IA) and methods for using such compounds for the prevention or treatment of diseases resulting from abnormal cell adhesion to the extracellular matrix which comprises administering to a host in need of such treatment a therapeutically effective amount of such compound of Formula (IA).

In the present invention it has also been discovered that the compounds of Formula (IA) above are useful as inhibitors of the $\alpha_v\beta_3$ integrin and/or the glycoprotein IIb/IIIa (GPIIbIIIa) integrin. The compounds of the present invention inhibit the binding of vitronectin and other RGD containing ligands to $\alpha_v\beta_3$ and/or to GPIIb/IIIa and inhibit cell adhesion.

The present invention also provides pharmaceutical compositions comprising a compound of Formula (IA) and a pharmaceutically acceptable carrier.

The compounds of Formula (IA) of the present invention are useful for the treatment (including prevention) of angiogenic disorders. The term "angiogenic disorders" as used herein includes conditions involving abnormal neovascularization, such as tumor metastasis and ocular neovascularization, including, for example, diabetic retinopathy, neovascular glaucoma, age-related macular degeneration, and retinal vein occlusion, comprising administering to a mammal in need of such treatment a therapeutically effective amount of a compound of Formula (IA) described above.

The compounds of Formula (IA) or the present invention may be useful for the treatment (including prevention) of thromboembolic disorders. The term "thromboembolic disorders" as used herein includes conditions involving platelet activation and aggregation, such as arterial or venous cardiovascular or cerebrovascular thromboembolic disorders, including, for example, thrombosis, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or such disorders associated with diabetes, comprising administering to a mammal in need of such treatment a therapeutically effective amount of a compound of Formula (IA) described above.

The compounds of Formula (IA) of the present invention may be useful for the treatment or prevention of other diseases which involve cell adhesion processes, including, but not limited to, inflammation, bone degradation, thromboembolic disorders, restenosis, rheumatoid arthritis, asthma, allergies, adult respiratory distress syndrome, graft versus host disease, organ transplantation rejection, septic shock, psoriasis, eczema, contact dermatitis, osteoporosis, osteoarthritis, atherosclerosis, inflammatory bowel disease and other autoimmune diseases. The compounds of Formula (IA) of the present invention may also be useful for wound healing.

Compounds of the invention may be administered to patients where prevention of thrombosis by inhibiting binding of fibrinogen to the platelet membrane glycoprotein complex IIb/IIIa receptor id desired. They are useful in surgery on peripheral arteries, (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemoli. The compounds of the present invention may be administered to these surgical patents to prevent the formation of thrombi and thromboemboli.

Extracorporeal circulation is routinely used during cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the extracorporeal circuit. Platelets released from artificial surfaces show impaired homeostatic function. The compounds of the invention may be administered to prevent such ex vivo adhesion.

Other applications for these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction.

The compounds of the present invention may be used for other ex vivo applications to prevent cellular adhesion in biological samples.

The compounds of the present invention can also be administered in combination with one or more additional therapeutic agents selected from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula (IA) of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula (IA) that when administered alone or in combination with an additional therapeutic agent to a cell or mammal is effective to prevent or ameliorate the thromboembolic disease condition or the progression of the disease.

By "administered in combination" it is meant that the compound of Formula (IA) and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as COUMADIN®) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs such as aspirin, ibuprofen, naproxen, sulindac, indomethacin, mefenamate, droxicam, diclofenac, sulfinpyrazone, and piroxicam, including pharmaceutically acceptable salts or prodrugs thereof. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boroarginine derivatives and boropeptides, hirudin and argatroban, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881 A2, the disclosures of which are hereby incorporated herein by reference. Other suitable boroarginine derivatives and boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. The term urokinase, as used herein, is intended to denote both dual and single chain urokinase, the latter also being referred to herein as prourokinase.

Administration of the compounds of Formula (IA) of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

The compounds of the present invention are also useful as standard or reference compounds, for example as a quality standard or control, in tests or assays involving the binding of vitronectin or fibrinogen to $\alpha_v\beta_3$. Such compounds may be provided in a commercial kit, for example, for use in pharmaceutical research involving $\alpha_v\beta_3$. The compounds of the present invention may also be used in diagnostic assays involving $\alpha_v\beta_3$.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention that contain asymmetrically substituted carbon atoms may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable (for example but not limited to, $R^2$, $R^3$, $R^4$, $R^{10}$, $R^{11}$, $R^{12}$, $R^{17}$, h, i, n, m, r, etc.) occurs more than one time in any constituent or in any formula, its definition on each occurrence is independent of its definition at every other occurrence. Thus, for example, if a group is shown to be substituted with 0–2 $R^4$, then said group may optionally be substituted with up to two $R^4$ and $R^4$ at each occurrence is selected independently from the defined list of possible $R^4$. Also, by way of example, for the group —N($R^2$)$_2$, each of the two $R^2$ substituents on N is independently selected from the defined list of possible $R^2$. Similarly, by way of example, for the group —C($R^{12}$)$_2$—, each of the two $R^{12}$ substituents on C is independently selected from the defined list of possible $R^{12}$.

When a bond to a substituent is shown to cross the bond connecting two atoms in a ring, then such substituent may be bonded to any atom on the ring. When a bond joining a substituent to another group is not specifically shown or the atom in such other group to which the bond joins is not specifically shown, then such substituent may form a bond with any atom on such other group.

When a substituent is listed without indicating the atom via which such substituent is bonded to the rest of the compound of Formula (IA), then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula (IA) via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms. For example, "$C_0$–$C_{10}$ alkyl" denotes alkyl having 0 to 10 carbon atoms; thus, $C_0$ denotes a direct bond between the groups linked by the $C_0$ alkyl group. Similarly, "$C_1$–$C_6$ alkyl" denotes methyl, ethyl, propyl, butyl, pentyl, hexyl; wherein, for example, butyl is intended to include n-butyl, i-butyl, s-butyl, and t-butyl.

"Haloalkyl" is intended to include both branched and straight-chain saturated aliphatic hydrocarbon groups having the specified number of carbon atoms, substituted with 1 or more halogen (for example -$C_vF_w$ where v=1 to 3 and w=1 to (2v+1)). "Alkoxy" represents an alkyl group of indicated number of carbon atoms attached through an oxygen bridge (for example, "$C_0$–$C_{10}$ alkoxy" denotes alkoxy having 0 to 10 carbon atoms; thus, $C_0$ denotes an oxygen atom between the groups linked by the $C_0$ alkoxy group). "Cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl, and adamantyl.

"Alkenyl" is intended to include hydrocarbon chains of either a straight or branched configuration and one or more unsaturated carbon-carbon bonds which may occur in any stable point along the chain, such as ethenyl, propenyl, butenyl and the like. "Alkynyl" is intended to include hydrocarbon chains of either a straight or branched configuration and one or more triple carbon-carbon bonds which may occur in any stable point along the chain, such as ethynyl, propynyl, butynyl and the like.

The terms "alkylene", "alkenylene", "phenylene", and the like, refer to alkyl, alkenyl, and phenyl groups, respectively, which are connected by two bonds to the rest of the structure of Formula (IA). Such "alkylene", "-alkenylene", "phenylene", and the like, may alternatively and equivalently be denoted herein as "-(alkyl)-", "-(alkyenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge. For example, "aryl $C_1$–$C_4$ alkyl" represents phenylmethyl, phenylethyl, phenylpropyl, phenylbutyl, and the like.

As used herein, "carbocycle" or "carbocyclic ring" is intended to mean any stable 3- to 7- membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heterocyclic ring" is intended to mean a stable 5- to 7- membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, indolenyl, isoxazolinyl, isoxazolyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl or octahydroisoquinolinyl, azocinyl, triazinyl, 6H-1, 2, 5-thiadiazinyl, 2H, 6H-1, 5, 2-dithiazinyl, thianthrenyl, pyranyl, isobenzofuranyl, chromenyl, xanthenyl, phenoxathiinyl, 2H-pyrrolyl, pyrrolyl, imidazolyl, pyrazolyl, isothiazolyl, isoxazolinyl, isoxazolyl, oxazolyl, pyridinyl, pyrazinyl, pyrimidinyl, pyridazinyl, indolizinyl, isoindolyl, 3H-indolyl, indolyl, 1H-indazolyl, purinyl, 4H-quinolizinyl, isoquinolinyl, quinolinyl, phthalazinyl, naphthyridinyl, quinoxalinyl, quinazolinyl, cinnolinyl, pteridinyl, 4aH-carbazole, carbazole, β-carbolinyl, phenanthridinyl, acridinyl, perimidinyl, phenanthrolinyl, phenazinyl, phenarsazinyl, phenothiazinyl, furazanyl, phenoxazinyl, isochromanyl, chromanyl, pyrrolidinyl, pyrrolinyl, imidazolidinyl, imidazolinyl, pyrazolidinyl, pyrazolinyl, piperidinyl, piperazinyl, indolinyl, isoindolinyl, quinuclidinyl, morpholinyl or oxazolidinyl. Also included are fused ring and spiro compounds containing, for example, the above heterocycles.

As used herein, the term "heteroaryl" refers to aromatic heterocyclic groups. Such heteroaryl groups are preferably 5–6 membered monocyclic groups or 8–10 membered fused bicyclic groups. Examples of such heteroaryl groups include, but are not limited to pyridyl (pyridinyl), pyrimidinyl, furanyl (furyl), thiazolyl, thienyl, pyrrolyl, pyrazolyl, imidazolyl, indolyl, isoxazolyl, oxazolyl, pyrazinyl, pyrimidinyl, pyridazinyl, benzofuranyl, benzothienyl, benzimidazolyl, quinolinyl, or isoquinolinyl.

The term "integrin" as used herein refers to any of the many cell surface receptor proteins, also referred to as adhesion protein receptors, which have been identified which bind to extracellular matrix ligands or other cell adhesion protein ligands thereby mediating cell-cell and cell-matrix adhesion processes. The integrins are encoded by genes belonging to a gene superfamily and are typically composed of heterodimeric transmembrane glycoproteins containing α- and β-subunits. Integrin subfamilies contain a common β-subunit combined with different α-subunits to form adhesion protein receptors with different specificities.

The integrin glycoprotein IIb/IIIa (referred to herein as GPIIb/IIIa or IIb/IIIa or the fibrinogen receptor) is the membrane protein mediating platelet aggregation. GPIIb/IIIa in activated platelets is known to bind four soluble RGD-containing adhesive proteins, namely fibrinogen, von Willebrand factor, fibronectin, and vitronectin. In addition to GPIIb/IIIa, a number of other integrin cell surface receptors have been identified, for example, αvβ3 and The term "integrin antagonists" as referred to herein (also referred to herein as integrin inhibitors) includes compounds (including peptidomimetic compounds and other small molecule compounds) which act as inhibitors of the binding of the integrin protein to endogenous protein ligands of such integrin. Preferred integrin inhibitors used in the present invention are RGD-peptidomimetic compounds. As used herein, the term "RGD-peptidomimetic compounds" refers to chemical compounds which bind to the RGD-binding region of the integrin and which block RGD-mediated binding of one or more adhesive proteins to such integrin. Preferred in the present invention are antagonists of the αvβ3 nad GPIIb/IIIa integrin.

As used herein, "prodrugs" refer to any covalently bonded carriers which release the active parent drug according to Formula (IA) in vivo when such prodrug is administered to a mammalian subject. Prodrugs of the compounds of Formula (IA) are prepared by modifying functional groups present in the compounds in such a way that the modifications are cleaved, either in routine manipulation or in vivo, to the parent compounds. Prodrugs include compounds of Formula (IA) wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula (IA), and the like.

As used herein, "pharmaceutically acceptable salts" refer to derivatives of the disclosed compounds wherein the parent compound of Formula (IA) is modified by making acid or base salts of the compound of Formula (IA). Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the compounds of Formula (IA) include the conventional non-toxic salts or the quaternary ammonium salts of the compounds of Formula (IA) formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula (IA) which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula (IA) with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. The templates of Formula (IB) and (IC) can be synthesized by methods disclosed in U.S. patent application Ser. No. 08/647132 filed May 9, 1996 or published in WO 96/37492 on Nov. 28, 1996. The templates of Formula (ID) and (IE) can be synthesized by methods disclosed in U.S. patent application Ser. No. 08/816580 filed Mar. 13, 1997 or published in WO 97/33887 on Sep. 18, 1997. The template of Formula (IG) can be synthesized by methods disclosed in U.S. patent application Ser. No. 08/770538 filed Dec. 20, 1996 or published in WO 97/23480 on Jul. 3, 1997. Preferred methods include, but are not limited to, those described below. All references cited herein are hereby incorporated in their entirety herein by reference.

The synthesis of compounds of formula I with various heterocycles represented by G may be prepared by many methods. For reviews on the synthesis of pyrimidines see Brown, D. J., in Comprehensive Heterocyclic Chemistry Vol. 3, pp. 57–157, (Katritzky A. R., and Rees, C. W ed's) Pergamon Press Ltd., New York, 1984, and Brown, D. J., in The Pyrimidines Vol 16. with supplements I and II. in the series Chemistry of Heterocyclic Compounds (Weissberger A., and Taylor, E. C. ed's) John Wiley and Sons, New York, 1970. For reviews on the synthesis of triazines see Quirke, J. M. E., in Comprehensive Heterocyclic Chemistry Vol. 3, pp. 457–531, (Katritzky A. R., and Rees, C. W ed's) Pergamon Press Ltd., New York, 1984.

Some of the methods which may be used to prepare the heterocyclic moieties represented by G in formula I are illustrated below in schemes Ia through Id and IIa through IIh. In schemes Ia through Id and IIa through IIh the substituent J represents a group appropriate for eventual elaboration to a compound of formula I. Typical examples of such groups are represented by formulas J1 through J4. The examples J1 through J4 are for illustration purposes and do not represent a limitation on the scope of the invention.

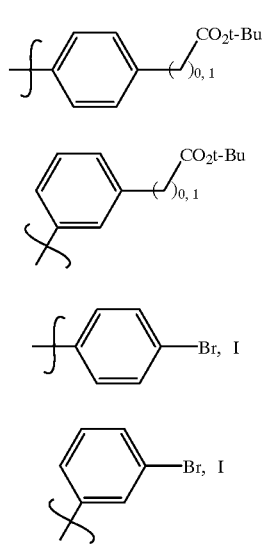

One general method of synthesis of the G portion of the compounds of formula I involves the displacement of an activated halogen atom substituent on an electron deficient heterocycle with nucleophiles including but not limited to amines, hydroxide, alkoxide salts, mercaptan salts, alkylthio salts, or Grignard reagents as outlined in schemes Ia - Id. The examples shown in schemes Ia-Id are for illustration purposes and do not constitute a limitation on the scope of the invention. The halogen containing heterocycles are obtained from commercial sources or can be readily prepared by one skilled in the art of organic synthesis from several means including direct halogenation or by conversion of the available oxo precursors. The oxo derivative may be converted to the halide by treatment with a phosphorous halide, for example phosphorous oxychloride, at temperatures from room temperature to reflux, with or without addition of a co-solvent, and with or without the addition of a basic catalyst, for example N,N-dimethylaniline. Fluorine containing heterocycles may be produced by several methods including transhalogenation of the chloro derivatives by treatment with a fluoride salt such as sodium fluoride, potassium fluoride or silver fluoride at elevated temperatures.

The nucleophilic displacement of activated multiple halogen containing electron deficient heterocycles has been shown to be generally applicable to multistep substitution procedures. The level of substitution may be controlled by choice of the proper sequence of reactions and reaction conditions such as stochiometry, temperature, pressure and solvent. The choice of the proper conditions would be known to one skilled in the art of organic synthesis, for pyrimidines this process is outlined in Brown, D. J., in The Pyrimidines Vol 16 supplements II, pp.184–188 in the series Chemistry of Heterocyclic Compounds (Weissberger A., and Taylor, E. C. ed's) John Wiley and Sons, New York, 1970. This iterative substitution process has also been illustrated for triazines starting from cyanuric chloride; for example, monosubstitution is depicted in Cambell, J. R., and Hatton, R. E., J. Org. Chem., 26, 2786, 1961, and for example, disubstitution is shown in Thurston, J. T., Dudley, J. R, Kaiser, D. W., Schaefer, F. C, et. al. J. Amer. Chem. Soc. 73, 2981, 1954, and for example, trisubstitution is shown in Controulis, J., Banks, C. K., J. Amer. Chem. Soc. 67, 1946, 1945. Other polyhalogenated heterocycles contained in this scope might be expected to behave in a similar manner.

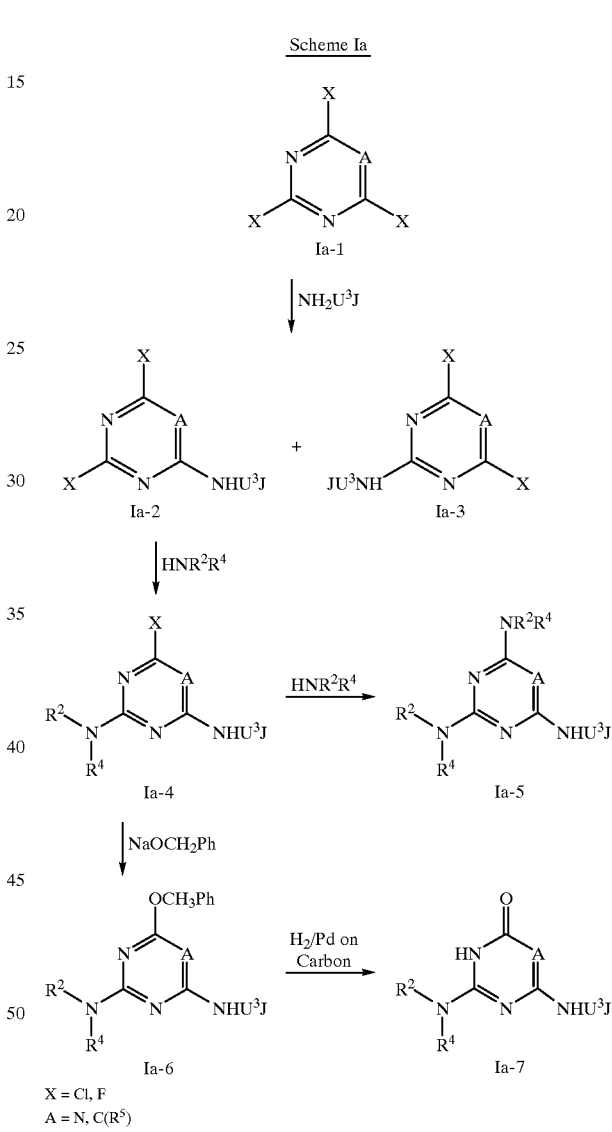

Scheme Ia represents a means of sequentially introducing nucleophiles into the heterocyclic core. The starting heterocycles cyanuric chloride, 2,4,6 trifluoropyrimidine, 2,4,6-trichloropyrimidine and the intermediate 2-amino-4,6-dichloropyrimidine are commercially available. In this case the amine containing $U^3J$ is treated with the trihaloheterocycle first, although the sequence of addition may be altered. The reaction may be carried out in an alcoholic solvent or N,N-dimethylformamide, from 0° C. to 100° C. In the case where the heterocycle is a pyrimidine two isomers will generally be produced (Ia-2 and Ia-3) and may be separated by several methods including chromatography, crystallization or distillation. Scheme Ia depicts Ia-2 as being carried through the remainder of the reaction sequence although isomer Ia-3 may be carried through the same reaction sequence. Isomer Ia-2 is then allowed to react with a second amine, by heating the components in an alcoholic solvent or N,N-dimethylformamide, from 25° C. to 140° C. to provide Ia-4. The diaminoheterocycle may be treated with a third amine component be heating in a sealed tube at a temperature of 80° C. to 210° C. to provide Ia-5. Alternatively, Ia-4 may be treated with an alkoxide such as sodium benzylalkoxide possible with the addition of an inert solvent such as mesitylene at a temperature from 100° C. to 160° C. to provide Ia-6, or alternatively Ia-4 might be treated with a sodium alkylthio salt (not shown) by heating in an alcoholic solvent. The benzyl group in compound Ia-6 may be removed by hydrogenation in the presence of a suitable catalyst such as palladium on carbon at a pressure from atmospheric to 55 psi to provide Ia-7. The hydroxy substituted heterocycles may exist in either the hydroxy tautomer or the keto tautomer or may exist as a mixture of both tautomers.

In some pyrimidine cases produced in scheme Ia, the final nucleophilic addition may be difficult to achieve, the rate of the reaction can be accelerated by first adding an electron withdrawing substituent to the ring such as a nitro or bromo substituent as illustrated in scheme Ib.

Nitration or halogenation of the 5-position of pyrimidine Ib-1 which contain one or two amino substituents or hydroxy or alkoxy substituents occurs readily as described in Brown, D. J., in The Pyrimidines Vol 16 supplements II, pp.135–39 and suppliment I pp. 119–122, the series Chemistry of Heterocyclic Compounds (Weissberger A., and Taylor, E. C. ed's) John Wiley and Sons, New York, 1970. Nitration occurs in a temperature range from 0° C. to 50° C. with a variety of nitrating reagents such as fuming nitric acid in acetic acid or sodium nitrate in sulfuric acid to provide Ib-5. Alternatively, the pyrimidines may be halogenated for example with bromine in acetic acid to provide Ib-2. After addition of the electron withdrawing substituent treatment with an amine can proceed at an acceptable rate at elevated temperature to produce either Ib-3 or Ib-6. In the case of Ib-2 nucleophilic attack usually only occurs at the 6-position and does not displace the 5-bromo substituent. The bromine atom in Ib-3 may be removed by catalytic hydrogenation for example by using palladium or platinum on carbon as the catalyst. In the case of a 5-nitro substituent Ib-6, reduction with palladium on carbon, or use of a metal such as zinc, provides the 5-amino substituent Ib-7.

Scheme Ib

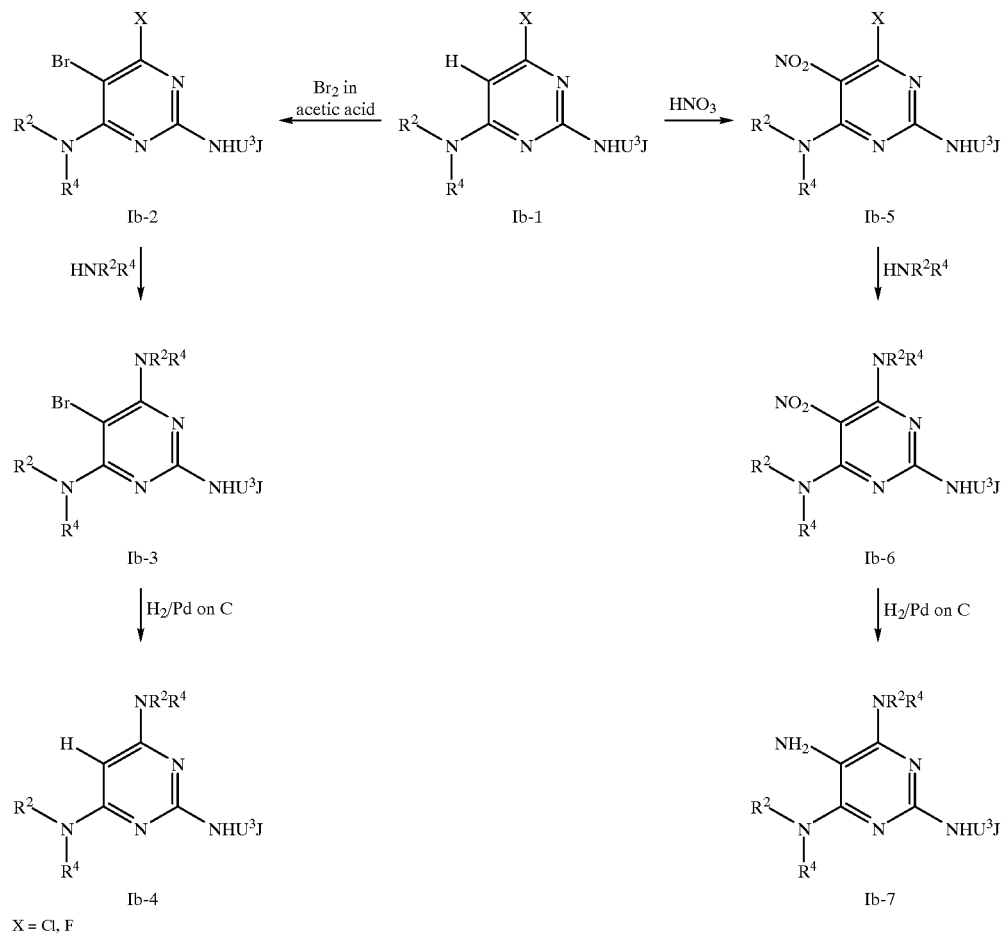

In scheme Ic the dihaloheterocycle Ic-1 is reacted with a nucleophilic amine in an alcoholic solvent or a solvent such as N,N-dimethylacetamide. Isolation of the product Ic-2 may also require the separation of isomers. Each isomer may be carried through the reaction sequence. Reaction of Ic-2 with a second amine substituent usually requires elevated temperatures and in some cases high pressure to provide Ic-3. Alternatively, the monohalo derivative Ic-2 may be treated with an alkoxide or alkylthio salt to provide Ic-4. Removal of the alkyl group may be accomplished by treatment with reagents such as hydrobromic acid, or $AlCl_3$ or $BBr_3$. If a benzylalkoxide is used the benzyl group may be remove by hydrogenolysis using a catalyst such as Pd/C, or Pt/C, in the presence or absence of an added base such as NaOH, or a tertiary amine base. The oxygen or sulfur sustituent may exist in either the enol (Ic-5a) or keto(Ic-5b) form or a mixture of both.

such as methylene chloride or N,N-dimethylformamide to prepare the activated sulfonate IIa-2.

Scheme IIa

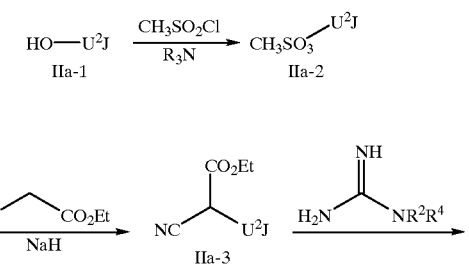

Method 1

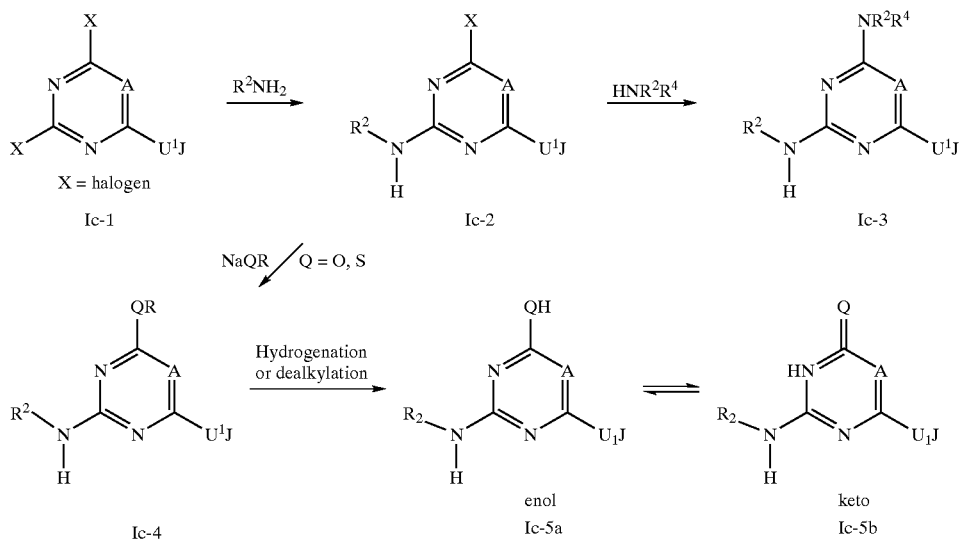

Scheme Ic

A second general method of synthesis of the G portion of compounds of formula I, involves ring forming reactions. The many ring forming reactions for pyrimidines, triazines, and other heterocycles which can be used to prepare the compounds in this invention, are outlined in the reviews cited above. The examples shown in schemes IIa through IIg are for illustration purposes and do not constitute a limitation on the scope of the invention.

Scheme IIa shows a general condensation route to pyrimidines based on the method of Taylor, E. C., Harrington, P. M., and Shih, C., in Heterocycles, 28, 1169, 1989. Taylor starts with an alcohol which can be obtained by a variety of methods well known to one skilled in the art of organic chemistry some examples are shown in schemes IIIa-IIIc, other precursors such as an aklylhalide is also permissible, which may be readily prepared from the alcohols. The group $U^2J$ is used in this general method, but for this synthetic scheme, $U^2J$ is meant to include only those cases in which the terminal methylene group is an alcohol. For example $U^2J$ is a compound like IIIa-6. In this case the alcohol is reacted with a sulfonyl chloride such as mesyl chloride or tosyl chloride in the presence of a tertiary amine, such as triethylamine, or a base such pyridine, in a suitable solvent, -continued Method 2

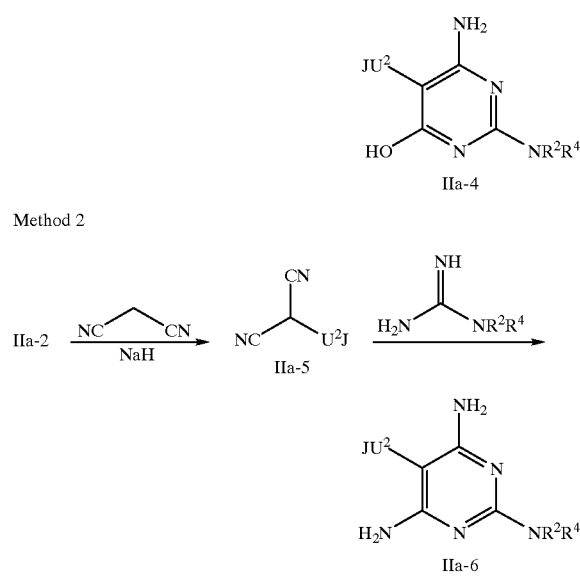

Method 3

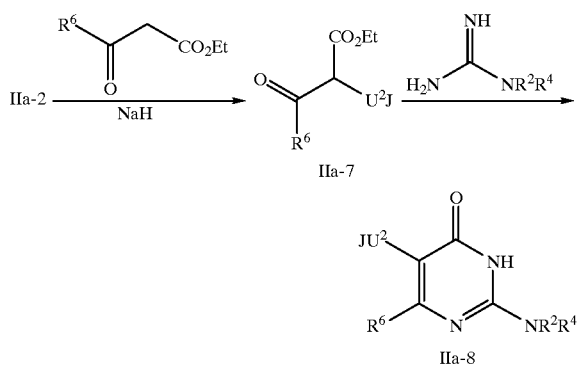

Activated methylene compounds are either, commercially available, or are readily prepared by methods known to one skilled in the art of organic synthesis, for example preparation by acylation of an ester enolate. Alkylation of active methylene compounds are well known in organic chemistry for example, see "The alkylation of active methylene compounds" in Modern Synthetic Reactions 2nd ed. House, H. O., Chapter 9, Benjamin/Cummings Publishing Co, Menlo Park, Calif., 1972. Briefly alkylation may be accomplished by treatment of an activated methylene compound with a suitable base such as sodium hydride, in a suitable solvent such as anhydrous tetrahydrofuran, or anhydrous dioxane at a temperature ranging from −5° C. to solvent reflux will form an anion. This is accompanied by the evolution of hydrogen gas (caution). A solution of the anion is generally cooled to −10° C. –0° C. and the alkylsulfonate ester is added. The reaction mixture is allowed to stir at a temperature ranging from 0° C. to solvent reflux, until the reaction is deemed to have progressed to completion or as far as practical.

In scheme IIa method I, the intermediate cyanoacetate IIa-3 is heated with a guanidine to provide pyrimidine IIa-4. In scheme IIa method 2 the intermediate malononitrile IIa-5 is heated with a guanidine provides pyrimidine IIa-6, and in scheme IIa method 3, the intermediate ketoester IIa-7 is heated with a guanidine to provide pyrimide IIa-8.

Scheme IIb methods 1–3 utilize guanidines which are either commercially available or are readily prepared by methods known to one skilled in the art of organic synthesis, for example as illustrated in scheme IIId. It has been suggested in the method of Taylor that guanidine salts should first be treated with sodium alkoxide/alcohol and filtered to prepare a "salt free" solution of the guanidine base. At this point the solvent may be removed and the gaunidine redissolved in a appropriate solvent, the choice of which is determined by by considerations such as desired reaction temperature and solubility of the reactants, and includes alcohols, N,N-dimethylformamide, and N,N-dimethylacetamide and would be known to one skilled in the art of organic synthesis. Reaction of the guanidine base with the active methylene compounds in methods 1–3, at a temperature from room temperature to solvent reflux provides the desired pyrimidines.

In cases where there is a single alkyl group on the guanidine base it can be envisioned that there will be two possible condensation products, one the desired pyrimidine and one which is the ring nitrogen substituted iminopyrimidine. These products may be separated to provide the desired product. In some cases the ring nitrogen substituted iminopyrimidine may undergo the Dimroth rearragement to provide the desired aminosubstituted pyrimidine (for a discussion of the Dimroth rearrangement see Brown, D. J., in The Pyrimidines Vol 16 supplements I, pp.287–294 in the series Chemistry of Heterocyclic Compounds (Weissberger A., and Taylor, E. C. ed's) John Wiley and Sons, New York, 1970. Alternatively, iminopyrimidines may be hydrolyzed to the pyrimidone (or hydroxypyrimidine tautomer) by treatment with aqueous acid.

Scheme IIb illustrates the use of activated methylene compounds to generate the isomeric pyrimidines which are also within the scope of this invention. In scheme IIb method 1 the guanidine is condensed with a β-ester nitrile in a ethanolic solvent or N,N-dimethylformamide, at 40° c. to 120° C. to give the pyrimidine. In scheme IIb method 2 a malononitrile derivative is condenesed with a guanidine derivative to produce the desired pyrimidine. Scheme IIb method 3 illustrates the condensation of a β-ketoester with a guanidine to produce the desired pyrimidine.

Scheme IIb

Method 1

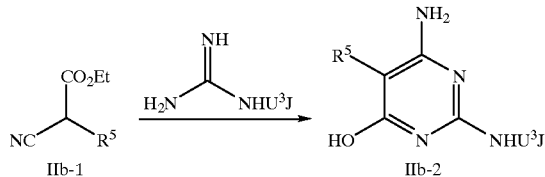

Method 2

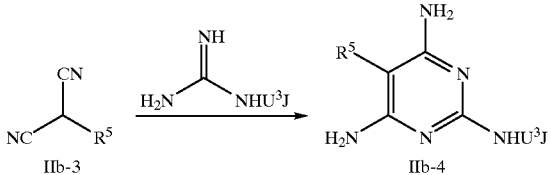

Method 3

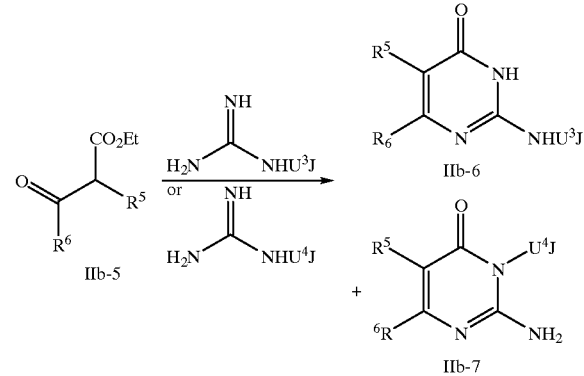

Amidines are either commercially available or readily prepared by one skilled in the art of organic chemistry from readily available nitriles by several methods including a method commonly refered to as the Pinner synthesis of amidines which involves treatment of the nitrile with methanol and anhydrous HCl either with or without an added solvent such as methylene chloride or chloroform followed by the addition of an amine. Amidines readily condense with a variety of activated methylene groups to form pyrimidines. Scheme IIc ilustrates the condensation of an amidine with and active methylene group. In scheme IIc method 1, a malonic ester is heated in a ethanolic solvent or N,N- dimethylformamide, at 40° c. to 120° C. with an amidine to provide pyrimidine IIc-2. In scheme IIc method 2, a malonitrile is heated in a ethanolic solvent or N,N-dimethylformamide, at 40° c. to 120° C. with an amidine to provide pyrimidine IIc-4. In a similar manner intermediate IIc-6 may be treated with phosphourous oxychloride at reflux either with ot without a cosolvent to produce the intermediate dichloropyrimidine IIc-7, which is a useful intermediate, capable of reacting with a variety of nucleophiles in a manner similar to those depicted in schemes Ia through Ic.

Scheme IIc

Method 1

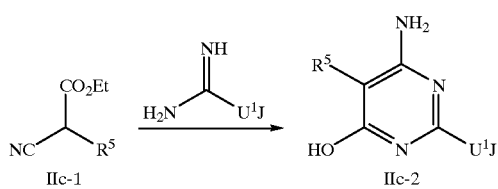

IIc-1 → IIc-2

Method 2

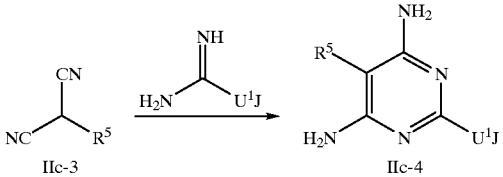

IIc-3 → IIc-4

Method 3

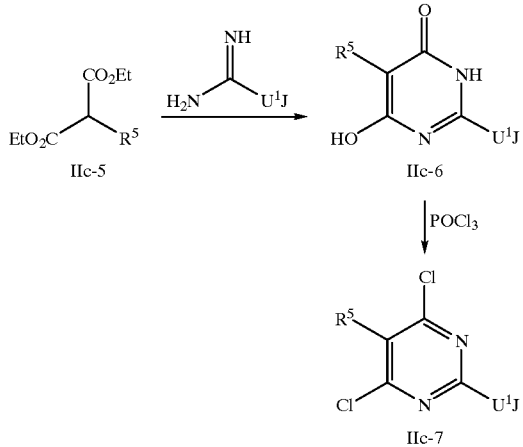

IIc-5 → IIc-6 → IIc-7

Scheme IId illustrates the synthesis of b-ketoesters from a carboxylic acid which is available by many routes known to one skilled in the art of organic chemistry, for example hydrolysis of an ester. An illustration of a carboxylic acid intermediate useful in the preparation of compounds of formula I is shown in scheme IIIc. A convenient preparation of β-ketoester and β-ketonitriles, from N-methoxy-N-methylamides has been reported by Turner, J. A., and Jacks, W. S in J. Org. Chem., 54, 4229–31, 1989. The carboxylic acid may be converted to the acid chloride by many methods for example treatment with oxalyl chloride in an inert solvent such a methylene chloride with a catalytic amount of N,N-dimethylformamide. Alternatively, the carboxylic acid may be activated by reaction with many available reagents such as BOP reagent (benzotriazol-1-yloxytris (dimethylamino)phosphonium hexafluorophosphate) or a a carbodiimide reagent such as dicyclohexylcarbodiimide with the addition of 1-hydroxybenzotriazole.

Scheme IId

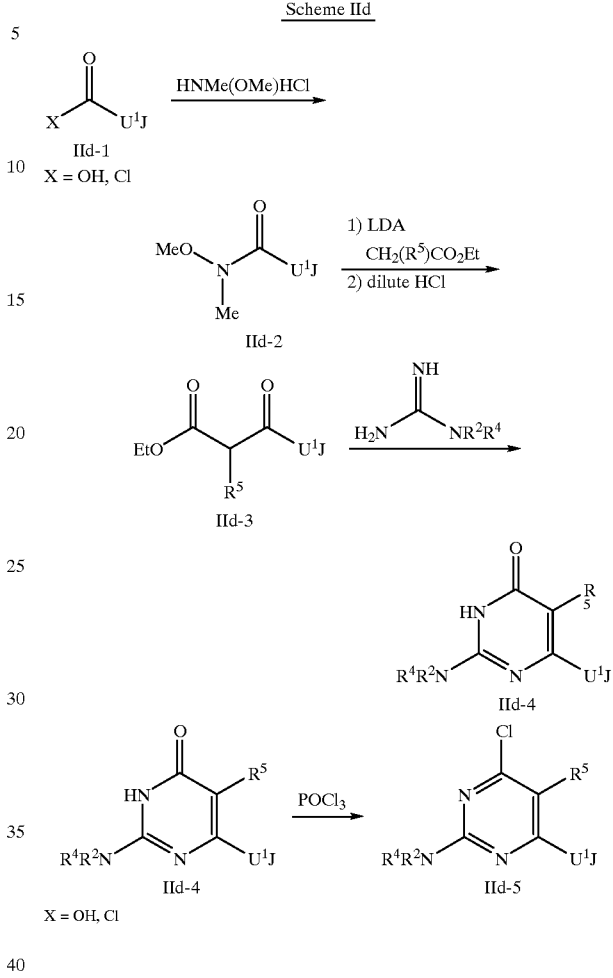

X = OH, Cl

Once the carboxylic acid has been activated reaction can occur with N,O-dimethylhydroxylamine hydrochloride or and a suitable base such as triethylamine or pyridine to produce N-methoxy-N-methylamide IId-2. A suitable ester which is either commercially available or readily prepared by a variety of methods known to one skilled in the art of organic synthesis is dissolved in a dry solvent such as tetrahydrofuran and cooled to a temperature in the range of −78° C. to −20° C., and is added to a precooled solution of a suitable base is added such as lithium diisopropylamide or lithium bis(trimethylsilyl)amide. Addition of the N-methoxy-N-methylamide to the enolate solution at low temperature for a sufficient amount of time then allowing the reaction mixture to reach room temperature, and quenching with dilute aqueous acid to provide the ketoester IId-3. There are many other means of preparing 5-keto esters, for example, a synthesis of ketoesters from the acid chloride and meldrums acid followed by treatment with alcohol has been reported by Oikawa, Y., Sugano, K., Yonemitsu, O., J. Org. Chem, 43, 2087, 1978.

The ketoester IId-3 is treated with guanidine free base, prepared as described previously, or guanidine carbonate in an alcholic solvent or N,N-dimethylformamide from room temperature to 120° C., until the reaction is deemed to have progressed by an analytical method such as TLC or HPLC, to provide the pyrimidone IId-4. Additionally the pyrimidone IId-4 may be treated with phosphorous oxychloride to provide intermediate IId-5. As illustrated in schemes Ia-Ic, the chloropyrimidine is a useful intermediate in the synthesis of additional compounds via a nucleophilic displacement.

Scheme IIe

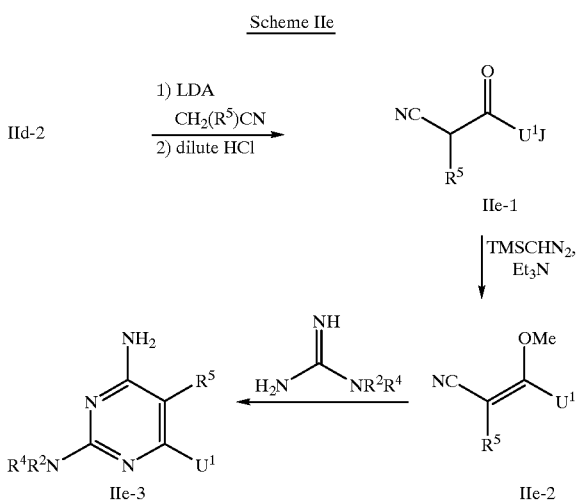

Scheme IIe illustrates the preparation of a pyrimidine from a β-ketonitrile. The intermediate IId-2 is reacted with the anion of a nitrile to produce IIe-1. Reaction of IIe-1 with either diazomethane or trimethylsilyldiazomethane in the presence of a suitable base such as triethylamine provides the β-methoxyacrylate derivative IIe-2. Treatment of intermediate IIe-2 with a guanidine at temperatures ranging from 100° C. to 200° C. in a sealed tube generally provides the desired pyrimidine derivative IIe-3.

Another synthetic route to pyrimidines is also useful for the preparation of compounds in this invention, and is depicted in scheme IIf. For a review of this approach to the synthesis of pyrimidines see Brown, D. J., in Comprehensive Heterocyclic Chemistry Vol. 3, pp. 107–108, (Katritzky A. R., and Rees, C. W ed's) Pergamon Press Ltd., New York, 1984. Malondiamidine and substituted malondiamidines are readily prepared by one skilled in the art of organic synthesis from the readily available malononitriles by the Pinner reaction (for example see Meyer, H., Kurz, J., in Justus Liebigs Ann. Chem. (9) 1491–1504, 1978). Malonamamidine, the mixed amide amidine, is commercially available. Malondiamidine IIf-1 is heated with an appropriate ester IIf-2 in a suitable solvent such as an alcohol or N,N-dimethylformamidine to provide the desired pyrimidines IIf-3. In a similar manner malonamamidine IIf-4 may be heated with an ester to provide pyrimidine IIf-5.

Scheme IIf

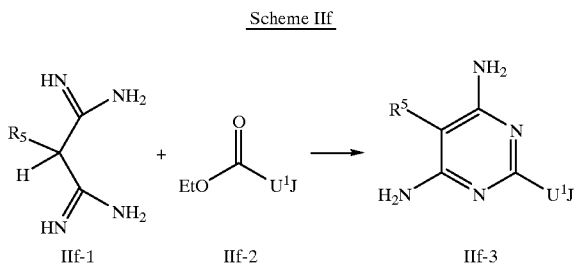

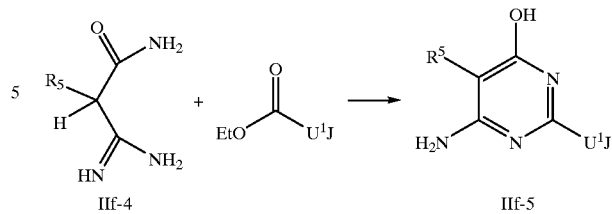

In Scheme IIg, a triazine IIg-2 is prepared from a carboxylic ester by heating with biguanide IIg-1, (Karipides, D. and Fernelius, W. C., in Inorganic Synthesis 7, pp 56–59, 1962, John Wiley and Sons, New York.) in either an alcoholic solvent or N,N-dimethylformamide at a temperature ranging from 25° C. to 80° C.

Scheme IIg

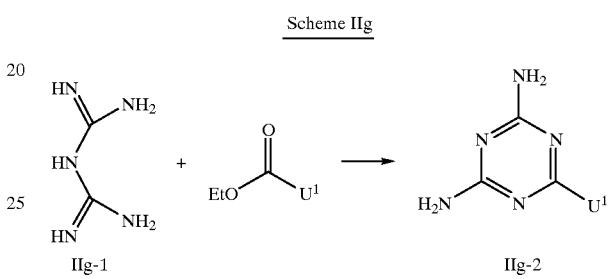

Another synthetic route to pyrimidines is also useful for the preparation of compounds in this invention, and is depicted in scheme IIh. Compounds which contain an aryl or heteroaryl ring with an ortho-aminocarboxamides (IIh-1) are either commercially available or readily available by methods known to one skilled in the art of organic chemistry. Reaction of IIh-1 with either an acid chloride in the presence of a base such as pyridine or an acid group in the presence of a suitable coupling agent such as N,N'-dicyclohexylcarbodiimide, provide intermediate IIh-3. Intermediates of type IIh-3 are readily cyclized to the pyrimidines IIh-4 under a wide variety of conditions which are known to one skilled in the art of organic chemistry, including heating in the presence of pyridine followed by treatment with acid.

Scheme IIh

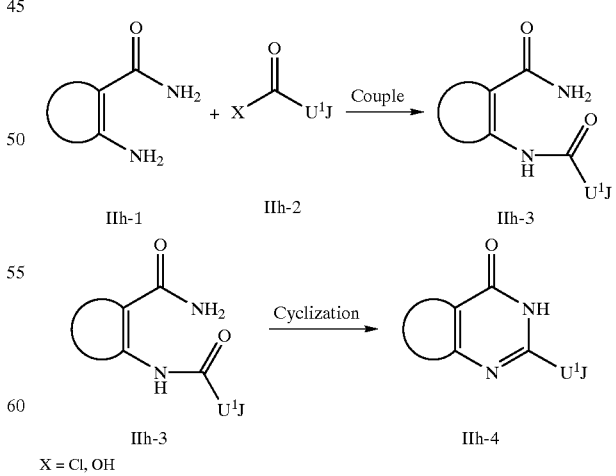

The synthesis of additional intermediates useful in the preparation of compounds of formula I is shown in schemes IIIa–IIId.

Scheme IIIa illustrates one method for the preparation of esters useful as intermediates in the preparation of compounds of formula I it should be noted that these and similar compounds including the meta substituted analogs can be prepared by a wide variety of methods known to one skilled in the art of organic synthesis.

Aminomethylbenzoic acid (IIIa-1) and hydroxyaminobenzoic acid (IIIa-6) are commercially available. Aminomethylbenzoic acid (IIIa-1) is reacted with benzylchloroformate in the presence of sodium hydroxide with or without a cosolvent such as dioxane. Acidification of the reaction mixture provides IIIa-2. Treatment of the acid with isobutylene and catalytic sulfuric acid in dioxane in a sealed pressure vessel provides IIIa-3. Hydrogenation in an alcoholic solvent with palladium on carbon provides the intermediate IIIa-4. Arndt-Eistert homologation of IIIa-2 followed by removal of the benzylcarbamate by hydrogenation in the presence of palladium on carbon provides the intermediate IIIa-5.

Hydroxyaminobenzoic acid (IIIa-6) is reacted with tert-butyldimethylsilyl chloride (TBDMS-Cl) in the presence of imidazole in a solvent such as tetrahydrofuran. Treatment of the the reaction mixture with dilute base followed by acidification provides the acid IIIa-7. Reaction of the acid with oxalyl chloride in a suitable solvent such as methylenechloride with a catalytic amount of N,N-dimethylformamide provides the acid chloride. The acid chloride is reacted with t-butanol in the presence of pyridine to provide IIIa-8. Treatment of IIIa-8 with tetrabutylammonium fluoride (TBAF) provides the intermediate alcohol IIIa-6.Arndt-Eistert homologation of IIIa-2 followed by removal of the TBDMS group to provide intermediate IIIa-10.

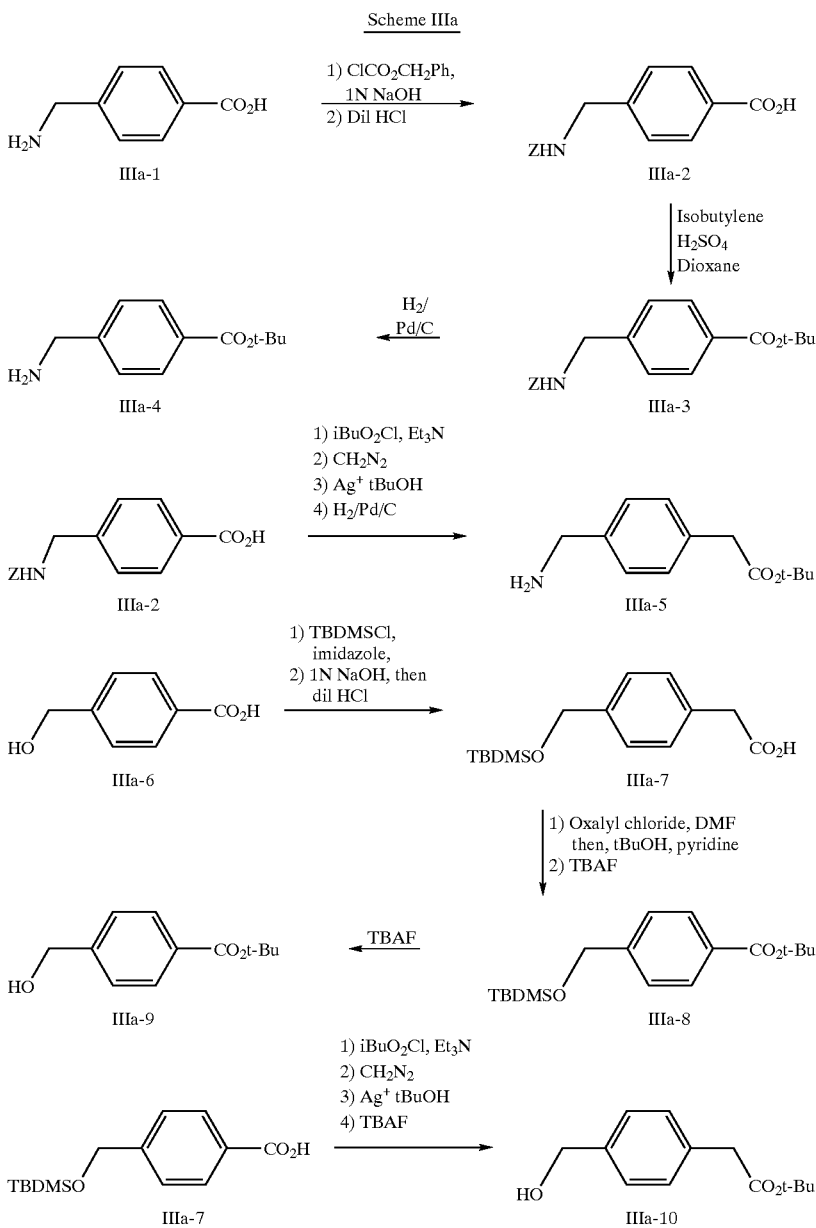

Scheme IIIb illustrates one method for the preparation of additional esters useful as intermediates in the preparation of compounds of formula I it should be noted that these and similar compounds including the meta substituted analogs can be prepared by a wide variety of methods known to one skilled in the art of organic synthesis.

4-Bromophenethylamine (IIIb-1) is commercially available. Reaction with benzyl chloroformate in dioxane in the presence of sodium hydroxide, followed by aryl coupling with commercially available 2-furanboronic acid in the presence of a suitable catalyst such as tetrakistriphenylphosphine palladium (0) to provide IIIb-2. The furan may be converted to the carboxylic acid IIIb-3 by several method including treatment with nitric acid and a vanadium salt (see Carbateas, P. M., and Williams, G. L., in J. Heterocycl. Chem. 11, 819–821, 1974) or by ozonolysis (see, Tsukamoto, T., Yoshiyama, T., Kitazume, T., in Tetrahedron: Asymmetry 2(8), 759–62, 1991). Treatment of the acid with isobutylene in dioxane with a catalytic amount of sulfuric acid followed by catalytic hydrogenation in the presence of palladium on carbon provides intermediate IIIb-4. Alternatively, the acid IIIb-3 may be be subjected to an Arndt-Eistert homologation followed by catalytic hydrogenation to provide intermediate IIIb-5.

4-Bromophenethylalcohol (IIIb-6) is commercially available. Treatment with TBDMSCl and imidazole, followed by aryl coupling with commercially available 2-furanboronic acid in the presence of a suitable catalyst such as tetrakistriphenylphosphine palladium (0) to provide IIIb-7. Oxidation of furan in a manner similar for IIIb-2, provides the acid IIIb-8. The acid can be converted to the acid chloride with oxalyl chloride in methylene chloride with a catalytic amount of N,N-dimethylformamide. Treatment of the acid chloride with t-butanol and pyridine, followed by treatment with tetrabutylammonium fluoride solution provides the intermediate IIIb-9. Alternatively, the acid IIIb-8 may be be subjected to an Arndt-Eistert homologation followed by catalytic hydrogenation to provide intermediate IIIb-10.

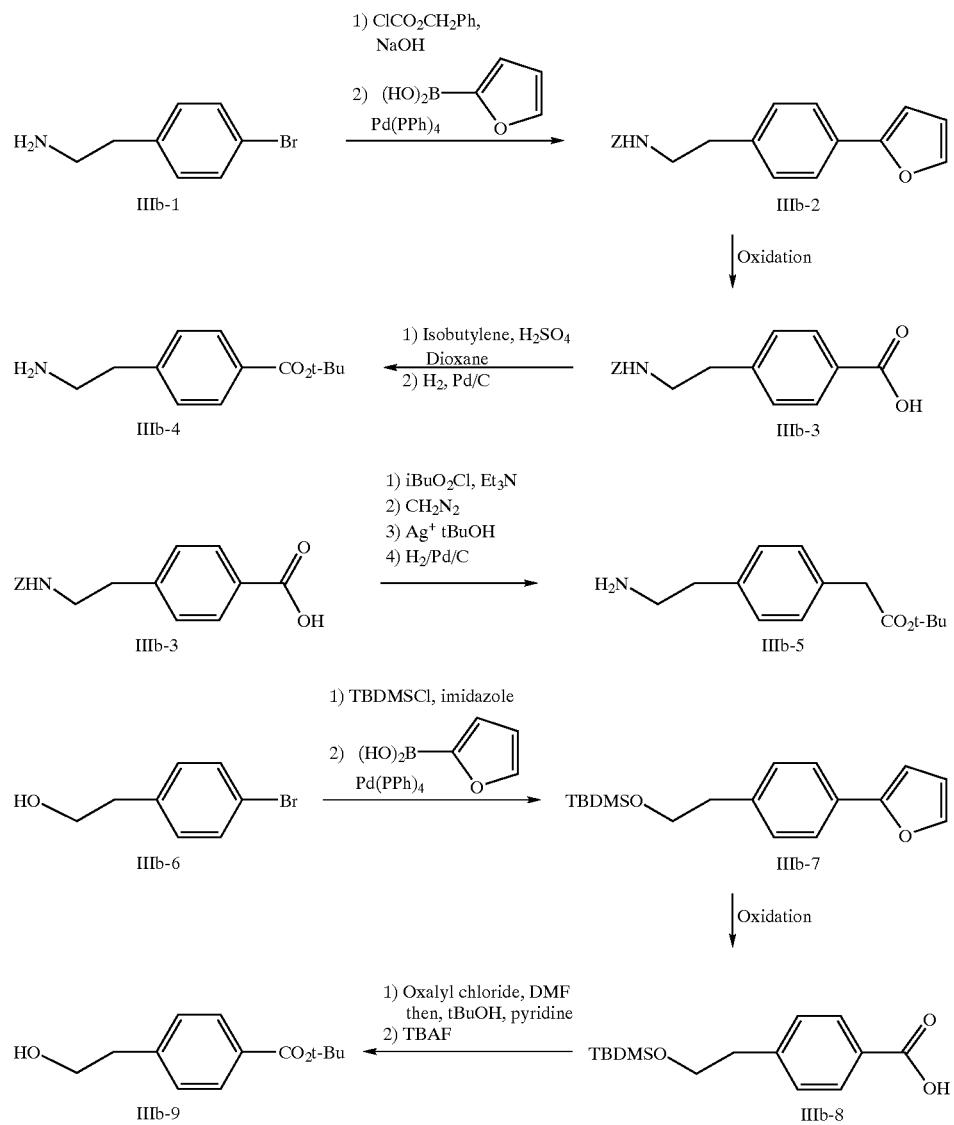

Scheme IIIb

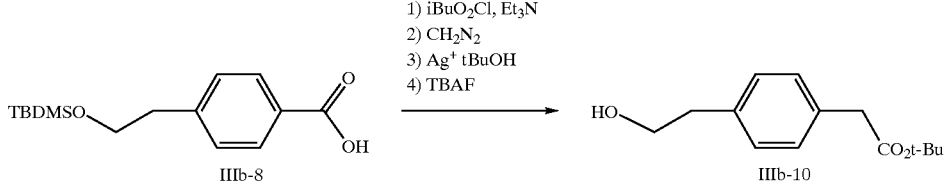

Scheme IIIc illustrates one method for the preparation of additional esters useful as intermediates in the preparation of compounds of formula I. It should be noted that these and similar compounds including the meta substituted analogs can be prepared by a wide variety of methods known to one skilled in the art of organic synthesis.illustrates the synthesis of some esters and acids useful as intermediates in the preparation of compounds of formula I.

4-Iodobenzoic acid (IIIc-1) and 3-iodobenzoic acid are commercially available. The preparation of t-Butyl esters can be accomplished by many methods, for example treatment of the the acid with isobutylene in the presence of an acid such as sulfuric acid. The 4-iodoester is subjected to a Heck reaction with methyl acrylate in the presence of palladium acetate according to the method of Jeffrey (Jeffrey, T., J. Chem. Soc., Chem. Commun. 1287–89, 1984.) to provide IIIc-2. Reduction of the double bond can be accomplished under a variety of catalytic hydrogenation conditions for example, palladium on carbon with ammonium formate in methanol at reflux (Tam, S., Spicer, L. D. Syn. Comm. 22(18), 2683–2690, 1992) to provide intermediate IIIc-3. Hydrolysis of the methyl ester in the presence of the t-butyl ester usually requires basic conditions such as lithium or sodium hydroxide, followed by acidification with dilute to provide the mono-acid IIIc-4. The carboxylic acid may be reduced with borane in THF (see Yoon, N. M., Pak, C. S., Brown, H. C., Krishnamurthy, S., Stocky, T. P., in J.Org. Chem. 38, 2786–92, 1973.) to provide the alcohol IIIc-5. Treatment of the alcohol with methansulfonyl chloride and triethylamine to provide the mesylate, which may be reacted with sodium azide in N,N-dimethylformamide, to provide the alkylazide. Reduction of the azide to the intermediate amine IIIc-6 can be accomplished by several methods including hydrogenation with palladium on carbon as the catalyst, or by the Staudinger reaction which involves treatment of the azide with triphenylphosphine followed by treatment with water.

Scheme IIIc

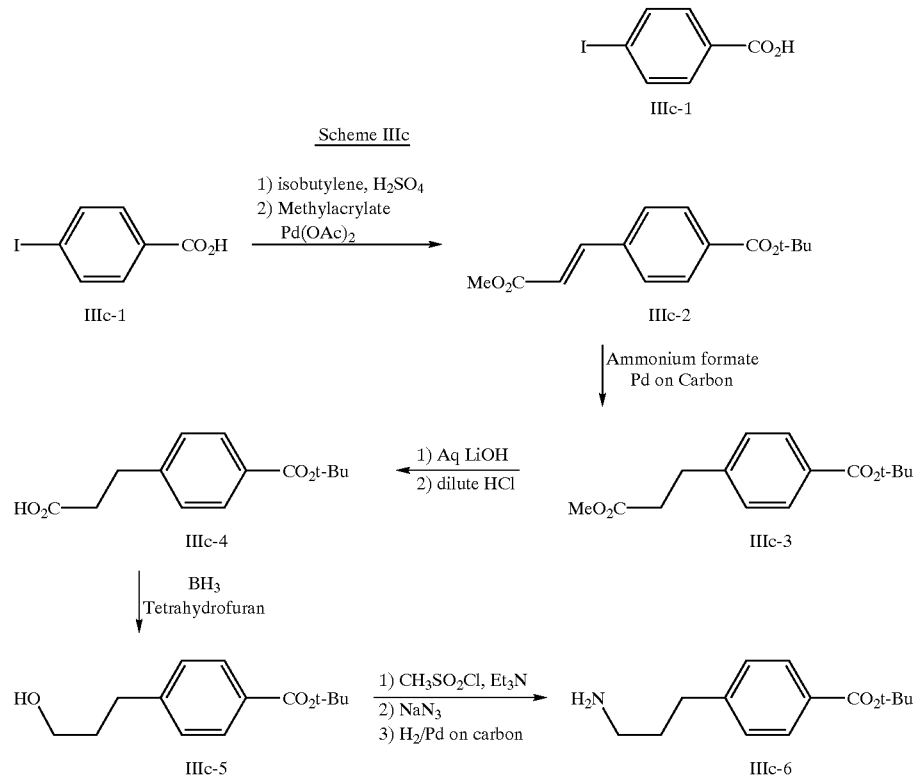

Alternatively the amines prepared in schemes IIIa-c may be converted to the guanidine by several methods including treatment with the commercially available 2–3,5-dimethylpyrazole-1-carboxamidine nitrate.

Scheme IIId

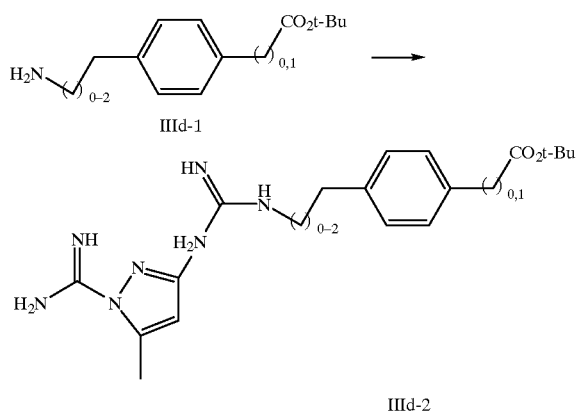

IIId-1

IIId-2

Scheme IIIe illustrates the synthesis of amidines useful as intermediates in this invention. Alcohols IIIe-1 for example such as IIIa-6, and IIIb-6 are readily converted to the corresponding nitrile IIIe-2 by formation of the sulfate ester followed by treatment with sodium or potassium cyanide. Amidines IIIc-3 are readily prepared by one skilled in the art of organic chemistry by several methods including a method commonly refered to as the Pinner synthesis of amidines which involves treatment of the nitrile with methanol and anhydrous HCl, either with or without, an added solvent such as methylene chloride or chloroform followed by the addition of an amine.

Scheme IIIe

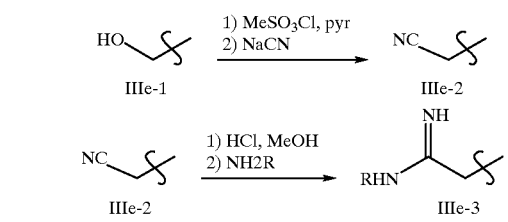

R = alkyl, aryl

The appropriately substituted racemic β-amino acids may be purchased commercially or, as is shown in Scheme IV, Method 1, prepared from the appropriate aldehyde, malonic acid and ammonium acetate according to the procedure of Johnson and Livak (*J. Am. Chem. Soc.* 1936, 58, 299). Racemic β-substituted-β-amino esters may be prepared through the reaction of dialkylcuprates or alkyllithiums with 4-benzoyloxy-2-azetidinone followed by treatment with anhydrous ethanol Scheme IV, Method 2,or by reductive amination of β-keto esters as is described in published PCT patent application WO9316038. (Also see Rico et al., J. Org. Chem. 1993, 58, 7948–51.) Enantiomerically pure β-substituted-β-amino acids can be obtained through the optical resolution of the racemic mixture or can be prepared using numerous methods, including: Arndt-Eistert homologation of the corresponding α-amino acids as shown in Scheme IV, Method 3 (see Meier, and Zeller, *Angew. Chem. Int. Ed. Enal.* 1975, 14, 32; Rodriguez, et al. *Tetrahedron Lett.* 1990, 31, 5153; Greenlee, *J. Med. Chem.* 1985, 28, 434 and references cited within); and through an enantioselective hydrogenation of a dehydroamino acid as is shown in Scheme IV, Method 4 (see Asymmetric Synthesis, Vol. 5, (Morrison, ed.) Academic Press, New York, 1985). A comprehensive treatise on the preparation of β-amino acid derivatives may be found in published PCT patent application WO 9307867, the disclosure of which is hereby incorporated by reference. The synthesis of $N^2$-substituted diaminopropionic acid derivatives as shown in Scheme IV method 5 can be carried out via Hoffman rearrangement of a wide variety of asparagine derivatives as described in Synthesis, 266–267, (1981).

Scheme IV

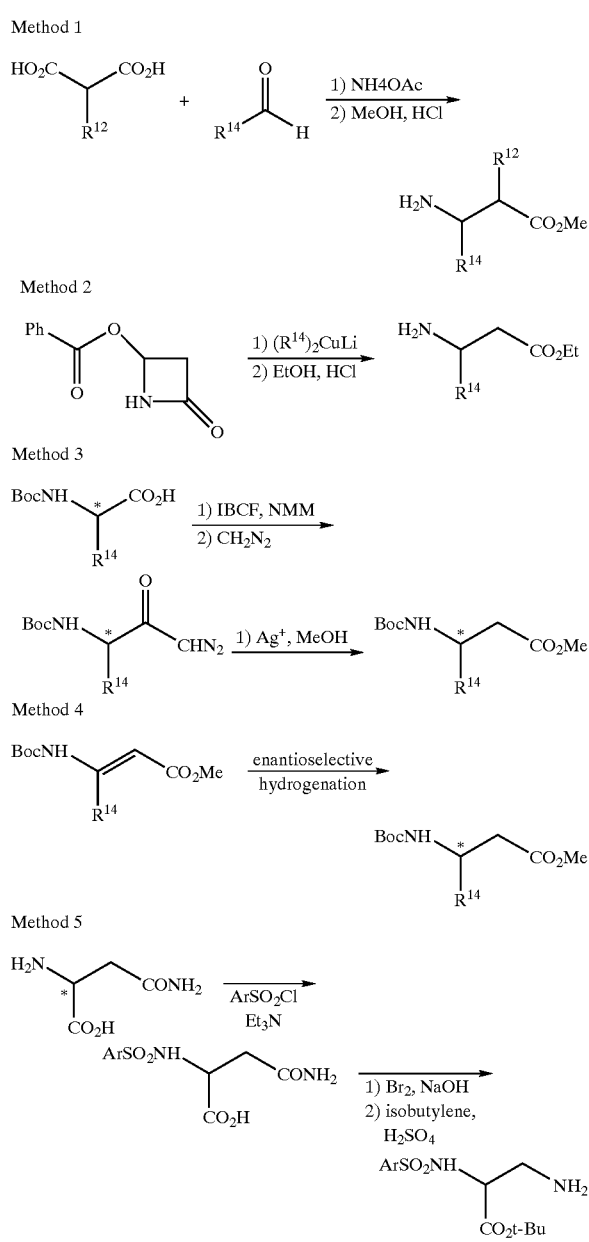

Scheme V depicts the coupling acids prepared in Schemes IIIa and IIIb with the amines prepared in sheme IV Coupling of the resulting acids to appropriately substituted α- or β-amino esters affords an intermediate which can be deprotected to give compounds of Formula (IA). The coupling is carried out using any of the many methods for the formation of amide bonds known to one skilled in the art of organic synthesis. These methods include but are not limited to conversion of the acid to the corresponding acid chloride, or use of standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, carbonyldiimidazole method, phosphorus reagents such as BOP-Cl. Some of these methods (especially the carbodiimide) can be enhanced by the addition of 1-hydroxybenzotriazole.

Scheme V

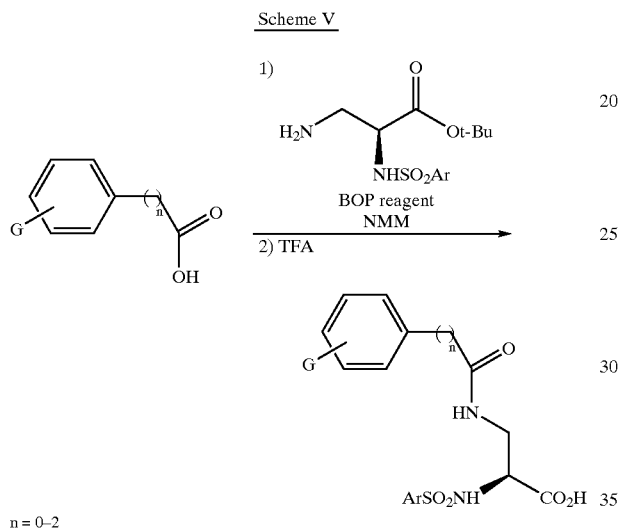

n = 0–2

The detailed processes for preparing the compounds of Formula (IA) are illustrated by the following Examples. It is, however, understood that this invention is not limited to the specific details of these examples. Melting points are uncorrected. Proton nuclear magnetic resonance spectra ($^1$H NMR) were measured in chloroform-d (CDCl$_3$) unless otherwise specified and the peaks are reported in parts per million (ppm) downfield from tetramethylsilane (TMS). The coupling patterns are reported as follows: s, singlet; d, doublet; t, triplet; q, quartet; qt, quintet; m, multiplet.

EXAMPLE A-23

2-[(S)-((2,4,6-Trimethylphenyl)sulfonyl)amino]3-[4-(2-(2,4-diaminopyrimidin-6-yl)ethylphenylcarbonyl] aminopropionic acid trifluoroacetate salt A. N-(2,4,6 trimethylphenyl)sulfonyl-L-asparagine L-Asparagine (20.0 g, 0.15M) was suspended in a mixture of tetrahydrofuran (130 mL) and water (250 mL). Triethylamine (49 g, 0.48M) was added followed by mesitylenesulfonyl chloride (49.7 g, 0.227M), The reaction mixture became slightly exothermic and the solids dissolved over a period of 0.5 h. to yield a yellow solution. The reaction mixture was stirred for 3 h at room temperature, then washed with ether, and methylene chloride. The aqueous layer was separated, and acidified to ca. pH=1.5 with conc. HCl, during which time a thick precipitate formed. After 0.5 h. the product was filtered, washed with water and dried to yield a white solid (34 g, 72%). m.p.=193.5 - 1950C $^1$H NMR (DMSO) δ 2.24 (s, 3H), 2.28 (dd, 1H), 2.45 (dd, 1H), 2.55 (s, 6H), 3.98 (m, 1H), 6.88 (br s, 1H), 6.99 (s, 2H), 7.32 (br s, 1H), 7.82 (d, 2H), 12.58 (br s, 1H). Mass spectrum ESI m/z 315.2, (M+H base peak).

B. 3-Amino-2-(S)-N-(2,4,6 trimethylphenyl) sulfonylaminopropionic acid

Sodium hydroxide (32 g, 0.80 M), was dissolved in water (200 mL) and cooled in an ice bath. Bromine (19.2 g, 0.12 M) was added dropwise over 5 min. and the mixture allowed to stir for 15 min. The product of Ex. A-23, Part A, (31.44 g, 0.10 M), was added in several portions over a period of ca. 10 min. during which time the yellow color faded. The reaction mixture was gently heated on a steam bath during which time the internal temperature rose to ca. 85° C. After 1 h, the reaction mixture was allowed to cool to room temperature then cooled in an ice bath. The reaction mixture was cautiously acidified to pH=6 with conc. HCl, during which time a solid formed and gas was evolved. The solid was filtered, washed with cold water, and allowed to dry overnight, to yield the product as a white solid (23.9 g, 83%). $^1$H NMR (DMSO) δ 2.26 (s, 3H), 2.59 (s, 6H), 2.80 (dd, 1H), 2.94 (dd, 1H), 3.07 (dd, 1H), 7.06 (s, 2H) . Mass spectrum ESI m/z 287.2 (M+H, base peak).

C. tert-Butyl-3-Amino-2-(S)-N-(2,4,6-trimethylphenyl) sulfonylaminopropionate

The product of Ex.A-23, Part B, (11.45 g, 0.04M), was placed in a Parr bottle, and dissolved in dioxane (170 mL), and conc. sulfuric acid (11 mL) was added. The reaction mixture was cooled in a dry ice / acetone bath and ca. 185 ml of isobutylene was added. The bottle was sealed and agitated for 114 h. The bottle was depressurized then purged with nitrogen for a brief time. The reaction mixture was poured into a rapidly stirred mixture of water (225 mL) containing sodium hydroxide (17 g) and ether (600 mL) which had been pre-cooled in an ice bath. The layers were separated. The aqueous layer was extracted with additional ether. The pH of the aqueous layer was carefully adjusted with conc. HCl to pH=11 and extracted four times with ether. The organic layers from the pH 11 adjusted extraction were combined, dried with anhydrous sodium sulfate, filtered and evaporated to yield the product as a viscous oil which solidified (8.64 g, 63%). $^1$H NMR (CDCl$_3$) δ 1.28 (s, 9H), 2.28 (s, 3H), 2.67 (s, 6H), 2.93 (m, 2H), 3.69 (m, 1H), 6.95 (s, 2H).

D. 4-Iodobenzoic acid tert-butyl ester

4-Iodobenzoic Acid (25 g, 0.10M) was suspended in 200 ml of anhydrous dioxane containing 14 ml of concentrated sulfuric acid. Isobutylene (200 ml) was condensed and added to the suspension. The reaction vessel was sealed and stirred at room temperature for 3 days, during which time most of the material dissolved. The reaction mixture was cautiously poured into saturated sodium bicarbonate solution and extracted with ethyl acetate. The organic layer was dried with anhydrous sodium carbonate, filtered and evaporated to a colorless oil (18 g, (60%). $^1$H NMR (CDCl$_3$) δ 1.59 (s, 9H), 7.68 (d, J=8 Hz, 2H), 7.75 (d, J=8 Hz, 2H).

E. 4-(tert-Butyloxycarbonyl)trans-cinnamic acid methyl ester

The product of Ex. A-23, Part D, (10.5 g, 34.5 mM) was dissolved in N,N-dimethylformamide (30 mL). Tetra n-butylammonium chloride monohydrate (9.56 g, 34.5 mM), sodium bicarbonate (9.32 g, 86.2 mM), methyl acrylate (5.92 g, 69.0 mM), and palladium acetate (155 mg, 0.69 mM) was added. The reaction was stirred at 30° C., overnight. The reaction mixture was poured into 300 mL of water and the precipitate collected. The crude product was dissolved in methylene chloride and passed through a pad of silica gel until all the product had eluted from the pad. The solvent was evaporated to yeild a light redish-brown solid (9.0 g, 99%). $^1$H NMR (CDCl$_3$) δ 1.60 (s, 9H), 3.81 (s, 3H), 6.51 (d, 16 Hz, 1H), 7.58 (d, J=8 Hz, 2H), 7.70, (d, J=16 Hz, 1), 7.98, (d, J=8 Hz, 2H), mass spec (CI) m/z=263 (M+H)+ base peak.

F. 4-(tert-Butyloxycarbonyl)hydrocinnamic acid methyl ester

The product of Ex. A-23, Part E, (from a different run) (14 g, 56.0 mM) was dissolved in methanol. Palladium on carbon 10% (2.2 g) was wetted with approximately 3 mL of water and added cautiously to the methonol solution followed by ammonium formate (18 g, 0.285M). The reaction mixture was refluxed for 3 h, filtered through celite and evaporated to yield a colorless oil (14 g, 99%). $^1$H NMR (CDCl$_3$) δ 1.59 (s, 9H), 2.64 (t, J=7 Hz, 2H), 3.00 (t, J=7 Hz, 2H), 3.64 (s, 3H), 7.24 (d, J=8 Hz, 2H), 7.90, (d, J=8 Hz, 2H).

G. 4-(tert-Butyloxycarbonyl)hydrocinnamic acid

The product of Ex. A-23, Part F, (14 g, 55.5 mM) was dissolved in 90 mL of tetrahydrofuran. 1N Lithium hydroxide (90 ml) was added and the reaction stirred at room temperature for 20 min. The reaction mixture was poured into 200 mL of 1:1 mixture of 1N HCl and saturated citric acid, and extracted with ethyl acetate. The organic layer was dried over magnesium sulfate, filtered and evaporated to yield a white solid (13 g 100%). $^1$H NMR (CDCl$_3$) δ 1.59 (s, 9H), 2.70 (t, J=7 Hz, 2H), 3.00 (t, J=7 Hz, 2H), 7.24 (d, J=8 Hz, 2H), 7.90, (d, J=8 Hz, 2H).

H. 4-(tert-Butyloxycarbonyl)hydrocinnamic acid N-methyl-O-methylamide

The product of Ex. A-23, Part G, (5.2 g, 22.2 mM) was dissolved in 10 mL of N,N-dimethylformamide. N,O-dimethylhydroxylamine hydrochloride (2.60 g, 22.6 mM), N-methylmorpholine (6.73 g, 66.6 mM), and benzotriazole-1-yloxy-tris(dimethylamino)phosphonium hexafluorophosphate (BOP reagent) (11.78 g, 26.6 mM) was added and the reaction mixture stirred at room temperature overnight. The reaction mixture was poured into 100 mL of water and extracted with ethyl acetate. The organic layer was separated, dried over magnesium sulfate, filtered and evaporated to yield a brown oil which was purified by flash column chromatography (hexane/ethyl acetate 3:1) to yield a tan oil (4.2 g, 65%).$^1$H NMR (CDCl$_3$) δ 1.59 (s, 9H), 2.75 (t, J=7 Hz, 2H), 3.00 (t, J=7 Hz, 2H), 3.18 (s, 3H), 3.60 (s, 3H), 7.24 (d, J=8 Hz, 2H), 7.90, (d, J=8 Hz, 2H).

I. 5-[4-(tert-Butyloxycarbonyl)phenyl]-3-oxopentanitrile

Lithium bis(trimethylsilyl)amide 1M solution in hexane (12 ml, 12.0 mM) was added to 12 mL of anhydrous tetrahydrofuran, and cooled to −78° C. After 0.5 h, anhydrous acetonitrile (492 mg, 12.0 mM) was added dropwise. After 0.25 h, the product of Ex. A-23, Part H, (2.93 g, 10.0 mM) was dissolved in 3 mL of anhydrous tetrahydrofuran and added dropwise to the rapidly stirred reaction mixture. After 3 h at −78° C. the reaction mixture was warmed to 0° C. for 1 h, the quenched by pouring into 1N HCl. The product was extracted with ethyl acetate. The organic layer was separated, dried over magnesium sulfate, filtered and evaporated to yield a yellow oil (2.7 g, 99%). $^1$H NMR (CDCl$_3$) δ 1.59 (s, 9H), 2.98 (m, 4H) 3.22 (s, 2H), 7.22 (d, J=8 Hz, 2H), 7.92, (d, J=8 Hz, 2H).

J. 5-[4-(tert-Butyloxycarbonyl)phenyl]-3-methoxy-2-pentenitrile

The product of Ex. A-23, Part I, (2.70 g, 9.89 mM) was dissolved in 100 mL of a 1:1 mixture of methanol and acetonitrile. N,N-diisopropyl-N-ethylamine (1.53 g, 11.8 mM) was added followed by trimethylsilyldiazomethane 2M solution in hexane (30 mL, 60 mM) was added, and the reaction mixture stirred overnight at room temperature. The reaction was quenched by the dropwise addition of glacial acetic acid until gas evolution subsided, and the solvent evaporated. The crude oil was purified by flash column chromatography (hexane/ethyl acetate 3:1). The product appears by NMR to be a mixture of cis and trans isomers. The data for the major isomer is reported. $^1$H NMR (CDCl$_3$) δ 1.59 (s, 9H), 2.42 (t, J=7 Hz, 2H), 2.82, (t, J=7 Hz, 2H), 4.10 (s, 3H), 6.84 (d, J=8 Hz, 1H) 7.22 (d, J=8 Hz, 2H), 7.92, (d, J=8 Hz, 2H).

K. 4-[2-(2,4-Diaminopyrimidin-6-yl)ethyl]benzoic acid

The product of Ex. A-23, Part J, (1.0 g, 3.48 mM) was dissolved in ethanol. Guanidine hydrochloride (1.09 g, 10.4 mM) and potassium tert-butoxide (1.38 g, 11.1 mM) was added and the reaction mixture refluxed overnight. NMR analysis of an aliquot did not show evidence of pyrimidine formation. The solvent was removed and the residue was heated at 160° C. for 1 h. NMR analysis of an aliquot showed that the pyrimidine ring had formed but the tert-butyl ester had cleaved. The solid residue was dissolved in 1:1 mixture of water and acetonitrile and purified by reverse phase (C18 water-acetonitrile linear gradient) HPLC. Evaporation of the appropriate fractions yielded a white solid (270 mg, 30%). $^1$H NMR (CD$_3$OD) δ 2.84 (t, J=7 Hz, 2H), 3.02, (t, J=7 Hz, 2H), 4.10 (s, 3H), 5.80 (s, 1H) 7.30 (d, J=8 Hz, 2H), 7.92, (d, J=8 Hz, 2H). mass spec (ESI) m/z=259 (M+H)$^+$ base peak.

L. 2-[(S)-((2,4,6-Trimethylphenyl)sulfonyl)amino]3-[4-(2-(2,4-diaminopyrimidin-6-yl)ethylphenylcarbonyl] aminopropionic acid tert-butyl ester The product of Ex. A-23, Part K, (65 mg, 0.25 mM) and the product of Ex. 1, Part C (103 mg, 0.03 mM) were dissolved in 1 mL of N,N-dimethylformamide. Benzotriazole-1-yloxy-tris(dimethylamono)phosphonium hexafluorophosphate (133 mg, 0.30 mM) and N-methylmorpholine (76.3 mg, 0.75 mM) were added and the reaction mixture was stirred overnight at room temperature. The reaction mixture was poured into 30 mL of water and allowed to stand for 1 h. The precipitate was collected, washed with an additional 20 mL of water and dried to yield a white solid (145 mg, 99%). $^1$H NMR (CD$_3$OD) δ 1. 19, (s, 9H), 2.20, (s, 3H), 2.58, (s, 6H), 2.75 (t, J=7 Hz, 2H), 2.98, (t, J=7 Hz, 2H), 3.45 (dd, J=13 Hz, 8 Hz, 1H), 3.65 (dd, J=13 Hz, 6 Hz, 1H), 4.01 (dd, J=8 Hz, 5 Hz, 1H) 5.75 (s, 1H), 6.88 (s, 2H), 7.27 (d, J=8 Hz, 2H), 7.65, (d, J=8 Hz, 2H). mass spec (ESI) m/z=583 (M+H)$^+$ base peak.

M. 2-[(S)-((2,4,6-Trimethylphenyl)sulfonyl)amino]3-[4-(2-(2,4-diaminopyrimidin-6-yl)ethylphenylcarbonyl] aminopropionic acid trifluoroacetate salt The product of Ex. A-23, Part L, (144 mg, 0.24 mM) was dissolved in 2 mL of trifluroacetic acid and stirred for 1 h. at room temperature. The solvent was removed and the residue purified by reverse phase (C$_{18}$ water-acetonitrile linear gradient) HPLC. The appropriate fractions were evaporated to remove the volatile solvents and then the water removed by lyophilization to yield a white solid. mp 145–150° C. $^1$H NMR (CD$_3$OD) δ 1. 19, (s, 9H), 2.18, (s, 3H), 2.58, (s, 6H), 2.85 (t, J=7 Hz, 2H), 3.05, (t, J=7 Hz, 2H), 3.45 (dd, J=13 Hz, 8 Hz, 1H), 3.70 (dd, J=13 Hz, 6 Hz, 1H), 4.06 (dd, J=8 Hz, 5 Hz, 1H) 5.84 (s, 1H), 6.82 (s, 2H), 7.30 (d, J=8 Hz, 2H), 7.64, (d, J=8 Hz, 2H). mass spec (ESI negative ion) m/z=640 (M+TFA)$^-$, 526 (M−H)$^-$ base peak, HRMS calc'd for C$_{25}$H$_3$N$_6$O$_5$S+H: 527.2076, found 527.2064. Anal. calc'd for $C_{27}H_{31}F_3N_6O_7S$: C, 50.62, H, 4.89, N, 13.12, found: C, 50.77, H, 4.89, N, 12.91.

EXAMPLE A-272

2-[(S)-((2,4.6-trimethylphenyl)sulfonyl)amino]3-[4-(2-(2-aminopyrimid-4-one-6-yl)ethylphenylcarbonyl]aminopropionic acid sodium salt A. 5-[4-(tert-Butyloxycarbonyl)phenyl]-3-oxopentanoic acid ethyl ester Lithium bis(trimethylsilyl)amide 1M solution in hexane (12 ml, 12.0 mM) was added to 12 mL of anhydrous tetrahydrofuran, and cooled to −78° C. After 0.5 h, anhydrous ethyl acetate (1.06 g, 12.0 mM) was added dropwise. After 0.25 h, the product of Ex. A-23, Part H, (2.93 g, 10.0 mM) was dissolved in 3 mL of anhydrous tetrahydrofuran and added dropwise to the rapidly stirred reaction mixture. After 3 h at −78° C. the reaction mixture was warmed to 0° C. for 1 h, the quenched by pouring into 1N HCl. The product was extracted with ethyl acetate. The organic layer was separated, dried over magnesium sulfate, filtered and evaporated to yield a colorless oil (1.7 g, 54%). $^1$H NMR (CDCl$_3$) δ 1.60 (s, 9H), 2.98 (m, 4H) 3.41 (s, 2H), 7.22 (d, J=8 Hz, 2H), 7.92, (d, J=8 Hz, 2H).

B. 4-[2-(2-Aminopyrimid-4-one-6-yl)ethyl]benzoic acid tert-butyl ester

The product of Ex. A-272, Part A, (1.73 g, 5.41 mM) and guanidine carbonate (485 mg, 2.69 mM) were dissolved in ethanol and refluxed overnight. The reaction mixture was cooled to room temperature and a white solid was collected by filtration and dried under vacuum (1.60 g, 94%). $^1$H NMR (d$_6$-DMSO) δ 1.48 (s, 9H), 2.50 (t, J=7 Hz, 2H), 2.88 (t, J=7 Hz, 2H), 5.34 (s, 1H), 6.48 (br s, 2H), 7.24 (d, J=8 Hz, 2H), 7.76 (d, J=8 Hz, 2H), 10.60 (br s, 1H).

C. 4-[2-(2-Aminopyrimid-4-one-6-yl)ethyl]benzoic acid trifluoroacetate salt

The product of Ex. A-272, Part B, (300 mg, 0.95 mM) was dissolved in 5 mL of trifluoroacetic acid and stirred for 1 h at room temperature. The solvent was evaporated to yield a white solid. (355 mg, 100%) $^1$H NMR (CD$_{30}$D) δ 2.82 (t, J=7 Hz, 2H), 3.02 (t, J=7 Hz, 2H), 5.80 (s, 1H), 7.34 (d, J=8 Hz, 2H), 7.92 (d, J=8 Hz, 2H).

D. 2-[(S)-((2,4,6-trimethylphenyl)sulfonyl)amino]3-[4-(2-(2-aminopyrimid-4-one-6-yl)ethylphenylcarbonyl]aminopropionic acid tert-butyl ester The product of Ex. A-272, Part C, (from a different batch) (500 mg, 1.34 mM) and the product of Ex. A-23, Part C (551 mg, 1.34 mM) were dissolved in 3 mL of N,N-dimethylformamide. Benzotriazole-1-yloxy-tris(dimethylamino)phosphonium hexafluorophosphate (712 mg, 1.61 mM) and N-methylmorpholine (406 mg, 4.02 mM) were added and the reaction mixture was stirred overnight at room temperature. The reaction mixture was poured into 30 mL of water and allowed to stand for 1 h. The precipitate was collected, dissolved in methanol and evaporated to yield a white solid (830 mg, 106%) $^1$H NMR (CD$_{30}$D) δ 1. 20, (s, 9H), 2.18, (s, 3H), 2.58, (s, 6H), 2.68 (t, J=7 Hz, 2H), 2.98, (t, J=7 Hz, 2H), 3.43 (dd, J=13 Hz, 8 Hz, 1H), 3.64 (dd, J=13 Hz, 6 Hz, 1H), 4.02 (dd, J=8 Hz, 5 Hz, 1H) 5.54 (s, 1H), 6.86 (s, 2H), 7.24 (d, J=8 Hz, 2H), 7.61 (d, J=8 Hz, 2H). mass spec (ESI neg ion) m/z=582 base peak.

E. 2-[(S)-((2,4,6-trimethylphenyl)sulfonyl)amino]3-[4-(2-(2-aminopyrimid-4-one-6-yl)ethylphenylcarbonyl]aminopropionic acid The product of Ex. A-272, Part D, (280 mg, 0.45 mM) was dissolved in trifluoroacetic acid and stirred at room temperature for 1 h. The solvent was evaporated and the residue suspended in toluene and the solvent evaporated. The residue was purified by reverse phase (C$_{18}$ water-acetonitrile linear gradient) HPLC. Evaporation of the solvent (bath <45° C.) provided a white solid (240 mg, 101%) $^1$H NMR (CD$_{30}$D) δ 2.18, (s, 3H), 2.58, (s, 6H), 2.82 (t, J=7 Hz, 2H), 3.02, (t, J=7 Hz, 2H), 3.43 (dd, J=13 Hz, 8 Hz, 1H), 3.70 (dd, J=13 Hz, 6 Hz, 1H), 4.05 (dd, J=7 Hz, 5 Hz, 1H) 5.64 (s, 1H), 6.80 (s, 2H), 7.30 (d, J=8 Hz, 2H), 7.62 (d, J=8 Hz, 2H). mass spec (ESI) m/z=528.1, (M+H)$^+$ base peak.

F. 2-[(S)-((2,4,6-trimethylphenyl)sulfonyl)amino]3-[4-(2-(2-aminopyrimid-4-one-6-yl)ethylphenylcarbonyl]aminopropionic acid sodium salt The product of Ex. A-272, Part E, (100 mg, 0.19 mM) was suspended in 5 mL of ethanol and 1N sodium hydroxide (0.19 ml, 0.19 mM) was added. The reaction was shaken until all of the material dissolved. The solution was filtered and evaporated. The residue was triturated with a 1:1 mixture of ethanol and ether, and the white solid was dried under vacuum (98 mg, 94%). $^1$H NMR (CD$_3$OD) δ 2.18, (s, 3H), 2.58, (s, 6H), 2.64 (t, J=7 Hz, 2H), 2.98, (t, J=7 Hz, 2H), 3.50 - 3.70 (m, 3H) 5.58 (s, 1H), 6.82 (s, 2H), 7.24 (d, J=8 Hz, 2H), 7.62 (d, J=8 Hz, 2H). mass spec (ESI) m/z=528.1, (M+H)$^+$ base peak.

EXAMPLE A-482

2-[(S)-((2,4,6-Trimethylphenyl)sulfonyl)amino]3-[4-(2-(2,4-diaminotriazin-6-yl)ethylphenylcarbonyl] aminopropionic acid A. 4-[2-(2,4-Diaminotriazin-6-yl)ethyl]benzoic acid Biguanide sulfate (1.3 g 6.53 mM) (prepared according to the method of Karipides, D., and Fernelius, W. C. in Inorg. Synth. 7, pp. 56–58, 1962) is dissolved in a solution of sodium hydroxide (1.0 g, 25 mM) and methanol 20 mL. The reaction mixture is stirred at room temperarue for 0.5 h then at reflux for 0.5 h. The hot solution is filtered and most of the solvent removed until a precipitate forms. 10 mL of ether is added and the solvent is decanted. The residue is redissolved in 40 ml of warm (approx. 50° C.) methanol. The product of Ex. A-23, Part F, (1.40 g, 5.55 mM) was added and the reaction mixture allowed to stir at room temperature overnight. The product, 4-[2-(2,4-Diaminotriazin-6-yl)ethyl] benzoic acid tert-butyl ester, was filtered and dried under vacuum to yield a white solid (1.1 g, 62%).$^1$H NMR (d$_6$-DMSO) δ 1.46 (s, 9H), 2.60 (t, J=7 Hz, 2H), 2.96 (t, J=7 Hz, 2H), 7.24 (d, J=8 Hz, 2H), 7.76 (d, J=8 Hz, 2H). The ester (500 mg, 1.59 mM) was dissolved in 5 mL of trifluoroacetic acid, stirred for 1 h. at room temperature and the solvent evaporated. The residue was purified by reverse phase (C$_{18}$ water-acetonitrile linear gradient) HPLC. Evaporation of the solvent (bath <45° C.) provided a white solid (325 mg, 79%) $^1$H NMR (CD$_3$OD) δ 2.92 (t, J=7 Hz, 2H), 3.12, (t, J=7 Hz, 2H), 7.32 (d, J=8 Hz, 2H), 7.92, (d, J=8 Hz, 2H). mass spec (ESI) m/z=260 (M+H)$^+$ base peak.

B. 2-[(S)-((2,4,6-Trimethylphenyl)sulfonyl)amino]3-[4-(2-(2,4-diaminotriazin-6-yl)ethylphenylcarbonyl] aminopropionic acid tert-butyl ester The product of Ex. A-482, Part A, (65 mg, 0.25 mM) and the product of Ex. A-23, Part C (102 mg, 0.03 mM) were dissolved in 1 mL of N,N-dimethylformamide.

Benzotriazole-1-yloxy-tris(dimethylamono)phosphonium hexafluorophosphate (133 mg, 0.30 mM) and N-methylmorpholine (76.3 mg, 0.75 mM) were added and the reaction mixture was stirred overnight at room temperature. The reaction mixture was poured into 30 mL of water and allowed to stand for 1 h. The precipitate was collected, washed with an additional 20 mL of water and dried to yield a white solid (137 mg, 93%). $^1$H NMR (CD$_3$OD) δ 1. 19, (s, 9H), 2.20, (s, 3H), 2.58, (s, 6H), 2.75 (t, J=7 Hz, 2H), 3.02, (t, J=7 Hz, 2H), 3.42 (dd, J=13 Hz, 8 Hz, 1H), 3.62 (dd, J=13 Hz, 6 Hz, 1H), 3.99 (t, J=7 Hz, 1H), 6.82 (s, 2H), 7.24 (d, J=8 Hz, 2H), 7.60, (d, J=8 Hz, 2H). mass spec (ESI) m/z=584 (M+H)$^+$.

C. 2-[(S)-((2,4,6-Trimethylphenyl)sulfonyl)amino]3-[4-(2-(2,4-diaminotriazin-6-yl)ethylphenylcarbonyl]aminopropionic acid The product of Ex. A-482, Part B, (137 mg, 0.23 mM) was dissolved in 4 mL of trifluoroacetic acid, stirred for 1 h. at room temperature and the solvent evaporated. The residue was purified by reverse phase (C$_{18}$ water-acetonitrile linear gradient) HPLC. Evaporation of the solvent (bath <45° C.) provided a white solid (110 mg, 88%) $^1$H NMR (CD$_3$OD) δ 2.18, (s, 3H), 2.58, (s, 6H), 2.82 (t, J=7 Hz, 2H), 3.10, (t, J=7 Hz, 2H), 3.42 (dd, J=13 Hz, 8 Hz, 1H), 3.70 (dd, J=13 Hz, 6 Hz, 1H), 4.07 (dd, J=7 Hz, 5 Hz, 1H), 6.80 (s, 2H), 7.30 (d, J=8 Hz, 2H), 7.62 (d, J=8 Hz, 2H). mass spec (ESI) m/z=528.1, (M+H)$^+$, mass spec (ESI negative ion) m/z=526.2, (M+H)$^+$, base peak.

EXAMPLE A-650

2-[(S)-((2,4,6-Trimethylphenyl)sulfonyl)amino]3-[4-(2-(4-aminoquinazolin-2-yl)aminomethyl)phenylcarbonyl]aminopropionic acid A. 2,4-Dichloroquinazoline Benzoyleneurea (732 mg, 4.5 mmol) and 4 mL of phosphorous oxychloride were refluxed under nitrogen over night. The reaction mixture was poured into 50 mL of ice water, and the precipitate filtered. The precipitate was washed with additional cold water and triturated with petroleum ether. The solid was dried to yield 510 mg (57%) mp 114–115° C. mass spec (ESI) m/z=199, (M+H)$^+$ base.

B. 2-Chloro-4-aminoquinazoline

The product of Ex. A-650, Part A, (2.07 g, 10.4 mmol) was heated with 32 mL of conc. ammonium hydroxide in an oil bath between 90–100° C. for 1.5 h. The reaction was cooled to room temperature and stirred overnight. The reaction mixture was filtered and dissolved in boiling 1N HCl and filtered. The filtrate was neutralized with 1N NaOH. The producte precipitated and was filtered, washed with cold water and dried to yield 831 mg (46%) of a light yellow solid, mp 232° C.

C. 4-Benzyloxycarbonylaminomethylbenzoic acid 4-(Aminomethyl)benzoic acid 15.1 g (100 mmol) was dissolved in 200 mL dioxane and 100 mL 1.000 N NaOH and cooled in a 0° C. ice bath. The mixture was treated dropwise with benzylchloroformate 14.3 mL (100 mmol) followed by the dropwise addition of 100 mL of 1.000 N NaOH. The mixture was stirred at room temperature for 18 hours. The mixture was neutralized by adding 100 mL of 1.000 N HCl followed by dilution with dichloromethane. A white solid precipitated out which was filtered. The solid was dried in vacuo to afford 10.8 g (38.9%). $^1$H NMR (300 MHz, DMSO-d$_6$): δ 4.24 (d, 2H, J=6.2 Hz); 5.01 (s, 2H); 7.31–7.34 (m, 7H); 7.84–7.88 (m, 3H); 12.85 (s, 1H).

D. 4-Benzyloxycarbonylaminomethylbenzoic acid t-butyl ester

The product of Ex. A-650, Part C 5.0 g (17.5 mmol) was suspended in 30 mL of dioxane and treated with conc. sulfuric acid 3.0 mL (56.3 mmol). 50 mL of isobutylene was then condensed into the mixture and the pressure vessel sealed and stirred at room temperature for 66 hours (the pressure reaches approximately 20 psi). The solution never becomes clear. The unreacted isobutylene was then removed in vacuo and the mixture neutralised to pH 10 with NaOH and extracted with dichloromethane (2×100 mL). The organic layer was dried (MgSO$_4$), filtered, concentrated and the residue purified by flash chromatography (200 g silica gel) using 1:3 EtOAc:hexane to elute 3.7 g of a colorless oil (61.8%). $^1$H NMR (300 MHz, CDCl$_3$): δ 1.59 (s, 9H); 4.43 (d, 2H, J=5.9 Hz); 5.14 (s, 2H); 7.3–7.36 (m, 7H); 7.94 (d, 2H, J=8.1 Hz).

E. Aminomethylbenzoic acid t-butyl ester

A solution of Ex. A-650, Part D 3.6 g (10.6 mmol) in 50 mL ethanol was shaken with a suspension of 300 mg of 10% Palladium on carbon under 1 atm hydrogen pressure at room temperature for 15 hours. TLC in 1:3 EtOAc:hexane indicated disappearance of starting material. The mixture was filtered through a celite pad. The filtrate was concentrated to provide 1.6 g of a colorless oil(72.9%). $^1$H NMR (300 MHz, CDCl$_3$): δ 1.59 (s, 9H); 3.93 (s, 2H); 7.37 (d, 2H, J=8.5 Hz); 7.96 (d, 2H, J=8.4 Hz).

F. 4-(2-(4-Aminoquinazolin-2-yl)aminomethyl)benzoic acid t-butyl ester

The intermediate Ex. A-650, Part E, 103 mg (0.5 mmol), and the product of Ex. A-650, Part B, 90 mg (0.5 mmol), and diisopropylethylamine 71 mg (0.6 mmol) were dissolved in 5 mL dimethyformamide and heated at 100° C. for 18 hours. TLC in 1:8 MeOH:CHCl$_3$ indicated disappearance of starting material. The mixture was poured into water and extracted with ethyl acetate. The organic layer was washed with water (2×50 mL). The organic layer was separated, dried (MgSO$_4$), filtered, and concentrated. The residue was triturated with dichloromethane:ether mixture to provide 83 mg of as an off-white solid (24% yield). $^1$H NMR (300 MHz, CDCl$_3$): δ 1.55 (s, 9H); 4.75 (d, J=3 Hz, 2H), 5.66 (br s, 2H); 7.15 (t, J=7 Hz, 1H); 7.60–7.82 (m, 5H); 7.85 (d, 2H, J=8 Hz).

G. 2-[(S)-((2,4.6-Trimethylphenyl)sulfonyl)amino]3-r4-(2-(4-aminoquinazolin-2-yl) aminomethyl) phenylcarbonyl aminopropionic acid t-butyl ester The product of Ex. A-650, Part F, (65 mg, 0.22 mM) and the product of Ex. A-23, Part C (171 mg, 0.26 mM) were dissolved in 1mL of N,N-dimethylformamide. Benzotriazole-1-yloxy-tris(dimethylamono)phosphonium hexafluorophosphate (133 mg, 0.30 mM) and N-methylmorpholine (76.3 mg, 0.75 mM) were added and the reaction mixture was stirred overnight at room temperature. The reaction mixture was poured into 30 mL of water and extracted with ethyl acetate. The organic layer was dried with magnesium sulfate, filtered and evaporated. The residue was purified by flash column chromatography to yield 77 mg (55%).HRMS calc for C$_{32}$H$_{39}$N$_6$O$_5$S=619.270266 found 619.270249.

H. 2-[(S)-((2,4,6-Trimethylphenyl)sulfonyl)amino]3-[4-(2-(4-aminoquinazolin-2-yl)aminomethyl)phenylcarbonyl]aminopropionic acid The product of Ex. A-650, Part G, (70 mg, 0.11 mM) was dissolved in 4 mL of 1:1 mixture of trifluoroacetic acid and methylene chloride and stirred for 2 hours. The solvent was removed under reduced pressure and the residue purified by reverse phase HPLC to yield 38 mg as a white solid (50% yield). $^1$H NMR (300 MHz, DMSO-d$_6$): 2.13 (s, 3H); 2.51 (s, 6H); 3.31–3.40 (m, 1H); 3.46–3.55 (m, 1H); 3.93–3.98 (m, 1H); 4.73 (d, 2H, J=5.9 Hz); 6.86 (s, 2H); 7.44 (d, 2H, J=8.4 Hz); 7.70 (d, 2H, J=8.4 Hz); 7.82 (t, 1H, J=7.3 Hz); 8.03 (d, 1H, J=9.5 Hz); 8.21 (d, 1H, J=8.0Hz); 8.42 (t, 1H, J=5.9 Hz). HRMS calcd for C$_{28}$H$_{31}$N$_6$O$_5$S [M+H]$^+$ 563.207665, found 563.207600.

EXAMPLE A-1210

3-[4[2-(Imidazo-4-oxopyrimidin-2-yl)ethyl] phenylcarbonyl]-amino]-2-[(2,4,6-trimethylphenyl) sulfonyl]aminopropanoic acid A. 4-(4-(t-Butoxycarbonyl)phenylethylcarbonylamino) imidazole-5-carboxamide A mixture of the product of Ex. A-23, Part G (400 mg, 1.6 mmole), 4-aminoimidazole-5-carboxamide hydrochloride (312 mg, 1.92 mmol), diisopropylethylamine (0.8 ml, 4.6 mmol) and Castro's reagent (1.08 g, 2.4 mmol) in 5 ml anhydrous DMF was stirred overnight under N$_2$ in a 70° C. oil bath. After cooling to room temperature, the dark brown reaction mixture was poured into 50 ml water and extracted 3× with ethyl acetate. The combined extracts were washed with brine, dried over anhydrous sodium sulfate, filtered and evaporated. The crude was purified by filtration through a pad of silica get eluted with ethyl acetate/methylene chloride/ethanol 10/10/0.5 to 10/10/1 to give the amide in 68% yield (0.39 g). MS 303.1 (M+H-tBu)$^+$ 359.2 (M+H)$^+$ 381.1 (M+Na)$^+$(base peak).

B. 3-[4-[2-(Imidazo-4-oxopyrimidin-2-yl)ethyl]benzoic acid

A mixture of 6 ml 2N NaOH and 0.2 ml pyridine was brought to reflux and 0.36 gm of the product of Ex. A-1210 Part A, was added in one portion. The whole was maintained at reflux for 15 min whereupon the hot reaction mixture was poured into ice. The pH was adjusted to acid with conc HCl and the mixture swirled occasional until the ice was melted. The solid which resulted was collected by filtration and washed thoroughly with water then dried in vacuo at 50° C. overnight to give the cyclized product as the free acid, 0.198 g white solid (69%). MS m/z 284.9 (M+H)$^+$ 306.9 (M+Na)$^+$.

C. 3-[4-[2-(Imidazo-4-oxopyrimidin-2-yl)ethyl] phenylcarbonyl]amino]-2-[(2,4,6-trimethylphenyl) sulfonyl]-aminopropanoic acid A mixture of the product of Ex. A-1210 Part B (65 mg, 0.23 mmol), and the product of Ex. A-23, Part C (86 mg, 0.25 mmol), 50 microliters N-methylmorpholine (0.45 mmol), and Castro's reagent (0.15 mg, 0.34 mmol) in 2 ml DMF was stirred overnight at room temperature under N$_2$. Reaction was poured into water and resulting solid collected and washed thoroughly with water then dried overnight in vacuo at 50° C. to provide 0.14 g desired product as an off white solid. The crude solid was dissolved in a mixture of 2–3 ml methylene chloride and 0.5 ml trifluoroacetic acid and the solution stirred overnight at room temperature. The solution was evaporated and triturated with ether to give a solid. Purification by reverse phase HPLC and conversion to the corresponding sodium salt by treatment with gave the title compound as a fluffy white solid, 30 mg. NMR: (D$_2$) δ 1.65 (3H, s) 2.10 (6H, s) 3.05, 5H, m), 3.43 (1H, dd), 3.55 (1H, dd), 6.03, 2H, s) 7.13 (4H, s) 7.83 (1H, s). HRMS calcd for C$_{26}$H$_{29}$N$_6$O$_6$S: 553.186930. Found: 553.186600.

EXAMPLE A-1266

2-[(S)-((2,4,6-Trimethylphenyl)sulfonyl)amino]3-[4-(2-(2-aminopyrimidin-4-yl)aminomethyl) phenylcarbonyl]aminopropionic acid A. 4-[2-(2-Amino-6-chloropyrimidin-4-yl)aminomethyl] benzoic acid t-butyl ester The product of Ex. A-650, Part E, (207 mg, 1.0 mmol), 2-amino-4,6-dichloropyrimidine (164 mg, 1.0 mmol), and diisopropylethylamine (388 mg, 3.0 mmol) were dissolved in N,N-dimethylformamide (5 mL) and refluxed for 18 h.THe reaction mixture was diluted with ethyl acetate and washed with water. The organic layer was washed with brine, separated, dried over magnesium sulfate, filtered and evaporated. The product was purified by flash column chromatography (methanol/chloroform gradient 0.5% to 3%) the provide the product (318 mg, 95%) as a yellow oil. $^1$H NMR (300 MHz, DMSO-d$_6$): [M+H]$^+$ 334.8.

B. 4-[2-(2-Amino-6-chloropyrimidin-4-yl)aminomethyl] benzoic acid

The product of Ex. A-1266, Part A, (318 mg, 0.95 mmol) was dissolved in methylene chloride (2 mL) and trifluoroacetic acid (2 mL) was added. THe reaction mixture was stirred at room temperature for 4 h. The solvent was removed under reduced pressure to provide the product.

C. 2-[(S)-((2,4,6-Trimethylphenyl)sulfonyl)amino]3-[4-(2-(2-amino-6-chloropyrimidin-4-yl)aminomethyl)phenyl] carbonylaminopropionic acid t-butyl ester The product of Ex. A-1266, Part B, (280 mg, 1.0 mmol), the product of Ex. A-23, Part C (342 mg, 1.0 mmol), N-methylmorpholine (400 mg, 4.0 mmol), and Benzotriazole-1-yloxy-tris(dimethylamono)phosphonium hexafluorophosphate, were dissolved in N,N-dimethylformamide (10 mL), and stirred at room temperature for 18 h. The reaction mixture was diluted with ethyl acetate and washed with water. The organic layer was washed with brine, separated , dried over magnesium sulfate, filtered and the solvent removed under reduced pressure. The product was purified by flash column chromatography (methanol/chloroform gradient 1% to 3%) to provide the product (512 mg, 85%).

D. 2-[(S)-((2,4,6-Trimethylphenyl)sulfonyl)amino]3-[4-(2-(2-aminopyrimidin-4-yl)aminomethyl)phenyl] carbonylaminopropionic acid t-butyl ester The product of Ex. A-1266, Part C, (300 mg, 0.5 mmol) and 10% palladium on carbon (30 mg), was dissolved in ethyl alcohol (5 mL). The reaction mixture was stirred under an atmosphere of hydrogen (balloon), for 18 h. The reactiom mixture was filtered through celite, evaporated and purified by column chromatography (methanol/chloroform gradient 1% to 3%) to provide the product (183 mg, 65%) HRMS calcd for C$_{28}$H$_{37}$N$_7$O$_5$S [M+H]$^+$ 569.254616, found 569.255236.

E. 2-[(S)-((2,4,6-Trimethylphenyl)sulfonyl)amino]3-[4-(2-(2-aminopyrimidin-4-yl)aminomethyl)phenyl]carbonyl aminopropionic acid The product of Ex. A-1266, Part D, was dissolved in methylene chloride (2 mL), and trifluoroacetic acid (2 mL) was added. The reaction mixture was stirred for 2 h, and the solvent evaporated under reduced pressure. The residue purified by reverse phase HPLC to yield 151 mg (93%) of the product. $^1$H NMR (300 MHz, DMSO-d$_6$): 2.15 (s, 3H); 2.52 (s, 6H); 3.31–3.40 (m, 1H); 3.49–3.57 (m, 1H); 3.94–4.01 (m, 1H); 4.63 (d, 2H, J=5.8 Hz); 6.15 (d, 1H, J=6.9 Hz); 6.87 (s, 2H); 7.38 (d, 2H, J=8.1 Hz); 7.68–7.71

(d, 3H); 8.05 (d, 1H, J=9.5 Hz); 8.43 (t, 1H, J=5.9 Hz); 9.21 (t, 1H, J=5.9 Hz). HRMS calcd for $C_{24}H_{29}N_6O_5S$ [M+H]$^+$ 513.192015, found 513.191100.

EXAMPLE T14–1

11-(2-aminopyridin-4-yl)-11-aza-8-oxo-7-aza-7-methyl-5-oxo-4-aza-3-((R)-phenethyl)undecanoic acid trifluoroacetate salt A. 3-[(N-tertbutyloxycarbonyl-N-methylgylcinyl)amino]-3-((R)-phenylethyl)propionic acid methyl ester.

5-Phenyl-3-(R)-aminovaleric acid methyl ester acetate salt (see U.S. Pat. No. 5,264,420, Nov. 23, 1993) (550 mg, 2.06 mmol) was dissolved in water (10 mL) and sodium carbonate was added until the reaction mixture was basic to lithmus paper. The mixture was extracted with methylene chloride, dried over potassium carbonate and evaporated, and the residue was dissolved in 2 mL of N,N-dimethylformamide. Boc Sarcosine (290 mg, 1.53 mmol), BOP-reagent (730 mg, 1.65 mmol) and diisopropylethylamine (234 mg, 1.81 mmol) was added, and the reaction mixture was stirred overnight at room temperature. The reaction mixture was poured into 0.1N HCl and extracted with ethyl acetate. The organic layer was dried over magnesium sulfate, evaporated and purified by flash column chromatography (hexane - ethyl acetate 3:1) to yield 300 mg (52%) of product. $^1$H NMR (CDCl$_3$) δ 7.30–7.05 (m, SH), 4.36–4.24 (m, 1H), 3.84 (s, 2H), 3.64 (s, 3H), 2.94 (s, 3H), 2.58–2.52 (m, 2H), 2.00–1.60 (m, 4H), 1.44 (s, 9H). mass spectrum m/z=401.0 (M+Na)$^+$ base peak, 381.0 (M+H)$^+$.

B. 3-[(N-methylglycinyl)amino]-3-((R)phenylethyl)propionic acid methyl ester trifluoroacetate salt The product of example T14–1, part A, (300 mg, 0.79 mmol) was dissolved in methylene chloride (1 mL). Trifluoroacetic acid (1 mL) was added and the reaction mixture was stirred at room temperature for 0.5 h. The solvent was evaporated and the residue purified by reverse phase HPLC.$^1$H NMR (CD$_3$OD) δ 7.30–7.12 (m, 5H), 4.28–4.18 (m, 1H), 3.72 (s, 2H), 3.62 (s, 3H), 2.70 (s, 3H), 2.68–2.44 (m, 4H), 1.90–1.78 (m, 2H). mass spectrum m/z 279.0 (M+H)$^+$, base peak.

C. 3-[(2-amino-6-chlocopyridin-4-yl)amino]propionic acid tert-butyl ester 2-amino-4,6-dichloropyrimidine (164 mg, 1.0 mmol), beta-alanine tert-butyl ester hydrochloride (181 mg, 1.0 mmol) and diisopropylethylamine (148 mg, 1.1 mmol) was dissolved in N,N-dimethylacetamide and heated at 130° C. for 3 h. The reaction mixture was allowed to cool to room temperature and poured into water (5 mL), and the precipitate collected and dried to yield 100 mg (37%) of the product as a white solid.$^1$H NMR (CD$_3$OD) δ 5.80 (S, 1H), 3.52 (br t, 2H), 2.44 (t, J=7 Hz, 2H), 1.22 (s, 9H). mass spectrum m/z 273.1 (M+H)$^+$, base peak.

D. 3-[(2-amino-6-chloropyrimidin-4-yl)amino]propionic acid

The product of example T14–1, part C, (100 mg, 0.37 mmol) was dissolved in 4N HCl in dioxane (2 mL), and stirred at room temperature for 1 h., and the solvent evaporated to yield the product as a white solid. $^1$H NMR (CD$_3$OD) δ 6.18 (s, 1H), 3.70 (br t, 2H), 2.60 (t, J=7 Hz, 2H). mass spectrum m/z 217.0 (M+H)$^+$, base peak.

E. 11-(2-amino-6-chloropyridin-4-yl)-11-aza-8-oxo-7-aza-7-methyl-5-oxo-4-aza-3-((R)-phenethyl)undecanoic acid methyl ester The product of Example T14–1, part B, (50 mg, 0.20 mmol), the product of Example T14–1, part D, (78 mg, 0.20 mmol) Bop-reagent (105 mg, 0.24 mmol), and diisopropylethyl amine was dissolved in 0.5 ml of N,N-dimethylformamide and stirred at room temperature over night. The reaction mixture was poured into water and extracted with ethyl acetate. The organic layer was evaporated to yield the product. $^1$H NMR (CD$_3$OD) δ 7.28–7.10 (m, 5H), 5.80 (s, 1H), 4.28–4.18 (m, 1H), 4.10–4.00 (m, 1H), 3.60 (3, 3H), 2.88 (s, 3H), 2.78–2.42 (m, 8H), 1.90–1.78 (m, 2H) . mass spectrum m/z 477.0 (M+H)$^+$, (35%).

F. 11-(2-amino-6-chloropyridin-4-yl)-11-aza-8-oxo-7-aza-7-methyl-5-oxo-4-aza-3-((R)-phenethyl)undecanoic acid trifluoroacetate salt The product of Example T14–1, part E, was dissolved in tetrahydrofuran (0.5 mL) and 1N lithium hydroxide was added, and the mixture stirred at room temperature for 15 min. The reaction was quenched with excess trifluoroacetic acid and the solvent evaporated. The residue was purified by reverse phase HPLC to yield 50 mg of a white solid. $^1$H NMR (CD$_3$OD) δ 7.30–7.10 (m, 5H), 6.10 (s, 1H), 4.28–4.18 (m, 1H), 4.10–4.00 (m, 1H), 3.78–3.60 (m, 2H), 2.88 (s, 3H), 2.78–2.42 (m, 8H), 1.90–1.78 (m, 2H). mass spectrum m/z 485.0 (M+Na)$^+$ (35%), 463.0 (M+H)+, (80%).

G. 11-(2-amino-6-pyridin-4-yl)-11-aza-8-oxo-7-aza-7-methyl-5-oxo-4-aza-3-((R)-phenethyl)undecanoic acid trifluoroacetate salt The product of Example T14–1, part F (40 mg, 0.11 mmol) was dissolved in ethyl alcohol (5 mL), and palldium on carbon 10% (15 mg) was added. The reaction mixture was stirred under a balloon of hydrogen over night. The reaction mixture was filtered and evaporated to yield the product. $^1$H NMR (CD$_3$OD) δ 7.50–7.42 (m, 1H), 7.28–7.10 (m, 5H), 6.06–6.00 (m, 1H), 4.32–4.20 (m, 1H), 4.12–3.98 (m, 1H), 3.78–3.60 (m, 4H), 3.06 (s, 3H), 2.80–2.50 (m, 6H), 1.90–1.78 (m, 2H). mass spectrum m/z 429.0 (M+H)$^+$, base peak.

EXAMPLE E-19

3-[1-[2-(2-Amino-4-oxopyrimidin-6-yl)ethyl]indazol-5-ylcarbonylamino]-2(S)-(2,4,6-trimethylbenzenesulfonylamino)propionic acid A. Ethyl 3-methyl-4-nitrobenzoate. A mixture of 3-methyl-4-nitrobenzoic acid (362.3 g, 2.0 mol), N,N-dimethylformamide (2000mL), sodium bicarbonate (200 g, 2.38 mol) and iodoethane (623.9 g, 4.0 mol) was stirred at 70° C. for 18 h. The mixture was allowed to cool to room temperature and poured into water (2000 mL). The resulting solid was collected by filtration, washed with water and dried. The solid was washed further with hexane and dried to provide the title product (382.1 g, 91%) as an off-white solid, mp 51–52.5 ° C.: $^1$H NMR (CDCl$_3$) d 8.04–7.98 (m, 3H), 4.42 (q, 2H), 2.63 (s, 3H), 1.42 (t, 3H); Mass spectrum (NH$_3$-CI) m/z 210 (100%, M+H$^+$).

B. Ethyl 3-methyl-4-aminobenzoate. A mixture of the product prepared according to Example E-19 Part A (183.96 g, 880 mmol), tin (II) chloride hydrate (1025 g, 4.54 mol) and ethanol (3500 mL) was heated at reflux for 2 h. The mixture was cooled and diluted with water (3500 mL) and the pH was adjusted to 8.5. The mixture was diluted further with additional water, and extracted with ethyl acetate. The organic extracts were dried (MgSO$_4$), filtered and concentrated to provide the title product (136.62 g, 87%) as an off-white solid, mp 76–78 ° C.: $^1$H NMR (CDCl$_3$) d 7.78 (s, 1H), 7.76 (d, 1H), 6.63 (d, 1H), 4.31 (q, 2H), 3.99 (bs, 2H), 2.19 (s, 3H), 1.38 (t, 3H); High resolution mass spectrum (NH$_3$-CI) calculated (M+H$^+$) 180.1025, found 180.1023.

C. 5-Ethoxycarbonylindazole. A mixture of the product prepared according to Example E-19 Part B (250.55 g, 1.4 mol), potassium acetate (143.3 g, 1.46 mol), acetic anhydride (285.9 g, 2.8 mol) and chloroform (ethanol-free; 2700 mL) was stirred at room temperature. The temperature rose to 40° C., then started to decline, at which time no starting material was detected by TLC. A mixture of 18-crown-6 (75 g, 280 mmol) and n-amyl nitrite (364.5 g, 3.1 mol) was added and the mixture was heated at reflux overnight. The cooled mixture was washed with saturated aqueous sodium bicarbonate, then with water, and was dried ($MgSO_4$), filtered and concentrated. The residue was combined with that from another batch (711.3 g) and distilled through a 10 cm vigreaux column under vacuum to provide 1-Acetyl-5-ethoxycarbonyl-indazole (576 g, 82%), bp 115–165 ° C. (1.0 Torr). This intermediate was combined with hydrochloric acid (6N; 2000 mL) and ethanol (2000 mL), and the mixture was stirred overnight at room temperature. The mixture was concentrated under vacuum, and the solid was combined with water. The pH of the mixture was adjusted to 8 with aqueous ammonia, and the mixture was extracted with dichloromethane. The organic phase was dried ($MgSO_4$), filtered and concentrated to provide a solid (460 g). This was recrystallized from acetonitrile (1000 mL), and the crystals were washed with ethanol, then hexane, and dried to provide the title product (281 g, 60%) as a tan solid, mp 122–124° C.: $^1$H NMR ($CDCl_3$) d 10.23 (bs, 1H), 8.57 (s, 1H), 8.20 (s, 1H), 8.10 (d, 1H), 7.53 (d, 1H), 4.42 (q, 2H), 1.42 (t, 3H); High resolution mass spectrum ($NH_3$-CI) calculated ($M+H^+$) 191.0821, found 191.0838.

D. 1-(2-Methoxycarbonylethyl)-5-ethoxycarbonylindazole. A mixture of the product prepared according to Example E-19 Part C (9.51 g, 50 mmol), methyl acrylate (4.5 mL, 50 mmol), tert-butanol (4.78 mL, 50 mmol) and tetrahydrofuran (1000 mL) was treated with potassium tert-butoxide (1.0 M in tetrahydrofuran; 2.5 mL, 2.5 mmol) and the resulting solution was heated at reflux for 1 h. The mixture was cooled to room temperature, treated with hydrochloric acid (1.0 M; 5 mL, 5 mmol) and concentrated to provide a viscous oil which slowly crystallized. The solid mass was broken up and dried further under vacuum to provide the title product (14.0 g, 100%) which was used without further purification: $^1$H NMR ($CDCl_3$) d 8.51 (s, 1H), 8.10 (s, 1H), 8.08 (d, 1H), 7.51 (d, 1H), 4.68 (t, 2H), 4.41 (q, 2H), 3.63 (s, 3H), 3.01 (t, 2H), 1.42 (t, 3H); High resolution mass spectrum ($NH_3$-CI) calculated ($M+H^+$) 277.1188, found 277.1188.

E. 1-(2-Carboxyethyl)-5-ethoxycarbonylindazole. The product prepared according to Example E-19 Part D (14 g, 50 mmol) was dissolved in tetrahydrofuran (100 mL) and treated at room temperature with a solution of lithium hydroxide monohydrate (4.2 g, 100 mmol) in water (100 mL). The solution was stirred for 10 min, then was treated with hydrochloric acid (1.0 M, 110 mL, 110 mmol). The tetrahydrofuran was removed to provide a sticky solid which became powdery after stirring the slurry at room temperature. The solid was collected by filtration, washed with water and dried to provide the title product (12 g, 91%) as a white solid, mp 102–110 C.; 1H NMR ($CDCl_3$) d 8.50 (s, 1H), 8.12 (s, 1H), 8.08 (d, 1H), 7.48 (d, 1H), 4.67 (t, 2H), 4.41 (q, 2H), 3.05 (t, 2H), 1.41 (t, 3H); High resolution mass spectrum ($NH_3$-CI) calculated (M+H+) 263.1032, found 263.1014.

F. 1-(4-Ethoxycarbonyl-3-oxobutyl)-5-ethoxycarbonylindazole.

A suspension of the product prepared according to Example E-19 Part E (8.0 g, 30.5 mmol) in dichloromethane (175 mL) was treated dropwise over 5 min at room temperature with oxalyl chloride (4.0mL, 45.8 mmol). Gas evolution was noted, which gradually slowed. After 1 h, N,N-dimethylformamide (1 drop) was added, causing renewed gas evolution. After 16 h, the mixture was heated briefly to reflux, then cooled and concentrated. In a separate flask, a solution of 2,2-dimethyl-4,6-dioxo-1,3-dioxane (Meldrum's acid; 4.62 g, 32 mmol) in dichloromethane (15 mL) was cooled to 0° C. and treated with pyridine (6.2 mL, 76.3 mmol) over 5 min. The acid chloride prepared above was dissolved in dichloromethane (50 mL) and added dropwise to the cooled solution over 50 min. The mixture was then allowed to warm to room temperature with stirring. After 4.25 h, the mixture was poured into hydrochloric acid (1.0 M, 120 mL) and ice, and the mixture was stirred until the ice melted. The layers were separated, and the aqueous phase was extracted twice with dichloromethane. The combined organic phases were washed with hydrochloric acid (1.0 M), dried ($Na_2SO_4$), filtered and concentrated. The residual orange gum was dissolved in ethanol (300 mL) and heated to reflux with stirring. After 5.5 h, the solution was cooled to room temperature and concentrated to a volume of about 50 mL. The precipitate was isolated by filtration, washed with a small amount of ethanol, and dried to provide the title compound (6.85 g, 68%) as a cream-colored solid: $^1$H NMR ($CDCl_3$) d 8.50 (s, 1H), 8.08 (s+d, 2H), 7.53 (d, 1H), 4.66 (t, 2H), 4.40 (q, 2H), 4.15 (q, 2H), 3.46 (s, 2H), 3.28 (t, 2H), 1.42 (t, 3H), 1.23 (t, 3H); High resolution mass spectrum ($NH_3$-CI) calculated ($M+H^+$) 333.1450, found 333.1460.

G. 1-(2-(2-Amino-4-oxopyrimidin-6-yl)ethyl)-5-ethoxycarbonylindazole. A suspension of the product prepared according to Example E-19 Part F (350 mg, 1.05 mmol) and guanidine carbonate (90 mg, 0.5 mmol) in ethanol (10 mL) was heated at reflux with stirring. The solids dissolved as reflux was achieved, then a precipitate formed within 3 h. After 19 h, the mixture was cooled to room temperature and filtered. The solid was rinsed with ethanol and dried to provide the title product (278 mg, 85%) as a white solid, mp 231–234° C.: $^1$H NMR (DMSO-$d_6$) d 10.61 (bs, 1H), 8.45 (s, 1H), 8.26 (s, 1H), 7.90 (d, 1H), 7.70 (d, 1H), 6.53 (bs, 2H), 5.25 (s, 1H), 4.69 (t, 2H), 4.33 (q, 2H), 2.83 (t, 2H), 1.35 (t, 3H); Mass spectrum (ESI) m/z 328.1 ($M+H^+$, 98%), 350.0 ($M+Na^+$, 100%).

H. 1-(2-(2-Amino-4-oxopyrimidin-6-yl) ethyl)-5-carboxyindazole. The product prepared according to Example E-19 Part G (100 mg, 305 μmol) was treated with aqueous sodium hydroxide (1.0 M; 5 mL) and the resulting solution was stirred for 30 min. Hydrochloric acid (1.0 M; 10 mL) was added, and the resulting suspension was stirred for 30 min. The solid was collected by filtration, rinsed with water and dried to provide the title product (88 mg, 96%) as a white solid, mp >250° C.: $^1$H NMR (DMSO-$d_6$) d 12.78 (b), 10.60 (b), 8.41 (s, 1H), 8.23 (s, 1H), 7.89 (d, 1H), 7.66 (d, 1H), 6.54 (bs, 2H), 5.27 (s, 1H), 4.68 (t, 2H), 2.82 (t, 2H); High resolution mass spectrum ($NH_3$-CI) calculated ($M+H^+$) 300.1097, found 300.1085.

I. $N^2$-(2,4,6 Trimethylbenzenesulfonyl)-L-asparagine.

L-Asparagine (20.0 g, 0.15 mol) was suspended in a mixture of tetrahydrofuran (13OmL) and water (250 mL). Triethylamine (68 mL, 0.48 mol) was added, followed by mesitylenesulfonyl chloride (49.7 g, 0.23 mol) added over 20 min. The reaction mixture became slightly warmer and the solids dissolved to yield a yellow solution. The reaction mixture was stirred for 3 h at room temperature, then washed twice with ether, and twice with dichloromethane. The aqueous layer was acidified to pH 1.5 with concentrated aqueous HCl, during which time a thick precipitate formed.

After being stirred for 30 min the solid was collected by filtration, washed with water and dried to yield the title product (34.1 g, 72%) as a white solid: m.p. 193.5–195° C.; $^1$H NMR (DMSO-$d_6$) d 12.58 (bs, 1H), 7.82 (d, 1H), 7.32 (bs, 1H), 6.99 (s, 2H), 6.88 (bs, 1H), 3.98 (m, 1H), 2.55 (s, 6H), 2.45 (dd, 1H), 2.28 (dd, 1H), 2.24 (s, 3H); Mass spectrum (ESI) m/z 315.2, (100%, M+H$^+$).

J. 3-Amino-2-(S)-(2,4,6-trimethylbenzenesulfonylamino)-propionic acid. Sodium hydroxide (32 g, 0.80 mol), was dissolved in water (200 mL) and cooled in an ice bath. Bromine (6.2 mL, 0.12 mol) was added dropwise over 5 min and the mixture was allowed to stir for 15 min. The product prepared according to Example E-19 Part I (31.44 g, 0.10 mol) was added in several portions over a period of ca. 10 min, during which time the yellow color faded. After stirring for 15 min more, the mixture was heated rapidly to an internal temperature of ca. 85° C. After 1 h, the mixture was allowed to cool to room temperature, then cooled in an ice bath. The mixture was cautiously acidified to pH 6 with concentrated hydrochloric acid, during which time a solid formed and gas was evolved. The solid was collected by filtration, washed with cold water, and dried to provide the title product (23.9 g, 83%) as a white solid: $^1$H NMR (DMSO-$d_6$) d 7.06 (s, 2H), 3.07 (dd, 1H), 3.35 (b), 2.94 (dd, 1H), 2.80 (dd, 1H), 2.59 (s, 6H), 2.26 (s, 3H); Mass spectrum (ESI) m/z 287.2 (100%, M+H$^+$).

K. tert-Butyl 3-amino-2-(S)-(2,4,6-trimethylbenzenesulfonylamino)propionate. The product prepared according to Example E-19 Part J (11.45 g, 0.04 mol) was placed in a pressure bottle and dissolved in dioxane (170 mL). Concentrated sulfuric acid (11 mL) was added and the reaction mixture was cooled in a dry ice-acetone bath. Liquid isobutylene (ca. 185 mL) was added, and the bottle was sealed and agitated for 114 h. The bottle was de-pressurized, then purged with nitrogen for a brief time. The reaction mixture was poured into a rapidly stirred mixture of water (225 mL) and sodium hydroxide (17 g) and ether (600 mL) which had been pre-cooled in an ice bath. The layers were separated, and the aqueous layer was extracted with additional ether. The organic extracts were discarded. The pH of the aqueous layer was carefully adjusted with concentrated aqueous HCl to pH 11.0 and extracted four times with ether. The organic layers from the pH 11 extraction were combined, dried (Na$_2$SO$_4$), filtered and concentrated to yield the title product (8.64 g, 63%) as a viscous oil which gradually solidified: $^1$H NMR (CDCl$_3$) d 6.95 (s, 2H), 3.69 (m, 1H), 2.93 (m, 2H), 2.67 (s, 6H), 2.28 (s, 3H), 1.28 (s, 9H); Mass spectrum (ESI) m/z 343.3 (100%, M+H$^+$).

L. 3-[1-[2-(2-Amino-4-oxopyrimidin-6-yl)ethyl]indazol-5-ylcarbonylamino]-2(S)-(2,4,6-trimethylbenzenesulfonylamino)propionic acid. A mixture of the product prepared according to Example E-19 Part H (92 mg, 300 μmol), the product prepared according to Example E-19 Part K (102 mg, 300 μmol) and 4-methylmorpholine (3 drops) in N,N-dimethylformamide (5 mL) was treated with BOP reagent (160 mg, 360 μmol). The mixture was stirred for 18 h at room temperature, then was concentrated. The residue was purified by flash chromatography (dichloromethane-methanol 95:5, then 85:15) to provide the tert-butyl ester of the title product as a white solid (20 mg, 43%) which contained impurities but was used without further purification: Mass spectrum (NH$_3$-CI) m/z 428.2 (100%, M+H$^+$). This material was stirred in a mixture of dichloromethane (2 mL) and trifluoroacetic acid (1 mL) for 3 h. The mixture was concentrated and the residue was subjected to preparative HPLC to provide the title product as a white solid: $^1$H NMR (MeOH-$d_4$) d 8.18 (s, 1H), 8.13 (s, 1H), 7.82 (d, 1H), 7.65 (d, 1H), 6.78 (s, 2H), 5.63 (s, 1H), 4.78 (t, 2H), 4.13 (dd, 1H), 3.74 (dd, 1H), 3.47 (dd, 1H), 3.10 (t, 2H), 2.58 (s, 6H), 2.03 (s, 3H); High resolution mass spectrum (FAB) calculated (M+H$^+$) 568.1978, found 568.1997. This material was dissolved in water (2 mL) and acetonitrile (1mL), and treated with aqueous sodium hydroxide (1.0 M; 128 μL, 128 μmol). The solution was frozen at −78° C. and lyophilized to provide the sodium salt of the title product (60 mg, 80%) as a fluffy white powder.

EXAMPLE E-24

3-[1-[2-Amino-4-oxopyrimidin-6-ylmethyl]indazol-5-ylcarbonylamino]-2(S)-(1-naphthalenesulfonylamino)-propionic acid A. 1-Methoxycarbonylmethyl-5-ethoxycarbonylindazole. A solution of the product prepared according to Example E-19 Part C (5.71 g, 30 mmol) in tetrahydrofuran (100 mL) was treated with sodium bis(trimethylsilyl)-amide (1.0 M in tetrahydrofuran; 33 mL, 33 mmol) to give an orange solution. Methyl bromoacetate (3.2 mL, 33 mmol) was added, causing a mild exotherm and a lightening of the color. After 20 min, the solution was heated to reflux. After 1 h, additional methyl bromoacetate (2.0 mL) was added, and heating was continued for 19 h. Thin-layer chromatography suggested residual starting material, so additional sodium bis(trimethylsilyl)amide (20 mL, 20 mmol) was added, causing the residual color to disappear. After heating for 1 h more, the solution was cooled, diluted with hydrochloric acid (1.0 M) and extracted with ethyl acetate. The extracts were dried (Na$_2$SO$_4$), filtered and concentrated. The residual gum was purified by flash chromatography (toluene-ethyl acetate, 8:2) to provide the title product (3.13 g, 40%) as a waxy white solid, which could be recrystallized (hexanes/1-chlorobutane) to give white crystals, mp 94–95° C.: $^1$H NMR (CDCl$_3$) d 8.54 (s, 1H), 8.16 (s, 1H), 8.12 (d, 1H), 7.35 (d, 1H), 5.19 (s, 2H), 4.42 (q, 2H), 3.76 (s, 3H), 1.43 (t, 3H); High resolution mass spectrum (NH$_3$-CI) calculated (M+H$^+$) 262.0954, found 262.0938.

B. 1-Carboxymethyl-5-ethoxycarbonylindazole. A solution of the product prepared according to Example E-24 Part A (2.84 g, 10.8 mmol) in tetrahydrofuran (20 mL) was treated with a solution of lithium hydroxide monohydrate (0.91 g, 21.6 mmol) in water (20 mL). The mixture was initially two liquid phases, and gradually became a thick slurry. After 15 min, hydrochloric acid (1.0 M, 30 mL) was added and the tetrahydrofuran removed under vacuum. The resulting precipitate was collected by filtration, washed with water and dried to provide the title product (2.045 g, 76%) as a white solid: $^1$H NMR (DMSO-$d_6$) d 13.17 (bs, 1H), 8.50 (s, 1H), 8.30 (s, 1H), 7.96 (d, 1H), 7.75 (d, 1H), 5.33 (s, 2H), 4.34 (q, 2H), 1.34 (t, 3H); High resolution mass spectrum (NH$_3$-CI) calculated (M+H$^+$) 249.0875, found 249.0865.

C. 1-(N-Methyl-N-methoxyamino)carbonylmethyl-5-ethoxycarbonylindazole. A solution of the product prepared according to Example E-24 Part B (1.8 g, 7.25 mmol), N,O-dimethylhydroxylamine hydrochloride (849 mg, 8.7 mmol) and triethylamine (2.53 mL, 18.1 mmol) in N,N-dimethylformamide (30 mL) was treated with BOP reagent (3.85 g, 8.7 mmol) and stirred at room temperature for 20 h. Most of the solvent was removed, and the residue was taken up in water. The mixture was extracted three times with ethyl acetate, and the combined organic phases were washed with hydrochloric acid (1.0 M) and water, then were dried (Na$_2$SO$_4$), filtered and concentrated. The residue was purified by flash chromatography (ethyl acetate-toluene 2:1) to provide the title product (1.85 g, 88%) as a white solid: $^1$H NMR (DMSO-d$_6$) d 8.48 (s, 1H), 8.28 (s, 1H), 7.94 (d, 1H), 7.72 (d, 1H), 5.52 (s, 2H), 4.34 (q, 2H), 3.82 (s, 3H), 3.15 (s, 3H), 1.36 (t, 3H); High resolution mass spectrum (NH$_3$-CI) calculated (M+H$^+$) 292.1297, found 292.1279.

D. 1-(3-Ethoxycarbonyl-2-oxopropyl)-5-ethoxycarbonylindazole. A solution of lithium bis(trimethylsilyl)-amide (1.0 M in hexane; 8.7 mL, 8.7 mmol) in tetrahydrofuran (9 mL) was cooled to −78° C. and treated dropwise with a solution of ethyl acetate (0.85 mL, 8.7 mmol) in tetrahydrofuran (2 mL) over 10 min. The resulting solution was stirred for 15 min more, then was treated over 2 min with a solution of the product prepared according to Example E-24 Part C (1.69 g, 5.80 mmol) in tetrahydrofuran (8 mL). A bright yellow color resulted. The solution was stirred at -78° C. for 3.5 h, then the cooling bath was removed. After 45 min, the mixture was poured into hydrochloric acid (1.0 M). The mixture was extracted three times with ethyl acetate, and the combined organic phases were dried (Na$_2$SO$_4$), filtered and concentrated. The residue was purified by flash chromatography (hexanes-ethyl acetate, 6:4) to provide the title product (636 mg, 34%) as a white solid which appeared to be a mixture (about 8:2) of keto and enol forms: $^1$H NMR (CDCl$_3$) d 12.13 (s, 0.2 H), 8.54 (s, 1H), 8.18 (s, 0.8 H), 8.15 (s, 0.2 H), 8.11 (d, 1H), 7.43 (d, 0.2 H), 7.35 (d, 0.8 H), 5.33 (s, 1.6 H), 5.13 (s, 0.4 H), 4.65 (s 0.2 H), 4.41 (q, 2H), 4.15 (q, 0.4 H), 4.11 (q, 1.6 H), 3.44 (s, 1.6 H), 1.42 (t, 3H), 1.22 (t, 3H); High resolution mass spectrum (NH$_3$-CI) calculated (M+H$^+$) 319.1294, found 319.1303.

E. 1-(2-Amino-4-oxopyrimidin-6-ylmethyl)-5-ethoxycarbonylindazole. Using the procedure of Example E-19 Part G, the product prepared according to Example E-24 Part D (318 mg, 1.0 mmol) was converted to the title product (258 mg, 82%) as a white solid: $^1$H NMR (DMSO-d$_6$) d 8.52 (s, 1H), 8.33 (s, 1H), 7.96 (d, 1H), 7.74 (d, 1H), 5.32 (s, 2H), 4.78 (s, 1H), 4.33 (q, 2H), 1.35 (t, 3H); Mass spectrum (ESI) m/z 314.2 (M+H$^+$, 100%).

F. 1-(2-Amino-4-oxopyrimidin-6-ylmethyl)-5-carboxyindazole.

Using the procedure of Example E-19 Part H, the product prepared according to Example E-24 Part E (100 mg, 319 μmol) was converted to the title product (84 mg, 92%) as a white solid: $^1$H NMR (DMSO-d$_6$) d 8.48 (s, 1H), 8.31 (s, 1H), 7.95 (d, 1H), 7.73 (d, 1H), 6.92 (bs), 5.37 (s, 2H), 4.87 (s, 1H).

G. Methyl 3-(tert-butyloxycarbonylamino)-2-(S)-(1-naphthalenesulfonylamino)propionate. A solution of methyl 3-(tert-butyloxycarbonylamino)-2-(S)-amino-propionate hydrochloride (7.64 g, 30 mmol) and diisopropylethylamine (7.76 g, 60 mmol) in dichloromethane (100 mL) was cooled on ice and treated slowly with 1-naphthalenesulfonyl chloride (6.80 g, 30 mmol). The resulting mixture was warmed to room temperature and stirred for 18 h. Water was added and the layers were separated. The aqueous phase was extracted with dichloromethane, and the combined organic phases were washed with brine, dried (MgSO$_4$), filtered and concentrated. The residue was purified by flash chromatography (hexanes-ethyl acetate, 5:1, then 3:1, then 2:1, then 3:2) to provide the title product (11.0 g, 90%) as a white solid: $^1$H NMR (CDCl$_3$) d 8.65 (d, 1H), 8.24 (d, 1H), 8.09 (d, 1H), 7.96 (d, 1H), 7.72 (t, 1H), 7.62 (t, 1H), 7.54 (t, 1H), 5.88 (bd, 1H), 4.78 (bt, 1H), 3.97 (m, 1H), 3.40 (m, 1H), 3.35 (s, 3H), 1.39 (s, 9H).

H. Methyl 3-amino-2-(S)-(1-naphthalenesulfonylamino)-propionate hydrochloride. The product prepared according to the procedure of Example E-24 Part G (11.0 g, 26.9 mmol) was dissolved in a dioxane solution of hydrogen chloride (4.0 M; 50mL). The mixture was stirred at room temperature for 18 h, and the resulting slurry was diluted with ether. The precipitate was collected by filtration, washed with ether and dried to provide the title product (10.6 g) as a white solid: $^1$H NMR (DMSO-d$_6$) d 8.90 (d, 1H), 8.57 (d, 1H), 8.23 (d, 1H), 8.15 (bs, 3H), 8.09 (t, 1H), 7.66 (m, 3H), 4.16 (bq, 1H), 3.34 (s, 3H), 3.01 (b, 1H), 2.90 (b, 1H).

I. Methyl 3-[1-[2-amino-4-oxopyrimidin-6-ylmethyl]-indazol-5-yl-carbonylamino]-2(S)-(1-naphthalenesulfonylamino)propionate. A mixture of the product prepared according to Example E-24 Part F (85 mg, 298 μmol) and the product prepared according to Example E-24 Part H (113 mg, 328 μmol) in N,N-dimethylformamide (3 mL) was treated sequentially with triethylamine (52 μL, 373 μmol), 1-hydroxybenzotriazole hydrate (40 mg, 298 μmol) and dicyclohexylcarbodiimide (68 mg, 328 μmol). The mixture was stirred at room temperature for 24 h and concentrated. The residue was purified by flash chromatography (dichloromethane-methanol, 97:3 then 9:1) to provide the title product (154 mg, 89%) as a gum: $^1$H NMR (MeOH-d$_4$) d 8.64 (d, 1H), 8.15 (s, 2H), 7.92 (d, 1H), 7.89 (s, 1H), 7.71 (d, 1H), 7.6–7.3 (4H), 5.35 (s, 2H), 5.03 (s, 1H), 4.20 (dd, 1H), 3.64 (dd, 1H), 3.46 (dd, 1H); ester methyl signal obscured by residual MeOH signal.

J. 3-[1-[2-Amino-4-oxopyrimidin-6-ylmethyll-indazol-5-ylcarbonylamino]-2(S)-(1-naphthalenesulfonylamino)-propionic acid. The product prepared according to Example E-24 Part I (154 mg, 267 μmol) was dissolved in formic acid (4 mL) and treated with concentrated hydrochloric acid (2 mL). The solution was stirred at room temperature for 67 h, then was concentrated. The residue was purified by preparative HPLC to provide the title product (83 mg, 55%) as a white solid: $^1$H NMR (DMSO-d$_6$) d 8.63 (d, 1H), 8.58 (d, 1H), 8.32 (bt, 1H), 8.25 (s, 1H), 8.12 (d, 1H), 8.07 (d, 1H), 7.98 (s, 1H), 7.87 (d, 1H), 7.7–7.4 (5H), 6.80 (b, 2H), 5.35 (s, 2H), 4.81 (s, 1H), 4.07 (m, 1H), 3.52 (m, 1H), 3.34 (m, 1H); High resolution mass spectrum (FAB) calculated (M+H$^+$) 562.1509, found 562.1516. This material (51 mg, 90.8 μmol) was dissolved in water (2 mL) and acetonitrile (1 mL) and treated with aqueous sodium hydroxide (1.0 M; 100 μL, 100 μmol). After stirring overnight, the solution was diluted with, water, frozen at −78° C. and lyophilized to provide the sodium salt of the title product (5 mg, 96%) as a fluffy white solid.

EXAMPLE E-42

3-[1-[2-(2–4-Diaminopyrimidin-6-yl)ethyl]indazol-5-ylcarbonylamino]-2(S)-benzenesulfonylaminopropionic acid A. 1-(2-(2-Amino-4-chloropyrimidin-6-yl)ethyl)-5-ethoxycarbonylindazole. A mixture of the product prepared according to Example E-l9 Part G (840 mg, 2.57 mmol) and phosphorus oxychloride (18 mL) was heated to reflux and stirred for 70 min. The solvent was allowed to distil off, and the residue was dried under vacuum. This material was triturated in water and aqueous ammonia (2 mL), and the resulting solid was collected by filtration, washed with water and dried to provide the title product (725 mg, 82%) as a cream-colored solid: $^1$H NMR (CDCl$_3$) d 8.49 (s, 1H), 8.10 (s, 1H), 8.03 (d, 1H), 7.38 (d, 1H), 6.36 (s, 1H), 5.10 (b, 2H), 4.78 (t, 2H), 4.40 (q, 2H), 3.20 (t, 2H), 1.43 (t, 3H); High resolution mass spectrum (NH$_3$-CI) calculated (M+H$^+$) 346.1071, found 346.1077.

B. 1-(2-(2,4-Diaminopyrimidin-6-yl)ethyl)-5-ethoxycarbonylindazole. A mixture of the product prepared according to Example E-42 Part A (350 mg, 1.02 mmol) and ethanol saturated with ammonia gas (20mL) was heated in a sealed tube for 44 h, starting at 100° C. and increasing to 155° C. The mixture was then concentrated. The residue was purified by flash chromatography (dichloromethane-methanol 9:1) to provide the title product (157 mg, 47%) as a solid: $^1$H NMR (DMSO-d$_6$) d 8.44 (s, 1H), 8.25 (s, 1H), 7.89 (d, 1H), 7.68 (d, 1H), 6.12 (bs, 2H), 5.87 (bs, 2H), 5.44 (s, 1H), 4.70 (t, 2H), 4.32 (q, 2H), 2.84 (t, 2H), 1.34 (t, 3H); High resolution mass spectrum (NH$_3$-CI) calculated (M+H$^+$) 327.1569, found 327.1589.

C. 1-(2-(2,4-Diaminopyrimidin-6-yl)ethyl)-5-carboxyindazole. A mixture of the product prepared according to Example E-42 Part B (157 mg, 480 μmol) and aqueous sodium hydroxide (1.0 M; 5 mL) was heated at reflux for 4 h. The solution was cooled to room temperature and treated with hydrochloric acid (1.0 M; 10 mL). The resulting solution was concentrated and the residue, containing sodium chloride, was used without further purification or characterization.

D. Methyl 3-amino-2-(S)-benzenesulfonylaminopropionate hydrochloride. Using procedures analogous to those outlined in Example E-24 Parts G and H, methyl 3-(tert-butyloxycarbonylamino)-2-(S)-aminopropionate hydrochloride (5.82 g, 26.6 mmol) was converted to the title product (7.5 g, 95% for two steps) as a white solid: $^1$H NMR (DMSO-d$_6$) d 8.70 (d, 1H), 8.38 (bs, 3H), 7.78 (m, 2H), 7.60 (m, 3H), 4.25 (dd, 1H), 3.03 (dd, 1H), 2.89 (dd, 1H).

E. Methyl 3-[1-[2-(2–4-diaminopyrimidin-6-yl)ethyl]-indazol-5-ylcarbonylamino]-2(S)-benzenesulfonylaminopropionate. A mixture of the crude product prepared according to Example E-42 Part C (80 mg, 234 μmol), the product prepared according to Example E-42 Part D (90 mg, 304 μmol) and 4-methylmorpholine (3 drops) in N,N-dimethylformamide (5 mL) was treated with BOP reagent (134 mg, 304 μmol) and stirred for 18 hr. The solution was diluted with water and extracted with dichloromethane. The organic phase was dried (MgSO$_4$), filtered and concentrated. The residue was purified by flash chromatography (dichloromethane-methanol 9:1, then 85:15) to provide the title product (80 mg, 66%) as a white solid: 1H NMR (MeOH-d$_4$) d 8.11 (s, 1H), 8.10 (s, 1H), 7.78 (m, 2H), 7.70 (d, 1H), 7.48 (d, 1H), 7.40 (m, 3H), 5.47 (s, 1H), 4.71 (t, 2H), 4.23 (dd, 1H), 3.66 (dd, 1H), 3.53 (dd, 1H), 3.46 (s, 3H), 2.93 (t, 2H); Mass spectrum (NH$_3$-CI) m/z 540.1 (100%, M+H$^+$).

F. 3-[1-[2-(2–4-Diaminopyrimidin-6-yl)ethyl]indazol-5-ylcarbonylamino]-2(S)-benzenesulfonylaminopropionic acid. The product prepared according to Example E-42 Part E (30 mg, 60 μmol) was dissolved in a mixture of formic acid (1 mL) and concentrated hydrochloric acid (0.5 mL) and stirred for 48 h. The solution was concentrated and purified by preparative HPLC to provide the title product as the trifluoroacetate salt (20 mg, 52%) as a white solid: $^1$H NMR (MeOH-d$_4$) d 8.19 (s, 1H), 8.15 (s, 1H), 7.82 (m, 3H), 7.58 (d, 1H), 7.40 (m, 3H), 5.65 (s, 1H), 4.78 (t, 2H), 4.20 (dd, 1H), 3.77 (dd, 1H), 3.49 (dd, 1H), 3.12 (t, 2H); High resolution mass spectrum (NH$_3$-CI) calculated (M+H$^+$) 525.1669, found 525.1680.

EXAMPLE E-43

3-[1-[2-(2,3-Dihydro-5-oxo-imidazo[1,2-a [pyrimidin-7-yl)ethyl]indazol-5-ylcarbonylamino]-2 (S)-(1-naphthalenesulfonyl)aminopropionic acid A. 1-(2-(2,3-Dihydro-5-oxo-imidazo[1,2-alpyrimidin-7-yl)ethyl)-5-ethoxycarbonylindazole. A mixture of the product prepared according to Example E-19 Part F (540 mg, 1.63 mmol), 2-amino-4,5-dihydroimidazole hydrobromide (297 mg, 1.79 mmol) and sodium bicarbonate (150 mg, 1.79 mmol) in ethanol (20 mL) was heated at reflux for 17 h. The mixture was cooled, and the precipitate was isolated by filtration, rinsed with ethanol, and dried to provide the title product (423 mg, 73%) as an off-white solid: $^1$H NMR (DMSO-d6) d 8.45 (s, 1H), 8.26 (s, 1H), 7.97 (s, 1H), 7.93 (d, 1H), 7.70 (d, 1H), 5.36 (s, 1H), 4.68 (t, 2H), 4.32 (q, 2H), 3.93 (t, 2H), 3.57 (t, 2H), 2.85 (t, 2H), 1.34 (t, 3H); High resolution mass spectrum (NH$_3$-CI) calculated (M+H$^+$) 354.1566, found 354.1555. Also recovered from the filtrate was starting ketoester (29 mg, 21%).

B. 1-(2-(2,3-Dihydro-5-oxo-imidazo[1,2-a]pyrimidin-7-yl)ethyl)-5-carboxyindazole. The product prepared according to Example E-43 Part A (402 mg, 1.14 mmol) was dissolved in aqueous sodium hydroxide (12 mL) and stirred at room temperature for 3 h. The mixture was acidified with hydrochloric acid (1.0 M, 13.5 mL) and the resulting solid was collected by filtration, washed with water, and dried to provide the title product (250 mg, 68%) as an off-white solid: $^1$H NMR (DMSO-d$_6$) d 8.42 (s, 1H), 8.23 (s, 1H), 7.99 (bs, 1H), 7.92 (d, 1H), 7.67 (d, 1H), 5.37 (s, 1H), 4.68 (t, 2H), 3.93 (t, 2H), 3.58 (t, 2H), 2.85 (t, 2H). $^1$H NMR (CD$_3$OD) δ 6 2.84 (t, J=7 Hz, 2H), 3.02, (t, J=7 Hz, 2H).

C. Methyl 3-[1-[2-(2,3-dihydro-5-oxo-imidazo[1,2-a]-pyrimidin-7-yl)ethyllindazol-5-ylcarbonylamino]-2(S)-(1-naphthalenesulfonyl)aminopropionate. A mixture of the product prepared according to Example E-43 Part B (50 mg, 154 μmol) and the product prepared according to Example E-24 Part H (67 mg, 185 μmol) was dissolved in N,N-dimethylformamide (3 mL). The solution was treated sequentially with triethylamine (67 μL, 462 μmol), 1-hydroxybenzotriazole hydrate (22 mg, 154 μmol) and dicyclohexylcarbodiimide (44 mg, 200 μmol). The resulting mixture was stirred at room temperature for 22 h. The solvent was removed and the residue was purified by flash chromatography (dichloromethane, gradually changing to dichloromethane-methanol-aqueous ammonia 93:7:0.7) to provide the title product (60 mg, 63%) as a solid: $^1$H NMR (MeOH-d$_4$) d 8.64 (d, 1H), 8.16 (d, 1H), 8.04 (s, 1H), 7.91 (d, 1H), 7.81 (s, 1H), 7.70 (d, 1H), 7.58 (m, 2H), 7.42 (m, 4H), 5.32 (s, 1H), 4.71 (t, 2H), 4.19 (dd, 1H), 3.97 (t, 2H), 3.64 (m, 3H), 3.45 (dd, 1H), 3.25 (s, 3H), 2.93 (t, 2H); Mass spectrum (FAB) m/z 616.2 (100%, M+H$^+$).

D. 3-[1-[2-(2,3-Dihydro-5-oxo-imidazo[1,2-a]pyrimidin-7-yl)ethyl]-indazol-5-ylcarbonylamino]-2(S)-(1-naphthalenesulfonyl)aminopropionic acid. The product prepared according to Example E-43 Part C (36 mg, 58 μmol) was dissolved in tetrahydrofuran (3 mL) and treated with lithium hydroxide monohydrate (18 mg) dissolved in water (1 mL). The mixture was stirred for 2 h, concentrated, and purified by preparative HPLC to provide the title product (17.3 mg) as a white solid: $^1$H NMR (MeOH-d$_4$) d 8.64 (d, 1H), 8.16 (d, 1H), 8.06 (s, 1H), 7.87 (d, 1H), 7.76 (s, 1H), 7.64 (d, 1H), 7.6–7.3 (5H), 5.47 (s, 1H), 4.75 (t, 2H), 4.19 (dd, 1H), 4.05 (t, 2H), 3.77 (t, 2H), 3.69 (dd, 1H), 3.43 (dd, 1H), 3.01 (t, 2H); High resolution mass spectrum (NH$_3$-CI) calculated (M+H$^+$) 602.1822, found 602.1818. This material was dissolved in water (1 mL) and acetonitrile (1 mL), and treated with sodium hydroxide (1.0 M; 28 μL, 28 μmol). The solution was frozen at −78° C. and lyophilized to provide the sodium salt of the title product (19.6 mg, 34%) as a white solid.

EXAMPLE E-48

3-[1-[2-(5-Oxo-imidazo[1,2-a]pyrimidin-7-yl)ethyl]-indazol-5-ylcarbonylamino]-2(S)-benzenesulfonylaminopropionic acid A. 1-(2-(5-Oxo-imidazo[1,2-a]pyrimidin-7-yl)ethyl)-5-ethoxycarbonylindazole. A mixture of the product prepared according to Example E-19 Part F (665 mg, 2.0 mmol), 2-aminoimidazole sulfate (291 mg, 2.2 mmol) and ammonium acetate (340 mg, 4.4 mmol) was heated on an oil bath at 150° C. After 2 h, the mixture was cooled and triturated in ethanol. The resulting solid was collected by filtration, washed with ethanol and dried to provide the title product (459 mg, 65%) as a gray-tan powder: $^1$H NMR (DMSO-$d_6$) d 12.7 (bs, 1H), 8.44 (s, 1H), 8.25 (s, 1H), 7.88 (d, 1H), 7.71 (d, 1H), 7.52 (s, 1H), 7.47 (s, 1H), 5.69 (s, 1H), 4.80 (t, 2H), 4.32 (q, 2H), 3.10 (t, 2H), 1.33 (t, 3H); High resolution mass spectrum (NH$_3$-CI) calculated (M+H$^+$) 351.1331, found 351.1325.

B. 1-(2-(5-Oxo-imidazo[1,2-a]pyrimidin-7-yl)ethyl)-5-carboxyindazole. The product prepared according to Example E-48 Part A (43.7 mg, 124 µmol) was stirred in aqueous sodium hydroxide (1.0 M, 2 mL), during which time the solid slowly dissolved. After 45 min, the solution was treated with hydrochloric acid (1.0 M, 3 mL) to form a dense precipitate. The solid was collected by filtration, washed with water and ethanol, and dried to provide the title product (33 mg, 82%) as a white solid: $^1$H NMR (DMSO-$d_6$) d 12.76 (bs, 2H), 8.40 (s, 1H), 8.23 (s, 1H), 7.87 (d, 1H), 7.68 (d, 1H), 7.51 (d, 1H), 7.45 (d, 1H), 5.64 (s, 1H), 4.79 (t, 2H), 3.09 (t, 2H); Mass spectrum (ESI) m/z 321.7 (100%, M+H$^+$).

C. Methyl 3-[1-]2-(5-oxo-imidazo[1,2-a]pyrimidin-7-yl)-ethyl]indazol-5-ylcarbonylamino]-2(S)-benzenesulfonylaminopropionate. Using the procedure of Example E-43 Part C, the product prepared according to Example E-48 Part B (61 mg, 188 µmol) and the product prepared according to Example E-42 Part D (67 mg, 227 µmol) were converted to the title product (96 mg, 90%) as a solid: $^1$H NMR (MeOH-$d_4$) d 8.07 (s, 2H), 7.77 (m, 2H), 7.61 (d, 1H), 7.46 (d, 1H), 7.36 (m, 2H), 7.26 (m, 1H), 5.54 (s, 1H), 4.80 (t, 2H), 4.22 (dd, 1H), 3.65 (dd, 1H), 3.52 (dd, 1H), 3.45 (s, 3H), 3.14 (t, 2H); Mass spectrum (ESI) m/z 561.8 (100%, M+H$^+$).

D. 3-[1-[2-(5-Oxo-imidazo[1,2-a]pyrimidin-7-yl)ethyl]-indazol-5-ylcarbonylamino1-2(S)-benzenesulfonylaminopropionic acid. The product prepared according to Example E-48 Part C (95 mg, 169 µmol) was dissolved in tetrahydrofuran (4 mL) and water (1.5 mL) and treated with lithium hydroxide monohydrate (30 mg, 715 µmol). After stirring for 46 h at room temperature, the solution was concentrated under vacuum and the residue was purified by preparative HPLC to provide the title product (45 mg) as a white solid: $^1$H NMR (MeOH-$d_4$) d 8.10 (s, 2H), 7.78 (m, 2H), 7.69 (d, 1H), 7.52 (d, 1H), 7.35 (m, 3H), 5.71 (s, 1H), 4.84 (t, 2H), 4.20 (dd, 1H), 3.73 (dd, 1H), 3.49 (dd, 1H), 3.21 (t, 2H); High resolution mass spectrum (FAB) calculated (M+H$^+$) 550.1509, found 550.1508.

EXAMPLE F-26

3-[1-Methyl-3-[2-(2-amino-4-oxopyrimidin-6-yl)ethyl]-indazol-6-ylcarbonylamino]-2(S)-(isoquinoline-5-sulfonylamino)propionic acid A. 6-Methoxycarbonylindazole. A solution of methyl 3-amino-4-methylbenzoate (12.39 g, 75 mmol) in water (85 mL) and concentrated hydrochloric acid (15 mL) was treated with ammonium fluoborate (10.48 g, 100 mmol) and cooled to −3° C. A solution of sodium nitrite (5.18 g, 75 mmol) in water (12 mL) was added dropwise over 25 min, producing a thick slurry. After stirring for 35 min more, the solid was collected by filtration, and was washed with water (100 mL), methanol (50 mL) and ether (50 mL), and dried. This material was added to a stirred mixture of potassium acetate (8.1 g, 82.5 mmol), 18-crown-6 (0.5 g, 1.9 mmol) and chloroform (170 mL) at room temperature, and stirring was continued for 70 min. Water (170 mL) was added and stirring was continued until the solid was dissolved. The layers were separated, and the aqueous phase was extracted with chloroform. The combined organic phases were washed with water, dried (MgSO$_4$), filtered and concentrated. The resulting solid was stirred in hexane overnight, collected by filtration, rinsed with hexane and dried to provide the title product (8.85 g, 67%) as a dull yellow powder, which could be recrystallized from acetonitrile to give pale orange crystals, mp 142–144° C.: $^1$H NMR (CDCl$_3$) d 11.17 (bs, 1H), 8.30 (s, 1H), 8.18 (s, 1H), 7.83 (m, 2H), 3.97 (s, 3H); Mass spectrum (NH$_3$-CI) m/z 177 (100%, M+H$^+$).

B. 3-Bromo-6-methoxycarbonylindazole. A solution of the product prepared according to Example F-26 Part A (3.52 g, 20 mmol) in acetic acid (100 mL) was treated with bromine (1.55 mL, 30 mmol) and stirred in the dark for 18 h. The solution was poured into water (600 mL) to form a dense orange slurry. Solid sodium bisulfite was added in small portions, causing the color to lighten, until no further change was observed. The slurry was then stirred for 20 min, and the solid was collected by filtration, washed thoroughly with water and dried to provide the title product (4.46 g, 87%) as a light yellow powder: mp 186–189° C.; $^1$H NMR (CDCl$_3$) d 8.24 (s, 1H), 7.91 (d, 1H), 7.70 (d, 1H), 3.92 (s, 3H); Mass spectrum (NH$_3$-CI) m/z 255 (100%), 257 (96%) (M+H$^+$); High resolution mass spectrum (EI) calculated (M$^+$) 253.9691, found 253.9694.

C. 1-Methyl-3-bromo-6-methoxycarbonylindazole. Sodium hydride (60% in mineral oil; 600 mg, 15 mmol) was placed in a dry flask under nitrogen and suspended in dry N,N-dimethylformamide (20 mL). The suspension was stirred on an ice bath and treated with a solution of the product prepared according to Example F-26 Part B (2.55 g, 10 mmol) in dry N,N-dimethylformamide (20 mL) over about 3 min. The resulting yellow solution was stirred for 10 min more, then was treated with iodomethane (0.7 mL, 11 mmol). The mixture was stirred at room temperature for 22.5 h, then was poured into water (ca. 600 mL). After being stirred for 10 min, the suspension was filtered, and the solid was washed with water and dried to provide the title product (2.57 g, 95%) as a yellow solid, which could be recrystallized from ethanol, mp 122–125° C.: $^1$H NMR (CDCl$_3$) d 8.16 (s, 1H), 7.87 (d, 1H), 7.65 (d, 1H), 4.13 (s, 3H), 3.99 (s, 3H); Mass spectrum (NH$_3$-CI) m/z 269 (100%), 271 (92%) (M+H$^+$); High resolution mass spectrum (NH$_3$-CI) calculated 268.9926, found 268.9914.

D. 1-Methyl-3-(3,3-diethoxypropynyl)-6-methoxycarbonylindazole. A mixture of the product prepared according to Example F-26 Part C (1.93 g, 7.2 mmol), 3,3-diethoxypropyne (1.65 mL, 11.5 mmol), triphenylphosphine (190 mg, 720 µmol), copper(I) iodide (68 mg, 360 µmol) and triethylamine (60 mL) was purged of oxygen by bubbling with nitrogen for 25 min. Bis(triphenyl-phosphine)palladium(II) chloride (126 mg, 180 µmol) was added, and the mixture was heated at 100° C. After 14 h, the mixture was concentrated. The residue was purified by flash chromatography (hexanes-ethyl acetate 85:15) to provide an orange, sticky solid. This was recrystallized (methanol) to provide the title product (1.26 g, 56%) as light yellow fibrous needles, mp 91–93° C.: $^1$H NMR (CDCl$_3$) d 8.18 (s, 1H), 7.88 (d, 1H), 7.83 (d, 1H), 5.59 (s, 1H), 4.14 (s, 3H), 3.98 (s, 3H), 3.89 (m, 2H), 3.72 (m, 2H), 1.30 (t, 6H); Mass spectrum (ESI) m/z 317.4 (100%, M+H$^+$).

E. 1-Methyl-3-(3,3-diethoxypropyl)-6-methoxycarbonylindazole. A mixture of the product prepared according to Example F-26 Part D (1.24 g, 3.92 mmol), 10% palladium on charcoal (130 mg), methanol (40 mL) and tetrahydrofuran (60 mL) was placed in a pressure bottle and shaken under an atmosphere of hydrogen (60 psig). After 60 min, the bottle was vented and the mixture was filtered through Celite.® The solids were rinsed with methanol and tetrahydrofuran, and the filtrate was concentrated to provide the title product (1.31 g) as a slightly cloudy oil which was not purified further: 1H NMR (CDCl$_3$) d 8.11 (s, 1H), 7.77 (d, 1H), 7.72 (d, 1H), 4.57 (t, 1H), 4.08 (s, 3H), 3.97 (s, 3H), 3.69 (m, 2H), 3.52 (m, 2H), 3.06 (t, 2H), 2.13 (m, 2H), 1.22 (t, 6H); High resolution mass spectrum (NH$_3$-CI) calculated (M+H$^+$) 321,1814, found 321.1830.

F. 1-Methyl-3-(3-oxopropyl)-6-methoxycarbonylindazole. A mixture of the product prepared according to Example F-26 Part E (1.29 g, 4.0 mmol), acetic acid (20 mL) and water (30 mL) was heated on an oil bath at 80° C. After 30 min, the solvent was removed, and the residue was dissolved in ethyl acetate. The solution was washed with saturated aqueous sodium bicarbonate, dried (MgSO$_4$), filtered and concentrated under vacuum to provide a light brown oil. On further drying under vacuum, a tan solid slowly formed, which was the title product (982 mg, 98%), mp 80–83° C.: 1H NMR (CDCl$_3$) d 9.92 (s, 1H), 8.11 (s, 1H), 7.79 (d, 1H), 7.71 (d, 1H), 4.07 (s, 3H), 3.98 (s, 3H), 3.31 (t, 2H), 3.03 (t, 2H); High resolution mass spectrum (NH$_3$-CI) calculated (M+H$^+$) 247.1083, found 247.1077.

G. 1-Methyl-3-(2-carboxyethyl)-6-methoxycarbonyl-indazole. The product prepared according to Example F-26 Part F (1.04 g, 4.22 mmol) was dissolved in N,N-dimethylformamide (10 mL) and treated with pyridinium dichromate (3.19 g, 8.48 mmol). The resulting dark-colored mixture was stirred at room temperature for 5 h, then was poured into water. The mixture was extracted four times with ethyl acetate. The combined organic phases were dried (Na$_2$SO$_4$), filtered and concentrated under vacuum to provide the title product (1.06 g, 96%) as a pale greenish solid: 1H NMR (CDCl$_3$) d 8.11 (s, 1H), 7.78 (d, 1H), 7.72 (d, 1H), 4.06 (s, 3H), 3.97 (s, 3H), 3.31 (t, 2H), 2.89 (t, 2H); High resolution mass spectrum (NH$_3$-CI) calculated (M+H$^+$) 263.1032, found 263.1013.

H. 1-Methyl-3-(4-ethoxycarbonyl-3-oxobutyl)-6-methoxycarbonylindazole. Following the procedure of Example E-19 Part F, the product prepared according to the procedure of Example F-26 Part G (998 mg, 3.81 mmol) was converted to the title product (720 mg, 57%) as a light yellow solid: $^1$H NMR (CDCl$_3$) d 8.09 (s, 1H), 7.77 (d, 1H), 7.71 (d, 1H), 4.19 (q, 2H), 4.05 (s, 3H), 3.97 (s, 3H), 3.53 (s, 2H), 3.26 (t, 2H), 3.13 (t, 2H), 1.27 (t, 3H).

I. 1-Methyl-3-(2-(2-amino-4-oxopyrimidin-6-yl)ethyl)-6-methoxycarbonylindazole. A suspension of the product prepared according to Example F-26 Part H (260 mg, 820 μmol) in ethanol (10 mL) was treated with guanidine carbonate (74 mg, 410 μmol) and the mixture was heated to reflux for 3.5 h. The mixture was cooled to room temperature and the precipitate was isolated by filtration, washed with ethanol and dried to provide the title product (149 mg, 56%) as a white solid: $^1$H NMR (DMSO-d$_6$) d 8.17 (s, 1H), 7.79 (d, 1H), 7.61 (d, 1H), 6.47 (bs, 2H), 5.37 (s, 1H), 4.02 (s, 3H), 3.86 (s, 3H), 3.17 (t, 2H), 2.67 (s, 3H); High resolution mass spectrum (NH$_3$-CI) calculated (M+H$^+$) 328.1410, found 328.1408.

J. 1-Methyl-3-(2-(2-amino-4-oxopyvrimidin-6-yl)ethyl)-6-carboxyindazole. The product prepared according to Example F-26 Part I (139 mg, 427 μmol) was dissolved in aqueous sodium hydroxide (1.0 M, 6 mL) and stirred at room temperature for 50 min. Hydrochloric acid (1.0 M, 6.5 mL) was added and the resulting precipitate was isolated by filtration, washed with ethanol and water, and dried to provide the title product (128 mg, 96%) as a white solid: $^1$H NMR (DMSO-d$_6$) d 8.14 (s, 1H), 7.76 (d, 1H), 7.60 (d, 1H), 6.52 (bs, 2H), 5.38 (s, 1H), 4.00 (s, 3H), 3.16 (t, 2H), 2.67 (s, 3H); High resolution mass spectrum (NH3-CI) calculated (M+H$^+$) 314.1253, found 314.1239.

K. Methyl 3-(tert-butyloxycarbonylamino)-2-(S)-(isoquinoline-5-sulfonylamino)propionate. A solution of methyl 3-(tert-butyloxycarbonylamino)-2-(S)-aminopropionate hydrochloride (7.06 g, 27.8 mmol) in pyridine (30 mL) was treated with N,N-dimethylamino-pyridine (3.40 g, 27.8 mmol) and cooled on ice. Isoquinoline-5-sulfonyl chloride (12.68 g, 55.7 mmol) was added portionwise over 5 min, and the mixture was warmed to room temperature and stirred for 5 h. The solvent was removed under vacuum and the residue was partitioned between water and ethyl acetate. The organic phase was dried (Na$_2$SO$_4$), filtered and concentrated. The residue was purified by flash chromatography to provide the title product (8.93 g, 79%) as a solid: $^1$H NMR (CDCl$_3$) d 9.37 (s, 1H), 8.73 (d, 1H), 8.42 (d, 2H), 8.23 (d, 1H), 7.69 (t, 1H), 4.86 (bt, 1H), 4.05 (t, 1H), 3.44 (t, 2H), 3.39 (s, 3H), 1.39 (s, 9H); High resolution mass spectrum (NH$_3$-CI) calculated (M+H$^+$) 410.1386, found 410.1378.

L. Methyl 3-amino-2-(S)-(isoauinoline-5-sulfonylamino)-propionate bis-trifluoroacetate. A solution of the product prepared according to Example F-26 Part K (8.02 g, 19.6 mmol) in dichloromethane (85 mL) was treated with trifluoroacetic acid (40 mL). The solution was stirred at room temperature for 60 min, then was concentrated under vacuum to provide the title product (12.0 g) as a solid, used without further purification: $^1$H NMR (MeOH-d$_4$) d 9.36 (s, 1H), 8.59 (m, 2H), 8.42 (d, 2H), 8.35 (d, 1H), 7.76 (t, 1H), 3.93 (dd, 1H), 3.10 (s, 3H), 2.86 (dd, 1H), 2.74 (dd, 1H).

M. Methyl 3-[1-methyl-3-[2-(2-amino-4-oxopyrimidin-6-yl)ethyl]-indazol-6-ylcarbonylamino]-2(S)-(isoauinoline-5-sulfonylamino)propionate. Using the procedure of Example E-43 Part C, the product prepared according to Example F-26 Part J (52.3 mg, 167 μmol) and the product prepared according to Example F-26 Part L (70 mg, 226 μmol) were converted to the title product (60 mg, 60%) as a solid: $^1$H NMR (MeOH-d$_4$) d 8.49 (m, 2H), 8.36 (d, 1H), 7.98 (d, 1H), 7.62 (t, 2H), 7.55 (s, 1H), 7.38 (m, 1H), 7.16 (d, 1H), 5.55 (s, 1H), 4.30 (dd, 1H), 3.97 (s, 3H), 3.67 (dd, 1H), 3.49 (dd, 1H), 3.41 (s, 3H), 2.87 (t, 2H); High resolution mass spectrum (FAB) calculated (M+H$^+$) 605.1931, found 605.1916.

N. 3-[1-Methyl-3-[2-(2-amino-4-oxopyrimidin-6-yl)ethyl [-indazol-6-ylcarbonylamino]-2(S) -(isoquinoline-5-sulfonylamino)propionic acid. A solution of the product prepared according to Example F-26 Part M (57 mg, 93 μmol) in tetrahydrofuran (4 mL) and water (1.5 mL) was treated with lithium hydroxide monohydrate (16 mg, 380 μmol). The solution was stirred for 24 h, then acidified with hydrochloric acid (1.0 M) and concentrated under vacuum.

The residue was purified by preparative HPLC to provide the title product as the trifluoroacetate salt (33 mg, 56%) as a light yellow solid: $^1$H NMR (MeOH-d$_4$) d 9.32 (bs, 1H), 8.92 (d, 1H), 8.66 (d, 1H), 8.62 (bm, 1H), 8.30 (d, 1H), 7.90 (t, 1H), 7.75 (d, 1H), 7.66 (s, 1H), 7.24 (d, 1H), 5.78 (s, 1H), 4.31 (dd, 1H), 4.01 (s, 3H), 3.73 (dd, 1H), 3.52 (dd, 1H), 3.36 (t, 2H), 3.04 (t, 2H); High resolution mass spectrum (FAB) calculated (M+H$^+$) 591.1774, found 591.1764.

Using the methods described above and modifications thereof known to one skilled in the art of organic synthesis, additional compounds of the present invention can be prepared, including, but not limited to the representative compounds listed in the Tables below.

Utility

The compounds of Formula (IA) of the present invention possess activity as antagonists of integrins such as, for example, the $\alpha_v\beta_3$ or vitronectin receptor, $\alpha_v\beta_5$ or $\alpha_5\beta_1$, and as such have utility in the treatment and diagnosis of cell adhesion, angiogenic disorders, inflammation, bone degradation, cancer metastases, diabetic retinopathy, thrombosis, restenosis, macular degeneration, and other conditions mediated by cell adhesion and/or cell migration and/or angiogenesis. The integrin antagonist activity of the compounds of the present invention is demonstrated using assays which measure the binding of a specific integrin to a native ligand, for example, using the ELISA assay described below for the binding of vitronectin to the $\alpha_v\beta_3$ receptor.

The compounds of the present invention possess selectivity for the $\alpha_v\beta_3$ receptor relative to the GPIIb/IIIa receptor as demonstrated by their lack of activity in standard assays of platelet aggregation, such as the platelet aggregation assay described below.

One of the major roles of integrins in vivo is to mediate cellular interactions with adjacent cells. Cell based adhesion assays can be used to mimic these interactions in vitro. A cell based assay is more representative of the in vivo situation than an ELISA since the receptor is maintained in membranes in the native state. The compounds of the present invention have activity in cell-based assays of adhesion, for example as demonstrated in using the cell adhesion assays described below.

The compounds of Formula (IA) of the present invention may be useful for the treatment or prevention of other diseases which involve cell adhesion processes, including, but not limited to, osteoporosis, rheumatoid arthritis, autoimmune disorders, bone degradation, rheumatoid arthritis, asthma, allergies, adult respiratory distress syndrome, graft versus host disease, organ transplantation, septic shock, psoriasis, eczema, contact dermatitis, osteoarthritis, atherosclerosis, metastasis, wound healing, inflammatory bowel disease and other angiogenic disorders.

The compounds of Formula (IA) have the ability to suppress/inhibit angiogenesis in vivo, for example, as demonstrated using animal models of ocular neovascularization.

The compounds provided by this invention are also useful as standards and reagents in determining the ability of a potential pharmaceutical to inhibit integrin-ligand binding. These may be provided in a commercial kit comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanometer. "Sigma" stands for the Sigma-Aldrich Corp. of St. Louis, Mo.

The utility of the compounds of the present invention may be assessed by testing in one or more of the following assays as described in detail below: Purified $\alpha_v\beta_3$ (human placenta) - Vitronectin ELISA, $\alpha_v\beta_3$-Vitronectin Binding Assay, Human Aortic Smooth Muscle Cell Migration Assay, In Vivo Angiogenesis Model, Pig Restenosis Model, Mouse Retinopathy Model. A compound of the present invention is considered to be active if it has an IC$_{50}$ or K$_i$ value of less than about 10 μM for the inhibition of $\alpha_v\beta_3$-Vitronectin Binding Assay, with compounds preferably having K$_i$ values of less than about 0.1 μM. Tested compounds of the present invention are active in the $\alpha_v\beta_3$-Vitronectin Binding Assay as well as in cell-based assays of integrin adhesion mediated by the $\alpha_v\beta_3$-receptor.

Purified $\alpha_v\beta_3$ (human placenta) - Vitronectin ELISA

The $\alpha_v\beta_3$ receptor was isolated from human placental extracts prepared using octylglucoside. The extracts were passed over an affinity column composed of anti-$\alpha_v\beta_3$ monoclonal antibody (LM609) to Affigel. The column was subsequently washed extensively at pH 7 and pH 4.5 followed by elution at pH 3. The resulting sample was concentrated by wheat germ agglutinin chromatography to provide gave two bands on SDS gel which were confirmed as $\alpha_v\beta_3$ by western blotting.

Affinity purified protein was diluted at different levels and plated to 96 well plates. ELISA was performed using fixed concentration of biotinylated vitronectin (approximately 80 nM/well). This receptor preparation contains the $\alpha_v\beta_3$ with no detectable levels of $\alpha_v\beta_5$ according to the gel ($\alpha_v\beta_3$) and according to effects of blocking antibodies for the $\alpha_v\beta_3$ or $\alpha_v\beta_5$ in the ELISA.

A submaximal concentration of biotinylated vitronectin was selected based on conc. response curve with fixed receptor conc. and variable concentrations of biotinylated vitronectin.

$\alpha_v\beta_3$-Vitronectin Binding Assay

The purified receptor is diluted with coating buffer (20 mM Tris HCl, 150 mM NaCl, 2.0 mM CaCl$_2$, 1.0 mM MgCl$_2$.6H$_2$O, 1.0 mM MnCl$_2$.4H$_2$O) and coated (100 μL/well) on Costar (3590) high capacity binding plates overnight at 4° C. The coating solution is discarded and the plates washed once with blocking/binding buffer (B/B buffer, 50 mM Tris HCl, 100 mM NaCl, 2.0 mM CaCl$_2$,1.0 mM MgCl$_2$.6H$_2$O, 1.0 mM MnCl$_2$.4H$_2$O). Receptor is then blocked (200 μL/well) with 3.5% BSA in B/B buffer for 2 hours at room temperature. After washing once with 1.0% BSA in B/B buffer, biotinylated vitronectin (100 μL) and either inhibitor (11 μL) or B/B buffer w/1.0% BSA (11 μL) is added to each well. The plates are incubated 2 hours at room temperature. The plates are washed twice with B/B buffer and incubated 1 hour at room temperature with anti-biotin alkaline phosphatase (100 μL/well) in B/B buffer containing 1.0% BSA. The plates are washed twice with B/B buffer and alkaline phosphatase substrate (100 μL) is added. Color is developed at room temperature. Color development is stopped by addition of 2N NaOH (25 μL/well) and absorbance is read at 405 nm. The IC$_{50}$ is the concentration of test substance needed to block 50% of the vitronectin binding to the receptor. A compound is considered to be active if it has a IC$_{50}$ value of less than about ≦10 μM in the $\alpha_v\beta_3$-Vitronectin Binding Assay. Compounds with a IC$_{50}$ less than 100 nM for the inhibition of vitronectin are desirable. Using the methodology described above, a number of compounds of the present invention were found to exhibit a IC$_{50}$ of ≦10 μM, thereby confirming the utility of the compounds of the present invention as effective $\alpha_v\beta_3$ integrin inhibitors.

Integrin Cell-Based Adhesion Assays

In the adhesion assays, a 96 well plate was coated with the ligand (i.e., fibrinogen) and incubated overnight at 4° C. The following day, the cells were harvested, washed and loaded with a fluorescent dye. Compounds and cells were added together and then were immediately added to the coated plate. After incubation, loose cells are removed from the plate, and the plate (with adherent cells) is counted on a fluorometer. The ability of test compounds to inhibit cell adhesion by 50% is given by the $IC_{50}$ value and represents a measure of potency of inhibition of integrin mediated binding. Compounds were tested for their ability to block cell adhesion using assays specific for $\alpha_v\beta_3$, $\alpha_v\beta_5$ and $\alpha_5\beta_1$ integrin interactions.

Platelet Aggregation Assay

Venous blood was obtained from anesthetized mongrel dogs or from healthy human donors who were drug- and aspirin-free for at least two weeks prior to blood collection. Blood was collected into citrated Vacutainer tubes. The blood was centrifuged for 15 minutes at 150×g (850 RPM in a Sorvall RT6000 Tabletop Centrifuge with H-1000 B rotor) at room temperature, and platelet-rich plasma (PRP) was removed. The remaining blood was centrifuged for 15 minutes at 1500×g (26,780 RPM) at room temperature, and platelet-poor plasma (PPP) was removed. Samples were assayed on a PAP-4 Platelet Aggregation Profiler, using PPP as the blank (100% transmittance). 200 $\mu$L of PRP ($5\times10^8$ platelets/mL) were added to each micro test tube, and transmittance was set to 0%. 20 $\mu$L of ADP (10 $\mu$M) was added to each tube, and the aggregation profiles were plotted (% transmittance versus time). Test agent (20 $\mu$L) was added at different concentrations prior to the addition of the platelet agonist. Results are expressed as % inhibition of agonist-induced platelet aggregation.

Human Aortic Smooth Muscle Cell Migration Assay

A method for assessing $\alpha_v\beta_3$-mediated smooth muscle cell migration and agents which inhibit $\alpha_v\beta_3$-mediated smooth muscle cell migration is described in Liaw et al., J. Clin. Invest. (1995) 95:713–724).

In Vivo Angiogenesis Model

A quantitative method for assessing angiogenesis and antiangiogenic agents is described in Passaniti et al., Laboratory Investigation (1992) 67:519–528

Pig Restenosis Model

A method for assessing restenosis and agents which inhibit restenosis is described in Schwartz et al., J. Am. College of Cardiology (1992) 19:267–274.

Mouse Retinopathy Model

A method for assessing retinopathy and agents which inhibit retinopathy is described in Smith et al., Invest. Ophthal. & Visual Science (1994) 35:101–111.

Dosage and Formulation

The compounds of this invention can be administered by any means that produces contact of the active agent with the agent's site of action, the $\alpha_v\beta_3$ integrin, in the body of a mammal. They can be administered by any conventional means available for use in conjunction with pharmaceuticals, either as individual therapeutic agents or in a combination of therapeutic agents, such as a antiplatelet agent such as aspirin, piroxicam, or ticlopidine which are agonist-specific, or an anti-coagulant such as warfarin or heparin, or a thrombin inhibitor such as a boropeptide, hirudin or argatroban, or a thrombolytic agent such as tissue plasminogen activator, anistreplase, urokinase or streptokinase, or combinations thereof. The compounds of the invention, or compounds of the invention in combination with other therapeutic agents, can be administered alone, but generally administered with a pharmaceutical carrier selected on the basis of the chosen route of administration and standard pharmaceutical practice.

The dosage of the novel cyclic compounds of this invention administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to 10 milligrams per kilogram of body weight.

Dosage forms (compositions suitable for administration) contain from about 0.1 milligram to about 100 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 10 milligrams of the active ingredient. The capsules are washed and dried.

Tablets

A large number of tablets are prepared by conventional procedures so that the dosage unit was 10 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

The combination products of this invention, such as the novel $\alpha_v\beta_3$ antagonist compounds of this invention in combination with an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, can be in any dosage form, such as those described above, and can also be administered in various ways, as described above.

In a preferred embodiment, the combination products of the invention are formulated together, in a single dosage form (that is, combined together in one capsule, tablet, powder, or liquid, etc.). When the combination products are not formulated together in a single dosage form, the $\alpha_v\beta_3$ antagonist compounds of this invention and the anti-coagulant agent, anti-platelet agent, thrombin inhibitor, and/or thrombolytic agent may be administered at the same time (that is, together), or in any order, for example the compounds of this invention are administered first, followed by administration of the anti-coagulant agent, anti-platelet agent, thrombin inhibitor, and/or thrombolytic agent. When not administered at the same time, preferably the administration of the compound of this invention and any anti-coagulant agent, anti-platelet agent, thrombin inhibitor, and/or thrombolytic agent occurs less than about one hour apart, more preferably less than about 30 minutes apart, even more preferably less than about 15 minutes apart, and most preferably less than about 5 minutes apart. Preferably, administration of the combination products of the invention is oral. The terms oral agent, oral inhibitor, oral compound, or the like, as used herein, denote compounds which may be orally administered. Although it is preferable that the $\alpha_v\beta_3$ antagonist compounds of this invention and the anti-coagulant agent, anti-platelet agent, thrombin inhibitor, and/or thrombolytic agent are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

As discussed above, where two or more of the foregoing therapeutic agents are combined or co-administered with the compounds of this invention, generally the amount of each component in a typical daily dosage and typical dosage form may be reduced relative to the usual dosage of the agent when administered alone, in view of the additive or synergistic effect which would be obtained as a result of addition of further agents in accordance with the present invention.

Particularly when provided as a single dosage form, the potential exists for a chemical interaction between the combined active ingredients (for example, a novel compound of this invention and an anti-coagulant such as warfarin or heparin, or a novel compound of this invention and an anti-platelet agent such as aspirin, piroxicam or ticlopidine, or a novel compound of this invention and a thrombin inhibitor such as a boropeptide, hirudin or argatroban, or a novel compound of this invention and a thrombolytic agent such as tissue plasminogen activator, anistreplase, urokinase or streptokinase, or combinations thereof). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

Pharmaceutical kits useful in, for example, the inhibition of thrombus formation, the prevention of blood clots, and/or the treatment of thromboembolic disorders, which comprise a therapeutically effective amount of a compound according to the method of the present invention along with a therapeutically effective amount of an anti-coagulant agent such as warfarin or heparin, or an anti-platelet agent such as aspirin, piroxicam or ticlopidine, or a thrombin inhibitor such as a boropeptide, hirudin or argatroban, or a thrombolytic agent such as tissue plasminogen activator, anistreplase, urokinase or streptokinase, or combinations thereof, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compounds according to the method of the invention and the anti-coagulant agent, anti-platelet agent, thrombin inhibitor, thrombolytic agent, and/or combinations thereof, may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

In Tables 1–4 below the structures which correspond to the names for the group $R^1$, eg Het-1, Het-2, Het-3, etc., are depicted below. Some of the heterocycles may exist as either a single prototropic tautomer or a mixture of prototropic tautomers. Additionally some of the heterocycles may exist as either a keto or enol tautomer or a mixture of both. The structure drawn does not constitute a limitation on the tautomeric form of the heterocycle. Structures defined under the heading $R^1$ are:

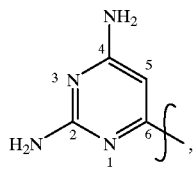

Het-1

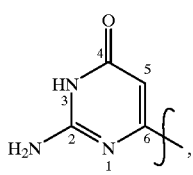

Het-2

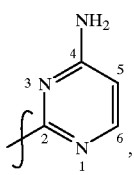

Het-3

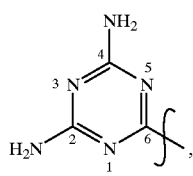

Het-4

-continued

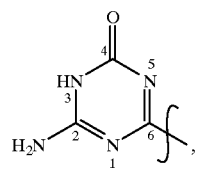

Het-5

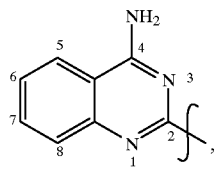

Het-6

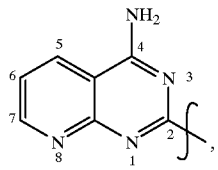

Het-7

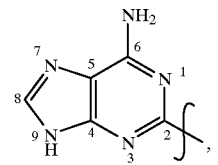

Het-8

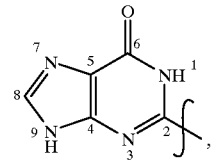

Het-9

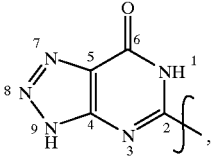

Het-10

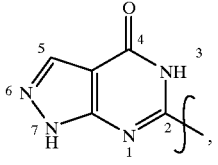

Het-11

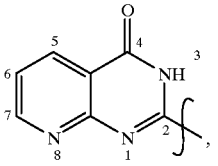

Het-12

-continued

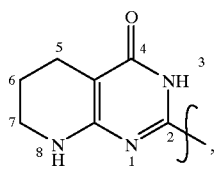
Het-13

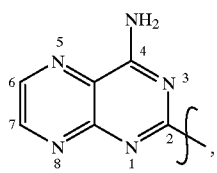
Het-14

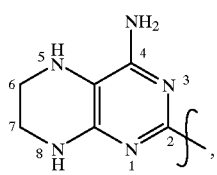
Het-15

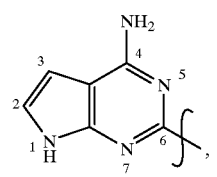
Het-16

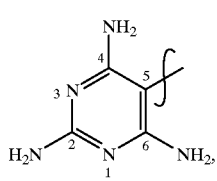
Het-17

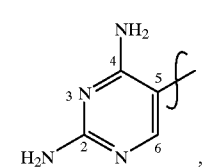
Het-18

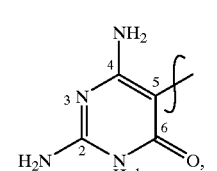
Het-19

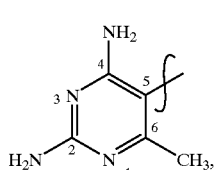
Het-20

-continued

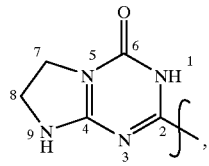
Het-21

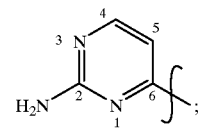
Het-22

Representative compounds of the present invention are listed in Tables 1–4 below.

TABLE 1

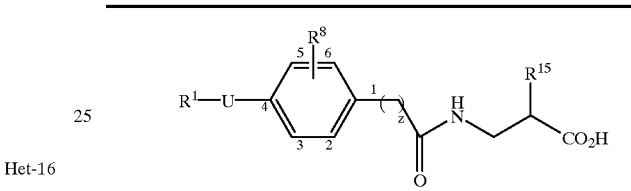

| Ex. No. | $R^1$ | U | $R^8$ | z | $R^{15}$ | MS |
|---|---|---|---|---|---|---|
| A-1 | Het-1 | $CH_2CH_2$ | H | 0 | $NHCO_2Et$ | |
| A-2 | Het-1 | $CH_2CH_2$ | H | 0 | $NHCO_2CH_2Ph$ | |
| A-3 | Het-1 | $CH_2CH_2$ | H | 0 | $NHCO_2$-n-Pr | |
| A-4 | Het-1 | $CH_2CH_2$ | H | 0 | $NHCO_2$-i-Pr | |
| A-5 | Het-1 | $CH_2CH_2$ | H | 0 | $NHCO_2$-n-Bu | |
| A-6 | Het-1 | $CH_2CH_2$ | H | 0 | $NHCO_2$-i-Bu | |
| A-7 | Het-1 | $CH_2CH_2$ | H | 0 | $NHCO_2$-n-$C_5H_{11}$ | |
| A-8 | Het-1 | $CH_2CH_2$ | H | 0 | $NHSO_2Ph$ | 485.0 |
| A-9 | Het-1 | $CH_2CH_2$ | H | 0 | $NHSO_2Ph(o-CH_3)$ | |
| A-10 | Het-1 | $CH_2CH_2$ | H | 0 | $NHSO_2Ph(m-CH_3)$ | |
| A-11 | Het-1 | $CH_2CH_2$ | H | 0 | $NHSO_2Ph(p-CH_3)$ | |
| A-12 | Het-1 | $CH_2CH_2$ | H | 0 | $NHSO_2Ph(o-Cl)$ | |
| A-13 | Het-1 | $CH_2CH_2$ | H | 0 | $NHSO_2Ph(m-Cl)$ | |
| A-14 | Het-1 | $CH_2CH_2$ | H | 0 | $NHSO_2Ph(p-Cl)$ | |
| A-15 | Het-1 | $CH_2CH_2$ | H | 0 | $NHSO_2Ph(m-F)$ | |
| A-16 | Het-1 | $CH_2CH_2$ | H | 0 | $NHSO_2Ph(p-F)$ | |
| A-17 | Het-1 | $CH_2CH_2$ | H | 0 | $NHSO_2Ph(o-F)$ | |
| A-18 | Het-1 | $CH_2CH_2$ | H | 0 | $NHSO_2Ph(m-Br)$ | |
| A-19 | Het-1 | $CH_2CH_2$ | H | 0 | $NHSO_2Ph(p-Br)$ | |
| A-20 | Het-1 | $CH_2CH_2$ | H | 0 | $NHSO_2Ph(o-OCH_3)$ | |
| A-21 | Het-1 | $CH_2CH_2$ | H | 0 | $NHSO_2Ph(m-OCH_3)$ | |
| A-22 | Het-1 | $CH_2CH_2$ | H | 0 | $NHSO_2Ph(p-OCH_3)$ | |
| A-23 | Het-1 | $CH_2CH_2$ | H | 0 | $NHSO_2$(2,4,6-trimethylphenyl) | 527.1 |
| A-24 | Het-1 | $CH_2CH_2$ | H | 0 | $NHSO_2$(2,4,6-trichlorophenyl) | |
| A-25 | Het-1 | $CH_2CH_2$ | H | 0 | $NHSO_2$(2,6-dichlorophenyl) | |
| A-26 | Het-1 | $CH_2CH_2$ | H | 0 | $NHSO_2$(2-chloro-6-methylphenyl) | |
| A-27 | Het-1 | $CH_2CH_2$ | H | 0 | NHSO2[4-(2,6-dimethylphenyl)phenyl | |
| A-28 | Het-1 | $CH_2CH_2$ | H | 0 | $NHSO_2C_6H_4$(4-Ph) | |
| A-29 | Het-1 | $CH_2CH_2$ | H | 0 | $NHSO_2$[4-(3,5-dimethyl)isoxazolyl] | |
| A-30 | Het-1 | $CH_2CH_2$ | H | 0 | $NHSO_2$(1-naphthyl) | |
| A-31 | Het-1 | $CH_2CH_2$ | H | 0 | $NHSO_2$(2-naphthyl) | |
| A-32 | Het-1 | $CH_2CH_2$ | H | 0 | $NHSO_2CH_2Ph$ | |
| A-33 | Het-1 | $CH_2CH_2$ | H | 0 | $NHSO_2NHCH_2Ph$ | |
| A-34 | Het-1 | $CH_2CH_2$ | H | 0 | $NHSO_2NHPh$ | |
| A-35 | Het-1 | $NHCH_2$ | H | 0 | $NHCO_2Et$ | |
| A-36 | Het-1 | $NHCH_2$ | H | 0 | $NHCO_2CH_2Ph$ | |
| A-37 | Het-1 | $NHCH_2$ | H | 0 | $NHCO_2$-n-Pr | |
| A-38 | Het-1 | $NHCH_2$ | H | 0 | $NHCO_2$-i-Pr | |
| A-39 | Het-1 | $NHCH_2$ | H | 0 | $NHCO_2$-n-Bu | |

TABLE 1-continued

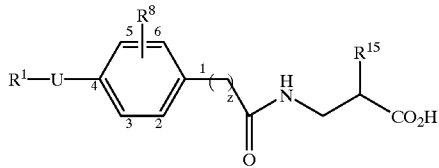

| Ex. No. | R¹ | U | R⁸ | z | R¹⁵ | MS |
|---|---|---|---|---|---|---|
| A-40 | Het-1 | NHCH₂ | H | 0 | NHCO₂-i-Bu | |
| A-41 | Het-1 | NHCH₂ | H | 0 | NHCO₂-n-C₅H₁₁ | |
| A-42 | Het-1 | NHCH₂ | H | 0 | NHSO₂Ph | |
| A-43 | Het-1 | NHCH₂ | H | 0 | NHSO₂Ph(o-CH₃) | |
| A-44 | Het-1 | NHCH₂ | H | 0 | NHSO₂Ph(m-CH₃) | |
| A-45 | Het-1 | NHCH₂ | H | 0 | NHSO₂Ph(p-CH₃) | |
| A-46 | Het-1 | NHCH₂ | H | 0 | NHSO₂Ph(o-Cl) | |
| A-47 | Het-1 | NHCH₂ | H | 0 | NHSO₂Ph(m-Cl) | |
| A-48 | Het-1 | NHCH₂ | H | 0 | NHSO₂Ph(p-Cl) | |
| A-49 | Het-1 | NHCH₂ | H | 0 | NHSO₂Ph(m-F) | |
| A-50 | Het-1 | NHCH₂ | H | 0 | NHSO₂Ph(p-F) | |
| A-51 | Het-1 | NHCH₂ | H | 0 | NHSO₂Ph(o-F) | |
| A-52 | Het-1 | NHCH₂ | H | 0 | NHSO₂Ph(m-Br) | |
| A-53 | Het-1 | NHCH₂ | H | 0 | NHSO₂Ph(p-Br) | |
| A-54 | Het-1 | NHCH₂ | H | 0 | NHSO₂Ph(o-OCH₃) | |
| A-55 | Het-1 | NHCH₂ | H | 0 | NHSO₂Ph(m-OCH₃) | |
| A-56 | Het-1 | NHCH₂ | H | 0 | NHSO₂Ph(p-OCH₃) | |
| A-57 | Het-1 | NHCH₂ | H | 0 | NHSO₂(2,4,6-trimethylphenyl) | |
| A-58 | Het-1 | NHCH₂ | H | 0 | NHSO₂(2,4,6-trichlorophenyl) | |
| A-59 | Het-1 | NHCH₂ | H | 0 | NHSO₂(2,6-dichlorophenyl) | |
| A-60 | Het-1 | NHCH₂ | H | 0 | NHSO₂(2-chloro-6-methylphenyl) | |
| A-61 | Het-1 | NHCH₂ | H | 0 | NHSO2[4-(2,6-dimethylphenyl)phenyl | |
| A-62 | Het-1 | NHCH₂ | H | 0 | NHSO₂C₆H₄(4-Ph) | |
| A-63 | Het-1 | NHCH₂ | H | 0 | NHSO₂[4-(3,5-dimethyl)isoxazolyl] | |
| A-64 | Het-1 | NHCH₂ | H | 0 | NHSO₂(1-naphthyl) | |
| A-65 | Het-1 | NHCH₂ | H | 0 | NHSO₂(2-naphthyl) | |
| A-66 | Het-1 | NHCH₂ | H | 0 | NHSO₂CH₂Ph | |
| A-67 | Het-1 | NHCH₂ | H | 0 | NHSO₂NHCH₂Ph | |
| A-68 | Het-1 | NHCH₂ | H | 0 | NHSO₂NHPh | |
| A-69 | Het-1 | OCH₂ | H | 0 | NHCO₂Et | |
| A-70 | Het-1 | OCH₂ | H | 0 | NHCO₂CH₂Ph | |
| A-71 | Het-1 | OCH₂ | H | 0 | NHCO₂-n-Pr | |
| A-72 | Het-1 | OCH₂ | H | 0 | NHCO₂-i-Pr | |
| A-73 | Het-1 | OCH₂ | H | 0 | NHCO₂-n-Bu | |
| A-74 | Het-1 | OCH₂ | H | 0 | NHCO₂-i-Bu | |
| A-75 | Het-1 | OCH₂ | H | 0 | NHCO₂-n-C₅H₁₁ | |
| A-76 | Het-1 | OCH₂ | H | 0 | NHSO₂Ph | |
| A-77 | Het-1 | OCH₂ | H | 0 | NHSO₂Ph(o-CH₃) | |
| A-78 | Het-1 | OCH₂ | H | 0 | NHSO₂Ph(m-CH₃) | |
| A-79 | Het-1 | OCH₂ | H | 0 | NHSO₂Ph(p-CH₃) | |
| A-80 | Het-1 | OCH₂ | H | 0 | NHSO₂Ph(o-Cl) | |
| A-81 | Het-1 | OCH₃ | H | 0 | NHSO₂Ph(m-Cl) | |
| A-82 | Het-1 | OCH₂ | H | 0 | NHSO₂Ph(p-Cl) | |
| A-83 | Het-1 | OCH₂ | H | 0 | NHSO₂Ph(m-F) | |
| A-84 | Het-1 | OCH₂ | H | 0 | NHSO₂Ph(p-F) | |
| A-85 | Het-1 | OCH₂ | H | 0 | NHSO₂Ph(o-F) | |
| A-86 | Het-1 | OCH₂ | H | 0 | NHSO₂Ph(m-Br) | |
| A-87 | Het-1 | OCH₂ | H | 0 | NHSO₂Ph(p-Br) | |
| A-88 | Het-1 | OCH₂ | H | 0 | NHSO₂Ph(o-OCH₃) | |
| A-89 | Het-1 | OCH₂ | H | 0 | NHSO₂Ph(m-OCH₃) | |
| A-90 | Het-1 | OCH₂ | H | 0 | NHSO₂Ph(p-OCH₃) | |
| A-91 | Het-1 | OCH₂ | H | 0 | NHSO₂(2,4,6-trimethylphenyl) | |
| A-92 | Het-1 | OCH₂ | H | 0 | NHSO₂(2,4,6-trichlorophenyl) | |
| A-93 | Het-1 | OCH₂ | H | 0 | NHSO₂(2,6-dichlorophenyl) | |
| A-94 | Het-1 | OCH₂ | H | 0 | NHSO₂(2-chloro-6-methylphenyl) | |
| A-95 | Het-1 | OCH₂ | H | 0 | NHSO2[4-(2,6-dimethylphenyl)phenyl | |
| A-96 | Het-1 | OCH₂ | H | 0 | NHSO₂C₆H₄(4-Ph) | |
| A-97 | Het-1 | OCH₂ | H | 0 | NHSO₂[4-(3,5-dimethyl)isoxazolyl] | |
| A-98 | Het-1 | OCH₂ | H | 0 | NHSO₂(1-naphthyl) | |
| A-99 | Het-1 | OCH₂ | H | 0 | NHSO₂(2-naphthyl) | |
| A-100 | Het-1 | OCH₂ | H | 0 | NHSO₂CH₂Ph | |
| A-101 | Het-1 | OCH₂ | H | 0 | NHSO₂NHCH₂Ph | |
| A-102 | Het-1 | OCH₂ | H | 0 | NHSO₂NHPh | |
| A-103 | Het-1 | CH₂CH₂CH₂ | H | 0 | NHCO₂Et | |
| A-104 | Het-1 | CH₂CH₂CH₂ | H | 0 | NHCO₂CH₂Ph | |
| A-105 | Het-1 | CH₂CH₂CH₂ | H | 0 | NHCO₂-n-Pr | |
| A-106 | Het-1 | CH₂CH₂CH₂ | H | 0 | NHCO₂-i-Pr | |
| A-107 | Het-1 | CH₂CH₂CH₂ | H | 0 | NHCO₂-n-Bu | |
| A-108 | Het-1 | CH₂CH₂CH₂ | H | 0 | NHCO₂-i-Bu | |
| A-109 | Het-1 | CH₂CH₂CH₂ | H | 0 | NHCO₂-n-C₅H₁₁ | |
| A-110 | Het-1 | CH₂CH₂CH₂ | H | 0 | NHSO₂Ph | |
| A-111 | Het-1 | CH₂CH₂CH₂ | H | 0 | NHSO₂Ph(o-CH₃) | |
| A-112 | Het-1 | CH₂CH₂CH₂ | H | 0 | NHSO₂Ph(m-CH₃) | |
| A-113 | Het-1 | CH₂CH₂CH₂ | H | 0 | NHSO₂Ph(p-CH₃) | |
| A-114 | Het-1 | CH₂CH₂CH₂ | H | 0 | NHSO₂Ph(o-Cl) | |
| A-115 | Het-1 | CH₂CH₂CH₂ | H | 0 | NHSO₂Ph(m-Cl) | |
| A-116 | Het-1 | CH₂CH₂CH₂ | H | 0 | NHSO₂Ph(p-Cl) | |
| A-117 | Het-1 | CH₂CH₂CH₂ | H | 0 | NHSO₂Ph(m-F) | |
| A-118 | Het-1 | CH₂CH₂CH₂ | H | 0 | NHSO₂Ph(p-F) | |
| A-119 | Het-1 | CH₂CH₂CH₂ | H | 0 | NHSO₂Ph(o-F) | |
| A-120 | Het-1 | CH₂CH₂CH₂ | H | 0 | NHSO₂Ph(m-Br) | |
| A-121 | Het-1 | CH₂CH₂CH₂ | H | 0 | NHSO₂Ph(p-Br) | |
| A-122 | Het-1 | CH₂CH₂CH₂ | H | 0 | NHSO₂Ph(o-OCH₃) | |
| A-123 | Het-1 | CH₂CH₂CH₂ | H | 0 | NHSO₂Ph(m-OCH₃) | |
| A-124 | Het-1 | CH₂CH₂CH₂ | H | 0 | NHSO₂Ph(p-OCH₃) | |
| A-125 | Het-1 | CH₂CH₂CH₂ | H | 0 | NHSO₂(2,4,6-trimethylphenyl) | |
| A-126 | Het-1 | CH₂CH₂CH₂ | H | 0 | NHSO₂(2,4,6-trichlorophenyl) | |
| A-127 | Het-1 | CH₂CH₂CH₂ | H | 0 | NHSO₂(2,6-dichlorophenyl) | |
| A-128 | Het-1 | CH₂CH₂CH₂ | H | 0 | NHSO₂(2-chloro-6-methylphenyl) | |
| A-129 | Het-1 | CH₂CH₂CH₂ | H | 0 | NHSO2[4-(2,6-dimethylphenyl)phenyl | |
| A-130 | Het-1 | CH₂CH₂CH₂ | H | 0 | NHSO₂C₆H₄(4-Ph) | |
| A-131 | Het-1 | CH₂CH₂CH₂ | H | 0 | NHSO₂[4-(3,5-dimethyl)isoxazolyl] | |
| A-132 | Het-1 | CH₂CH₂CH₂ | H | 0 | NHSO₂(1-naphthyl) | |
| A-133 | Het-1 | CH₂CH₂CH₂ | H | 0 | NHSO₂(2-naphthyl) | |
| A-134 | Het-1 | CH₂CH₂CH₂ | H | 0 | NHSO₂CH₂Ph | |
| A-135 | Het-1 | CH₂CH₂CH₂ | H | 0 | NHSO₂NHCH₂Ph | |
| A-136 | Het-1 | CH₂CH₂CH₂ | H | 0 | NHSO₂NHPh | |
| A-137 | Het-1 | NHCH₂CH₂ | H | 0 | NHCO₂Et | |
| A-138 | Het-1 | NHCH₂CH₂ | H | 0 | NHCO₂CH₂Ph | |
| A-139 | Het-1 | NHCH₂CH₂ | H | 0 | NHCO₂-n-Pr | |
| A-140 | Het-1 | NHCH₂CH₂ | H | 0 | NHCO₂-i-Pr | |
| A-141 | Het-1 | NHCH₂CH₂ | H | 0 | NHCO₂-n-Bu | |
| A-142 | Het-1 | NHCH₂CH₂ | H | 0 | NHCO₂-i-Bu | |
| A-143 | Het-1 | NHCH₂CH₂ | H | 0 | NHCO₂-n-C₅H₁₁ | |
| A-144 | Het-1 | NHCH₂CH₂ | H | 0 | NHSO₂Ph | |
| A-145 | Het-1 | NHCH₂CH₂ | H | 0 | NHSO₂Ph(o-CH₃) | |
| A-146 | Het-1 | NHCH₂CH₂ | H | 0 | NHSO₂Ph(m-CH₃) | |
| A-147 | Het-1 | NHCH₂CH₂ | H | 0 | NHSO₂Ph(p-CH₃) | |
| A-148 | Het-1 | NHCH₂CH₂ | H | 0 | NHSO₂Ph(o-Cl) | |
| A-149 | Het-1 | NHCH₂CH₂ | H | 0 | NHSO₂Ph(m-Cl) | |
| A-150 | Het-1 | NHCH₂CH₂ | H | 0 | NHSO₂Ph(p-Cl) | |
| A-151 | Het-1 | NHCH₂CH₂ | H | 0 | NHSO₂Ph(m-F) | |
| A-152 | Het-1 | NHCH₂CH₂ | H | 0 | NHSO₂Ph(p-F) | |
| A-153 | Het-1 | NHCH₂CH₂ | H | 0 | NHSO₂Ph(o-F) | |
| A-154 | Het-1 | NHCH₂CH₂ | H | 0 | NHSO₂Ph(m-Br) | |
| A-155 | Het-1 | NHCH₂CH₂ | H | 0 | NHSO₂Ph(p-Br) | |

TABLE 1-continued

R¹—U—[phenyl with R⁸ at 5,6 positions]—(CH₂)z—C(O)—NH—CH(R¹⁵)—CO₂H (with ring positions 1,2,3,4,5,6)

| Ex. No. | R¹ | U | R⁸ | z | R¹⁵ | MS |
|---|---|---|---|---|---|---|
| A-156 | Het-1 | NHCH$_2$CH$_2$ | H | 0 | NHSO$_2$Ph(o-OCH$_3$) | |
| A-157 | Het-1 | NHCH$_2$CH$_2$ | H | 0 | NHSO$_2$Ph(m-OCH$_3$) | |
| A-158 | Het-1 | NHCH$_2$CH$_2$ | H | 0 | NHSO$_2$Ph(p-OCH$_3$) | |
| A-159 | Het-1 | NHCH$_2$CH$_2$ | H | 0 | NHSO$_2$(2,4,6-trimethylphenyl) | |
| A-160 | Het-1 | NHCH$_2$CH$_2$ | H | 0 | NHSO$_2$(2,4,6-trichlorophenyl) | |
| A-161 | Het-1 | NHCH$_2$CH$_2$ | H | 0 | NHSO$_2$(2,6-dichlorophenyl) | |
| A-162 | Het-1 | NHCH$_2$CH$_2$ | H | 0 | NHSO$_2$(2-chloro-6-methylphenyl) | |
| A-163 | Het-1 | NHCH$_2$CH$_2$ | H | 0 | NHSO2[4-(2,6-dimethylphenyl)phenyl | |
| A-164 | Het-1 | NHCH$_2$CH$_2$ | H | 0 | NHSO$_2$C$_6$H$_4$(4-Ph) | |
| A-165 | Het-1 | NHCH$_2$CH$_2$ | H | 0 | NHSO$_2$[4-(3,5-dimethyl)isoxazolyl] | |
| A-166 | Het-1 | NHCH$_2$CH$_2$ | H | 0 | NHSO$_2$(1-naphthyl) | |
| A-167 | Het-1 | NHCH$_2$CH$_2$ | H | 0 | NHSO$_2$(2-naphthyl) | |
| A-168 | Het-1 | NHCH$_2$CH$_2$ | H | 0 | NHSO$_2$CH$_2$Ph | |
| A-169 | Het-1 | NHCH$_2$CH$_2$ | H | 0 | NHSO$_2$NHCH$_2$Ph | |
| A-170 | Het-1 | NHCH$_2$CH$_2$ | H | 0 | NHSO$_2$NHPh | |
| A-171 | Het-1 | OCH$_2$CH$_2$ | H | 0 | NHCO$_2$Et | |
| A-172 | Het-1 | OCH$_2$CH$_2$ | H | 0 | NHCO$_2$CH$_2$Ph | |
| A-173 | Het-1 | OCH$_2$CH$_2$ | H | 0 | NHCO$_2$-n-Pr | |
| A-174 | Het-1 | OCH$_2$CH$_2$ | H | 0 | NHCO$_2$-i-Pr | |
| A-175 | Het-1 | OCH$_2$CH$_2$ | H | 0 | NHCO$_2$-n-Bu | |
| A-176 | Het-1 | OCH$_2$CH$_2$ | H | 0 | NHCO$_2$-i-Bu | |
| A-177 | Het-1 | OCH$_2$CH$_2$ | H | 0 | NHCO$_2$-n-C$_5$H$_{11}$ | |
| A-178 | Het-1 | OCH$_2$CH$_2$ | H | 0 | NHSO$_2$Ph | |
| A-179 | Het-1 | OCH$_2$CH$_2$ | H | 0 | NHSO$_2$Ph(o-CH$_3$) | |
| A-180 | Het-1 | OCH$_2$CH$_2$ | H | 0 | NHSO$_2$Ph(m-CH$_3$) | |
| A-181 | Het-1 | OCH$_2$CH$_2$ | H | 0 | NHSO$_2$Ph(p-CH$_3$) | |
| A-182 | Het-1 | OCH$_2$CH$_2$ | H | 0 | NHSO$_2$Ph(o-Cl) | |
| A-183 | Het-1 | OCH$_2$CH$_2$ | H | 0 | NHSO$_2$Ph(m-Cl) | |
| A-184 | Het-1 | OCH$_2$CH$_2$ | H | 0 | NHSO$_2$Ph(p-Cl) | |
| A-185 | Het-1 | OCH$_2$CH$_2$ | H | 0 | NHSO$_2$Ph(m-F) | |
| A-186 | Het-1 | OCH$_2$CH$_2$ | H | 0 | NHSO$_2$Ph(p-F) | |
| A-187 | Het-1 | OCH$_2$CH$_2$ | H | 0 | NHSO$_2$Ph(o-F) | |
| A-188 | Het-1 | OCH$_2$CH$_2$ | H | 0 | NHSO$_2$Ph(m-Br) | |
| A-189 | Het-1 | OCH$_2$CH$_2$ | H | 0 | NHSO$_2$Ph(p-Br) | |
| A-190 | Het-1 | OCH$_2$CH$_2$ | H | 0 | NHSO$_2$Ph(o-OCH$_3$) | |
| A-191 | Het-1 | OCH$_2$CH$_2$ | H | 0 | NHSO$_2$Ph(m-OCH$_3$) | |
| A-192 | Het-1 | OCH$_2$CH$_2$ | H | 0 | NHSO$_2$Ph(p-OCH$_3$) | |
| A-193 | Het-1 | OCH$_2$CH$_2$ | H | 0 | NHSO$_2$(2,4,6-trimethylphenyl) | |
| A-194 | Het-1 | OCH$_2$CH$_2$ | H | 0 | NHSO$_2$(2,4,6-trichlorophenyl) | |
| A-195 | Het-1 | OCH$_2$CH$_2$ | H | 0 | NHSO$_2$(2,6-dichlorophenyl) | |
| A-196 | Het-1 | OCH$_2$CH$_2$ | H | 0 | NHSO$_2$(2-chloro-6-methylphenyl) | |
| A-197 | Het-1 | OCH$_2$CH$_2$ | H | 0 | NHSO2[4-(2,6-dimethylphenyl)phenyl | |
| A-198 | Het-1 | OCH$_2$CH$_2$ | H | 0 | NHSO$_2$C$_6$H$_4$(4-Ph) | |
| A-199 | Het-1 | OCH$_2$CH$_2$ | H | 0 | NHSO$_2$[4-(3,5-dimethyl)isoxazolyl] | |
| A-200 | Het-1 | OCH$_2$CH$_2$ | H | 0 | NHSO$_2$(1-naphthyl) | |
| A-201 | Het-1 | OCH$_2$CH$_2$ | H | 0 | NHSO$_2$(2-naphthyl) | |
| A-202 | Het-1 | OCH$_2$CH$_2$ | H | 0 | NHSO$_2$CH$_2$Ph | |
| A-203 | Het-1 | OCH$_2$CH$_2$ | H | 0 | NHSO$_2$NHCH$_2$Ph | |
| A-204 | Het-1 | OCH$_2$CH$_2$ | H | 0 | NHSO$_2$NHPh | |
| A-205 | Het-2 | CH$_2$CH$_2$ | H | 0 | NHCO$_2$Et | |
| A-206 | Het-2 | CH$_2$CH$_2$ | H | 0 | NHCO$_2$CH$_2$Ph | 479.9 |
| A-207 | Het-2 | CH$_2$CH$_2$ | H | 0 | NHCO$_2$-n-Pr | |
| A-208 | Het-2 | CH$_2$CH$_2$ | H | 0 | NHCO$_2$-i-Pr | |
| A-209 | Het-2 | CH$_2$CH$_2$ | H | 0 | NHCO$_2$-n-Bu | |
| A-210 | Het-2 | CH$_2$CH$_2$ | H | 0 | NHCO$_2$-i-Bu | 446.1 |
| A-211 | Het-2 | CH$_2$CH$_2$ | H | 0 | NHCO$_2$-n-C$_5$H$_{11}$ | |
| A-212 | Het-2 | CH$_2$CH$_2$ | H | 0 | NHSO$_2$Ph | |
| A-213 | Het-2 | CH$_2$CH$_2$ | H | 0 | NHSO$_2$Ph(o-CH$_3$) | |
| A-214 | Het-2 | CH$_2$CH$_2$ | H | 0 | NHSO$_2$Ph(m-CH$_3$) | |
| A-215 | Het-2 | CH$_2$CH$_2$ | H | 0 | NHSO$_2$Ph(p-CH$_3$) | |
| A-216 | Het-2 | CH$_2$CH$_2$ | H | 0 | NHSO$_2$Ph(o-Cl) | |
| A-217 | Het-2 | CH$_2$CH$_2$ | H | 0 | NHSO$_2$Ph(m-Cl) | |
| A-218 | Het-2 | CH$_2$CH$_2$ | H | 0 | NHSO$_2$Ph(p-Cl) | |
| A-219 | Het-2 | CH$_2$CH$_2$ | H | 0 | NHSO$_2$Ph(m-F) | |
| A-220 | Het-2 | CH$_2$CH$_2$ | H | 0 | NHSO$_2$Ph(p-F) | |
| A-221 | Het-2 | CH$_2$CH$_2$ | H | 0 | NHSO$_2$Ph(o-F) | |
| A-222 | Het-2 | CH$_2$CH$_2$ | H | 0 | NHSO$_2$Ph(m-Br) | |
| A-223 | Het-2 | CH$_2$CH$_2$ | H | 0 | NHSO$_2$Ph(p-Br) | |
| A-224 | Het-2 | CH$_2$CH$_2$ | H | 0 | NHSO$_2$Ph(o-OCH$_3$) | |
| A-225 | Het-2 | CH$_2$CH$_2$ | H | 0 | NHSO$_2$Ph(m-OCH$_3$) | |
| A-226 | Het-2 | CH$_2$CH$_2$ | H | 0 | NHSO$_2$Ph(p-OCH$_3$) | |
| A-227 | Het-2 | CH$_2$CH$_2$ | H | 0 | NHSO$_2$(2,4,6-trimethylphenyl) | 528.1 |
| A-228 | Het-2 | CH$_2$CH$_2$ | H | 0 | NHSO$_2$(2,4,6-trichlorophenyl) | |
| A-229 | Het-2 | CH$_2$CH$_2$ | H | 0 | NHSO$_2$(2,6-dichlorophenyl) | |
| A-230 | Het-2 | CH$_2$CH$_2$ | H | 0 | NHSO$_2$(2-chloro-6-methylphenyl) | |
| A-231 | Het-2 | CH$_2$CH$_2$ | H | 0 | NHSO2[4-(2,6-dimethylphenyl)phenyl | |
| A-232 | Het-2 | CH$_2$CH$_2$ | H | 0 | NHSO$_2$C$_6$H$_4$(4-Ph) | |
| A-233 | Het-2 | CH$_2$CH$_2$ | H | 0 | NHSO$_2$[4-(3,5-dimethyl)isoxazolyl] | |
| A-234 | Het-2 | CH$_2$CH$_2$ | H | 0 | NHSO$_2$(1-naphthyl) | |
| A-235 | Het-2 | CH$_2$CH$_2$ | H | 0 | NHSO$_2$(2-naphthyl) | |
| A-236 | Het-2 | CH$_2$CH$_2$ | H | 0 | NHSO$_2$CH$_2$Ph | |
| A-237 | Het-2 | CH$_2$CH$_2$ | H | 0 | NHSO$_2$NHCH$_2$Ph | |
| A-238 | Het-2 | CH$_2$CH$_2$ | H | 0 | NHSO$_2$NHPh | |
| A-239 | Het-2 | NHCH$_2$ | H | 0 | NHCO$_2$Et | |
| A-240 | Het-2 | NHCH$_2$ | H | 0 | NHCO$_2$CH$_2$Ph | |
| A-241 | Het-2 | NHCH$_2$ | H | 0 | NHCO$_2$-n-Pr | |
| A-242 | Het-2 | NHCH$_2$ | H | 0 | NHCO$_2$-i-Pr | |
| A-243 | Het-2 | NHCH$_2$ | H | 0 | NHCO$_2$-n-Bu | |
| A-244 | Het-2 | NHCH$_2$ | H | 0 | NHCO$_2$-i-Bu | |
| A-245 | Het-2 | NHCH$_2$ | H | 0 | NHCO$_2$-n-C$_5$H$_{11}$ | |
| A-246 | Het-2 | NHCH$_2$ | H | 0 | NHSO$_2$Ph | |
| A-247 | Het-2 | NHCH$_2$ | H | 0 | NHSO$_2$Ph(o-CH$_3$) | |
| A-248 | Het-2 | NHCH$_2$ | H | 0 | NHSO$_2$Ph(m-CH$_3$) | |
| A-249 | Het-2 | NHCH$_2$ | H | 0 | NHSO$_2$Ph(p-CH$_3$) | |
| A-250 | Het-2 | NHCH$_2$ | H | 0 | NHSO$_2$Ph(o-Cl) | |
| A-251 | Het-2 | NHCH$_2$ | H | 0 | NHSO$_2$Ph(m-Cl) | |
| A-252 | Het-2 | NHCH$_2$ | H | 0 | NHSO$_2$Ph(p-Cl) | |
| A-253 | Het-2 | NHCH$_2$ | H | 0 | NHSO$_2$Ph(m-F) | |
| A-254 | Het-2 | NHCH$_2$ | H | 0 | NHSO$_2$Ph(p-F) | |
| A-255 | Het-2 | NHCH$_2$ | H | 0 | NHSO$_2$Ph(o-F) | |
| A-256 | Het-2 | NHCH$_2$ | H | 0 | NHSO$_2$Ph(m-Br) | |
| A-257 | Het-2 | NHCH$_2$ | H | 0 | NHSO$_2$Ph(p-Br) | |
| A-258 | Het-2 | NHCH$_2$ | H | 0 | NHSO$_2$Ph(o-OCH$_3$) | |
| A-259 | Het-2 | NHCH$_2$ | H | 0 | NHSO$_2$Ph(m-OCH$_3$) | |
| A-260 | Het-2 | NHCH$_2$ | H | 0 | NHSO$_2$Ph(p-OCH$_3$) | |
| A-261 | Het-2 | NHCH$_2$ | H | 0 | NHSO$_2$(2,4,6-trimethylphenyl) | |
| A-262 | Het-2 | NHCH$_2$ | H | 0 | NHSO$_2$(2,4,6-trichlorophenyl) | |
| A-263 | Het-2 | NHCH$_2$ | H | 0 | NHSO$_2$(2,6-dichlorophenyl) | |
| A-264 | Het-2 | NHCH$_2$ | H | 0 | NHSO$_2$(2-chloro-6-methylphenyl) | |
| A-265 | Het-2 | NHCH$_2$ | H | 0 | NHSO2[4-(2,6-dimethylphenyl)phenyl | |
| A-266 | Het-2 | NHCH$_2$ | H | 0 | NHSO$_2$C$_6$H$_4$(4-Ph) | |

TABLE 1-continued $R^1-U$—[phenyl with $R^8$ at 5,6 positions]—$(C)_z$—C(O)—NH—CH($R^{15}$)—$CO_2H$

| Ex. No. | $R^1$ | U | $R^8$ | z | $R^{15}$ | MS |
|---|---|---|---|---|---|---|
| A-267 | Het-2 | $NHCH_2$ | H | 0 | $NHSO_2$[4-(3,5-dimethyl)isoxazolyl] | |
| A-268 | Het-2 | $NHCH_2$ | H | 0 | $NHSO_2$(1-naphthyl) | |
| A-269 | Het-2 | $NHCH_2$ | H | 0 | $NHSO_2$(2-naphthyl) | |
| A-270 | Het-2 | $NHCH_2$ | H | 0 | $NHSO_2CH_2Ph$ | |
| A-271 | Het-2 | $NHCH_2$ | H | 0 | $NHSO_2NHCH_2Ph$ | |
| A-272 | Het-2 | $NHCH_2$ | H | 0 | $NHSO_2NHPh$ | |
| A-273 | Het-2 | $OCH_2$ | H | 0 | $NHCO_2Et$ | |
| A-274 | Het-2 | $OCH_2$ | H | 0 | $NHCO_2CH_2Ph$ | |
| A-275 | Het-2 | $OCH_2$ | H | 0 | $NHCO_2$-n-Pr | |
| A-276 | Het-2 | $OCH_2$ | H | 0 | $NHCO_2$-i-Pr | |
| A-277 | Het-2 | $OCH_2$ | H | 0 | $NHCO_2$-n-Bu | |
| A-278 | Het-2 | $OCH_2$ | H | 0 | $NHCO_2$-i-Bu | |
| A-279 | Het-2 | $OCH_2$ | H | 0 | $NHCO_2$-n-$C_5H_{11}$ | |
| A-280 | Het-2 | $OCH_2$ | H | 0 | $NHSO_2Ph$ | |
| A-281 | Het-2 | $OCH_2$ | H | 0 | $NHSO_2Ph(o-CH_3)$ | |
| A-282 | Het-2 | $OCH_2$ | H | 0 | $NHSO_2Ph(m-CH_3)$ | |
| A-283 | Het-2 | $OCH_2$ | H | 0 | $NHSO_2Ph(p-CH_3)$ | |
| A-284 | Het-2 | $OCH_2$ | H | 0 | $NHSO_2Ph(o-Cl)$ | |
| A-285 | Het-2 | $OCH_2$ | H | 0 | $NHSO_2Ph(m-Cl)$ | |
| A-286 | Het-2 | $OCH_2$ | H | 0 | $NHSO_2Ph(p-Cl)$ | |
| A-287 | Het-2 | $OCH_2$ | H | 0 | $NHSO_2Ph(m-F)$ | |
| A-288 | Het-2 | $OCH_2$ | H | 0 | $NHSO_2Ph(p-F)$ | |
| A-289 | Het-2 | $OCH_2$ | H | 0 | $NHSO_2Ph(o-F)$ | |
| A-290 | Het-2 | $OCH_2$ | H | 0 | $NHSO_2Ph(m-Br)$ | |
| A-291 | Het-2 | $OCH_2$ | H | 0 | $NHSO_2Ph(p-Br)$ | |
| A-292 | Het-2 | $OCH_2$ | H | 0 | $NHSO_2Ph(o-OCH_3)$ | |
| A-293 | Het-2 | $OCH_2$ | H | 0 | $NHSO_2Ph(m-OCH_3)$ | |
| A-294 | Het-2 | $OCH_2$ | H | 0 | $NHSO_2Ph(p-OCH_3)$ | |
| A-295 | Het-2 | $OCH_2$ | H | 0 | $NHSO_2$(2,4,6-trimethylphenyl) | |
| A-296 | Het-2 | $OCH_2$ | H | 0 | $NHSO_2$(2,4,6-trichlorophenyl) | |
| A-297 | Het-2 | $OCH_2$ | H | 0 | $NHSO_2$(2,6-dichlorophenyl) | |
| A-298 | Het-2 | $OCH_2$ | H | 0 | $NHSO_2$(2-chloro-6-methylphenyl) | |
| A-299 | Het-2 | $OCH_2$ | H | 0 | NHSO2[4-(2,6-dimethylphenyl)phenyl | |
| A-300 | Het-2 | $OCH_2$ | H | 0 | $NHSO_2C_6H_4$(4-Ph) | |
| A-301 | Het-2 | $OCH_2$ | H | 0 | $NHSO_2$[4-(3,5-dimethyl)isoxazolyl] | |
| A-302 | Het-2 | $OCH_2$ | H | 0 | $NHSO_2$(1-naphthyl) | |
| A-303 | Het-2 | $OCH_2$ | H | 0 | $NHSO_2$(2-naphthyl) | |
| A-304 | Het-2 | $OCH_2$ | H | 0 | $NHSO_2CH_2Ph$ | |
| A-305 | Het-2 | $OCH_2$ | H | 0 | $NHSO_2NHCH_2Ph$ | |
| A-306 | Het-2 | $OCH_2$ | H | 0 | $NHSO_2NHPh$ | |
| A-307 | Het-2 | $CH_2CH_2CH_2$ | H | 0 | $NHCO_2Et$ | |
| A-308 | Het-2 | $CH_2CH_2CH_2$ | H | 0 | $NHCO_2CH_2Ph$ | |
| A-309 | Het-2 | $CH_2CH_2CH_2$ | H | 0 | $NHCO_2$-n-Pr | |
| A-310 | Het-2 | $CH_2CH_2CH_2$ | H | 0 | $NHCO_2$-i-Pr | |
| A-311 | Het-2 | $CH_2CH_2CH_2$ | H | 0 | $NHCO_2$-n-Bu | |
| A-312 | Het-2 | $CH_2CH_2CH_2$ | H | 0 | $NHCO_2$-i-Bu | |
| A-313 | Het-2 | $CH_2CH_2CH_2$ | H | 0 | $NHCO_2$-n-$C_5H_{11}$ | |
| A-314 | Het-2 | $CH_2CH_2CH_2$ | H | 0 | $NHSO_2Ph$ | |
| A-315 | Het-2 | $CH_2CH_2CH_2$ | H | 0 | $NHSO_2Ph(o-CH_3)$ | |
| A-316 | Het-2 | $CH_2CH_2CH_2$ | H | 0 | $NHSO_2Ph(m-CH_3)$ | |
| A-317 | Het-2 | $CH_2CH_2CH_2$ | H | 0 | $NHSO_2Ph(p-CH_3)$ | |
| A-318 | Het-2 | $CH_2CH_2CH_2$ | H | 0 | $NHSO_2Ph(o-Cl)$ | |
| A-319 | Het-2 | $CH_2CH_2CH_2$ | H | 0 | $NHSO_2Ph(m-Cl)$ | |
| A-320 | Het-2 | $CH_2CH_2CH_2$ | H | 0 | $NHSO_2Ph(p-Cl)$ | |
| A-321 | Het-2 | $CH_2CH_2CH_2$ | H | 0 | $NHSO_2Ph(m-F)$ | |
| A-322 | Het-2 | $CH_2CH_2CH_2$ | H | 0 | $NHSO_2Ph(p-F)$ | |
| A-323 | Het-2 | $CH_2CH_2CH_2$ | H | 0 | $NHSO_2Ph(o-F)$ | |
| A-324 | Het-2 | $CH_2CH_2CH_2$ | H | 0 | $NHSO_2Ph(m-Br)$ | |
| A-325 | Het-2 | $CH_2CH_2CH_2$ | H | 0 | $NHSO_2Ph(p-Br)$ | |
| A-326 | Het-2 | $CH_2CH_2CH_2$ | H | 0 | $NHSO_2Ph(o-OCH_3)$ | |
| A-327 | Het-2 | $CH_2CH_2CH_2$ | H | 0 | $NHSO_2Ph(m-OCH_3)$ | |
| A-328 | Het-2 | $CH_2CH_2CH_2$ | H | 0 | $NHSO_2Ph(p-OCH_3)$ | |
| A-329 | Het-2 | $CH_2CH_2CH_2$ | H | 0 | $NHSO_2$(2,4,6-trimethylphenyl) | |
| A-330 | Het-2 | $CH_2CH_2CH_2$ | H | 0 | $NHSO_2$(2,4,6-trichlorophenyl) | |
| A-331 | Het-2 | $CH_2CH_2CH_2$ | H | 0 | $NHSO_2$(2,6-dichlorophenyl) | |
| A-332 | Het-2 | $CH_2CH_2CH_2$ | H | 0 | $NHSO_2$(2-chloro-6-methylphenyl) | |
| A-333 | Het-2 | $CH_2CH_2CH_2$ | H | 0 | NHSO2[4-(2,6-dimethylphenyl)phenyl | |
| A-334 | Het-2 | $CH_2CH_2CH_2$ | H | 0 | $NHSO_2C_6H_4$(4-Ph) | |
| A-335 | Het-2 | $CH_2CH_2CH_2$ | H | 0 | $NHSO_2$[4-(3,5-dimethyl)isoxazolyl] | |
| A-336 | Het-2 | $CH_2CH_2CH_2$ | H | 0 | $NHSO_2$(1-naphthyl) | |
| A-337 | Het-2 | $CH_2CH_2CH_2$ | H | 0 | $NHSO_2$(2-naphthyl) | |
| A-338 | Het-2 | $CH_2CH_2CH_2$ | H | 0 | $NHSO_2CH_2Ph$ | |
| A-339 | Het-2 | $CH_2CH_2CH_2$ | H | 0 | $NHSO_2NHCH_2Ph$ | |
| A-340 | Het-2 | $CH_2CH_2CH_2$ | H | 0 | $NHSO_2NHPh$ | |
| A-341 | Het-2 | $NHCH_2CH_2$ | H | 0 | $NHCO_2Et$ | |
| A-342 | Het-2 | $NHCH_2CH_2$ | H | 0 | $NHCO_2CH_2Ph$ | |
| A-343 | Het-2 | $NHCH_2CH_2$ | H | 0 | $NHCO_2$-n-Pr | |
| A-344 | Het-2 | $NHCH_2CH_2$ | H | 0 | $NHCO_2$-i-Pr | |
| A-345 | Het-2 | $NHCH_2CH_2$ | H | 0 | $NHCO_2$-n-Bu | |
| A-346 | Het-2 | $NHCH_2CH_2$ | H | 0 | $NHCO_2$-i-Bu | |
| A-347 | Het-2 | $NHCH_2CH_2$ | H | 0 | $NHCO_2$-n-$C_5H_{11}$ | |
| A-348 | Het-2 | $NHCH_2CH_2$ | H | 0 | $NHSO_2Ph$ | |
| A-349 | Het-2 | $NHCH_2CH_2$ | H | 0 | $NHSO_2Ph(o-CH_3)$ | |
| A-350 | Het-2 | $NHCH_2CH_2$ | H | 0 | $NHSO_2Ph(m-CH_3)$ | |
| A-351 | Het-2 | $NHCH_2CH_2$ | H | 0 | $NHSO_2Ph(p-CH_3)$ | |
| A-352 | Het-2 | $NHCH_2CH_2$ | H | 0 | $NHSO_2Ph(o-Cl)$ | |
| A-353 | Het-2 | $NHCH_2CH_2$ | H | 0 | $NHSO_2Ph(m-Cl)$ | |
| A-354 | Het-2 | $NHCH_2CH_2$ | H | 0 | $NHSO_2Ph(p-Cl)$ | |
| A-355 | Het-2 | $NHCH_2CH_2$ | H | 0 | $NHSO_2Ph(m-F)$ | |
| A-356 | Het-2 | $NHCH_2CH_2$ | H | 0 | $NHSO_2Ph(p-F)$ | |
| A-357 | Het-2 | $NHCH_2CH_2$ | H | 0 | $NHSO_2Ph(o-F)$ | |
| A-358 | Het-2 | $NHCH_2CH_2$ | H | 0 | $NHSO_2Ph(m-Br)$ | |
| A-359 | Het-2 | $NHCH_2CH_2$ | H | 0 | $NHSO_2Ph(p-Br)$ | |
| A-360 | Het-2 | $NHCH_2CH_2$ | H | 0 | $NHSO_2Ph(o-OCH_3)$ | |
| A-361 | Het-2 | $NHCH_2CH_2$ | H | 0 | $NHSO_2Ph(m-OCH_3)$ | |
| A-362 | Het-2 | $NHCH_2CH_2$ | H | 0 | $NHSO_2Ph(p-OCH_3)$ | |
| A-363 | Het-2 | $NHCH_2CH_2$ | H | 0 | $NHSO_2$(2,4,6-trimethylphenyl) | |
| A-364 | Het-2 | $NHCH_2CH_2$ | H | 0 | $NHSO_2$(2,4,6-trichlorophenyl) | |
| A-365 | Het-2 | $NHCH_2CH_2$ | H | 0 | $NHSO_2$(2,6-dichlorophenyl) | |
| A-366 | Het-2 | $NHCH_2CH_2$ | H | 0 | $NHSO_2$(2-chloro-6-methylphenyl) | |
| A-367 | Het-2 | $NHCH_2CH_2$ | H | 0 | NHSO2[4-(2,6-dimethylphenyl)phenyl | |
| A-368 | Het-2 | $NHCH_2CH_2$ | H | 0 | $NHSO_2C_6H_4$(4-Ph) | |
| A-369 | Het-2 | $NHCH_2CH_2$ | H | 0 | $NHSO_2$[4-(3,5-dimethyl)isoxazolyl] | |
| A-370 | Het-2 | $NHCH_2CH_2$ | H | 0 | $NHSO_2$(1-naphthyl) | |
| A-371 | Het-2 | $NHCH_2CH_2$ | H | 0 | $NHSO_2$(2-naphthyl) | |
| A-372 | Het-2 | $NHCH_2CH_2$ | H | 0 | $NHSO_2CH_2Ph$ | |
| A-373 | Het-2 | $NHCH_2CH_2$ | H | 0 | $NHSO_2NHCH_2Ph$ | |
| A-374 | Het-2 | $NHCH_2CH_2$ | H | 0 | $NHSO_2NHPh$ | |
| A-375 | Het-2 | $OCH_2CH_2$ | H | 0 | $NHCO_2Et$ | |
| A-376 | Het-2 | $OCH_2CH_2$ | H | 0 | $NHCO_2CH_2Ph$ | |
| A-377 | Het-2 | $OCH_2CH_2$ | H | 0 | $NHCO_2$-n-Pr | |
| A-378 | Het-2 | $OCH_2CH_2$ | H | 0 | $NHCO_2$-i-Pr | |
| A-379 | Het-2 | $OCH_2CH_2$ | H | 0 | $NHCO_2$-n-Bu | |
| A-380 | Het-2 | $OCH_2CH_2$ | H | 0 | $NHCO_2$-i-Bu | |
| A-381 | Het-2 | $OCH_2CH_2$ | H | 0 | $NHCO_2$-n-$C_5H_{11}$ | |

TABLE 1-continued

Structure: R¹—U—[phenyl with positions 2,3,4,5,6 and R⁸]—(CH₂)z—C(=O)—NH—CH(R¹⁵)—CO₂H

| Ex. No. | R¹ | U | R⁸ | z | R¹⁵ | MS |
|---|---|---|---|---|---|---|
| A-382 | Het-2 | OCH₂CH₂ | H | 0 | NHSO₂Ph | |
| A-383 | Het-2 | OCH₂CH₂ | H | 0 | NHSO₂Ph(o-CH₃) | |
| A-384 | Het-2 | OCH₂CH₂ | H | 0 | NHSO₂Ph(m-CH₃) | |
| A-385 | Het-2 | OCH₂CH₂ | H | 0 | NHSO₂Ph(p-CH₃) | |
| A-386 | Het-2 | OCH₂CH₂ | H | 0 | NHSO₂Ph(o-Cl) | |
| A-387 | Het-2 | OCH₂CH₂ | H | 0 | NHSO₂Ph(m-Cl) | |
| A-388 | Het-2 | OCH₂CH₂ | H | 0 | NHSO₂Ph(p-Cl) | |
| A-389 | Het-2 | OCH₂CH₂ | H | 0 | NHSO₂Ph(m-F) | |
| A-390 | Het-2 | OCH₂CH₂ | H | 0 | NHSO₂Ph(p-F) | |
| A-391 | Het-2 | OCH₂CH₂ | H | 0 | NHSO₂Ph(o-F) | |
| A-392 | Het-2 | OCH₂CH₂ | H | 0 | NHSO₂Ph(m-Br) | |
| A-393 | Het-2 | OCH₂CH₂ | H | 0 | NHSO₂Ph(p-Br) | |
| A-394 | Het-2 | OCH₂CH₂ | H | 0 | NHSO₂Ph(o-OCH₃) | |
| A-395 | Het-2 | OCH₂CH₂ | H | 0 | NHSO₂Ph(m-OCH₃) | |
| A-396 | Het-2 | OCH₂CH₂ | H | 0 | NHSO₂Ph(p-OCH₃) | |
| A-397 | Het-2 | OCH₂CH₂ | H | 0 | NHSO₂(2,4,6-trimethylphenyl) | |
| A-398 | Het-2 | OCH₂CH₂ | H | 0 | NHSO₂(2,4,6-trichlorophenyl) | |
| A-399 | Het-2 | OCH₂CH₂ | H | 0 | NHSO₂(2,6-dichlorophenyl) | |
| A-400 | Het-2 | OCH₂CH₂ | H | 0 | NHSO₂(2-chloro-6-methylphenyl) | |
| A-401 | Het-2 | OCH₂CH₂ | H | 0 | NHSO2[4-(2,6-dimethylphenyl)phenyl | |
| A-402 | Het-2 | OCH₂CH₂ | H | 0 | NHSO₂C₆H₄(4-Ph) | |
| A-403 | Het-2 | OCH₂CH₂ | H | 0 | NHSO₂[4-(3,5-dimethyl)isoxazolyl] | |
| A-404 | Het-2 | OCH₂CH₂ | H | 0 | NHSO₂(1-naphthyl) | |
| A-405 | Het-2 | OCH₂CH₂ | H | 0 | NHSO₂(2-naphthyl) | |
| A-406 | Het-2 | OCH₂CH₂ | H | 0 | NHSO₂CH₂Ph | |
| A-407 | Het-2 | OCH₂CH₂ | H | 0 | NHSO₂NHCH₂Ph | |
| A-408 | Het-2 | OCH₂CH₂ | H | 0 | NHSO₂NHPh | |
| A-409 | Het-3 | NHCH₂ | H | 0 | NHCO₂Et | |
| A-410 | Het-3 | NHCH₂ | H | 0 | NHCO₂CH₂Ph | |
| A-411 | Het-3 | NHCH₂ | H | 0 | NHCO₂-n-Pr | |
| A-412 | Het-3 | NHCH₂ | H | 0 | NHCO₂-i-Pr | |
| A-413 | Het-3 | NHCH₂ | H | 0 | NHCO₂-n-Bu | |
| A-414 | Het-3 | NHCH₂ | H | 0 | NHCO₂-i-Bu | |
| A-415 | Het-3 | NHCH₂ | H | 0 | NHCO₂-n-C₅H₁₁ | |
| A-416 | Het-3 | NHCH₂ | H | 0 | NHSO₂Ph | |
| A-417 | Het-3 | NHCH₂ | H | 0 | NHSO₂Ph(o-CH₃) | |
| A-418 | Het-3 | NHCH₂ | H | 0 | NHSO₂Ph(m-CH₃) | |
| A-419 | Het-3 | NHCH₂ | H | 0 | NHSO₂Ph(p-CH₃) | |
| A-420 | Het-3 | NHCH₂ | H | 0 | NHSO₂Ph(o-Cl) | |
| A-421 | Het-3 | NHCH₂ | H | 0 | NHSO₂Ph(m-Cl) | |
| A-422 | Het-3 | NHCH₂ | H | 0 | NHSO₂Ph(p-Cl) | |
| A-423 | Het-3 | NHCH₂ | H | 0 | NHSO₂Ph(m-F) | |
| A-424 | Het-3 | NHCH₂ | H | 0 | NHSO₂Ph(p-F) | |
| A-425 | Het-3 | NHCH₂ | H | 0 | NHSO₂Ph(o-F) | |
| A-426 | Het-3 | NHCH₂ | H | 0 | NHSO₂Ph(m-Br) | |
| A-427 | Het-3 | NHCH₂ | H | 0 | NHSO₂Ph(p-Br) | |
| A-428 | Het-3 | NHCH₂ | H | 0 | NHSO₂Ph(o-OCH₃) | |
| A-429 | Het-3 | NHCH₂ | H | 0 | NHSO₂Ph(m-OCH₃) | |
| A-430 | Het-3 | NHCH₂ | H | 0 | NHSO₂Ph(p-OCH₃) | |
| A-431 | Het-3 | NHCH₂ | H | 0 | NHSO₂(2,4,6-trimethylphenyl) | |
| A-432 | Het-3 | NHCH₂ | H | 0 | NHSO₂(2,4,6-trichlorophenyl) | |
| A-433 | Het-3 | NHCH₂ | H | 0 | NHSO₂(2,6-dichlorophenyl) | |
| A-434 | Het-3 | NHCH₂ | H | 0 | NHSO₂(2-chloro-6-methylphenyl) | |
| A-435 | Het-3 | NHCH₂ | H | 0 | NHSO2[4-(2,6-dimethylphenyl)phenyl | |
| A-436 | Het-3 | NHCH₂ | H | 0 | NHSO₂C₆H₄(4-Ph) | |
| A-437 | Het-3 | NHCH₂ | H | 0 | NHSO₂[4-(3,5-dimethyl)isoxazolyl] | |
| A-438 | Het-3 | NHCH₂ | H | 0 | NHSP₂(1-naphthyl) | |
| A-439 | Het-3 | NHCH₂ | H | 0 | NHSO₂(2-naphthyl) | |
| A-440 | Het-3 | NHCH₂ | H | 0 | NHSO₂CH₂Ph | |
| A-441 | Het-3 | NHCH₂CH₂ | H | 0 | NHCO₂Et | |
| A-442 | Het-3 | NHCH₂CH₂ | H | 0 | NHCO₂CH₂Ph | |
| A-443 | Het-3 | NHCH₂CH₂ | H | 0 | NHCO₂-n-Pr | |
| A-444 | Het-3 | NHCH₂CH₂ | H | 0 | NHCO₂-i-Pr | |
| A-445 | Het-3 | NHCH₂CH₂ | H | 0 | NHCO₂-n-Bu | |
| A-446 | Het-3 | NHCH₂CH₂ | H | 0 | NHCO₂-i-Bu | |
| A-447 | Het-3 | NHCH₂CH₂ | H | 0 | NHCO₂-n-C₅H₁₁ | |
| A-448 | Het-3 | NHCH₂CH₂ | H | 0 | NHSO₂Ph | |
| A-449 | Het-3 | NHCH₂CH₂ | H | 0 | NHSO₂Ph(o-CH₃) | |
| A-450 | Het-3 | NHCH₂CH₂ | H | 0 | NHSO₂Ph(m-CH₃) | |
| A-451 | Het-3 | NHCH₂CH₂ | H | 0 | NHSO₂Ph(p-CH₃) | |
| A-452 | Het-3 | NHCH₂CH₂ | H | 0 | NHSO₂Ph(o-Cl) | |
| A-453 | Het-3 | NHCH₂CH₂ | H | 0 | NHSO₂Ph(m-Cl) | |
| A-454 | Het-3 | NHCH₂CH₂ | H | 0 | NHSO₂Ph(p-Cl) | |
| A-455 | Het-3 | NHCH₂CH₂ | H | 0 | NHSO₂Ph(m-F) | |
| A-456 | Het-3 | NHCH₂CH₂ | H | 0 | NHSO₂Ph(p-F) | |
| A-457 | Het-3 | NHCH₂CH₂ | H | 0 | NHSO₂Ph(o-F) | |
| A-458 | Het-3 | NHCH₂CH₂ | H | 0 | NHSO₂Ph(m-Br) | |
| A-459 | Het-3 | NHCH₂CH₂ | H | 0 | NHSO₂Ph(p-Br) | |
| A-460 | Het-3 | NHCH₂CH₂ | H | 0 | NHSO₂Ph(o-OCH₃) | |
| A-461 | Het-3 | NHCH₂CH₂ | H | 0 | NHSO₂Ph(m-OCH₃) | |
| A-462 | Het-3 | NHCH₂CH₂ | H | 0 | NHSO₂Ph(p-OCH₃) | |
| A-463 | Het-3 | NHCH₂CH₂ | H | 0 | NHSO₂(2,4,6-trimethylphenyl) | |
| A-464 | Het-3 | NHCH₂CH₂ | H | 0 | NHSO₂(2,4,6-trichlorophenyl) | |
| A-465 | Het-3 | NHCH₂CH₂ | H | 0 | NHSO₂(2,6-dichlorophenyl) | |
| A-466 | Het-3 | NHCH₂CH₂ | H | 0 | NHSO₂(2-chloro-6-methylphenyl) | |
| A-467 | Het-3 | NHCH₂CH₂ | H | 0 | NHSO2[4-(2,6-dimethylphenyl)phenyl | |
| A-468 | Het-3 | NHCH₂CH₂ | H | 0 | NHSO₂C₆H₄(4-Ph) | |
| A-469 | Het-3 | NHCH₂CH₂ | H | 0 | NHSO₂[4-(3,5-dimethyl)isoxazolyl] | |
| A-470 | Het-3 | NHCH₂CH₂ | H | 0 | NHSO₂(1-naphthyl) | |
| A-471 | Het-3 | NHCH₂CH₂ | H | 0 | NHSO₂(2-naphthyl) | |
| A-472 | Het-3 | NHCH₂CH₂ | H | 0 | NHSO₂CH₂Ph | |
| A-473 | Het-3 | NHCH₂CH₂ | H | 0 | NHSO₂NHCH₂Ph | |
| A-474 | Het-3 | NHCH₂CH₂ | H | 0 | NHSO₂NHPh | |
| A-475 | Het-4 | CH₂CH₂ | H | 0 | NHCO₂-n-Pr | |
| A-476 | Het-4 | CH₂CH₂ | H | 0 | NHCO₂-i-Pr | |
| A-477 | Het-4 | CH₂CH₂ | H | 0 | NHCO₂-n-Bu | |
| A-478 | Het-4 | CH₂CH₂ | H | 0 | NHCO₂-i-Bu | |
| A-479 | Het-4 | CH₂CH₂ | H | 0 | NHSO₂Ph | |
| A-480 | Het-4 | CH₂CH₂ | H | 0 | NHSO₂Ph(p-Cl) | |
| A-481 | Het-4 | CH₂CH₂ | H | 0 | NHSO₂Ph(p-F) | |
| A-482 | Het-4 | CH₂CH₂ | H | 0 | NHSO₂(2,4,6-trimethylphenyl) | 528.1 |
| A-483 | Het-4 | CH₂CH₂ | H | 0 | NHSO₂(2,4,6-trichlorophenyl) | |
| A-484 | Het-4 | CH₂CH₂ | H | 0 | NHSO₂(2,6-dichlorophenyl) | |
| A-485 | Het-4 | CH₂CH₂ | H | 0 | NHSO2[4-(2,6-dimethylphenyl)phenyl | |
| A-486 | Het-4 | CH₂CH₂ | H | 0 | NHSO₂C₆H₄(4-Ph) | |
| A-487 | Het-4 | CH₂CH₂ | H | 0 | NHSO₂[4-(3,5-dimethyl)isoxazolyl] | |
| A-488 | Het-4 | CH₂CH₂ | H | 0 | NHSO₂(1-naphthyl) | |
| A-489 | Het-4 | NHCH₂ | H | 0 | NHCO₂-n-Pr | |
| A-490 | Het-4 | NHCH₂ | H | 0 | NHCO₂-i-Pr | |
| A-491 | Het-4 | NHCH₂ | H | 0 | NHCO₂-n-Bu | |

TABLE 1-continued

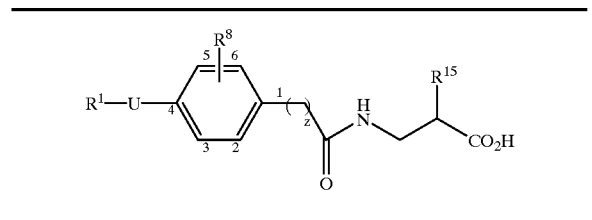

| Ex. No. | $R^1$ | U | $R^8$ | z | $R^{15}$ | MS |
|---|---|---|---|---|---|---|
| A-492 | Het-4 | NHCH$_2$ | H | 0 | NHCO$_2$-i-Bu | |
| A-493 | Het-4 | NHCH$_2$ | H | 0 | NHSO$_2$Ph | |
| A-494 | Het-4 | NHCH$_2$ | H | 0 | NHSO$_2$Ph(p-Cl) | |
| A-495 | Het-4 | NHCH$_2$ | H | 0 | NHSO$_2$Ph(p-F) | |
| A-496 | Het-4 | NHCH$_2$ | H | 0 | NHSO$_2$(2,4,6-trimethylphenyl) | |
| A-497 | Het-4 | NHCH$_2$ | H | 0 | NHSO$_2$(2,4,6-trichlorophenyl) | |
| A-498 | Het-4 | NHCH$_2$ | H | 0 | NHSO$_2$(2,6-dichlorophenyl) | |
| A-499 | Het-4 | NHCH$_2$ | H | 0 | NHSO2[4-(2,6-dimethylphenyl)phenyl | |
| A-500 | Het-4 | NHCH$_2$ | H | 0 | NHSO$_2$C$_6$H$_4$(4-Ph) | |
| A-501 | Het-4 | NHCH$_2$ | H | 0 | NHSO$_2$[4-(3,5-dimethyl)isoxazolyl] | |
| A-502 | Het-4 | NHCH$_2$ | H | 0 | NHSO$_2$(1-naphthyl) | |
| A-503 | Het-4 | OCH$_2$ | H | 0 | NHCO$_2$-n-Pr | |
| A-504 | Het-4 | OCH$_2$ | H | 0 | NHCO$_2$-i-Pr | |
| A-505 | Het-4 | OCH$_2$ | H | 0 | NHCO$_2$-n-Bu | |
| A-506 | Het-4 | OCH$_2$ | H | 0 | NHCO$_2$-i-Bu | |
| A-507 | Het-4 | OCH$_2$ | H | 0 | NHSO$_2$Ph | |
| A-508 | Het-4 | OCH$_2$ | H | 0 | NHSO$_2$Ph(p-Cl) | |
| A-509 | Het-4 | OCH$_2$ | H | 0 | NHSO$_2$Ph(p-F) | |
| A-510 | Het-4 | OCH$_2$ | H | 0 | NHSO$_2$(2,4,6-trimethylphenyl) | |
| A-511 | Het-4 | OCH$_2$ | H | 0 | NHSO$_2$(2,4,6-trichlorophenyl) | |
| A-512 | Het-4 | OCH$_2$ | H | 0 | NHSO$_2$(2,6-dichlorophenyl) | |
| A-513 | Het-4 | OCH$_2$ | H | 0 | NHSO2[4-(2,6-dimethylphenyl)phenyl | |
| A-514 | Het-4 | OCH$_2$ | H | 0 | NHSO$_2$C$_6$H$_4$(4-Ph) | |
| A-515 | Het-4 | OCH$_2$ | H | 0 | NHSO$_2$[4-(3,5-dimethyl)isoxazolyl] | |
| A-516 | Het-4 | OCH$_2$ | H | 0 | NHSO$_2$(1-naphthyl) | |
| A-517 | Het-4 | CH$_2$CH$_2$CH$_2$ | H | 0 | NHCO$_2$-n-Pr | |
| A-518 | Het-4 | CH$_2$CH$_2$CH$_2$ | H | 0 | NHCO$_2$-i-Pr | |
| A-519 | Het-4 | CH$_2$CH$_2$CH$_2$ | H | 0 | NHCO$_2$-n-Bu | |
| A-520 | Het-4 | CH$_2$CH$_2$CH$_2$ | H | 0 | NHCO$_2$-i-Bu | |
| A-521 | Het-4 | CH$_2$CH$_2$CH$_2$ | H | 0 | NHSO$_2$Ph | |
| A-522 | Het-4 | CH$_2$CH$_2$CH$_2$ | H | 0 | NHSO$_2$Ph(p-Cl) | |
| A-523 | Het-4 | CH$_2$CH$_2$CH$_2$ | H | 0 | NHSO$_2$Ph(p-F) | |
| A-524 | Het-4 | CH$_2$CH$_2$CH$_2$ | H | 0 | NHSO$_2$(2,4,6-trimethylphenyl) | |
| A-525 | Het-4 | CH$_2$CH$_2$CH$_2$ | H | 0 | NHSO$_2$(2,4,6-trichlorophenyl) | |
| A-526 | Het-4 | CH$_2$CH$_2$CH$_2$ | H | 0 | NHSO$_2$(2,6-dichlorophenyl) | |
| A-527 | Het-4 | CH$_2$CH$_2$CH$_2$ | H | 0 | NHSO2[4-(2,6-dimethylphenyl)phenyl | |
| A-528 | Het-4 | CH$_2$CH$_2$CH$_2$ | H | 0 | NHSO$_2$C$_6$H$_4$(4-Ph) | |
| A-529 | Het-4 | CH$_2$CH$_2$CH$_2$ | H | 0 | NHSO$_2$[4-(3,5-dimethyl)isoxazolyl] | |
| A-530 | Het-4 | CH$_2$CH$_2$CH$_2$ | H | 0 | NHSO$_2$(1-naphthyl) | |
| A-531 | Het-4 | NHCH$_2$CH$_2$ | H | 0 | NHCO$_2$-n-Pr | |
| A-532 | Het-4 | NHCH$_2$CH$_2$ | H | 0 | NHCO$_2$-i-Pr | |
| A-533 | Het-4 | NHCH$_2$CH$_2$ | H | 0 | NHCO$_2$-n-Bu | |
| A-534 | Het-4 | NHCH$_2$CH$_2$ | H | 0 | NHCO$_2$-i-Bu | |
| A-535 | Het-4 | NHCH$_2$CH$_2$ | H | 0 | NHSO$_2$Ph | |
| A-536 | Het-4 | NHCH$_2$CH$_2$ | H | 0 | NHSO$_2$Ph(p-Cl) | |
| A-537 | Het-4 | NHCH$_2$CH$_2$ | H | 0 | NHSO$_2$Ph(p-F) | |
| A-538 | Het-4 | NHCH$_2$CH$_2$ | H | 0 | NHSO$_2$(2,4,6-trimethylphenyl) | |
| A-539 | Het-4 | NHCH$_2$CH$_2$ | H | 0 | NHSO$_2$(2,4,6-trichlorophenyl) | |
| A-540 | Het-4 | NHCH$_2$CH$_2$ | H | 0 | NHSO$_2$(2,6-dichlorophenyl) | |
| A-541 | Het-4 | NHCH$_2$CH$_2$ | H | 0 | NHSO2[4-(2,6-dimethylphenyl)phenyl | |
| A-542 | Het-4 | NHCH$_2$CH$_2$ | H | 0 | NHSO$_2$C$_6$H$_4$(4-Ph) | |
| A-543 | Het-4 | NHCH$_2$CH$_2$ | H | 0 | NHSO$_2$[4-(3,5-dimethyl)isoxazolyl] | |
| A-544 | Het-4 | NHCH$_2$CH$_2$ | H | 0 | NHSO$_2$(1-naphthyl) | |
| A-545 | Het-4 | OCH$_2$CH$_2$ | H | 0 | NHCO$_2$-n-Pr | |
| A-546 | Het-4 | OCH$_2$CH$_2$ | H | 0 | NHCO$_2$-i-Pr | |
| A-547 | Het-4 | OCH$_2$CH$_2$ | H | 0 | NHCO$_2$-n-Bu | |
| A-548 | Het-4 | OCH$_2$CH$_2$ | H | 0 | NHCO$_2$-i-Bu | |
| A-549 | Het-4 | OCH$_2$CH$_2$ | H | 0 | NHSO$_2$Ph | |
| A-550 | Het-4 | OCH$_2$CH$_2$ | H | 0 | NHSO$_2$Ph(p-Cl) | |
| A-551 | Het-4 | OCH$_2$CH$_2$ | H | 0 | NHSO$_2$Ph(p-F) | |
| A-552 | Het-4 | OCH$_2$CH$_2$ | H | 0 | NHSO$_2$(2,4,6-trimethylphenyl) | |
| A-553 | Het-4 | OCH$_2$CH$_2$ | H | 0 | NHSO$_2$(2,4,6-trichlorophenyl) | |
| A-554 | Het-4 | OCH$_2$CH$_2$ | H | 0 | NHSO$_2$(2,6-dichlorophenyl) | |
| A-555 | Het-4 | OCH$_2$CH$_2$ | H | 0 | NHSO2[4-(2,6-dimethylphenyl)phenyl | |
| A-556 | Het-4 | OCH$_2$CH$_2$ | H | 0 | NHSO$_2$C$_6$H$_4$(4-Ph) | |
| A-557 | Het-4 | OCH$_2$CH$_2$ | H | 0 | NHSO$_2$[4-(3,5-dimethyl)isoxazolyl] | |
| A-558 | Het-4 | OCH$_2$CH$_2$ | H | 0 | NHSO$_2$(1-naphthyl) | |
| A-559 | Het-5 | CH$_2$CH$_2$ | H | 0 | NHCO$_2$-n-Pr | |
| A-560 | Het-5 | CH$_2$CH$_2$ | H | 0 | NHCO$_2$-i-Pr | |
| A-561 | Het-5 | CH$_2$CH$_2$ | H | 0 | NHCO$_2$-n-Bu | |
| A-562 | Het-5 | CH$_2$CH$_2$ | H | 0 | NHCO$_2$-i-Bu | |
| A-563 | Het-5 | CH$_2$CH$_2$ | H | 0 | NHSO$_2$Ph | |
| A-564 | Het-5 | CH$_2$CH$_2$ | H | 0 | NHSO$_2$Ph(p-Cl) | |
| A-565 | Het-5 | CH$_2$CH$_2$ | H | 0 | NHSO$_2$Ph(p-F) | |
| A-566 | Het-5 | CH$_2$CH$_2$ | H | 0 | NHSO$_2$(2,4,6-trimethylphenyl) | |
| A-567 | Het-5 | CH$_2$CH$_2$ | H | 0 | NHSO$_2$(2,4,6-trichlorophenyl) | |
| A-568 | Het-5 | CH$_2$CH$_2$ | H | 0 | NHSO$_2$(2,6-dichlorophenyl) | |
| A-569 | Het-5 | CH$_2$CH$_2$ | H | 0 | NHSO2[4-(2,6-dimethylphenyl)phenyl | |
| A-570 | Het-5 | CH$_2$CH$_2$ | H | 0 | NHSO$_2$C$_6$H$_4$(4-Ph) | |
| A-571 | Het-5 | CH$_2$CH$_2$ | H | 0 | NHSO$_2$[4-(3,5-dimethyl)isoxazolyl] | |
| A-572 | Het-5 | CH$_2$CH$_2$ | H | 0 | NHSO$_2$(1-naphthyl) | |
| A-573 | Het-5 | NHCH$_2$ | H | 0 | NHCO$_2$-n-Pr | |
| A-574 | Het-5 | NHCH$_2$ | H | 0 | NHCO$_2$-i-Pr | |
| A-575 | Het-5 | NHCH$_2$ | H | 0 | NHCO$_2$-n-Bu | |
| A-576 | Het-5 | NHCH$_2$ | H | 0 | NHCO$_2$-i-Bu | |
| A-577 | Het-5 | NHCH$_2$ | H | 0 | NHSO$_2$Ph | |
| A-578 | Het-5 | NHCH$_2$ | H | 0 | NHSO$_2$Ph(p-Cl) | |
| A-579 | Het-5 | NHCH$_2$ | H | 0 | NHSO$_2$Ph(p-F) | |
| A-580 | Het-5 | NHCH$_2$ | H | 0 | NHSO$_2$(2,4,6-trimethylphenyl) | |
| A-581 | Het-5 | NHCH$_2$ | H | 0 | NHSO$_2$(2,4,6-trichlorophenyl) | |
| A-582 | Het-5 | NHCH$_2$ | H | 0 | NHSO$_2$(2,6-dichlorophenyl) | |
| A-583 | Het-5 | NHCH$_2$ | H | 0 | NHSO2[4-(2,6-dimethylphenyl)phenyl | |
| A-584 | Het-5 | NHCH$_2$ | H | 0 | NHSO$_2$C$_6$H$_4$(4-Ph) | |
| A-585 | Het-5 | NHCH$_2$ | H | 0 | NHSO$_2$[4-(3,5-dimethyl)isoxazolyl] | |
| A-586 | Het-5 | NHCH$_2$ | H | 0 | NHSO$_2$(1-naphthyl) | |
| A-587 | Het-5 | OCH$_2$ | H | 0 | NHCO$_2$-n-Pr | |
| A-588 | Het-5 | OCH$_2$ | H | 0 | NHCO$_2$-i-Pr | |
| A-589 | Het-5 | OCH$_2$ | H | 0 | NHCO$_2$-n-Bu | |
| A-590 | Het-5 | OCH$_2$ | H | 0 | NHCO$_2$-i-Bu | |

TABLE 1-continued

| Ex. No. | R¹ | U | R⁸ | z | R¹⁵ | MS |
|---|---|---|---|---|---|---|
| A-591 | Het-5 | OCH$_2$ | H | 0 | NHSO$_2$Ph | |
| A-592 | Het-5 | OCH$_2$ | H | 0 | NHSO$_2$Ph(p-Cl) | |
| A-593 | Het-5 | OCH$_2$ | H | 0 | NHSO$_2$Ph(p-F) | |
| A-594 | Het-5 | OCH$_2$ | H | 0 | NHSO$_2$(2,4,6-trimethylphenyl) | |
| A-595 | Het-5 | OCH$_2$ | H | 0 | NHSO$_2$(2,4,6-trichlorophenyl) | |
| A-596 | Het-5 | OCH$_2$ | H | 0 | NHSO$_2$(2,6-dichlorophenyl) | |
| A-597 | Het-5 | OCH$_2$ | H | 0 | NHSO2[4-(2,6-dimethylphenyl)phenyl | |
| A-598 | Het-5 | OCH$_2$ | H | 0 | NHSO$_2$C$_6$H$_4$(4-Ph) | |
| A-599 | Het-5 | OCH$_2$ | H | 0 | NHSO$_2$[4-(3,5-dimethyl)isoxazolyl] | |
| A-600 | Het-5 | OCH$_2$ | H | 0 | NHSO$_2$(1-naphthyl) | |
| A-601 | Het-5 | CH$_2$CH$_2$CH$_2$ | H | 0 | NHCO$_2$-n-Pr | |
| A-602 | Het-5 | CH$_2$CH$_2$CH$_2$ | H | 0 | NHCO$_2$-i-Pr | |
| A-603 | Het-5 | CH$_2$CH$_2$CH$_2$ | H | 0 | NHCO$_2$-n-Bu | |
| A-604 | Het-5 | CH$_2$CH$_2$CH$_2$ | H | 0 | NHCO$_2$-i-Bu | |
| A-605 | Het-5 | CH$_2$CH$_2$CH$_2$ | H | 0 | NHSO$_2$Ph | |
| A-606 | Het-5 | CH$_2$CH$_2$CH$_2$ | H | 0 | NHSO$_2$Ph(p-Cl) | |
| A-607 | Het-5 | CH$_2$CH$_2$CH$_2$ | H | 0 | NHSO$_2$Ph(p-F) | |
| A-608 | Het-5 | CH$_2$CH$_2$CH$_2$ | H | 0 | NHSO$_2$(2,4,6-trimethylphenyl) | |
| A-609 | Het-5 | CH$_2$CH$_2$CH$_2$ | H | 0 | NHSO$_2$(2,4,6-trichlorophenyl) | |
| A-610 | Het-5 | CH$_2$CH$_2$CH$_2$ | H | 0 | NHSO$_2$(2,6-dichlorophenyl) | |
| A-611 | Het-5 | CH$_2$CH$_2$CH$_2$ | H | 0 | NHSO2[4-(2,6-dimethylphenyl)phenyl | |
| A-612 | Het-5 | CH$_2$CH$_2$CH$_2$ | H | 0 | NHSO$_2$C$_6$H$_4$(4-Ph) | |
| A-613 | Het-5 | CH$_2$CH$_2$CH$_2$ | H | 0 | NHSO$_2$[4-(3,5-dimethyl)isoxazolyl] | |
| A-614 | Het-5 | CH$_2$CH$_2$CH$_2$ | H | 0 | NHSO$_2$(1-naphthyl) | |
| A-615 | Het-5 | NHCH$_2$CH$_2$ | H | 0 | NHCO$_2$-n-Pr | |
| A-616 | Het-5 | NHCH$_2$CH$_2$ | H | 0 | NHCO$_2$-i-Pr | |
| A-617 | Het-5 | NHCH$_2$CH$_2$ | H | 0 | NHCO$_2$-n-Bu | |
| A-618 | Het-5 | NHCH$_2$CH$_2$ | H | 0 | NHCO$_2$-i-Bu | |
| A-619 | Het-5 | NHCH$_2$CH$_2$ | H | 0 | NHSO$_2$Ph | |
| A-620 | Het-5 | NHCH$_2$CH$_2$ | H | 0 | NHSO$_2$Ph(p-Cl) | |
| A-621 | Het-5 | NHCH$_2$CH$_2$ | H | 0 | NHSO$_2$Ph(p-F) | |
| A-622 | Het-5 | NHCH$_2$CH$_2$ | H | 0 | NHSO$_2$(2,4,6-trimethylphenyl) | |
| A-623 | Het-5 | NHCH$_2$CH$_2$ | H | 0 | NHSO$_2$(2,4,6-trichlorophenyl) | |
| A-624 | Het-5 | NHCH$_2$CH$_2$ | H | 0 | NHSO$_2$(2,6-dichlorophenyl) | |
| A-625 | Het-5 | NHCH$_2$CH$_2$ | H | 0 | NHSO2[4-(2,6-dimethylphenyl)phenyl | |
| A-626 | Het-5 | NHCH$_2$CH$_2$ | H | 0 | NHSO$_2$C$_6$H$_4$(4-Ph) | |
| A-627 | Het-5 | NHCH$_2$CH$_2$ | H | 0 | NHSO$_2$[4-(3,5-dimethyl)isoxazolyl] | |
| A-628 | Het-5 | NHCH$_2$CH$_2$ | H | 0 | NHSO$_2$(1-naphthyl) | |
| A-629 | Het-5 | OCH$_2$CH$_2$ | H | 0 | NHCO$_2$-n-Pr | |
| A-630 | Het-5 | OCH$_2$CH$_2$ | H | 0 | NHCO$_2$-i-Pr | |
| A-631 | Het-5 | OCH$_2$CH$_2$ | H | 0 | NHCO$_2$-n-Bu | |
| A-632 | Het-5 | OCH$_2$CH$_2$ | H | 0 | NHCO$_2$-i-Bu | |
| A-633 | Het-5 | OCH$_2$CH$_2$ | H | 0 | NHSO$_2$Ph | |
| A-634 | Het-5 | OCH$_2$CH$_2$ | H | 0 | NHSO$_2$Ph(p-Cl) | |
| A-635 | Het-5 | OCH$_2$CH$_2$ | H | 0 | NHSO$_2$Ph(p-F) | |
| A-636 | Het-5 | OCH$_2$CH$_2$ | H | 0 | NHSO$_2$(2,4,6-trimethylphenyl) | |
| A-637 | Het-5 | OCH$_2$CH$_2$ | H | 0 | NHSO$_2$(2,4,6-trichlorophenyl) | |
| A-638 | Het-5 | OCH$_2$CH$_2$ | H | 0 | NHSO$_2$(2,6-dichlorophenyl) | |
| A-639 | Het-5 | OCH$_2$CH$_2$ | H | 0 | NHSO2[4-(2,6-dimethylphenyl)phenyl | |
| A-640 | Het-5 | OCH$_2$CH$_2$ | H | 0 | NHSO$_2$C$_6$H$_4$(4-Ph) | |
| A-641 | Het-5 | OCH$_2$CH$_2$ | H | 0 | NHSO$_2$[4-(3,5-dimethyl)isoxazolyl] | |
| A-642 | Het-5 | OCH$_2$CH$_2$ | H | 0 | NHSO$_2$(1-naphthyl) | |
| A-643 | Het-6 | NHCH$_2$ | H | 0 | NHCO$_2$-n-Pr | |
| A-644 | Het-6 | NHCH$_2$ | H | 0 | NHCO$_2$-i-Pr | |
| A-645 | Het-6 | NHCH$_2$ | H | 0 | NHCO$_2$-n-Bu | |
| A-646 | Het-6 | NHCH$_2$ | H | 0 | NHCO$_2$-i-Bu | |
| A-647 | Het-6 | NHCH$_2$ | H | 0 | NHSO$_2$Ph | |
| A-648 | Het-6 | NHCH$_2$ | H | 0 | NHSO$_2$Ph(p-Cl) | |
| A-649 | Het-6 | NHCH$_2$ | H | 0 | NHSO$_2$Ph(p-F) | |
| A-650 | Het-6 | NHCH$_2$ | H | 0 | NHSO$_2$(2,4,6-trimethylphenyl) | 563.2 |
| A-651 | Het-6 | NHCH$_2$ | H | 0 | NHSO$_2$(2,4,6-trichlorophenyl) | |
| A-652 | Het-6 | NHCH$_2$ | H | 0 | NHSO$_2$(2,6-dichlorophenyl) | |
| A-653 | Het-6 | NHCH$_2$ | H | 0 | NHSO2[4-(2,6-dimethylphenyl)phenyl | |
| A-654 | Het-6 | NHCH$_2$ | H | 0 | NHSO$_2$C$_6$H$_4$(4-Ph) | |
| A-655 | Het-6 | NHCH$_2$ | H | 0 | NHSO$_2$[4-(3,5-dimethyl)isoxazolyl] | |
| A-656 | Het-6 | NHCH$_2$ | H | 0 | NHSO$_2$(1-naphthyl) | |
| A-657 | Het-6 | NHCH$_2$CH$_2$ | H | 0 | NHCO$_2$-n-Pr | |
| A-658 | Het-6 | NHCH$_2$CH$_2$ | H | 0 | NHCO$_2$-i-Pr | |
| A-659 | Het-6 | NHCH$_2$CH$_2$ | H | 0 | NHCO$_2$-n-Bu | |
| A-660 | Het-6 | NHCH$_2$CH$_2$ | H | 0 | NHCO$_2$-i-Bu | |
| A-661 | Het-6 | NHCH$_2$CH$_2$ | H | 0 | NHSO$_2$Ph | |
| A-662 | Het-6 | NHCH$_2$CH$_2$ | H | 0 | NHSO$_2$Ph(p-Cl) | |
| A-663 | Het-6 | NHCH$_2$CH$_2$ | H | 0 | NHSO$_2$Ph(p-F) | |
| A-664 | Het-6 | NHCH$_2$CH$_2$ | H | 0 | NHSO$_2$(2,4,6-trimethylphenyl) | |
| A-665 | Het-6 | NHCH$_2$CH$_2$ | H | 0 | NHSO$_2$(2,4,6-trichlorophenyl) | |
| A-666 | Het-6 | NHCH$_2$CH$_2$ | H | 0 | NHSO$_2$(2,6-dichlorophenyl) | |
| A-667 | Het-6 | NHCH$_2$CH$_2$ | H | 0 | NHSO2[4-(2,6-dimethylphenyl)phenyl | |
| A-668 | Het-6 | NHCH$_2$CH$_2$ | H | 0 | NHSO$_2$C$_6$H$_4$(4-Ph) | |
| A-669 | Het-6 | NHCH$_2$CH$_2$ | H | 0 | NHSO$_2$[4-(3,5-dimethyl)isoxazolyl] | |
| A-670 | Het-6 | NHCH$_2$CH$_2$ | H | 0 | NHSO$_2$(1-naphthyl) | |
| A-671 | Het-7 | NHCH$_2$ | H | 0 | NHCO$_2$-n-Pr | |
| A-672 | Het-7 | NHCH$_2$ | H | 0 | NHCO$_2$-i-Pr | |
| A-673 | Het-7 | NHCH$_2$ | H | 0 | NHCO$_2$-n-Bu | |
| A-674 | Het-7 | NHCH$_2$ | H | 0 | NHCO$_2$-i-Bu | |
| A-675 | Het-7 | NHCH$_2$ | H | 0 | NHSO$_2$Ph | |
| A-676 | Het-7 | NHCH$_2$ | H | 0 | NHSO$_2$Ph(p-Cl) | |
| A-677 | Het-7 | NHCH$_2$ | H | 0 | NHSO$_2$Ph(p-F) | |
| A-678 | Het-7 | NHCH$_2$ | H | 0 | NHSO$_2$(2,4,6-trimethylphenyl) | |
| A-679 | Het-7 | NHCH$_2$ | H | 0 | NHSO$_2$(2,4,6-trichlorophenyl) | |
| A-680 | Het-7 | NHCH$_2$ | H | 0 | NHSO$_2$(2,6-dichlorophenyl) | |
| A-681 | Het-7 | NHCH$_2$ | H | 0 | NHSO2[4-(2,6-dimethylphenyl)phenyl | |
| A-682 | Het-7 | NHCH$_2$ | H | 0 | NHSO$_2$C$_6$H$_4$(4-Ph) | |
| A-683 | Het-7 | NHCH$_2$ | H | 0 | NHSO$_2$[4-(3,5-dimethyl)isoxazolyl] | |
| A-684 | Het-7 | NHCH$_2$ | H | 0 | NHSO$_2$(1-naphthyl) | |
| A-685 | Het-7 | NHCH$_2$CH$_2$ | H | 0 | NHCO$_2$-n-Pr | |
| A-686 | Het-7 | NHCH$_2$CH$_2$ | H | 0 | NHCO$_2$-i-Pr | |
| A-687 | Het-7 | NHCH$_2$CH$_2$ | H | 0 | NHCO$_2$-n-Bu | |
| A-688 | Het-7 | NHCH$_2$CH$_2$ | H | 0 | NHCO$_2$-i-Bu | |

TABLE 1-continued

| Ex. No. | R¹ | U | R⁸ | z | R¹⁵ | MS |
|---|---|---|---|---|---|---|
| A-689 | Het-7 | NHCH₂CH₂ | H | 0 | NHSO₂Ph | |
| A-690 | Het-7 | NHCH₂CH₂ | H | 0 | NHSO₂Ph(p-Cl) | |
| A-691 | Het-7 | NHCH₂CH₂ | H | 0 | NHSO₂Ph(p-F) | |
| A-692 | Het-7 | NHCH₂CH₂ | H | 0 | NHSO₂(2,4,6-trimethylphenyl) | |
| A-693 | Het-7 | NHCH₂CH₂ | H | 0 | NHSO₂(2,4,6-trichlorophenyl) | |
| A-694 | Het-7 | NHCH₂CH₂ | H | 0 | NHSO₂(2,6-dichlorophenyl) | |
| A-695 | Het-7 | NHCH₂CH₂ | H | 0 | NHSO2[4-(2,6-dimethylphenyl)phenyl | |
| A-696 | Het-7 | NHCH₂CH₂ | H | 0 | NHSO₂C₆H₄(4-Ph) | |
| A-697 | Het-7 | NHCH₂CH₂ | H | 0 | NHSO₂[4-(3,5-dimethyl)isoxazolyl] | |
| A-698 | Het-7 | NHCH₂CH₂ | H | 0 | NHSO₂(1-naphthyl) | |
| A-699 | Het-8 | NHCH₂ | H | 0 | NHCO₂-n-Pr | |
| A-700 | Het-8 | NHCH₂ | H | 0 | NHCO₂-i-Pr | |
| A-701 | Het-8 | NHCH₂ | H | 0 | NHCO₂-n-Bu | |
| A-702 | Het-8 | NHCH₂ | H | 0 | NHCO₂-i-Bu | |
| A-703 | Het-8 | NHCH₂ | H | 0 | NHSO₂Ph | |
| A-704 | Het-8 | NHCH₂ | H | 0 | NHSO₂Ph(p-Cl) | |
| A-705 | Het-8 | NHCH₂ | H | 0 | NHSO₂Ph(p-F) | |
| A-706 | Het-8 | NHCH₂ | H | 0 | NHSO₂(2,4,6-trimethylphenyl) | |
| A-707 | Het-8 | NHCH₂ | H | 0 | NHSO₂(2,4,6-trichlorophenyl) | |
| A-708 | Het-8 | NHCH₂ | H | 0 | NHSO₂(2,6-dichlorophenyl) | |
| A-709 | Het-8 | NHCH₂ | H | 0 | NHSO2[4-(2,6-dimethylphenyl)phenyl | |
| A-710 | Het-8 | NHCH₂ | H | 0 | NHSO₂C₆H₄(4-Ph) | |
| A-711 | Het-8 | NHCH₂ | H | 0 | NHSO₂[4-(3,5-dimethyl)isoxazolyl] | |
| A-712 | Het-8 | NHCH₂ | H | 0 | NHSO₂(1-naphthyl) | |
| A-713 | Het-8 | NHCH₂CH₂ | H | 0 | NHCO₂-n-Pr | |
| A-714 | Het-8 | NHCH₂CH₂ | H | 0 | NHCO₂-i-Pr | |
| A-715 | Het-8 | NHCH₂CH₂ | H | 0 | NHCO₂-n-Bu | |
| A-716 | Het-8 | NHCH₂CH₂ | H | 0 | NHCO₂-i-Bu | |
| A-717 | Het-8 | NHCH₂CH₂ | H | 0 | NHSO₂Ph | |
| A-718 | Het-8 | NHCH₂CH₂ | H | 0 | NHSO₂Ph(p-Cl) | |
| A-719 | Het-8 | NHCH₂CH₂ | H | 0 | NHSO₂Ph(p-F) | |
| A-720 | Het-8 | NHCH₂CH₂ | H | 0 | NHSO₂(2,4,6-trimethylphenyl) | |
| A-721 | Het-8 | NHCH₂CH₂ | H | 0 | NHSO₂(2,4,6-trichlorophenyl) | |
| A-722 | Het-8 | NHCH₂CH₂ | H | 0 | NHSO₂(2,6-dichlorophenyl) | |
| A-723 | Het-8 | NHCH₂CH₂ | H | 0 | NHSO2[4-(2,6-dimethylphenyl)phenyl | |
| A-724 | Het-8 | NHCH₂CH₂ | H | 0 | NHSO₂C₆H₄(4-Ph) | |
| A-725 | Het-8 | NHCH₂CH₂ | H | 0 | NHSO₂[4-(3,5-dimethyl)isoxazolyl] | |
| A-726 | Het-8 | NHCH₂CH₂ | H | 0 | NHSO₂(1-naphthyl) | |
| A-727 | Het-9 | NHCH₂ | H | 0 | NHCO₂-n-Pr | |
| A-728 | Het-9 | NHCH₂ | H | 0 | NHCO₂-i-Pr | |
| A-729 | Het-9 | NHCH₂ | H | 0 | NHCO₂-n-Bu | |
| A-730 | Het-9 | NHCH₂ | H | 0 | NHCO₂-i-Bu | |
| A-731 | Het-9 | NHCH₂ | H | 0 | NHSO₂Ph | |
| A-732 | Het-9 | NHCH₂ | H | 0 | NHSO₂Ph(p-Cl) | |
| A-733 | Het-9 | NHCH₂ | H | 0 | NHSO₂Ph(p-F) | |
| A-734 | Het-9 | NHCH₂ | H | 0 | NHSO₂(2,4,6-trimethylphenyl) | |
| A-735 | Het-9 | NHCH₂ | H | 0 | NHSO₂(2,4,6-trichlorophenyl) | |
| A-736 | Het-9 | NHCH₂ | H | 0 | NHSO₂(2,6-dichlorophenyl) | |
| A-737 | Het-9 | NHCH₂ | H | 0 | NHSO2[4-(2,6-dimethylphenyl)phenyl | |
| A-738 | Het-9 | NHCH₂ | H | 0 | NHSO₂C₆H₄(4-Ph) | |
| A-739 | Het-9 | NHCH₂ | H | 0 | NHSO₂[4-(3,5-dimethylisoxazolyl] | |
| A-740 | Het-9 | NHCH₂ | H | 0 | NHSO₂(1-naphthyl) | |
| A-741 | Het-9 | NHCH₂CH₂ | H | 0 | NHCO₂-n-Pr | |
| A-742 | Het-9 | NHCH₂CH₂ | H | 0 | NHCO₂-i-Pr | |
| A-743 | Het-9 | NHCH₂CH₂ | H | 0 | NHCO₂-n-Bu | |
| A-744 | Het-9 | NHCH₂CH₂ | H | 0 | NHCO₂-i-Bu | |
| A-745 | Het-9 | NHCH₂CH₂ | H | 0 | NHSO₂Ph | |
| A-746 | Het-9 | NHCH₂CH₂ | H | 0 | NHSO₂Ph(p-Cl) | |
| A-747 | Het-9 | NHCH₂CH₂ | H | 0 | NHSO₂Ph(p-F) | |
| A-748 | Het-9 | NHCH₂CH₂ | H | 0 | NHSO₂(2,4,6-trimethylphenyl) | |
| A-749 | Het-9 | NHCH₂CH₂ | H | 0 | NHSO₂(2,4,6-trichlorophenyl) | |
| A-750 | Het-9 | NHCH₂CH₂ | H | 0 | NHSO₂(2,6-dichlorophenyl) | |
| A-751 | Het-9 | NHCH₂CH₂ | H | 0 | NHSO2[4-(2,6-dimethylphenyl)phenyl | |
| A-752 | Het-9 | NHCH₂CH₂ | H | 0 | NHSO₂C₆H₄(4-Ph) | |
| A-753 | Het-9 | NHCH₂CH₂ | H | 0 | NHSO₂[4-(3,5-dimethyl isoxazolyl] | |
| A-754 | Het-9 | NHCH₂CH₂ | H | 0 | NHSO₂(1-naphthyl) | |
| A-755 | Het-10 | NHCH₂ | H | 0 | NHCO₂-n-Pr | |
| A-756 | Het-10 | NHCH₂ | H | 0 | NHCO₂-i-Pr | |
| A-757 | Het-10 | NHCH₂ | H | 0 | NHCO₂-n-Bu | |
| A-758 | Het-10 | NHCH₂ | H | 0 | NHCO₂-i-Bu | |
| A-759 | Het-10 | NHCH₂ | H | 0 | NHSO₂Ph | |
| A-760 | Het-10 | NHCH₂ | H | 0 | NHSO₂Ph(p-Cl) | |
| A-761 | Het-10 | NHCH₂ | H | 0 | NHSO₂Ph(p-F) | |
| A-762 | Het-10 | NHCH₂ | H | 0 | NHSO₂(2,4,6-trimethylphenyl) | |
| A-763 | Het-10 | NHCH₂ | H | 0 | NHSO₂(2,4,6-trichlorophenyl) | |
| A-764 | Het-10 | NHCH₂ | H | 0 | NHSO₂(2,6-dichlorophenyl) | |
| A-765 | Het-10 | NHCH₂ | H | 0 | NHSO2[4-(2,6-dimethylphenyl)phenyl | |
| A-766 | Het-10 | NHCH₂ | H | 0 | NHSO₂C₆H₄(4-Ph) | |
| A-767 | Het-10 | NHCH₂ | H | 0 | NHSO₂[4-(3,5-dimethyl isoxazolyl] | |
| A-768 | Het-10 | NHCH₂ | H | 0 | NHSO₂(1-naphthyl) | |
| A-769 | Het-10 | NHCH₂CH₂ | H | 0 | NHCO₂-n-Pr | |
| A-770 | Het-10 | NHCH₂CH₂ | H | 0 | NHCO₂-i-Pr | |
| A-771 | Het-10 | NHCH₂CH₂ | H | 0 | NHCO₂-n-Bu | |
| A-772 | Het-10 | NHCH₂CH₂ | H | 0 | NHCO₂-i-Bu | |
| A-773 | Het-10 | NHCH₂CH₂ | H | 0 | NHSO₂Ph | |
| A-774 | Het-10 | NHCH₂CH₂ | H | 0 | NHSO₂Ph(p-Cl) | |
| A-775 | Het-10 | NHCH₂CH₂ | H | 0 | NHSO₂Ph(p-F) | |
| A-776 | Het-10 | NHCH₂CH₂ | H | 0 | NHSO₂(2,4,6-trimethylphenyl) | |
| A-777 | Het-10 | NHCH₂CH₂ | H | 0 | NHSO₂(2,4,6-trichlorophenyl) | |
| A-778 | Het-10 | NHCH₂CH₂ | H | 0 | NHSO₂(2,6-dichlorophenyl) | |
| A-779 | Het-10 | NHCH₂CH₂ | H | 0 | NHSO2[4-(2,6-dimethylphenyl)phenyl | |
| A-780 | Het-10 | NHCH₂CH₂ | H | 0 | NHSO₂C₆H₄(4-Ph) | |
| A-781 | Het-10 | NHCH₂CH₂ | H | 0 | NHSO₂[4-(3,5-dimethyl isoxazolyl] | |
| A-782 | Het-10 | NHCH₂CH₂ | H | 0 | NHSO₂(1-naphthyl) | |
| A-783 | Het-11 | NHCH₂ | H | 0 | NHCO₂-n-Pr | |
| A-784 | Het-11 | NHCH₂ | H | 0 | NHCO₂-i-Pr | |
| A-785 | Het-11 | NHCH₂ | H | 0 | NHCO₂-n-Bu | |
| A-786 | Het-11 | NHCH₂ | H | 0 | NHCO₂-i-Bu | |

TABLE 1-continued

[Structure: R¹—U—[phenyl ring with positions 3,2 and 5,6, R⁸ substituent]—(CH₂)z—C(O)—NH—CH(R¹⁵)—CO₂H]

| Ex. No. | R¹ | U | R⁸ | z | R¹⁵ | MS |
|---|---|---|---|---|---|---|
| A-787 | Het-11 | NHCH₂ | H | 0 | NHSO₂Ph | |
| A-788 | Het-11 | NHCH₂ | H | 0 | NHSO₂Ph(p-Cl) | |
| A-789 | Het-11 | NHCH₂ | H | 0 | NHSO₂Ph(p-F) | |
| A-790 | Het-11 | NHCH₂ | H | 0 | NHSO₂(2,4,6-trimethylphenyl) | |
| A-791 | Het-11 | NHCH₂ | H | 0 | NHSO₂(2,4,6-trichlorophenyl) | |
| A-792 | Het-11 | NHCH₂ | H | 0 | NHSO₂(2,6-dichlorophenyl) | |
| A-793 | Het-11 | NHCH₂ | H | 0 | NHSO2[4-(2,6-dimethylphenyl)phenyl | |
| A-794 | Het-11 | NHCH₂ | H | 0 | NHSO₂C₆H₄(4-Ph) | |
| A-795 | Het-11 | NHCH₂ | H | 0 | NHSO₂[4-(3,5-dimethyl)isoxazolyl] | |
| A-796 | Het-11 | NHCH₂ | H | 0 | NHSO₂(1-naphthyl) | |
| A-797 | Het-11 | NHCH₂CH₂ | H | 0 | NHCO₂-n-Pr | |
| A-798 | Het-11 | NHCH₂CH₂ | H | 0 | NHCO₂-i-Pr | |
| A-799 | Het-11 | NHCH₂CH₂ | H | 0 | NHCO₂-n-Bu | |
| A-800 | Het-11 | NHCH₂CH₂ | H | 0 | NHCO₂-i-Bu | |
| A-801 | Het-11 | NHCH₂CH₂ | H | 0 | NHSO₂Ph | |
| A-802 | Het-11 | NHCH₂CH₂ | H | 0 | NHSO₂Ph(p-Cl) | |
| A-803 | Het-11 | NHCH₂CH₂ | H | 0 | NHSO₂Ph(p-F) | |
| A-804 | Het-11 | NHCH₂CH₂ | H | 0 | NHSO₂(2,4,6-trimethylphenyl) | |
| A-805 | Het-11 | NHCH₂CH₂ | H | 0 | NHSO₂(2,4,6-trichlorophenyl) | |
| A-806 | Het-11 | NHCH₂CH₂ | H | 0 | NHSO₂(2,6-dichlorophenyl) | |
| A-807 | Het-11 | NHCH₂CH₂ | H | 0 | NHSO2[4-(2,6-dimethylphenyl)phenyl | |
| A-808 | Het-11 | NHCH₂CH₂ | H | 0 | NHSO₂C₆H₄(4-Ph) | |
| A-809 | Het-11 | NHCH₂CH₂ | H | 0 | NHSO₂[4-(3,5-dimethyl)isoxazolyl] | |
| A-810 | Het-11 | NHCH₂CH₂ | H | 0 | NHSO₂(1-naphthyl) | |
| A-811 | Het-12 | NHCH₂ | H | 0 | NHCO₂-n-Pr | |
| A-812 | Het-12 | NHCH₂ | H | 0 | NHCO₂-i-Pr | |
| A-813 | Het-12 | NHCH₂ | H | 0 | NHCO₂-n-Bu | |
| A-814 | Het-12 | NHCH₂ | H | 0 | NHCO₂-i-Bu | |
| A-815 | Het-12 | NHCH₂ | H | 0 | NHSO₂Ph | |
| A-816 | Het-12 | NHCH₂ | H | 0 | NHSO₂Ph(p-Cl) | |
| A-817 | Het-12 | NHCH₂ | H | 0 | NHSO₂Ph(p-F) | |
| A-818 | Het-12 | NHCH₂ | H | 0 | NHSO₂(2,4,6-trimethylphenyl) | |
| A-819 | Het-12 | NHCH₂ | H | 0 | NHSO₂(2,4,6-trichlorophenyl) | |
| A-820 | Het-12 | NHCH₂ | H | 0 | NHSO₂(2,6-dichlorophenyl) | |
| A-821 | Het-12 | NHCH₂ | H | 0 | NHSO2[4-(2,6-dimethylphenyl)phenyl | |
| A-822 | Het-12 | NHCH₂ | H | 0 | NHSO₂C₆H₄(4-Ph) | |
| A-823 | Het-12 | NHCH₂ | H | 0 | NHSO₂[4-(3,5-dimethyl)isoxazolyl] | |
| A-824 | Het-12 | NHCH₂ | H | 0 | NHSO₂(1-naphthyl) | |
| A-825 | Het-12 | NHCH₂CH₂ | H | 0 | NHCO₂-n-Pr | |
| A-826 | Het-12 | NHCH₂CH₂ | H | 0 | NHCO₂-i-Pr | |
| A-827 | Het-12 | NHCH₂CH₂ | H | 0 | NHCO₂-n-Bu | |
| A-828 | Het-12 | NHCH₂CH₂ | H | 0 | NHCO₂-i-Bu | |
| A-829 | Het-12 | NHCH₂CH₂ | H | 0 | NHSO₂Ph | |
| A-830 | Het-12 | NHCH₂CH₂ | H | 0 | NHSO₂Ph(p-Cl) | |
| A-831 | Het-12 | NHCH₂CH₂ | H | 0 | NHSO₂Ph(p-F) | |
| A-832 | Het-12 | NHCH₂CH₂ | H | 0 | NHSO₂(2,4,6-trimethylphenyl) | |
| A-833 | Het-12 | NHCH₂CH₂ | H | 0 | NHSO₂(2,4,6-trichlorophenyl) | |
| A-834 | Het-12 | NHCH₂CH₂ | H | 0 | NHSO₂(2,6-dichlorophenyl) | |
| A-835 | Het-12 | NHCH₂CH₂ | H | 0 | NHSO2[4-(2,6-dimethylphenyl)phenyl | |
| A-836 | Het-12 | NHCH₂CH₂ | H | 0 | NHSO₂C₆H₄(4-Ph) | |
| A-837 | Het-12 | NHCH₂CH₂ | H | 0 | NHSO₂[4-(3,5-dimethylisoxazolyl] | |
| A-838 | Het-12 | NHCH₂CH₂ | H | 0 | NHSO₂(1-naphthyl) | |
| A-839 | Het-13 | NHCH₂ | H | 0 | NHCO₂-n-Pr | |
| A-840 | Het-13 | NHCH₂ | H | 0 | NHCO₂-i-Pr | |
| A-841 | Het-13 | NHCH₂ | H | 0 | NHCO₂-n-Bu | |
| A-842 | Het-13 | NHCH₂ | H | 0 | NHCO₂-i-Bu | |
| A-843 | Het-13 | NHCH₂ | H | 0 | NHSO₂Ph | |
| A-844 | Het-13 | NHCH₂ | H | 0 | NHSO₂Ph(p-Cl) | |
| A-845 | Het-13 | NHCH₂ | H | 0 | NHSO₂Ph(p-F) | |
| A-846 | Het-13 | NHCH₂ | H | 0 | NHSO₂(2,4,6-trimethylphenyl) | |
| A-847 | Het-13 | NHCH₂ | H | 0 | NHSO₂(2,4,6-trichlorophenyl) | |
| A-848 | Het-13 | NHCH₂ | H | 0 | NHSO₂(2,6-dichlorophenyl) | |
| A-849 | Het-13 | NHCH₂ | H | 0 | NHSO2[4-(2,6-dimethylphenyl)phenyl | |
| A-850 | Het-13 | NHCH₂ | H | 0 | NHSO₂C₆H₄(4-Ph) | |
| A-851 | Het-13 | NHCH₂ | H | 0 | NHSO₂[4-(3,5-dimethylisoxazolyl] | |
| A-852 | Het-13 | NHCH₂ | H | 0 | NHSO₂(1-naphthyl) | |
| A-853 | Het-13 | NHCH₂CH₂ | H | 0 | NHCO₂-n-Pr | |
| A-854 | Het-13 | NHCH₂CH₂ | H | 0 | NHCO₂-i-Pr | |
| A-855 | Het-13 | NHCH₂CH₂ | H | 0 | NHCO₂-n-Bu | |
| A-856 | Het-13 | NHCH₂CH₂ | H | 0 | NHCO₂-i-Bu | |
| A-857 | Het-13 | NHCH₂CH₂ | H | 0 | NHSO₂Ph | |
| A-858 | Het-13 | NHCH₂CH₂ | H | 0 | NHSO₂Ph(p-Cl) | |
| A-859 | Het-13 | NHCH₂CH₂ | H | 0 | NHSO₂Ph(p-F) | |
| A-860 | Het-13 | NHCH₂CH₂ | H | 0 | NHSO₂(2,4,6-trimethylphenyl) | |
| A-861 | Het-13 | NHCH₂CH₂ | H | 0 | NHSO₂(2,4,6-trichlorophenyl) | |
| A-862 | Het-13 | NHCH₂CH₂ | H | 0 | NHSO₂(2,6-dichlorophenyl) | |
| A-863 | Het-13 | NHCH₂CH₂ | H | 0 | NHSO2[4-(2,6-dimethylphenyl)phenyl | |
| A-864 | Het-13 | NHCH₂CH₂ | H | 0 | NHSO₂C₆H₄(4-Ph) | |
| A-865 | Het-13 | NHCH₂CH₂ | H | 0 | NHSO₂[4-(3,5-dimethyl)isoxazolyl] | |
| A-866 | Het-13 | NHCH₂CH₂ | H | 0 | NHSO₂(1-naphthyl) | |
| A-867 | Het-14 | NHCH₂ | H | 0 | NHCO₂-n-Pr | |
| A-868 | Het-14 | NHCH₂ | H | 0 | NHCO₂-i-Pr | |
| A-869 | Het-14 | NHCH₂ | H | 0 | NHCO₂-n-Bu | |
| A-870 | Het-14 | NHCH₂ | H | 0 | NHCO₂-i-Bu | |
| A-871 | Het-14 | NHCH₂ | H | 0 | NHSO₂Ph | |
| A-872 | Het-14 | NHCH₂ | H | 0 | NHSO₂Ph(p-Cl) | |
| A-873 | Het-14 | NHCH₂ | H | 0 | NHSO₂Ph(p-F) | |
| A-874 | Het-14 | NHCH₂ | H | 0 | NHSO₂(2,4,6-trimethylphenyl) | |
| A-875 | Het-14 | NHCH₂ | H | 0 | NHSO₂(2,4,6-trichlorophenyl) | |
| A-876 | Het-14 | NHCH₂ | H | 0 | NHSO₂(2,6-dichlorophenyl) | |
| A-877 | Het-14 | NHCH₂ | H | 0 | NHSO2[4-(2,6-dimethylphenyl)phenyl | |
| A-878 | Het-14 | NHCH₂ | H | 0 | NHSO₂C₆H₄(4-Ph) | |
| A-879 | Het-14 | NHCH₂ | H | 0 | NHSO₂[4-(3,5-dimethyl)isoxazolyl] | |
| A-880 | Het-14 | NHCH₂ | H | 0 | NHSO₂(1-naphthyl) | |
| A-881 | Het-14 | NHCH₂CH₂ | H | 0 | NHCO₂-n-Pr | |
| A-882 | Het-14 | NHCH₂CH₂ | H | 0 | NHCO₂-i-Pr | |
| A-883 | Het-14 | NHCH₂CH₂ | H | 0 | NHCO₂-n-Bu | |
| A-884 | Het-14 | NHCH₂CH₂ | H | 0 | NHCO₂-i-Bu | |

TABLE 1-continued $R^1-U-\text{(phenyl with positions 1-6, R}^8\text{)}-(CH_2)_z-C(O)-NH-CH(R^{15})-CO_2H$

| Ex. No. | $R^1$ | U | $R^8$ | z | $R^{15}$ | MS |
|---|---|---|---|---|---|---|
| A-885 | Het-14 | NHCH$_2$CH$_2$ | H | 0 | NHSO$_2$Ph | |
| A-886 | Het-14 | NHCH$_2$CH$_2$ | H | 0 | NHSO$_2$Ph(p-Cl) | |
| A-887 | Het-14 | NHCH$_2$CH$_2$ | H | 0 | NHSO$_2$Ph(p-F) | |
| A-888 | Het-14 | NHCH$_2$CH$_2$ | H | 0 | NHSO$_2$(2,4,6-trimethylphenyl) | |
| A-889 | Het-14 | NHCH$_2$CH$_2$ | H | 0 | NHSO$_2$(2,4,6-trichlorophenyl) | |
| A-890 | Het-14 | NHCH$_2$CH$_2$ | H | 0 | NHSO$_2$(2,6-dichlorophenyl) | |
| A-891 | Het-14 | NHCH$_2$CH$_2$ | H | 0 | NHSO2[4-(2,6-dimethylphenyl)phenyl | |
| A-892 | Het-14 | NHCH$_2$CH$_2$ | H | 0 | NHSO$_2$C$_6$H$_4$(4-Ph) | |
| A-893 | Het-14 | NHCH$_2$CH$_2$ | H | 0 | NHSO$_2$[4-(3,5-dimethyl)isoxazolyl] | |
| A-894 | Het-14 | NHCH$_2$CH$_2$ | H | 0 | NHSO$_2$(1-naphthyl) | |
| A-895 | Het-15 | NHCH$_2$ | H | 0 | NHCO$_2$-n-Pr | |
| A-896 | Het-15 | NHCH$_2$ | H | 0 | NHCO$_2$-i-Pr | |
| A-897 | Het-15 | NHCH$_2$ | H | 0 | NHCO$_2$-n-Bu | |
| A-898 | Het-15 | NHCH$_2$ | H | 0 | NHCO$_2$-i-Bu | |
| A-899 | Het-15 | NHCH$_2$ | H | 0 | NHSO$_2$Ph | |
| A-900 | Het-15 | NHCH$_2$ | H | 0 | NHSO$_2$Ph(p-Cl) | |
| A-901 | Het-15 | NHCH$_2$ | H | 0 | NHSO$_2$Ph(p-F) | |
| A-902 | Het-15 | NHCH$_2$ | H | 0 | NHSO$_2$(2,4,6-trimethylphenyl) | |
| A-903 | Het-15 | NHCH$_2$ | H | 0 | NHSO$_2$(2,4,6-trichlorophenyl) | |
| A-904 | Het-15 | NHCH$_2$ | H | 0 | NHSO$_2$(2,6-dichlorophenyl) | |
| A-905 | Het-15 | NHCH$_2$ | H | 0 | NHSO2[4-(2,6-dimethylphenyl)phenyl | |
| A-906 | Het-15 | NHCH$_2$ | H | 0 | NHSO$_2$C$_6$H$_4$(4-Ph) | |
| A-907 | Het-15 | NHCH$_2$ | H | 0 | NHSO$_2$[4-(3,5-dimethyl)isoxazolyl] | |
| A-908 | Het-15 | NHCH$_2$ | H | 0 | NHSO$_2$(1-naphthyl) | |
| A-909 | Het-15 | NHCH$_2$CH$_2$ | H | 0 | NHCO$_2$-n-Pr | |
| A-910 | Het-15 | NHCH$_2$CH$_2$ | H | 0 | NHCO$_2$-i-Pr | |
| A-911 | Het-15 | NHCH$_2$CH$_2$ | H | 0 | NHCO$_2$-n-Bu | |
| A-912 | Het-15 | NHCH$_2$CH$_2$ | H | 0 | NHCO$_2$-i-Bu | |
| A-913 | Het-15 | NHCH$_2$CH$_2$ | H | 0 | NHSO$_2$Ph | |
| A-914 | Het-15 | NHCH$_2$CH$_2$ | H | 0 | NHSO$_2$Ph(p-Cl) | |
| A-915 | Het-15 | NHCH$_2$CH$_2$ | H | 0 | NHSO$_2$Ph(p-F) | |
| A-916 | Het-15 | NHCH$_2$CH$_2$ | H | 0 | NHSO$_2$(2,4,6-trimethylphenyl) | |
| A-917 | Het-15 | NHCH$_2$CH$_2$ | H | 0 | NHSO$_2$(2,4,6-trichlorophenyl) | |
| A-918 | Het-15 | NHCH$_2$CH$_2$ | H | 0 | NHSO$_2$(2,6-dichlorophenyl) | |
| A-919 | Het-15 | NHCH$_2$CH$_2$ | H | 0 | NHSO2[4-(2,6-dimethylphenyl)phenyl | |
| A-920 | Het-15 | NHCH$_2$CH$_2$ | H | 0 | NHSO$_2$C$_6$H$_4$(4-Ph) | |
| A-921 | Het-15 | NHCH$_2$CH$_2$ | H | 0 | NHSO$_2$[4-(3,5-dimethyl)isoxazolyl] | |
| A-922 | Het-15 | NHCH$_2$CH$_2$ | H | 0 | NHSO$_2$(1-naphthyl) | |
| A-923 | Het-8 | CH$_2$CH$_2$ | H | 0 | NHCO$_2$-n-Pr | |
| A-924 | Het-8 | CH$_2$CH$_2$ | H | 0 | NHCO$_2$-i-Pr | |
| A-925 | Het-8 | CH$_2$CH$_2$ | H | 0 | NHCO$_2$-n-Bu | |
| A-926 | Het-8 | CH$_2$CH$_2$ | H | 0 | NHCO$_2$-i-Bu | |
| A-927 | Het-8 | CH$_2$CH$_2$ | H | 0 | NHSO$_2$Ph | |
| A-928 | Het-8 | CH$_2$CH$_2$ | H | 0 | NHSO$_2$Ph(p-Cl) | |
| A-929 | Het-8 | CH$_2$CH$_2$ | H | 0 | NHSO$_2$Ph(p-F) | |
| A-930 | Het-8 | CH$_2$CH$_2$ | H | 0 | NHSO$_2$(2,4,6-trimethylphenyl) | |
| A-931 | Het-8 | CH$_2$CH$_2$ | H | 0 | NHSO$_2$(2,4,6-trichlorophenyl) | |
| A-932 | Het-8 | CH$_2$CH$_2$ | H | 0 | NHSO$_2$(2,6-dichlorophenyl) | |
| A-933 | Het-8 | CH$_2$CH$_2$ | H | 0 | NHSO2[4-(2,6-dimethylphenyl)phenyl | |
| A-934 | Het-8 | CH$_2$CH$_2$ | H | 0 | NHSO$_2$C$_6$H$_4$(4-Ph) | |
| A-935 | Het-8 | CH$_2$CH$_2$ | H | 0 | NHSO$_2$[4-(3,5-dimethyyl)isoxazolyl] | |
| A-936 | Het-8 | CH$_2$CH$_2$ | H | 0 | NHSO$_2$(1-naphthyl) | |
| A-937 | Het-8 | CH$_2$CH$_2$CH$_2$ | H | 0 | NHCO$_2$-n-Pr | |
| A-938 | Het-8 | CH$_2$CH$_2$CH$_2$ | H | 0 | NHCO$_2$-i-Pr | |
| A-939 | Het-8 | CH$_2$CH$_2$CH$_2$ | H | 0 | NHCO$_2$-n-Bu | |
| A-940 | Het-8 | CH$_2$CH$_2$CH$_2$ | H | 0 | NHCO$_2$-i-Bu | |
| A-941 | Het-8 | CH$_2$CH$_2$CH$_2$ | H | 0 | NHSO$_2$Ph | |
| A-942 | Het-8 | CH$_2$CH$_2$CH$_2$ | H | 0 | NHSO$_2$Ph(p-Cl) | |
| A-943 | Het-8 | CH$_2$CH$_2$CH$_2$ | H | 0 | NHSO$_2$Ph(p-F) | |
| A-944 | Het-8 | CH$_2$CH$_2$CH$_2$ | H | 0 | NHSO$_2$(2,4,6-trimethylphenyl) | |
| A-945 | Het-8 | CH$_2$CH$_2$CH$_2$ | H | 0 | NHSO$_2$(2,4,6-trichlorophenyl) | |
| A-946 | Het-8 | CH$_2$CH$_2$CH$_2$ | H | 0 | NHSO$_2$(2,6-dichlorophenyl) | |
| A-947 | Het-8 | CH$_2$CH$_2$CH$_2$ | H | 0 | NHSO2[4-(2,6-dimethylphenyl)phenyl | |
| A-948 | Het-8 | CH$_2$CH$_2$CH$_2$ | H | 0 | NHSO$_2$C$_6$H$_4$(4-Ph) | |
| A-949 | Het-8 | CH$_2$CH$_2$CH$_2$ | H | 0 | NHSO$_2$[4-(3,5-dimethyl isoxazolyl] | |
| A-950 | Het-8 | CH$_2$CH$_2$CH$_2$ | H | 0 | NHSO$_2$(1-naphthyl) | |
| A-951 | Het-16 | CH$_2$CH$_2$ | H | 0 | NHCO$_2$-n-Pr | |
| A-952 | Het-16 | CH$_2$CH$_2$ | H | 0 | NHCO$_2$-i-Pr | |
| A-953 | Het-16 | CH$_2$CH$_2$ | H | 0 | NHCO$_2$-n-Bu | |
| A-954 | Het-16 | CH$_2$CH$_2$ | H | 0 | NHCO$_2$-i-Bu | |
| A-955 | Het-16 | CH$_2$CH$_2$ | H | 0 | NHSO$_2$Ph | |
| A-956 | Het-16 | CH$_2$CH$_2$ | H | 0 | NHSO$_2$Ph(p-Cl) | |
| A-957 | Het-16 | CH$_2$CH$_2$ | H | 0 | NHSO$_2$Ph(p-F) | |
| A-958 | Het-16 | CH$_2$CH$_2$ | H | 0 | NHSO$_2$(2,4,6-trimethylphenyl) | |
| A-959 | Het-16 | CH$_2$CH$_2$ | H | 0 | NHSO$_2$(2,4,6-trichlorophenyl) | |
| A-960 | Het-16 | CH$_2$CH$_2$ | H | 0 | NHSO$_2$(2,6-dichlorophenyl) | |
| A-961 | Het-16 | CH$_2$CH$_2$ | H | 0 | NHSO2[4-(2,6-dimethylphenyl)phenyl | |
| A-962 | Het-16 | CH$_2$CH$_2$ | H | 0 | NHSO$_2$C$_6$H$_4$(4-Ph) | |
| A-963 | Het-16 | CH$_2$CH$_2$ | H | 0 | NHSP$_2$[4-(3,5-dimethyl isoxazolyl] | |
| A-964 | Het-16 | CH$_2$CH$_2$ | H | 0 | NHSO$_2$(1-naphthyl) | |
| A-965 | Het-16 | CH$_2$CH$_2$CH$_2$ | H | 0 | NHCO$_2$-n-Pr | |
| A-966 | Het-16 | CH$_2$CH$_2$CH$_2$ | H | 0 | NHCO$_2$-i-Pr | |
| A-967 | Het-16 | CH$_2$CH$_2$CH$_2$ | H | 0 | NHCO$_2$-n-Bu | |
| A-968 | Het-16 | CH$_2$CH$_2$CH$_2$ | H | 0 | NHCO$_2$-i-Bu | |
| A-969 | Het-16 | CH$_2$CH$_2$CH$_2$ | H | 0 | NHSO$_2$Ph | |
| A-970 | Het-16 | CH$_2$CH$_2$CH$_2$ | H | 0 | NHSO$_2$Ph(p-Cl) | |
| A-971 | Het-16 | CH$_2$CH$_2$CH$_2$ | H | 0 | NHSO$_2$Ph(p-F) | |
| A-972 | Het-16 | CH$_2$CH$_2$CH$_2$ | H | 0 | NHSO$_2$(2,4,6-trimethylphenyl) | |
| A-973 | Het-16 | CH$_2$CH$_2$CH$_2$ | H | 0 | NHSO$_2$(2,4,6-trichlorophenyl) | |
| A-974 | Het-16 | CH$_2$CH$_2$CH$_2$ | H | 0 | NHSO$_2$(2,6-dichlorophenyl) | |
| A-975 | Het-16 | CH$_2$CH$_2$CH$_2$ | H | 0 | NHSO2[4-(2,6-dimethylphenyl)phenyl | |
| A-976 | Het-16 | CH$_2$CH$_2$CH$_2$ | H | 0 | NHSO$_2$C$_6$H$_4$(4-Ph) | |
| A-977 | Het-16 | CH$_2$CH$_2$CH$_2$ | H | 0 | NHSO$_2$[4-(3,5-dimethyl)isoxazolyl] | |
| A-978 | Het-16 | CH$_2$CH$_2$CH$_2$ | H | 0 | NHSO$_2$(1-naphthyl) | |
| A-979 | Het-17 | CH$_2$CH$_2$ | H | 0 | NHCO$_2$-n-Pr | |
| A-980 | Het-17 | CH$_2$CH$_2$ | H | 0 | NHCO$_2$-i-Pr | |
| A-981 | Het-17 | CH$_2$CH$_2$ | H | 0 | NHCO$_2$-n-Bu | |
| A-982 | Het-17 | CH$_2$CH$_2$ | H | 0 | NHCO$_2$-i-Bu | |

TABLE 1-continued

R¹—U—[phenyl ring with positions 2,3,4,5,6 and R⁸]—(CH₂)z—C(=O)—NH—CH(R¹⁵)—CO₂H

| Ex. No. | R¹ | U | R⁸ | z | R¹⁵ | MS |
|---|---|---|---|---|---|---|
| A-983 | Het-17 | CH₂CH₂ | H | 0 | NHSO₂Ph | |
| A-984 | Het-17 | CH₂CH₂ | H | 0 | NHSO₂Ph(p-Cl) | |
| A-985 | Het-17 | CH₂CH₂ | H | 0 | NHSO₂Ph(p-F) | |
| A-986 | Het-17 | CH₂CH₂ | H | 0 | NHSO₂(2,4,6-trimethylphenyl) | |
| A-987 | Het-17 | CH₂CH₂ | H | 0 | NHSO₂(2,4,6-trichlorophenyl) | |
| A-988 | Het-17 | CH₂CH₂ | H | 0 | NHSO₂(2,6-dichlorophenyl) | |
| A-989 | Het-17 | CH₂CH₂ | H | 0 | NHSO2[4-(2,6-dimethylphenyl)phenyl | |
| A-990 | Het-17 | CH₂CH₂ | H | 0 | NHSO₂C₆H₄(4-Ph) | |
| A-991 | Het-17 | CH₂CH₂ | H | 0 | NHSO₂ 4-(3,5-dimethyl)isoxazolyl] | |
| A-992 | Het-17 | CH₂CH₂ | H | 0 | NHSO₂(1-naphthyl) | |
| A-993 | Het-17 | CH₂CH₂CH₂ | H | 0 | NHCO₂-n-Pr | |
| A-994 | Het-17 | CH₂CH₂CH₂ | H | 0 | NHCO₂-i-Pr | |
| A-995 | Het-17 | CH₂CH₂CH₂ | H | 0 | NHCO₂-n-Bu | |
| A-996 | Het-17 | CH₂CH₂CH₂ | H | 0 | NHCO₂-i-Bu | |
| A-997 | Het-17 | CH₂CH₂CH₂ | H | 0 | NHSO₂Ph | |
| A-998 | Het-17 | CH₂CH₂CH₂ | H | 0 | NHSO₂Ph(p-Cl) | |
| A-999 | Het-17 | CH₂CH₂CH₂ | H | 0 | NHSO₂Ph(p-F) | |
| A-1000 | Het-17 | CH₂CH₂CH₂ | H | 0 | NHSO₂(2,4,6-trimethylphenyl) | |
| A-1001 | Het-17 | CH₂CH₂CH₂ | H | 0 | NHSO₂(2,4,6-trichlorophenyl) | |
| A-1002 | Het-17 | CH₂CH₂CH₂ | H | 0 | NHSO₂(2,6-dichlorophenyl) | |
| A-1003 | Het-17 | CH₂CH₂CH₂ | H | 0 | NHSO2[4-(2,6-dimethylphenyl)phenyl | |
| A-1004 | Het-17 | CH₂CH₂CH₂ | H | 0 | NHSO₂C₆H₄(4-Ph) | |
| A-1005 | Het-17 | CH₂CH₂CH₂ | H | 0 | NHSO₂[4-(3,5-dimethyl)isoxazolyl] | |
| A-1006 | Het-17 | CH₂CH₂CH₂ | H | 0 | NHSO₂(1-naphthyl) | |
| A-1007 | Het-18 | CH₂CH₂ | H | 0 | NHCO₂-n-Pr | |
| A-1008 | Het-18 | CH₂CH₂ | H | 0 | NHCO₂-i-Pr | |
| A-1009 | Het-18 | CH₂CH₂ | H | 0 | NHCO₂-n-Bu | |
| A-1010 | Het-18 | CH₂CH₂ | H | 0 | NHCO₂-i-Bu | |
| A-1011 | Het-18 | CH₂CH₂ | H | 0 | NHSO₂Ph | |
| A-1012 | Het-18 | CH₂CH₂ | H | 0 | NHSO₂Ph(p-Cl) | |
| A-1013 | Het-18 | CH₂CH₂ | H | 0 | NHSO₂Ph(p-F) | |
| A-1014 | Het-18 | CH₂CH₂ | H | 0 | NHSO₂(2,4,6-trimethylphenyl) | |
| A-1015 | Het-18 | CH₂CH₂ | H | 0 | NHSO₂(2,4,6-trichlorophenyl) | |
| A-1016 | Het-18 | CH₂CH₂ | H | 0 | NHSO₂(2,6-dichlorophenyl) | |
| A-1017 | Het-18 | CH₂CH₂ | H | 0 | NHSO2[4-(2,6-dimethylphenyl)phenyl | |
| A-1018 | Het-18 | CH₂CH₂ | H | 0 | NHSO₂C₆H₄(4-Ph) | |
| A-1019 | Het-18 | CH₂CH₂ | H | 0 | NHSO₂[4-(3,5-dimethyl)isoxazolyl] | |
| A-1020 | Het-18 | CH₂CH₂ | H | 0 | NHSO₂(1-naphthyl) | |
| A-1021 | Het-18 | CH₂CH₂CH₂ | H | 0 | NHCO₂-n-Pr | |
| A-1022 | Het-18 | CH₂CH₂CH₂ | H | 0 | NHCO₂-i-Pr | |
| A-1023 | Het-18 | CH₂CH₂CH₂ | H | 0 | NHCO₂-n-Bu | |
| A-1024 | Het-18 | CH₂CH₂CH₂ | H | 0 | NHCO₂-i-Bu | |
| A-1025 | Het-18 | CH₂CH₂CH₂ | H | 0 | NHSO₂Ph | |
| A-1026 | Het-18 | CH₂CH₂CH₂ | H | 0 | NHSO₂Ph(p-Cl) | |
| A-1027 | Het-18 | CH₂CH₂CH₂ | H | 0 | NHSO₂Ph(p-F) | |
| A-1028 | Het-18 | CH₂CH₂CH₂ | H | 0 | NHSO₂(2,4,6-trimethylphenyl) | |
| A-1029 | Het-18 | CH₂CH₂CH₂ | H | 0 | NHSO₂(2,4,6-trichlorophenyl) | |
| A-1030 | Het-18 | CH₂CH₂CH₂ | H | 0 | NHSO₂(2,6-dichlorophenyl) | |
| A-1031 | Het-18 | CH₂CH₂CH₂ | H | 0 | NHSO2[4-(2,6-dimethylphenyl)phenyl | |
| A-1032 | Het-18 | CH₂CH₂CH₂ | H | 0 | NHSO₂C₆H₄(4-Ph) | |
| A-1033 | Het-18 | CH₂CH₂CH₂ | H | 0 | NHSO₂[4-(3,5-dimethylisoxazolyl] | |
| A-1034 | Het-18 | CH₂CH₂CH₂ | H | 0 | NHSO₂(1-naphthyl) | |
| A-1035 | Het-13 | CH₂CH₂ | H | 0 | NHCO₂-n-Pr | |
| A-1036 | Het-13 | CH₂CH₂ | H | 0 | NHCO₂-i-Pr | |
| A-1037 | Het-13 | CH₂CH₂ | H | 0 | NHCO₂-n-Bu | |
| A-1038 | Het-13 | CH₂CH₂ | H | 0 | NHCO₂-i-Bu | |
| A-1039 | Het-13 | CH₂CH₂ | H | 0 | NHSO₂Ph | |
| A-1040 | Het-13 | CH₂CH₂ | H | 0 | NHSO₂Ph(p-Cl) | |
| A-1041 | Het-13 | CH₂CH₂ | H | 0 | NHSO₂Ph(p-F) | |
| A-1042 | Het-13 | CH₂CH₂ | H | 0 | NHSO₂(2,4,6-trimethylphenyl) | |
| A-1043 | Het-13 | CH₂CH₂ | H | 0 | NHSO₂(2,4,6-trichlorophenyl) | |
| A-1044 | Het-13 | CH₂CH₂ | H | 0 | NHSO₂(2,6-dichlorophenyl) | |
| A-1045 | Het-13 | CH₂CH₂ | H | 0 | NHSO2[4-(2,6-dimethylphenyl)phenyl | |
| A-1046 | Het-13 | CH₂CH₂ | H | 0 | NHSO₂C₆H₄(4-Ph) | |
| A-1047 | Het-13 | CH₂CH₂ | H | 0 | NHSO₂[4-(3,5-dimethylisoxazolyl] | |
| A-1048 | Het-13 | CH₂CH₂ | H | 0 | NHSO₂(1-naphthyl) | |
| A-1049 | Het-13 | CH₂CH₂CH₂ | H | 0 | NHCO₂-n-Pr | |
| A-1050 | Het-13 | CH₂CH₂CH₂ | H | 0 | NHCO₂-i-Pr | |
| A-1051 | Het-13 | CH₂CH₂CH₂ | H | 0 | NHCO₂-n-Bu | |
| A-1052 | Het-13 | CH₂CH₂CH₂ | H | 0 | NHCO₂-i-Bu | |
| A-1053 | Het-13 | CH₂CH₂CH₂ | H | 0 | NHSO₂Ph | |
| A-1054 | Het-13 | CH₂CH₂CH₂ | H | 0 | NHSO₂Ph(p-Cl) | |
| A-1055 | Het-13 | CH₂CH₂CH₂ | H | 0 | NHSO₂Ph(p-F) | |
| A-1056 | Het-13 | CH₂CH₂CH₂ | H | 0 | NHSO₂(2,4,6-trimethylphenyl) | |
| A-1057 | Het-13 | CH₂CH₂CH₂ | H | 0 | NHSO₂(2,4,6-trichlorophenyl) | |
| A-1058 | Het-13 | CH₂CH₂CH₂ | H | 0 | NHSO₂(2,6-dichlorophenyl) | |
| A-1059 | Het-13 | CH₂CH₂CH₂ | H | 0 | NHSO2[4-(2,6-dimethylphenyl)phenyl | |
| A-1060 | Het-13 | CH₂CH₂CH₂ | H | 0 | NHSO₂C₆H₄(4-Ph) | |
| A-1061 | Het-13 | CH₂CH₂CH₂ | H | 0 | NHSO₂[4-(3,5-dimethyl)isoxazolyl] | |
| A-1062 | Het-13 | CH₂CH₂CH₂ | H | 0 | NHSO₂(1-naphthyl) | |
| A-1063 | Het-19 | CH₂CH₂ | H | 0 | NHCO₂-n-Pr | |
| A-1064 | Het-19 | CH₂CH₂ | H | 0 | NHCO₂-i-Pr | |
| A-1065 | Het-19 | CH₂CH₂ | H | 0 | NHCO₂-n-Bu | |
| A-1066 | Het-19 | CH₂CH₂ | H | 0 | NHCO₂-i-Bu | |
| A-1067 | Het-19 | CH₂CH₂ | H | 0 | NHSO₂Ph | |
| A-1068 | Het-19 | CH₂CH₂ | H | 0 | NHSO₂Ph(p-Cl) | |
| A-1069 | Het-19 | CH₂CH₂ | H | 0 | NHSO₂Ph(p-F) | |
| A-1070 | Het-19 | CH₂CH₂ | H | 0 | NHSO₂(2,4,6-trimethylphenyl) | |
| A-1071 | Het-19 | CH₂CH₂ | H | 0 | NHSO₂(2,4,6-trichlorophenyl) | |
| A-1072 | Het-19 | CH₂CH₂ | H | 0 | NHSO₂(2,6-dichlorophenyl) | |
| A-1073 | Het-19 | CH₂CH₂ | H | 0 | NHSO2[4-(2,6-dimethylphenyl)phenyl | |
| A-1074 | Het-19 | CH₂CH₂ | H | 0 | NHSO₂C₆H₄(4-Ph) | |
| A-1075 | Het-19 | CH₂CH₂ | H | 0 | NHSO₂[4-(3,5-dimethyl)isoxazolyl] | |
| A-1076 | Het-19 | CH₂CH₂ | H | 0 | NHSO₂(1-naphthyl) | |
| A-1077 | Het-19 | CH₂CH₂CH₂ | H | 0 | NHCO₂-n-Pr | |
| A-1078 | Het-19 | CH₂CH₂CH₂ | H | 0 | NHCO₂-i-Pr | |
| A-1079 | Het-19 | CH₂CH₂CH₂ | H | 0 | NHCO₂-n-Bu | |
| A-1080 | Het-19 | CH₂CH₂CH₂ | H | 0 | NHCO₂-i-Bu | |

TABLE 1-continued

| Ex. No. | R¹ | U | R⁸ | z | R¹⁵ | MS |
|---|---|---|---|---|---|---|
| A-1081 | Het-19 | $CH_2CH_2CH_2$ | H | 0 | $NHSO_2Ph$ | |
| A-1082 | Het-19 | $CH_2CH_2CH_2$ | H | 0 | $NHSO_2Ph(p-Cl)$ | |
| A-1083 | Het-19 | $CH_2CH_2CH_2$ | H | 0 | $NHSO_2Ph(p-F)$ | |
| A-1084 | Het-19 | $CH_2CH_2CH_2$ | H | 0 | $NHSO_2(2,4,6-trimethylphenyl)$ | |
| A-1085 | Het-19 | $CH_2CH_2CH_2$ | H | 0 | $NHSO_2(2,4,6-trichlorophenyl)$ | |
| A-1086 | Het-19 | $CH_2CH_2CH_2$ | H | 0 | $NHSO_2(2,6-dichlorophenyl)$ | |
| A-1087 | Het-19 | $CH_2CH_2CH_2$ | H | 0 | NHSO2[4-(2,6-dimethylphenyl)phenyl | |
| A-1088 | Het-19 | $CH_2CH_2CH_2$ | H | 0 | $NHSO_2C_6H_4(4-Ph)$ | |
| A-1089 | Het-19 | $CH_2CH_2CH_2$ | H | 0 | $NHSO_2[4-(3,5-dimethyl)isoxazolyl]$ | |
| A-1090 | Het-19 | $CH_2CH_2CH_2$ | H | 0 | $NHSO_2(1-naphthyl)$ | |
| A-1091 | Het-20 | $CH_2CH_2$ | H | 0 | $NHCO_2$-n-Pr | |
| A-1092 | Het-20 | $CH_2CH_2$ | H | 0 | $NHCO_2$-i-Pr | |
| A-1093 | Het-20 | $CH_2CH_2$ | H | 0 | $NHCO_2$-n-Bu | |
| A-1094 | Het-20 | $CH_2CH_2$ | H | 0 | $NHCO_2$-i-Bu | |
| A-1095 | Het-20 | $CH_2CH_2$ | H | 0 | $NHSO_2Ph$ | |
| A-1096 | Het-20 | $CH_2CH_2$ | H | 0 | $NHSO_2Ph(p-Cl)$ | |
| A-1097 | Het-20 | $CH_2CH_2$ | H | 0 | $NHSO_2Ph(p-F)$ | |
| A-1098 | Het-20 | $CH_2CH_2$ | H | 0 | $NHSO_2(2,4,6-trimethylphenyl)$ | |
| A-1099 | Het-20 | $CH_2CH_2$ | H | 0 | $NHSO_2(2,4,6-trichlorophenyl)$ | |
| A-1100 | Het-20 | $CH_2CH_2$ | H | 0 | $NHSO_2(2,6-dichlorophenyl)$ | |
| A-1101 | Het-20 | $CH_2CH_2$ | H | 0 | NHSO2[4-(2,6-dimethylphenyl)phenyl | |
| A-1102 | Het-20 | $CH_2CH_2$ | H | 0 | $NHSO_2C_6H_4(4-Ph)$ | |
| A-1103 | Het-20 | $CH_2CH_2$ | H | 0 | $NHSO_2[4-(3,5-dimethyl)isoxazolyl]$ | |
| A-1104 | Het-20 | $CH_2CH_2$ | H | 0 | $NHSO_2(1-naphthyl)$ | |
| A-1105 | Het-20 | $CH_2CH_2CH_2$ | H | 0 | $NHCO_2$-n-Pr | |
| A-1106 | Het-20 | $CH_2CH_2CH_2$ | H | 0 | $NHCO_2$-i-Pr | |
| A-1107 | Het-20 | $CH_2CH_2CH_2$ | H | 0 | $NHCO_2$-n-Bu | |
| A-1108 | Het-20 | $CH_2CH_2CH_2$ | H | 0 | $NHCO_2$-i-Bu | |
| A-1109 | Het-20 | $CH_2CH_2CH_2$ | H | 0 | $NHSO_2Ph$ | |
| A-1110 | Het-20 | $CH_2CH_2CH_2$ | H | 0 | $NHSO_2Ph(p-Cl)$ | |
| A-1111 | Het-20 | $CH_2CH_2CH_2$ | H | 0 | $NHSO_2Ph(p-F)$ | |
| A-1112 | Het-20 | $CH_2CH_2CH_2$ | H | 0 | $NHSO_2(2,4,6-trimethylphenyl)$ | |
| A-1113 | Het-20 | $CH_2CH_2CH_2$ | H | 0 | $NHSO_2(2,4,6-trichlorophenyl)$ | |
| A-1114 | Het-20 | $CH_2CH_2CH_2$ | H | 0 | $NHSO_2(2,6-dichlorophenyl)$ | |
| A-1115 | Het-20 | $CH_2CH_2CH_2$ | H | 0 | NHSO2[4-(2,6-dimethylphenyl)phenyl | |
| A-1116 | Het-20 | $CH_2CH_2CH_2$ | H | 0 | $NHSO_2C_6H_4(4-Ph)$ | |
| A-1117 | Het-20 | $CH_2CH_2CH_2$ | H | 0 | $NHSO_2[4-(3,5-dimethyyl)isoxazolyl]$ | |
| A-1118 | Het-20 | $CH_2CH_2CH_2$ | H | 0 | $NHSO_2(1-naphthyl)$ | |
| A-1119 | Het-1 | $CH_2CH_2$ | H | 1 | $NHCO_2$-n-Pr | |
| A-1120 | Het-1 | $CH_2CH_2$ | H | 1 | $NHCO_2$-i-Pr | |
| A-1121 | Het-1 | $CH_2CH_2$ | H | 1 | $NHCO_2$-n-Bu | |
| A-1122 | Het-1 | $CH_2CH_2$ | H | 1 | $NHCO_2$-i-Bu | |
| A-1123 | Het-1 | $CH_2CH_2$ | H | 1 | $NHSO_2Ph$ | |
| A-1124 | Het-1 | $CH_2CH_2$ | H | 1 | $NHSO_2Ph(p-Cl)$ | |
| A-1125 | Het-1 | $CH_2CH_2$ | H | 1 | $NHSO_2Ph(p-F)$ | |
| A-1126 | Het-1 | $CH_2CH_2$ | H | 1 | $NHSO_2(2,4,6-trimethylphenyl)$ | |
| A-1127 | Het-1 | $CH_2CH_2$ | H | 1 | $NHSO_2(2,4,6-trichlorophenyl)$ | |
| A-1128 | Het-1 | $CH_2CH_2$ | H | 1 | $NHSO_2(2,6-dichlorophenyl)$ | |
| A-1129 | Het-1 | $CH_2CH_2$ | H | 1 | NHSO2[4-(2,6-dimethylphenyl)phenyl | |
| A-1130 | Het-1 | $CH_2CH_2$ | H | 1 | $NHSO_2C_6H_4(4-Ph)$ | |
| A-1131 | Het-1 | $CH_2CH_2$ | H | 1 | $NHSO_2[4-(3,5-dimethylisoxazolyl]$ | |
| A-1132 | Het-1 | $CH_2CH_2$ | H | 1 | $NHSO_2(1-naphthyl)$ | |
| A-1133 | Het-1 | $CH_2CH_2$ | 3-Me | 0 | $NHCO_2$-n-Pr | |
| A-1134 | Het-1 | $CH_2CH_2$ | 3-Me | 0 | $NHCO_2$-i-Pr | |
| A-1135 | Het-1 | $CH_2CH_2$ | 3-Me | 0 | $NHCO_2$-n-Bu | |
| A-1136 | Het-1 | $CH_2CH_2$ | 3-Me | 0 | $NHCO_2$-i-Bu | |
| A-1137 | Het-1 | $CH_2CH_2$ | 3-Me | 0 | $NHSO_2Ph$ | |
| A-1138 | Het-1 | $CH_2CH_2$ | 3-Me | 0 | $NHSO_2Ph(p-Cl)$ | |
| A-1139 | Het-1 | $CH_2CH_2$ | 3-Me | 0 | $NHSO_2Ph(p-F)$ | |
| A-1140 | Het-1 | $CH_2CH_2$ | 3-Me | 0 | $NHSO_2(2,4,6-trimethylphenyl)$ | |
| A-1141 | Het-1 | $CH_2CH_2$ | 3-Me | 0 | $NHSO_2(2,4,6-trichlorophenyl)$ | |
| A-1142 | Het-1 | $CH_2CH_2$ | 3-Me | 0 | $NHSO_2(2,6-dichlorophenyl)$ | |
| A-1143 | Het-1 | $CH_2CH_2$ | 3-Me | 0 | NHSO2[4-(2,6-dimethylphenyl)phenyl | |
| A-1144 | Het-1 | $CH_2CH_2$ | 3-Me | 0 | $NHSO_2C_6H_4(4-Ph)$ | |
| A-1145 | Het-1 | $CH_2CH_2$ | 3-Me | 0 | $NHSO_2[4-(3,5-dimethyl)isoxazolyl]$ | |
| A-1146 | Het-1 | $CH_2CH_2$ | 3-Me | 0 | $NHSO_2(1-naphthyl)$ | |
| A-1147 | Het-1 | $CH_2CH_2$ | 2-Cl | 0 | $NHCO_2$-n-Pr | |
| A-1148 | Het-1 | $CH_2CH_2$ | 2-Cl | 0 | $NHCO_2$-i-Pr | |
| A-1149 | Het-1 | $CH_2CH_2$ | 2-Cl | 0 | $NHCO_2$-n-Bu | |
| A-1150 | Het-1 | $CH_2CH_2$ | 2-Cl | 0 | $NHCO_2$-i-Bu | |
| A-1151 | Het-1 | $CH_2CH_2$ | 2-Cl | 0 | $NHSO_2Ph$ | |
| A-1152 | Het-1 | $CH_2CH_2$ | 2-Cl | 0 | $NHSO_2Ph(p-Cl)$ | |
| A-1153 | Het-1 | $CH_2CH_2$ | 2-Cl | 0 | $NHSO_2Ph(p-F)$ | |
| A-1154 | Het-1 | $CH_2CH_2$ | 2-Cl | 0 | $NHSO_2(2,4,6-trimethylphenyl)$ | |
| A-1155 | Het-1 | $CH_2CH_2$ | 2-Cl | 0 | $NHSO_2(2,4,6-trichlorophenyl)$ | |
| A-1156 | Het-1 | $CH_2CH_2$ | 2-Cl | 0 | $NHSO_2(2,6-dichlorophenyl)$ | |
| A-1157 | Het-1 | $CH_2CH_2$ | 2-Cl | 0 | NHSO2[4-(2,6-dimethylphenyl)phenyl | |
| A-1158 | Het-1 | $CH_2CH_2$ | 2-Cl | 0 | $NHSO_2C_6H_4(4-Ph)$ | |
| A-1159 | Het-1 | $CH_2CH_2$ | 2-Cl | 0 | $NHSO_2[4-(3,5-dimethyl)isoxazolyl]$ | |
| A-1160 | Het-1 | $CH_2CH_2$ | 2-Cl | 0 | $NHSO_2(1-naphthyl)$ | |
| A-1161 | Het-2 | $CH_2CH_2$ | H | 1 | $NHCO_2$-n-Pr | |
| A-1162 | Het-2 | $CH_2CH_2$ | H | 1 | $NHCO_2$-i-Pr | |
| A-1163 | Het-2 | $CH_2CH_2$ | H | 1 | $NHCO_2$-n-Bu | |
| A-1164 | Het-2 | $CH_2CH_2$ | H | 1 | $NHCO_2$-i-Bu | |
| A-1165 | Het-2 | $CH_2CH_2$ | H | 1 | $NHSO_2Ph$ | |

TABLE 1-continued $$R^1-U-\underset{\underset{3}{}}{\overset{\overset{R^8}{\underset{5}{\overset{6}{\diagup}}}}{\diagdown}}\underset{2}{\diagdown}(\ )_z\overset{O}{\underset{\|}{C}}-N(H)-CH(R^{15})-CO_2H$$

| Ex. No. | R¹ | U | R⁸ | z | R¹⁵ | MS |
|---|---|---|---|---|---|---|
| A-1166 | Het-2 | CH₂CH₂ | H | 1 | NHSO₂Ph(p-Cl) | |
| A-1167 | Het-2 | CH₂CH₂ | H | 1 | NHSO₂Ph(p-F) | |
| A-1168 | Het-2 | CH₂CH₂ | H | 1 | NHSO₂(2,4,6-trimethylphenyl) | |
| A-1169 | Het-2 | CH₂CH₂ | H | 1 | NHSO₂(2,4,6-trichlorophenyl) | |
| A-1170 | Het-2 | CH₂CH₂ | H | 1 | NHSO₂(2,6-dichlorophenyl) | |
| A-1171 | Het-2 | CH₂CH₂ | H | 1 | NHSO2[4-(2,6-dimethylphenyl)phenyl | |
| A-1172 | Het-2 | CH₂CH₂ | H | 1 | NHSO₂C₆H₄(4-Ph) | |
| A-1173 | Het-2 | CH₂CH₂ | H | 1 | NHSO₂[4-(3,5-dimethyl)isoxazolyl] | |
| A-1174 | Het-2 | CH₂CH₂ | H | 1 | NHSO₂(1-naphthyl) | |
| A-1175 | Het-2 | CH₂CH₂ | 3-Me | 0 | NHCO₂-n-Pr | |
| A-1176 | Het-2 | CH₂CH₂ | 3-Me | 0 | NHCO₂-i-Pr | |
| A-1177 | Het-2 | CH₂CH₂ | 3-Me | 0 | NHCO₂-n-Bu | |
| A-1178 | Het-2 | CH₂CH₂ | 3-Me | 0 | NHCO₂-i-Bu | |
| A-1179 | Het-2 | CH₂CH₂ | 3-Me | 0 | NHSO₂Ph | |
| A-1180 | Het-2 | CH₂CH₂ | 3-Me | 0 | NHSO₂Ph(p-Cl) | |
| A-1181 | Het-2 | CH₂CH₂ | 3-Me | 0 | NHSO₂Ph(p-F) | |
| A-1182 | Het-2 | CH₂CH₂ | 3-Me | 0 | NHSO₂(2,4,6-trimethylphenyl) | |
| A-1183 | Het-2 | CH₂CH₂ | 3-Me | 0 | NHSO₂(2,4,6-trichlorophenyl) | |
| A-1184 | Het-2 | CH₂CH₂ | 3-Me | 0 | NHSO₂(2,6-dichlorophenyl) | |
| A-1185 | Het-2 | CH₂CH₂ | 3-Me | 0 | NHSO2[4-(2,6-dimethylphenyl)phenyl | |
| A-1186 | Het-2 | CH₂CH₂ | 3-Me | 0 | NHSO₂C₆H₄(4-Ph) | |
| A-1187 | Het-2 | CH₂CH₂ | 3-Me | 0 | NHSO₂[4-(3,5-dimethyl)isoxazolyl] | |
| A-1188 | Het-2 | CH₂CH₂ | 3-Me | 0 | NHSO₂(1-naphthyl) | |
| A-1189 | Het-2 | CH₂CH₂ | 2-Cl | 0 | NHCO₂-n-Pr | |
| A-1190 | Het-2 | CH₂CH₂ | 2-Cl | 0 | NHCO₂-i-Pr | |
| A-1191 | Het-2 | CH₂CH₂ | 2-Cl | 0 | NHCO₂-n-Bu | |
| A-1192 | Het-2 | CH₂CH₂ | 2-Cl | 0 | NHCO₂-i-Bu | |
| A-1193 | Het-2 | CH₂CH₂ | 2-Cl | 0 | NHSO₂Ph | |
| A-1194 | Het-2 | CH₂CH₂ | 2-Cl | 0 | NHSO₂Ph(p-Cl) | |
| A-1195 | Het-2 | CH₂CH₂ | 2-Cl | 0 | NHSO₂Ph(p-F) | |
| A-1196 | Het-2 | CH₂CH₂ | 2-Cl | 0 | NHSO₂(2,4,6-trimethylphenyl) | |
| A-1197 | Het-2 | CH₂CH₂ | 2-Cl | 0 | NHSO₂(2,4,6-trichlorophenyl) | |
| A-1198 | Het-2 | CH₂CH₂ | 2-Cl | 0 | NHSO₂(2,6-dichlorophenyl) | |
| A-1199 | Het-2 | CH₂CH₂ | 2-Cl | 0 | NHSO2[4-(2,6-dimethylphenyl)phenyl | |
| A-1200 | Het-2 | CH₂CH₂ | 2-Cl | 0 | NHSO₂C₆H₄(4-Ph) | |
| A-1201 | Het-2 | CH₂CH₂ | 2-Cl | 0 | NHSO₂[4-(3,5-dimethyl)isoxazolyl] | |
| A-1202 | Het-2 | CH₂CH₂ | 2-Cl | 0 | NHSO₂(1-naphthyl) | |
| A-1203 | Het-9 | CH₂CH₂ | H | 0 | NHCO₂-n-Pr | |
| A-1204 | Het-9 | CH₂CH₂ | H | 0 | NHCO₂-i-Pr | |
| A-1205 | Het-9 | CH₂CH₂ | H | 0 | NHCO₂-n-Bu | |
| A-1206 | Het-9 | CH₂CH₂ | H | 0 | NHCO₂-i-Bu | |
| A-1207 | Het-9 | CH₂CH₂ | H | 0 | NHSO₂Ph | |
| A-1208 | Het-9 | CH₂CH₂ | H | 0 | NHSO₂Ph(p-Cl) | |
| A-1209 | Het-9 | CH₂CH₂ | H | 0 | NHSO₂Ph(p-F) | |
| A-1210 | Het-9 | CH₂CH₂ | H | 0 | NHSO₂(2,4,6-trimethylphenyl) | 553.6 |
| A-1211 | Het-9 | CH₂CH₂ | H | 0 | NHSO₂(2,4,6-trichlorophenyl) | |
| A-1212 | Het-9 | CH₂CH₂ | H | 0 | NHSO₂(2,6-dichlorophenyl) | |
| A-1213 | Het-9 | CH₂CH₂ | H | 0 | NHSO2[4-(2,6-dimethylphenyl)phenyl | |
| A-1214 | Het-9 | CH₂CH₂ | H | 0 | NHSO₂C₆H₄(4-Ph) | |
| A-1215 | Het-9 | CH₂CH₂ | H | 0 | NHSO₂[4-(3,5-dimethyl)isoxazolyl] | |
| A-1216 | Het-9 | CH₂CH₂ | H | 0 | NHSO₂(1-naphthyl) | |
| A-1217 | Het-9 | CH₂CH₂CH₂ | H | 0 | NHCO₂-n-Pr | |
| A-1218 | Het-9 | CH₂CH₂CH₂ | H | 0 | NHCO₂-i-Pr | |
| A-1219 | Het-9 | CH₂CH₂CH₂ | H | 0 | NHCO₂-n-Bu | |
| A-1220 | Het-9 | CH₂CH₂CH₂ | H | 0 | NHCO₂-i-Bu | |
| A-1221 | Het-9 | CH₂CH₂CH₂ | H | 0 | NHSO₂Ph | |
| A-1222 | Het-9 | CH₂CH₂CH₂ | H | 0 | NHSO₂Ph(p-Cl) | |
| A-1223 | Het-9 | CH₂CH₂CH₂ | H | 0 | NHSO₂Ph(p-F) | |
| A-1224 | Het-9 | CH₂CH₂CH₂ | H | 0 | NHSO₂(2,4,6-trimethylphenyl) | |
| A-1225 | Het-9 | CH₂CH₂CH₂ | H | 0 | NHSO₂(2,4,6-trichlorophenyl) | |
| A-1226 | Het-9 | CH₂CH₂CH₂ | H | 0 | NHSO₂(2,6-dichlorophenyl) | |
| A-1227 | Het-9 | CH₂CH₂CH₂ | H | 0 | NHSO2[4-(2,6-dimethylphenyl)phenyl | |
| A-1228 | Het-9 | CH₂CH₂CH₂ | H | 0 | NHSO₂C₆H₄(4-Ph) | |
| A-1229 | Het-9 | CH₂CH₂CH₂ | H | 0 | NHSO₂[4-(3,5-dimethyl)isoxazolyl] | |
| A-1230 | Het-9 | CH₂CH₂CH₂ | H | 0 | NHSO₂(1-naphthyl) | |
| A-1231 | Het-21 | CH₂CH₂ | H | 0 | NHCO₂-n-Pr | |
| A-1232 | Het-21 | CH₂CH₂ | H | 0 | NHCO₂-i-Pr | |
| A-1233 | Het-21 | CH₂CH₂ | H | 0 | NHCO₂-n-Bu | |
| A-1234 | Het-21 | CH₂CH₂ | H | 0 | NHCO₂-i-Bu | |
| A-1235 | Het-21 | CH₂CH₂ | H | 0 | NHSO₂Ph | |
| A-1236 | Het-21 | CH₂CH₂ | H | 0 | NHSO₂Ph(p-Cl) | |
| A-1237 | Het-21 | CH₂CH₂ | H | 0 | NHSO₂Ph(p-F) | |
| A-1238 | Het-21 | CH₂CH₂ | H | 0 | NHSO₂(2,4,6-trimethylphenyl) | 554.2 |
| A-1239 | Het-21 | CH₂CH₂ | H | 0 | NHSO₂(2,4,6-trichlorophenyl) | |
| A-1240 | Het-21 | CH₂CH₂ | H | 0 | NHSO₂(2,6-dichlorophenyl) | |
| A-1241 | Het-21 | CH₂CH₂ | H | 0 | NHSO2[4-(2,6-dimethylphenyl)phenyl | |
| A-1242 | Het-21 | CH₂CH₂ | H | 0 | NHSO₂C₆H₄(4-Ph) | |
| A-1243 | Het-21 | CH₂CH₂ | H | 0 | NHSO₂[4-(3,5-dimethyl)isoxazolyl] | |
| A-1244 | Het-21 | CH₂CH₂ | H | 0 | NHSO₂(1-naphthyl) | |
| A-1245 | Het-21 | CH₂CH₂CH₂ | H | 0 | NHCO₂-n-Pr | |
| A-1246 | Het-21 | CH₂CH₂CH₂ | H | 0 | NHCO₂-i-Pr | |
| A-1247 | Het-21 | CH₂CH₂CH₂ | H | 0 | NHCO₂-n-Bu | |
| A-1248 | Het-21 | CH₂CH₂CH₂ | H | 0 | NHCO₂-i-Bu | |
| A-1249 | Het-21 | CH₂CH₂CH₂ | H | 0 | NHSO₂Ph | |
| A-1250 | Het-21 | CH₂CH₂CH₂ | H | 0 | NHSO₂Ph(p-Cl) | |

TABLE 1-continued

Structure: $R^1-U-$[phenyl ring with positions 5,6,3,2 around position 4 (U) and position 1]$-CH_z-C(=O)-NH-CH(R^{15})-CO_2H$, with $R^8$ on the phenyl ring.

| Ex. No. | $R^1$ | U | $R^8$ | z | $R^{15}$ | MS |
|---|---|---|---|---|---|---|
| A-1251 | Het-21 | $CH_2CH_2CH_2$ | H | 0 | $NHSO_2Ph(p-F)$ | |
| A-1252 | Het-21 | $CH_2CH_2CH_2$ | H | 0 | $NHSO_2$(2,4,6-trimethylphenyl) | |
| A-1253 | Het-21 | $CH_2CH_2CH_2$ | H | 0 | $NHSO_2$(2,4,6-trichlorophenyl) | |
| A-1254 | Het-21 | $CH_2CH_2CH_2$ | H | 0 | $NHSO_2$(2,6-dichlorophenyl) | |
| A-1255 | Het-21 | $CH_2CH_2CH_2$ | H | 0 | $NHSO_2$[4-(2,6-dimethylphenyl)phenyl | |
| A-1256 | Het-21 | $CH_2CH_2CH_2$ | H | 0 | $NHSO_2C_6H_4$(4-Ph) | |
| A-1257 | Het-21 | $CH_2CH_2CH_2$ | H | 0 | $NHSO_2$[4-(3,5-dimthyl)isoxazolyl] | |
| A-1258 | Het-21 | $CH_2CH_2CH_2$ | H | 0 | $NHSO_2$(1-naphthyl) | |
| A-1259 | Het-22 | $NHCH_2$ | H | 0 | $NHCO_2$-n-Pr | |
| A-1260 | Het-22 | $NHCH_2$ | H | 0 | $NHCO_2$-i-Pr | |
| A-1261 | Het-22 | $NHCH_2$ | H | 0 | $NHCO_2$-n-Bu | |
| A-1262 | Het-22 | $NHCH_2$ | H | 0 | $NHCO_2$-i-Bu | |
| A-1263 | Het-22 | $NHCH_2$ | H | 0 | $NHSO_2Ph$ | |
| A-1264 | Het-22 | $NHCH_2$ | H | 0 | $NHSO_2Ph$(p-Cl) | |
| A-1265 | Het-22 | $NHCH_2$ | H | 0 | $NHSO_2Ph$(p-F) | |
| A-1266 | Het-22 | $NHCH_2$ | H | 0 | $NHSO_2$(2,4,6-trimethylphenyl) | 513.2 |
| A-1267 | Het-22 | $NHCH_2$ | H | 0 | $NHSO_2$(2,4,6-trichlorophenyl) | |
| A-1268 | Het-22 | $NHCH_2$ | H | 0 | $NHSO_2$(2,6-dichlorophenyl) | |
| A-1269 | Het-22 | $NHCH_2$ | H | 0 | $NHSO_2$[4-(2,6-dimethylphenyl)phenyl | |
| A-1270 | Het-22 | $NHCH_2$ | H | 0 | $NHSO_2C_6H_4$(4-Ph) | |
| A-1271 | Het-22 | $NHCH_2$ | H | 0 | $NHSO_2$[4-(3,5-dimethyl)isoxazolyl] | |
| A-1272 | Het-22 | $NHCH_2$ | H | 0 | $NHSO_2$(1-naphthyl) | |
| A-1273 | Het-22 | $NHCH_2CH_2$ | H | 0 | $NHCO_2$-n-Pr | |
| A-1274 | Het-22 | $NHCH_2CH_2$ | H | 0 | $NHCO_2$-i-Pr | |
| A-1275 | Het-22 | $NHCH_2CH_2$ | H | 0 | $NHCO_2$-n-Bu | |
| A-1276 | Het-22 | $NHCH_2CH_2$ | H | 0 | $NHCO_2$-i-Bu | |
| A-1277 | Het-22 | $NHCH_2CH_2$ | H | 0 | $NHSO_2Ph$ | |
| A-1278 | Het-22 | $NHCH_2CH_2$ | H | 0 | $NHSO_2Ph$(p-Cl) | |
| A-1279 | Het-22 | $NHCH_2CH_2$ | H | 0 | $NHSO_2Ph$(p-F) | |
| A-1280 | Het-22 | $NHCH_2CH_2$ | H | 0 | $NHSO_2$(2,4,6-trimethylphenyl) | |
| A-1281 | Het-22 | $NHCH_2CH_2$ | H | 0 | $NHSO_2$(2,4,6-trichlorophenyl) | |
| A-1282 | Het-22 | $NHCH_2CH_2$ | H | 0 | $NHSO_2$(2,6-dichlorophenyl) | |
| A-1283 | Het-22 | $NHCH_2CH_2$ | H | 0 | $NHSO_2$[4-(2,6-dimethylphenyl)phenyl | |
| A-1284 | Het-22 | $NHCH_2CH_2$ | H | 0 | $NHSO_2C_6H_4$(4-Ph) | |
| A-1285 | Het-22 | $NHCH_2CH_2$ | H | 0 | $NHSO_2$[4-(3,5-dimethyl)isoxazolyl] | |
| A-1286 | Het-22 | $NHCH_2CH_2$ | H | 0 | $NHSO_2$(1-naphthyl) | |

TABLE 2

Structure: $R^1-U-$[phenyl ring]$-CH_z-C(=O)-NH-CH(R^{14})-CH_2-CO_2H$, with $R^8$ on the phenyl ring.

| Ex. No. | $R^1$ | U | $R^8$ | z | $R^{14}$ | MS |
|---|---|---|---|---|---|---|
| B-1 | Het-1 | $CH_2CH_2$ | H | 0 | $CH=CH2$ | |
| B-2 | Het-1 | $CH_2CH_2$ | H | 0 | $C{\equiv}CH$ | |
| B-3 | Het-1 | $CH_2CH_2$ | H | 0 | cyclopropyl | |
| B-4 | Het-1 | $CH_2CH_2$ | H | 0 | cyclohexyl | |
| B-5 | Het-1 | $CH_2CH_2$ | H | 0 | Ph | |
| B-6 | Het-1 | $CH_2CH_2$ | H | 0 | Ph(p-F) | |
| B-7 | Het-1 | $CH_2CH_2$ | H | 0 | Ph (3,5-dichloro) | |
| B-8 | Het-1 | $CH_2CH_2$ | H | 0 | $CH_2Ph$ | |
| B-9 | Het-1 | $CH_2CH_2$ | H | 0 | $CH_2CH_2Ph$ | |
| B-10 | Het-1 | $CH_2CH_2$ | H | 0 | 3-pyridyl | |
| B-11 | Het-1 | $CH_2CH_2$ | H | 0 | 5-pyrimidinyl | |
| B-12 | Het-1 | $CH_2CH_2$ | H | 0 | 3-quinolyl | |
| B-13 | Het-1 | $CH_2CH_2$ | H | 1 | $CH=CH2$ | |
| B-14 | Het-1 | $CH_2CH_2$ | H | 1 | $C{\equiv}CH$ | |
| B-15 | Het-1 | $CH_2CH_2$ | H | 1 | cyclopropyl | |
| B-16 | Het-1 | $CH_2CH_2$ | H | 1 | cyclohexyl | |
| B-17 | Het-1 | $CH_2CH_2$ | H | 1 | Ph | |
| B-18 | Het-1 | $CH_2CH_2$ | H | 1 | Ph(p-F) | |
| B-19 | Het-1 | $CH_2CH_2$ | H | 1 | Ph (3,5-dichloro) | |
| B-20 | Het-1 | $CH_2CH_2$ | H | 0 | $CH_2Ph$ | |
| B-21 | Het-1 | $CH_2CH_2$ | H | 0 | $CH_2CH_2Ph$ | |
| B-22 | Het-1 | $CH_2CH_2$ | H | 1 | 3-pyridyl | |
| B-23 | Het-1 | $CH_2CH_2$ | H | 1 | 5-pyrimidinyl | |
| B-24 | Het-1 | $CH_2CH_2$ | H | 1 | 3-quinolyl | |
| B-25 | Het-1 | $NHCH_2$ | H | 0 | $CH=CH2$ | |
| B-26 | Het-1 | $NHCH_2$ | H | 0 | $CH{\equiv}CH$ | |
| B-27 | Het-1 | $NHCH_2$ | H | 0 | cyclopropyl | |
| B-28 | Het-1 | $NHCH_2$ | H | 0 | Ph | |
| B-29 | Het-1 | $NHCH_2$ | H | 0 | Ph | |
| B-30 | Het-1 | $NHCH_2$ | H | 0 | Ph(p-F) | |
| B-31 | Het-1 | $NHCH_2$ | H | 0 | Ph (3,5-dichloro) | |
| B-32 | Het-1 | $NHCH_2$ | H | 0 | $CH_2Ph$ | |
| B-33 | Het-1 | $NHCH_2$ | H | 0 | $CH_2CH_2Ph$ | |
| B-34 | Het-1 | $NHCH_2$ | H | 0 | 3-pyridyl | |
| B-35 | Het-1 | $NHCH_2$ | H | 0 | 5-pyridiminyl | |
| B-36 | Het-1 | $NHCH_2$ | H | 0 | 3-quinolyl | |
| B-37 | Het-1 | $NHCH_2$ | H | 1 | $CH=CH2$ | |
| B-38 | Het-1 | $NHCH_2$ | H | 1 | $C{\equiv}CH$ | |
| B-39 | Het-1 | $NHCH_2$ | H | 1 | cyclopropyl | |
| B-40 | Het-1 | $NHCH_2$ | H | 1 | cyclohexyl | |
| B-41 | Het-1 | $NHCH_2$ | H | 1 | Ph | |
| B-42 | Het-1 | $NHCH_2$ | H | 1 | Ph(p-F) | |
| B-43 | Het-1 | $NHCH_2$ | H | 1 | Ph (3,5-dichloro) | |
| B-44 | Het-1 | $NHCH_2$ | H | 1 | $CH_2Ph$ | |
| B-45 | Het-1 | $NHCH_2$ | H | 1 | $CH_2CH_2Ph$ | |
| B-46 | Het-1 | $NHCH_2$ | H | 1 | 3-pyridyl | |
| B-47 | Het-1 | $NHCH_2$ | H | 1 | 5-pyrimidinyl | |
| B-48 | Het-1 | $NHCH_2$ | H | 1 | 3-quinolyl | |
| B-49 | Het-1 | $OCH_2$ | H | 0 | $CH=CH2$ | |
| B-50 | Het-1 | $OCH_2$ | H | 0 | $C{\equiv}CH$ | |
| B-51 | Het-1 | $OCH_2$ | H | 0 | cyclopropyl | |
| B-52 | Het-1 | $OCH_2$ | H | 0 | cyclohexyl | |
| B-53 | Het-1 | $OCH_2$ | H | 0 | Ph | |
| B-54 | Het-1 | $OCH_2$ | H | 0 | Ph(p-F) | |
| B-55 | Het-1 | $OCH_2$ | H | 0 | Ph (3,5-dichloro) | |
| B-56 | Het-1 | $OCH_2$ | H | 0 | $CH_2Ph$ | |
| B-57 | Het-1 | $OCH_2$ | H | 0 | $CH_2CH_2Ph$ | |
| B-58 | Het-1 | $OCH_2$ | H | 0 | 3-pyridyl | |
| B-59 | Het-1 | $OCH_2$ | H | 0 | 5-pyrimidinyl | |
| B-60 | Het-1 | $OCH_2$ | H | 0 | 3-quinolyl | |
| B-61 | Het-1 | $OCH_2$ | H | 1 | $CH=CH2$ | |
| B-62 | Het-1 | $OCH_2$ | H | 1 | $C{\equiv}CH$ | |
| B-63 | Het-1 | $OCH_2$ | H | 1 | cyclopropyl | |
| B-64 | Het-1 | $OCH_2$ | H | 1 | cyclohexyl | |
| B-65 | Het-1 | $OCH_2$ | H | 1 | Ph | |
| B-66 | Het-1 | $OCH_2$ | H | 1 | Ph(p-F) | |
| B-67 | Het-1 | $OCH_2$ | H | 1 | Ph (3,5-dichloro) | |

TABLE 2-continued

| Ex. No. | R¹ | U | R⁸ | z | R¹⁴ | MS |
|---|---|---|---|---|---|---|
| B-68 | Het-1 | OCH₂ | H | 1 | CH₂Ph | |
| B-69 | Het-1 | OCH₂ | H | 1 | CH₂CH₂Ph | |
| B-70 | Het-1 | OCH₂ | H | 1 | 3-pyridyl | |
| B-71 | Het-1 | OCH₂ | H | 1 | 5-pyrimidinyl | |
| B-72 | Het-1 | OCH₂ | H | 1 | 3-quinolyl | |
| B-73 | Het-1 | CH₂CH₂CH₂ | H | 0 | CH=CH2 | |
| B-74 | Het-1 | CH₂CH₂CH₂ | H | 0 | C≡CH | |
| B-75 | Het-1 | CH₂CH₂CH₂ | H | 0 | cyclopropyl | |
| B-76 | Het-1 | CH₂CH₂CH₂ | H | 0 | cyclohexyl | |
| B-77 | Het-1 | CH₂CH₂CH₂ | H | 0 | Ph | |
| B-78 | Het-1 | CH₂CH₂CH₂ | H | 0 | Ph(p-F) | |
| B-79 | Het-1 | CH₂CH₂CH₂ | H | 0 | Ph (3,5-dichloro) | |
| B-80 | Het-1 | CH₂CH₂CH₂ | H | 0 | CH₂Ph | |
| B-81 | Het-1 | CH₂CH₂CH₂ | H | 0 | CH₂CH₂Ph | |
| B-82 | Het-1 | CH₂CH₂CH₂ | H | 0 | 3-pyridyl | |
| B-83 | Het-1 | CH₂CH₂CH₂ | H | 0 | 5-pyrimidinyl | |
| B-84 | Het-1 | CH₂CH₂CH₂ | H | 0 | 3-quinolyl | |
| B-85 | Het-1 | CH₂CH₂CH₂ | H | 1 | CH=CH2 | |
| B-86 | Het-1 | CH₂CH₂CH₂ | H | 1 | C≡CH | |
| B-87 | Het-1 | CH₂CH₂CH₂ | H | 1 | cyclopropyl | |
| B-88 | Het-1 | CH₂CH₂CH₂ | H | 1 | cyclohexyl | |
| B-89 | Het-1 | CH₂CH₂CH₂ | H | 1 | Ph | |
| B-90 | Het-1 | CH₂CH₂CH₂ | H | 1 | Ph(p-F) | |
| B-91 | Het-1 | CH₂CH₂CH₂ | H | 1 | Ph (3,5-dichloro) | |
| B-92 | Het-1 | CH₂CH₂CH₂ | H | 1 | CH₂Ph | |
| B-93 | Het-1 | CH₂CH₂CH₂ | H | 1 | CH₂CH₂Ph | |
| B-94 | Het-1 | CH₂CH₂CH₂ | H | 1 | 3-pyridyl | |
| B-95 | Het-1 | CH₂CH₂CH₂ | H | 1 | 5-pyrimidinyl | |
| B-96 | Het-1 | CH₂CH₂CH₂ | H | 1 | 3-quinolyl | |
| B-97 | Het-1 | NHCH₂CH₂ | H | 0 | CH=CH2 | |
| B-98 | Het-1 | NHCH₂CH₂ | H | 0 | C≡CH | |
| B-99 | Het-1 | NHCH₂CH₂ | H | 0 | cyclopropyl | |
| B-100 | Het-1 | NHCH₂CH₂ | H | 0 | cyclohexyl | |
| B-101 | Het-1 | NHCH₂CH₂ | H | 0 | Ph | |
| B-102 | Het-1 | NHCH₂CH₂ | H | 0 | Ph(p-F) | |
| B-103 | Het-1 | NHCH₂CH₂ | H | 0 | Ph (3,5-dichloro) | |
| B-104 | Het-1 | NHCH₂CH₂ | H | 0 | CH₂Ph | |
| B-105 | Het-1 | NHCH₂CH₂ | H | 0 | CH₂CH₂Ph | |
| B-106 | Het-1 | NHCH₂CH₂ | H | 0 | 3-pyridyl | |
| B-107 | Het-1 | NHCH₂CH₂ | H | 0 | 5-pyrimidinyl | |
| B-108 | Het-1 | NHCH₂CH₂ | H | 0 | 3-quinolyl | |
| B-109 | Het-1 | NHCH₂CH₂ | H | 1 | CH=CH2 | |
| B-110 | Het-1 | NHCH₂CH₂ | H | 1 | C≡CH | |
| B-111 | Het-1 | NHCH₂CH₂ | H | 1 | cyclopropyl | |
| B-112 | Het-1 | NHCH₂CH₂ | H | 1 | cyclohexyl | |
| B-113 | Het-1 | NHCH₂CH₂ | H | 1 | Ph | |
| B-114 | Het-1 | NHCH₂CH₂ | H | 1 | Ph(p-F) | |
| B-115 | Het-1 | NHCH₂CH₂ | H | 1 | Ph (3,5-dichloro) | |
| B-116 | Het-1 | NHCH₂CH₂ | H | 1 | CH₂Ph | |
| B-117 | Het-1 | NHCH₂CH₂ | H | 1 | CH₂CH₂Ph | |
| B-118 | Het-1 | NHCH₂CH₂ | H | 1 | 3-pyridyl | |
| B-119 | Het-1 | NHCH₂CH₂ | H | 1 | 5-pyrimidinyl | |
| B-120 | Het-1 | NHCH₂CH₂ | H | 1 | 3-quinolyl | |
| B-121 | Het-1 | OCH₂CH₂ | H | 0 | CH=CH2 | |
| B-122 | Het-1 | OCH₂CH₂ | H | 0 | C≡CH | |
| B-123 | Het-1 | OCH₂CH₂ | H | 0 | cyclopropyl | |
| B-124 | Het-1 | OCH₂CH₂ | H | 0 | cyclohexyl | |
| B-125 | Het-1 | OCH₂CH₂ | H | 0 | Ph | |
| B-126 | Het-1 | OCH₂CH₂ | H | 0 | Ph(p-F) | |
| B-127 | Het-1 | OCH₂CH₂ | H | 0 | Ph (3,5-dichloro) | |
| B-128 | Het-1 | OCH₂CH₂ | H | 0 | CH₂Ph | |
| B-129 | Het-1 | OCH₂CH₂ | H | 0 | CH₂CH₂Ph | |
| B-130 | Het-1 | OCH₂CH₂ | H | 0 | 3-pyridyl | |
| B-131 | Het-1 | OCH₂CH₂ | H | 0 | 5-pyridiminyl | |
| B-132 | Het-1 | OCH₂CH₂ | H | 0 | 3-quinolyl | |
| B-133 | Het-1 | OCH₂CH₂ | H | 1 | CH=CH2 | |
| B-134 | Het-1 | OCH₂CH₂ | H | 1 | C≡CH | |
| B-135 | Het-1 | OCH₂CH₂ | H | 1 | cyclopropyl | |
| B-136 | Het-1 | OCH₂CH₂ | H | 1 | cyclohexyl | |
| B-137 | Het-1 | OCH₂CH₂ | H | 1 | Ph | |
| B-138 | Het-1 | OCH₂CH₂ | H | 1 | Ph(p-F) | |
| B-139 | Het-1 | OCH₂CH₂ | H | 1 | Ph (3,5-dichloro) | |
| B-140 | Het-1 | OCH₂CH₂ | H | 1 | CH₂Ph | |
| B-141 | Het-1 | OCH₂CH₂ | H | 1 | CH₂CH₂Ph | |
| B-142 | Het-1 | OCH₂CH₂ | H | 1 | 3-pyridyl | |
| B-143 | Het-1 | OCH₂CH₂ | H | 1 | 5-pyrimidinyl | |
| B-144 | Het-1 | OCH₂CH₂ | H | 1 | 3-quinolyl | |
| B-145 | Het-2 | CH₂CH₂ | H | 0 | CH=CH2 | |
| B-146 | Het-2 | CH₂CH₂ | H | 0 | C≡CH | |
| B-147 | Het-2 | CH₂CH₂ | H | 0 | cyclopropyl | |
| B-148 | Het-2 | CH₂CH₂ | H | 0 | cyclohexyl | |
| B-149 | Het-2 | CH₂CH₂ | H | 0 | Ph | |
| B-150 | Het-2 | CH₂CH₂ | H | 0 | Ph(p-F) | |
| B-151 | Het-2 | CH₂CH₂ | H | 0 | Ph (3,5-dichloro) | |
| B-152 | Het-2 | CH₂CH₂ | H | 0 | CH₂Ph | |
| B-153 | Het-2 | CH₂CH₂ | H | 0 | CH₂CH₂Ph | |
| B-154 | Het-2 | CH₂CH₂ | H | 0 | 3-pyridyl | |
| B-155 | Het-2 | CH₂CH₂ | H | 0 | 5-pyrimidinyl | |
| B-156 | Het-2 | CH₂CH₂ | H | 0 | 3-quinolyl | |
| B-157 | Het-2 | CH₂CH₂ | H | 1 | CH=CH2 | |
| B-158 | Het-2 | CH₂CH₂ | H | 1 | C≡CH | |
| B-159 | Het-2 | CH₂CH₂ | H | 1 | cyclopropyl | |
| B-160 | Het-2 | CH₂CH₂ | H | 1 | cyclohexyl | |
| B-161 | Het-2 | CH₂CH₂ | H | 1 | Ph | |
| B-162 | Het-2 | CH₂CH₂ | H | 1 | Ph(p-F) | |
| B-163 | Het-2 | CH₂CH₂ | H | 1 | Ph (3,5-dichloro) | |
| B-164 | Het-2 | CH₂CH₂ | H | 0 | CH₂Ph | |
| B-165 | Het-2 | CH₂CH₂ | H | 0 | CH₂CH₂Ph | |
| B-166 | Het-2 | CH₂CH₂ | H | 1 | 3-pyridyl | |
| B-167 | Het-2 | CH₂CH₂ | H | 1 | 5-pyrimidinyl | |
| B-168 | Het-2 | CH₂CH₂ | H | 1 | 3-quinolyl | |
| B-169 | Het-2 | NHCH₂ | H | 0 | CH=CH2 | |
| B-170 | Het-2 | NHCH₂ | H | 0 | C≡CH | |
| B-171 | Het-2 | NHCH₂ | H | 0 | cyclopropyl | |
| B-172 | Het-2 | NHCH₂ | H | 0 | cyclohexyl | |
| B-173 | Het-2 | NHCH₂ | H | 0 | Ph | |
| B-174 | Het-2 | NHCH₂ | H | 0 | Ph(p-F) | |
| B-175 | Het-2 | NHCH₂ | H | 0 | Ph (3,5-dichloro) | |
| B-176 | Het-2 | NHCH₂ | H | 0 | CH₂Ph | |
| B-177 | Het-2 | NHCH₂ | H | 0 | CH₂CH₂Ph | |
| B-178 | Het-2 | NHCH₂ | H | 0 | 3-pyridyl | |
| B-179 | Het-2 | NHCH₂ | H | 0 | 5-pyrimidinyl | |
| B-180 | Het-2 | NHCH₂ | H | 0 | 3-quinolyl | |
| B-181 | Het-2 | NHCH₂ | H | 1 | CH=CH2 | |
| B-182 | Het-2 | NHCH₂ | H | 1 | C≡CH | |
| B-183 | Het-2 | NHCH₂ | H | 1 | cyclopropyl | |
| B-184 | Het-2 | NHCH₂ | H | 1 | cyclohexyl | |
| B-185 | Het-2 | NHCH₂ | H | 1 | Ph | |
| B-186 | Het-2 | NHCH₂ | H | 1 | Ph(p-F) | |
| B-187 | Het-2 | NHCH₂ | H | 1 | Ph (3,5-dichloro) | |
| B-188 | Het-2 | NHCH₂ | H | 1 | CH₂Ph | |
| B-189 | Het-2 | NHCH₂ | H | 1 | CH₂CH₂Ph | |
| B-190 | Het-2 | NHCH₂ | H | 1 | 3-pyridyl | |
| B-191 | Het-2 | NHCH₂ | H | 1 | 5-pyrimidinyl | |
| B-192 | Het-2 | NHCH₂ | H | 1 | 3-quinolyl | |
| B-193 | Het-2 | OCH₂ | H | 0 | CH=CH2 | |
| B-194 | Het-2 | OCH₂ | H | 0 | C≡CH | |
| B-195 | Het-2 | OCH₂ | H | 0 | cyclopropyl | |
| B-196 | Het-2 | OCH₂ | H | 0 | cyclohexyl | |
| B-197 | Het-2 | OCH₂ | H | 0 | Ph | |
| B-198 | Het-2 | OCH₂ | H | 0 | Ph(p-F) | |
| B-199 | Het-2 | OCH₂ | H | 0 | Ph (3,5-dichloro) | |
| B-200 | Het-2 | OCH₂ | H | 0 | CH₂Ph | |
| B-201 | Het-2 | OCH₂ | H | 0 | CH₂CH₂Ph | |

TABLE 2-continued

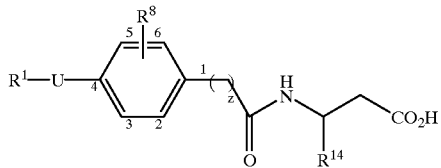
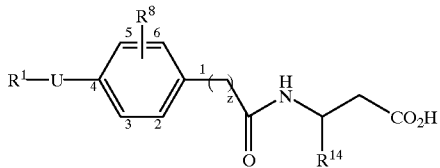

| Ex. No. | R¹ | U | R⁸ | z | R¹⁴ | MS |
|---|---|---|---|---|---|---|
| B-202 | Het-2 | OCH₂ | H | 0 | 3-pyridyl | |
| B-203 | Het-2 | OCH₂ | H | 0 | 5-pyrimidinyl | |
| B-204 | Het-2 | OCH₂ | H | 0 | 3-quinolyl | |
| B-205 | Het-2 | OCH₂ | H | 1 | CH=CH2 | |
| B-206 | Het-2 | OCH₂ | H | 1 | C≡CH | |
| B-207 | Het-2 | OCH₂ | H | 1 | cyclopropyl | |
| B-208 | Het-2 | OCH₂ | H | 1 | cyclohexyl | |
| B-209 | Het-2 | OCH₂ | H | 1 | Ph | |
| B-210 | Het-2 | OCH₂ | H | 1 | Ph(p-F) | |
| B-211 | Het-2 | OCH₂ | H | 1 | Ph (3,5-dichloro) | |
| B-212 | Het-2 | OCH₂ | H | 1 | CH₂Ph | |
| B-213 | Het-2 | OCH₂ | H | 1 | CH₂CH₂Ph | |
| B-214 | Het-2 | OCH₂ | H | 1 | 3-pyridyl | |
| B-215 | Het-2 | OCH₂ | H | 1 | 5-pyrimidinyl | |
| B-216 | Het-2 | OCH₂ | H | 1 | 3-quinolyl | |
| B-217 | Het-2 | CH₂CH₂CH₂ | H | 0 | CH=CH2 | |
| B-218 | Het-2 | CH₂CH₂CH₂ | H | 0 | C≡CH | |
| B-219 | Het-2 | CH₂CH₂CH₂ | H | 0 | cyclopropyl | |
| B-220 | Het-2 | CH₂CH₂CH₂ | H | 0 | cyclohexyl | |
| B-221 | Het-2 | CH₂CH₂CH₂ | H | 0 | Ph | |
| B-222 | Het-2 | CH₂CH₂CH₂ | H | 0 | Ph(p-F) | |
| B-223 | Het-2 | CH₂CH₂CH₂ | H | 0 | Ph (3,5-dichloro) | |
| B-224 | Het-2 | CH₂CH₂CH₂ | H | 0 | CH₂Ph | |
| B-225 | Het-2 | CH₂CH₂CH₂ | H | 0 | CH₂CH₂Ph | |
| B-226 | Het-2 | CH₂CH₂CH₂ | H | 0 | 3-pyridyl | |
| B-227 | Het-2 | CH₂CH₂CH₂ | H | 0 | 5-pyrimidinyl | |
| B-228 | Het-2 | CH₂CH₂CH₂ | H | 0 | 3-quinolyl | |
| B-229 | Het-2 | CH₂CH₂CH₂ | H | 1 | CH=CH2 | |
| B-230 | Het-2 | CH₂CH₂CH₂ | H | 1 | C≡CH | |
| B-231 | Het-2 | CH₂CH₂CH₂ | H | 1 | cyclopropyl | |
| B-232 | Het-2 | CH₂CH₂CH₂ | H | 1 | cyclohexyl | |
| B-233 | Het-2 | CH₂CH₂CH₂ | H | 1 | Ph | |
| B-234 | Het-2 | CH₂CH₂CH₂ | H | 1 | Ph(p-F) | |
| B-235 | Het-2 | CH₂CH₂CH₂ | H | 1 | Ph (3,5-dichloro) | |
| B-236 | Het-2 | CH₂CH₂CH₂ | H | 1 | CH₂Ph | |
| B-237 | Het-2 | CH₂CH₂CH₂ | H | 1 | CH₂CH₂Ph | |
| B-238 | Het-2 | CH₂CH₂CH₂ | H | 1 | 3-pyridyl | |
| B-239 | Het-2 | CH₂CH₂CH₂ | H | 1 | 5-pyrimidinyl | |
| B-240 | Het-2 | CH₂CH₂CH₂ | H | 1 | 1-quinolyl | |
| B-241 | Het-2 | NHCH₂CH₂ | H | 0 | CH=CH2 | |
| B-242 | Het-2 | NHCH₂CH₂ | H | 0 | C≡CH | |
| B-243 | Het-2 | NHCH₂CH₂ | H | 0 | cyclopropyl | |
| B-244 | Het-2 | NHCH₂CH₂ | H | 0 | cyclohexyl | |
| B-245 | Het-2 | NHCH₂CH₂ | H | 0 | Ph | |
| B-246 | Het-2 | NHCH₂CH₂ | H | 0 | Ph(p-F) | |
| B-247 | Het-2 | NHCH₂CH₂ | H | 0 | Ph (3,5-dichloro) | |
| B-248 | Het-2 | NHCH₂CH₂ | H | 0 | CH₂Ph | |
| B-249 | Het-2 | NHCH₂CH₂ | H | 0 | CH₂CH₂Ph | |
| B-250 | Het-2 | NHCH₂CH₂ | H | 0 | 3-pyridyl | |
| B-251 | Het-2 | NHCH₂CH₂ | H | 0 | 5-pyrimidinyl | |
| B-252 | Het-2 | NHCH₂CH₂ | H | 0 | 3-quinolyl | |
| B-253 | Het-2 | NHCH₂CH₂ | H | 1 | CH=CH2 | |
| B-254 | Het-2 | NHCH₂CH₂ | H | 1 | C≡CH | |
| B-255 | Het-2 | NHCH₂CH₂ | H | 1 | cyclopropyl | |
| B-256 | Het-2 | NHCH₂CH₂ | H | 1 | cyclohexyl | |
| B-257 | Het-2 | NHCH₂CH₂ | H | 1 | Ph | |
| B-258 | Het-2 | NHCH₂CH₂ | H | 1 | Ph(p-F) | |
| B-259 | Het-2 | NHCH₂CH₂ | H | 1 | Ph (3,5-dichloro) | |
| B-260 | Het-2 | NHCH₂CH₂ | H | 1 | CH₂Ph | |
| B-261 | Het-2 | NHCH₂CH₂ | H | 1 | CH₂CH₂Ph | |
| B-262 | Het-2 | NHCH₂CH₂ | H | 1 | 3-pyridyl | |
| B-263 | Het-2 | NHCH₂CH₂ | H | 1 | 5-pyrimidinyl | |
| B-264 | Het-2 | NHCH₂CH₂ | H | 1 | 3-quinolyl | |
| B-265 | Het-2 | OCH₂CH₂ | H | 0 | CH=CH2 | |
| B-266 | Het-2 | OCH₂CH₂ | H | 0 | C≡CH | |
| B-267 | Het-2 | OCH₂CH₂ | H | 0 | cyclopropyl | |
| B-268 | Het-2 | OCH₂CH₂ | H | 0 | cyclohexyl | |
| B-269 | Het-2 | OCH₂CH₂ | H | 0 | Ph | |
| B-270 | Het-2 | OCH₂CH₂ | H | 0 | Ph(p-F) | |
| B-271 | Het-2 | OCH₂CH₂ | H | 0 | Ph (3,5-dichloro) | |
| B-272 | Het-2 | OCH₂CH₂ | H | 0 | CH₂Ph | |
| B-273 | Het-2 | OCH₂CH₂ | H | 0 | CH₂CH₂Ph | |
| B-274 | Het-2 | OCH₂CH₂ | H | 0 | 3-pyridyl | |
| B-275 | Het-2 | OCH₂CH₂ | H | 0 | 5-pyrimidinyl | |
| B-276 | Het-2 | OCH₂CH₂ | H | 0 | 3-quinolyl | |
| B-277 | Het-3 | NHCH₂ | H | 0 | CH=CH2 | |
| B-278 | Het-3 | NHCH₂ | H | 0 | C≡CH | |
| B-279 | Het-3 | NHCH₂ | H | 0 | cyclopropyl | |
| B-280 | Het-3 | NHCH₂ | H | 0 | cyclohexyl | |
| B-281 | Het-3 | NHCH₂ | H | 0 | Ph | |
| B-282 | Het-3 | NHCH₂ | H | 0 | Ph(p-F) | |
| B-283 | Het-3 | NHCH₂ | H | 0 | Ph (3,5-dichloro) | |
| B-284 | Het-3 | NHCH₂ | H | 0 | CH₂Ph | |
| B-285 | Het-3 | NHCH₂ | H | 0 | CH₂CH₂Ph | |
| B-286 | Het-3 | NHCH₂ | H | 0 | 3-pyridyl | |
| B-287 | Het-3 | NHCH₂ | H | 0 | 5-pyrimidinyl | |
| B-288 | Het-3 | NHCH₂ | H | 0 | 3-quinolyl | |
| B-289 | Het-3 | NHCH₂ | H | 1 | CH=CH2 | |
| B-290 | Het-3 | NHCH₂ | H | 1 | C≡CH | |
| B-291 | Het-3 | NHCH₂ | H | 1 | cyclopropyl | |
| B-292 | Het-3 | NHCH₂ | H | 1 | cyclohexyl | |
| B-293 | Het-3 | NHCH₂ | H | 1 | Ph | |
| B-294 | Het-3 | NHCH₂ | H | 1 | Ph(p-F) | |
| B-295 | Het-3 | NHCH₂ | H | 1 | Ph (3,5-dichloro) | |
| B-296 | Het-3 | NHCH₂ | H | 1 | CH₂Ph | |
| B-297 | Het-3 | NHCH₂ | H | 1 | CH₂CH₂Ph | |
| B-298 | Het-3 | NHCH₂ | H | 1 | 3-pyridyl | |
| B-299 | Het-3 | NHCH₂ | H | 1 | 5-pyrimidinyl | |
| B-300 | Het-3 | NHCH₂ | H | 1 | 3-quinolyl. | |
| B-301 | Het-3 | NHCH₂CH₂ | H | 0 | CH=CH2 | |
| B-302 | Het-3 | NHCH₂CH₂ | H | 0 | C≡CH | |
| B-303 | Het-3 | NHCH₂CH₂ | H | 0 | cyclopropyl | |
| B-304 | Het-3 | NHCH₂CH₂ | H | 0 | cyclohexyl | |
| B-305 | Het-3 | NHCH₂CH₂ | H | 0 | Ph | |
| B-306 | Het-3 | NHCH₂CH₂ | H | 0 | Ph(p-F) | |
| B-307 | Het-3 | NHCH₂CH₂ | H | 0 | Ph (3,5-dichloro) | |
| B-308 | Het-3 | NHCH₂CH₂ | H | 0 | CH₂Ph | |
| B-309 | Het-3 | NHCH₂CH₂ | H | 0 | CH₂CH₂Ph | |
| B-310 | Het-3 | NHCH₂CH₂ | H | 0 | 3-pyridyl | |
| B-311 | Het-3 | NHCH₂CH₂ | H | 0 | 5-pyrimidinyl | |
| B-312 | Het-3 | NHCH₂CH₂ | H | 0 | 3-quinolyl | |
| B-313 | Het-3 | NHCH₂CH₂ | H | 1 | CH=CH2 | |
| B-314 | Het-3 | NHCH₂CH₂ | H | 1 | C≡CH | |
| B-315 | Het-3 | NHCH₂CH₂ | H | 1 | cyclopropyl | |
| B-316 | Het-3 | NHCH₂CH₂ | H | 1 | cyclohexyl | |
| B-317 | Het-3 | NHCH₂CH₂ | H | 1 | Ph | |
| B-318 | Het-3 | NHCH₂CH₂ | H | 1 | Ph(p-F) | |
| B-319 | Het-3 | NHCH₂CH₂ | H | 1 | Ph (3,5-dichloro) | |
| B-320 | Het-3 | NHCH₂CH₂ | H | 1 | CH₂Ph | |
| B-321 | Het-3 | NHCH₂CH₂ | H | 1 | CH₂CH₂Ph | |
| B-322 | Het-3 | NHCH₂CH₂ | H | 1 | 3-pyridyl | |
| B-323 | Het-3 | NHCH₂CH₂ | H | 1 | 5-pyrimidinyl | |
| B-324 | Het-3 | NHCH₂CH₂ | H | 1 | 3-quinolyl | |
| B-325 | Het-4 | CH₂CH₂ | H | 1 | CH=CH2 | |
| B-326 | Het-4 | CH₂CH₂ | H | 1 | C≡CH | |
| B-327 | Het-4 | CH₂CH₂ | H | 1 | cyclopropyl | |
| B-328 | Het-4 | CH₂CH₂ | H | 1 | cyclohexyl | |
| B-329 | Het-4 | CH₂CH₂ | H | 1 | Ph | |
| B-330 | Het-4 | CH₂CH₂ | H | 1 | Ph(p-F) | |
| B-331 | Het-4 | CH₂CH₂ | H | 1 | Ph (3,5-dichloro) | |
| B-332 | Het-4 | CH₂CH₂ | H | 1 | CH₂Ph | |
| B-333 | Het-4 | CH₂CH₂ | H | 1 | CH₂CH₂Ph | |
| B-334 | Het-4 | CH₂CH₂ | H | 1 | 3-pyridyl | |
| B-335 | Het-4 | CH₂CH₂ | H | 1 | 5-pyrimidinyl | |

TABLE 2-continued $R^1-U-\underset{\underset{3}{\overset{4}{\bigcirc}}}{\overset{R^8}{\bigcirc}}(\underset{z}{)_1}\underset{\underset{O}{\overset{\|}{C}}}{\overset{H}{N}}\underset{R^{14}}{\overset{}{C}}CO_2H$

| Ex. No. | $R^1$ | U | $R^8$ | z | $R^{14}$ | MS |
|---|---|---|---|---|---|---|
| B-336 | Het-4 | $CH_2CH_2$ | H | 1 | 3-quinolyl | |
| B-337 | Het-4 | $NHCH_2$ | H | 1 | $CH=CH2$ | |
| B-338 | Het-4 | $NHCH_2$ | H | 1 | $C\equiv CH$ | |
| B-339 | Het-4 | $NHCH_2$ | H | 1 | cyclopropyl | |
| B-340 | Het-4 | $NHCH_2$ | H | 1 | cyclohexyl | |
| B-341 | Het-4 | $NHCH_2$ | H | 1 | Ph | |
| B-342 | Het-4 | $NHCH_2$ | H | 1 | Ph(p-F) | |
| B-343 | Het-4 | $NHCH_2$ | H | 1 | Ph (3,5-dichloro) | |
| B-344 | Het-4 | $NHCH_2$ | H | 1 | $CH_2Ph$ | |
| B-345 | Het-4 | $NHCH_2$ | H | 1 | $CH_2CH_2Ph$ | |
| B-346 | Het-4 | $NHCH_2$ | H | 1 | 3-pyridyl | |
| B-347 | Het-4 | $NHCH_2$ | H | 1 | 5-pyrimidinyl | |
| B-348 | Het-4 | $NHCH_2$ | H | 1 | 3-quinolyl | |
| B-349 | Het-4 | $OCH_2$ | H | 1 | $CH=CH2$ | |
| B-350 | Het-4 | $OCH_2$ | H | 1 | $C\equiv CH$ | |
| B-351 | Het-4 | $OCH_2$ | H | 1 | cyclopropyl | |
| B-352 | Het-4 | $OCH_2$ | H | 1 | cyclohexyl | |
| B-353 | Het-4 | $OCH_2$ | H | 1 | Ph | |
| B-354 | Het-4 | $OCH_2$ | H | 1 | Ph(p-F) | |
| B-355 | Het-4 | $OCH_2$ | H | 1 | Ph (3,5-dichloro) | |
| B-356 | Het-4 | $OCH_2$ | H | 1 | $CH_2Ph$ | |
| B-357 | Het-4 | $OCH_2$ | H | 1 | $CH_2CH_2Ph$ | |
| B-358 | Het-4 | $OCH_2$ | H | 1 | 3-pyridyl | |
| B-359 | Het-4 | $OCH_2$ | H | 1 | 5-pyrimidinyl | |
| B-360 | Het-4 | $OCH_2$ | H | 1 | 3-quinolyl | |
| B-361 | Het-5 | $CH_2CH_2$ | H | 1 | $CH=CH2$ | |
| B-362 | Het-5 | $CH_2CH_2$ | H | 1 | $C\equiv CH$ | |
| B-363 | Het-5 | $CH_2CH_2$ | H | 1 | cyclopropyl | |
| B-364 | Het-5 | $CH_2CH_2$ | H | 1 | cyclohexyl | |
| B-365 | Het-5 | $CH_2CH_2$ | H | 1 | Ph(p-F) | |
| B-367 | Het-5 | $CH_2CH_2$ | H | 1 | Ph (3,5-dichloro) | |
| B-368 | Het-5 | $CH_2CH_2$ | H | 1 | $CH_2Ph$ | |
| B-369 | Het-5 | $CH_2CH_2$ | H | 1 | $CH_2CH_2Ph$ | |
| B-370 | Het-5 | $CH_2CH_2$ | H | 1 | 3-pyridyl | |
| B-371 | Het-5 | $CH_2CH_2$ | H | 1 | 5-pyrimidinyl | |
| B-372 | Het-5 | $CH_2CH_2$ | H | 1 | 3-quinolyl | |
| B-373 | Het-5 | $NHCH_2$ | H | 1 | $CH=CH2$ | |
| B-374 | Het-5 | $NHCH_2$ | H | 1 | $C\equiv CH$ | |
| B-375 | Het-5 | $NHCH_2$ | H | 1 | cyclopropyl | |
| B-376 | Het-5 | $NHCH_2$ | H | 1 | cyclohexyl | |
| B-377 | Het-5 | $NHCH_2$ | H | 1 | Ph | |
| B-378 | Het-5 | $NHCH_2$ | H | 1 | Ph(p-F) | |
| B-379 | Het-5 | $NHCH_2$ | H | 1 | Ph (3,5-dichloro) | |
| B-380 | Het-5 | $NHCH_2$ | H | 1 | $CH_2Ph$ | |
| B-381 | Het-5 | $NHCH_2$ | H | 1 | $CH_2CH_2Ph$ | |
| B-382 | Het-5 | $NHCH_2$ | H | 1 | 3-pyridyl | |
| B-383 | Het-5 | $NHCH_2$ | H | 1 | 5-pyrimidinyl | |
| B-384 | Het-5 | $NHCH_2$ | H | 1 | 3-quinolyl | |
| B-385 | Het-5 | $OCH_2$ | H | 1 | $C\equiv CH$ | |
| B-387 | Het-5 | $OCH_2$ | H | 1 | cyclopropyl | |
| B-388 | Het-5 | $OCH_2$ | H | 1 | cyclohexyl | |
| B-389 | Het-5 | $OCH_2$ | H | 1 | Ph | |
| B-390 | Het-5 | $OCH_2$ | H | 1 | Ph(p-F) | |
| B-391 | Het-5 | $OCH_2$ | H | 1 | Ph (3,5-dichloro) | |
| B-392 | Het-5 | $OCH_2$ | H | 1 | $CH_2Ph$ | |
| B-393 | Het-5 | $OCH_2$ | H | 1 | $CH_2CH_2Ph$ | |
| B-394 | Het-5 | $OCH_2$ | H | 1 | 3-pyridyl | |
| B-395 | Het-5 | $OCH_2$ | H | 1 | 5-pyrimidinyl | |
| B-396 | Het-5 | $OCH_2$ | H | 1 | 3-quinolyl | |
| B-397 | Het-6 | $NHCH_2$ | H | 1 | $CH=CH2$ | |
| B-398 | Het-6 | $NHCH_2$ | H | 1 | $C\equiv CH$ | |
| B-399 | Het-6 | $NHCH_2$ | H | 1 | cyclopropyl | |
| B-400 | Het-6 | $NHCH_2$ | H | 1 | cyclohexyl | |
| B-401 | Het-6 | $NHCH_2$ | H | 1 | Ph | |
| B-402 | Het-6 | $NHCH_2$ | H | 1 | Ph(p-F) | |
| B-403 | Het-6 | $NHCH_2$ | H | 1 | Ph (3,5-dichloro) | |
| B-404 | Het-6 | $NHCH_2$ | H | 1 | $CH_2Ph$ | |
| B-405 | Het-6 | $NHCH_2$ | H | 1 | $CH_2CH_2Ph$ | |
| B-406 | Het-6 | $NHCH_2$ | H | 1 | 3-pyridyl | |
| B-407 | Het-6 | $NHCH_2$ | H | 1 | 5-pyrimidinyl | |
| B-408 | Het-6 | $NHCH_2$ | H | 1 | 3-quinolyl | |
| B-409 | Het-7 | $NHCH_2$ | H | 1 | $CH=CH2$ | |
| B-410 | Het-7 | $NHCH_2$ | H | 1 | cyclopropyl | |
| B-412 | Het-7 | $NHCH_2$ | H | 1 | cyclohexyl | |
| B-413 | Het-7 | $NHCH_2$ | H | 1 | Ph | |
| B-414 | Het-7 | $NHCH_2$ | H | 1 | Ph(p-F) | |
| B-415 | Het-7 | $NHCH_2$ | H | 1 | Ph (3,5-dichloro) | |
| B-416 | Het-7 | $NHCH_2$ | H | 1 | $CH_2Ph$ | |
| B-417 | Het-7 | $NHCH_2$ | H | 1 | $CH_2CH_2Ph$ | |
| B-418 | Het-7 | $NHCH_2$ | H | 1 | 3-pyridyl | |
| B-419 | Het-7 | $NHCH_2$ | H | 1 | 5-pyrimidinyl | |
| B-420 | Het-7 | $NHCH_2$ | H | 1 | 3-quinolyl | |
| B-421 | Het-8 | $NHCH_2$ | H | 1 | $CH=CH2$ | |
| B-422 | Het-8 | $NHCH_2$ | H | 1 | $C\equiv CH$ | |
| B-423 | Het-8 | $NHCH_2$ | H | 1 | cyclopropyl | |
| B-424 | Het-8 | $NHCH_2$ | H | 1 | cyclohexyl | |
| B-425 | Het-8 | $NHCH_2$ | H | 1 | Ph | |
| B-426 | Het-8 | $NHCH_2$ | H | 1 | Ph(p-F) | |
| B-427 | Het-8 | $NHCH_2$ | H | 1 | Ph (3,5-dichloro) | |
| B-428 | Het-8 | $NHCH_2$ | H | 1 | $CH_2Ph$ | |
| B-429 | Het-8 | $NHCH_2$ | H | 1 | $CH_2CH_2Ph$ | |
| B-430 | Het-8 | $NHCH_2$ | H | 1 | 3-pyridyl | |
| B-431 | Het-8 | $NHCH_2$ | H | 1 | 5-pyrimidinyl | |
| B-432 | Het-8 | $NHCH_2$ | H | 1 | 3-quinolyl | |
| B-433 | Het-9 | $NHCH_2$ | H | 1 | $CH=CH2$ | |
| B-434 | Het-9 | $NHCH_2$ | H | 1 | $C\equiv CH$ | |
| B-435 | Het-9 | $NHCH_2$ | H | 1 | cyclopropyl | |
| B-436 | Het-9 | $NHCH_2$ | H | 1 | cyclohexyl | |
| B-437 | Het-9 | $NHCH_2$ | H | 1 | Ph | |
| B-438 | Het-9 | $NHCH_2$ | H | 1 | Ph(p-F) | |
| B-439 | Het-9 | $NHCH_2$ | H | 1 | Ph (3,5-dichloro) | |
| B-440 | Het-9 | $NHCH_2$ | H | 1 | $CH_2Ph$ | |
| B-441 | Het-9 | $NHCH_2$ | H | 1 | $CH_2CH_2Ph$ | |
| B-442 | Het-9 | $NHCH_2$ | H | 1 | 3-pyridtl | |
| B-443 | Het-9 | $NHCH_2$ | H | 1 | 5-pyrimidinyl | |
| B-444 | Het-9 | $NHCH_2$ | H | 1 | 3-quinolyl | |
| B-445 | Het-10 | $NHCH_2$ | H | 1 | $CH=CH2$ | |
| B-446 | Het-10 | $NHCH_2$ | H | 1 | $C\equiv CH$ | |
| B-447 | Het-10 | $NHCH_2$ | H | 1 | cyclopropyl | |
| B-448 | Het-10 | $NHCH_2$ | H | 1 | cyclohexyl | |
| B-449 | Het-10 | $NHCH_2$ | H | 1 | Ph | |
| B-450 | Het-10 | $NHCH_2$ | H | 1 | Ph(p-F) | |
| B-451 | Het-10 | $NHCH_2$ | H | 1 | Ph (3,5-dichloro) | |
| B-452 | Het-10 | $NHCH_2$ | H | 1 | $CH_2Ph$ | |
| B-453 | Het-10 | $NHCH_2$ | H | 1 | $CH_2CH_2Ph$ | |
| B-454 | Het-10 | $NHCH_2$ | H | 1 | 3-pyridyl | |
| B-455 | Het-10 | $NHCH_2$ | H | 1 | 5-pyrimidinyl | |
| B-456 | Het-10 | $NHCH_2$ | H | 1 | 3-quinolyl | |
| B-457 | Het-11 | $NHCH_2$ | H | 1 | $CH=CH2$ | |
| B-458 | Het-11 | $NHCH_2$ | H | 1 | $C\equiv CH$ | |
| B-459 | Het-11 | $NHCH_2$ | H | 1 | cyclopropyl | |
| B-460 | Het-11 | $NHCH_2$ | H | 1 | cyclohexyl | |
| B-461 | Het-11 | $NHCH_2$ | H | 1 | Ph | |
| B-462 | Het-11 | $NHCH_2$ | H | 1 | Ph(p-F) | |
| B-463 | Het-11 | $NHCH_2$ | H | 1 | Ph (3,5-dichloro) | |
| B-464 | Het-11 | $NHCH_2$ | H | 1 | $CH_2Ph$ | |
| B-465 | Het-11 | $NHCH_2$ | H | 1 | $CH_2CH_2Ph$ | |
| B-466 | Het-11 | $NHCH_2$ | H | 1 | 3-pyridyl | |
| B-467 | Het-11 | $NHCH_2$ | H | 1 | 5-pyrimidinyl | |
| B-468 | Het-11 | $NHCH_2$ | H | 1 | 3-quinolyl | |
| B-469 | Het-12 | $NHCH_2$ | H | 1 | $CH=CH2$ | |
| B-470 | Het-12 | $NHCH_2$ | H | 1 | $C\equiv CH$ | |
| B-471 | Het-12 | $NHCH_2$ | H | 1 | cyclopropyl | |
| B-472 | Het-12 | $NHCH_2$ | H | 1 | cyclohexyl | |

TABLE 2-continued

| Ex. No. | R¹ | U | R⁸ | z | R¹⁴ | MS |
|---|---|---|---|---|---|---|
| B-473 | Het-12 | NHCH$_2$ | H | 1 | Ph | |
| B-474 | Het-12 | NHCH$_2$ | H | 1 | Ph(p-F) | |
| B-475 | Het-12 | NHCH$_2$ | H | 1 | Ph (3,5-dichloro) | |
| B-476 | Het-12 | NHCH$_2$ | H | 1 | CH$_2$Ph | |
| B-477 | Het-12 | NHCH$_2$ | H | 1 | CH$_2$CH$_2$Ph | |
| B-478 | Het-12 | NHCH$_2$ | H | 1 | 3-pyridyl | |
| B-479 | Het-12 | NHCH$_2$ | H | 1 | 5-pyrimidinyl | |
| B-480 | Het-12 | NHCH$_2$ | H | 1 | 3-quinolyl | |
| B-481 | Het-13 | NHCH$_2$ | H | 1 | CH=CH2 | |
| B-482 | Het-13 | NHCH$_2$ | H | 1 | C≡CH | |
| B-483 | Het-13 | NHCH$_2$ | H | 1 | cyclopropyl | |
| B-484 | Het-13 | NHCH$_2$ | H | 1 | cyclohexyl | |
| B-485 | Het-13 | NHCH$_2$ | H | 1 | Ph | |
| B-486 | Het-13 | NHCH$_2$ | H | 1 | Ph(p-F) | |
| B-487 | Het-13 | NHCH$_2$ | H | 1 | Ph (3,5-dichloro) | |
| B-488 | Het-13 | NHCH$_2$ | H | 1 | CH$_2$Ph | |
| B-489 | Het-13 | NHCH$_2$ | H | 1 | CH$_2$CH$_2$Ph | |
| B-490 | Het-13 | NHCH$_2$ | H | 1 | 3-pyridyl | |
| B-491 | Het-13 | NHCH$_2$ | H | 1 | 5-pyrimidinyl | |
| B-492 | Het-13 | NHCH$_2$ | H | 1 | 3-quinolyl | |
| B-493 | Het-14 | NHCH$_2$ | H | 1 | CH=CH2 | |
| B-494 | Het-14 | NHCH$_2$ | H | 1 | C≡CH | |
| B-495 | Het-14 | NHCH$_2$ | H | 1 | cyclopropyl | |
| B-496 | Het-14 | NHCH$_2$ | H | 1 | cyclohexyl | |
| B-497 | Het-14 | NHCH$_2$ | H | 1 | Ph | |
| B-498 | Het-14 | NHCH$_2$ | H | 1 | Ph(p-F) | |
| B-499 | Het-14 | NHCH$_2$ | H | 1 | Ph (3,5-dichloro) | |
| B-500 | Het-14 | NHCH$_2$ | H | 1 | CH$_2$Ph | |
| B-501 | Het-14 | NHCH$_2$ | H | 1 | CH$_2$CH$_2$Ph | |
| B-502 | Het-14 | NHCH$_2$ | H | 1 | 3-pyridyl | |
| B-503 | Het-14 | NHCH$_2$ | H | 1 | 5-pyrimidinyl | |
| B-504 | Het-14 | NHCH$_2$ | H | 1 | 3-quinolyl | |
| B-505 | Het-15 | NHCH$_2$ | H | 1 | CH=CH2 | |
| B-506 | Het-15 | NHCH$_2$ | H | 1 | C≡CH | |
| B-507 | Het-15 | NHCH$_2$ | H | 1 | cyclopropyl | |
| B-508 | Het-15 | NHCH$_2$ | H | 1 | cyclohexyl | |
| B-509 | Het-15 | NHCH$_2$ | H | 1 | Ph | |
| B-510 | Het-15 | NHCH$_2$ | H | 1 | Ph(p-F) | |
| B-511 | Het-15 | NHCH$_2$ | H | 1 | Ph (3,5-dichloro) | |
| B-512 | Het-15 | NHCH$_2$ | H | 1 | CH$_2$Ph | |
| B-513 | Het-15 | NHCH$_2$ | H | 1 | CH$_2$CH$_2$Ph | |
| B-514 | Het-15 | NHCH$_2$ | H | 1 | 3-pyridyl | |
| B-515 | Het-15 | NHCH$_2$ | H | 1 | 5-pyrimidinyl | |
| B-516 | Het-15 | NHCH$_2$ | H | 1 | 3-quinolyl | |
| B-517 | Het-8 | CH$_2$CH$_2$ | H | 1 | CH=CH2 | |
| B-518 | Het-8 | CH$_2$CH$_2$ | H | 1 | C≡CH | |
| B-519 | Het-8 | CH$_2$CH$_2$ | H | 1 | cyclopropyl | |
| B-520 | Het-8 | CH$_2$CH$_2$ | H | 1 | cyclohexyl | |
| B-521 | Het-8 | CH$_2$CH$_2$ | H | 1 | Ph | |
| B-522 | Het-8 | CH$_2$CH$_2$ | H | 1 | Ph(p-F) | |
| B-523 | Het-8 | CH$_2$CH$_2$ | H | 1 | Ph (3,5-dichloro) | |
| B-524 | Het-8 | CH$_2$CH$_2$ | H | 1 | CH$_2$Ph | |
| B-525 | Het-8 | CH$_2$CH$_2$ | H | 1 | CH$_2$CH$_2$Ph | |
| B-526 | Het-8 | CH$_2$CH$_2$ | H | 1 | 3-pyridyl | |
| B-527 | Het-8 | CH$_2$CH$_2$ | H | 1 | 5-pyrimidinyl | |
| B-528 | Het-8 | CH$_2$CH$_2$ | H | 1 | 3-quinolyl | |
| B-529 | Het-16 | CH$_2$CH$_2$ | H | 1 | CH=CH2 | |
| B-530 | Het-16 | CH$_2$CH$_2$ | H | 1 | C≡CH | |
| B-531 | Het-16 | CH$_2$CH$_2$ | H | 1 | cyclopropyl | |
| B-532 | Het-16 | CH$_2$CH$_2$ | H | 1 | cyclohexyl | |
| B-533 | Het-16 | CH$_2$CH$_2$ | H | 1 | Ph | |
| B-534 | Het-16 | CH$_2$CH$_2$ | H | 1 | Ph(p-F) | |
| B-535 | Het-16 | CH$_2$CH$_2$ | H | 1 | Ph (3,5-dichloro) | |
| B-536 | Het-16 | CH$_2$CH$_2$ | H | 1 | CH$_2$Ph | |
| B-537 | Het-16 | CH$_2$CH$_2$ | H | 1 | CH$_2$CH$_2$Ph | |
| B-538 | Het-16 | CH$_2$CH$_2$ | H | 1 | 3-pyridyl | |
| B-539 | Het-16 | CH$_2$CH$_2$ | H | 1 | 5-pyrimidinyl | |
| B-540 | Het-16 | CH$_2$CH$_2$ | H | 1 | 3-quinolyl | |
| B-541 | Het-17 | CH$_2$CH$_2$ | H | 1 | CH=CH2 | |
| B-542 | Het-17 | CH$_2$CH$_2$ | H | 1 | C≡CH | |
| B-543 | Het-17 | CH$_2$CH$_2$ | H | 1 | cyclopropyl | |
| B-544 | Het-17 | CH$_2$CH$_2$ | H | 1 | cyclohexyl | |
| B-545 | Het-17 | CH$_2$CH$_2$ | H | 1 | Ph | |
| B-546 | Het-17 | CH$_2$CH$_2$ | H | 1 | Ph(p-F) | |
| B-547 | Het-17 | CH$_2$CH$_2$ | H | 1 | Ph (3,5-dichloro) | |
| B-548 | Het-17 | CH$_2$CH$_2$ | H | 1 | CH$_2$Ph | |
| B-549 | Het-17 | CH$_2$CH$_2$ | H | 1 | CH$_2$CH$_2$Ph | |
| B-550 | Het-17 | CH$_2$CH$_2$ | H | 1 | 3-pyridyl | |
| B-551 | Het-17 | CH$_2$CH$_2$ | H | 1 | 5-pyrimidinyl | |
| B-552 | Het-17 | CH$_2$CH$_2$ | H | 1 | 3-quinolyl | |
| B-553 | Het-18 | CH$_2$CH$_2$ | H | 1 | CH=CH2 | |
| B-554 | Het-18 | CH$_2$CH$_2$ | H | 1 | C≡CH | |
| B-555 | Het-18 | CH$_2$CH$_2$ | H | 1 | cyclopropyl | |
| B-556 | Het-18 | CH$_2$CH$_2$ | H | 1 | cyclohexyl | |
| B-557 | Het-18 | CH$_2$CH$_2$ | H | 1 | Ph | |
| B-558 | Het-18 | CH$_2$CH$_2$ | H | 1 | Ph(p-F) | |
| B-559 | Het-18 | CH$_2$CH$_2$ | H | 1 | Ph (3,5-dichloro) | |
| B-560 | Het-18 | CH$_2$CH$_2$ | H | 1 | CH$_2$Ph | |
| B-561 | Het-18 | CH$_2$CH$_2$ | H | 1 | CH$_2$CH$_2$Ph | |
| B-562 | Het-18 | CH$_2$CH$_2$ | H | 1 | 3-pyridyl | |
| B-563 | Het-18 | CH$_2$CH$_2$ | H | 1 | 5-pyrimidinyl | |
| B-564 | Het-18 | CH$_2$CH$_2$ | H | 1 | 3-quinolyl | |
| B-565 | Het-13 | CH$_2$CH$_2$ | H | 1 | CH=CH2 | |
| B-566 | Het-13 | CH$_2$CH$_2$ | H | 1 | C≡CH | |
| B-567 | Het-13 | CH$_2$CH$_2$ | H | 1 | cyclopropyl | |
| B-568 | Het-13 | CH$_2$CH$_2$ | H | 1 | cyclohexyl | |
| B-569 | Het-13 | CH$_2$CH$_2$ | H | 1 | Ph | |
| B-570 | Het-13 | CH$_2$CH$_2$ | H | 1 | Ph(p-F) | |
| B-571 | Het-13 | CH$_2$CH$_2$ | H | 1 | Ph (3,5-dichloro) | |
| B-572 | Het-13 | CH$_2$CH$_2$ | H | 1 | CH$_2$Ph | |
| B-573 | Het-13 | CH$_2$CH$_2$ | H | 1 | CH$_2$CH$_2$Ph | |
| B-574 | Het-13 | CH$_2$CH$_2$ | H | 1 | 3-pyridyl | |
| B-575 | Het-13 | CH$_2$CH$_2$ | H | 1 | 5-pyrimidinyl | |
| B-576 | Het-13 | CH$_2$CH$_2$ | H | 1 | 3-quinolyl | |
| B-577 | Het-19 | CH$_2$CH$_2$ | H | 1 | CH=CH2 | |
| B-578 | Het-19 | CH$_2$CH$_2$ | H | 1 | C≡CH | |
| B-579 | Het-19 | CH$_2$CH$_2$ | H | 1 | cyclopropyl | |
| B-580 | Het-19 | CH$_2$CH$_2$ | H | 1 | cyclohexyl | |
| B-581 | Het-19 | CH$_2$CH$_2$ | H | 1 | Ph | |
| B-582 | Het-19 | CH$_2$CH$_2$ | H | 1 | Ph(p-F) | |
| B-583 | Het-19 | CH$_2$CH$_2$ | H | 1 | Ph (3,5-dichloro) | |
| B-584 | Het-19 | CH$_2$CH$_2$ | H | 1 | CH$_2$Ph | |
| B-585 | Het-19 | CH$_2$CH$_2$ | H | 1 | CH$_2$CH$_2$Ph | |
| B-586 | Het-19 | CH$_2$CH$_2$ | H | 1 | 3-pyridyl | |
| B-587 | Het-19 | CH$_2$CH$_2$ | H | 1 | 5-pyrimidinyl | |
| B-588 | Het-19 | CH$_2$CH$_2$ | H | 1 | 3-quinolyl | |
| B-589 | Het-20 | CH$_2$CH$_2$ | H | 1 | CH=CH2 | |
| B-590 | Het-20 | CH$_2$CH$_2$ | H | 1 | C≡CH | |
| B-591 | Het-20 | CH$_2$CH$_2$ | H | 1 | cyclopropyl | |
| B-592 | Het-20 | CH$_2$CH$_2$ | H | 1 | cyclohexyl | |
| B-593 | Het-20 | CH$_2$CH$_2$ | H | 1 | Ph | |
| B-594 | Het-20 | CH$_2$CH$_2$ | H | 1 | Ph(p-F) | |
| B-595 | Het-20 | CH$_2$CH$_2$ | H | 1 | Ph (3,5-dichloro) | |
| B-596 | Het-20 | CH$_2$CH$_2$ | H | 1 | CH$_2$Ph | |
| B-597 | Het-20 | CH$_2$CH$_2$ | H | 1 | CH$_2$CH$_2$Ph | |
| B-598 | Het-20 | CH$_2$CH$_2$ | H | 1 | 3-pyridyl | |
| B-599 | Het-20 | CH$_2$CH$_2$ | H | 1 | 5-pyrimidinyl | |
| B-600 | Het-20 | CH$_2$CH$_2$ | H | 1 | 3-quinolyl | |
| B-601 | Het-1 | CH$_2$CH$_2$ | 3-Me | 1 | CH=CH2 | |
| B-602 | Het-1 | CH$_2$CH$_2$ | 3-Me | 1 | C≡CH | |
| B-603 | Het-1 | CH$_2$CH$_2$ | 3-Me | 1 | cyclopropyl | |
| B-604 | Het-1 | CH$_2$CH$_2$ | 3-Me | 1 | cyclohexyl | |
| B-605 | Het-1 | CH$_2$CH$_2$ | 3-Me | 1 | Ph | |
| B-606 | Het-1 | CH$_2$CH$_2$ | 3-Me | 1 | Ph(p-F) | |

TABLE 2-continued

Structure: $R^1-U$ attached at position 4 of phenyl ring with positions 2,3,5,6 labeled, $R^8$ at position 6, CH group with subscript z connecting to C(=O)NH-CH($R^{14}$)-CO$_2$H

| Ex. No. | $R^1$ | U | $R^8$ | z | $R^{14}$ | MS |
|---|---|---|---|---|---|---|
| B-607 | Het-1 | CH$_2$CH$_2$ | 3-Me | 1 | Ph(3,5-dichloro) | |
| B-608 | Het-1 | CH$_2$CH$_2$ | 3-Me | 1 | CH$_2$Ph | |
| B-609 | Het-1 | CH$_2$CH$_2$ | 3-Me | 1 | CH$_2$CH$_2$Ph | |
| B-610 | Het-1 | CH$_2$CH$_2$ | 3-Me | 1 | 3-pyridyl | |
| B-611 | Het-1 | CH$_2$CH$_2$ | 3-Me | 1 | 5-pyrimidinyl | |
| B-612 | Het-1 | CH$_2$CH$_2$ | 3-Me | 1 | 3-quinolyl | |
| B-613 | Het-1 | CH$_2$CH$_2$ | 2-Cl | 1 | CH=CH2 | |
| B-614 | Het-1 | CH$_2$CH$_2$ | 2-Cl | 1 | C≡CH | |
| B-615 | Het-1 | CH$_2$CH$_2$ | 2-Cl | 1 | cyclopropyl | |
| B-616 | Het-1 | CH$_2$CH$_2$ | 2-Cl | 1 | cyclohexyl | |
| B-617 | Het-1 | CH$_2$CH$_2$ | 2-Cl | 1 | Ph | |
| B-618 | Het-1 | CH$_2$CH$_2$ | 2-Cl | 1 | Ph(p-F) | |
| B-619 | Het-1 | CH$_2$CH$_2$ | 2-Cl | 1 | Ph (3,5-dichloro) | |
| B-620 | Het-1 | CH$_2$CH$_2$ | 2-Cl | 1 | CH$_2$Ph | |
| B-621 | Het-1 | CH$_2$CH$_2$ | 2-Cl | 1 | CH$_2$CH$_2$Ph | |
| B-622 | Het-1 | CH$_2$CH$_2$ | 2-Cl | 1 | 3-pyridyl | |
| B-623 | Het-1 | CH$_2$CH$_2$ | 2-Cl | 1 | 5-pyrimidinyl | |
| B-624 | Het-1 | CH$_2$CH$_2$ | 2-Cl | 1 | 3-quinolyl | |
| B-625 | Het-2 | CH$_2$CH$_2$ | 3-Me | 1 | CH=CH2 | |
| B-626 | Het-2 | CH$_2$CH$_2$ | 3-Me | 1 | C≡CH | |
| B-627 | Het-2 | CH$_2$CH$_2$ | 3-Me | 1 | cyclopropyl | |
| B-628 | Het-2 | CH$_2$CH$_2$ | 3-Me | 1 | cyclohexyl | |
| B-629 | Het-2 | CH$_2$CH$_2$ | 3-Me | 1 | Ph | |
| B-630 | Het-2 | CH$_2$CH$_2$ | 3-Me | 1 | Ph(p-F) | |
| B-631 | Het-2 | CH$_2$CH$_2$ | 3-Me | 1 | Ph (3,5-dichloro) | |
| B-632 | Het-2 | CH$_2$CH$_2$ | 3-Me | 1 | CH$_2$Ph | |
| B-633 | Het-2 | CH$_2$CH$_2$ | 3-Me | 1 | CH$_2$CH$_2$Ph | |
| B-634 | Het-2 | CH$_2$CH$_2$ | 3-Me | 1 | 3-pyridyl | |
| B-635 | Het-2 | CH$_2$CH$_2$ | 3-Me | 1 | 5-pyrimidinyl | |
| B-636 | Het-2 | CH$_2$CH$_2$ | 3-Me | 1 | 3-quinolyl | |
| B-637 | Het-2 | CH$_2$CH$_2$ | 2-Cl | 1 | CH=CH2 | |
| B-638 | Het-2 | CH$_2$CH$_2$ | 2-Cl | 1 | C≡CH | |
| B-639 | Het-2 | CH$_2$CH$_2$ | 2-Cl | 1 | cyclopropyl | |
| B-640 | Het-2 | CH$_2$CH$_2$ | 2-Cl | 1 | cyclohexyl | |
| B-641 | Het-2 | CH$_2$CH$_2$ | 2-Cl | 1 | Ph | |
| B-642 | Het-2 | CH$_2$CH$_2$ | 2-Cl | 1 | Ph(p-F) | |
| B-643 | Het-2 | CH$_2$CH$_2$ | 2-Cl | 1 | CH$_2$Ph | |
| B-644 | Het-2 | CH$_2$CH$_2$ | 2-Cl | 1 | CH$_2$CH$_2$Ph | |
| B-645 | Het-2 | CH$_2$CH$_2$ | 2-Cl | 1 | Ph (3,5-dichloro) | |
| B-646 | Het-2 | CH$_2$CH$_2$ | 2-Cl | 1 | 3-pyridyl | |
| B-647 | Het-2 | CH$_2$CH$_2$ | 2-Cl | 1 | 5-pyrimidinyl | |
| B-648 | Het-2 | CH$_2$CH$_2$ | 2-Cl | 1 | 3-quinolyl | |
| B-649 | Het-9 | CH$_2$CH$_2$ | H | 1 | CH=CH2 | |
| B-650 | Het-9 | CH$_2$CH$_2$ | H | 1 | C≡CH | |
| B-651 | Het-9 | CH$_2$CH$_2$ | H | 1 | cyclopropyl | |
| B-652 | Het-9 | CH$_2$CH$_2$ | H | 1 | cyclohexyl | |
| B-653 | Het-9 | CH$_2$CH$_2$ | H | 1 | Ph | |
| B-654 | Het-9 | CH$_2$CH$_2$ | H | 1 | Ph(p-F) | |
| B-655 | Het-9 | CH$_2$CH$_2$ | H | 1 | Ph (3,5-dichloro) | |
| B-656 | Het-9 | CH$_2$CH$_2$ | H | 1 | CH$_2$Ph | |
| B-657 | Het-9 | CH$_2$CH$_2$ | H | 1 | CH$_2$CH$_2$Ph | |
| B-658 | Het-9 | CH$_2$CH$_2$ | H | 1 | 3-pyridyl | |
| B-659 | Het-9 | CH$_2$CH$_2$ | H | 1 | 5-pyrimidinyl | |
| B-660 | Het-9 | CH$_2$CH$_2$ | H | 1 | 3-quinolyl | |
| B-661 | Het-21 | CH$_2$CH$_2$ | H | 1 | CH=CH2 | |
| B-662 | Het-21 | CH$_2$CH$_2$ | H | 1 | C≡CH | |
| B-663 | Het-21 | CH$_2$CH$_2$ | H | 1 | cyclopropyl | |
| B-664 | Het-21 | CH$_2$CH$_2$ | H | 1 | cyclohexyl | |
| B-665 | Het-21 | CH$_2$CH$_2$ | H | 1 | Ph | |
| B-666 | Het-21 | CH$_2$CH$_2$ | H | 1 | Ph(p-F) | |
| B-667 | Het-21 | CH$_2$CH$_2$ | H | 1 | Ph (3,5-dichloro) | |
| B-668 | Het-21 | CH$_2$CH$_2$ | H | 1 | CH$_2$Ph | |
| B-669 | Het-21 | CH$_2$CH$_2$ | H | 1 | CH$_2$CH$_2$Ph | |
| B-670 | Het-21 | CH$_2$CH$_2$ | H | 1 | 3-pyridyl | |
| B-671 | Het-21 | CH$_2$CH$_2$ | H | 1 | 5-pyrimidinyl | |
| B-672 | Het-21 | CH$_2$CH$_2$ | H | 1 | 3-quinolyl | |

TABLE 3

Structure: $R^1-U$ attached at position 4 of phenyl ring, $R^8$ at position 6, CH group with subscript z connecting to C(=O)NH-CH$_2$-CH($R^{15}$)-CO$_2$H

| Ex. No. | $R^1$ | U | $R^8$ | z | $R^{15}$ | MS |
|---|---|---|---|---|---|---|
| C-1 | Het-1 | CH$_2$CH$_2$ | H | 0 | NHCO$_2$Et | |
| C-2 | Het-1 | CH$_2$CH$_2$ | H | 0 | NHCO$_2$CH$_2$Ph | |
| C-3 | Het-1 | CH$_2$CH$_2$ | H | 0 | NHCO$_2$-n-Pr | |
| C-4 | Het-1 | CH$_2$CH$_2$ | H | 0 | NHCO$_2$-i-Pr | |
| C-5 | Het-1 | CH$_2$CH$_2$ | H | 0 | NHCO$_2$-n-Bu | |
| C-6 | Het-1 | CH$_2$CH$_2$ | H | 0 | NHCO$_2$-i-Bu | |
| C-7 | Het-1 | CH$_2$CH$_2$ | H | 0 | NHCO$_2$-n-C$_5$H$_{11}$ | |
| C-8 | Het-1 | CH$_2$CH$_2$ | H | 0 | NHSO$_2$Ph | 485.0 |
| C-9 | Het-1 | CH$_2$CH$_2$ | H | 0 | NHSO$_2$Ph(o-CH$_3$) | |
| C-10 | Het-1 | CH$_2$CH$_2$ | H | 0 | NHSO$_2$Ph(m-CH$_3$) | |
| C-11 | Het-1 | CH$_2$CH$_2$ | H | 0 | NHSO$_2$Ph(p-CH$_3$) | |
| C-12 | Het-1 | CH$_2$CH$_2$ | H | 0 | NHSO$_2$Ph(o-Cl) | |
| C-13 | Het-1 | CH$_2$CH$_2$ | H | 0 | NHSO$_2$Ph(m-Cl) | |
| C-14 | Het-1 | CH$_2$CH$_2$ | H | 0 | NHSO$_2$Ph(p-Cl) | |
| C-15 | Het-1 | CH$_2$CH$_2$ | H | 0 | NHSO$_2$Ph(m-F) | |
| C-16 | Het-1 | CH$_2$CH$_2$ | H | 0 | NHSO$_2$Ph(p-F) | |
| C-17 | Het-1 | CH$_2$CH$_2$ | H | 0 | NHSO$_2$Ph(o-F) | |
| C-18 | Het-1 | CH$_2$CH$_2$ | H | 0 | NHSO$_2$Ph(m-Br) | |
| C-19 | Het-1 | CH$_2$CH$_2$ | H | 0 | NHSO$_2$Ph(p-Br) | |
| C-20 | Het-1 | CH$_2$CH$_2$ | H | 0 | NHSO$_2$Ph(o-OCH$_3$) | |
| C-21 | Het-1 | CH$_2$CH$_2$ | H | 0 | NHSO$_2$Ph(m-OCH$_3$) | |
| C-22 | Het-1 | CH$_2$CH$_2$ | H | 0 | NHSO$_2$Ph(p-OCH$_3$) | |
| C-23 | Het-1 | CH$_2$CH$_2$ | H | 0 | NHSO$_2$(2,4,6-trimethylphenyl) | 527.1 |
| C-24 | Het-1 | CH$_2$CH$_2$ | H | 0 | NHSO$_2$(2,4,6-trichlorophenyl) | |
| C-25 | Het-1 | CH$_2$CH$_2$ | H | 0 | NHSO$_2$(2,6-dichlorophenyl) | |
| C-26 | Het-1 | CH$_2$CH$_2$ | H | 0 | NHSO$_2$(2-chloro-6-methylphenyl) | |
| C-27 | Het-1 | CH$_2$CH$_2$ | H | 0 | NHSO2[4-(2,6-dimethylphenyl)phenyl | |
| C-28 | Het-1 | CH$_2$CH$_2$ | H | 0 | NHSO$_2$C$_6$H$_4$(4-Ph) | |
| C-29 | Het-1 | CH$_2$CH$_2$ | H | 0 | NHSO$_2$[4-(3,5-dimethyl)isoxazolyl] | |
| C-30 | Het-1 | CH$_2$CH$_2$ | H | 0 | NHSO$_2$(1-naphthyl) | |
| C-31 | Het-1 | CH$_2$CH$_2$ | H | 0 | NHSO$_2$(2-naphthyl) | |
| C-32 | Het-1 | CH$_2$CH$_2$ | H | 0 | NHSO$_2$CH$_2$Ph | |
| C-33 | Het-1 | CH$_2$CH$_2$ | H | 0 | NHSO$_2$NHCH$_2$Ph | |
| C-34 | Het-1 | CH$_2$CH$_2$ | H | 0 | NHSO$_2$NHPh | |
| C-35 | Het-1 | NHCH$_2$ | H | 0 | NHCO$_2$Et | |
| C-36 | Het-1 | NHCH$_2$ | H | 0 | NHCO$_2$CH$_2$Ph | |
| C-37 | Het-1 | NHCH$_2$ | H | 0 | NHCO$_2$-n-Pr | |
| C-38 | Het-1 | NHCH$_2$ | H | 0 | NHCO$_2$-i-Pr | |
| C-39 | Het-1 | NHCH$_2$ | H | 0 | NHCO$_2$-n-Bu | |
| C-40 | Het-1 | NHCH$_2$ | H | 0 | NHCO$_2$-i-Bu | |
| C-41 | Het-1 | NHCH$_2$ | H | 0 | NHCO$_2$-n-C$_5$H$_{11}$ | |
| C-42 | Het-1 | NHCH$_2$ | H | 0 | NHSO$_2$Ph | |
| C-43 | Het-1 | NHCH$_2$ | H | 0 | NHSO$_2$Ph(o-CH$_3$) | |
| C-44 | Het-1 | NHCH$_2$ | H | 0 | NHSO$_2$Ph(m-CH$_3$) | |
| C-45 | Het-1 | NHCH$_2$ | H | 0 | NHSO$_2$Ph(p-CH$_3$) | |
| C-46 | Het-1 | NHCH$_2$ | H | 0 | NHSO$_2$Ph(o-Cl) | |
| C-47 | Het-1 | NHCH$_2$ | H | 0 | NHSO$_2$Ph(m-Cl) | |
| C-48 | Het-1 | NHCH$_2$ | H | 0 | NHSO$_2$Ph(p-Cl) | |
| C-49 | Het-1 | NHCH$_2$ | H | 0 | NHSO$_2$Ph(m-F) | |
| C-50 | Het-1 | NHCH$_2$ | H | 0 | NHSO$_2$Ph(p-F) | |
| C-51 | Het-1 | NHCH$_2$ | H | 0 | NHSO$_2$Ph(o-F) | |
| C-52 | Het-1 | NHCH$_2$ | H | 0 | NHSO$_2$Ph(m-Br) | |
| C-53 | Het-1 | NHCH$_2$ | H | 0 | NHSO$_2$Ph(p-Br) | |
| C-54 | Het-1 | NHCH$_2$ | H | 0 | NHSO$_2$Ph(o-OCH$_3$) | |
| C-55 | Het-1 | NHCH$_2$ | H | 0 | NHSO$_2$Ph(m-OCH$_3$) | |
| C-56 | Het-1 | NHCH$_2$ | H | 0 | NHSO$_2$Ph(p-OCH$_3$) | |
| C-57 | Het-1 | NHCH$_2$ | H | 0 | NHSO$_2$(2,4,6-trimethylphenyl) | |
| C-58 | Het-1 | NHCH$_2$ | H | 0 | NHSO$_2$(2,4,6-trichlorophenyl) | |

TABLE 3-continued

| Ex. No. | R$^1$ | U | R$^8$ | z | R$^{15}$ | MS |
|---|---|---|---|---|---|---|
| C-59 | Het-1 | NHCH$_2$ | H | 0 | NHSO$_2$(2,6-dichlorophenyl) | |
| C-60 | Het-1 | NHCH$_2$ | H | 0 | NHSO$_2$(2-chloro-6-methylphenyl) | |
| C-61 | Het-1 | NHCH$_2$ | H | 0 | NHSO2[4-(2,6-dimethylphenyl)phenyl | |
| C-62 | Het-1 | NHCH$_2$ | H | 0 | NHSO$_2$C$_6$H$_4$(4-Ph) | |
| C-63 | Het-1 | NHCH$_2$ | H | 0 | NHSO$_2$[4-(3,5-dimethyl)isoxazolyl] | |
| C-64 | Het-1 | NHCH$_2$ | H | 0 | NHSO$_2$(1-naphthyl) | |
| C-65 | Het-1 | NHCH$_2$ | H | 0 | NHSO$_2$(2-naphthyl) | |
| C-66 | Het-1 | NHCH$_2$ | H | 0 | NHSO$_2$CH$_2$Ph | |
| C-67 | Het-1 | NHCH$_2$ | H | 0 | NHSO$_2$NHCH$_2$Ph | |
| C-68 | Het-1 | NHCH$_2$ | H | 0 | NHSO$_2$NHPh | |
| C-69 | Het-1 | OCH$_2$ | H | 0 | NHCO$_2$Et | |
| C-70 | Het-1 | OCH$_2$ | H | 0 | NHCO$_2$CH$_2$Ph | |
| C-71 | Het-1 | OCH$_2$ | H | 0 | NHCO$_2$-n-Pr | |
| C-72 | Het-1 | OCH$_2$ | H | 0 | NHCO$_2$-i-Pr | |
| C-73 | Het-1 | OCH$_2$ | H | 0 | NHCO$_2$-n-Bu | |
| C-74 | Het-1 | OCH$_2$ | H | 0 | NHCO$_2$-i-Bu | |
| C-75 | Het-1 | OCH$_2$ | H | 0 | NHCO$_2$-n-C$_5$H$_{11}$ | |
| C-76 | Het-1 | OCH$_2$ | H | 0 | NHSO$_2$Ph | |
| C-77 | Het-1 | OCH$_2$ | H | 0 | NHSO$_2$Ph(o-CH$_3$) | |
| C-78 | Het-1 | OCH$_2$ | H | 0 | NHSO$_2$Ph(m-CH$_3$) | |
| C-79 | Het-1 | OCH$_2$ | H | 0 | NHSO$_2$Ph(p-CH$_3$) | |
| C-80 | Het-1 | OCH$_2$ | H | 0 | NHSO$_2$Ph(o-Cl) | |
| C-81 | Het-1 | OCH$_2$ | H | 0 | NHSO$_2$Ph(m-Cl) | |
| C-82 | Het-1 | OCH$_2$ | H | 0 | NHSO$_2$Ph(p-Cl) | |
| C-83 | Het-1 | OCH$_2$ | H | 0 | NHSO$_2$Ph(m-F) | |
| C-84 | Het-1 | OCH$_2$ | H | 0 | NHSO$_2$Ph(p-F) | |
| C-85 | Het-1 | OCH$_2$ | H | 0 | NHSO$_2$Ph(o-F) | |
| C-86 | Het-1 | OCH$_2$ | H | 0 | NHSO$_2$Ph(m-Br) | |
| C-87 | Het-1 | OCH$_2$ | H | 0 | NHSO$_2$Ph(p-Br) | |
| C-88 | Het-1 | OCH$_2$ | H | 0 | NHSO$_2$Ph(o-OCH$_3$) | |
| C-89 | Het-1 | OCH$_2$ | H | 0 | NHSO$_2$Ph(m-OCH$_3$) | |
| C-90 | Het-1 | OCH$_2$ | H | 0 | NHSO$_2$Ph(p-OCH$_3$) | |
| C-91 | Het-1 | OCH$_2$ | H | 0 | NHSO$_2$(2,4,6-trimethylphenyl) | |
| C-92 | Het-1 | OCH$_2$ | H | 0 | NHSO$_2$(2,4,6-trichlorophenyl) | |
| C-93 | Het-1 | OCH$_2$ | H | 0 | NHSO$_2$(2,6-dichlorophenyl) | |
| C-94 | Het-1 | OCH$_2$ | H | 0 | NHSO$_2$(2-chloro-6-methylphenyl) | |
| C-95 | Het-1 | OCH$_2$ | H | 0 | NHSO2[4-(2,6-dimethylphenyl)phenyl | |
| C-96 | Het-1 | OCH$_2$ | H | 0 | NHSO$_2$C$_6$H$_4$(4-Ph) | |
| C-97 | Het-1 | OCH$_2$ | H | 0 | NHSO$_2$[4-(3,5-dimethyl)isoxazolyl] | |
| C-98 | Het-1 | OCH$_2$ | H | 0 | NHSO$_2$(1-naphthyl) | |
| C-99 | Het-1 | OCH$_2$ | H | 0 | NHSO$_2$(2-naphthyl) | |
| C-100 | Het-1 | OCH$_2$ | H | 0 | NHSO$_2$CH$_2$Ph | |
| C-101 | Het-1 | OCH$_2$ | H | 0 | NHSO$_2$NHCH$_2$Ph | |
| C-102 | Het-1 | OCH$_2$ | H | 0 | NHSO$_2$NHPh | |
| C-103 | Het-1 | CH$_2$CH$_2$CH$_2$ | H | 0 | NHCO$_2$Et | |
| C-104 | Het-1 | CH$_2$CH$_2$CH$_2$ | H | 0 | NHCO$_2$CH$_2$Ph | |
| C-105 | Het-1 | CH$_2$CH$_2$CH$_2$ | H | 0 | NHCO$_2$-n-Pr | |
| C-106 | Het-1 | CH$_2$CH$_2$CH$_2$ | H | 0 | NHCO$_2$-i-Pr | |
| C-107 | Het-1 | CH$_2$CH$_2$CH$_2$ | H | 0 | NHCO$_2$-n-Bu | |
| C-108 | Het-1 | CH$_2$CH$_2$CH$_2$ | H | 0 | NHCO$_2$-i-Bu | |
| C-109 | Het-1 | CH$_2$CH$_2$CH$_2$ | H | 0 | NHCO$_2$-n-C$_5$H$_{11}$ | |
| C-110 | Het-1 | CH$_2$CH$_2$CH$_2$ | H | 0 | NHSO$_2$Ph | |
| C-111 | Het-1 | CH$_2$CH$_2$CH$_2$ | H | 0 | NHSO$_2$Ph(o-CH$_3$) | |
| C-112 | Het-1 | CH$_2$CH$_2$CH$_2$ | H | 0 | NHSO$_2$Ph(m-CH$_3$) | |
| C-113 | Het-1 | CH$_2$CH$_2$CH$_2$ | H | 0 | NHSO$_2$Ph(p-CH$_3$) | |
| C-114 | Het-1 | CH$_2$CH$_2$CH$_2$ | H | 0 | NHSO$_2$Ph(o-Cl) | |
| C-115 | Het-1 | CH$_2$CH$_2$CH$_2$ | H | 0 | NHSO$_2$Ph(m-Cl) | |
| C-116 | Het-1 | CH$_2$CH$_2$CH$_2$ | H | 0 | NHSO$_2$Ph(p-Cl) | |
| C-117 | Het-1 | CH$_2$CH$_2$CH$_2$ | H | 0 | NHSO$_2$Ph(m-F) | |
| C-118 | Het-1 | CH$_2$CH$_2$CH$_2$ | H | 0 | NHSO$_2$Ph(p-F) | |
| C-119 | Het-1 | CH$_2$CH$_2$CH$_2$ | H | 0 | NHSO$_2$Ph(o-F) | |
| C-120 | Het-1 | CH$_2$CH$_2$CH$_2$ | H | 0 | NHSO$_2$Ph(m-Br) | |
| C-121 | Het-1 | CH$_2$CH$_2$CH$_2$ | H | 0 | NHSO$_2$Ph(p-Br) | |
| C-122 | Het-1 | CH$_2$CH$_2$CH$_2$ | H | 0 | NHSO$_2$Ph(o-OCH$_3$) | |
| C-123 | Het-1 | CH$_2$CH$_2$CH$_2$ | H | 0 | NHSO$_2$Ph(m-OCH$_3$) | |
| C-124 | Het-1 | CH$_2$CH$_2$CH$_2$ | H | 0 | NHSO$_2$Ph(p-OCH$_3$) | |
| C-125 | Het-1 | CH$_2$CH$_2$CH$_2$ | H | 0 | NHSO$_2$(2,4,6-trimethylphenyl) | |
| C-126 | Het-1 | CH$_2$CH$_2$CH$_2$ | H | 0 | NHSO$_2$(2,4,6-trichlorophenyl) | |
| C-127 | Het-1 | CH$_2$CH$_2$CH$_2$ | H | 0 | NHSO$_2$(2,6-dichlorophenyl) | |
| C-128 | Het-1 | CH$_2$CH$_2$CH$_2$ | H | 0 | NHSO$_2$(2-chloro-6-methylphenyl) | |
| C-129 | Het-1 | CH$_2$CH$_2$CH$_2$ | H | 0 | NHSO2[4-(2,6-dimethylphenyl)phenyl | |
| C-130 | Het-1 | CH$_2$CH$_2$CH$_2$ | H | 0 | NHSO$_2$C$_6$H$_4$(4-Ph) | |
| C-131 | Het-1 | CH$_2$CH$_2$CH$_2$ | H | 0 | NHSO$_2$[4-(3,5-dimethyl)isoxazolyl] | |
| C-132 | Het-1 | CH$_2$CH$_2$CH$_2$ | H | 0 | NHSO$_2$(1-naphthyl) | |
| C-133 | Het-1 | CH$_2$CH$_2$CH$_2$ | H | 0 | NHSO$_2$(2-naphthyl) | |
| C-134 | Het-1 | CH$_2$CH$_2$CH$_2$ | H | 0 | NHSO$_2$CH$_2$Ph | |
| C-135 | Het-1 | CH$_2$CH$_2$CH$_2$ | H | 0 | NHSO$_2$NHCH$_2$Ph | |
| C-136 | Het-1 | CH$_2$CH$_2$CH$_2$ | H | 0 | NHSO$_2$NHPh | |
| C-137 | Het-1 | NHCH$_2$CH$_2$ | H | 0 | NHCO$_2$Et | |
| C-138 | Het-1 | NHCH$_2$CH$_2$ | H | 0 | NHCO$_2$CH$_2$Ph | |
| C-139 | Het-1 | NHCH$_2$CH$_2$ | H | 0 | NHCO$_2$-n-Pr | |
| C-140 | Het-1 | NHCH$_2$CH$_2$ | H | 0 | NHCO$_2$-i-Pr | |
| C-141 | Het-1 | NHCH$_2$CH$_2$ | H | 0 | NHCO$_2$-n-Bu | |
| C-142 | Het-1 | NHCH$_2$CH$_2$ | H | 0 | NHSO$_2$-i-Bu | |
| C-143 | Het-1 | NHCH$_2$CH$_2$ | H | 0 | NHCO$_2$-n-C$_5$H$_{11}$ | |
| C-144 | Het-1 | NHCH$_2$CH$_2$ | H | 0 | NHSO$_2$Ph | |
| C-145 | Het-1 | NHCH$_2$CH$_2$ | H | 0 | NHSO$_2$Ph(o-CH$_3$) | |
| C-146 | Het-1 | NHCH$_2$CH$_2$ | H | 0 | NHSO$_2$Ph(m-CH$_3$) | |
| C-147 | Het-1 | NHCH$_2$CH$_2$ | H | 0 | NHSO$_2$Ph(p-CH$_3$) | |
| C-148 | Het-1 | NHCH$_2$CH$_2$ | H | 0 | NHSO$_2$Ph(o-Cl) | |
| C-149 | Het-1 | NHCH$_2$CH$_2$ | H | 0 | NHSO$_2$Ph(m-Cl) | |
| C-150 | Het-1 | NHCH$_2$CH$_2$ | H | 0 | NHSO$_2$Ph(p-Cl) | |
| C-151 | Het-1 | NHCH$_2$CH$_2$ | H | 0 | NHSO$_2$Ph(m-F) | |
| C-152 | Het-1 | NHCH$_2$CH$_2$ | H | 0 | NHSO$_2$Ph(p-F) | |
| C-153 | Het-1 | NHCH$_2$CH$_2$ | H | 0 | NHSO$_2$Ph(o-F) | |
| C-154 | Het-1 | NHCH$_2$CH$_2$ | H | 0 | NHSO$_2$Ph(m-Br) | |
| C-155 | Het-1 | NHCH$_2$CH$_2$ | H | 0 | NHSO$_2$Ph(p-Br) | |
| C-156 | Het-1 | NHCH$_2$CH$_2$ | H | 0 | NHSO$_2$Ph(o-OCH$_3$) | |
| C-157 | Het-1 | NHCH$_2$CH$_2$ | H | 0 | NHSO$_2$Ph(m-OCH$_3$) | |
| C-158 | Het-1 | NHCH$_2$CH$_2$ | H | 0 | NHSO$_2$Ph(p-OCH$_3$) | |
| C-159 | Het-1 | NHCH$_2$CH$_2$ | H | 0 | NHSO$_2$(2,4,6-trimethylphenyl) | |
| C-160 | Het-1 | NHCH$_2$CH$_2$ | H | 0 | NHSO$_2$(2,4,6-trichlorophenyl) | |
| C-161 | Het-1 | NHCH$_2$CH$_2$ | H | 0 | NHSO$_2$(2,6-dichlorophenyl) | |
| C-162 | Het-1 | NHCH$_2$CH$_2$ | H | 0 | NHSO$_2$(2-chloro-6-methylphenyl) | |
| C-163 | Het-1 | NHCH$_2$CH$_2$ | H | 0 | NHSO2[4-(2,6-dimethylphenyl)phenyl | |
| C-164 | Het-1 | NHCH$_2$CH$_2$ | H | 0 | NHSO$_2$C$_6$H$_4$(4-Ph) | |
| C-165 | Het-1 | NHCH$_2$CH$_2$ | H | 0 | NHSO$_2$[4-(3,5-dimethyl)isoxazolyl] | |
| C-166 | Het-1 | NHCH$_2$CH$_2$ | H | 0 | NHSO$_2$(1-naphthyl) | |
| C-167 | Het-1 | NHCH$_2$CH$_2$ | H | 0 | NHSO$_2$(2-naphthyl) | |
| C-168 | Het-1 | NHCH$_2$CH$_2$ | H | 0 | NHSO$_2$CH$_2$Ph | |
| C-169 | Het-1 | NHCH$_2$CH$_2$ | H | 0 | NHSO$_2$NHCH$_2$Ph | |
| C-170 | Het-1 | NHCH$_2$CH$_2$ | H | 0 | NHSO$_2$NHPh | |

TABLE 3-continued

| Ex. No. | R¹ | U | R⁸ | z | R¹⁵ | MS |
|---|---|---|---|---|---|---|
| C-171 | Het-1 | OCH$_2$CH$_2$ | H | 0 | NHCO$_2$Et | |
| C-172 | Het-1 | OCH$_2$CH$_2$ | H | 0 | NHCO$_2$CH$_2$Ph | |
| C-173 | Het-1 | OCH$_2$CH$_2$ | H | 0 | NHCO$_2$-n-Pr | |
| C-174 | Het-1 | OCH$_2$CH$_2$ | H | 0 | NHCO$_2$-i-Pr | |
| C-175 | Het-1 | OCH$_2$CH$_2$ | H | 0 | NHCO$_2$-n-Bu | |
| C-176 | Het-1 | OCH$_2$CH$_2$ | H | 0 | NHCO$_2$-i-Bu | |
| C-177 | Het-1 | OCH$_2$CH$_2$ | H | 0 | NHCO$_2$-n-C$_5$H$_{11}$ | |
| C-178 | Het-1 | OCH$_2$CH$_2$ | H | 0 | NHSO$_2$Ph | |
| C-179 | Het-1 | OCH$_2$CH$_2$ | H | 0 | NHSO$_2$Ph(o-CH$_3$) | |
| C-180 | Het-1 | OCH$_2$CH$_2$ | H | 0 | NHSO$_2$Ph(m-CH$_3$) | |
| C-181 | Het-1 | OCH$_2$CH$_2$ | H | 0 | NHSO$_2$Ph(p-CH$_3$) | |
| C-182 | Het-1 | OCH$_2$CH$_2$ | H | 0 | NHSO$_2$Ph(o-Cl) | |
| C-183 | Het-1 | OCH$_2$CH$_2$ | H | 0 | NHSO$_2$Ph(m-Cl) | |
| C-184 | Het-1 | OCH$_2$CH$_2$ | H | 0 | NHSO$_2$Ph(p-Cl) | |
| C-185 | Het-1 | OCH$_2$CH$_2$ | H | 0 | NHSO$_2$Ph(m-F) | |
| C-186 | Het-1 | OCH$_2$CH$_2$ | H | 0 | NHSO$_2$Ph(p-F) | |
| C-187 | Het-1 | OCH$_2$CH$_2$ | H | 0 | NHSO$_2$Ph(o-F) | |
| C-188 | Het-1 | OCH$_2$CH$_2$ | H | 0 | NHSO$_2$Ph(m-Br) | |
| C-189 | Het-1 | OCH$_2$CH$_2$ | H | 0 | NHSO$_2$Ph(p-Br) | |
| C-190 | Het-1 | OCH$_2$CH$_2$ | H | 0 | NHSO$_2$Ph(o-OCH$_3$) | |
| C-191 | Het-1 | OCH$_2$CH$_2$ | H | 0 | NHSO$_2$Ph(m-OCH$_3$) | |
| C-192 | Het-1 | OCH$_2$CH$_2$ | H | 0 | NHSO$_2$Ph(p-OCH$_3$) | |
| C-193 | Het-1 | OCH$_2$CH$_2$ | H | 0 | NHSO$_2$(2,4,6-trimethylphenyl) | |
| C-194 | Het-1 | OCH$_2$CH$_2$ | H | 0 | NHSO$_2$(2,4,6-trichlorophenyl) | |
| C-195 | Het-1 | OCH$_2$CH$_2$ | H | 0 | NHSO$_2$(2,6-dichlorophenyl) | |
| C-196 | Het-1 | OCH$_2$CH$_2$ | H | 0 | NHSO$_2$(2-chloro-6-methylphenyl) | |
| C-197 | Het-1 | OCH$_2$CH$_2$ | H | 0 | NHSO2[4-(2,6-dimethylphenyl)phenyl | |
| C-198 | Het-1 | OCH$_2$CH$_2$ | H | 0 | NHSO$_2$C$_6$H$_4$(4-Ph) | |
| C-199 | Het-1 | OCH$_2$CH$_2$ | H | 0 | NHSO$_2$[4-(3,5-dimethyl)isoxazolyl] | |
| C-200 | Het-1 | OCH$_2$CH$_2$ | H | 0 | NHSO$_2$(1-naphthyl) | |
| C-201 | Het-1 | OCH$_2$CH$_2$ | H | 0 | NHSO$_2$(2-naphthyl) | |
| C-202 | Het-1 | OCH$_2$CH$_2$ | H | 0 | NHSO$_2$CH$_2$Ph | |
| C-203 | Het-1 | OCH$_2$CH$_2$ | H | 0 | NHSO$_2$NHCH$_2$Ph | |
| C-204 | Het-1 | OCH$_2$CH$_2$ | H | 0 | NHSO$_2$NHPh | |
| C-205 | Het-2 | CH$_2$CH$_2$ | H | 0 | NHCO$_2$Et | |
| C-206 | Het-2 | CH$_2$CH$_2$ | H | 0 | NHCO$_2$CH$_2$Ph | |
| C-207 | Het-2 | CH$_2$CH$_2$ | H | 0 | NHCO$_2$-n-Pr | |
| C-208 | Het-2 | CH$_2$CH$_2$ | H | 0 | NHCO$_2$-i-Pr | |
| C-209 | Het-2 | CH$_2$CH$_2$ | H | 0 | NHCO$_2$-n-Bu | |
| C-210 | Het-2 | CH$_2$CH$_2$ | H | 0 | NHCO$_2$-i-Bu | |
| C-211 | Het-2 | CH$_2$CH$_2$ | H | 0 | NHCO$_2$-n-C$_5$H$_{11}$ | |
| C-212 | Het-2 | CH$_2$CH$_2$ | H | 0 | NHSO$_2$Ph | |
| C-213 | Het-2 | CH$_2$CH$_2$ | H | 0 | NHSO$_2$Ph(o-CH$_3$) | |
| C-214 | Het-2 | CH$_2$CH$_2$ | H | 0 | NHSO$_2$Ph(m-CH$_3$) | |
| C-215 | Het-2 | CH$_2$CH$_2$ | H | 0 | NHSO$_2$Ph(p-CH$_3$) | |
| C-216 | Het-2 | CH$_2$CH$_2$ | H | 0 | NHSO$_2$Ph(o-Cl) | |
| C-217 | Het-2 | CH$_2$CH$_2$ | H | 0 | NHSO$_2$Ph(m-Cl) | |
| C-218 | Het-2 | CH$_2$CH$_2$ | H | 0 | NHSO$_2$Ph(p-Cl) | |
| C-219 | Het-2 | CH$_2$CH$_2$ | H | 0 | NHSO$_2$Ph(m-F) | |
| C-220 | Het-2 | CH$_2$CH$_2$ | H | 0 | NHSO$_2$Ph(p-F) | |
| C-221 | Het-2 | CH$_2$CH$_2$ | H | 0 | NHSO$_2$Ph(o-F) | |
| C-222 | Het-2 | CH$_2$CH$_2$ | H | 0 | NHSO$_2$Ph(m-Br) | |
| C-223 | Het-2 | CH$_2$CH$_2$ | H | 0 | NHSO$_2$Ph(p-Br) | |
| C-224 | Het-2 | CH$_2$CH$_2$ | H | 0 | NHSO$_2$Ph(o-OCH$_3$) | |
| C-225 | Het-2 | CH$_2$CH$_2$ | H | 0 | NHSO$_2$Ph(m-OCH$_3$) | |
| C-226 | Het-2 | CH$_2$CH$_2$ | H | 0 | NHSO$_2$Ph(p-OCH$_3$) | |
| C-227 | Het-2 | CH$_2$CH$_2$ | H | 0 | NHSO$_2$(2,4,6-trimethylphenyl) | 528.1 |
| C-228 | Het-2 | CH$_2$CH$_2$ | H | 0 | NHSO$_2$(2,4,6-trichlorophenyl) | |
| C-229 | Het-2 | CH$_2$CH$_2$ | H | 0 | NHSO$_2$(2,6-dichlorophenyl) | |
| C-230 | Het-2 | CH$_2$CH$_2$ | H | 0 | NHSO$_2$(2-chloro-6-methylphenyl) | |
| C-231 | Het-2 | CH$_2$CH$_2$ | H | 0 | NHSO2[4-(2,6-dimethylphenyl)phenyl | |
| C-232 | Het-2 | CH$_2$CH$_2$ | H | 0 | NHSO$_2$C$_6$H$_4$(4-Ph) | |
| C-233 | Het-2 | CH$_2$CH$_2$ | H | 0 | NHSO$_2$[4-(3,5-dimethyl)isoxazolyl] | |
| C-234 | Het-2 | CH$_2$CH$_2$ | H | 0 | NHSO$_2$(1-naphthyl) | |
| C-235 | Het-2 | CH$_2$CH$_2$ | H | 0 | NHSO$_2$(2-naphthyl) | |
| C-236 | Het-2 | CH$_2$CH$_2$ | H | 0 | NHSO$_2$CH$_2$Ph | |
| C-237 | Het-2 | CH$_2$CH$_2$ | H | 0 | NHSO$_2$NHCH$_2$Ph | |
| C-238 | Het-2 | CH$_2$CH$_2$ | H | 0 | NHSO$_2$NHPh | |
| C-239 | Het-2 | NHCH$_2$ | H | 0 | NHCO$_2$Et | |
| C-240 | Het-2 | NHCH$_2$ | H | 0 | NHCO$_2$CH$_2$Ph | |
| C-241 | Het-2 | NHCH$_2$ | H | 0 | NHCO$_2$-n-Pr | |
| C-242 | Het-2 | NHCH$_2$ | H | 0 | NHCO$_2$-i-Pr | |
| C-243 | Het-2 | NHCH$_2$ | H | 0 | NHCO$_2$-n-Bu | |
| C-244 | Het-2 | NHCH$_2$ | H | 0 | NHCO$_2$-i-Bu | |
| C-245 | Het-2 | NHCH$_2$ | H | 0 | NHCO$_2$-n-C$_5$H$_{11}$ | |
| C-246 | Het-2 | NHCH$_2$ | H | 0 | NHSO$_2$Ph | |
| C-247 | Het-2 | NHCH$_2$ | H | 0 | NHSO$_2$Ph(o-CH$_3$) | |
| C-248 | Het-2 | NHCH$_2$ | H | 0 | NHSO$_2$Ph(m-CH$_3$) | |
| C-249 | Het-2 | NHCH$_2$ | H | 0 | NHSO$_2$Ph(p-CH$_3$) | |
| C-250 | Het-2 | NHCH$_2$ | H | 0 | NHSO$_2$Ph(o-Cl) | |
| C-251 | Het-2 | NHCH$_2$ | H | 0 | NHSO$_2$Ph(m-Cl) | |
| C-252 | Het-2 | NHCH$_2$ | H | 0 | NHSO$_2$Ph(p-Cl) | |
| C-253 | Het-2 | NHCH$_2$ | H | 0 | NHSO$_2$Ph(m-F) | |
| C-254 | Het-2 | NHCH$_2$ | H | 0 | NHSO$_2$Ph(p-F) | |
| C-255 | Het-2 | NHCH$_2$ | H | 0 | NHSO$_2$Ph(o-F) | |
| C-256 | Het-2 | NHCH$_2$ | H | 0 | NHSP$_2$Ph(m-Br) | |
| C-257 | Het-2 | NHCH$_2$ | H | 0 | NHSO$_2$Ph(p-Br) | |
| C-258 | Het-2 | NHCH$_2$ | H | 0 | NHSO$_2$Ph(o-OCH$_3$) | |
| C-259 | Het-2 | NHCH$_2$ | H | 0 | NHSO$_2$Ph(m-OCH$_3$) | |
| C-260 | Het-2 | NHCH$_2$ | H | 0 | NHSO$_2$Ph(p-OCH$_3$) | |
| C-261 | Het-2 | NHCH$_2$ | H | 0 | NHSO$_2$(2,4,6-trimethylphenyl) | |
| C-262 | Het-2 | NHCH$_2$ | H | 0 | NHSO$_2$(2,4,6-trichlorophenyl) | |
| C-263 | Het-2 | NHCH$_2$ | H | 0 | NHSO$_2$(2,6-dichlorophenyl) | |
| C-264 | Het-2 | NHCH$_2$ | H | 0 | NHSO$_2$(2-chloro-6-methylphenyl) | |
| C-265 | Het-2 | NHCH$_2$ | H | 0 | NHSO2[4-(2,6-dimethylphenyl)phenyl | |
| C-266 | Het-2 | NHCH$_2$ | H | 0 | NHSO$_2$C$_6$H$_4$(4-Ph) | |
| C-267 | Het-2 | NHCH$_2$ | H | 0 | NHSO$_2$[4-(3,5-dimethyl)isoxazolyl] | |
| C-268 | Het-2 | NHCH$_2$ | H | 0 | NHSO$_2$(1-naphthyl) | |
| C-269 | Het-2 | NHCH$_2$ | H | 0 | NHSO$_2$(2-naphthyl) | |
| C-270 | Het-2 | NHCH$_2$ | H | 0 | NHSO$_2$CH$_2$Ph | |
| C-271 | Het-2 | NHCH$_2$ | H | 0 | NHSO$_2$NHCH$_2$Ph | |
| C-272 | Het-2 | NHCH$_2$ | H | 0 | NHSO$_2$NHPh | |
| C-273 | Het-2 | OCH$_2$ | H | 0 | NHCO$_2$Et | |
| C-274 | Het-2 | OCH$_2$ | H | 0 | NHCO$_2$CH$_2$Ph | |
| C-275 | Het-2 | OCH$_2$ | H | 0 | NHCO$_2$-n-Pr | |
| C-276 | Het-2 | OCH$_2$ | H | 0 | NHCO$_2$-i-Pr | |
| C-277 | Het-2 | OCH$_2$ | H | 0 | NHCO$_2$-n-Bu | |
| C-278 | Het-2 | OCH$_2$ | H | 0 | NHCO$_2$-i-Bu | |
| C-279 | Het-2 | OCH$_2$ | H | 0 | NHCO$_2$-n-C$_5$H$_{11}$ | |
| C-280 | Het-2 | OCH$_2$ | H | 0 | NHSO$_2$Ph | |
| C-281 | Het-2 | OCH$_2$ | H | 0 | NHSO$_2$Ph(o-CH$_3$) | |
| C-282 | Het-2 | OCH$_2$ | H | 0 | NHSO$_2$Ph(m-CH$_3$) | |
| C-283 | Het-2 | OCH$_2$ | H | 0 | NHSO$_2$Ph(p-CH$_3$) | |
| C-284 | Het-2 | OCH$_2$ | H | 0 | NHSO$_2$Ph(o-Cl) | |
| C-285 | Het-2 | OCH$_2$ | H | 0 | NHSO$_2$Ph(m-Cl) | |

TABLE 3-continued

| Ex. No. | R¹ | U | R⁸ | z | R¹⁵ | MS |
|---|---|---|---|---|---|---|
| C-286 | Het-2 | OCH₂ | H | 0 | NHSO₂Ph(p-Cl) | |
| C-287 | Het-2 | OCH₂ | H | 0 | NHSO₂Ph(m-F) | |
| C-288 | Het-2 | OCH₂ | H | 0 | NHSO₂Ph(p-F) | |
| C-289 | Het-2 | OCH₂ | H | 0 | NHSO₂Ph(o-F) | |
| C-290 | Het-2 | OCH₂ | H | 0 | NHSO₂Ph(m-Br) | |
| C-291 | Het-2 | OCH₂ | H | 0 | NHSO₂Ph(p-Br) | |
| C-292 | Het-2 | OCH₂ | H | 0 | NHSO₂Ph(o-OCH₃) | |
| C-293 | Het-2 | OCH₂ | H | 0 | NHSO₂Ph(m-OCH₃) | |
| C-294 | Het-2 | OCH₂ | H | 0 | NHSO₂Ph(p-OCH₃) | |
| C-295 | Het-2 | OCH₂ | H | 0 | NHSO₂(2,4,6-trimethylphenyl) | |
| C-296 | Het-2 | OCH₂ | H | 0 | NHSO₂(2,4,6-trichlorophenyl) | |
| C-297 | Het-2 | OCH₂ | H | 0 | NHSO₂(2,6-dichlorophenyl) | |
| C-298 | Het-2 | OCH₂ | H | 0 | NHSO₂(2-chloro-6-methylphenyl) | |
| C-299 | Het-2 | OCH₂ | H | 0 | NHSO2[4-(2,6-dimethylphenyl)phenyl | |
| C-300 | Het-2 | OCH₂ | H | 0 | NHSO₂C₆H₄(4-Ph) | |
| C-301 | Het-2 | OCH₂ | H | 0 | NHSO₂[4-(3,5-dimethyl)isoxazolyl] | |
| C-302 | Het-2 | OCH₂ | H | 0 | NHSO₂(1-naphthyl) | |
| C-303 | Het-2 | OCH₂ | H | 0 | NHSO₂(2-naphthyl) | |
| C-304 | Het-2 | OCH₂ | H | 0 | NHSO₂CH₂Ph | |
| C-305 | Het-2 | OCH₂ | H | 0 | NHSO₂NHCH₂Ph | |
| C-306 | Het-2 | OCH₂ | H | 0 | NHSO₂NHPh | |
| C-307 | Het-2 | CH₂CH₂CH₂ | H | 0 | NHCO₂Et | |
| C-308 | Het-2 | CH₂CH₂CH₂ | H | 0 | NHCO₂CH₂Ph | |
| C-309 | Het-2 | CH₂CH₂CH₂ | H | 0 | NHCO₂-n-Pr | |
| C-310 | Het-2 | CH₂CH₂CH₂ | H | 0 | NHCO₂-i-Pr | |
| C-311 | Het-2 | CH₂CH₂CH₂ | H | 0 | NHCO₂-n-Bu | |
| C-312 | Het-2 | CH₂CH₂CH₂ | H | 0 | NHCO₂-i-Bu | |
| C-313 | Het-2 | CH₂CH₂CH₂ | H | 0 | NHCO₂-n-C₅H₁₁ | |
| C-314 | Het-2 | CH₂CH₂CH₂ | H | 0 | NHSO₂Ph | |
| C-315 | Het-2 | CH₂CH₂CH₂ | H | 0 | NHSO₂Ph(o-CH₃) | |
| C-316 | Het-2 | CH₂CH₂CH₂ | H | 0 | NHSO₂Ph(m-CH₃) | |
| C-317 | Het-2 | CH₂CH₂CH₂ | H | 0 | NHSO₂Ph(p-CH₃) | |
| C-318 | Het-2 | CH₂CH₂CH₂ | H | 0 | NHSO₂Ph(o-Cl) | |
| C-319 | Het-2 | CH₂CH₂CH₂ | H | 0 | NHSO₂Ph(m-Cl) | |
| C-320 | Het-2 | CH₂CH₂CH₂ | H | 0 | NHSO₂Ph(p-Cl) | |
| C-321 | Het-2 | CH₂CH₂CH₂ | H | 0 | NHSO₂Ph(m-F) | |
| C-322 | Het-2 | CH₂CH₂CH₂ | H | 0 | NHSO₂Ph(p-F) | |
| C-323 | Het-2 | CH₂CH₂CH₂ | H | 0 | NHSO₂Ph(o-F) | |
| C-324 | Het-2 | CH₂CH₂CH₂ | H | 0 | NHSO₂Ph(m-Br) | |
| C-325 | Het-2 | CH₂CH₂CH₂ | H | 0 | NHSO₂Ph(p-Br) | |
| C-326 | Het-2 | CH₂CH₂CH₂ | H | 0 | NHSO₂Ph(o-OCH₃) | |
| C-327 | Het-2 | CH₂CH₂CH₂ | H | 0 | NHSO₂Ph(m-OCH₃) | |
| C-328 | Het-2 | CH₂CH₂CH₂ | H | 0 | NHSO₂Ph(p-OCH₃) | |
| C-329 | Het-2 | CH₂CH₂CH₂ | H | 0 | NHSO₂(2,4,6-trimethylphenyl) | |
| C-330 | Het-2 | CH₂CH₂CH₂ | H | 0 | NHSO₂(2,4,6-trichlorophenyl) | |
| C-331 | Het-2 | CH₂CH₂CH₂ | H | 0 | NHSO₂(2,6-dichlorophenyl) | |
| C-332 | Het-2 | CH₂CH₂CH₂ | H | 0 | NHSO₂(2-chloro-6-methylphenyl) | |
| C-333 | Het-2 | CH₂CH₂CH₂ | H | 0 | NHSO2[4-(2,6-dimethylphenyl)phenyl | |
| C-334 | Het-2 | CH₂CH₂CH₂ | H | 0 | NHSO₂C₆H₄(4-Ph) | |
| C-335 | Het-2 | CH₂CH₂CH₂ | H | 0 | NHSO₂[4-(3,5-dimethyl)isoxazolyl] | |
| C-336 | Het-2 | CH₂CH₂CH₂ | H | 0 | NHSO₂(1-naphthyl) | |
| C-337 | Het-2 | CH₂CH₂CH₂ | H | 0 | NHSO₂(2-naphthyl) | |
| C-338 | Het-2 | CH₂CH₂CH₂ | H | 0 | NHSO₂CH₂Ph | |
| C-339 | Het-2 | CH₂CH₂CH₂ | H | 0 | NHSO₂NHCH₂Ph | |
| C-340 | Het-2 | CH₂CH₂CH₂ | H | 0 | NHSO₂NHPh | |
| C-341 | Het-2 | NHCH₂CH₂ | H | 0 | NHCO₂Et | |
| C-342 | Het-2 | NHCH₂CH₂ | H | 0 | NHCO₂CH₂Ph | |
| C-343 | Het-2 | NHCH₂CH₂ | H | 0 | NHCO₂-n-Pr | |
| C-344 | Het-2 | NHCH₂CH₂ | H | 0 | NHCO₂-i-Pr | |
| C-345 | Het-2 | NHCH₂CH₂ | H | 0 | NHCO₂-n-Bu | |
| C-346 | Het-2 | NHCH₂CH₂ | H | 0 | NHCO₂-i-Bu | |
| C-347 | Het-2 | NHCH₂CH₂ | H | 0 | NHCO₂-n-C₅H₁₁ | |
| C-348 | Het-2 | NHCH₂CH₂ | H | 0 | NHSO₂Ph | |
| C-349 | Het-2 | NHCH₂CH₂ | H | 0 | NHSO₂Ph(o-CH₃) | |
| C-350 | Het-2 | NHCH₂CH₂ | H | 0 | NHSO₂Ph(m-CH₃) | |
| C-351 | Het-2 | NHCH₂CH₂ | H | 0 | NHSO₂Ph(p-CH₃) | |
| C-352 | Het-2 | NHCH₂CH₂ | H | 0 | NHSO₂Ph(o-Cl) | |
| C-353 | Het-2 | NHCH₂CH₂ | H | 0 | NHSO₂Ph(m-Cl) | |
| C-354 | Het-2 | NHCH₂CH₂ | H | 0 | NHSO₂Ph(p-Cl) | |
| C-355 | Het-2 | NHCH₂CH₂ | H | 0 | NHSO₂Ph(m-F) | |
| C-356 | Het-2 | NHCH₂CH₂ | H | 0 | NHSO₂Ph(p-F) | |
| C-357 | Het-2 | NHCH₂CH₂ | H | 0 | NHSO₂Ph(o-F) | |
| C-358 | Het-2 | NHCH₂CH₂ | H | 0 | NHSO₂Ph(m-Br) | |
| C-359 | Het-2 | NHCH₂CH₂ | H | 0 | NHSO₂Ph(p-Br) | |
| C-360 | Het-2 | NHCH₂CH₂ | H | 0 | NHSO₂Ph(o-OCH₃) | |
| C-361 | Het-2 | NHCH₂CH₂ | H | 0 | NHSO₂Ph(m-OCH₃) | |
| C-362 | Het-2 | NHCH₂CH₂ | H | 0 | NHSO₂Ph(p-OCH₃) | |
| C-363 | Het-2 | NHCH₂CH₂ | H | 0 | NHSO₂(2,4,6-trimethylphenyl) | |
| C-364 | Het-2 | NHCH₂CH₂ | H | 0 | NHSO₂(2,4,6-trichlorophenyl) | |
| C-365 | Het-2 | NHCH₂CH₂ | H | 0 | NHSO₂(2,6-dichlorophenyl) | |
| C-366 | Het-2 | NHCH₂CH₂ | H | 0 | NHSO₂(2-chloro-6-methylphenyl) | |
| C-367 | Het-2 | NHCH₂CH₂ | H | 0 | NHSO2[4-(2,6-dimethylphenyl)phenyl | |
| C-368 | Het-2 | NHCH₂CH₂ | H | 0 | NHSO₂C₆H₄(4-Ph) | |
| C-369 | Het-2 | NHCH₂CH₂ | H | 0 | NHSO₂[4-(3,5-dimethyl)isoxazolyl] | |
| C-370 | Het-2 | NHCH₂CH₂ | H | 0 | NHSO₂(1-naphthyl) | |
| C-371 | Het-2 | NHCH₂CH₂ | H | 0 | NHSO₂(2-naphthyl) | |
| C-372 | Het-2 | NHCH₂CH₂ | H | 0 | NHSO₂CH₂Ph | |
| C-373 | Het-2 | NHCH₂CH₂ | H | 0 | NHSO₂NHCH₂Ph | |
| C-374 | Het-2 | NHCH₂CH₂ | H | 0 | NHSO₂NHPh | |
| C-375 | Het-2 | OCH₂CH₂ | H | 0 | NHCO₂Et | |
| C-376 | Het-2 | OCH₂CH₂ | H | 0 | NHCO₂CH₂Ph | |
| C-377 | Het-2 | OCH₂CH₂ | H | 0 | NHCO₂-n-Pr | |
| C-378 | Het-2 | OCH₂CH₂ | H | 0 | NHCO₂-i-Pr | |
| C-379 | Het-2 | OCH₂CH₂ | H | 0 | NHCO₂-n-Bu | |
| C-380 | Het-2 | OCH₂CH₂ | H | 0 | NHCO₂-i-Bu | |
| C-381 | Het-2 | OCH₂CH₂ | H | 0 | NHCO₂-n-C₅H₁₁ | |
| C-382 | Het-2 | OCH₂CH₂ | H | 0 | NHSO₂Ph | |
| C-383 | Het-2 | OCH₂CH₂ | H | 0 | NHSO₂Ph(o-CH₃) | |
| C-384 | Het-2 | OCH₂CH₂ | H | 0 | NHSO₂Ph(m-CH₃) | |
| C-385 | Het-2 | OCH₂CH₂ | H | 0 | NHSO₂Ph(p-CH₃) | |
| C-386 | Het-2 | OCH₂CH₂ | H | 0 | NHSO₂Ph(o-Cl) | |
| C-387 | Het-2 | OCH₂CH₂ | H | 0 | NHSO₂Ph(m-Cl) | |
| C-388 | Het-2 | OCH₂CH₂ | H | 0 | NHSO₂Ph(p-Cl) | |
| C-389 | Het-2 | OCH₂CH₂ | H | 0 | NHSO₂Ph(m-F) | |
| C-390 | Het-2 | OCH₂CH₂ | H | 0 | NHSO₂Ph(p-F) | |
| C-391 | Het-2 | OCH₂CH₂ | H | 0 | NHSO₂Ph(o-F) | |
| C-392 | Het-2 | OCH₂CH₂ | H | 0 | NHSO₂Ph(m-Br) | |
| C-393 | Het-2 | OCH₂CH₂ | H | 0 | NHSO₂Ph(p-Br) | |
| C-394 | Het-2 | OCH₂CH₂ | H | 0 | NHSO₂Ph(o-OCH₃) | |
| C-395 | Het-2 | OCH₂CH₂ | H | 0 | NHSO₂Ph(m-OCH₃) | |
| C-396 | Het-2 | OCH₂CH₂ | H | 0 | NHSO₂Ph(p-OCH₃) | |
| C-397 | Het-2 | OCH₂CH₂ | H | 0 | NHSO₂(2,4,6-trimethylphenyl) | |
| C-398 | Het-2 | OCH₂CH₂ | H | 0 | NHSO₂(2,4,6-trichlorophenyl) | |

TABLE 3-continued

| Ex. No. | R$^1$ | U | R$^8$ | z | R$^{15}$ | MS |
|---|---|---|---|---|---|---|
| C-399 | Het-2 | OCH$_2$CH$_2$ | H | 0 | NHSO$_2$(2,6-dichlorophenyl) | |
| C-400 | Het-2 | OCH$_2$CH$_2$ | H | 0 | NHSO$_2$(2-chloro-6-methylphenyl) | |
| C-401 | Het-2 | OCH$_2$CH$_2$ | H | 0 | NHSO2[4-(2,6-dimethylphenyl)phenyl | |
| C-402 | Het-2 | OCH$_2$CH$_2$ | H | 0 | NHSO$_2$C$_6$H$_4$(4-Ph) | |
| C-403 | Het-2 | OCH$_2$CH$_2$ | H | 0 | NHSO$_2$[4-(3,5-dimethyl)isoxazolyl] | |
| C-404 | Het-2 | OCH$_2$CH$_2$ | H | 0 | NHSO$_2$(1-naphthyl) | |
| C-405 | Het-2 | OCH$_2$CH$_2$ | H | 0 | NHSO$_2$(2-naphthyl) | |
| C-406 | Het-2 | OCH$_2$CH$_2$ | H | 0 | NHSO$_2$CH$_2$Ph | |
| C-407 | Het-2 | OCH$_2$CH$_2$ | H | 0 | NHSO$_2$NHCH$_2$Ph | |
| C-408 | Het-2 | OCH$_2$CH$_2$ | H | 0 | NHSO$_2$NHPh | |
| C-409 | Het-3 | NHCH$_2$ | H | 0 | NHCO$_2$Et | |
| C-410 | Het-3 | NHCH$_2$ | H | 0 | NHCO$_2$CH$_2$Ph | |
| C-411 | Het-3 | NHCH$_2$ | H | 0 | NHCO$_2$-n-Pr | |
| C-412 | Het-3 | NHCH$_2$ | H | 0 | NHCO$_2$-i-Pr | |
| C-413 | Het-3 | NHCH$_2$ | H | 0 | NHCO$_2$-n-Bu | |
| C-414 | Het-3 | NHCH$_2$ | H | 0 | NHCO$_2$-i-Bu | |
| C-415 | Het-3 | NHCH$_2$ | H | 0 | NHCO$_2$-n-C$_5$H$_{11}$ | |
| C-416 | Het-3 | NHCH$_2$ | H | 0 | NHSO$_2$Ph | |
| C-417 | Het-3 | NHCH$_2$ | H | 0 | NHSO$_2$Ph(o-CH$_3$) | |
| C-418 | Het-3 | NHCH$_2$ | H | 0 | NHSO$_2$Ph(m-CH$_3$) | |
| C-419 | Het-3 | NHCH$_2$ | H | 0 | NHSO$_2$Ph(p-CH$_3$) | |
| C-420 | Het-3 | NHCH$_2$ | H | 0 | NHSO$_2$Ph(o-Cl) | |
| C-421 | Het-3 | NHCH$_2$ | H | 0 | NHSO$_2$Ph(m-Cl) | |
| C-422 | Het-3 | NHCH$_2$ | H | 0 | NHSO$_2$Ph(p-Cl) | |
| C-423 | Het-3 | NHCH$_2$ | H | 0 | NHSO$_2$Ph(m-F) | |
| C-424 | Het-3 | NHCH$_2$ | H | 0 | NHSO$_2$Ph(p-F) | |
| C-425 | Het-3 | NHCH$_2$ | H | 0 | NHSO$_2$Ph(o-F) | |
| C-426 | Het-3 | NHCH$_2$ | H | 0 | NHSO$_2$Ph(m-Br) | |
| C-427 | Het-3 | NHCH$_2$ | H | 0 | NHSO$_2$Ph(p-Br) | |
| C-428 | Het-3 | NHCH$_2$ | H | 0 | NHSO$_2$Ph(o-OCH$_3$) | |
| C-429 | Het-3 | NHCH$_2$ | H | 0 | NHSO$_2$Ph(m-OCH$_3$) | |
| C-430 | Het-3 | NHCH$_2$ | H | 0 | NHSO$_2$Ph(p-OCH$_3$) | |
| C-431 | Het-3 | NHCH$_2$ | H | 0 | NHSO$_2$(2,4,6-trimethylphenyl) | |
| C-432 | Het-3 | NHCH$_2$ | H | 0 | NHSO$_2$(2,4,6-trichlorophenyl) | |
| C-433 | Het-3 | NHCH$_2$ | H | 0 | NHSO$_2$(2,6-dichlorophenyl) | |
| C-434 | Het-3 | NHCH$_2$ | H | 0 | NHSO$_2$(2-chloro-6-methylphenyl) | |
| C-435 | Het-3 | NHCH$_2$ | H | 0 | NHSO2[4-(2,6-dimethylphenyl)phenyl | |
| C-436 | Het-3 | NHCH$_2$ | H | 0 | NHSO$_2$C$_6$H$_4$(4-Ph) | |
| C-437 | Het-3 | NHCH$_2$ | H | 0 | NHSO$_2$[4-(3,5-dimethyl)isoxazolyl] | |
| C-438 | Het-3 | NHCH$_2$ | H | 0 | NHSO$_2$(1-naphthyl) | |
| C-439 | Het-3 | NHCH$_2$ | H | 0 | NHSO$_2$(2-naphthyl) | |
| C-440 | Het-3 | NHCH$_2$ | H | 0 | NHSO$_2$CH$_2$Ph | |
| C-441 | Het-3 | NHCH$_2$CH$_2$ | H | 0 | NHCO$_2$Et | |
| C-442 | Het-3 | NHCH$_2$CH$_2$ | H | 0 | NHCO$_2$CH$_2$Ph | |
| C-443 | Het-3 | NHCH$_2$CH$_2$ | H | 0 | NHCO$_2$-n-Pr | |
| C-444 | Het-3 | NHCH$_2$CH$_2$ | H | 0 | NHCO$_2$-i-Pr | |
| C-445 | Het-3 | NHCH$_2$CH$_2$ | H | 0 | NHCO$_2$-n-Bu | |
| C-446 | Het-3 | NHCH$_2$CH$_2$ | H | 0 | NHCO$_2$-i-Bu | |
| C-447 | Het-3 | NHCH$_2$CH$_2$ | H | 0 | NHCO$_2$-n-C$_5$H$_{11}$ | |
| C-448 | Het-3 | NHCH$_2$CH$_2$ | H | 0 | NHSO$_2$Ph | |
| C-449 | Het-3 | NHCH$_2$CH$_2$ | H | 0 | NHSO$_2$Ph(o-CH$_3$) | |
| C-450 | Het-3 | NHCH$_2$CH$_2$ | H | 0 | NHSO$_2$Ph(m-CH$_3$) | |
| C-451 | Het-3 | NHCH$_2$CH$_2$ | H | 0 | NHSO$_2$Ph(p-CH$_3$) | |
| C-452 | Het-3 | NHCH$_2$CH$_2$ | H | 0 | NHSO$_2$Ph(o-Cl) | |
| C-453 | Het-3 | NHCH$_2$CH$_2$ | H | 0 | NHSO$_2$Ph(m-Cl) | |
| C-454 | Het-3 | NHCH$_2$CH$_2$ | H | 0 | NHSO$_2$Ph(p-Cl) | |
| C-455 | Het-3 | NHCH$_2$CH$_2$ | H | 0 | NHSO$_2$Ph(m-F) | |
| C-456 | Het-3 | NHCH$_2$CH$_2$ | H | 0 | NHSO$_2$Ph(p-F) | |
| C-457 | Het-3 | NHCH$_2$CH$_2$ | H | 0 | NHSO$_2$Ph(o-F) | |
| C-458 | Het-3 | NHCH$_2$CH$_2$ | H | 0 | NHSO$_2$Ph(m-Br) | |
| C-459 | Het-3 | NHCH$_2$CH$_2$ | H | 0 | NHSO$_2$Ph(p-Br) | |
| C-460 | Het-3 | NHCH$_2$CH$_2$ | H | 0 | NHSO$_2$Ph(o-OCH$_3$) | |
| C-461 | Het-3 | NHCH$_2$CH$_2$ | H | 0 | NHSO$_2$Ph(m-OCH$_3$) | |
| C-462 | Het-3 | NHCH$_2$CH$_2$ | H | 0 | NHSO$_2$Ph(p-OCH$_3$) | |
| C-463 | Het-3 | NHCH$_2$CH$_2$ | H | 0 | NHSO$_2$(2,4,6-trimethylphenyl) | |
| C-464 | Het-3 | NHCH$_2$CH$_2$ | H | 0 | NHSO$_2$(2,4,6-trichlorophenyl) | |
| C-465 | Het-3 | NHCH$_2$CH$_2$ | H | 0 | NHSO$_2$(2,6-dichlorophenyl) | |
| C-466 | Het-3 | NHCH$_2$CH$_2$ | H | 0 | NHSO$_2$(2-chloro-6-methylphenyl) | |
| C-467 | Het-3 | NHCH$_2$CH$_2$ | H | 0 | NHSO2[4-(2,6-dimethylphenyl)phenyl | |
| C-468 | Het-3 | NHCH$_2$CH$_2$ | H | 0 | NHSO$_2$C$_6$H$_4$(4-Ph) | |
| C-469 | Het-3 | NHCH$_2$CH$_2$ | H | 0 | NHSO$_2$[4-(3,5-dimethyl)isoxazolyl] | |
| C-470 | Het-3 | NHCH$_2$CH$_2$ | H | 0 | NHSO$_2$(1-naphthyl) | |
| C-471 | Het-3 | NHCH$_2$CH$_2$ | H | 0 | NHSO$_2$(2-naphthyl) | |
| C-472 | Het-3 | NHCH$_2$CH$_2$ | H | 0 | NHSO$_2$CH$_2$Ph | |
| C-473 | Het-3 | NHCH$_2$CH$_2$ | H | 0 | NHSO$_2$NHCH$_2$Ph | |
| C-474 | Het-3 | NHCH$_2$CH$_2$ | H | 0 | NHSO$_2$NHPh | |
| C-475 | Het-4 | CH$_2$CH$_2$ | H | 0 | NHCO$_2$-n-Pr | |
| C-476 | Het-4 | CH$_2$CH$_2$ | H | 0 | NHCO$_2$-i-Pr | |
| C-477 | Het-4 | CH$_2$CH$_2$ | H | 0 | NHCO$_2$-n-Bu | |
| C-478 | Het-4 | CH$_2$CH$_2$ | H | 0 | NHCO$_2$-i-Bu | |
| C-479 | Het-4 | CH$_2$CH$_2$ | H | 0 | NHSO$_2$Ph | |
| C-480 | Het-4 | CH$_2$CH$_2$ | H | 0 | NHSO$_2$Ph(p-Cl) | |
| C-481 | Het-4 | CH$_2$CH$_2$ | H | 0 | NHSO$_2$Ph(p-F) | |
| C-482 | Het-4 | CH$_2$CH$_2$ | H | 0 | NHSO$_2$(2,4,6-trimethylphenyl) | 528.1 |
| C-483 | Het-4 | CH$_2$CH$_2$ | H | 0 | NHSO$_2$(2,4,6-trichlorophenyl) | |
| C-484 | Het-4 | CH$_2$CH$_2$ | H | 0 | NHSO$_2$(2,6-dichlorophenyl) | |
| C-485 | Het-4 | CH$_2$CH$_2$ | H | 0 | NHSO2[4-(2,6-dimethylphenyl)phenyl | |
| C-486 | Het-4 | CH$_2$CH$_2$ | H | 0 | NHSO$_2$C$_6$H$_4$(4-Ph) | |
| C-487 | Het-4 | CH$_2$CH$_2$ | H | 0 | NHSO$_2$[4-(3,5-dimethyl)isoxazolyl] | |
| C-488 | Het-4 | CH$_2$CH$_2$ | H | 0 | NHSO$_2$(1-naphthyl) | |
| C-489 | Het-4 | NHCH$_2$ | H | 0 | NHCO$_2$-n-Pr | |
| C-490 | Het-4 | NHCH$_2$ | H | 0 | NHCO$_2$-i-Pr | |
| C-491 | Het-4 | NHCH$_2$ | H | 0 | NHCO$_2$-n-Bu | |
| C-492 | Het-4 | NHCH$_2$ | H | 0 | NHCO$_2$-i-Bu | |
| C-493 | Het-4 | NHCH$_2$ | H | 0 | NHSO$_2$Ph | |
| C-494 | Het-4 | NHCH$_2$ | H | 0 | NHSO$_2$Ph(p-Cl) | |
| C-495 | Het-4 | NHCH$_2$ | H | 0 | NHSO$_2$Ph(p-F) | |
| C-496 | Het-4 | NHCH$_2$ | H | 0 | NHSO$_2$(2,4,6-trimethylphenyl) | |
| C-497 | Het-4 | NHCH$_2$ | H | 0 | NHSO$_2$(2,4,6-trichlorophenyl) | |
| C-498 | Het-4 | NHCH$_2$ | H | 0 | NHSO$_2$(2,6-dichlorophenyl) | |
| C-499 | Het-4 | NHCH$_2$ | H | 0 | NHSO2[4-(2,6-dimethylphenyl)phenyl | |
| C-500 | Het-4 | NHCH$_2$ | H | 0 | NHSO$_2$C$_6$H$_4$(4-Ph) | |
| C-501 | Het-4 | NHCH$_2$ | H | 0 | NHSO$_2$[4-(3,5-dimethyl)isoxazolyl] | |
| C-502 | Het-4 | NHCH$_2$ | H | 0 | NHSO$_2$(1-naphthyl) | |
| C-503 | Het-4 | OCH$_2$ | H | 0 | NHCO$_2$-n-Pr | |
| C-504 | Het-4 | OCH$_2$ | H | 0 | NHCO$_2$-i-Pr | |
| C-505 | Het-4 | OCH$_2$ | H | 0 | NHCO$_2$-n-Bu | |
| C-506 | Het-4 | OCH$_2$ | H | 0 | NHCO$_2$-i-Bu | |

TABLE 3-continued

| Ex. No. | R[1] | U | R[8] | z | R[15] | MS |
|---|---|---|---|---|---|---|
| C-507 | Het-4 | OCH$_2$ | H | 0 | NHSO$_2$Ph | |
| C-508 | Het-4 | OCH$_2$ | H | 0 | NHSO$_2$Ph(p-Cl) | |
| C-509 | Het-4 | OCH$_2$ | H | 0 | NHSO$_2$Ph(p-F) | |
| C-510 | Het-4 | OCH$_2$ | H | 0 | NHSO$_2$(2,4,6-trimethylphenyl) | |
| C-511 | Het-4 | OCH$_2$ | H | 0 | NHSO$_2$(2,4,6-trichlorophenyl) | |
| C-512 | Het-4 | OCH$_2$ | H | 0 | NHSO$_2$(2,6-dichlorophenyl) | |
| C-513 | Het-4 | OCH$_2$ | H | 0 | NHSO2[4-(2,6-dimethylphenyl)phenyl | |
| C-514 | Het-4 | OCH$_2$ | H | 0 | NHSO$_2$C$_6$H$_4$(4-Ph) | |
| C-515 | Het-4 | OCH$_2$ | H | 0 | NHSO$_2$[4-(3,5-dimethyl)isoxazolyl] | |
| C-516 | Het-4 | OCH$_2$ | H | 0 | NHSO$_2$(1-naphthyl) | |
| C-517 | Het-4 | CH$_2$CH$_2$CH$_2$ | H | 0 | NHCO$_2$-n-Pr | |
| C-518 | Het-4 | CH$_2$CH$_2$CH$_2$ | H | 0 | NHCO$_2$-i-Pr | |
| C-519 | Het-4 | CH$_2$CH$_2$CH$_2$ | H | 0 | NHCO$_2$-n-Bu | |
| C-520 | Het-4 | CH$_2$CH$_2$CH$_2$ | H | 0 | NHCO$_2$-i-Bu | |
| C-521 | Het-4 | CH$_2$CH$_2$CH$_2$ | H | 0 | NHSO$_2$Ph | |
| C-522 | Het-4 | CH$_2$CH$_2$CH$_2$ | H | 0 | NHSO$_2$Ph(p-Cl) | |
| C-523 | Het-4 | CH$_2$CH$_2$CH$_2$ | H | 0 | NHSO$_2$Ph(p-F) | |
| C-524 | Het-4 | CH$_2$CH$_2$CH$_2$ | H | 0 | NHSO$_2$(2,4,6-trimethylphenyl) | |
| C-525 | Het-4 | CH$_2$CH$_2$CH$_2$ | H | 0 | NHSO$_2$(2,4,6-trichlorophenyl) | |
| C-526 | Het-4 | CH$_2$CH$_2$CH$_2$ | H | 0 | NHSO$_2$(2,6-dichlorophenyl) | |
| C-527 | Het-4 | CH$_2$CH$_2$CH$_2$ | H | 0 | NHSO2[4-(2,6-dimethylphenyl)phenyl | |
| C-528 | Het-4 | CH$_2$CH$_2$CH$_2$ | H | 0 | NHSO$_2$C$_6$H$_4$(4-Ph) | |
| C-529 | Het-4 | CH$_2$CH$_2$CH$_2$ | H | 0 | NHSO$_2$[4-(3,5-dimethyl)isoxazolyl] | |
| C-530 | Het-4 | CH$_2$CH$_2$CH$_2$ | H | 0 | NHSO$_2$(1-naphthyl) | |
| C-531 | Het-4 | NHCH$_2$CH$_2$ | H | 0 | NHCO$_2$-n-Pr | |
| C-532 | Het-4 | NHCH$_2$CH$_2$ | H | 0 | NHCO$_2$-i-Pr | |
| C-533 | Het-4 | NHCH$_2$CH$_2$ | H | 0 | NHCO$_2$-n-Bu | |
| C-534 | Het-4 | NHCH$_2$CH$_2$ | H | 0 | NHCO$_2$-i-Bu | |
| C-535 | Het-4 | NHCH$_2$CH$_2$ | H | 0 | NHSO$_2$Ph | |
| C-536 | Het-4 | NHCH$_2$CH$_2$ | H | 0 | NHSO$_2$Ph(p-Cl) | |
| C-537 | Het-4 | NHCH$_2$CH$_2$ | H | 0 | NHSO$_2$Ph(p-F) | |
| C-538 | Het-4 | NHCH$_2$CH$_2$ | H | 0 | NHSO$_2$(2,4,6-trimethylphenyl) | |
| C-539 | Het-4 | NHCH$_2$CH$_2$ | H | 0 | NHSO$_2$(2,4,6-trichlorophenyl) | |
| C-540 | Het-4 | NHCH$_2$CH$_2$ | H | 0 | NHSO$_2$(2,6-dichlorophenyl) | |
| C-541 | Het-4 | NHCH$_2$CH$_2$ | H | 0 | NHSO2[4-(2,6-dimethylphenyl)phenyl | |
| C-542 | Het-4 | NHCH$_2$CH$_2$ | H | 0 | NHSO$_2$C$_6$H$_4$(4-Ph) | |
| C-543 | Het-4 | NHCH$_2$CH$_2$ | H | 0 | NHSO$_2$[4-(3,5-dimethyl)isoxazolyl] | |
| C-544 | Het-4 | NHCH$_2$CH$_2$ | H | 0 | NHSO$_2$(1-naphthyl) | |
| C-545 | Het-4 | OCH$_2$CH$_2$ | H | 0 | NHCO$_2$-n-Pr | |
| C-546 | Het-4 | OCH$_2$CH$_2$ | H | 0 | NHCO$_2$-i-Pr | |
| C-547 | Het-4 | OCH$_2$CH$_2$ | H | 0 | NHCO$_2$-n-Bu | |
| C-548 | Het-4 | OCH$_2$CH$_2$ | H | 0 | NHCO$_2$-i-Bu | |
| C-549 | Het-4 | OCH$_2$CH$_2$ | H | 0 | NHSO$_2$Ph | |
| C-550 | Het-4 | OCH$_2$CH$_2$ | H | 0 | NHSO$_2$Ph(p-Cl) | |
| C-551 | Het-4 | OCH$_2$CH$_2$ | H | 0 | NHSO$_2$Ph(p-F) | |
| C-552 | Het-4 | OCH$_2$CH$_2$ | H | 0 | NHSO$_2$(2,4,6-trimethylphenyl) | |
| C-553 | Het-4 | OCH$_2$CH$_2$ | H | 0 | NHSO$_2$(2,4,6-trichlorophenyl) | |
| C-554 | Het-4 | OCH$_2$CH$_2$ | H | 0 | NHSO$_2$(2,6-dichlorophenyl) | |
| C-555 | Het-4 | OCH$_2$CH$_2$ | H | 0 | NHSO2[4-(2,6-dimethylphenyl)phenyl | |
| C-556 | Het-4 | OCH$_2$CH$_2$ | H | 0 | NHSO$_2$C$_6$H$_4$(4-Ph) | |
| C-557 | Het-4 | OCH$_2$CH$_2$ | H | 0 | NHSO$_2$[4-(3,5-dimethylisoxazolyl] | |
| C-558 | Het-4 | OCH$_2$CH$_2$ | H | 0 | NHSO$_2$(1-naphthyl) | |
| C-559 | Het-5 | CH$_2$CH$_2$ | H | 0 | NHCO$_2$-n-Pr | |
| C-560 | Het-5 | CH$_2$CH$_2$ | H | 0 | NHCO$_2$-i-Pr | |
| C-561 | Het-5 | CH$_2$CH$_2$ | H | 0 | NHCO$_2$-n-Bu | |
| C-562 | Het-5 | CH$_2$CH$_2$ | H | 0 | NHCO$_2$-i-Bu | |
| C-563 | Het-5 | CH$_2$CH$_2$ | H | 0 | NHSO$_2$Ph | |
| C-564 | Het-5 | CH$_2$CH$_2$ | H | 0 | NHSO$_2$Ph(p-Cl) | |
| C-565 | Het-5 | CH$_2$CH$_2$ | H | 0 | NHSO$_2$Ph(p-F) | |
| C-566 | Het-5 | CH$_2$CH$_2$ | H | 0 | NHSO$_2$(2,4,6-trimethylphenyl) | |
| C-567 | Het-5 | CH$_2$CH$_2$ | H | 0 | NHSO$_2$(2,4,6-trichlorophenyl) | |
| C-568 | Het-5 | CH$_2$CH$_2$ | H | 0 | NHSO$_2$(2,6-dichlorophenyl) | |
| C-569 | Het-5 | CH$_2$CH$_2$ | H | 0 | NHSO2[4-(2,6-dimethylphenyl)phenyl | |
| C-570 | Het-5 | CH$_2$CH$_2$ | H | 0 | NHSO$_2$C$_6$H$_4$(4-Ph) | |
| C-571 | Het-5 | CH$_2$CH$_2$ | H | 0 | NHSO$_2$[4-(3,5-dimethylisoxazolyl] | |
| C-572 | Het-5 | CH$_2$CH$_2$ | H | 0 | NHSO$_2$(1-naphthyl) | |
| C-573 | Het-5 | NHCH$_2$ | H | 0 | NHCO$_2$-n-Pr | |
| C-574 | Het-5 | NHCH$_2$ | H | 0 | NHCO$_2$-i-Pr | |
| C-575 | Het-5 | NHCH$_2$ | H | 0 | NHCO$_2$-n-Bu | |
| C-576 | Het-5 | NHCH$_2$ | H | 0 | NHCO$_2$-i-Bu | |
| C-577 | Het-5 | NHCH$_2$ | H | 0 | NHSO$_2$Ph | |
| C-578 | Het-5 | NHCH$_2$ | H | 0 | NHSO$_2$Ph(p-Cl) | |
| C-579 | Het-5 | NHCH$_2$ | H | 0 | NHSO$_2$Ph(p-F) | |
| C-580 | Het-5 | NHCH$_2$ | H | 0 | NHSO$_2$(2,4,6-trimethylphenyl) | |
| C-581 | Het-5 | NHCH$_2$ | H | 0 | NHSO$_2$(2,4,6-trichlorophenyl) | |
| C-582 | Het-5 | NHCH$_2$ | H | 0 | NHSO$_2$(2,6-dichlorophenyl) | |
| C-583 | Het-5 | NHCH$_2$ | H | 0 | NHSO2[4-(2,6-dimethylphenyl)phenyl | |
| C-584 | Het-5 | NHCH$_2$ | H | 0 | NHSO$_2$C$_6$H$_4$(4-Ph) | |
| C-585 | Het-5 | NHCH$_2$ | H | 0 | NHSO$_2$[4-(3,5-dimethylisoxazolyl] | |
| C-586 | Het-5 | NHCH$_2$ | H | 0 | NHSO$_2$(1-naphthyl) | |
| C-587 | Het-5 | OCH$_2$ | H | 0 | NHCO$_2$-n-Pr | |
| C-588 | Het-5 | OCH$_2$ | H | 0 | NHCO$_2$-i-Pr | |
| C-589 | Het-5 | OCH$_2$ | H | 0 | NHCO$_2$-n-Bu | |
| C-590 | Het-5 | OCH$_2$ | H | 0 | NHCO$_2$-i-Bu | |
| C-591 | Het-5 | OCH$_2$ | H | 0 | NHSO$_2$Ph | |
| C-592 | Het-5 | OCH$_2$ | H | 0 | NHSO$_2$Ph(p-Cl) | |
| C-593 | Het-5 | OCH$_2$ | H | 0 | NHSO$_2$Ph(p-F) | |
| C-594 | Het-5 | OCH$_2$ | H | 0 | NHSO$_2$(2,4,6-trimethylphenyl) | |
| C-595 | Het-5 | OCH$_2$ | H | 0 | NHSO$_2$(2,4,6-trichlorophenyl) | |
| C-596 | Het-5 | OCH$_2$ | H | 0 | NHSO$_2$(2,6-dichlorophenyl) | |
| C-597 | Het-5 | OCH$_2$ | H | 0 | NHSO2[4-(2,6-dimethylphenyl)phenyl | |
| C-598 | Het-5 | OCH$_2$ | H | 0 | NHSO$_2$C$_6$H$_4$(4-Ph) | |
| C-599 | Het-5 | OCH$_2$ | H | 0 | NHSO$_2$[4-(3,5-dimethyl)isoxazolyl] | |
| C-600 | Het-5 | OCH$_2$ | H | 0 | NHSO$_2$(1-naphthyl) | |
| C-601 | Het-5 | CH$_2$CH$_2$CH$_2$ | H | 0 | NHCO$_2$-n-Pr | |
| C-602 | Het-5 | CH$_2$CH$_2$CH$_2$ | H | 0 | NHCO$_2$-i-Pr | |
| C-603 | Het-5 | CH$_2$CH$_2$CH$_2$ | H | 0 | NHCO$_2$-n-Bu | |
| C-604 | Het-5 | CH$_2$CH$_2$CH$_2$ | H | 0 | NHCO$_2$-i-Bu | |

TABLE 3-continued

| Ex. No. | R$^1$ | U | R$^8$ | z | R$^{15}$ | MS |
|---|---|---|---|---|---|---|
| C-605 | Het-5 | CH$_2$CH$_2$CH$_2$ | H | 0 | NHSO$_2$Ph | |
| C-606 | Het-5 | CH$_2$CH$_2$CH$_2$ | H | 0 | NHSO$_2$Ph(p-Cl) | |
| C-607 | Het-5 | CH$_2$CH$_2$CH$_2$ | H | 0 | NHSO$_2$Ph(p-F) | |
| C-608 | Het-5 | CH$_2$CH$_2$CH$_2$ | H | 0 | NHSO$_2$(2,4,6-trimethylphenyl) | |
| C-609 | Het-5 | CH$_2$CH$_2$CH$_2$ | H | 0 | NHSO$_2$(2,4,6-trichlorophenyl) | |
| C-610 | Het-5 | CH$_2$CH$_2$CH$_2$ | H | 0 | NHSO$_2$(2,6-dichlorophenyl) | |
| C-611 | Het-5 | CH$_2$CH$_2$CH$_2$ | H | 0 | NHSO2[4-(2,6-dimethylphenyl)phenyl | |
| C-612 | Het-5 | CH$_2$CH$_2$CH$_2$ | H | 0 | NHSO$_2$C$_6$H$_4$(4-Ph) | |
| C-613 | Het-5 | CH$_2$CH$_2$CH$_2$ | H | 0 | NHSO$_2$[4-(3,5-dimethyl)isoxazolyl] | |
| C-614 | Het-5 | CH$_2$CH$_2$CH$_2$ | H | 0 | NHSO$_2$(1-naphthyl) | |
| C-615 | Het-5 | NHCH$_2$CH$_2$ | H | 0 | NHCO$_2$-n-Pr | |
| C-616 | Het-5 | NHCH$_2$CH$_2$ | H | 0 | NHCO$_2$-i-Pr | |
| C-617 | Het-5 | NHCH$_2$CH$_2$ | H | 0 | NHCO$_2$-n-Bu | |
| C-618 | Het-5 | NHCH$_2$CH$_2$ | H | 0 | NHCO$_2$-i-Bu | |
| C-619 | Het-5 | NHCH$_2$CH$_2$ | H | 0 | NHSO$_2$Ph | |
| C-620 | Het-5 | NHCH$_2$CH$_2$ | H | 0 | NHSO$_2$Ph(p-Cl) | |
| C-621 | Het-5 | NHCH$_2$CH$_2$ | H | 0 | NHSO$_2$Ph(p-F) | |
| C-622 | Het-5 | NHCH$_2$CH$_2$ | H | 0 | NHSO$_2$(2,4,6-trimethylphenyl) | |
| C-623 | Het-5 | NHCH$_2$CH$_2$ | H | 0 | NHSO$_2$(2,4,6-trichlorophenyl) | |
| C-624 | Het-5 | NHCH$_2$CH$_2$ | H | 0 | NHSO$_2$(2,6-dichlorophenyl) | |
| C-625 | Het-5 | NHCH$_2$CH$_2$ | H | 0 | NHSO2[4-(2,6-dimethylphenyl)phenyl | |
| C-626 | Het-5 | NHCH$_2$CH$_2$ | H | 0 | NHSO$_2$C$_6$H$_4$(4-Ph) | |
| C-627 | Het-5 | NHCH$_2$CH$_2$ | H | 0 | NHSO$_2$[4-(3,5-dimethyl)isoxazolyl] | |
| C-628 | Het-5 | NHCH$_2$CH$_2$ | H | 0 | NHSO$_2$(1-naphthyl) | |
| C-629 | Het-5 | OCH$_2$CH$_2$ | H | 0 | NHCO$_2$-n-Pr | |
| C-630 | Het-5 | OCH$_2$CH$_2$ | H | 0 | NHCO$_2$-i-Pr | |
| C-631 | Het-5 | OCH$_2$CH$_2$ | H | 0 | NHCO$_2$-n-Bu | |
| C-632 | Het-5 | OCH$_2$CH$_2$ | H | 0 | NHCO$_2$-i-Bu | |
| C-633 | Het-5 | OCH$_2$CH$_2$ | H | 0 | NHSO$_2$Ph | |
| C-634 | Het-5 | OCH$_2$CH$_2$ | H | 0 | NHSO$_2$Ph(p-Cl) | |
| C-635 | Het-5 | OCH$_2$CH$_2$ | H | 0 | NHSO$_2$Ph(p-F) | |
| C-636 | Het-5 | OCH$_2$CH$_2$ | H | 0 | NHSO$_2$(2,4,6-trimethylphenyl) | |
| C-637 | Het-5 | OCH$_2$CH$_2$ | H | 0 | NHSO$_2$(2,4,6-trichlorophenyl) | |
| C-638 | Het-5 | OCH$_2$CH$_2$ | H | 0 | NHSO$_2$(2,6-dichlorophenyl) | |
| C-639 | Het-5 | OCH$_2$CH$_2$ | H | 0 | NHSO2[4-(2,6-dimethylphenyl)phenyl | |
| C-640 | Het-5 | OCH$_2$CH$_2$ | H | 0 | NHSO$_2$C$_6$H$_4$(4-Ph) | |
| C-641 | Het-5 | OCH$_2$CH$_2$ | H | 0 | NHSO$_2$[4-(3,5-dimethyl)isoxazolyl] | |
| C-642 | Het-5 | OCH$_2$CH$_2$ | H | 0 | NHSO$_2$(1-naphthyl) | |
| C-643 | Het-6 | NHCH$_2$ | H | 0 | NHCO$_2$-n-Pr | |
| C-644 | Het-6 | NHCH$_2$ | H | 0 | NHCO$_2$-i-Pr | |
| C-645 | Het-6 | NHCH$_2$ | H | 0 | NHCO$_2$-n-Bu | |
| C-646 | Het-6 | NHCH$_2$ | H | 0 | NHCO$_2$-i-Bu | |
| C-647 | Het-6 | NHCH$_2$ | H | 0 | NHSO$_2$Ph | |
| C-648 | Het-6 | NHCH$_2$ | H | 0 | NHSO$_2$Ph(p-Cl) | |
| C-649 | Het-6 | NHCH$_2$ | H | 0 | NHSO$_2$Ph(p-F) | |
| C-650 | Het-6 | NHCH$_2$ | H | 0 | NHSO$_2$(2,4,6-trimethylphenyl) | |
| C-651 | Het-6 | NHCH$_2$ | H | 0 | NHSO$_2$(2,4,6-trichlorophenyl) | |
| C-652 | Het-6 | NHCH$_2$ | H | 0 | NHSO$_2$(2,6-dichlorophenyl) | |
| C-653 | Het-6 | NHCH$_2$ | H | 0 | NHSO2[4-(2,6-dimethylphenyl)phenyl | |
| C-654 | Het-6 | NHCH$_2$ | H | 0 | NHSO$_2$C$_6$H$_4$(4-Ph) | |
| C-655 | Het-6 | NHCH$_2$ | H | 0 | NHSO$_2$[4-(3,5-dimethylisoxazolyl] | |
| C-656 | Het-6 | NHCH$_2$ | H | 0 | NHSO$_2$(1-naphthyl) | |
| C-657 | Het-6 | NHCH$_2$CH$_2$ | H | 0 | NHCO$_2$-n-Pr | |
| C-658 | Het-6 | NHCH$_2$CH$_2$ | H | 0 | NHCO$_2$-i-Pr | |
| C-659 | Het-6 | NHCH$_2$CH$_2$ | H | 0 | NHCO$_2$-n-Bu | |
| C-660 | Het-6 | NHCH$_2$CH$_2$ | H | 0 | NHCO$_2$-i-Bu | |
| C-661 | Het-6 | NHCH$_2$CH$_2$ | H | 0 | NHSO$_2$Ph | |
| C-662 | Het-6 | NHCH$_2$CH$_2$ | H | 0 | NHSO$_2$Ph(p-Cl) | |
| C-663 | Het-6 | NHCH$_2$CH$_2$ | H | 0 | NHSO$_2$Ph(p-F) | |
| C-664 | Het-6 | NHCH$_2$CH$_2$ | H | 0 | NHSO$_2$(2,4,6-trimethylphenyl) | |
| C-665 | Het-6 | NHCH$_2$CH$_2$ | H | 0 | NHSO$_2$(2,4,6-trichlorophenyl) | |
| C-666 | Het-6 | NHCH$_2$CH$_2$ | H | 0 | NHSO$_2$(2,6-dichlorophenyl) | |
| C-667 | Het-6 | NHCH$_2$CH$_2$ | H | 0 | NHSO2[4-(2,6-dimethylphenyl)phenyl | |
| C-668 | Het-6 | NHCH$_2$CH$_2$ | H | 0 | NHSO$_2$C$_6$H$_4$(4-Ph) | |
| C-669 | Het-6 | NHCH$_2$CH$_2$ | H | 0 | NHSO$_2$[4-(3,5-dimethylisoxazolyl] | |
| C-670 | Het-6 | NHCH$_2$CH$_2$ | H | 0 | NHSO$_2$(1-naphthyl) | |
| C-671 | Het-7 | NHCH$_2$ | H | 0 | NHCO$_2$-n-Pr | |
| C-672 | Het-7 | NHCH$_2$ | H | 0 | NHCO$_2$-i-Pr | |
| C-673 | Het-7 | NHCH$_2$ | H | 0 | NHCO$_2$-n-Bu | |
| C-674 | Het-7 | NHCH$_2$ | H | 0 | NHCO$_2$-i-Bu | |
| C-675 | Het-7 | NHCH$_2$ | H | 0 | NHSO$_2$Ph | |
| C-676 | Het-7 | NHCH$_2$ | H | 0 | NHSO$_2$Ph(p-Cl) | |
| C-677 | Het-7 | NHCH$_2$ | H | 0 | NHSO$_2$Ph(p-F) | |
| C-678 | Het-7 | NHCH$_2$ | H | 0 | NHSO$_2$(2,4,6-trimethylphenyl) | |
| C-679 | Het-7 | NHCH$_2$ | H | 0 | NHSO$_2$(2,4,6-trichlorophenyl) | |
| C-680 | Het-7 | NHCH$_2$ | H | 0 | NHSO$_2$(2,6-dichlorophenyl) | |
| C-681 | Het-7 | NHCH$_2$ | H | 0 | NHSO2[4-(2,6-dimethylphenyl)phenyl | |
| C-682 | Het-7 | NHCH$_2$ | H | 0 | NHSO$_2$C$_6$H$_4$(4-Ph) | |
| C-683 | Het-7 | NHCH$_2$ | H | 0 | NHSO$_2$(1-naphthyl) | |
| C-685 | Het-7 | NHCH$_2$CH$_2$ | H | 0 | NHCO$_2$-n-Pr | |
| C-686 | Het-7 | NHCH$_2$CH$_2$ | H | 0 | NHCO$_2$-i-Pr | |
| C-687 | Het-7 | NHCH$_2$CH$_2$ | H | 0 | NHCO$_2$-n-Bu | |
| C-688 | Het-7 | NHCH$_2$CH$_2$ | H | 0 | NHCO$_2$-i-Bu | |
| C-689 | Het-7 | NHCH$_2$CH$_2$ | H | 0 | NHSO$_2$Ph | |
| C-690 | Het-7 | NHCH$_2$CH$_2$ | H | 0 | NHSO$_2$Ph(p-Cl) | |
| C-691 | Het-7 | NHCH$_2$CH$_2$ | H | 0 | NHSO$_2$Ph(p-F) | |
| C-692 | Het-7 | NHCH$_2$CH$_2$ | H | 0 | NHSO$_2$(2,4,6-trimethylphenyl) | |
| C-693 | Het-7 | NHCH$_2$CH$_2$ | H | 0 | NHSO$_2$(2,4,6-trichlorophenyl) | |
| C-694 | Het-7 | NHCH$_2$CH$_2$ | H | 0 | NHSO$_2$(2,6-dichlorophenyl) | |
| C-695 | Het-7 | NHCH$_2$CH$_2$ | H | 0 | NHSO2[4-(2,6-dimethylphenyl)phenyl | |
| C-696 | Het-7 | NHCH$_2$CH$_2$ | H | 0 | NHSO$_2$C$_6$H$_4$(4-Ph) | |
| C-697 | Het-7 | NHCH$_2$CH$_2$ | H | 0 | NHSO$_2$[4-(3,5-dimethyl)isoxazolyl] | |
| C-698 | Het-7 | NHCH$_2$CH$_2$ | H | 0 | NHSO$_2$(1-naphthyl) | |
| C-699 | Het-8 | NHCH$_2$ | H | 0 | NHCO$_2$-n-Pr | |
| C-700 | Het-8 | NHCH$_2$ | H | 0 | NHCO$_2$-i-Pr | |
| C-701 | Het-8 | NHCH$_2$ | H | 0 | NHCO$_2$-n-Bu | |
| C-702 | Het-8 | NHCH$_2$ | H | 0 | NHCO$_2$-i-Bu | |
| C-703 | Het-8 | NHCH$_2$ | H | 0 | NHSO$_2$Ph | |
| C-704 | Het-8 | NHCH$_2$ | H | 0 | NHSO$_2$Ph(p-Cl) | |

TABLE 3-continued

| Ex. No. | R¹ | U | R⁸ | z | R¹⁵ | MS |
|---|---|---|---|---|---|---|
| C-705 | Het-8 | NHCH$_2$ | H | 0 | NHSO$_2$Ph(p-F) | |
| C-706 | Het-8 | NHCH$_2$ | H | 0 | NHSO$_2$(2,4,6-trimethylphenyl) | |
| C-707 | Het-8 | NHCH$_2$ | H | 0 | NHSO$_2$(2,4,6-trichlorophenyl) | |
| C-708 | Het-8 | NHCH$_2$ | H | 0 | NHSO$_2$(2,6-dichlorophenyl) | |
| C-709 | Het-8 | NHCH$_2$ | H | 0 | NHSO2[4-(2,6-dimethylphenyl)phenyl | |
| C-710 | Het-8 | NHCH$_2$ | H | 0 | NHSO$_2$C$_6$H$_4$(4-Ph) | |
| C-711 | Het-8 | NHCH$_2$ | H | 0 | NHSO$_2$[4-(3,5-dimethyl)isoxazolyl] | |
| C-712 | Het-8 | NHCH$_2$ | H | 0 | NHSO$_2$(1-naphthyl) | |
| C-713 | Het-8 | NHCH$_2$CH$_2$ | H | 0 | NHCO$_2$-n-Pr | |
| C-714 | Het-8 | NHCH$_2$CH$_2$ | H | 0 | NHCO$_2$-i-Pr | |
| C-715 | Het-8 | NHCH$_2$CH$_2$ | H | 0 | NHCO$_2$-n-Bu | |
| C-716 | Het-8 | NHCH$_2$CH$_2$ | H | 0 | NHCO$_2$-i-Bu | |
| C-717 | Het-8 | NHCH$_2$CH$_2$ | H | 0 | NHSO$_2$Ph | |
| C-718 | Het-8 | NHCH$_2$CH$_2$ | H | 0 | NHSO$_2$Ph(p-Cl) | |
| C-719 | Het-8 | NHCH$_2$CH$_2$ | H | 0 | NHSO$_2$Ph(p-F) | |
| C-720 | Het-8 | NHCH$_2$CH$_2$ | H | 0 | NHSO$_2$(2,4,6-trimethyylphenyl) | |
| C-721 | Het-8 | NHCH$_2$CH$_2$ | H | 0 | NHSO$_2$(2,4,6-trichlorophenyl) | |
| C-722 | Het-8 | NHCH$_2$CH$_2$ | H | 0 | NHSO$_2$(2,6-dichlorophenyl) | |
| C-723 | Het-8 | NHCH$_2$CH$_2$ | H | 0 | NHSO2[4-(2,6-dimethylphenyl)phenyl | |
| C-724 | Het-8 | NHCH$_2$CH$_2$ | H | 0 | NHSO$_2$C$_6$H$_4$(4-Ph) | |
| C-725 | Het-8 | NHCH$_2$CH$_2$ | H | 0 | NHSO$_2$[4-(3,5-dimethyl)isoxazolyl] | |
| C-726 | Het-8 | NHCH$_2$CH$_2$ | H | 0 | NHSO$_2$(1-naphthyl) | |
| C-727 | Het-9 | NHCH$_2$ | H | 0 | NHCO$_2$-n-Pr | |
| C-728 | Het-9 | NHCH$_2$ | H | 0 | NHCO$_2$-i-Pr | |
| C-729 | Het-9 | NHCH$_2$ | H | 0 | NHCO$_2$-n-Bu | |
| C-730 | Het-9 | NHCH$_2$ | H | 0 | NHCO$_2$-i-Bu | |
| C-731 | Het-9 | NHCH$_2$ | H | 0 | NHSO$_2$Ph | |
| C-732 | Het-9 | NHCH$_2$ | H | 0 | NHSO$_2$Ph(p-Cl) | |
| C-733 | Het-9 | NHCH$_2$ | H | 0 | NHSO$_2$Ph(p-F) | |
| C-734 | Het-9 | NHCH$_2$ | H | 0 | NHSO$_2$(2,4,6-trimethylphenyl) | |
| C-735 | Het-9 | NHCH$_2$ | H | 0 | NHSO$_2$(2,4,6-trichlorophenyl) | |
| C-736 | Het-9 | NHCH$_2$ | H | 0 | NHSO$_2$(2,6-dichlorophenyl) | |
| C-737 | Het-9 | NHCH$_2$ | H | 0 | NHSO$_2$[4-(2,6-dimethylphenyl)phenyl | |
| C-738 | Het-9 | NHCH$_2$ | H | 0 | NHSO$_2$C$_6$H$_4$(4-Ph) | |
| C-739 | Het-9 | NHCH$_2$ | H | 0 | NHSO$_2$[4-(3,5-dimethyl)isoxazolyl] | |
| C-740 | Het-9 | NHCH$_2$ | H | 0 | NHSO$_2$(1-naphthyl) | |
| C-741 | Het-9 | NHCH$_2$CH$_2$ | H | 0 | NHCO$_2$-n-Pr | |
| C-742 | Het-9 | NHCH$_2$CH$_2$ | H | 0 | NHCO$_2$-i-Pr | |
| C-743 | Het-9 | NHCH$_2$CH$_2$ | H | 0 | NHCO$_2$-n-Bu | |
| C-744 | Het-9 | NHCH$_2$CH$_2$ | H | 0 | NHCO$_2$-i-Bu | |
| C-745 | Het-9 | NHCH$_2$CH$_2$ | H | 0 | NHSO$_2$Ph | |
| C-746 | Het-9 | NHCH$_2$CH$_2$ | H | 0 | NHSO$_2$Ph(p-Cl) | |
| C-747 | Het-9 | NHCH$_2$CH$_2$ | H | 0 | NHSO$_2$Ph(p-F) | |
| C-748 | Het-9 | NHCH$_2$CH$_2$ | H | 0 | NHSO$_2$(2,4,6-trimethylphenyl) | |
| C-749 | Het-9 | NHCH$_2$CH$_2$ | H | 0 | NHSO$_2$(2,4,6-trichlorophenyl) | |
| C-750 | Het-9 | NHCH$_2$CH$_2$ | H | 0 | NHSO$_2$(2,6-dichlorophenyl) | |
| C-751 | Het-9 | NHCH$_2$CH$_2$ | H | 0 | NHSO2[4-(2,6-dimethylphenyl)phenyl | |
| C-752 | Het-9 | NHCH$_2$CH$_2$ | H | 0 | NHSO$_2$C$_6$H$_4$(4-Ph) | |
| C-753 | Het-9 | NHCH$_2$CH$_2$ | H | 0 | NHSO$_2$[4-(3,5-dimethyl)isoxazolyl] | |
| C-754 | Het-9 | NHCH$_2$CH$_2$ | H | 0 | NHSO$_2$(1-naphthyl) | |
| C-755 | Het-10 | NHCH$_2$ | H | 0 | NHCO$_2$-n-Pr | |
| C-756 | Het-10 | NHCH$_2$ | H | 0 | NHCO$_2$-i-Pr | |
| C-757 | Het-10 | NHCH$_2$ | H | 0 | NHCO$_2$-n-Bu | |
| C-758 | Het-10 | NHCH$_2$ | H | 0 | NHCO$_2$-i-Bu | |
| C-759 | Het-10 | NHCH$_2$ | H | 0 | NHSO$_2$Ph | |
| C-760 | Het-10 | NHCH$_2$ | H | 0 | NHSO$_2$Ph(p-Cl) | |
| C-761 | Het-10 | NHCH$_2$ | H | 0 | NHSO$_2$Ph(p-F) | |
| C-762 | Het-10 | NHCH$_2$ | H | 0 | NHSO$_2$(2,4,6-trimethylphenyl) | |
| C-763 | Het-10 | NHCH$_2$ | H | 0 | NHSO$_2$(2,4,6-trichlorophenyl) | |
| C-764 | Het-10 | NHCH$_2$ | H | 0 | NHSO$_2$(2,6-dichlorophenyl) | |
| C-765 | Het-10 | NHCH$_2$ | H | 0 | NHSO2[4-(2,6-dimethylphenyl)phenyl | |
| C-766 | Het-10 | NHCH$_2$ | H | 0 | NHSO$_2$C$_6$H$_4$(4-Ph) | |
| C-767 | Het-10 | NHCH$_2$ | H | 0 | NHSO$_2$[4-(3,5-dimethyl)isoxazolyl] | |
| C-768 | Het-10 | NHCH$_2$ | H | 0 | NHSO$_2$(1-naphthyl) | |
| C-769 | Het-10 | NHCH$_2$CH$_2$ | H | 0 | NHCO$_2$-n-Pr | |
| C-770 | Het-10 | NHCH$_2$CH$_2$ | H | 0 | NHCO$_2$-i-Pr | |
| C-771 | Het-10 | NHCH$_2$CH$_2$ | H | 0 | NHCO$_2$-n-Bu | |
| C-772 | Het-10 | NHCH$_2$CH$_2$ | H | 0 | NHCO$_2$-i-Bu | |
| C-773 | Het-10 | NHCH$_2$CH$_2$ | H | 0 | NHSO$_2$Ph | |
| C-774 | Het-10 | NHCH$_2$CH$_2$ | H | 0 | NHSO$_2$Ph(p-Cl) | |
| C-775 | Het-10 | NHCH$_2$CH$_2$ | H | 0 | NHSO$_2$Ph(p-F) | |
| C-776 | Het-10 | NHCH$_2$CH$_2$ | H | 0 | NHSO$_2$(2,4,6-trimethylphenyl) | |
| C-777 | Het-10 | NHCH$_2$CH$_2$ | H | 0 | NHSO$_2$(2,4,6-trichlorophenyl) | |
| C-778 | Het-10 | NHCH$_2$CH$_2$ | H | 0 | NHSO$_2$(2,6-dichlorophenyl) | |
| C-779 | Het-10 | NHCH$_2$CH$_2$ | H | 0 | NHSO2[4-(2,6-dimethylphenyl)phenyl | |
| C-780 | Het-10 | NHCH$_2$CH$_2$ | H | 0 | NHSO$_2$C$_6$H$_4$(4-Ph) | |
| C-781 | Het-10 | NHCH$_2$CH$_2$ | H | 0 | NHSO$_2$[4-(3,5-dimethyl)isoxazolyl] | |
| C-782 | Het-10 | NHCH$_2$CH$_2$ | H | 0 | NHSO$_2$(1-naphthyl) | |
| C-783 | Het-11 | NHCH$_2$ | H | 0 | NHCO$_2$-n-Pr | |
| C-784 | Het-11 | NHCH$_2$ | H | 0 | NHCO$_2$-i-Pr | |
| C-785 | Het-11 | NHCH$_2$ | H | 0 | NHCO$_2$-n-Bu | |
| C-786 | Het-11 | NHCH$_2$ | H | 0 | NHCO$_2$-i-Bu | |
| C-787 | Het-11 | NHCH$_2$ | H | 0 | NHSO$_2$Ph | |
| C-788 | Het-11 | NHCH$_2$ | H | 0 | NHSO$_2$Ph(p-Cl) | |
| C-789 | Het-11 | NHCH$_2$ | H | 0 | NHSO$_2$Ph(p-F) | |
| C-790 | Het-11 | NHCH$_2$ | H | 0 | NHSO$_2$(2,4,6-trimethylphenyl) | |
| C-791 | Het-11 | NHCH$_2$ | H | 0 | NHSO$_2$(2,4,6-trichlorophenyl) | |
| C-792 | Het-11 | NHCH$_2$ | H | 0 | NHSO$_2$(2,6-dichlorophenyl) | |
| C-793 | Het-11 | NHCH$_2$ | H | 0 | NHSO2[4-(2,6-dimethylphenyl)phenyl | |
| C-794 | Het-11 | NHCH$_2$ | H | 0 | NHSO$_2$C$_6$H$_4$(4-Ph) | |
| C-795 | Het-11 | NHCH$_2$ | H | 0 | NHSO$_2$[4-(3,5-dimethyl(isoxazolyl] | |
| C-796 | Het-11 | NHCH$_2$ | H | 0 | NHSO$_2$(1-naphthyl) | |
| C-797 | Het-11 | NHCH$_2$CH$_2$ | H | 0 | NHCO$_2$-n-Pr | |
| C-798 | Het-11 | NHCH$_2$CH$_2$ | H | 0 | NHCO$_2$-i-Pr | |
| C-799 | Het-11 | NHCH$_2$CH$_2$ | H | 0 | NHCO$_2$-n-Bu | |
| C-800 | Het-11 | NHCH$_2$CH$_2$ | H | 0 | NHCO$_2$-i-Bu | |
| C-801 | Het-11 | NHCH$_2$CH$_2$ | H | 0 | NHSO$_2$Ph | |
| C-802 | Het-11 | NHCH$_2$CH$_2$ | H | 0 | NHSO$_2$Ph(p-Cl) | |
| C-803 | Het-11 | NHCH$_2$CH$_2$ | H | 0 | NHSO$_2$Ph(p-F) | |

TABLE 3-continued

| Ex. No. | R¹ | U | R⁸ | z | R¹⁵ | MS |
|---|---|---|---|---|---|---|
| C-804 | Het-11 | NHCH$_2$CH$_2$ | H | 0 | NHSO$_2$(2,4,6-trimethylphenyl) | |
| C-805 | Het-11 | NHCH$_2$CH$_2$ | H | 0 | NHSO$_2$(2,4,6-trichlorophenyl) | |
| C-806 | Het-11 | NHCH$_2$CH$_2$ | H | 0 | NHSO$_2$(2,6-dichlorophenyl) | |
| C-807 | Het-11 | NHCH$_2$CH$_2$ | H | 0 | NHSO2[4-(2,6-dimethylphenyl)phenyl | |
| C-808 | Het-11 | NHCH$_2$CH$_2$ | H | 0 | NHSO$_2$C$_6$H$_4$(4-Ph) | |
| C-809 | Het-11 | NHCH$_2$CH$_2$ | H | 0 | NHSO$_2$[4-(3,5-dimethyl)isoxazolyl] | |
| C-810 | Het-11 | NHCH$_2$CH$_2$ | H | 0 | NHSO$_2$(1-naphthyl) | |
| C-811 | Het-12 | NHCH$_2$ | H | 0 | NHCO$_2$-n-Pr | |
| C-812 | Het-12 | NHCH$_2$ | H | 0 | NHCO$_2$-i-Pr | |
| C-813 | Het-12 | NHCH$_2$ | H | 0 | NHCO$_2$-n-Bu | |
| C-814 | Het-12 | NHCH$_2$ | H | 0 | NHCO$_2$-i-Bu | |
| C-815 | Het-12 | NHCH$_2$ | H | 0 | NHSO$_2$Ph | |
| C-816 | Het-12 | NHCH$_2$ | H | 0 | NHSO$_2$Ph(p-Cl) | |
| C-817 | Het-12 | NHCH$_2$ | H | 0 | NHSO$_2$Ph(p-F) | |
| C-818 | Het-12 | NHCH$_2$ | H | 0 | NHSO$_2$(2,4,6-trimethylphenyl) | |
| C-819 | Het-12 | NHCH$_2$ | H | 0 | NHSO$_2$(2,4,6-trichlorophenyl) | |
| C-820 | Het-12 | NHCH$_2$ | H | 0 | NHSO$_2$(2,6-dichlorophenyl) | |
| C-821 | Het-12 | NHCH$_2$ | H | 0 | NHSO2[4-(2,6-dimethylphenyl)phenyl | |
| C-822 | Het-12 | NHCH$_2$ | H | 0 | NHSO$_2$C$_6$H$_4$(4-Ph) | |
| C-823 | Het-12 | NHCH$_2$ | H | 0 | NHSO$_2$[4-(3,5-dimethyl)isoxazolyl] | |
| C-824 | Het-12 | NHCH$_2$ | H | 0 | NHSO$_2$(1-naphthyl) | |
| C-825 | Het-12 | NHCH$_2$CH$_2$ | H | 0 | NHCO$_2$-n-Pr | |
| C-826 | Het-12 | NHCH$_2$CH$_2$ | H | 0 | NHCO$_2$-i-Pr | |
| C-827 | Het-12 | NHCH$_2$CH$_2$ | H | 0 | NHCO$_2$-n-Bu | |
| C-828 | Het-12 | NHCH$_2$CH$_2$ | H | 0 | NHCO$_2$-i-Bu | |
| C-829 | Het-12 | NHCH$_2$CH$_2$ | H | 0 | NHSO$_2$Ph | |
| C-830 | Het-12 | NHCH$_2$CH$_2$ | H | 0 | NHSO$_2$Ph(p-Cl) | |
| C-831 | Het-12 | NHCH$_2$CH$_2$ | H | 0 | NHSO$_2$Ph(p-F) | |
| C-832 | Het-12 | NHCH$_2$CH$_2$ | H | 0 | NHSO$_2$(2,4,6-trimethylphenyl) | |
| C-833 | Het-12 | NHCH$_2$CH$_2$ | H | 0 | NHSO$_2$(2,4,6-trichlorophenyl) | |
| C-834 | Het-12 | NHCH$_2$CH$_2$ | H | 0 | NHSO$_2$(2,6-dichlorophenyl) | |
| C-835 | Het-12 | NHCH$_2$CH$_2$ | H | 0 | NHSO2[4-(2,6-dimethylphenyl)phenyl | |
| C-836 | Het-12 | NHCH$_2$CH$_2$ | H | 0 | NHSO$_2$C$_6$H$_4$(4-Ph) | |
| C-837 | Het-12 | NHCH$_2$CH$_2$ | H | 0 | NHSO$_2$[4-(3,5-dimethyl)isoxazolyl] | |
| C-838 | Het-12 | NHCH$_2$CH$_2$ | H | 0 | NHSO$_2$(1-naphthyl) | |
| C-839 | Het-13 | NHCH$_2$ | H | 0 | NHCO$_2$-n-Pr | |
| C-840 | Het-13 | NHCH$_2$ | H | 0 | NHCO$_2$-i-Pr | |
| C-841 | Het-13 | NHCH$_2$ | H | 0 | NHCO$_2$-n-Bu | |
| C-842 | Het-13 | NHCH$_2$ | H | 0 | NHCO$_2$-i-Bu | |
| C-843 | Het-13 | NHCH$_2$ | H | 0 | NHSO$_2$Ph | |
| C-844 | Het-13 | NHCH$_2$ | H | 0 | NHSO$_2$Ph(p-Cl) | |
| C-845 | Het-13 | NHCH$_2$ | H | 0 | NHSO$_2$Ph(p-F) | |
| C-846 | Het-13 | NHCH$_2$ | H | 0 | NHSO$_2$(2,4,6-trimethylphenyl) | |
| C-847 | Het-13 | NHCH$_2$ | H | 0 | NHSO$_2$(2,4,6-trichlorophenyl) | |
| C-848 | Het-13 | NHCH$_2$ | H | 0 | NHSO$_2$(2,6-dichlorophenyl) | |
| C-849 | Het-13 | NHCH$_2$ | H | 0 | NHSO2[4-(2,6-dimethylphenyl)phenyl | |
| C-850 | Het-13 | NHCH$_2$ | H | 0 | NHSO$_2$C$_6$H$_4$(4-Ph) | |
| C-851 | Het-13 | NHCH$_2$ | H | 0 | NHSO$_2$[4-(3,5-dimethyl)isoxazolyl] | |
| C-852 | Het-13 | NHCH$_2$ | H | 0 | NHSO$_2$(1-naphthyl) | |
| C-853 | Het-13 | NHCH$_2$CH$_2$ | H | 0 | NHCO$_2$-n-Pr | |
| C-854 | Het-13 | NHCH$_2$CH$_2$ | H | 0 | NHCO$_2$-i-Pr | |
| C-855 | Het-13 | NHCH$_2$CH$_2$ | H | 0 | NHCO$_2$-n-Bu | |
| C-856 | Het-13 | NHCH$_2$CH$_2$ | H | 0 | NHCO$_2$-i-Bu | |
| C-857 | Het-13 | NHCH$_2$CH$_2$ | H | 0 | NHSO$_2$Ph | |
| C-858 | Het-13 | NHCH$_2$CH$_2$ | H | 0 | NHSO$_2$Ph(p-Cl) | |
| C-859 | Het-13 | NHCH$_2$CH$_2$ | H | 0 | NHSO$_2$Ph(p-F) | |
| C-860 | Het-13 | NHCH$_2$CH$_2$ | H | 0 | NHSO$_2$(2,4,6-trimethylphenyl) | |
| C-861 | Het-13 | NHCH$_2$CH$_2$ | H | 0 | NHSO$_2$(2,4,6-trichlorophenyl) | |
| C-862 | Het-13 | NHCH$_2$CH$_2$ | H | 0 | NHSO$_2$(2,6-dichlorophenyl) | |
| C-863 | Het-13 | NHCH$_2$CH$_2$ | H | 0 | NHSO2[4-(2,6-dimethylphenyl)phenyl | |
| C-864 | Het-13 | NHCH$_2$CH$_2$ | H | 0 | NHSO$_2$C$_6$H$_4$(4-Ph) | |
| C-865 | Het-13 | NHCH$_2$CH$_2$ | H | 0 | NHSO$_2$[4-(3,5-dimethyl)isoxazolyl] | |
| C-866 | Het-13 | NHCH$_2$CH$_2$ | H | 0 | NHSO$_2$(1-naphthyl) | |
| C-867 | Het-14 | NHCH$_2$ | H | 0 | NHCO$_2$-n-Pr | |
| C-868 | Het-14 | NHCH$_2$ | H | 0 | NHCO$_2$-i-Pr | |
| C-869 | Het-14 | NHCH$_2$ | H | 0 | NHCO$_2$-n-Bu | |
| C-870 | Het-14 | NHCH$_2$ | H | 0 | NHCO$_2$-i-Bu | |
| C-871 | Het-14 | NHCH$_2$ | H | 0 | NHSO$_2$Ph | |
| C-872 | Het-14 | NHCH$_2$ | H | 0 | NHSO$_2$Ph(p-Cl) | |
| C-873 | Het-14 | NHCH$_2$ | H | 0 | NHSO$_2$Ph(p-F) | |
| C-874 | Het-14 | NHCH$_2$ | H | 0 | NHSO$_2$(2,4,6-trimethylphenyl) | |
| C-875 | Het-14 | NHCH$_2$ | H | 0 | NHSO$_2$(2,4,6-trichlorophenyl) | |
| C-876 | Het-14 | NHCH$_2$ | H | 0 | NHSO$_2$(2,6-dichlorophenyl) | |
| C-877 | Het-14 | NHCH$_2$ | H | 0 | NHSO2[4-(2,6-dimethylphenyl)phenyl | |
| C-878 | Het-14 | NHCH$_2$ | H | 0 | NHSO$_2$C$_6$H$_4$(4-Ph) | |
| C-879 | Het-14 | NHCH$_2$ | H | 0 | NHSO$_2$[4-(3,5-dimethyl)isoxazolyl] | |
| C-880 | Het-14 | NHCH$_2$ | H | 0 | NHSO$_2$(1-naphthyl) | |
| C-881 | Het-14 | NHCH$_2$CH$_2$ | H | 0 | NHCO$_2$-n-Pr | |
| C-882 | Het-14 | NHCH$_2$CH$_2$ | H | 0 | NHCO$_2$-i-Pr | |
| C-883 | Het-14 | NHCH$_2$CH$_2$ | H | 0 | NHCO$_2$-n-Bu | |
| C-884 | Het-14 | NHCH$_2$CH$_2$ | H | 0 | NHCO$_2$-i-Bu | |
| C-885 | Het-14 | NHCH$_2$CH$_2$ | H | 0 | NHSO$_2$Ph | |
| C-886 | Het-14 | NHCH$_2$CH$_2$ | H | 0 | NHSO$_2$Ph(p-Cl) | |
| C-887 | Het-14 | NHCH$_2$CH$_2$ | H | 0 | NHSO$_2$Ph(p-F) | |
| C-888 | Het-14 | NHCH$_2$CH$_2$ | H | 0 | NHSO$_2$(2,4,6-trimethylphenyl) | |
| C-889 | Het-14 | NHCH$_2$CH$_2$ | H | 0 | NHSO$_2$(2,4,6-trichlorophenyl) | |
| C-890 | Het-14 | NHCH$_2$CH$_2$ | H | 0 | NHSO$_2$(2,6-dichlorophenyl) | |
| C-891 | Het-14 | NHCH$_2$CH$_2$ | H | 0 | NHSO2[4-(2,6-dimethylphenyl)phenyl | |
| C-892 | Het-14 | NHCH$_2$CH$_2$ | H | 0 | NHSO$_2$C$_6$H$_4$(4-Ph) | |
| C-893 | Het-14 | NHCH$_2$CH$_2$ | H | 0 | NHSO$_2$[4-(3,5-dimethyl)isoxazolyl] | |
| C-894 | Het-14 | NHCH$_2$CH$_2$ | H | 0 | NHSO$_2$(1-naphthyl) | |
| C-895 | Het-15 | NHCH$_2$ | H | 0 | NHCO$_2$-n-Pr | |
| C-896 | Het-15 | NHCH$_2$ | H | 0 | NHCO$_2$-i-Pr | |
| C-897 | Het-15 | NHCH$_2$ | H | 0 | NHCO$_2$-n-Bu | |
| C-898 | Het-15 | NHCH$_2$ | H | 0 | NHCO$_2$-i-Bu | |
| C-899 | Het-15 | NHCH$_2$ | H | 0 | NHSO$_2$Ph | |
| C-900 | Het-15 | NHCH$_2$ | H | 0 | NHSO$_2$Ph(p-Cl) | |
| C-901 | Het-15 | NHCH$_2$ | H | 0 | NHSO$_2$Ph(p-F) | |

TABLE 3-continued

| Ex. No. | R¹ | U | R⁸ | z | R¹⁵ | MS |
|---|---|---|---|---|---|---|
| C-902 | Het-15 | NHCH₂ | H | 0 | NHSO₂(2,4,6-trimethylphenyl) | |
| C-903 | Het-15 | NHCH₂ | H | 0 | NHSO₂(2,4,6-trichlorophenyl) | |
| C-904 | Het-15 | NHCH₂ | H | 0 | NHSO₂(2,6-dichlorophenyl) | |
| C-905 | Het-15 | NHCH₂ | H | 0 | NHSO2[4-(2,6-dimethylphenyl)phenyl | |
| C-906 | Het-15 | NHCH₂ | H | 0 | NHSO₂C₆H₄(4-Ph) | |
| C-907 | Het-15 | NHCH₂ | H | 0 | NHSO₂[4-(3,5-dimethyl)isoxazolyl] | |
| C-908 | Het-15 | NHCH₂ | H | 0 | NHSO₂(1-naphthyl) | |
| C-909 | Het-15 | NHCH₂CH₂ | H | 0 | NHCO₂-n-Pr | |
| C-910 | Het-15 | NHCH₂CH₂ | H | 0 | NHCO₂-i-Pr | |
| C-911 | Het-15 | NHCH₂CH₂ | H | 0 | NHCO₂-n-Bu | |
| C-912 | Het-15 | NHCH₂CH₂ | H | 0 | NHCO₂-i-Bu | |
| C-913 | Het-15 | NHCH₂CH₂ | H | 0 | NHSO₂Ph | |
| C-914 | Het-15 | NHCH₂CH₂ | H | 0 | NHSO₂Ph(p-Cl) | |
| C-915 | Het-15 | NHCH₂CH₂ | H | 0 | NHSO₂Ph(p-F) | |
| C-916 | Het-15 | NHCH₂CH₂ | H | 0 | NHSO₂(2,4,6-trimethylphenyl) | |
| C-917 | Het-15 | NHCH₂CH₂ | H | 0 | NHSO₂(2,4,6-trichlorophenyl) | |
| C-918 | Het-15 | NHCH₂CH₂ | H | 0 | NHSO₂(2,6-dichlorophenyl) | |
| C-919 | Het-15 | NHCH₂CH₂ | H | 0 | NHSO2[4-(2,6-dimethylphenyl)phenyl | |
| C-920 | Het-15 | NHCH₂CH₂ | H | 0 | NHSO₂C₆H₄(4-Ph) | |
| C-921 | Het-15 | NHCH₂CH₂ | H | 0 | NHSO₂[4-(3,5-dimethyl)isoxazolyl] | |
| C-922 | Het-15 | NHCH₂CH₂ | H | 0 | NHSO₂(1-naphthyl) | |
| C-923 | Het-8 | CH₂CH₂ | H | 0 | NHCO₂-n-Pr | |
| C-924 | Het-8 | CH₂CH₂ | H | 0 | NHCO₂-i-Pr | |
| C-925 | Het-8 | CH₂CH₂ | H | 0 | NHCO₂-n-Bu | |
| C-926 | Het-8 | CH₂CH₂ | H | 0 | NHCO₂-i-Bu | |
| C-927 | Het-8 | CH₂CH₂ | H | 0 | NHSO₂Ph | |
| C-928 | Het-8 | CH₂CH₂ | H | 0 | NHSO₂Ph(p-Cl) | |
| C-929 | Het-8 | CH₂CH₂ | H | 0 | NHSO₂Ph(p-F) | |
| C-930 | Het-8 | CH₂CH₂ | H | 0 | NHSO₂(2,4,6-trimethylphenyl) | |
| C-931 | Het-8 | CH₂CH₂ | H | 0 | NHSO₂(2,4,6-trichlorophenyl) | |
| C-932 | Het-8 | CH₂CH₂ | H | 0 | NHSO₂(2,6-dichlorophenyl) | |
| C-933 | Het-8 | CH₂CH₂ | H | 0 | NHSO2[4-(2,6-dimethylphenyl)phenyl | |
| C-934 | Het-8 | CH₂CH₂ | H | 0 | NHSO₂C₆H₄(4-Ph) | |
| C-935 | Het-8 | CH₂CH₂ | H | 0 | NHSO₂[4-(3,5-dimethyl(isoxazolyl] | |
| C-936 | Het-8 | CH₂CH₂ | H | 0 | NHSO₂(1-naphthyl) | |
| C-937 | Het-8 | CH₂CH₂CH₂ | H | 0 | NHCO₂-n-Pr | |
| C-938 | Het-8 | CH₂CH₂CH₂ | H | 0 | NHCO₂-i-Pr | |
| C-939 | Het-8 | CH₂CH₂CH₂ | H | 0 | NHCO₂-n-Bu | |
| C-940 | Het-8 | CH₂CH₂CH₂ | H | 0 | NHCO₂-i-Bu | |
| C-941 | Het-8 | CH₂CH₂CH₂ | H | 0 | NHSO₂Ph | |
| C-942 | Het-8 | CH₂CH₂CH₂ | H | 0 | NHSO₂Ph(p-Cl) | |
| C-943 | Het-8 | CH₂CH₂CH₂ | H | 0 | NHSO₂Ph(p-F) | |
| C-944 | Het-8 | CH₂CH₂CH₂ | H | 0 | NHSO₂(2,4,6-trimethylphenyl) | |
| C-945 | Het-8 | CH₂CH₂CH₂ | H | 0 | NHSO₂(2,4,6-trichlorophenyl) | |
| C-946 | Het-8 | CH₂CH₂CH₂ | H | 0 | NHSO₂(2,6-dichlorophenyl) | |
| C-947 | Het-8 | CH₂CH₂CH₂ | H | 0 | NHSO2[4-(2,6-dimethylphenyl)phenyl | |
| C-948 | Het-8 | CH₂CH₂CH₂ | H | 0 | NHSO₂C₆H₄(4-Ph) | |
| C-949 | Het-8 | CH₂CH₂CH₂ | H | 0 | NHSO₂[4-(3,5-dimethyl)isoxazolyl] | |
| C-950 | Het-8 | CH₂CH₂CH₂ | H | 0 | NHSO₂(1-naphthyl) | |
| C-951 | Het-16 | CH₂CH₂ | H | 0 | NHCO₂-n-Pr | |
| C-952 | Het-16 | CH₂CH₂ | H | 0 | NHCO₂-i-Pr | |
| C-953 | Het-16 | CH₂CH₂ | H | 0 | NHCO₂-n-Bu | |
| C-954 | Het-16 | CH₂CH₂ | H | 0 | NHCO₂-i-Bu | |
| C-955 | Het-16 | CH₂CH₂ | H | 0 | NHSO₂Ph | |
| C-956 | Het-16 | CH₂CH₂ | H | 0 | NHSO₂Ph(p-Cl) | |
| C-957 | Het-16 | CH₂CH₂ | H | 0 | NHSO₂Ph(p-F) | |
| C-958 | Het-16 | CH₂CH₂ | H | 0 | NHSO₂(2,4,6-trimethylphenyl) | |
| C-959 | Het-16 | CH₂CH₂ | H | 0 | NHSO₂(2,4,6-trichlorophenyl) | |
| C-960 | Het-16 | CH₂CH₂ | H | 0 | NHSO₂(2,6-dichlorophenyl) | |
| C-961 | Het-16 | CH₂CH₂ | H | 0 | NHSO2[4-(2,6-dimethylphenyl)phenyl | |
| C-962 | Het-16 | CH₂CH₂ | H | 0 | NHSO₂C₆H₄(4-Ph) | |
| C-963 | Het-16 | CH₂CH₂ | H | 0 | NHSO₂[4-(3,5-dimethyl)isoxazolyl] | |
| C-964 | Het-16 | CH₂CH₂ | H | 0 | NHSO₂(1-naphthyl) | |
| C-965 | Het-16 | CH₂CH₂CH₂ | H | 0 | NHCO₂-n-Pr | |
| C-966 | Het-16 | CH₂CH₂CH₂ | H | 0 | NHCO₂-i-Pr | |
| C-967 | Het-16 | CH₂CH₂CH₂ | H | 0 | NHCO₂-n-Bu | |
| C-968 | Het-16 | CH₂CH₂CH₂ | H | 0 | NHCO₂-i-Bu | |
| C-969 | Het-16 | CH₂CH₂CH₂ | H | 0 | NHSO₂Ph | |
| C-970 | Het-16 | CH₂CH₂CH₂ | H | 0 | NHSO₂Ph(p-Cl) | |
| C-971 | Het-16 | CH₂CH₂CH₂ | H | 0 | NHSO₂Ph(p-F) | |
| C-972 | Het-16 | CH₂CH₂CH₂ | H | 0 | NHSO₂(2,4,6-trimethylphenyl) | |
| C-973 | Het-16 | CH₂CH₂CH₂ | H | 0 | NHSO₂(2,4,6-trichlorophenyl) | |
| C-974 | Het-16 | CH₂CH₂CH₂ | H | 0 | NHSO₂(2,6-dichlorophenyl) | |
| C-975 | Het-16 | CH₂CH₂CH₂ | H | 0 | NHSO2[4-(2,6-dimethylphenyl)phenyl | |
| C-976 | Het-16 | CH₂CH₂CH₂ | H | 0 | NHSO₂C₆H₄(4-Ph) | |
| C-977 | Het-16 | CH₂CH₂CH₂ | H | 0 | NHSO₂[4-(3,5-dimethyl)isoxazolyl] | |
| C-978 | Het-16 | CH₂CH₂CH₂ | H | 0 | NHSO₂(1-naphthyl) | |
| C-979 | Het-17 | CH₂CH₂ | H | 0 | NHSO₂-n-Pr | |
| C-980 | Het-17 | CH₂CH₂ | H | 0 | NHCO₂-i-Pr | |
| C-981 | Het-17 | CH₂CH₂ | H | 0 | NHCO₂-n-Bu | |
| C-982 | Het-17 | CH₂CH₂ | H | 0 | NHCO₂-i-Bu | |
| C-983 | Het-17 | CH₂CH₂ | H | 0 | NHSO₂Ph | |
| C-984 | Het-17 | CH₂CH₂ | H | 0 | NHSO₂Ph(p-Cl) | |
| C-985 | Het-17 | CH₂CH₂ | H | 0 | NHSO₂Ph(p-F) | |
| C-986 | Het-17 | CH₂CH₂ | H | 0 | NHSO₂(2,4,6-trimethylphenyl) | |
| C-987 | Het-17 | CH₂CH₂ | H | 0 | NHSO₂(2,4,6-trichlorophenyl) | |
| C-988 | Het-17 | CH₂CH₂ | H | 0 | NHSO₂(2,6-dichlorophenyl) | |
| C-989 | Het-17 | CH₂CH₂ | H | 0 | NHSO2[4-(2,6-dimethylphenyl)phenyl | |
| C-990 | Het-17 | CH₂CH₂ | H | 0 | NHSO₂C₆H₄(4-Ph) | |
| C-991 | Het-17 | CH₂CH₂ | H | 0 | NHSO₂[4-(3,5-dimethyl)isoxazolyl] | |
| C-992 | Het-17 | CH₂CH₂ | H | 0 | NHSO₂(1-naphthyl) | |
| C-993 | Het-17 | CH₂CH₂CH₂ | H | 0 | NHCO₂-n-Pr | |
| C-994 | Het-17 | CH₂CH₂CH₂ | H | 0 | NHCO₂-i-Pr | |
| C-995 | Het-17 | CH₂CH₂CH₂ | H | 0 | NHCO₂-n-Bu | |
| C-996 | Het-17 | CH₂CH₂CH₂ | H | 0 | NHCO₂-i-Bu | |
| C-997 | Het-17 | CH₂CH₂CH₂ | H | 0 | NHSO₂Ph | |
| C-998 | Het-17 | CH₂CH₂CH₂ | H | 0 | NHSO₂Ph(p-Cl) | |
| C-999 | Het-17 | CH₂CH₂CH₂ | H | 0 | NHSO₂Ph(p-F) | |

TABLE 3-continued

![Structure: phenyl ring with positions 2,3,4,5,6; substituent $R^1-U$ at position 3; $R^8$ at position 6; side chain at position 1 as $(CH_2)_z$ linked to $-C(=O)-NH-CH(R^{15})-CO_2H$]

| Ex. No. | $R^1$ | U | $R^8$ | z | $R^{15}$ | MS |
|---|---|---|---|---|---|---|
| C-1000 | Het-17 | $CH_2CH_2CH_2$ | H | 0 | $NHSO_2$(2,4,6-trimethylphenyl) | |
| C-1001 | Het-17 | $CH_2CH_2CH_2$ | H | 0 | $NHSO_2$(2,4,6-trichlorophenyl) | |
| C-1002 | Het-17 | $CH_2CH_2CH_2$ | H | 0 | $NHSO_2$(2,6-dochlorophenyl) | |
| C-1003 | Het-17 | $CH_2CH_2CH_2$ | H | 0 | NHSO2[4-(2,6-dimethylphenyl)phenyl | |
| C-1004 | Het-17 | $CH_2CH_2CH_2$ | H | 0 | $NHSO_2C_6H_4$(4-Ph) | |
| C-1005 | Het-17 | $CH_2CH_2CH_2$ | H | 0 | $NHSO_2$[4-(3,5-dimethyl)isoxazolyl] | |
| C-1006 | Het-17 | $CH_2CH_2CH_2$ | H | 0 | $NHSO_2$(1-naphthyl) | |
| C-1007 | Het-18 | $CH_2CH_2$ | H | 0 | $NHCO_2$-n-Pr | |
| C-1008 | Het-18 | $CH_2CH_2$ | H | 0 | $NHCO_2$-i-Pr | |
| C-1009 | Het-18 | $CH_2CH_2$ | H | 0 | $NHCO_2$-n-Bu | |
| C-1010 | Het-18 | $CH_2CH_2$ | H | 0 | $NHCO_2$-i-Bu | |
| C-1011 | Het-18 | $CH_2CH_2$ | H | 0 | $NHSO_2$Ph | |
| C-1012 | Het-18 | $CH_2CH_2$ | H | 0 | $NHSO_2$Ph(p-Cl) | |
| C-1013 | Het-18 | $CH_2CH_2$ | H | 0 | $NHSO_2$Ph(p-F) | |
| C-1014 | Het-18 | $CH_2CH_2$ | H | 0 | $NHSO_2$(2,4,6-trimethylphenyl) | |
| C-1015 | Het-18 | $CH_2CH_2$ | H | 0 | $NHSO_2$(2,4,6-trichlorophenyl) | |
| C-1016 | Het-18 | $CH_2CH_2$ | H | 0 | $NHSO_2$(2,6-dichlorophenyl) | |
| C-1017 | Het-18 | $CH_2CH_2$ | H | 0 | NHSO2[4-(2,6-dimethylphenyl)phenyl | |
| C-1018 | Het-18 | $CH_2CH_2$ | H | 0 | $NHSO_2C_6H_4$(4-Ph) | |
| C-1019 | Het-18 | $CH_2CH_2$ | H | 0 | $NHSO_2$[4-(3,5-dimethyl)isoxazolyl] | |
| C-1020 | Het-18 | $CH_2CH_2$ | H | 0 | $NHSO_2$(1-naphthyl) | |
| C-1021 | Het-18 | $CH_2CH_2CH_2$ | H | 0 | $NHCO_2$-n-Pr | |
| C-1022 | Het-18 | $CH_2CH_2CH_2$ | H | 0 | $NHCO_2$-i-Pr | |
| C-1023 | Het-18 | $CH_2CH_2CH_2$ | H | 0 | $NHCO_2$-n-Bu | |
| C-1024 | Het-18 | $CH_2CH_2CH_2$ | H | 0 | $NHCO_2$-i-Bu | |
| C-1025 | Het-18 | $CH_2CH_2CH_2$ | H | 0 | $NHSO_2$Ph | |
| C-1026 | Het-18 | $CH_2CH_2CH_2$ | H | 0 | $NHSO_2$Ph(p-Cl) | |
| C-1027 | Het-18 | $CH_2CH_2CH_2$ | H | 0 | $NHSO_2$Ph(p-F) | |
| C-1028 | Het-18 | $CH_2CH_2CH_2$ | H | 0 | $NHSO_2$(2,4,6-trimethylphenyl) | |
| C-1029 | Het-18 | $CH_2CH_2CH_2$ | H | 0 | $NHSO_2$(2,4,6-trichlorophenyl) | |
| C-1030 | Het-18 | $CH_2CH_2CH_2$ | H | 0 | $NHSO_2$(2,6-dichlorophenyl) | |
| C-1031 | Het-18 | $CH_2CH_2CH_2$ | H | 0 | NHSO2[4-(2,6-dimethylphenyl)phenyl | |
| C-1032 | Het-18 | $CH_2CH_2CH_2$ | H | 0 | $NHSO_2C_6H_4$(4-Ph) | |
| C-1033 | Het-18 | $CH_2CH_2CH_2$ | H | 0 | $NHSO_2$[4-(3,5-dimethyl)isoxazolyl] | |
| C-1034 | Het-18 | $CH_2CH_2CH_2$ | H | 0 | $NHSO_2$(1-naphthyl) | |
| C-1035 | Het-13 | $CH_2CH_2$ | H | 0 | $NHCO_2$-n-Pr | |
| C-1036 | Het-13 | $CH_2CH_2$ | H | 0 | $NHCO_2$-i-Pr | |
| C-1037 | Het-13 | $CH_2CH_2$ | H | 0 | $NHCO_2$-n-Bu | |
| C-1038 | Het-13 | $CH_2CH_2$ | H | 0 | $NHCO_2$-i-Bu | |
| C-1039 | Het-13 | $CH_2CH_2$ | H | 0 | $NHSO_2$Ph | |
| C-1040 | Het-13 | $CH_2CH_2$ | H | 0 | $NHSO_2$Ph(p-Cl) | |
| C-1041 | Het-13 | $CH_2CH_2$ | H | 0 | $NHSO_2$Ph(p-F) | |
| C-1042 | Het-13 | $CH_2CH_2$ | H | 0 | $NHSO_2$(2,4,6-trimethylphenyl) | |
| C-1043 | Het-13 | $CH_2CH_2$ | H | 0 | $NHSO_2$(2,4,6-trichlorophenyl) | |
| C-1044 | Het-13 | $CH_2CH_2$ | H | 0 | $NHSO_2$(2,6-dichlorophenyl) | |
| C-1045 | Het-13 | $CH_2CH_2$ | H | 0 | NHSO2[4-(2,6-dimethylphenyl)phenyl | |
| C-1046 | Het-13 | $CH_2CH_2$ | H | 0 | $NHSO_2C_6H_4$(4-Ph) | |
| C-1047 | Het-13 | $CH_2CH_2$ | H | 0 | $NHSO_2$[4-(3,5-dimethyl)isoxazolyl] | |
| C-1048 | Het-13 | $CH_2CH_2$ | H | 0 | $NHSO_2$(1-naphthyl) | |
| C-1049 | Het-13 | $CH_2CH_2CH_2$ | H | 0 | $NHCO_2$-n-Pr | |
| C-1050 | Het-13 | $CH_2CH_2CH_2$ | H | 0 | $NHCO_2$-i-Pr | |
| C-1051 | Het-13 | $CH_2CH_2CH_2$ | H | 0 | $NHCO_2$-n-Bu | |
| C-1052 | Het-13 | $CH_2CH_2CH_2$ | H | 0 | $NHCO_2$-i-Bu | |
| C-1053 | Het-13 | $CH_2CH_2CH_2$ | H | 0 | $NHSO_2$Ph | |
| C-1054 | Het-13 | $CH_2CH_2CH_2$ | H | 0 | $NHSO_2$Ph(p-Cl) | |
| C-1055 | Het-13 | $CH_2CH_2CH_2$ | H | 0 | $NHSO_2$Ph(p-F) | |
| C-1056 | Het-13 | $CH_2CH_2CH_2$ | H | 0 | $NHSO_2$(2,4,6-trimethylphenyl) | |
| C-1057 | Het-13 | $CH_2CH_2CH_2$ | H | 0 | $NHSO_2$(2,4,6-trichlorophenyl) | |
| C-1058 | Het-13 | $CH_2CH_2CH_2$ | H | 0 | $NHSO_2$(2,6-dichlorophenyl) | |
| C-1059 | Het-13 | $CH_2CH_2CH_2$ | H | 0 | NHSO2[4-(2,6-dimethylphenyl)phenyl | |
| C-1060 | Het-13 | $CH_2CH_2CH_2$ | H | 0 | $NHSO_2C_6H_4$(4-Ph) | |
| C-1061 | Het-13 | $CH_2CH_2CH_2$ | H | 0 | $NHSO_2$[4-(3,5-dimethyl)isoxazolyl] | |
| C-1062 | Het-13 | $CH_2CH_2CH_2$ | H | 0 | $NHSO_2$(1-naphthyl) | |
| C-1063 | Het-19 | $CH_2CH_2$ | H | 0 | $NHCO_2$-n-Pr | |
| C-1064 | Het-19 | $CH_2CH_2$ | H | 0 | $NHCO_2$-i-Pr | |
| C-1065 | Het-19 | $CH_2CH_2$ | H | 0 | $NHCO_2$-n-Bu | |
| C-1066 | Het-19 | $CH_2CH_2$ | H | 0 | $NHCO_2$-i-Bu | |
| C-1067 | Het-19 | $CH_2CH_2$ | H | 0 | $NHSO_2$Ph | |
| C-1068 | Het-19 | $CH_2CH_2$ | H | 0 | $NHSO_2$Ph(p-Cl) | |
| C-1069 | Het-19 | $CH_2CH_2$ | H | 0 | $NHSO_2$Ph(p-F) | |
| C-1070 | Het-19 | $CH_2CH_2$ | H | 0 | $NHSO_2$(2,4,6-trimethylphenyl) | |
| C-1071 | Het-19 | $CH_2CH_2$ | H | 0 | $NHSO_2$(2,4,6-trichloophenyl) | |
| C-1072 | Het-19 | $CH_2CH_2$ | H | 0 | $NHSO_2$(2,6-dichlorophenyl) | |
| C-1073 | Het-19 | $CH_2CH_2$ | H | 0 | NHSO2[4-(2,6-dimethylphenyl)phenyl | |
| C-1074 | Het-19 | $CH_2CH_2$ | H | 0 | $NHSO_2C_6H_4$(4-Ph) | |
| C-1075 | Het-19 | $CH_2CH_2$ | H | 0 | $NHSO_2$[4-(3,5-dimethyl)isoxazolyl] | |
| C-1076 | Het-19 | $CH_2CH_2$ | H | 0 | $NHSO_2$(1-naphthyl) | |
| C-1077 | Het-19 | $CH_2CH_2CH_2$ | H | 0 | $NHCO_2$-n-Pr | |
| C-1078 | Het-19 | $CH_2CH_2CH_2$ | H | 0 | $NHCO_2$-i-Pr | |
| C-1079 | Het-19 | $CH_2CH_2CH_2$ | H | 0 | $NHCO_2$-n-Bu | |
| C-1080 | Het-19 | $CH_2CH_2CH_2$ | H | 0 | $NHCO_2$-i-Bu | |
| C-1081 | Het-19 | $CH_2CH_2CH_2$ | H | 0 | $NHSO_2$Ph | |
| C-1082 | Het-19 | $CH_2CH_2CH_2$ | H | 0 | $NHSO_2$Ph(p-Cl) | |
| C-1083 | Het-19 | $CH_2CH_2CH_2$ | H | 0 | $NHSO_2$Ph(p-F) | |
| C-1084 | Het-19 | $CH_2CH_2CH_2$ | H | 0 | $NHSO_2$(2,4,6-trimethylphenyl) | |
| C-1085 | Het-19 | $CH_2CH_2CH_2$ | H | 0 | $NHSO_2$(2,4,6-trichlorophenyl) | |
| C-1086 | Het-19 | $CH_2CH_2CH_2$ | H | 0 | $NHSO_2$(2,6-dichlorophenyl) | |
| C-1087 | Het-19 | $CH_2CH_2CH_2$ | H | 0 | NHSO2[4-(2,6-dimethylphenyl)phenyl | |
| C-1088 | Het-19 | $CH_2CH_2CH_2$ | H | 0 | $NHSO_2C_6H_4$(4-Ph) | |
| C-1089 | Het-19 | $CH_2CH_2CH_2$ | H | 0 | $NHSO_2$[4-(3,5-dimethyl)isoxazolyl] | |
| C-1090 | Het-19 | $CH_2CH_2CH_2$ | H | 0 | $NHSO_2$(1-naphthyl) | |
| C-1091 | Het-20 | $CH_2CH_2$ | H | 0 | $NHCO_2$-n-Pr | |
| C-1092 | Het-20 | $CH_2CH_2$ | H | 0 | $NHCO_2$-i-Pr | |
| C-1093 | Het-20 | $CH_2CH_2$ | H | 0 | $NHCO_2$-n-Bu | |
| C-1094 | Het-20 | $CH_2CH_2$ | H | 0 | $NHCO_2$-i-Bu | |
| C-1095 | Het-20 | $CH_2CH_2$ | H | 0 | $NHSO_2$Ph | |
| C-1096 | Het-20 | $CH_2CH_2$ | H | 0 | $NHSO_2$Ph(p-Cl) | |
| C-1097 | Het-20 | $CH_2CH_2$ | H | 0 | $NHSO_2$Ph(p-F) | |

TABLE 3-continued

| Ex. No. | R¹ | U | R⁸ | z | R¹⁵ | MS |
|---|---|---|---|---|---|---|
| C-1098 | Het-20 | $CH_2CH_2$ | H | 0 | $NHSO_2$(2,4,6-trimethylphenyl) | |
| C-1099 | Het-20 | $CH_2CH_2$ | H | 0 | $NHSO_2$(2,4,6-trichlorophenyl) | |
| C-1100 | Het-20 | $CH_2CH_2$ | H | 0 | $NHSO_2$(2,6-dichlorophenyl) | |
| C-1101 | Het-20 | $CH_2CH_2$ | H | 0 | $NHSO2$[4-(2,6-dimethylphenyl)phenyl | |
| C-1102 | Het-20 | $CH_2CH_2$ | H | 0 | $NHSO_2C_6H_4$(4-Ph) | |
| C-1103 | Het-20 | $CH_2CH_2$ | H | 0 | $NHSO_2$[4-(3,5-dimethyl)isoxazolyl] | |
| C-1104 | Het-20 | $CH_2CH_2$ | H | 0 | $NHSO_2$(1-naphthyl) | |
| C-1105 | Het-20 | $CH_2CH_2CH_2$ | H | 0 | $NHCO_2$-n-Pr | |
| C-1106 | Het-20 | $CH_2CH_2CH_2$ | H | 0 | $NHCO_2$-i-Pr | |
| C-1107 | Het-20 | $CH_2CH_2CH_2$ | H | 0 | $NHCO_2$-n-Bu | |
| C-1108 | Het-20 | $CH_2CH_2CH_2$ | H | 0 | $NHCO_2$-i-Bu | |
| C-1109 | Het-20 | $CH_2CH_2CH_2$ | H | 0 | $NHSO_2$Ph | |
| C-1110 | Het-20 | $CH_2CH_2CH_2$ | H | 0 | $NHSO_2$Ph(p-Cl) | |
| C-1111 | Het-20 | $CH_2CH_2CH_2$ | H | 0 | $NHSO_2$Ph(p-F) | |
| C-1112 | Het-20 | $CH_2CH_2CH_2$ | H | 0 | $NHSO_2$(2,4,6-trimethylphenyl) | |
| C-1113 | Het-20 | $CH_2CH_2CH_2$ | H | 0 | $NHSO_2$(2,4,6-trichlorophenyl) | |
| C-1114 | Het-20 | $CH_2CH_2CH_2$ | H | 0 | $NHSO_2$(2,6-dichlorophenyl) | |
| C-1115 | Het-20 | $CH_2CH_2CH_2$ | H | 0 | $NHSO2$[4-(2,6-dimethylphenyl)phenyl | |
| C-1116 | Het-20 | $CH_2CH_2CH_2$ | H | 0 | $NHSO_2C_6H_4$(4-Ph) | |
| C-1117 | Het-20 | $CH_2CH_2CH_2$ | H | 0 | $NHSO_2$[4-(3,5-dimethyl)isoxazolyl] | |
| C-1118 | Het-20 | $CH_2CH_2CH_2$ | H | 0 | $NHSO_2$(1-naphthyl) | |
| C-1119 | Het-1 | $CH_2CH_2$ | H | 1 | $NHCO_2$-n-Pr | |
| C-1120 | Het-1 | $CH_2CH_2$ | H | 1 | $NHCO_2$-i-Pr | |
| C-1121 | Het-1 | $CH_2CH_2$ | H | 1 | $NHCO_2$-n-Bu | |
| C-1122 | Het-1 | $CH_2CH_2$ | H | 1 | $NHCO_2$-i-Bu | |
| C-1123 | Het-1 | $CH_2CH_2$ | H | 1 | $NHSO_2$Ph | |
| C-1124 | Het-1 | $CH_2CH_2$ | H | 1 | $NHSO_2$Ph(p-Cl) | |
| C-1125 | Het-1 | $CH_2CH_2$ | H | 1 | $NHSO_2$Ph(p-F) | |
| C-1126 | Het-1 | $CH_2CH_2$ | H | 1 | $NHSO_2$(2,4,6-trimethylphenyl) | |
| C-1127 | Het-1 | $CH_2CH_2$ | H | 1 | $NHSO_2$(2,4,6-trichlorophenyl) | |
| C-1128 | Het-1 | $CH_2CH_2$ | H | 1 | $NHSO_2$(2,6-dichlorophenyl) | |
| C-1129 | Het-1 | $CH_2CH_2$ | H | 1 | $NHSO2$[4-(2,6-dimethylphenyl)phenyl | |
| C-1130 | Het-1 | $CH_2CH_2$ | H | 1 | $NHSO_2C_6H_4$(4-Ph) | |
| C-1131 | Het-1 | $CH_2CH_2$ | H | 1 | $NHSO_2$[4-(3,5-dimethyl)isoxazolyl] | |
| C-1132 | Het-1 | $CH_2CH_2$ | H | 1 | $NHSO_2$(1-naphthyl) | |
| C-1133 | Het-1 | $CH_2CH_2$ | 3-Me | 0 | $NHCO_2$-n-Pr | |
| C-1134 | Het-1 | $CH_2CH_2$ | 3-Me | 0 | $NHCO_2$-i-Pr | |
| C-1135 | Het-1 | $CH_2CH_2$ | 3-Me | 0 | $NHCO_2$-n-Bu | |
| C-1136 | Het-1 | $CH_2CH_2$ | 3-Me | 0 | $NHCO_2$-i-Bu | |
| C-1137 | Het-1 | $CH_2CH_2$ | 3-Me | 0 | $NHSO_2$Ph | |
| C-1138 | Het-1 | $CH_2CH_2$ | 3-Me | 0 | $NHSO_2$Ph(p-Cl) | |
| C-1139 | Het-1 | $CH_2CH_2$ | 3-Me | 0 | $NHSO_2$Ph(p-F) | |
| C-1140 | Het-1 | $CH_2CH_2$ | 3-Me | 0 | $NHSO_2$(2,4,6-trimethylphenyl) | |
| C-1141 | Het-1 | $CH_2CH_2$ | 3-Me | 0 | $NHSO_2$(2,4,6-trichlorophenyl) | |
| C-1142 | Het-1 | $CH_2CH_2$ | 3-Me | 0 | $NHSO_2$(2,6-dichlorophenyl) | |
| C-1143 | Het-1 | $CH_2CH_2$ | 3-Me | 0 | $NHSO2$[4-(2,6-dimethylphenyl)phenyl | |
| C-1144 | Het-1 | $CH_2CH_2$ | 3-Me | 0 | $NHSO_2C_6H_4$(4-Ph) | |
| C-1145 | Het-1 | $CH_2CH_2$ | 3-Me | 0 | $NHSO_2$[4-(3,5-dimethyl)isoxazolyl] | |
| C-1146 | Het-1 | $CH_2CH_2$ | 3-Me | 0 | $NHSO_2$(1-naphthyl) | |
| C-1147 | Het-1 | $CH_2CH_2$ | 2-Cl | 0 | $NHCO_2$-n-Pr | |
| C-1148 | Het-1 | $CH_2CH_2$ | 2-Cl | 0 | $NHCO_2$-i-Pr | |
| C-1149 | Het-1 | $CH_2CH_2$ | 2-Cl | 0 | $NHCO_2$-n-Bu | |
| C-1150 | Het-1 | $CH_2CH_2$ | 2-Cl | 0 | $NHCO_2$-i-Bu | |
| C-1151 | Het-1 | $CH_2CH_2$ | 2-Cl | 0 | $NHSO_2$Ph | |
| C-1152 | Het-1 | $CH_2CH_2$ | 2-Cl | 0 | $NHSO_2$Ph(p-Cl) | |
| C-1153 | Het-1 | $CH_2CH_2$ | 2-Cl | 0 | $NHSO_2$Ph(p-F) | |
| C-1154 | Het-1 | $CH_2CH_2$ | 2-Cl | 0 | $NHSO_2$(2,4,6-trimethylphenyl) | |
| C-1155 | Het-1 | $CH_2CH_2$ | 2-Cl | 0 | $NHSO_2$(2,4,6-trichlorophenyl) | |
| C-1156 | Het-1 | $CH_2CH_2$ | 2-Cl | 0 | $NHSO_2$(2,6-dichlorophenyl) | |
| C-1157 | Het-1 | $CH_2CH_2$ | 2-Cl | 0 | $NHSO2$[4-(2,6-dimethylphenyl)phenyl | |
| C-1158 | Het-1 | $CH_2CH_2$ | 2-Cl | 0 | $NHSO_2C_6H_4$(4-Ph) | |
| C-1159 | Het-1 | $CH_2CH_2$ | 2-Cl | 0 | $NHSO_2$[4-(3,5-dimethyl)isoxazolyl] | |
| C-1160 | Het-1 | $CH_2CH_2$ | 2-Cl | 0 | $NHSO_2$(1-naphthyl) | |
| C-1161 | Het-2 | $CH_2CH_2$ | H | 1 | $NHCO_2$-n-Pr | |
| C-1162 | Het-2 | $CH_2CH_2$ | H | 1 | $NHCO_2$-i-Pr | |
| C-1163 | Het-2 | $CH_2CH_2$ | H | 1 | $NHCO_2$-n-Bu | |
| C-1164 | Het-2 | $CH_2CH_2$ | H | 1 | $NHCO_2$-i-Bu | |
| C-1165 | Het-2 | $CH_2CH_2$ | H | 1 | $NHSO_2$Ph | |
| C-1166 | Het-2 | $CH_2CH_2$ | H | 1 | $NHSO_2$Ph(p-Cl) | |
| C-1167 | Het-2 | $CH_2CH_2$ | H | 1 | $NHSO_2$Ph(p-F) | |
| C-1168 | Het-2 | $CH_2CH_2$ | H | 1 | $NHSO_2$(2,4,6-trimethylphenyl) | |
| C-1169 | Het-2 | $CH_2CH_2$ | H | 1 | $NHSO_2$(2,4,6-trichlorophenyl) | |
| C-1170 | Het-2 | $CH_2CH_2$ | H | 1 | $NHSO_2$(2,6-dichlorophenyl) | |
| C-1171 | Het-2 | $CH_2CH_2$ | H | 1 | $NHSO2$[4-(2,6-dimethylphenyl)phenyl | |
| C-1172 | Het-2 | $CH_2CH_2$ | H | 1 | $NHSO_2C_6H_4$(4-Ph) | |
| C-1173 | Het-2 | $CH_2CH_2$ | H | 1 | $NHSO_2$[4-(3,5-dimethyl)isoxazolyl] | |
| C-1174 | Het-2 | $CH_2CH_2$ | H | 1 | $NHSO_2$(1-naphthyl) | |
| C-1175 | Het-2 | $CH_2CH_2$ | 3-Me | 0 | $NHCO_2$-n-Pr | |
| C-1176 | Het-2 | $CH_2CH_2$ | 3-Me | 0 | $NHCO_2$-i-Pr | |
| C-1177 | Het-2 | $CH_2CH_2$ | 3-Me | 0 | $NHCO_2$-n-Bu | |
| C-1178 | Het-2 | $CH_2CH_2$ | 3-Me | 0 | $NHCO_2$-i-Bu | |

TABLE 3-continued

| Ex. No. | R¹ | U | R⁸ | z | R¹⁵ | MS |
|---|---|---|---|---|---|---|
| C-1179 | Het-2 | $CH_2CH_2$ | 3-Me | 0 | $NHSO_2Ph$ | |
| C-1180 | Het-2 | $CH_2CH_2$ | 3-Me | 0 | $NHSO_2Ph(p-Cl)$ | |
| C-1181 | Het-2 | $CH_2CH_2$ | 3-Me | 0 | $NHSO_2Ph(p-F)$ | |
| C-1182 | Het-2 | $CH_2CH_2$ | 3-Me | 0 | $NHSO_2(2,4,6-trimethylphenyl)$ | |
| C-1183 | Het-2 | $CH_2CH_2$ | 3-Me | 0 | $NHSO_2(2,4,6-trichlorophenyl)$ | |
| C-1184 | Het-2 | $CH_2CH_2$ | 3-Me | 0 | $NHSO_2(2,6-dichlorophenyl)$ | |
| C-1185 | Het-2 | $CH_2CH_2$ | 3-Me | 0 | $NHSO2[4-(2,6-dimethylphenyl)phenyl$ | |
| C-1186 | Het-2 | $CH_2CH_2$ | 3-Me | 0 | $NHSO_2C_6H_4(4-Ph)$ | |
| C-1187 | Het-2 | $CH_2CH_2$ | 3-Me | 0 | $NHSO_2[4-(3,5-dimethyl)isoxazolyl]$ | |
| C-1188 | Het-2 | $CH_2CH_2$ | 3-Me | 0 | $NHSO_2(1-naphthyl)$ | |
| C-1189 | Het-2 | $CH_2CH_2$ | 2-Cl | 0 | $NHSO_2(-n-Pr)$ | |
| C-1190 | Het-2 | $CH_2CH_2$ | 2-Cl | 0 | $NHCO_2-i-Pr$ | |
| C-1191 | Het-2 | $CH_2CH_2$ | 2-Cl | 0 | $NHCO_2-n-Bu$ | |
| C-1192 | Het-2 | $CH_2CH_2$ | 2-Cl | 0 | $NHCO_2-i-Bu$ | |
| C-1193 | Het-2 | $CH_2CH_2$ | 2-Cl | 0 | $NHSO_2Ph$ | |
| C-1194 | Het-2 | $CH_2CH_2$ | 2-Cl | 0 | $NHSO_2Ph(p-Cl)$ | |
| C-1195 | Het-2 | $CH_2CH_2$ | 2-Cl | 0 | $NHSO_2Ph(p-F)$ | |
| C-1196 | Het-2 | $CH_2CH_2$ | 2-Cl | 0 | $NHSO_2(2,4,6-trimethylphenyl)$ | |
| C-1197 | Het-2 | $CH_2CH_2$ | 2-Cl | 0 | $NHSO_2(2,4,6-trichlorophenyl)$ | |
| C-1198 | Het-2 | $CH_2CH_2$ | 2-Cl | 0 | $NHSO_2(2,6-dichlorophenyl)$ | |
| C-1199 | Het-2 | $CH_2CH_2$ | 2-Cl | 0 | $NHSO2[4-(2,6-dichlorophenyl)$ | |
| C-1200 | Het-2 | $CH_2CH_2$ | 2-Cl | 0 | $NHSO_2C_6H_4(4-Ph)$ | |
| C-1201 | Het-2 | $CH_2CH_2$ | 2-Cl | 0 | $NHSO_2[4-(3,5-dimethyl)isoxazolyl]$ | |
| C-1202 | Het-2 | $CH_2CH_2$ | 2-Cl | 0 | $NHSO_2(1-naphthyl)$ | |
| C-1203 | Het-9 | $CH_2CH_2$ | H | 0 | $NHCO_2-n-Pr$ | |
| C-1204 | Het-9 | $CH_2CH_2$ | H | 0 | $NHCO_2-i-Pr$ | |
| C-1205 | Het-9 | $CH_2CH_2$ | H | 0 | $NHCO_2-n-Bu$ | |
| C-1206 | Het-9 | $CH_2CH_2$ | H | 0 | $NHCO_2-i-Bu$ | |
| C-1207 | Het-9 | $CH_2CH_2$ | H | 0 | $NHSO_2Ph$ | |
| C-1208 | Het-9 | $CH_2CH_2$ | H | 0 | $NHSO_2Ph(p-Cl)$ | |
| C-1209 | Het-9 | $CH_2CH_2$ | H | 0 | $NHSO_2Ph(p-F)$ | |
| C-1210 | Het-9 | $CH_2CH_2$ | H | 0 | $NHSO_2(2,4,6-trimethylphenyl)$ | |
| C-1211 | Het-9 | $CH_2CH_2$ | H | 0 | $NHSO_2(2,4,6-trichlorophenyl)$ | |
| C-1212 | Het-9 | $CH_2CH_2$ | H | 0 | $NHSO_2(2,6-dichlorophenyl)$ | |
| C-1213 | Het-9 | $CH_2CH_2$ | H | 0 | $NHSO2[4-(2,6-dimethylphenyl)phenyl$ | |
| C-1214 | Het-9 | $CH_2CH_2$ | H | 0 | $NHSO_2C_6H_4(4-Ph)$ | |
| C-1215 | Het-9 | $CH_2CH_2$ | H | 0 | $NHSO_2[4-(3,5-dimethyl)isoxazolyl]$ | |
| C-1216 | Het-9 | $CH_2CH_2$ | H | 0 | $NHSO_2(1-naphthyl)$ | |
| C-1217 | Het-9 | $CH_2CH_2CH_2$ | H | 0 | $NHCO_2-n-Pr$ | |
| C-1218 | Het-9 | $CH_2CH_2CH_2$ | H | 0 | $NHCO_2-i-Pr$ | |
| C-1219 | Het-9 | $CH_2CH_2CH_2$ | H | 0 | $NHCO_2-n-Bu$ | |
| C-1220 | Het-9 | $CH_2CH_2CH_2$ | H | 0 | $NHSO_2-i-Bu$ | |
| C-1221 | Het-9 | $CH_2CH_2CH_2$ | H | 0 | $NHSO_2Ph$ | |
| C-1222 | Het-9 | $CH_2CH_2CH_2$ | H | 0 | $NHSO_2Ph(p-Cl)$ | |
| C-1223 | Het-9 | $CH_2CH_2CH_2$ | H | 0 | $NHSO_2Ph(p-F)$ | |
| C-1224 | Het-9 | $CH_2CH_2CH_2$ | H | 0 | $NHSO_2(2,4,6-trimethylphenyl)$ | |
| C-1225 | Het-9 | $CH_2CH_2CH_2$ | H | 0 | $NHSO_2(2,4,6-trichlorophenyl)$ | |
| C-1226 | Het-9 | $CH_2CH_2CH_2$ | H | 0 | $NHSO_2(2,6-dichlorophenyl)$ | |
| C-1227 | Het-9 | $CH_2CH_2CH_2$ | H | 0 | $NHSO2[4-(2,6-dimethylphenyl)phenyl$ | |
| C-1228 | Het-9 | $CH_2CH_2CH_2$ | H | 0 | $NHSO_2C_6H_4(4-Ph)$ | |
| C-1229 | Het-9 | $CH_2CH_2CH_2$ | H | 0 | $NHSO_2[4-(3,5-dimethyl)isoxazolyl]$ | |
| C-1230 | Het-9 | $CH_2CH_2CH_2$ | H | 0 | $NHSO_2(1-naphthyl)$ | |
| C-1231 | Het-21 | $CH_2CH_2$ | H | 0 | $NHCO_2-n-Pr$ | |
| C-1232 | Het-21 | $CH_2CH_2$ | H | 0 | $NHCO_2-i-Pr$ | |
| C-1233 | Het-21 | $CH_2CH_2$ | H | 0 | $NHCO_2-n-Bu$ | |
| C-1234 | Het-21 | $CH_2CH_2$ | H | 0 | $NHCO_2-i-Bu$ | |
| C-1235 | Het-21 | $CH_2CH_2$ | H | 0 | $NHSO_2Ph$ | |
| C-1236 | Het-21 | $CH_2CH_2$ | H | 0 | $NHSO_2Ph(p-Cl)$ | |
| C-1237 | Het-21 | $CH_2CH_2$ | H | 0 | $NHSO_2Ph(p-F)$ | |
| C-1238 | Het-21 | $CH_2CH_2$ | H | 0 | $NHSO_2(2,4,6-trimethylphenyl)$ | |
| C-1239 | Het-21 | $CH_2CH_2$ | H | 0 | $NHSO_2(2,4,6-trichlorophenyl)$ | |
| C-1240 | Het-21 | $CH_2CH_2$ | H | 0 | $NHSO_2(2,6-dichlorophenyl)$ | |
| C-1241 | Het-21 | $CH_2CH_2$ | H | 0 | $NHSO2[4-(2,6-dimethylphenyl)phenyl$ | |
| C-1242 | Het-21 | $CH_2CH_2$ | H | 0 | $NHSO_2C_6H_4(4-Ph)$ | |
| C-1243 | Het-21 | $CH_2CH_2$ | H | 0 | $NHSO_2[4-(3,5-dimethyl(isoxazolyl)]$ | |
| C-1244 | Het-21 | $CH_2CH_2$ | H | 0 | $NHSO_2(1-naphthyl)$ | |
| C-1245 | Het-21 | $CH_2CH_2CH_2$ | H | 0 | $NHCO_2-n-Pr$ | |
| C-1246 | Het-21 | $CH_2CH_2CH_2$ | H | 0 | $NHCO_2-i-Pr$ | |
| C-1247 | Het-21 | $CH_2CH_2CH_2$ | H | 0 | $NHCO_2-n-Bu$ | |
| C-1248 | Het-21 | $CH_2CH_2CH_2$ | H | 0 | $NHCO_2-i-Bu$ | |
| C-1249 | Het-21 | $CH_2CH_2CH_2$ | H | 0 | $NHSO_2Ph$ | |
| C-1250 | Het-21 | $CH_2CH_2CH_2$ | H | 0 | $NHSO_2Ph(p-Cl)$ | |
| C-1251 | Het-21 | $CH_2CH_2CH_2$ | H | 0 | $NHSO_2Ph(p-F)$ | |
| C-1252 | Het-21 | $CH_2CH_2CH_2$ | H | 0 | $NHSO_2(2,4,6-trimethylphenyl)$ | |
| C-1253 | Het-21 | $CH_2CH_2CH_2$ | H | 0 | $NHSO_2(2,4,6-trichlorophenyl)$ | |
| C-1254 | Het-21 | $CH_2CH_2CH_2$ | H | 0 | $NHSO_2(2,6-dichlorophenyl)$ | |
| C-1255 | Het-21 | $CH_2CH_2CH_2$ | H | 0 | $NHSO2[4-(2,6-dimethylphenyl)phenyl$ | |
| C-1256 | Het-21 | $CH_2CH_2CH_2$ | H | 0 | $NHSO_2C_6H_4(4-Ph)$ | |
| C-1257 | Het-21 | $CH_2CH_2CH_2$ | H | 0 | $NHSO_2[4-(3,5-dimethyl)isoxazolyl]$ | |
| C-1258 | Het-21 | $CH_2CH_2CH_2$ | H | 0 | $NHSO_2(1-naphthyl)$ | |

TABLE 4

| Ex. No. | R¹ | U | R⁸ | z | R¹⁴ | MS |
|---|---|---|---|---|---|---|
| D-1 | Het-1 | $CH_2CH_2$ | H | 0 | CH=CH2 | |
| D-2 | Het-1 | $CH_2CH_2$ | H | 0 | C≡CH | |
| D-3 | Het-1 | $CH_2CH_2$ | H | 0 | cyclopropyl | |
| D-4 | Het-1 | $CH_2CH_2$ | H | 0 | cyclohexyl | |
| D-5 | Het-1 | $CH_2CH_2$ | H | 0 | Ph | |
| D-6 | Het-1 | $CH_2CH_2$ | H | 0 | Ph(p-F) | |
| D-7 | Het-1 | $CH_2CH_2$ | H | 0 | Ph (3,5-dichloro) | |
| D-8 | Het-1 | $CH_2CH_2$ | H | 0 | $CH_2Ph$ | |
| D-9 | Het-1 | $CH_2CH_2$ | H | 0 | $CH_2CH_2Ph$ | |
| D-10 | Het-1 | $CH_2CH_2$ | H | 0 | 3-pyridyl | |
| D-11 | Het-1 | $CH_2CH_2$ | H | 0 | 5-pyrimidinyl | |
| D-12 | Het-1 | $CH_2CH_2$ | H | 0 | 3-quinolyl | |
| D-13 | Het-1 | $CH_2CH_2$ | H | 1 | CH=CH2 | |
| D-14 | Het-1 | $CH_2CH_2$ | H | 1 | C≡CH | |
| D-15 | Het-1 | $CH_2CH_2$ | H | 1 | cyclopropyl | |
| D-16 | Het-1 | $CH_2CH_2$ | H | 1 | cyclohexyl | |
| D-17 | Het-1 | $CH_2CH_2$ | H | 1 | Ph | |
| D-18 | Het-1 | $CH_2CH_2$ | H | 1 | Ph(p-F) | |
| D-19 | Het-1 | $CH_2CH_2$ | H | 1 | Ph (3,5-dichloro) | |
| D-20 | Het-1 | $CH_2CH_2$ | H | 0 | $CH_2Ph$ | |
| D-21 | Het-1 | $CH_2CH_2$ | H | 0 | $CH_2CH_2Ph$ | |
| D-22 | Het-1 | $CH_2CH_2$ | H | 1 | 3-pyridyl | |
| D-23 | Het-1 | $CH_2CH_2$ | H | 1 | 5-pyrimidinyl | |
| D-24 | Het-1 | $CH_2CH_2$ | H | 1 | 3-quinolyl | |
| D-25 | Het-1 | $NHCH_2$ | H | 0 | CH=CH2 | |
| D-26 | Het-1 | $NHCH_2$ | H | 0 | C≡CH | |
| D-27 | Het-1 | $NHCH_2$ | H | 0 | cyclopropyl | |
| D-28 | Het-1 | $NHCH_2$ | H | 0 | cyclohexyl | |
| D-29 | Het-1 | $NHCH_2$ | H | 0 | Ph | |
| D-30 | Het-1 | $NHCH_2$ | H | 0 | Ph(p-F) | |
| D-31 | Het-1 | $NHCH_2$ | H | 0 | Ph (3,5-dichloro) | |
| D-32 | Het-1 | $NHCH_2$ | H | 0 | $CH_2Ph$ | |
| D-33 | Het-1 | $NHCH_2$ | H | 0 | $CH_2CH_2Ph$ | |
| D-34 | Het-1 | $NHCH_2$ | H | 0 | 3-pyridyl | |
| D-35 | Het-1 | $NHCH_2$ | H | 0 | 5-pyrimidinyl | |
| D-36 | Het-1 | $NHCH_2$ | H | 0 | 3-quinolyl | |
| D-37 | Het-1 | $NHCH_2$ | H | 1 | CH=CH2 | |
| D-38 | Het-1 | $NHCH_2$ | H | 1 | C≡CH | |
| D-39 | Het-1 | $NHCH_2$ | H | 1 | cyclopropyl | |
| D-40 | Het-1 | $NHCH_2$ | H | 1 | cyclohexyl | |
| D-41 | Het-1 | $NHCH_2$ | H | 1 | Ph | |
| D-42 | Het-1 | $NHCH_2$ | H | 1 | Ph(p-F) | |
| D-43 | Het-1 | $NHCH_2$ | H | 1 | Ph (3,5-dichloro) | |
| D-44 | Het-1 | $NHCH_2$ | H | 1 | $CH_2Ph$ | |
| D-45 | Het-1 | $NHCH_2$ | H | 1 | $CH_2CH_2Ph$ | |
| D-46 | Het-1 | $NHCH_2$ | H | 1 | 3-pyridyl | |
| D-47 | Het-1 | $NHCH_2$ | H | 1 | 5-pyrimidinyl | |
| D-48 | Het-1 | $NHCH_2$ | H | 1 | 3-quinolyl | |
| D-49 | Het-1 | $OCH_2$ | H | 0 | CH=CH2 | |
| D-50 | Het-1 | $OCH_2$ | H | 0 | C≡CH | |
| D-51 | Het-1 | $OCH_2$ | H | 0 | cyclopropyl | |
| D-52 | Het-1 | $OCH_2$ | H | 0 | cyclohexyl | |
| D-53 | Het-1 | $OCH_2$ | H | 0 | Ph | |
| D-54 | Het-1 | $OCH_2$ | H | 0 | Ph(p-F) | |
| D-55 | Het-1 | $OCH_2$ | H | 0 | Ph (3,5-dichloro) | |
| D-56 | Het-1 | $OCH_2$ | H | 0 | $CH_2Ph$ | |
| D-57 | Het-1 | $OCH_2$ | H | 0 | $CH_2CH_2Ph$ | |
| D-58 | Het-1 | $OCH_2$ | H | 0 | 3-pyridyl | |
| D-59 | Het-1 | $OCH_2$ | H | 0 | 5-pyrimidinyl | |
| D-60 | Het-1 | $OCH_2$ | H | 0 | 3-quinolyl | |
| D-62 | Het-1 | $OCH_2$ | H | 1 | CH=CH2 | |
| D-62 | Het-1 | $OCH_2$ | H | 1 | C≡CH | |
| D-63 | Het-1 | $OCH_2$ | H | 1 | cyclopropyl | |
| D-64 | Het-1 | $OCH_2$ | H | 1 | cyclohexyl | |
| D-65 | Het-1 | $OCH_2$ | H | 1 | Ph | |
| D-66 | Het-1 | $OCH_2$ | H | 1 | Ph(p-F) | |
| D-67 | Het-1 | $OCH_2$ | H | 1 | Ph (3,5-dichloro) | |
| D-68 | Het-1 | $OCH_2$ | H | 1 | $CH_2Ph$ | |
| D-69 | Het-1 | $OCH_2$ | H | 1 | $CH_2CH_2Ph$ | |
| D-70 | Het-1 | $OCH_2$ | H | 1 | 3-pyridyl | |
| D-71 | Het-1 | $OCH_2$ | H | 1 | 5-pyrimidinyl | |
| D-72 | Het-1 | $OCH_2$ | H | 1 | 3-quinolyl | |
| D-73 | Het-1 | $CH_2CH_2CH_2$ | H | 0 | CH=CH2 | |
| D-74 | Het-1 | $CH_2CH_2CH_2$ | H | 0 | C≡CH | |
| D-75 | Het-1 | $CH_2CH_2CH_2$ | H | 0 | cyclopropyl | |
| D-76 | Het-1 | $CH_2CH_2CH_2$ | H | 0 | cyclohexyl | |
| D-77 | Het-1 | $CH_2CH_2CH_2$ | H | 0 | Ph | |
| D-78 | Het-1 | $CH_2CH_2CH_2$ | H | 0 | Ph(p-F) | |
| D-79 | Het-1 | $CH_2CH_2CH_2$ | H | 0 | Ph (3,5-dichloro) | |
| D-80 | Het-1 | $CH_2CH_2CH_2$ | H | 0 | $CH_2Ph$ | |
| D-81 | Het-1 | $CH_2CH_2CH_2$ | H | 0 | $CH_2CH_2Ph$ | |
| D-82 | Het-1 | $CH_2CH_2CH_2$ | H | 0 | 3-pyridyl | |
| D-83 | Het-1 | $CH_2CH_2CH_2$ | H | 0 | 5-pyrimidinyl | |
| D-84 | Het-1 | $CH_2CH_2CH_2$ | H | 0 | 3-quinolyl | |
| D-85 | Het-1 | $CH_2CH_2CH_2$ | H | 1 | CH=CH2 | |
| D-86 | Het-1 | $CH_2CH_2CH_2$ | H | 1 | C≡CH | |
| D-87 | Het-1 | $CH_2CH_2CH_2$ | H | 1 | cyclopropyl | |
| D-88 | Het-1 | $CH_2CH_2CH_2$ | H | 1 | cyclohexyl | |
| D-89 | Het-1 | $CH_2CH_2CH_2$ | H | 1 | Ph | |
| D-90 | Het-1 | $CH_2CH_2CH_2$ | H | 1 | Ph(p-F) | |
| D-91 | Het-1 | $CH_2CH_2CH_2$ | H | 1 | Ph (3,5-dichloro) | |
| D-92 | Het-1 | $CH_2CH_2CH_2$ | H | 1 | $CH_2Ph$ | |
| D-93 | Het-1 | $CH_2CH_2CH_2$ | H | 1 | $CH_2CH_2Ph$ | |
| D-94 | Het-1 | $CH_2CH_2CH_2$ | H | 1 | 3-pyridyl | |
| D-95 | Het-1 | $CH_2CH_2CH_2$ | H | 1 | 5-pyrimidinyl | |
| D-96 | Het-1 | $CH_2CH_2CH_2$ | H | 1 | 3-quinolyl | |
| D-97 | Het-1 | $NHCH_2CH_2$ | H | 0 | CH=CH2 | |
| D-98 | Het-1 | $NHCH_2CH_2$ | H | 0 | C≡CH | |
| D-99 | Het-1 | $NHCH_2CH_2$ | H | 0 | cyclopropyl | |
| D-100 | Het-1 | $NHCH_2CH_2$ | H | 0 | cyclohexyl | |
| D-101 | Het-1 | $NHCH_2CH_2$ | H | 0 | Ph | |
| D-102 | Het-1 | $NHCH_2CH_2$ | H | 0 | Ph(p-F) | |
| D-103 | Het-1 | $NHCH_2CH_2$ | H | 0 | Ph (3,5-dichloro) | |
| D-104 | Het-1 | $NHCH_2CH_2$ | H | 0 | $CH_2Ph$ | |
| D-105 | Het-1 | $NHCH_2CH_2$ | H | 0 | $CH_2CH_2Ph$ | |
| D-106 | Het-1 | $NHCH_2CH_2$ | H | 0 | 3-pyridyl | |
| D-107 | Het-1 | $NHCH_2CH_2$ | H | 0 | 5-pyrimidinyl | |
| D-108 | Het-1 | $NHCH_2CH_2$ | H | 0 | 3-quinolyl | |
| D-109 | Het-1 | $NHCH_2CH_2$ | H | 1 | CH=CH2 | |
| D-110 | Het-1 | $NHCH_2CH_2$ | H | 1 | C≡CH | |
| D-111 | Het-1 | $NHCH_2CH_2$ | H | 1 | cyclopropyl | |
| D-112 | Het-1 | $NHCH_2CH_2$ | H | 1 | cyclohexyl | |
| D-113 | Het-1 | $NHCH_2CH_2$ | H | 1 | Ph | |
| D-114 | Het-1 | $NHCH_2CH_2$ | H | 1 | Ph(p-F) | |
| D-115 | Het-1 | $NHCH_2CH_2$ | H | 1 | Ph (3,5-dichloro) | |
| D-116 | Het-1 | $NHCH_2CH_2$ | H | 1 | $CH_2Ph$ | |
| D-117 | Het-1 | $NHCH_2CH_2$ | H | 1 | $CH_2CH_2Ph$ | |
| D-118 | Het-1 | $NHCH_2CH_2$ | H | 1 | 3-pyridyl | |
| D-119 | Het-1 | $NHCH_2CH_2$ | H | 1 | 5-pyrimidinyl | |
| D-120 | Het-1 | $NHCH_2CH_2$ | H | 1 | 3-quinolyl | |
| D-121 | Het-1 | $OCH_2CH_2$ | H | 0 | CH=CH2 | |
| D-122 | Het-1 | $OCH_2CH_2$ | H | 0 | C≡CH | |
| D-123 | Het-1 | $OCH_2CH_2$ | H | 0 | cyclopropyl | |
| D-124 | Het-1 | $OCH_2CH_2$ | H | 0 | cyclohexyl | |
| D-125 | Het-1 | $OCH_2CH_2$ | H | 0 | Ph | |
| D-126 | Het-1 | $OCH_2CH_2$ | H | 0 | Ph(p-F) | |
| D-127 | Het-1 | $OCH_2CH_2$ | H | 0 | Ph (3,5-dichloro) | |
| D-128 | Het-1 | $OCH_2CH_2$ | H | 0 | $CH_2Ph$ | |
| D-129 | Het-1 | $OCH_2CH_2$ | H | 0 | $CH_2CH_2Ph$ | |
| D-130 | Het-1 | $OCH_2CH_2$ | H | 0 | 3-pyridyl | |
| D-131 | Het-1 | $OCH_2CH_2$ | H | 0 | 5-pyrimidinyl | |
| D-132 | Het-1 | $OCH_2CH_2$ | H | 0 | 3-quinolyl | |
| D-133 | Het-1 | $OCH_2CH_2$ | H | 1 | CH=CH2 | |
| D-134 | Het-1 | $OCH_2CH_2$ | H | 1 | C≡CH | |

TABLE 4-continued

| Ex. No. | R¹ | U | R⁸ | z | R¹⁴ | MS |
|---|---|---|---|---|---|---|
| D-135 | Het-1 | OCH$_2$CH$_2$ | H | 1 | cyclopropyl | |
| D-136 | Het-1 | OCH$_2$CH$_2$ | H | 1 | cyclohexyl | |
| D-137 | Het-1 | OCH$_2$CH$_2$ | H | 1 | Ph | |
| D-138 | Het-1 | OCH$_2$CH$_2$ | H | 1 | Ph(p-F) | |
| D-139 | Het-1 | OCH$_2$CH$_2$ | H | 1 | Ph (3,5-dichloro) | |
| D-140 | Het-1 | OCH$_2$CH$_2$ | H | 1 | CH$_2$Ph | |
| D-141 | Het-1 | OCH$_2$CH$_2$ | H | 1 | CH$_2$CH$_2$Ph | |
| D-142 | Het-1 | OCH$_2$CH$_2$ | H | 1 | 3-pyridyl | |
| D-143 | Het-1 | OCH$_2$CH$_2$ | H | 1 | 5-pyrimdinyl | |
| D-144 | Het-1 | OCH$_2$CH$_2$ | H | 1 | 3-quinolyl | |
| D-145 | Het-2 | CH$_2$CH$_2$ | H | 0 | CH=CH2 | |
| D-146 | Het-2 | CH$_2$CH$_2$ | H | 0 | C≡CH | |
| D-147 | Het-2 | CH$_2$CH$_2$ | H | 0 | cyclopropyl | |
| D-148 | Het-2 | CH$_2$CH$_2$ | H | 0 | cyclohexyl | |
| D-149 | Het-2 | CH$_2$CH$_2$ | H | 0 | Ph | |
| D-150 | Het-2 | CH$_2$CH$_2$ | H | 0 | Ph(p-F) | |
| D-151 | Het-2 | CH$_2$CH$_2$ | H | 0 | Ph (3,5-dichloro) | |
| D-152 | Het-2 | CH$_2$CH$_2$ | H | 0 | CH$_2$Ph | |
| D-153 | Het-2 | CH$_2$CH$_2$ | H | 0 | CH$_2$CH$_2$Ph | |
| D-154 | Het-2 | CH$_2$CH$_2$ | H | 0 | 3-pyridyl | |
| D-155 | Het-2 | CH$_2$CH$_2$ | H | 0 | 5-pyrimidinyl | |
| D-156 | Het-2 | CH$_2$CH$_2$ | H | 0 | 3-quinolyl | |
| D-157 | Het-2 | CH$_2$CH$_2$ | H | 1 | CH=CH2 | |
| D-158 | Het-2 | CH$_2$CH$_2$ | H | 1 | C≡CH | |
| D-159 | Het-2 | CH$_2$CH$_2$ | H | 1 | cyclopropyl | |
| D-160 | Het-2 | CH$_2$CH$_2$ | H | 1 | cyclohexyl | |
| D-161 | Het-2 | CH$_2$CH$_2$ | H | 1 | Ph | |
| D-162 | Het-2 | CH$_2$CH$_2$ | H | 1 | Ph(p-F) | |
| D-163 | Het-2 | CH$_2$CH$_2$ | H | 1 | Ph (3,5-dichloro) | |
| D-164 | Het-2 | CH$_2$CH$_2$ | H | 0 | CH$_2$Ph | |
| D-165 | Het-2 | CH$_2$CH$_2$ | H | 0 | CH$_2$CH$_2$Ph | |
| D-166 | Het-2 | CH$_2$CH$_2$ | H | 1 | 3-pyridyl | |
| D-167 | Het-2 | CH$_2$CH$_2$ | H | 1 | 5-pyrimidinyl | |
| D-168 | Het-2 | CH$_2$CH$_2$ | H | 1 | 3-quinolyl | |
| D-169 | Het-2 | NHCH$_2$ | H | 0 | CH=CH2 | |
| D-170 | Het-2 | NHCH$_2$ | H | 0 | C≡CH | |
| D-171 | Het-2 | NHCH$_2$ | H | 0 | cyclopropyl | |
| D-172 | Het-2 | NHCH$_2$ | H | 0 | cyclohexyl | |
| D-173 | Het-2 | NHCH$_2$ | H | 0 | Ph | |
| D-174 | Het-2 | NHCH$_2$ | H | 0 | Ph(p-F) | |
| D-175 | Het-2 | NHCH$_2$ | H | 0 | Ph (3,5-dichloro) | |
| D-176 | Het-2 | NHCH$_2$ | H | 0 | CH$_2$Ph | |
| D-177 | Het-2 | NHCH$_2$ | H | 0 | CH$_2$CH$_2$Ph | |
| D-178 | Het-2 | NHCH$_2$ | H | 0 | 3-pyridyl | |
| D-179 | Het-2 | NHCH$_2$ | H | 0 | 5-pyrimidinyl | |
| D-180 | Het-2 | NHCH$_2$ | H | 0 | 3-quinolyl | |
| D-181 | Het-2 | NHCH$_2$ | H | 1 | CH=CH2 | |
| D-182 | Het-2 | NHCH$_2$ | H | 1 | C≡CH | |
| D-183 | Het-2 | NHCH$_2$ | H | 1 | cyclopropyl | |
| D-184 | Het-2 | NHCH$_2$ | H | 1 | cyclohexyl | |
| D-185 | Het-2 | NHCH$_2$ | H | 1 | Ph | |
| D-186 | Het-2 | NHCH$_2$ | H | 1 | Ph(p-F) | |
| D-187 | Het-2 | NHCH$_2$ | H | 1 | Ph (3,5-dichloro) | |
| D-188 | Het-2 | NHCH$_2$ | H | 1 | CH$_2$Ph | |
| D-189 | Het-2 | NHCH$_2$ | H | 1 | CH$_2$CH$_2$Ph | |
| D-190 | Het-2 | NHCH$_2$ | H | 1 | 3-pyridyl | |
| D-191 | Het-2 | NHCH$_2$ | H | 1 | 5-pyrimidinyl | |
| D-192 | Het-2 | NHCH$_2$ | H | 1 | 3-quinolyl | |
| D-193 | Het-2 | OCH$_2$ | H | 0 | CH=CH2 | |
| D-194 | Het-2 | OCH$_2$ | H | 0 | C≡CH | |
| D-195 | Het-2 | OCH$_2$ | H | 0 | cyclopropyl | |
| D-196 | Het-2 | OCH$_2$ | H | 0 | cyclohexyl | |
| D-197 | Het-2 | OCH$_2$ | H | 0 | Ph | |
| D-198 | Het-2 | OCH$_2$ | H | 0 | Ph(p-F) | |
| D-199 | Het-2 | OCH$_2$ | H | 0 | Ph (3,5-dichloro) | |
| D-200 | Het-2 | OCH$_2$ | H | 0 | CH$_2$Ph | |
| D-201 | Het-2 | OCH$_2$ | H | 0 | CH$_2$CH$_2$Ph | |
| D-202 | Het-2 | OCH$_2$ | H | 0 | 3-pyridyl | |
| D-203 | Het-2 | OCH$_2$ | H | 0 | 5-pyrimidinyl | |
| D-204 | Het-2 | OCH$_2$ | H | 0 | 3-quinolyl | |
| D-205 | Het-2 | OCH$_2$ | H | 1 | CH=CH2 | |
| D-206 | Het-2 | OCH$_2$ | H | 1 | C≡CH | |
| D-207 | Het-2 | OCH$_2$ | H | 1 | cyclopropyl | |
| D-208 | Het-2 | OCH$_2$ | H | 1 | cyclohexyl | |
| D-209 | Het-2 | OCH$_2$ | H | 1 | Ph | |
| D-210 | Het-2 | OCH$_2$ | H | 1 | Ph(p-F) | |
| D-211 | Het-2 | OCH$_2$ | H | 1 | Ph (3,5-dichloro) | |
| D-212 | Het-2 | OCH$_2$ | H | 1 | CH$_2$Ph | |
| D-213 | Het-2 | OCH$_2$ | H | 1 | CH$_2$CH$_2$Ph | |
| D-214 | Het-2 | OCH$_2$ | H | 1 | 3-pyridyl | |
| D-215 | Het-2 | OCH$_2$ | H | 1 | 5-pyrimidinyl | |
| D-216 | Het-2 | OCH$_2$ | H | 1 | 3-quinolyl | |
| D-217 | Het-2 | CH$_2$CH$_2$CH$_2$ | H | 0 | CH=CH2 | |
| D-218 | Het-2 | CH$_2$CH$_2$CH$_2$ | H | 0 | C≡CH | |
| D-219 | Het-2 | CH$_2$CH$_2$CH$_2$ | H | 0 | cyclopropyl | |
| D-220 | Het-2 | CH$_2$CH$_2$CH$_2$ | H | 0 | cyclohexyl | |
| D-221 | Het-2 | CH$_2$CH$_2$CH$_2$ | H | 0 | Ph | |
| D-222 | Het-2 | CH$_2$CH$_2$CH$_2$ | H | 0 | Ph(p-F) | |
| D-223 | Het-2 | CH$_2$CH$_2$CH$_2$ | H | 0 | Ph (3,5-dichloro) | |
| D-224 | Het-2 | CH$_2$CH$_2$CH$_2$ | H | 0 | CH$_2$Ph | |
| D-225 | Het-2 | CH$_2$CH$_2$CH$_2$ | H | 0 | CH$_2$CH$_2$Ph | |
| D-226 | Het-2 | CH$_2$CH$_2$CH$_2$ | H | 0 | 3-pyridyl | |
| D-227 | Het-2 | CH$_2$CH$_2$CH$_2$ | H | 0 | 5-pyrimidinyl | |
| D-228 | Het-2 | CH$_2$CH$_2$CH$_2$ | H | 0 | 3-quinolyl | |
| D-229 | Het-2 | CH$_2$CH$_2$CH$_2$ | H | 1 | CH=CH2 | |
| D-230 | Het-2 | CH$_2$CH$_2$CH$_2$ | H | 1 | C≡CH | |
| D-231 | Het-2 | CH$_2$CH$_2$CH$_2$ | H | 1 | cyclopropyl | |
| D-232 | Het-2 | CH$_2$CH$_2$CH$_2$ | H | 1 | cyclohexyl | |
| D-233 | Het-2 | CH$_2$CH$_2$CH$_2$ | H | 1 | Ph | |
| D-234 | Het-2 | CH$_2$CH$_2$CH$_2$ | H | 1 | Ph(p-F) | |
| D-235 | Het-2 | CH$_2$CH$_2$CH$_2$ | H | 1 | Ph (3,5-dichloro) | |
| D-236 | Het-2 | CH$_2$CH$_2$CH$_2$ | H | 1 | CH$_2$Ph | |
| D-237 | Het-2 | CH$_2$CH$_2$CH$_2$ | H | 1 | CH$_2$CH$_2$Ph | |
| D-238 | Het-2 | CH$_2$CH$_2$CH$_2$ | H | 1 | 3-pyridyl | |
| D-239 | Het-2 | CH$_2$CH$_2$CH$_2$ | H | 1 | 5-pyrimidinyl | |
| D-240 | Het-2 | CH$_2$CH$_2$CH$_2$ | H | 1 | 3-quinolyl | |
| D-241 | Het-2 | NHCH$_2$CH$_2$ | H | 0 | CH=CH2 | |
| D-242 | Het-2 | NHCH$_2$CH$_2$ | H | 0 | C≡CH | |
| D-243 | Het-2 | NHCH$_2$CH$_2$ | H | 0 | cyclopropyl | |
| D-244 | Het-2 | NHCH$_2$CH$_2$ | H | 0 | cyclohexyl | |
| D-245 | Het-2 | NHCH$_2$CH$_2$ | H | 0 | Ph | |
| D-246 | Het-2 | NHCH$_2$CH$_2$ | H | 0 | Ph(p-F) | |
| D-247 | Het-2 | NHCH$_2$CH$_2$ | H | 0 | Ph(3,5-dichloro) | |
| D-248 | Het-2 | NHCH$_2$CH$_2$ | H | 0 | CH$_2$Ph | |
| D-249 | Het-2 | NHCH$_2$CH$_2$ | H | 0 | CH$_2$CH$_2$Ph | |
| D-250 | Het-2 | NHCH$_2$CH$_2$ | H | 0 | 3-pyridyl | |
| D-251 | Het-2 | NHCH$_2$CH$_2$ | H | 0 | 5-pyrimidinyl | |
| D-252 | Het-2 | NHCH$_2$CH$_2$ | H | 0 | 3-quinolyl | |
| D-253 | Het-2 | NHCH$_2$CH$_2$ | H | 1 | CH=CH2 | |
| D-254 | Het-2 | NHCH$_2$CH$_2$ | H | 1 | C≡CH | |
| D-255 | Het-2 | NHCH$_2$CH$_2$ | H | 1 | cyclopropyl | |
| D-256 | Het-2 | NHCH$_2$CH$_2$ | H | 1 | cyclohexyl | |
| D-257 | Het-2 | NHCH$_2$CH$_2$ | H | 1 | Ph | |
| D-258 | Het-2 | NHCH$_2$CH$_2$ | H | 1 | Ph(p-F) | |
| D-259 | Het-2 | NHCH$_2$CH$_2$ | H | 1 | Ph (3,5-dichloro) | |
| D-260 | Het-2 | NHCH$_2$CH$_2$ | H | 1 | CH$_2$Ph | |
| D-261 | Het-2 | NHCH$_2$CH$_2$ | H | 1 | CH$_2$CH$_2$Ph | |
| S-262 | Het-2 | NHCH$_2$CH$_2$ | H | 1 | 3-pyridyl | |
| D-263 | Het-2 | NHCH$_2$CH$_2$ | H | 1 | 5-pyrimidinyl | |
| D-264 | Het-2 | NHCH$_2$CH$_2$ | H | 1 | 3-quinolyl | |
| D-265 | Het-2 | OCH$_2$CH$_2$ | H | 0 | CH=CH2 | |
| D-266 | Het-2 | OCH$_2$CH$_2$ | H | 0 | C≡CH | |
| D-267 | Het-2 | OCH$_2$CH$_2$ | H | 0 | cyclopropyl | |
| D-268 | Het-2 | OCH$_2$CH$_2$ | H | 0 | cyclohexyl | |

TABLE 4-continued

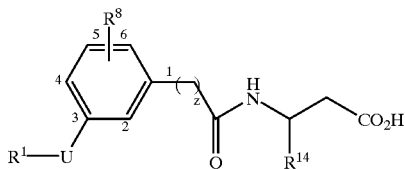

| Ex. No. | R¹ | U | R⁸ | z | R¹⁴ | MS |
|---|---|---|---|---|---|---|
| D-269 | Het-2 | OCH₂CH₂ | H | 0 | Ph | |
| D-270 | Het-2 | OCH₂CH₂ | H | 0 | Ph(p-F) | |
| D-271 | Het-2 | OCH₂CH₂ | H | 0 | Ph (3,5-dichloro) | |
| D-272 | Het-2 | OCH₂CH₂ | H | 0 | CH₂Ph | |
| D-273 | Het-2 | OCH₂CH₂ | H | 0 | CH₂CH₂Ph | |
| D-274 | Het-2 | OCH₂CH₂ | H | 0 | 3-pyridyl | |
| D-275 | Het-2 | OCH₂CH₂ | H | 0 | 5-pyrimidinyl | |
| D-276 | Het-2 | OCH₂CH₂ | H | 0 | 3-quinolyl | |
| D-277 | Het-3 | NHCH₂ | H | 0 | CH=CH2 | |
| D-278 | Het-3 | NHCH₂ | H | 0 | C≡CH | |
| D-279 | Het-3 | NHCH₂ | H | 0 | cyclopropyl | |
| D-280 | Het-3 | NHCH₂ | H | 0 | cyclohexyl | |
| D-281 | Het-3 | NHCH₂ | H | 0 | Ph | |
| D-282 | Het-3 | NHCH₂ | H | 0 | Ph(p-F) | |
| D-283 | Het-3 | NHCH₂ | H | 0 | Ph (3,5-dichloo) | |
| D-284 | Het-3 | NHCH₂ | H | 0 | CH₂Ph | |
| D-285 | Het-3 | NHCH₂ | H | 0 | CH₂CH₂Ph | |
| D-286 | Het-3 | NHCH₂ | H | 0 | 3-pyridyl | |
| D-287 | Het-3 | NHCH₂ | H | 0 | 5-pyrimidinyl | |
| D-288 | Het-3 | NHCH₂ | H | 0 | 3-quinolyl | |
| D-289 | Het-3 | NHCH₂ | H | 1 | CH=CH2 | |
| D-290 | Het-3 | NHCH₂ | H | 1 | C≡CH | |
| D-291 | Het-3 | NHCH₂ | H | 1 | cyclopropyl | |
| D-292 | Het-3 | NHCH₂ | H | 1 | cyclohexyl | |
| D-293 | Het-3 | NHCH₂ | H | 1 | Ph | |
| D-294 | Het-3 | NHCH₂ | H | 1 | Ph(p-F) | |
| D-295 | Het-3 | NHCH₂ | H | 1 | Ph (3,5-dichloro) | |
| D-296 | Het-3 | NHCH₂ | H | 1 | CH₂Ph | |
| D-297 | Het-3 | NHCH₂ | H | 1 | CH₂CH₂Ph | |
| D-298 | Het-3 | NHCH₂ | H | 1 | 3-pyridyl | |
| D-299 | Het-3 | NHCH₂ | H | 1 | 5-pyrimidinyl | |
| D-300 | Het-3 | NHCH₂ | H | 1 | 3-quinolyl | |
| D-301 | Het-3 | NHCH₂CH₂ | H | 0 | CH=CH2 | |
| D-302 | Het-3 | NHCH₂CH₂ | H | 0 | C≡CH | |
| D-303 | Het-3 | NHCH₂CH₂ | H | 0 | cyclopropyl | |
| D-304 | Het-3 | NHCH₂CH₂ | H | 0 | cyclohexyl | |
| D-305 | Het-3 | NHCH₂CH₂ | H | 0 | Ph | |
| D-306 | Het-3 | NHCH₂CH₂ | H | 0 | Ph(p-F) | |
| D-307 | Het-3 | NHCH₂CH₂ | H | 0 | Ph (3,5-dichloro) | |
| D-308 | Het-3 | NHCH₂CH₂ | H | 0 | CH₂Ph | |
| D-309 | Het-3 | NHCH₂CH₂ | H | 0 | CH₂CH₂Ph | |
| D-310 | Het-3 | NHCH₂CH₂ | H | 0 | 3-pyridyl | |
| D-311 | Het-3 | NHCH₂CH₂ | H | 0 | 5-pyrimidinyl | |
| D-312 | Het-3 | NHCH₂CH₂ | H | 0 | 3-quinolyl | |
| D-313 | Het-3 | NHCH₂CH₂ | H | 1 | CH=CH2 | |
| D-314 | Het-3 | NHCH₂CH₂ | H | 1 | C≡CH | |
| D-315 | Het-3 | NHCH₂CH₂ | H | 1 | cyclopropyl | |
| D-316 | Het-3 | NHCH₂CH₂ | H | 1 | cyclohexyl | |
| D-317 | Het-3 | NHCH₂CH₂ | H | 1 | Ph | |
| D-318 | Het-3 | NHCH₂CH₂ | H | 1 | Ph(p-F) | |
| D-319 | Het-3 | NHCH₂CH₂ | H | 1 | Ph (3,5-dichloro) | |
| D-320 | Het-3 | NHCH₂CH₂ | H | 1 | CH₂Ph | |
| D-321 | Het-3 | NHCH₂CH₂ | H | 1 | CH₂CH₂Ph | |
| D-322 | Het-3 | NHCH₂CH₂ | H | 1 | 3-pyridyl | |
| D-323 | Het-3 | NHCH₂CH₂ | H | 1 | 5-pyrimidinyl | |
| D-324 | Het-3 | NHCH₂CH₂ | H | 1 | 3-quinolyl | |
| D-325 | Het-4 | CH₂CH₂ | H | 1 | CH=CH2 | |
| D-326 | Het-4 | CH₂CH₂ | H | 1 | C≡CH | |
| D-327 | Het-4 | CH₂CH₂ | H | 1 | cyclopropyl | |
| D-328 | Het-4 | CH₂CH₂ | H | 1 | cyclohexyl | |
| D-329 | Het-4 | CH₂CH₂ | H | 1 | Ph | |
| D-330 | Het-4 | CH₂CH₂ | H | 1 | Ph(p-F) | |
| D-331 | Het-4 | CH₂CH₂ | H | 1 | Ph (3,5-dichloro) | |
| D-332 | Het-4 | CH₂CH₂ | H | 1 | CH₂Ph | |
| D-333 | Het-4 | CH₂CH₂ | H | 1 | CH₂CH₂Ph | |
| D-334 | Het-4 | CH₂CH₂ | H | 1 | 3-pyridyl | |
| D-335 | Het-4 | CH₂CH₂ | H | 1 | 5-pyrimidinyl | |

TABLE 4-continued

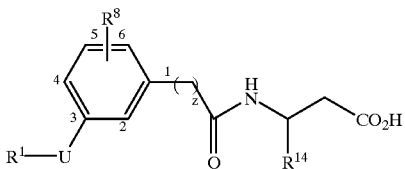

| Ex. No. | R¹ | U | R⁸ | z | R¹⁴ | MS |
|---|---|---|---|---|---|---|
| D-336 | Het-4 | CH₂CH₂ | H | 1 | 3-quinolyl | |
| D-337 | Het-4 | NHCH₂ | H | 1 | CH=CH2 | |
| D-338 | Het-4 | NHCH₂ | H | 1 | C≡CH | |
| D-339 | Het-4 | NHCH₂ | H | 1 | cyclopropyl | |
| D-340 | Het-4 | NHCH₂ | H | 1 | cyclohexyl | |
| D-341 | Het-4 | NHCH₂ | H | 1 | Ph | |
| D-342 | Het-4 | NHCH₂ | H | 1 | Ph(p-F) | |
| D-343 | Het-4 | NHCH₂ | H | 1 | Ph (3,5-dichloro) | |
| D-344 | Het-4 | NHCH₂ | H | 1 | CH₂Ph | |
| D-345 | Het-4 | NHCH₂ | H | 1 | CH₂CH₂Ph | |
| D-346 | Het-4 | NHCH₂ | H | 1 | 3-pyridyl | |
| D-347 | Het-4 | NHCH₂ | H | 1 | 5-pyrimidinyl | |
| D-348 | Het-4 | NHCH₂ | H | 1 | 3-quinolyl | |
| D-349 | Het-4 | OCH₂ | H | 1 | CH=CH2 | |
| D-350 | Het-4 | OCH₂ | H | 1 | C≡CH | |
| D-351 | Het-4 | OCH₂ | H | 1 | cyclopropyl | |
| D-352 | Het-4 | OCH₂ | H | 1 | cyclohexyl | |
| D-353 | Het-4 | OCH₂ | H | 1 | Ph | |
| D-354 | Het-4 | OCH₂ | H | 1 | Ph(p-F) | |
| D-355 | Het-4 | OCH₂ | H | 1 | Ph (3,5-dichloro) | |
| D-356 | Het-4 | OCH₂ | H | 1 | CH₂Ph | |
| D-357 | Het-4 | OCH₂ | H | 1 | CH₂CH₂Ph | |
| D-358 | Het-4 | OCH₂ | H | 1 | 3-pyridyl | |
| D-359 | Het-4 | OCH₂ | H | 1 | 5-pyrimidinyl | |
| D-360 | Het-4 | OCH₂ | H | 1 | 3-quinolyl | |
| D-361 | Het-5 | CH₂CH₂ | H | 1 | CH=CH2 | |
| D-362 | Het-5 | CH₂CH₂ | H | 1 | C≡CH | |
| D-363 | Het-5 | CH₂CH₂ | H | 1 | cyclopropyl | |
| D-364 | Het-5 | CH₂CH₂ | H | 1 | cyclohexyl | |
| D-365 | Het-5 | CH₂CH₂ | H | 1 | Ph | |
| D-366 | Het-5 | CH₂CH₂ | H | 1 | Ph(p-F) | |
| D-367 | Het-5 | CH₂CH₂ | H | 1 | Ph (3,5-dichloro) | |
| D-368 | Het-5 | CH₂CH₂ | H | 1 | CH₂Ph | |
| D-369 | Het-5 | CH₂CH₂ | H | 1 | CH₂CH₂Ph | |
| D-370 | Het-5 | CH₂CH₂ | H | 1 | 3-pyridyl | |
| D-371 | Het-5 | CH₂CH₂ | H | 1 | 5-pyrimidinyl | |
| D-372 | Het-5 | CH₂CH₂ | H | 1 | 3-quinolyl | |
| D-373 | Het-5 | NHCH₂ | H | 1 | CH=CH2 | |
| D-374 | Het-5 | NHCH₂ | H | 1 | C≡CH | |
| D-375 | Het-5 | NHCH₂ | H | 1 | cyclopropyl | |
| D-376 | Het-5 | NHCH₂ | H | 1 | cyclohexyl | |
| D-377 | Het-5 | NHCH₂ | H | 1 | Ph | |
| D-378 | Het-5 | NHCH₂ | H | 1 | Ph(p-F) | |
| D-379 | Het-5 | NHCH₂ | H | 1 | Ph (3,5-dichloro) | |
| D-380 | Het-5 | NHCH₂ | H | 1 | CH₂Ph | |
| D-381 | Het-5 | NHCH₂ | H | 1 | CH₂CH₂Ph | |
| D-382 | Het-5 | NHCH₂ | H | 1 | 3-pyridyl | |
| D-383 | Het-5 | NHCH₂ | H | 1 | 5-pyrimidinyl | |
| D-384 | Het-5 | NHCH₂ | H | 1 | 3-quinolyl | |
| D-385 | Het-5 | OCH₂ | H | 1 | CH=CH2 | |
| D-386 | Het-5 | OCH₂ | H | 1 | C≡CH | |
| D-387 | Het-5 | OCH₂ | H | 1 | cyclopropyl | |
| D-388 | Het-5 | OCH₂ | H | 1 | cyclohexyl | |
| D-389 | Het-5 | OCH₂ | H | 1 | Ph | |
| D-390 | Het-5 | OCH₂ | H | 1 | Ph(p-F) | |
| D-391 | Het-5 | OCH₂ | H | 1 | Ph (3,5-dichloro) | |
| D-392 | Het-5 | OCH₂ | H | 1 | CH₂Ph | |
| D-393 | Het-5 | OCH₂ | H | 1 | CH₂CH₂Ph | |
| D-394 | Het-5 | OCH₂ | H | 1 | 3-pyridyl | |
| D-395 | Het-5 | OCH₂ | H | 1 | 5-pyrimidinyl | |
| D-396 | Het-5 | OCH₂ | H | 1 | 3-quinolyl | |
| D-397 | Het-5 | CH₂CH₂CH₂ | H | 1 | CH=CH2 | |
| D-398 | Het-5 | CH₂CH₂CH₂ | H | 1 | C≡CH | |
| D-399 | Het-5 | CH₂CH₂CH₂ | H | 1 | cyclopropyl | |
| D-400 | Het-5 | CH₂CH₂CH₂ | H | 1 | cyclohexyl | |
| D-401 | Het-5 | CH₂CH₂CH₂ | H | 1 | Ph | |
| D-402 | Het-5 | CH₂CH₂CH₂ | H | 1 | Ph (p-F) | |

TABLE 4-continued

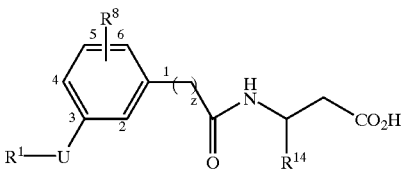

| Ex. No. | R¹ | U | R⁸ | z | R¹⁴ | MS |
|---|---|---|---|---|---|---|
| D-403 | Het-5 | CH₂CH₂CH₂ | H | 1 | Ph (3,5-dichlorol) | |
| D-404 | Het-5 | CH₂CH₂CH₂ | H | 1 | CH₂Ph | |
| D-405 | Het-5 | CH₂CH₂CH₂ | H | 1 | CH₂CH₂Ph | |
| D-406 | Het-5 | CH₂CH₂CH₂ | H | 1 | 3-pyridyl | |
| D-407 | Het-5 | CH₂CH₂CH₂ | H | 1 | 5-pyrimidinyl | |
| D-408 | Het-5 | CH₂CH₂CH₂ | H | 1 | 3-quinolyl | |
| D-409 | Het-5 | NHCH₂CH₂ | H | 1 | CH=CH2 | |
| D-410 | Het-5 | NHCH₂CH₂ | H | 1 | C≡CH | |
| D-411 | Het-5 | NHCH₂CH₂ | H | 1 | cyclopropyl | |
| D-412 | Het-5 | NHCH₂CH₂ | H | 1 | cyclohexyl | |
| D-413 | Het-5 | NHCH₂CH₂ | H | 1 | Ph | |
| D-414 | Het-5 | NHCH₂CH₂ | H | 1 | Ph(p-F) | |
| D-415 | Het-5 | NHCH₂CH₂ | H | 1 | Ph (3,5-dichloro) | |
| D-416 | Het-5 | NHCH₂CH₂ | H | 1 | CH₂Ph | |
| D-417 | Het-5 | NHCH₂CH₂ | H | 1 | CH₂CH₂Ph | |
| D-418 | Het-5 | NHCH₂CH₂ | H | 1 | 3-pyridyl | |
| D-419 | Het-5 | NHCH₂CH₂ | H | 1 | 5-pyrimidinyl | |
| D-420 | Het-5 | NHCH₂CH₂ | H | 1 | 3-quinolyl | |
| D-421 | Het-5 | OCH₂CH₂ | H | 1 | CH=CH2 | |
| D-422 | Het-5 | OCH₂CH₂ | H | 1 | C≡CH | |
| D-423 | Het-5 | OCH₂CH₂ | H | 1 | cyclopropyl | |
| D-424 | Het-5 | OCH₂CH₂ | H | 1 | cyclohexyl | |
| D-425 | Het-5 | OCH₂CH₂ | H | 1 | Ph | |
| D-426 | Het-5 | OCH₂CH₂ | H | 1 | Ph(p-F) | |
| D-427 | Het-5 | OCH₂CH₂ | H | 1 | Ph (3,5-dichloro) | |
| D-428 | Het-5 | OCH₂CH₂ | H | 1 | CH₂Ph | |
| D-429 | Het-5 | OCH₂CH₂ | H | 1 | CH₂CH₂Ph | |
| D-430 | Het-5 | OCH₂CH₂ | H | 1 | 3-pyridyl | |
| D-431 | Het-5 | OCH₂CH₂ | H | 1 | 5-pyrimidinyl | |
| D-432 | Het-5 | OCH₂CH₂ | H | 1 | 3-quinolyl | |
| D-433 | Het-6 | NHCH₂ | H | 1 | CH=CH2 | |
| D-434 | Het-6 | NHCH₂ | H | 1 | C≡CH | |
| D-435 | Het-6 | NHCH₂ | H | 1 | cyclopropyl | |
| D-436 | Het-6 | NHCH₂ | H | 1 | cyclohexyl | |
| D-437 | Het-6 | NHCH₂ | H | 1 | Ph | |
| D-438 | Het-6 | NHCH₂ | H | 1 | Ph(p-F) | |
| D-439 | Het-6 | NHCH₂ | H | 1 | Ph (3,5-dichloro) | |
| D-440 | Het-6 | NHCH₂ | H | 1 | CH₂Ph | |
| D-441 | Het-6 | NHCH₂ | H | 1 | CH₂CH₂Ph | |
| D-442 | Het-6 | NHCH₂ | H | 1 | 3-pyridyl | |
| D-443 | Het-6 | NHCH₂ | H | 1 | 5-pyrimidinyl | |
| D-444 | Het-6 | NHCH₂ | H | 1 | 3-quinolyl | |
| D-445 | Het-6 | NHCH₂CH₂ | H | 1 | CH=CH2 | |
| D-446 | Het-6 | NHCH₂CH₂ | H | 1 | C≡CH | |
| D-447 | Het-6 | NHCH₂CH₂ | H | 1 | cyclopropyl | |
| D-448 | Het-6 | NHCH₂CH₂ | H | 1 | cyclohexyl | |
| D-449 | Het-6 | NHCH₂CH₂ | H | 1 | Ph | |
| D-450 | Het-6 | NHCH₂CH₂ | H | 1 | Ph(p-F) | |
| D-451 | Het-6 | NHCH₂CH₂ | H | 1 | Ph (3,5-dichloro) | |
| D-452 | Het-6 | NHCH₂CH₂ | H | 1 | CH₂Ph | |
| D-453 | Het-6 | NHCH₂CH₂ | H | 1 | CH₂CH₂Ph | |
| D-454 | Het-6 | NHCH₂CH₂ | H | 1 | 3-pyridyl | |
| D-455 | Het-6 | NHCH₂CH₂ | H | 1 | 5-pyrimidinyl | |
| D-456 | Het-6 | NHCH₂CH₂ | H | 1 | 3-quinolyl | |
| D-457 | Het-7 | NHCH₂ | H | 1 | CH=CH2 | |
| D-458 | Het-7 | NHCH₂ | H | 1 | C≡CH | |
| D-459 | Het-7 | NHCH₂ | H | 1 | cyclopropyl | |
| D-460 | Het-7 | NHCH₂ | H | 1 | cyclohexyl | |
| D-461 | Het-7 | NHCH₂ | H | 1 | Ph | |
| D-462 | Het-7 | NHCH₂ | H | 1 | Ph(p-F) | |
| D-463 | Het-7 | NHCH₂ | H | 1 | Ph (3,5-dichloro) | |
| D-464 | Het-7 | NHCH₂ | H | 1 | CH₂Ph | |
| D-465 | Het-7 | NHCH₂ | H | 1 | CH₂CH₂Ph | |
| D-466 | Het-7 | NHCH₂ | H | 1 | 3-pyridyl | |
| D-467 | Het-7 | NHCH₂ | H | 1 | 5-pyrimindinyl | |
| D-468 | Het-7 | NHCH₂ | H | 1 | 3-quinolyl | |
| D-469 | Het-7 | NHCH₂CH₂ | H | 1 | CH=CH2 | |

TABLE 4-continued

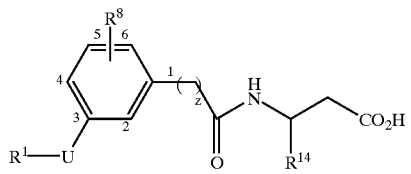

| Ex. No. | R¹ | U | R⁸ | z | R¹⁴ | MS |
|---|---|---|---|---|---|---|
| D-470 | Het-7 | NHCH₂CH₂ | H | 1 | C≡CH | |
| D-471 | Het-7 | NHCH₂CH₂ | H | 1 | cyclopropyl | |
| D-472 | Het-7 | NHCH₂CH₂ | H | 1 | cyclohexyl | |
| D-473 | Het-7 | NHCH₂CH₂ | H | 1 | Ph | |
| D-474 | Het-7 | NHCH₂CH₂ | H | 1 | Ph(p-F) | |
| D-475 | Het-7 | NHCH₂CH₂ | H | 1 | Ph (3,5-dichloro) | |
| D-476 | Het-7 | NHCH₂CH₂ | H | 1 | CH₂Ph | |
| D-477 | Het-7 | NHCH₂CH₂ | H | 1 | CH₂CH₂Ph | |
| D-478 | Het-7 | NHCH₂CH₂ | H | 1 | 3-pyridyl | |
| D-479 | Het-7 | NHCH₂CH₂ | H | 1 | 5-pyrimidinyl | |
| D-480 | Het-7 | NHCH₂CH₂ | H | 1 | 3-quinolyl | |
| D-481 | Het-8 | NHCH₂ | H | 1 | CH=CH2 | |
| D-482 | Het-8 | NHCH₂ | H | 1 | C≡CH | |
| D-483 | Het-8 | NHCH₂ | H | 1 | cyclopropyl | |
| D-484 | Het-8 | NHCH₂ | H | 1 | cyclohexyl | |
| D-485 | Het-8 | NHCH₂ | H | 1 | Ph | |
| D-486 | Het-8 | NHCH₂ | H | 1 | Ph(p-F) | |
| D-487 | Het-8 | NHCH₂ | H | 1 | Ph (3,5-dichloro) | |
| D-488 | Het-8 | NHCH₂ | H | 1 | CH₂Ph | |
| D-489 | Het-8 | NHCH₂ | H | 1 | CH₂CH₂Ph | |
| D-490 | Het-8 | NHCH₂ | H | 1 | 3-pyridyl | |
| D-491 | Het-8 | NHCH₂ | H | 1 | 5-pyrimidinyl | |
| D-492 | Het-8 | NHCH₂ | H | 1 | 3-quinolyl | |
| D-493 | Het-8 | NHCH₂CH₂ | H | 1 | CH=CH2 | |
| D-494 | Het-8 | NHCH₂CH₂ | H | 1 | C≡CH | |
| D-495 | Het-8 | NHCH₂CH₂ | H | 1 | cyclopropyl | |
| D-496 | Het-8 | NHCH₂CH₂ | H | 1 | cyclohexyl | |
| D-497 | Het-8 | NHCH₂CH₂ | H | 1 | Ph | |
| D-498 | Het-8 | NHCH₂CH₂ | H | 1 | Ph(p-F) | |
| D-499 | Het-8 | NHCH₂CH₂ | H | 1 | Ph (3,5-dichloro) | |
| D-500 | Het-8 | NHCH₂CH₂ | H | 1 | CH₂Ph | |
| D-501 | Het-8 | NHCH₂CH₂ | H | 1 | CH₂CH₂Ph | |
| D-502 | Het-8 | NHCH₂CH₂ | H | 1 | 3-pyridyl | |
| D-503 | Het-8 | NHCH₂CH₂ | H | 1 | 5-pyrimidinyl | |
| D-504 | Het-8 | NHCH₂CH₂ | H | 1 | 3-quinolyl | |
| D-505 | Het-9 | NHCH₂ | H | 1 | CH=CH2 | |
| D-506 | Het-9 | NHCH₂ | H | 1 | C≡CH | |
| D-507 | Het-9 | NHCH₂ | H | 1 | cyclopropyl | |
| D-508 | Het-9 | NHCH₂ | H | 1 | cyclohexyl | |
| D-509 | Het-9 | NHCH₂ | H | 1 | Ph | |
| D-510 | Het-9 | NHCH₂ | H | 1 | Ph(p-F) | |
| D-511 | Het-9 | NHCH₂ | H | 1 | Ph (3,5-dichloro) | |
| D-512 | Het-9 | NHCH₂ | H | 1 | CH₂Ph | |
| D-513 | Het-9 | NHCH₂ | H | 1 | CH₂CH₂Ph | |
| D-514 | Het-9 | NHCH₂ | H | 1 | 3-pyridyl | |
| D-515 | Het-9 | NHCH₂ | H | 1 | 5-pyrimidinyl | |
| D-516 | Het-9 | NHCH₂ | H | 1 | 3-quinolyl | |
| D-517 | Het-9 | NHCH₂CH₂ | H | 1 | CH=CH2 | |
| D-518 | Het-9 | NHCH₂CH₂ | H | 1 | C≡CH | |
| D-519 | Het-9 | NHCH₂CH₂ | H | 1 | cyclopropyl | |
| D-520 | Het-9 | NHCH₂CH₂ | H | 1 | cyclohexyl | |
| D-521 | Het-9 | NHCH₂CH₂ | H | 1 | Ph | |
| D-522 | Het-9 | NHCH₂CH₂ | H | 1 | Ph(p-F) | |
| D-523 | Het-9 | NHCH₂CH₂ | H | 1 | Ph (3,5-dichloro) | |
| D-524 | Het-9 | NHCH₂CH₂ | H | 1 | CH₂Ph | |
| D-525 | Het-9 | NHCH₂CH₂ | H | 1 | CH₂CH₂Ph | |
| D-526 | Het-9 | NHCH₂CH₂ | H | 1 | 3-pyridyl | |
| D-527 | Het-9 | NHCH₂CH₂ | H | 1 | 5-pyrimidinyl | |
| D-528 | Het-9 | NHCH₂CH₂ | H | 1 | 3-quinolyl | |
| D-529 | Het-10 | NHCH₂ | H | 1 | CH=CH2 | |
| D-530 | Het-10 | NHCH₂ | H | 1 | C≡CH | |
| D-531 | Het-10 | NHCH₂ | H | 1 | cyclopropyl | |
| D-532 | Het-10 | NHCH₂ | H | 1 | cyclohexyl | |
| D-533 | Het-10 | NHCH₂ | H | 1 | Ph | |
| D-534 | Het-10 | NHCH₂ | H | 1 | Ph(p-F) | |
| D-535 | Het-10 | NHCH₂ | H | 1 | Ph (3,5-dichloro) | |
| D-536 | Het-10 | NHCH₂ | H | 1 | CH₂Ph | |

TABLE 4-continued

| Ex. No. | R¹ | U | R⁸ | z | R¹⁴ | MS |
|---|---|---|---|---|---|---|
| D-537 | Het-10 | NHCH₂ | H | 1 | CH₂CH₂Ph | |
| D-538 | Het-10 | NHCH₂ | H | 1 | 3-pyridyl | |
| D-539 | Het-10 | NHCH₂ | H | 1 | 5-pyrimidinyl | |
| D-540 | Het-10 | NHCH₂ | H | 1 | 3-quinolyl | |
| D-541 | Het-10 | NHCH₂CH₂ | H | 1 | CH=CH2 | |
| D-542 | Het-10 | NHCH₂CH₂ | H | 1 | C≡CH | |
| D-543 | Het-10 | NHCH₂CH₂ | H | 1 | cyclopropyl | |
| D-544 | Het-10 | NHCH₂CH₂ | H | 1 | cyclohexyl | |
| D-545 | Het-10 | NHCH₂CH₂ | H | 1 | Ph | |
| D-546 | Het-10 | NHCH₂CH₂ | H | 1 | Ph(p-F) | |
| D-547 | Het-10 | NHCH₂CH₂ | H | 1 | Ph (3,5-dichloro) | |
| D-548 | Het-10 | NHCH₂CH₂ | H | 1 | CH₂Ph | |
| D-549 | Het-10 | NHCH₂CH₂ | H | 1 | CH₂CH₂Ph | |
| D-550 | Het-10 | NHCH₂CH₂ | H | 1 | 3-pyridyl | |
| D-551 | Het-10 | NHCH₂CH₂ | H | 1 | 5-pyrimidinyl | |
| D-552 | Het-10 | NHCH₂CH₂ | H | 1 | 3-quinolyl | |
| D-553 | Het-11 | NHCH₂ | H | 1 | CH=CH2 | |
| D-554 | Het-11 | NHCH₂ | H | 1 | C≡CH | |
| D-555 | Het-11 | NHCH₂ | H | 1 | cyclopropyl | |
| D-556 | Het-11 | NHCH₂ | H | 1 | cyclohexyl | |
| D-557 | Het-11 | NHCH₂ | H | 1 | Ph | |
| D-558 | Het-11 | NHCH₂ | H | 1 | Ph(p-F) | |
| D-559 | Het-11 | NHCH₂ | H | 1 | Ph (3,5-dichloro) | |
| D-560 | Het-11 | NHCH₂ | H | 1 | CH₂Ph | |
| D-561 | Het-11 | NHCH₂ | H | 1 | CH₂CH₂Ph | |
| D-562 | Het-11 | NHCH₂ | H | 1 | 3-pyridyl | |
| D-563 | Het-11 | NHCH₂ | H | 1 | 5-pyrimidinyl | |
| D-564 | Het-11 | NHCH₂ | H | 1 | 3-quinolyl | |
| D-565 | Het-11 | NHCH₂CH₂ | H | 1 | CH=CH2 | |
| D-566 | Het-11 | NHCH₂CH₂ | H | 1 | C≡CH | |
| D-567 | Het-11 | NHCH₂CH₂ | H | 1 | cyclopropyl | |
| D-568 | Het-11 | NHCH₂CH₂ | H | 1 | cyclohexyl | |
| D-569 | Het-11 | NHCH₂CH₂ | H | 1 | Ph | |
| D-570 | Het-11 | NHCH₂CH₂ | H | 1 | Ph(p-F) | |
| D-571 | Het-11 | NHCH₂CH₂ | H | 1 | Ph (3,5-dichloro) | |
| D-572 | Het-11 | NHCH₂CH₂ | H | 1 | CH₂Ph | |
| D-573 | Het-11 | NHCH₂CH₂ | H | 1 | CH₂CH₂Ph | |
| D-574 | Het-11 | NHCH₂CH₂ | H | 1 | 3-pyridyl | |
| D-575 | Het-11 | NHCH₂CH₂ | H | 1 | 5-pyrimidinyl | |
| D-576 | Het-11 | NHCH₂CH₂ | H | 1 | 3-quinolyl | |
| D-577 | Het-12 | NHCH₂ | H | 1 | CH=CH2 | |
| D-578 | Het-12 | NHCH₂ | H | 1 | C≡CH | |
| D-579 | Het-12 | NHCH₂ | H | 1 | cyclopropyl | |
| D-580 | Het-12 | NHCH₂ | H | 1 | cyclohexyl | |
| D-581 | Het-12 | NHCH₂ | H | 1 | Ph | |
| D-582 | Het-12 | NHCH₂ | H | 1 | Ph(p-F) | |
| D-583 | Het-12 | NHCH₂ | H | 1 | Ph (3,5-dichloro) | |
| D-584 | Het-12 | NHCH₂ | H | 1 | CH₂Ph | |
| D-585 | Het-12 | NHCH₂ | H | 1 | CH₂CH₂Ph | |
| D-586 | Het-12 | NHCH₂ | H | 1 | 3-pyridyl | |
| D-587 | Het-12 | NHCH₂ | H | 1 | 5-pyrimidinyl | |
| D-588 | Het-12 | NHCH₂ | H | 1 | 3-quinolyl | |
| D-589 | Het-12 | NHCH₂CH₂ | H | 1 | CH=CH2 | |
| D-590 | Het-12 | NHCH₂CH₂ | H | 1 | C≡CH | |
| D-591 | Het-12 | NHCH₂CH₂ | H | 1 | cyclopropyl | |
| D-592 | Het-12 | NHCH₂CH₂ | H | 1 | cyclohexyl | |
| D-593 | Het-12 | NHCH₂CH₂ | H | 1 | Ph | |
| D-594 | Het-12 | NHCH₂CH₂ | H | 1 | Ph(p-F) | |
| D-595 | Het-12 | NHCH₂CH₂ | H | 1 | Ph (3,5-dichloro) | |
| D-596 | Het-12 | NHCH₂CH₂ | H | 1 | CH₂Ph | |
| D-597 | Het-12 | NHCH₂CH₂ | H | 1 | CH₂CH₂Ph | |
| D-598 | Het-12 | NHCH₂CH₂ | H | 1 | 3-pyridyl | |
| D-599 | Het-12 | NHCH₂CH₂ | H | 1 | 5-pyrimidinyl | |
| D-600 | Het-12 | NHCH₂CH₂ | H | 1 | 3-quinolyl | |
| D-601 | Het-13 | NHCH₂ | H | 1 | CH=CH2 | |
| D-602 | Het-13 | NHCH₂ | H | 1 | C≡CH | |
| D-603 | Het-13 | NHCH₂ | H | 1 | cyclopropyl | |
| D-604 | Het-13 | NHCH₂ | H | 1 | cyclohexyl | |
| D-605 | Het-13 | NHCH₂ | H | 1 | Ph | |
| D-606 | Het-13 | NHCH₂ | H | 1 | Ph(p-F) | |
| D-607 | Het-13 | NHCH₂ | H | 1 | Ph (3,5-dichloro) | |
| D-608 | Het-13 | NHCH₂ | H | 1 | CH₂Ph | |
| D-609 | Het-13 | NHCH₂ | H | 1 | CH₂CH₂Ph | |
| D-610 | Het-13 | NHCH₂ | H | 1 | 3-pyridyl | |
| D-611 | Het-13 | NHCH₂ | H | 1 | 5-pyrimidinyl | |
| D-612 | Het-13 | NHCH₂ | H | 1 | 3-quinolyl | |
| D-613 | Het-13 | NHCH₂CH₂ | H | 1 | CH=CH2 | |
| D-614 | Het-13 | NHCH₂CH₂ | H | 1 | C≡CH | |
| D-615 | Het-13 | NHCH₂CH₂ | H | 1 | cyclopropyl | |
| D-616 | Het-13 | NHCH₂CH₂ | H | 1 | cyclohexyl | |
| D-617 | Het-13 | NHCH₂CH₂ | H | 1 | Ph | |
| D-618 | Het-13 | NHCH₂CH₂ | H | 1 | Ph(p-F) | |
| D-619 | Het-13 | NHCH₂CH₂ | H | 1 | Ph (3,5-dichloro) | |
| D-620 | Het-13 | NHCH₂CH₂ | H | 1 | CH₂Ph | |
| D-621 | Het-13 | NHCH₂CH₂ | H | 1 | CH₂CH₂Ph | |
| D-622 | Het-13 | NHCH₂CH₂ | H | 1 | 3-pyridyl | |
| D-623 | Het-13 | NHCH₂CH₂ | H | 1 | 5-pyrimidinyl | |
| D-624 | Het-13 | NHCH₂CH₂ | H | 1 | 3-quinolyl | |
| D-625 | Het-14 | NHCH₂ | H | 1 | CH=CH2 | |
| D-626 | Het-14 | NHCH₂ | H | 1 | C≡CH | |
| D-627 | Het-14 | NHCH₂ | H | 1 | cyclopropyl | |
| D-628 | Het-14 | NHCH₂ | H | 1 | cyclohexyl | |
| D-629 | Het-14 | NHCH₂ | H | 1 | Ph | |
| D-630 | Het-14 | NHCH₂ | H | 1 | Ph(p-F) | |
| D-631 | Het-14 | NHCH₂ | H | 1 | Ph (3,5-dichloro) | |
| D-632 | Het-14 | NHCH₂ | H | 1 | CH₂Ph | |
| D-633 | Het-14 | NHCH₂ | H | 1 | CH₂CH₂Ph | |
| D-634 | Het-14 | NHCH₂ | H | 1 | 3-pyridyl | |
| D-635 | Het-14 | NHCH₂ | H | 1 | 5-pyrimidinyl | |
| D-636 | Het-14 | NHCH₂ | H | 1 | 3-quinolyl | |
| D-637 | Het-14 | NHCH₂CH₂ | H | 1 | CH=CH2 | |
| D-638 | Het-14 | NHCH₂CH₂ | H | 1 | C≡CH | |
| D-639 | Het-14 | NHCH₂CH₂ | H | 1 | cyclopropyl | |
| D-640 | Het-14 | NHCH₂CH₂ | H | 1 | cyclohexyl | |
| D-641 | Het-14 | NHCH₂CH₂ | H | 1 | Ph | |
| D-642 | Het-14 | NHCH₂CH₂ | H | 1 | Ph(p-F) | |
| D-643 | Het-14 | NHCH₂CH₂ | H | 1 | Ph (3,5-dichloro) | |
| D-644 | Het-14 | NHCH₂CH₂ | H | 1 | CH₂Ph | |
| D-645 | Het-14 | NHCH₂CH₂ | H | 1 | CH₂CH₂Ph | |
| D-646 | Het-14 | NHCH₂CH₂ | H | 1 | 3-pyridyl | |
| D-647 | Het-14 | NHCH₂CH₂ | H | 1 | 5-pyrimidinyl | |
| D-648 | Het-14 | NHCH₂CH₂ | H | 1 | 3-quinolyl | |
| D-649 | Het-15 | NHCH₂ | H | 1 | CH=CH2 | |
| D-650 | Het-15 | NHCH₂ | H | 1 | C≡CH | |
| D-651 | Het-15 | NHCH₂ | H | 1 | cyclopropyl | |
| D-652 | Het-15 | NHCH₂ | H | 1 | cyclohexyl | |
| D-653 | Het-15 | NHCH₂ | H | 1 | Ph | |
| D-654 | Het-15 | NHCH₂ | H | 1 | Ph(p-F) | |
| D-655 | Het-15 | NHCH₂ | H | 1 | Ph (3,5-dichloro) | |
| D-656 | Het-15 | NHCH₂ | H | 1 | CH₂Ph | |
| D-657 | Het-15 | NHCH₂ | H | 1 | CH₂CH₂Ph | |
| D-658 | Het-15 | NHCH₂ | H | 1 | 3-pyridyl | |
| D-659 | Het-15 | NHCH₂ | H | 1 | 5-pyrimidinyl | |
| D-660 | Het-15 | NHCH₂ | H | 1 | 3-quinolyl | |
| D-661 | Het-15 | NHCH₂CH₂ | H | 1 | CH=CH2 | |
| D-662 | Het-15 | NHCH₂CH₂ | H | 1 | C≡CH | |
| D-663 | Het-15 | NHCH₂CH₂ | H | 1 | cyclopropyl | |
| D-664 | Het-15 | NHCH₂CH₂ | H | 1 | cyclohexyl | |
| D-665 | Het-15 | NHCH₂CH₂ | H | 1 | Ph | |
| D-666 | Het-15 | NHCH₂CH₂ | H | 1 | Ph(p-F) | |
| D-667 | Het-15 | NHCH₂CH₂ | H | 1 | Ph (3,5-dichloro) | |
| D-668 | Het-15 | NHCH₂CH₂ | H | 1 | CH₂Ph | |
| D-669 | Het-15 | NHCH₂CH₂ | H | 1 | CH₂CH₂Ph | |
| D-670 | Het-15 | NHCH₂CH₂ | H | 1 | 3-pyridyl | |

TABLE 4-continued

| Ex. No. | R¹ | U | R⁸ | z | R¹⁴ | MS |
|---|---|---|---|---|---|---|
| D-671 | Het-15 | NHCH$_2$CH$_2$ | H | 1 | 5-pyrimidinyl | |
| D-672 | Het-15 | NHCH$_2$CH$_2$ | H | 1 | 3-quinolyl | |
| D-673 | Het-8 | CH$_2$CH$_2$ | H | 1 | CH=CH2 | |
| D-674 | Het-8 | CH$_2$CH$_2$ | H | 1 | C≡CH | |
| D-675 | Het-8 | CH$_2$CH$_2$ | H | 1 | cyclopropyl | |
| D-676 | Het-8 | CH$_2$CH$_2$ | H | 1 | cyclohexyl | |
| D-677 | Het-8 | CH$_2$CH$_2$ | H | 1 | Ph | |
| D-678 | Het-8 | CH$_2$CH$_2$ | H | 1 | Ph(p-F) | |
| D-679 | Het-8 | CH$_2$CH$_2$ | H | 1 | Ph (3,5-dichloro) | |
| D-680 | Het-8 | CH$_2$CH$_2$ | H | 1 | CH$_2$Ph | |
| D-681 | Het-8 | CH$_2$CH$_2$ | H | 1 | CH$_2$CH$_2$Ph | |
| D-682 | Het-8 | CH$_2$CH$_2$ | H | 1 | 3-pyridyl | |
| D-683 | Het-8 | CH$_2$CH$_2$ | H | 1 | 5-pyrimidinyl | |
| D-684 | Het-8 | CH$_2$CH$_2$ | H | 1 | 3-quinolyl | |
| D-685 | Het-8 | CH$_2$CH$_2$CH$_2$ | H | 1 | CH=CH2 | |
| D-686 | Het-8 | CH$_2$CH$_2$CH$_2$ | H | 1 | C≡CH | |
| D-687 | Het-8 | CH$_2$CH$_2$CH$_2$ | H | 1 | cyclopropyl | |
| D-688 | Het-8 | CH$_2$CH$_2$CH$_2$ | H | 1 | cyclohexyl | |
| D-689 | Het-8 | CH$_2$CH$_2$CH$_2$ | H | 1 | Ph | |
| D-690 | Het-8 | CH$_2$CH$_2$CH$_2$ | H | 1 | Ph(p-F) | |
| D-691 | Het-8 | CH$_2$CH$_2$CH$_2$ | H | 1 | Ph (3,5-dichloro) | |
| D-692 | Het-8 | CH$_2$CH$_2$CH$_2$ | H | 1 | CH$_2$Ph | |
| D-693 | Het-8 | CH$_2$CH$_2$CH$_2$ | H | 1 | CH$_2$CH$_2$Ph | |
| D-694 | Het-8 | CH$_2$CH$_2$CH$_2$ | H | 1 | 3-pyridyl | |
| D-695 | Het-8 | CH$_2$CH$_2$CH$_2$ | H | 1 | 5-pyrimidinyl | |
| D-696 | Het-8 | CH$_2$CH$_2$CH$_2$ | H | 1 | 3-quinolyl | |
| D-697 | Het-16 | CH$_2$CH$_2$ | H | 1 | CH=CH2 | |
| D-698 | Het-16 | CH$_2$CH$_2$ | H | 1 | C≡CH | |
| D-699 | Het-16 | CH$_2$CH$_2$ | H | 1 | cyclopropyl | |
| D-700 | Het-16 | CH$_2$CH$_2$ | H | 1 | cyclohexyl | |
| D-701 | Het-16 | CH$_2$CH$_2$ | H | 1 | Ph | |
| D-702 | Het-16 | CH$_2$CH$_2$ | H | 1 | Ph(p-F) | |
| D-703 | Het-16 | CH$_2$CH$_2$ | H | 1 | Ph (3,5-dichloro) | |
| D-704 | Het-16 | CH$_2$CH$_2$ | H | 1 | CH$_2$Ph | |
| D-705 | Het-16 | CH$_2$CH$_2$ | H | 1 | CH$_2$CH$_2$Ph | |
| D-706 | Het-16 | CH$_2$CH$_2$ | H | 1 | 3-pyridyl | |
| D-707 | Het-16 | CH$_2$CH$_2$ | H | 1 | 5-pyrimidinyl | |
| D-708 | Het-16 | CH$_2$CH$_2$ | H | 1 | 3-quinolyl | |
| D-709 | Het-16 | CH$_2$CH$_2$CH$_2$ | H | 1 | CH=CH2 | |
| D-710 | Het-16 | CH$_2$CH$_2$CH$_2$ | H | 1 | C≡CH | |
| D-711 | Het-16 | CH$_2$CH$_2$CH$_2$ | H | 1 | cyclopropyl | |
| D-712 | Het-16 | CH$_2$CH$_2$CH$_2$ | H | 1 | cyclohexyl | |
| D-713 | Het-16 | CH$_2$CH$_2$CH$_2$ | H | 1 | Ph | |
| D-714 | Het-16 | CH$_2$CH$_2$CH$_2$ | H | 1 | Ph(p-F) | |
| D-715 | Het-16 | CH$_2$CH$_2$CH$_2$ | H | 1 | Ph (3,5-dichloro) | |
| D-716 | Het-16 | CH$_2$CH$_2$CH$_2$ | H | 1 | CH$_2$Ph | |
| D-717 | Het-16 | CH$_2$CH$_2$CH$_2$ | H | 1 | CH$_2$CH$_2$Ph | |
| D-718 | Het-16 | CH$_2$CH$_2$CH$_2$ | H | 1 | 3-pyridyl | |
| D-719 | Het-16 | CH$_2$CH$_2$CH$_2$ | H | 1 | 5-pyrimidinyl | |
| D-720 | Het-16 | CH$_2$CH$_2$CH$_2$ | H | 1 | 3-quinolyl | |
| D-721 | Het-17 | CH$_2$CH$_2$ | H | 1 | CH=CH2 | |
| D-722 | Het-17 | CH$_2$CH$_2$ | H | 1 | C≡CH | |
| D-723 | Het-17 | CH$_2$CH$_2$ | H | 1 | cyclopropyl | |
| D-724 | Het-17 | CH$_2$CH$_2$ | H | 1 | cyclohexyl | |
| D-725 | Het-17 | CH$_2$CH$_2$ | H | 1 | Ph | |
| D-726 | Het-17 | CH$_2$CH$_2$ | H | 1 | Ph(p-F) | |
| D-727 | Het-17 | CH$_2$CH$_2$ | H | 1 | Ph (3,5-dichloro) | |
| D-728 | Het-17 | CH$_2$CH$_2$ | H | 1 | CH$_2$Ph | |
| D-729 | Het-17 | CH$_2$CH$_2$ | H | 1 | CH$_2$CH$_2$Ph | |
| D-730 | Het-17 | CH$_2$CH$_2$ | H | 1 | 3-pyridyl | |
| D-731 | Het-17 | CH$_2$CH$_2$ | H | 1 | 5-pyrimidinyl | |
| D-732 | Het-17 | CH$_2$CH$_2$ | H | 1 | 3-quinolyl | |
| D-733 | Het-17 | CH$_2$CH$_2$CH$_2$ | H | 1 | CH=CH2 | |
| D-734 | Het-17 | CH$_2$CH$_2$CH$_2$ | H | 1 | C≡CH | |
| D-735 | Het-17 | CH$_2$CH$_2$CH$_2$ | H | 1 | cyclopropyl | |
| D-736 | Het-17 | CH$_2$CH$_2$CH$_2$ | H | 1 | cyclohexyl | |
| D-737 | Het-17 | CH$_2$CH$_2$CH$_2$ | H | 1 | Ph | |
| D-738 | Het-17 | CH$_2$CH$_2$CH$_2$ | H | 1 | Ph(p-F) | |
| D-739 | Het-17 | CH$_2$CH$_2$CH$_2$ | H | 1 | Ph (3,5-dichloro) | |
| D-740 | Het-17 | CH$_2$CH$_2$CH$_2$ | H | 1 | CH$_2$Ph | |
| D-741 | Het-17 | CH$_2$CH$_2$CH$_2$ | H | 1 | CH$_2$CH$_2$Ph | |
| D-742 | Het-17 | CH$_2$CH$_2$CH$_2$ | H | 1 | 3-pyridyl | |
| D-743 | Het-17 | CH$_2$CH$_2$CH$_2$ | H | 1 | 5-pyrimidinyl | |
| D-744 | Het-17 | CH$_2$CH$_2$CH$_2$ | H | 1 | 3-quinolyl | |
| D-745 | Het-18 | CH$_2$CH$_2$ | H | 1 | CH=CH2 | |
| D-746 | Het-18 | CH$_2$CH$_2$ | H | 1 | C≡CH | |
| D-747 | Het-18 | CH$_2$CH$_2$ | H | 1 | cyclopropyl | |
| D-748 | Het-18 | CH$_2$CH$_2$ | H | 1 | cyclohexyl | |
| D-749 | Het-18 | CH$_2$CH$_2$ | H | 1 | Ph | |
| D-750 | Het-18 | CH$_2$CH$_2$ | H | 1 | Ph(p-F) | |
| D-751 | Het-18 | CH$_2$CH$_2$ | H | 1 | Ph (3,5-dichloro) | |
| D-752 | Het-18 | CH$_2$CH$_2$ | H | 1 | CH$_2$Ph | |
| D-753 | Het-18 | CH$_2$CH$_2$ | H | 1 | CH$_2$CH$_2$Ph | |
| D-754 | Het-18 | CH$_2$CH$_2$ | H | 1 | 3-pyridyl | |
| D-755 | Het-18 | CH$_2$CH$_2$ | H | 1 | 5-pyrimidinyl | |
| D-756 | Het-18 | CH$_2$CH$_2$ | H | 1 | 3-quinolyl | |
| D-757 | Het-18 | CH$_2$CH$_2$CH$_2$ | H | 1 | CH=CH2 | |
| D-758 | Het-18 | CH$_2$CH$_2$CH$_2$ | H | 1 | C≡CH | |
| D-759 | Het-18 | CH$_2$CH$_2$CH$_2$ | H | 1 | cyclopropyl | |
| D-760 | Het-18 | CH$_2$CH$_2$CH$_2$ | H | 1 | cyclohexyl | |
| D-761 | Het-18 | CH$_2$CH$_2$CH$_2$ | H | 1 | Ph | |
| D-762 | Het-18 | CH$_2$CH$_2$CH$_2$ | H | 1 | Ph(p-F) | |
| D-763 | Het-18 | CH$_2$CH$_2$CH$_2$ | H | 1 | Ph (3,5-dichloro) | |
| D-764 | Het-18 | CH$_2$CH$_2$CH$_2$ | H | 1 | CH$_2$Ph | |
| D-765 | Het-18 | CH$_2$CH$_2$CH$_2$ | H | 1 | CH$_2$CH$_2$Ph | |
| D-766 | Het-18 | CH$_2$CH$_2$CH$_2$ | H | 1 | 3-pyridyl | |
| D-767 | Het-18 | CH$_2$CH$_2$CH$_2$ | H | 1 | 5-pyrimidinyl | |
| D-768 | Het-18 | CH$_2$CH$_2$CH$_2$ | H | 1 | 3-quinolyl | |
| D-769 | Het-13 | CH$_2$CH$_2$ | H | 1 | CH=CH2 | |
| D-770 | Het-13 | CH$_2$CH$_2$ | H | 1 | C≡CH | |
| D-771 | Het-13 | CH$_2$CH$_2$ | H | 1 | cyclopropyl | |
| D-772 | Het-13 | CH$_2$CH$_2$ | H | 1 | cyclohexyl | |
| D-773 | Het-13 | CH$_2$CH$_2$ | H | 1 | Ph | |
| D-774 | Het-13 | CH$_2$CH$_2$ | H | 1 | Ph(p-F) | |
| D-775 | Het-13 | CH$_2$CH$_2$ | H | 1 | Ph (3,5-dichloro) | |
| D-776 | Het-13 | CH$_2$CH$_2$ | H | 1 | CH$_2$Ph | |
| D-777 | Het-13 | CH$_2$CH$_2$ | H | 1 | CH$_2$CH$_2$Ph | |
| D-778 | Het-13 | CH$_2$CH$_2$ | H | 1 | 3-pyridyl | |
| D-779 | Het-13 | CH$_2$CH$_2$ | H | 1 | 5-pyrimidinyl | |
| D-780 | Het-13 | CH$_2$CH$_2$ | H | 1 | 3-quinolyl | |
| D-781 | Het-13 | CH$_2$CH$_2$CH$_2$ | H | 1 | CH=CH2 | |
| D-782 | Het-13 | CH$_2$CH$_2$CH$_2$ | H | 1 | C≡CH | |
| D-783 | Het-13 | CH$_2$CH$_2$CH$_2$ | H | 1 | cyclopropyl | |
| D-784 | Het-13 | CH$_2$CH$_2$CH$_2$ | H | 1 | cyclohexyl | |
| D-785 | Het-13 | CH$_2$CH$_2$CH$_2$ | H | 1 | Ph | |
| D-786 | Het-13 | CH$_2$CH$_2$CH$_2$ | H | 1 | Ph(p-F) | |
| D-787 | Het-13 | CH$_2$CH$_2$CH$_2$ | H | 1 | Ph (3,5-dichloro) | |
| D-788 | Het-13 | CH$_2$CH$_2$CH$_2$ | H | 1 | CH$_2$Ph | |
| D-789 | Het-13 | CH$_2$CH$_2$CH$_2$ | H | 1 | CH$_2$CH$_2$Ph | |
| D-790 | Het-13 | CH$_2$CH$_2$CH$_2$ | H | 1 | 3-pyridyl | |
| D-791 | Het-13 | CH$_2$CH$_2$CH$_2$ | H | 1 | 5-pyrimidinyl | |
| D-792 | Het-13 | CH$_2$CH$_2$CH$_2$ | H | 1 | 3-quinolyl | |
| D-793 | Het-19 | CH$_2$CH$_2$ | H | 1 | CH=CH2 | |
| D-794 | Het-19 | CH$_2$CH$_2$ | H | 1 | C≡CH | |
| D-795 | Het-19 | CH$_2$CH$_2$ | H | 1 | cyclopropyl | |
| D-796 | Het-19 | CH$_2$CH$_2$ | H | 1 | cyclohexyl | |
| D-797 | Het-19 | CH$_2$CH$_2$ | H | 1 | Ph | |
| D-798 | Het-19 | CH$_2$CH$_2$ | H | 1 | Ph(p-F) | |
| D-799 | Het-19 | CH$_2$CH$_2$ | H | 1 | Ph (3,5-dichloro) | |
| D-800 | Het-19 | CH$_2$CH$_2$ | H | 1 | CH$_2$Ph | |
| D-801 | Het-19 | CH$_2$CH$_2$ | H | 1 | CH$_2$CH$_2$Ph | |
| D-802 | Het-19 | CH$_2$CH$_2$ | H | 1 | 3-pyridyl | |
| D-803 | Het-19 | CH$_2$CH$_2$ | H | 1 | 5-pyrimidinyl | |
| D-804 | Het-19 | CH$_2$CH$_2$ | H | 1 | 3-quinolyl | |

TABLE 4-continued

| Ex. No. | R¹ | U | R⁸ | z | R¹⁴ | MS |
|---|---|---|---|---|---|---|
| D-805 | Het-19 | $CH_2CH_2CH_2$ | H | 1 | CH=CH2 | |
| D-806 | Het-19 | $CH_2CH_2CH_2$ | H | 1 | C≡CH | |
| D-807 | Het-19 | $CH_2CH_2CH_2$ | H | 1 | cyclopropyl | |
| D-808 | Het-19 | $CH_2CH_2CH_2$ | H | 1 | cyclohexyl | |
| D-809 | Het-19 | $CH_2CH_2CH_2$ | H | 1 | Ph | |
| D-810 | Het-19 | $CH_2CH_2CH_2$ | H | 1 | Ph(p-F) | |
| D-811 | Het-19 | $CH_2CH_2CH_2$ | H | 1 | Ph (3,5-dichloro) | |
| D-812 | Het-19 | $CH_2CH_2CH_2$ | H | 1 | $CH_2Ph$ | |
| D-813 | Het-19 | $CH_2CH_2CH_2$ | H | 1 | $CH_2CH_2Ph$ | |
| D-814 | Het-19 | $CH_2CH_2CH_2$ | H | 1 | 3-pyridyl | |
| D-815 | Het-19 | $CH_2CH_2CH_2$ | H | 1 | 5-pyrimidinyl | |
| D-816 | Het-19 | $CH_2CH_2CH_2$ | H | 1 | 3-quinolyl | |
| D-817 | Het-20 | $CH_2CH_2$ | H | 1 | CH=CH2 | |
| D-818 | Het-20 | $CH_2CH_2$ | H | 1 | C≡CH | |
| D-819 | Het-20 | $CH_2CH_2$ | H | 1 | cyclopropyl | |
| D-820 | Het-20 | $CH_2CH_2$ | H | 1 | cyclohexyl | |
| D-821 | Het-20 | $CH_2CH_2$ | H | 1 | Ph | |
| D-822 | Het-20 | $CH_2CH_2$ | H | 1 | Ph(p-F) | |
| D-823 | Het-20 | $CH_2CH_2$ | H | 1 | Ph (3,5-dichloro) | |
| D-824 | Het-20 | $CH_2CH_2$ | H | 1 | $CH_2Ph$ | |
| D-825 | Het-20 | $CH_2CH_2$ | H | 1 | $CH_2CH_2Ph$ | |
| D-826 | Het-20 | $CH_2CH_2$ | H | 1 | 3-pyridyl | |
| D-827 | Het-20 | $CH_2CH_2$ | H | 1 | 5-pyrimidinyl | |
| D-828 | Het-20 | $CH_2CH_2$ | H | 1 | 3-quinolyl | |
| D-829 | Het-20 | $CH_2CH_2CH_2$ | H | 1 | CH=CH2 | |
| D-830 | Het-20 | $CH_2CH_2CH_2$ | H | 1 | C≡CH | |
| D-831 | Het-20 | $CH_2CH_2CH_2$ | H | 1 | cyclopropyl | |
| D-832 | Het-20 | $CH_2CH_2CH_2$ | H | 1 | cyclohexyl | |
| D-833 | Het-20 | $CH_2CH_2CH_2$ | H | 1 | Ph | |
| D-834 | Het-20 | $CH_2CH_2CH_2$ | H | 1 | Ph(p-F) | |
| D-835 | Het-20 | $CH_2CH_2CH_2$ | H | 1 | Ph (3,5-dichloro) | |
| D-836 | Het-20 | $CH_2CH_2CH_2$ | H | 1 | $CH_2Ph$ | |
| D-837 | Het-20 | $CH_2CH_2CH_2$ | H | 1 | $CH_2CH_2Ph$ | |
| D-838 | Het-20 | $CH_2CH_2CH_2$ | H | 1 | 3-pyridyl | |
| D-839 | Het-20 | $CH_2CH_2CH_2$ | H | 1 | 5-pyrimidinyl | |
| D-840 | Het-20 | $CH_2CH_2CH_2$ | H | 1 | 3-quinolyl | |
| D-841 | Het-1 | $CH_2CH_2$ | 4-OMe | 1 | CH=CH2 | |
| D-842 | Het-1 | $CH_2CH_2$ | 4-OMe | 1 | C≡CH | |
| D-843 | Het-1 | $CH_2CH_2$ | 4-OMe | 1 | cyclopropyl | |
| D-844 | Het-1 | $CH_2CH_2$ | 4-OMe | 1 | cyclohexyl | |
| D-845 | Het-1 | $CH_2CH_2$ | 4-OMe | 1 | Ph | |
| D-846 | Het-1 | $CH_2CH_2$ | 4-OMe | 1 | Ph(p-F) | |
| D-847 | Het-1 | $CH_2CH_2$ | 4-OMe | 1 | Ph (3,5-dichloro) | |
| D-848 | Het-1 | $CH_2CH_2$ | 4-OMe | 1 | $CH_2Ph$ | |
| D-849 | Het-1 | $CH_2CH_2$ | 4-OMe | 1 | $CH_2CH_2Ph$ | |
| D-850 | Het-1 | $CH_2CH_2$ | 4-OMe | 1 | 3-pyridyl | |
| D-851 | Het-1 | $CH_2CH_2$ | 4-OMe | 1 | 5-pyrimidinyl | |
| D-852 | Het-1 | $CH_2CH_2$ | 4-OMe | 1 | 3-quinolyl | |
| D-853 | Het-1 | $CH_2CH_2$ | 6-OMe | 1 | CH=CH2 | |
| D-854 | Het-1 | $CH_2CH_2$ | 6-OMe | 1 | C≡CH | |
| D-855 | Het-1 | $CH_2CH_2$ | 6-OMe | 1 | cyclopropyl | |
| D-856 | Het-1 | $CH_2CH_2$ | 6-OMe | 1 | cyclohexyl | |
| D-857 | Het-1 | $CH_2CH_2$ | 6-OMe | 1 | Ph | |
| D-858 | Het-1 | $CH_2CH_2$ | 6-OMe | 1 | Ph(p-F) | |
| D-859 | Het-1 | $CH_2CH_2$ | 6-OMe | 1 | Ph (3,5-dichloro) | |
| D-860 | Het-1 | $CH_2CH_2$ | 6-OMe | 1 | $CH_2Ph$ | |
| D-861 | Het-1 | $CH_2CH_2$ | 6-OMe | 1 | $CH_2CH_2Ph$ | |
| D-862 | Het-1 | $CH_2CH_2$ | 6-OMe | 1 | 3-pyridyl | |
| D-863 | Het-1 | $CH_2CH_2$ | 6-OMe | 1 | 5-pyrimidinyl | |
| D-864 | Het-1 | $CH_2CH_2$ | 6-OMe | 1 | 3-quinolyl | |
| D-865 | Het-2 | $CH_2CH_2$ | 4-OMe | 1 | CH=CH2 | |
| D-866 | Het-2 | $CH_2CH_2$ | 4-OMe | 1 | C≡CH | |
| D-867 | Het-2 | $CH_2CH_2$ | 4-OMe | 1 | cyclopropyl | |
| D-868 | Het-2 | $CH_2CH_2$ | 4-OMe | 1 | cyclohexyl | |
| D-869 | Het-2 | $CH_2CH_2$ | 4-OMe | 1 | Ph | |
| D-870 | Het-2 | $CH_2CH_2$ | 4-OMe | 1 | Ph(p-F) | |
| D-871 | Het-2 | $CH_2CH_2$ | 4-OMe | 1 | Ph (3,5-dichloro) | |
| D-872 | Het-2 | $CH_2CH_2$ | 4-OMe | 1 | $CH_2Ph$ | |
| D-873 | Het-2 | $CH_2CH_2$ | 4-OMe | 1 | $CH_2CH_2Ph$ | |
| D-874 | Het-2 | $CH_2CH_2$ | 4-OMe | 1 | 3-pyridyl | |
| D-875 | Het-2 | $CH_2CH_2$ | 4-OMe | 1 | 5-pyrimidinyl | |
| D-876 | Het-2 | $CH_2CH_2$ | 4-OMe | 1 | 3-quinolyl | |
| D-877 | Het-2 | $CH_2CH_2$ | 6-OMe | 1 | CH=CH2 | |
| D-878 | Het-2 | $CH_2CH_2$ | 6-OMe | 1 | C≡CH | |
| D-879 | Het-2 | $CH_2CH_2$ | 6-OMe | 1 | cyclopropyl | |
| D-880 | Het-2 | $CH_2CH_2$ | 6-OMe | 1 | cyclohexyl | |
| D-881 | Het-2 | $CH_2CH_2$ | 6-OMe | 1 | Ph | |
| D-882 | Het-2 | $CH_2CH_2$ | 6-OMe | 1 | Ph(p-F) | |
| D-883 | Het-2 | $CH_2CH_2$ | 6-OMe | 1 | Ph (3,5-dichloro) | |
| D-884 | Het-2 | $CH_2CH_2$ | 6-OMe | 1 | $CH_2Ph$ | |
| D-885 | Het-2 | $CH_2CH_2$ | 6-OMe | 1 | $CH_2CH_2Ph$ | |
| D-886 | Het-2 | $CH_2CH_2$ | 6-OMe | 1 | 3-pyridyl | |
| D-887 | Het-2 | $CH_2CH_2$ | 6-OMe | 1 | 5-pyrimidinyl | |
| D-888 | Het-2 | $CH_2CH_2$ | 6-OMe | 1 | 3-quinolyl | |
| D-889 | Het-9 | $CH_2CH_2$ | H | 1 | CH=CH2 | |

TABLE 4-continued

| Ex. No. | R¹ | U | R⁸ | z | R¹⁴ | MS |
|---|---|---|---|---|---|---|
| D-890 | Het-9 | CH₂CH₂ | H | 1 | C≡CH | |
| D-891 | Het-9 | CH₂CH₂ | H | 1 | cyclopropyl | |
| D-892 | Het-9 | CH₂CH₂ | H | 1 | cyclohexyl | |
| D-893 | Het-9 | CH₂CH₂ | H | 1 | Ph | |
| D-894 | Het-9 | CH₂CH₂ | H | 1 | Ph(p-F) | |
| D-895 | Het-9 | CH₂CH₂ | H | 1 | Ph (3,5-dichloro) | |
| D-896 | Het-9 | CH₂CH₂ | H | 1 | CH₂Ph | |
| D-897 | Het-9 | CH₂CH₂ | H | 1 | CH₂CH₂Ph | |
| D-898 | Het-9 | CH₂CH₂ | H | 1 | 3-pyridyl | |
| D-899 | Het-9 | CH₂CH₂ | H | 1 | 5-pyrimidinyl | |
| D-900 | Het-9 | CH₂CH₂ | H | 1 | 3-quinolyl | |
| D-901 | Het-9 | CH₂CH₂CH₂ | H | 1 | CH=CH2 | |
| D-902 | Het-9 | CH₂CH₂CH₂ | H | 1 | C≡CH | |
| D-903 | Het-9 | CH₂CH₂CH₂ | H | 1 | cyclopropyl | |
| D-904 | Het-9 | CH₂CH₂CH₂ | H | 1 | cyclohexyl | |
| D-905 | Het-9 | CH₂CH₂CH₂ | H | 1 | Ph | |
| D-906 | Het-9 | CH₂CH₂CH₂ | H | 1 | Ph(p-F) | |
| D-907 | Het-9 | CH₂CH₂CH₂ | H | 1 | Ph (3,5-dichloro) | |
| D-908 | Het-9 | CH₂CH₂CH₂ | H | 1 | CH₂Ph | |
| D-909 | Het-9 | CH₂CH₂CH₂ | H | 1 | CH₂CH₂Ph | |
| D-910 | Het-9 | CH₂CH₂CH₂ | H | 1 | 3-pyridyl | |
| D-911 | Het-9 | CH₂CH₂CH₂ | H | 1 | 5-pyrimidinyl | |
| D-912 | Het-9 | CH₂CH₂CH₂ | H | 1 | 3-quinolyl | |
| D-913 | Het-12 | NHCH₂ | H | 1 | CH=CH2 | |
| D-914 | Het-12 | NHCH₂ | H | 1 | C≡CH | |
| D-915 | Het-12 | NHCH₂ | H | 1 | cyclopropyl | |
| D-916 | Het-12 | NHCH₂ | H | 1 | cyclohexyl | |
| D-917 | Het-12 | NHCH₂ | H | 1 | Ph | |
| D-918 | Het-12 | NHCH₂ | H | 1 | Ph(p-F) | |
| D-919 | Het-12 | NHCH₂ | H | 1 | Ph (3,5-dichloro) | |
| D-920 | Het-12 | NHCH₂ | H | 1 | 3-pyridyl | |
| D-921 | Het-12 | NHCH₂ | H | 1 | 5-pyrimidinyl | |
| D-922 | Het-12 | NHCH₂ | H | 1 | 3-quinolyl | |
| D-923 | Het-12 | NHCH₂CH₂ | H | 1 | CH=CH2 | |
| D-924 | Het-12 | NHCH₂CH₂ | H | 1 | C≡CH | |
| D-925 | Het-12 | NHCH₂CH₂ | H | 1 | cyclopropyl | |
| D-926 | Het-12 | NHCH₂CH₂ | H | 1 | cyclohexyl | |
| D-927 | Het-12 | NHCH₂CH₂ | H | 1 | Ph | |
| D-928 | Het-12 | NHCH₂CH₂ | H | 1 | Ph(p-F) | |
| D-929 | Het-12 | NHCH₂CH₂ | H | 1 | Ph (3,5-dichloro) | |
| D-930 | Het-12 | NHCH₂CH₂ | H | 1 | 3-pyridyl | |
| D-931 | Het-12 | NHCH₂CH₂ | H | 1 | 5-pyrimidinyl | |
| D-932 | Het-12 | NHCH₂CH₂ | H | 1 | 3-quinolyl | |

What is claimed is:

1. A compound of Formula (IG):

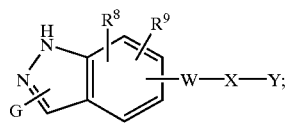

(IG)

or stereoisomeric forms thereof, tautomeric forms thereof, pharmaceutically acceptable salt forms thereof or prodrug forms thereof, wherein:

G is selected from:

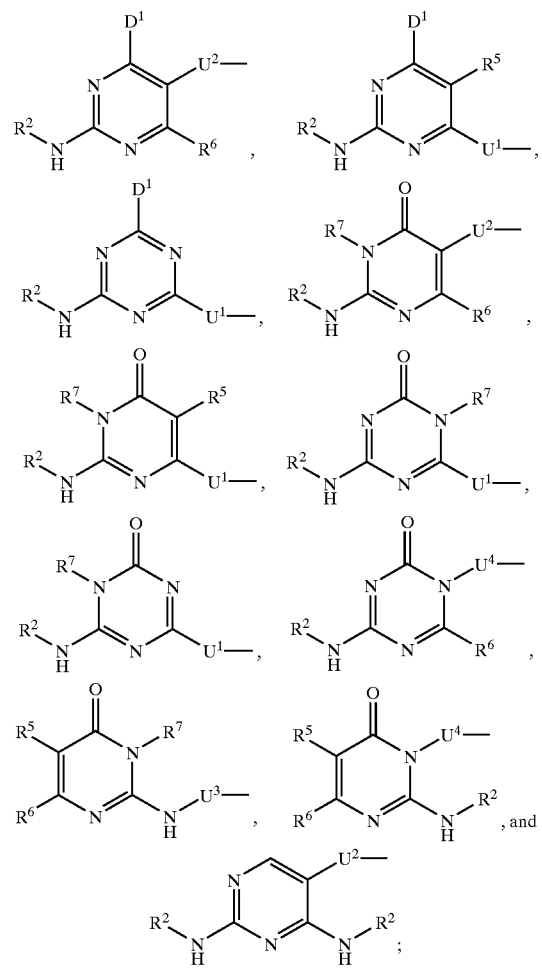

$D^1$ is selected from: $NR^2R^4$, $OR^3$, $SR^3$, F, Cl, Br, $CF_3$, and $C_1$–$C_4$ alkyl;

$R^2$ at each occurrence is independently selected from: H, $OR^3$, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl($C_0$–$C_4$ alkyl)carbonyl, $C_3$–$C_7$ cycloalkyl ($C_0$–$C_4$ alkoxy)carbonyl, aryl($C_0$–$C_6$ alkyl), heteroaryl ($C_0$–$C_6$ alkyl), aryl($C_0$–$C_6$alkyl)carbonyl, heteroaryl ($C_0$–$C_6$ alkyl)carbonyl, $C_1$–$C_6$ alkylsulfonyl, aryl ($C_0$–$C_6$ alkyl)sulfonyl, heteroaryl($C_0$–$C_6$ alkyl) sulfonyl, aryl($C_1$–$C_6$ alkoxy)carbonyl, and heteroaryl ($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^3$ at each occurrence is independently selected from: H, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl ($C_0$–$C_4$ alkyl) carbonyl, cycloalkyl ($C_0$–$C_4$ alkoxy)carbonyl, aryl($C_0$–$C_6$ alkyl), heteroaryl($C_0$–$C_6$ alkyl), aryl ($C_0$–$C_6$ alkyl) carbonyl, heteroaryl ($C_0$–$C_6$ alkyl)carbonyl, aryl ($C_1$–$C_6$ alkoxy)carbonyl, and heteroaryl($C_1$–$C_6$ alkoxy)carbonyl, wherein said aryl or heteroaryl groups are substituted with 0–2 substituents independently selected from the group consisting of $C_1-C_4$ alkyl, $C_1-C_4$ alkoxy, F, Cl, Br, $CF_3$, and $NO_2$;

$R^4$ is selected from:
  H, $C_1-C_6$ alkyl, $C_1-C_6$ alkylcarbonyl, $C_1-C_6$ alkoxycarbonyl, $C_3-C_7$ cycloalkyl($C_0-C_4$ alkyl), $C_3-C_7$ cycloalkyl($C_0-C_4$ alkyl)carbonyl, cycloalkyl ($C_0-C_4$ alkoxy)carbonyl, aryl($C_0-C_6$ alkyl), heteroaryl($C_0-C_6$ alkyl), aryl($C_0-C_6$ alkyl)carbonyl, heteroaryl($C_0-C_6$ alkyl)carbonyl, aryl($C_1-C_6$ alkoxy)carbonyl, and heteroaryl($C_1-C_6$ alkoxy)carbonyl, wherein said aryl or heteroaryl groups are substituted with 0–2 substituents independently selected from the group consisting of $C_1-C_4$ alkyl, $C_1-C_4$ alkoxy, F, Cl, Br, $CF_3$, and $NO_2$;

alternatively, $R^2$ and $R^4$ when both substituents on the same nitrogen atom as in ($—NR^2R^4$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1-C_6$ alkyl, $C_3-C_7$ cycloalkyl($C_0-C_4$ alkyl), $C_1-C_6$ alkylcarbonyl, $C_3-C_7$ cycloalkyl($C_0-C_5$ alkyl) carbonyl, $C_1-C_6$ alkoxycarbonyl, $C_3-C_7$ cycloalkyl ($C_0-C_5$ alkoxy)carbonyl, aryl($C_0-C_5$ alkyl), heteroaryl ($C_0-C_5$ alkyl), aryl($C_1-C_5$ alkoxy)carbonyl, heteroaryl ($C_1-C_5$ alkoxy)carbonyl, $C_1-C_6$ alkylsulfonyl, arylsulfonyl, and heteroarylsulfonyl;

$R^5$ is selected from:
  H, $NR^2R^4$, $OR^3$, $NO_2$, NO, $C_1-C_6$ alkyl, $C_3-C_7$ cycloalkyl($C_0-C_4$ alkyl), aryl($C_0-C_6$ alkyl), or heteroaryl($C_0-C_6$ alkyl), wherein said aryl and heteroaryl groups are substituted with 0–2 substituents independently selected from the group consisting of $C_1-C_4$ alkyl, $C_1-C_4$ alkoxy, F, Cl, Br, $CF_3$, and $NO_2$;

$R^6$ is selected from:
  H, $NR^2R^4$, $OR^3$, $C_1-C_6$ alkyl, aryl($C_0-C_5$ alkyl), heteroaryl($C_0-C_5$ alkyl), $CF_3$, F, Cl, and Br, wherein said aryl or heteroaryl groups are substituted with 0–2 substituents independently selected from the group consisting of $C_1-C_4$ alkyl, $C_1-C_4$ alkoxy, F, Cl, Br, $CF_3$, and $NO_2$;

alternatively, $R^5$ and $R^6$, when substituents on adjacent carbon atoms, are taken together with the carbon atoms to which they are attached to form a 5–7 membered heterocyclic ring containing 1, 2 or 3 nitrogen atoms or a 5–7 membered carbocyclic ring, said carbocyclic or heterocyclic ring being aromatic or nonaromatic, said carbocyclic or heterocyclic ring being substituted with 0–2 substituents independently selected from the group consisting of $C_1-C_4$ alkyl, $C_1-C_4$ alkoxy, F, Cl, Br, $CF_3$, $NO_2$ and aryl, wherein said aryl groups are substituted with 0–2 substituents independently selected from the group consisting of $C_1-C_4$ alkyl, $C_1-C_4$ alkoxy, F, Cl, Br, $CF_3$, and $NO_2$;

$R^7$ is selected from:
  H, $C_1-C_4$ alkyl, $C_3-C_6$ alkenyl, $C_3-C_6$ alkynyl, aryl ($C_0-C_4$ alkyl), and heteroaryl($C_0-C_4$ alkyl), wherein said aryl or heteroaryl groups are substituted with 0–2 substituents independently selected from the group consisting of $C_1-C_4$ alkyl, $C_1-C_4$ alkoxy, F, Cl, Br, $CF_3$, and $NO_2$;

alternatively, $—NHR^2$ and $R^7$, when substituents on adjacent atoms, are taken together with the atoms to which they are attached to form a 5–7 membered heterocyclic ring containing 2 or 3 nitrogen atoms, said heterocyclic ring being aromatic or nonaromatic, said heterocyclic ring being substituted with 0–2 substituents independently selected from the group consisting of $C_1-C_4$ alkyl, $C_1-C_4$ alkoxy, F, Cl, Br, $CF_3$, $NO_2$, and aryl, wherein said aryl groups are substituted with 0–2 substituents independently selected from the group consisting of $C_1-C_4$ alkyl, $C_1-C_4$ alkoxy, F, Cl, Br, $CF_3$, and $NO_2$;

$U^1$ is selected from:
  $—(CH_2)_n-$,
  $—Q^1-(CH_2)_m-$,
  $—(CH_2)_m-Q^2—$,
  $—(CH_2)_r-Q^2-CH_2—$,
  $—CH_2-Q^2-(CH_2)_r-$,
  $—(CH_2)_r-N(R^3)—C(=O)—$,
  $—(CH_2)_r-N(R^3)—S(=O)_2—$,
  $—(CH_2)_r-C(=O)—N(R^3)—$,
  $—(CH_2)_r-S(=O)_2—N(R^3)—$,
  $—C(=O)—N(R^4)—(CH_2)_r-$,
  $—N(R^4)—$,
  $—N(R^4)—(CH_2)_q-Q^2-$,
  $—N(R^4)—C(=O)—(CH_2)_r-$, and
  $—N(R^4)—(CH_2)_r-C(=O)—$;

$U^2$ is selected from:
  $—(CH_2)_h-$,
  $—Q^1-(CH_2)_r-$,
  $—(CH_2)_r-Q^2-$,
  $—(CH_2)_i-N(R^3)—C(=O)—$,
  $—(CH_2)_i-N(R^3)—S(=O)_2—$,
  $—(CH_2)_i-C(=O)—N(R^3)—$,
  $—(CH_2)_i-S(=O)_2—N(R^3)—$,
  $—(CH_2)_i-Q^2—CH_2—$,
  $—CH_2-Q^2-(CH_2)_i-$,
  $—C(=O)—N(R^4)—(CH_2)_i-$,
  $—N(R^4)—$,
  $—N(R^4)—(CH_2)_2-Q^2-$,
  $—N(R^4)—C(=O)—(CH_2)_i-$, and
  $—N(R^4)—(CH_2)_r-C(=O)—$;

$U^4$ is selected from:
  $—(CH_2)_h-$,
  $—(CH_2)_2-Q^2$,
  $—(CH_2)_2—O—CH_2—$,
  $—(CH_2)_r-C(=O)—$,
  $—C(=O)—(CH_2)_r-$, and
  $—C(=O)—N(R^4)—(CH_2)_r$;

$Q^1$ is $—O—$, $—S—$, or $N(R^4)$;
$Q^2$ is $—O—$, $—S—$, $—S(=O)—$, $—S(=O)_2—$, or $N(R^3)$;

$R^8$ and $R^9$ are independently selected from:
  H, $C_1-C_{10}$ alkyl, $NO_2$, $CF_3$, F, Cl, Br, $C_1-C_{10}$ alkylcarbonyl, $—NR^2R^4$, $OC(=O)OR^{10}$, $OR^{10}$, $OC(=O)NR^{10}R^{11}$, $OCH_2CO_2R^{10}$, $CO_2CH_2CO_2R^{10}$, $CO_2R^{10}$, $C(=O)R^{10}$, $NR^{10}C(=O)R^{11}$, $NR^7C(=O)OR^{10}$, $NR^7C(=O)NR^{10}R^{11}$, $NR^7SO_2NR^{10}R^{11}$, $NR^7SO_2R^{10}$, $SR^{10}$, $SR^{10}$, $S(=O)R^{10}$, $SO_2R^{10}$, $SO_2NR^{10}R^{11}$, $SiMe_3$, $R^{10}OOC(C_1-C_6$ alkyl), $R^2R^4N(C_2-C_6$ alkyl), $R^{10}OOC(C_1-C_6$ alkoxy), $R^2R^4N(C_2-C_6$ alkoxy), $C_2-C_6$ alkenyl, $C_3-C_{10}$ cycloalkyl, $C_3-C_{10}$ cycloalkylmethyl, aryl, and aryl($C_1-C_5$ alkyl)-, wherein said aryl groups are substituted with 0–2 substituents independentyl selected from a group consisting of $C_1-C_4$ alkyl, $C_1-C_4$ alkoxy, F, Cl, Br, $CF_3$, and $NO_2$;

$R^{10}$ and $R^{11}$ are independently selected from:
  H, $C_1-C_8$ alkyl, $C_3-C_6$ alkenyl, $C_3-C_{10}$ cycloalkyl ($C_0-C_4$ alkyl), aryl($C_0-C_4$ alkyl), and heteroaryl ($C_0$–$C_4$ alkyl), wherein said aryl or heteroaryl groups are substituted with 0–2 substitutents independently selected from the group consisting of $C_1$–$C_4$ alkyl, $C_1$–$C_4$ alkoxy, F, Cl, Br, $CF_3$, and $NO_2$, alternatively, $R^{10}$ and $R^{11}$ when both substituents on the same nitrogen atom an in (—$NR^{10}R^{11}$) can be taken together with the nitrogen atom to which are attached to form a heterocycle selected from 1-aziridinyl, 1-azetidinyl, 1-piperridinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$–$C_6$ alkyl, $C_3$–$C_7$ cycloalkyl($C_0$–$C_4$ alkyl), $C_1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl($C_0$–$C_5$ alkoxy) carbonyl, aryl($C_0$–$C_5$ alkyl), heteroaryl($C_0$–$C_5$ alkyl), aryl($C_1$–$C_5$ alkoxy)carbonyl, heteroaryl($C_1$–$C_5$ alkoxy) carbonyl, $C_1$–$C_6$ alkylsulfonyl arysulfonyl and heteroarysulfonyl;

W is selected form :
—$(C(R^{12})_2)_pC(=O)N(R^{13})$-, and
—$C(=O)$—$N(R^{13})$-$(C(R^{12})_2)_p$-;

X is —$(C(R^{12})_2)_pC(R^{12})(R^{14})$-$C(R^{12})_2$- or —$(C(R^{12})_2)_p$-$C(R^{12})(R^{15})$-;

alternatively, W and X can be taken together to be

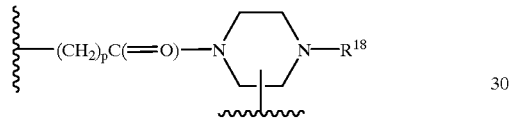

$R^{12}$ at each occurence is independently selected from:
H, $C_1$–$C_6$ alkyl, $C_2$–$C_6$ alkenyl, $C_2$–$C_6$ alkynyl, $C_3$–$C_7$ cycloalkyl($C_0$–$C_4$ alkyl)-, ($C_1$–$C_4$ alkyl)carbonyl, aryl($C_0$–$C_6$ alkyl), and heteroaryl($C_0$–$C_6$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^{13}$ is selected from:
H, $C_1$–$C_6$ alkyl, $C_3$–$C_7$ cycloalkyl($C_0$–$C_6$ alkyl), aryl ($C_0$–$C_6$ alkyl), or heteroaryl($C_0$–$C_6$ alkyl), wherein said aryl and heteroaryl groups substituted with 0–2 substituents independently selected from the group consisting of $C_1$–$C_4$ alkyl, $C_1$–$C_4$ alkoxy, F, Cl, Br, $CF_3$, and $NO_2$;

$R^{14}$ is selected from:
H, $C_1$–$C_{10}$ alkyl, $C_2$–$C_{10}$ alkenyl, $C_2$–$C_{10}$ alkynyl, $C_3$–$C_{10}$ cycloalkyl, $C_1$–$C_6$ hydroxyalkyl, $C_1$–$C_6$ alkoxy($C_1$–$C_6$ alkyl), aryl($C_0$–$C_6$ alkoxy $C_1$–$C_6$ alkyl), $C_1$–$C_6$ alkylthio($C_1$–$C_6$ alkyl), $C_1$–$C_6$ alkylsulfonyl($C_1$–$C_6$ alkyl), aryl($C_0$–$C_6$ alkylthio $C_1$–$C_6$ alkyl), aryl($C_0$–$C_6$ alkylsulfonyl $C_1$–$C_6$ alkyl), $C_3$–$C_{10}$ cycloalkyl($C_0$–$C_6$ alkyl), aryl($C_0$–$C_6$ alkyl), heteroaryl($C_0$–$C_6$ alkyl), $R^{17}R^{20}NC(=O)$ ($C_1$–$C_4$ alkyl), $R^{10}OC(=O)(C_1$–$C_4$ alkyl), and $R^{17}R^{20}N(C_1$–$C_4$ alkyl), provided that any of the above alkyl, cycloalkyl, aryl or heteroaryl groups may optionally by substituted independently with 0–1 $R^{16}$ or 0–2 $R^8$;

$R^{15}$ is selected from:
H, $R^{16}$, $C_1$–$C_{10}$ alkyl, $C_2$–$C_{10}$ alkenyl, $C_2$–$C_{10}$ alkynyl, $C_3$–$C_{10}$ cycloalkyl ($C_0$–$C_6$ alkyl), $C_1$–$C_6$ alkoxy ($C_1$–$C_6$ alkyl), $C_1$–$C_6$ alkylamino($C_1$–$C_6$ alkyl), $C_2$–$C_{10}$ dialkylamino ($C_1$–$C_6$ alkyl), ($C^1$–$C_{10}$ alkyl) carbonyl, aryl($C_0$–$C_6$ alkyl)carbonyl, heteroaryl ($C_0$–$C_6$ alkyl)carbonyl, aryl($C_0$–$C_6$ alkyl), heteroaryl ($C_0$–$C_6$ alkyl), $CO_2R^{17}$, $C(=O)R^{17}$, $CONR^{17}R^{20}$, $SO_2NR^{17}R^{20}$, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

Y is selected from —$C(=O)R^{19}$, —$SO_3H$, and —$PO_3H$;

$R^{16}$ is selected from:
—$N(R^{20})$-$C(=O)$-O-$R^{17}$,
—$N(R^{20})$-$C(=O)$-$R^{17}$,
—$N(R^{20})$-$C(=O)$-NH-$R^{17}$,
—$N(R^{20})SO_2$-$R^{17}$, and
—$N(R^{20})SO_2$-$NR^{20}R^{17}$;

$R^{17}$ is selected from:
$C_1$–$C_{10}$ alkyl, $C_3$–$C_{10}$ cycloalkyl, aryl($C_0$–$C_6$ ), heteroaryl($C_0$–$C_6$ alkyl), arylaryl($C_0$–$C_6$ alkyl), heteroarylaryl($C_0$–$C_6$ alkyl), arylheteroaryl($C_0$–$C_6$ alkyl), and heteroarylheteroaryl ($C_0$–$C_6$ ), wherein said aryl or heteroaryl groups are optionally substituted with 0–3 substituents independently selected from the group consisting of: $C_1$–$C_4$ alkyl, $C_1$–$C_4$ alkoxy, aryl, F, Cl, Br, CN, $NH_2$, $CF_3$, and $NO_2$;

$R^{18}$ is selected from:
H,
—$C(=O)OR^{17}$,
—$C(=O)R^{17}$,
—$C(=O)NHR^{17}$,
—$SO_2R^{17}$.
—$SO_2NR^{20}R^{17}$,
$C_1$–$C_{10}$ alkyl,
$C_3$–$C_{10}$ cycloalkyl ($C_0$–$C_6$ alkyl),
aryl ($C_0$–$C_6$ alkyl), and
heteroaryl($C_0$–$C_6$ alkyl),
wherein said aryl group is optionally substituted with 0–3 substituents independently selected from the group consisting of: $C_1$–$C_4$ alkyl, $C_1$–$C_4$ alkoxy, aryl, F, Cl, Br, —CN, —$NH_2$, —$CF_3$, and —$NO_2$;

$R^{19}$ is selected from:
hydroxy,
$C_1$–$C_{10}$ alkoxy,
$C_3$–$C_{10}$ cycloalkyloxy,
aryloxy,
aryl($C_1$–$C_6$ alkoxy),
$C_2$–$C_{10}$ alkylcarbonyloxy($C_1$–$C_2$ alkyl)oxy,
$C_2$–$C_{10}$ alkoxycarbonyloxy($C_1$–$C_2$ alkyl)oxy,
$C_2$–$C_{10}$ alkoxycarbonyl($C_1$–$C_2$ alkyl)oxy,
$C_3$–$C_{10}$ cycloalkylcarbonyloxy($C_1$–$C_2$ )oxy,
$C_3$–$C_{10}$ cycloalkoxycarbonylox($C_1$–$C_2$ alkyl)oxy,
$C_3$–$C_{10}$ cycloalkoxycarbonyl($C_1$–$C_2$ alkyl)oxy,
aryloxycarbonyl($C_1$–$C_2$ alkyl)oxy,
aryloxycarbonyloxy($C_1$–$C_2$ alkyl)oxy,
arylcarbonyloxy($C_1$–$C_2$ alkyl)oxy,
$C_1$–$C_5$ alkoxy($C_1$–$C_5$ alkyl)carbonyloxy($C_1$–$C_1$–$C_2$ alkyl)oxy,
(5-($C_1$–$C_5$ alkyl)-1,3-dioxa-cyclopenten-2-one-yl) methoxyloxy,
(5-aryl-1,3-dioxa-cyclopenten-2-one-yl)methyloxy,
$(R^{10})(R^{11})N$-$(C_1$–$C_{10}$ alkoxy) and
—$(CH_2)_kN^+(R^{21})(R^{22})(R^{23})z$-;

$R^{20}$ is selected from:
H, $C_1$–$C_6$ alkyl, $C_3$–$C_7$ cycloalkyl($C_0$–$C_6$ alkyl)-, aryl, aryl($C_0$–$C_6$ alkyl)-, and heteroaryl($C_0$–$C_6$ alkyl), wherein said aryl or hetroaryl groups are optionally substituted with 0–3 substituents independently selected from the group consisting of: $C_1$–$C_4$ alkyl, $C_1$–$C_4$ alkoxy, F, Cl, Br, $CF_3$, and $NO_2$;

z- is a pharmaceutically acceptable anion selected from halide, bisulfate, sulfae, hydrogenphosphate, phosphate, toluenesulfonate, methanesulfonate, ethanesulfonate, acetate, trifluoroacetate, citrate, oxalate, succinate, and molonate;

$R^{22}$, $R^{22}$ and $R^{23}$ are independently selected from: H, $C_1$–$C_9$ alkyl, $C$–$C_7$ cycloalkyl($C_0$–$C_4$ alkyl), aryl ($C_0$–$C_6$ alkyl), heteroaryl, and heteroaryl($C_0$–$C_6$ alkyl), wherein said alkyl or aryl groups are substituted with 0–2 substituents selected from the group consisting of $C_1$–$C_4$ alkyl, $C_1$–$C_4$ alkoxy, OH, F, Cl, Br, $CF_3$, and $NO_2$;

alternatively $R^{21}$ and $R^{22}$ can be taken together to form a 5–7 membered heterocyclic aromatic or non-aromatic ring system containing 1–3 heteroatoms selected from N, O and S and $R^{23}$ is defined as above or $R^{21}$, $R^{22}$, and $R^{23}$ can be taken together to form a heterobicyclic ring system containing 1–3 heteroatoms selected from N, O and S, wherein said heterocyclic or heterobicyclic ring being substituted with 0–2 groups selected from $C_1$–$C_4$ alkyl, $C_1$–$C_4$ alkoxy, halo, —CN, —$NH_2$, —$CF_3$, and —$NO_2$;

h is 0–4;
i is 0–2;
k is 2–6;
m is 1–4;
n is 0–5;
q is 2–3;
r is 0–3;
t is 1–3; and
p is 0–2;

provided that h, i, m, n, q, r, t, and p at each occurrence, are chosen such that the number of in-chain atoms between Y and the pyrimidine, pyrimidone, triazine or triazinone of G is in the range of 8–12.

2. A compound of claim 1 wherein:

G is selected from:

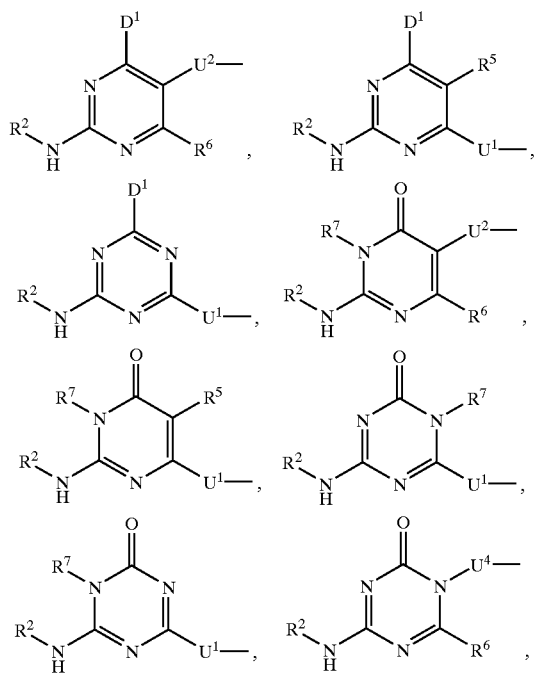

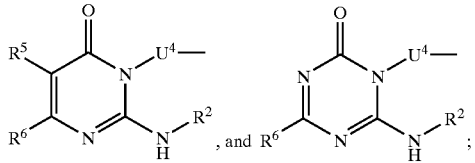

$D^1$ is selected from: $NR^2R^4$, $OR^3$, $SR^3$, F, Cl, Br, $CF_3$, methyl, ethyl, propyl, and butyl;

$R^2$ at each occurrence is independently selected from: H, $OR^3$, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl($C_0$–$C_4$ alkyl)carbonyl, $C_3$–$C_7$ cycloalkyl ($C_0$–$C_4$ alkoxy) carbonyl, aryl ($C_0$–$C_6$ alkyl), heteroaryl ($C_0$–$C_6$ alkyl), aryl($C_0$–$C_6$alkyl)carbonyl, heteroaryl($C_0$–$C_6$ alkyl)carbonyl, $C_1$–$C_6$ alkylsulfonyl, aryl($C_0$–$C_6$ alkyl)sulfonyl, heteroaryl($C_0$–$C_6$ alkyl) sulfonyl, aryl($C_1$–$C_6$ alkoxy)carbonyl, and heteroaryl ($C_1$–$C_6$ alkoxy)carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^3$ at each occurrence is independently selected from:
H, $C_1$–$C_6$ alkyl, ($C_1$–$C_6$ alkyl)carbonyl, ($C_1$–$C_6$ alkoxy)carbonyl, ($C_0$–$C_6$ alkyl)aminocarbonyl, $C_3$–$C_6$ alkenyl, $C_3$–$C_7$ cycloalkyl($C_0$–$C_4$ alkyl), $C_3$–$C_7$ cycloalkyl($C_0$–$C_4$ alkyl)carbonyl, cycloalkyl ($C_0$–$C_4$ alkoxy)carbonyl, aryl($C_0$–$C_6$ alkyl), heteroaryl($C_0$–$C_6$ alkyl), aryl($C_0$–$C_6$ alkyl)carbonyl, heteroaryl($C_0$–$C_6$ alkyl)carbonyl, aryl($C_1$–$C_6$ alkoxy)carbonyl, and heteroaryl($C_1$–$C_6$ alkoxy) carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^4$ is selected from:
H, $C_1$–$C_6$ alkyl, $C_1$–$C_6$ alkylcarbonyl, $C_1$–$C_6$ alkoxycarbonyl, $C_3$–$C_7$ cycloalkyl ($C_0$–$C_4$ alkyl), $C_3$–$C_7$ cycloalkyl($C_0$–$C_4$ alkyl)carbonyl, cycloalkyl ($C_0$–$C_4$ alkoxy)carbonyl, aryl($C_0$–$C_6$ alkyl), heteroaryl($C_0$–$C_6$ alkyl), aryl($C_0$–$C_6$ alkyl)carbonyl, heteroaryl($C_0$–$C_6$ alkyl)carbonyl, aryl($C_1$–$C_6$ alkoxy)carbonyl, and heteroaryl($C_1$–$C_6$ alkoxy) carbonyl, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^2$ and $R^4$ when both substituents on the same nitrogen atom as in (-$NR^2R^4$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$–$C_6$ alkyl, $C_3$–$C_7$ cycloalkyl($C_0$–$C_4$ alkyl), $C1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl ($C_0$–$C_5$ alkoxy)carbonyl, aryl($C_0$–$C_5$ alkyl), heteroaryl ($C_0$–$C_5$ alkyl), aryl ($C_1$–$C_5$ alkoxy)carbonyl, heteroaryl ($C_1$–$C_5$ alkoxy)carbonyl, $C_1$–$C_6$ alkylsulfonyl, arylsulfonyl, and heteroarylsulfonyl;

$R^5$ is selected from:
H, $NR^2R^4$, $OR^3$, $NO_2$, NO, $C_1$–$C_6$ alkyl, $C_3$–$C_7$ cycloalkyl($C_0$–$C_4$ alkyl), aryl($C_0$–$C_6$ alkyl), or heteroaryl($C_0$–$C_6$ alkyl), wherein said aryl and heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^6$ is selected from:
H, $NR^2R^4$, $OR^3$, $C_1$–$C_6$ alkyl, aryl($C_0$–$C_5$ alkyl), heteroaryl($C_0$–C5 alkyl), $CF_3$, F, Cl, and Br, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^5$ and $R^6$, when substituents on adjacent carbon atoms, are taken together with the carbon atoms to which they are attached to form a 5–7 membered heterocyclic ring containing 1, 2 or 3 nitrogen atoms or a 5–7 membered carbocyclic ring, said carbocyclic or heterocyclic ring being aromatic or nonaromatic, said carbocyclic or heterocyclic ring being substituted with 0–2 substituents independently selected from the group consisting of $C_1$–$C_4$ alkyl, $C_1$–$C_4$ alkoxy, F, Cl, Br, $CF_3$, $NO_2$ and phenyl, wherein said phenyl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^7$ is selected from:
H, $C_1$–$C_4$ alkyl, $C_3$–$C_6$ alkenyl, $C_3$–$C_6$ alkynyl, aryl ($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$NHR^2$ and $R^7$, when substituents on adjacent atoms, are taken together with the atoms to which they are attached to form a 5–7 membered heterocyclic ring containing 2 or 3 nitrogen atoms, said heterocyclic ring being aromatic or nonaromatic, said heterocyclic ring being substituted with 0–2 substituents independently selected from the group consisting of $C_1$–$C_4$ alkyl, $C_1$–$C_4$ alkoxy, F, Cl, Br, $CF_3$, $NO_2$, and phenyl, wherein said phenyl groups are substituted with 0–2 substituents independently selected from the group consisting of $C_1$–$C_4$ alkyl, $C_1$–$C_4$ alkoxy, F, Cl, Br, $CF_3$, and $NO_2$;

$U^1$ is selected from:
—$(CH_2)_n$-,
—O—$(CH_2)_m$-,
—$(CH_2)_m$-O—,
—$(CH_2)_m$-N($R^3$)—,
—S—$(CH_2)_m$-,
—$(CH_2)_m$-S—,
—$(CH_2)_m$-S(=O)—,
—$(CH_2)_m$-S(=O)$_2$—,
—$(CH_2)_t$-N($R^3$)—$CH_2$—,
—$(CH_2)_t$-N($R^3$)—C(=O)—,
—$(CH_2)_t$-N($R^3$)—S(=O)$_2$—,
—$(CH_2)_t$-C(=O)—N($R^3$)—,
—$(CH_2)_t$-S(=O)$_2$—N($R^3$)—,
—$(CH_2)_t$-O—$CH_2$—,
—$(CH_2)_t$-S—$CH_2$—,
—$(CH_2)_t$-S-(=O)—$CH_2$—,
—$(CH_2)_t$-S(=O)$_2$—$CH_2$—,
—$CH_2$—O—$(CH_2)_t$-,
—$CH_2$—S—$(CH_2)_t$-,
—$CH_2$—S(=O)—$(CH_2)_t$-,
—$CH_2$—S(=O)$_2$—$(CH_2)_t$-,
—$CH_2$—N($R^3$)—$(CH_2)_t$-,
—C(=O)—N($R^4$)—$(CH_2)_t$-,
—N($R^4$)—,
—N($R^4$)—$(CH_2)_m$-,
—N($R^4$)—$(CH_2)_q$-N($R^3$)—,
—N($R^4$)—$(CH_2)_q$-O—,
—N($R^4$)—$(CH_2)_q$-S—,
—N($R^4$)—$(CH_2)_q$-S(O)—,
—N($R^4$)—$(CH_2)_q$-S(O)$_2$—,
—N($R^4$)—C(=O)—$(CH_2)_r$-, and
—N($R^4$)—$(CH_2)_r$-C(=O)—;

$U^2$ is selected from:
—$(CH_2)_h$-,
—O—$(CH_2)_r$-,
—$(CH_2)_r$-O—,
—$(CH_2)_r$-N($R^3$)—,
—S—$(CH_2)_r$-,
$(CH_2)_r$-S—,
—$(CH_2)_r$-S(=O)—,
—$(CH_2)_r$-S(=O)$_2$—,
—$(CH_2)_i$-N($R^3$)—$CH_2$—,
—$(CH_2)_i$-N($R^3$)—C(=O)—,
—$(CH_2)_i$-N($R^3$)—S(=O)$_2$—,
—$(CH_2)_i$-C(=O)—N($R^3$)—,
—$(CH_2)_i$-S (=O)$_2$—N($R^3$)—,
—$(CH_2)_i$-O—$CH_2$—,
—$(CH_2)_i$-S—$CH_2$—,
—$(CH_2)_i$-S(=O)—$CH_2$—,
—$(CH_2)_i$-S(=O)$_2$—$CH_2$—,
—$CH_2$—O—$(CH_2)_i$-,
—$CH_2$—S—$(CH_2)_i$-,
—$CH_2$—S(=O)—$(CH_2)_i$-,
—$CH_2$—S(=O)$_2$-$(CH_2)_i$-,
—$CH_2$—N($R^3$)—$(CH_2)_i$,
—C(=O)—N($R^4$)—$(CH_2)_i$-,
—N($R^4$)—,
—N($R^4$)—$(CH_2)_r$-,
—N($R^4$)—$(CH_2)_2$—N($R^3$)—,
—N($R^4$)—$(CH_2)_2$—O—,
—N($R^4$)—$(CH_2)_2$—S—,
—N($R^4$)—$(CH_2)_2$—S(O)—,
—N($R^4$)—$(CH_2)_2$—S(O)$_2$—,
—N($R^4$)—C(=O)—$(CH_2)_i$-, and
—N($R^4$)—$(CH_2)_r$-C(=O)—;

$U^3$ is selected from:
—$(CH_2)_h$-,
—$(CH_2)_q$-O—,
—$(CH_2)_q$N($R^3$)—,
—$(CH_2)_q$-N($R^3$)—C(=O)—,
—$(CH_2)_r$-C(=O)—N($R^3$)—,
—$(CH_2)_q$-S—,
—$(CH_2)_q$-S(O)—,
—$(CH_2)_q$-S(O)$_2$,
—$(CH_2)_q$-S(O)$_2$—N($R^3$),
—$(CH_2)_q$-N($R^3$)—S(O)$_2$—,
—$(CH_2)_q$-N($R^3$)—$CH_2$—,
—$(CH_2)_q$-O-13 $CH_2$—,
—$(CH_2)_h$-C(=O)—,
—C(=O)—$(CH_2)_r$-, and
—C(=O)—N($R^4$)—$(CH_2)_p$;

$U^4$ is selected from:
—$(CH_2)_h$-,
—$(CH_2)_2$—O—,
—$(CH_2)_2$—N($R^3$)—,
—$(CH_2)_2$—S—,
—$(CH_2)_2$—S(O)—,
—$(CH_2)_2$—S(O)$_2$—,
—$(CH_2)_2$—O—$CH_2$—, —$(CH_2)_r$-C(=O)—,
—C(=O)—$(CH_2)_r$, and
—C(=O)—N($R^4$)—$(CH_2)_r$;

$R^8$ and $R^9$ are independently selected from: H, $C_1$–$C_4$ alkyl, $CF_3$, F, Cl, Br, and $OR^{10}$;

$R^{10}$ and $R^{11}$ are independently selected from:
H, $C_1$–$C_8$ alkyl, $C_3$–$C_6$ alkenyl, $C_3$–$C_{10}$ cycloalkyl ($C_0$–$C_4$ alkyl), aryl ($C_0$–$C_4$ alkyl), and heteroaryl ($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^{10}$ and $R^{11}$ when both substituents on the same nitrogen atom as in (—$NR^{10}R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl; said heterocycle being optionally substituted with 0–3 groups selected from oxo, $C_1$–$C_6$ alkyl, $C_3$–$C_7$ cycloalkyl($C_0$–$C_4$ alkyl), $C_1$–$C_6$ alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl ($C_0$–$C_5$ alkoxy)carbonyl, aryl($C_0$–$C_5$ alkyl), heteroaryl ($C_0$–$C_5$ alkyl), aryl($C_1$–C5 alkoxy)carbonyl, heteroaryl ($C_1$–C5 alkoxy)carbonyl, $C_1$–$C_6$ alkylsulfonyl arylsulfonyl and heteroarylsulfonyl;

W is —$(CHR^{12})_p C(=O)N(R^{13})$— or —C(=O)—N($R^{13}$)—$(CHR^{12})_p$-;

X is —CH($R^{14}$)—$CHR^{12}$— or —$CHR^{12}$—CH($R^{15}$)—;

$R^{12}$ at each occurrence is independently selected from: H or $C_1$–$C_6$ alkyl;

$R^{13}$ is selected from:
H, $C_1$–$C_6$ alkyl, $C_3$–$C_7$ cycloalkyl($C_0$–$C_6$ alkyl), aryl ($C_0$–$C_6$ alkyl), or heteroaryl($C_0$–$C_6$ alkyl), wherein said aryl and heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^{14}$ is selected from:
H, $C_1$–$C_{10}$ alkyl, $C_2$–$C_{10}$ alkenyl, $C_2$–$C_{10}$ alkynyl, $C_3$–$C_{10}$ cycloalkyl, $C_1$–$C_6$ hydroxyalkyl, $C_1$–$C_6$ alkoxy($C_1$–$C_6$ alkyl), aryl($C_0$–$C_6$ alkoxy $C_1$–$C_6$ alkyl), $C_1$–$C_6$ alkylthio($C_1$–$C_6$ alkyl), $C_1$–$C_6$ alkylsulfonyl($C_1$–$C_6$ alkyl), aryl($C_0$–$C_6$ alkylthio $C_1$–$C_6$ alkyl), aryl($C_0$–$C_6$ alkylsulfonyl $C_1$–$C_6$ alkyl), $C_3$–$C_{10}$ cycloalkyl($C_0$–$C_6$ alkyl), aryl($C_0$–$C_6$ alkyl), heteroaryl($C_0$–$C_6$ alkyl), $R^{17}R^{20}NC(=O)$ ($C_1$–$C_4$ alkyl), $R^{10}OC(=O)$ ($C_1$–$C_4$ alkyl), and $R^{17}R^{20}N(C_1$–$C_4$ alkyl), provided that any of the above alkyl, cycloalkyl, aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

$R^{15}$ is selected from:
—NH—C(=O)—O—$R^{17}$,
—NH—C(=O)—$R^{17}$,
—NH—C(=O)—NH—$R^{17}$,
—$NHSO_2$—$R^{17}$, and
—$NHSO_2$—$NR^{20}R^{17}$;

Y is —C(=O)$R^{19}$;

$R^{17}$ is selected from:
$C_1$–$C_{10}$ alkyl, $C_3$–$C_{10}$ cycloalkyl, aryl($C_0$–$C_6$ alkyl), heteroaryl($C_0$–$C_6$ alkyl), arylaryl($C_0$–$C_6$ alkyl), heteroarylaryl($C_0$–$C_6$ alkyl), arylheteroaryl($C_0$–$C_6$ alkyl), and heteroarylheteroaryl ($C_0$–$C_6$ alkyl), wherein said aryl or heteroaryl groups are optionally substituted with 0–3 substituents independently selected from the group consisting of: $C_1$–$C_4$ alkyl, $C_1$–$C_4$ alkoxy, aryl, F, Cl, Br, CN, NH2, $CF_3$, and $NO_2$;

$R^{19}$ is selected from:
hydroxy,
$C_1$–$C_{10}$ alkyloxy,
$C_3$–$C_{10}$ cycloalkyloxy,
aryloxy,
aryl ($C_1$–$C_6$ alkoxy)
$C_2$–$C_{10}$ alkylcarbonyloxy($C_1$–$C_2$ alkyl)oxy-,
$C_2$–$C_{10}$ alkoxycarbonyloxy(Cl-C2 alkyl)oxy-,
$C_2$–$C_{10}$ alkoxycarbonyl ($C_1$–$C_2$ alkyl)oxy-,
$C_3$–$C_{10}$ cycloalkylcarbonyloxy($C_1$–$C_2$ alkyl)oxy-,
$C_3$–$C_{10}$ cycloalkoxycarbonyloxy($C_1$–$C_2$ alkyl) oxy-,
$C_3$–$C_{10}$ cycloalkoxycarbonyl($C_1$–$C_2$ alkyl)oxy-,
aryloxycarbonyl($C_1$–$C_2$ alkyl)oxy-,
aryloxycarbonyloxy($C_1$–$C_2$ alkyl)oxy-,
arylcarbonyloxy($C_1$–$C_2$ alkyl)oxy-,
$C_1$–$C_5$ alkoxy($C_1$–$C_5$ alkyl)carbonyloxy($C_1$–$C_2$ alkyl) oxy-,
(5-($C_1$–$C_5$ alkyl)-1,3-dioxa-cyclopenten-2-one-yl) methyloxy,
(5-aryl-1,3-dioxa-cyclopenten-2-one-yl)methyloxy,
($R^{10}$) ($R^{11}$)N-($C_1$–$C_{10}$ alkoxy)- and
—$O(CH_2)_k N^+(R^{21}) (R^{22}) (R^{23})Z^-$;

$R^{20}$ is selected from H, methyl, ethyl, propyl, and butyl;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{21}$, $R^{22}$ and $R^{23}$ are independently selected from:
H, $C_1$–$C_6$ alkyl, $C_3$–$C_7$ cycloalkyl($C_0$–$C_4$ alkyl)-, aryl, aryl ($C_1$–$C_6$ alkyl) -, heteroaryl, and heteroaryl ($C_1$–$C_6$ alkyl)- wherein said alkyl or aryl groups are substituted with 0–2 substituents selected from the group consisting of $C_1$–$C_4$ alkyl, $C_1$–$C_4$ alkoxy, OH, F, Cl, Br, $CF_3$, and $NO_2$;

alternatively $R^{21}$ and $R^{22}$ can be taken together to form a 5–7 membered heterocyclic aromatic or non-aromatic ring system containing 1–3 heteroatoms selected from N, O and S and $R^{23}$ is defined as above or $R^{21} R^{22}$, and $R^{23}$ can be taken together to form a heterobicyclic ring system containing 1–3 heteroatoms selected from N, O and S, wherein said heterocyclic or heterobicyclic ring being substituted with 0–2 groups selected from $C_1$–$C_4$ alkyl, $C_1$–$C_4$ alkoxy, halo, —CN, —$NH_2$, —$CF_3$, and —$NO_2$;

h is 0–4;
i is 0–2;
k is 2–6;
m is 1–4;
n is 0–5;
q is 2–3;
r is 0–3;
t is 1–3; and
p is 0–2;

provided that h, i, m, n, q, r, t, and p at each occurrence, are chosen such that the number of in-chain atoms between Y and the pyrimidine, pyrimidone, triazine or triazinone of G is in the range of 8–12.

3. A compound of claim 2 wherein:
G is selected from:

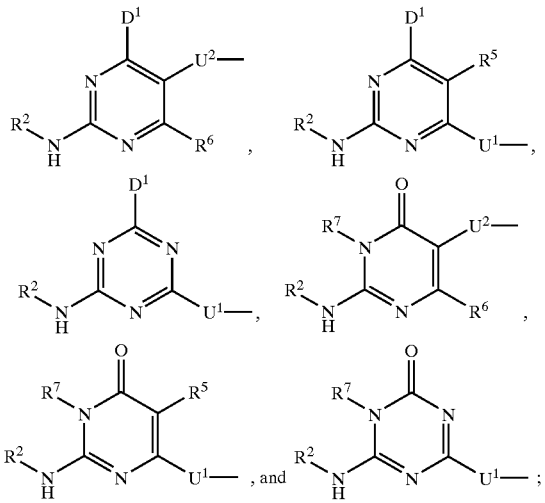

$D^1$ is $NR^2R^4$ or $OR^3$;

$R^2$ at each occurrence is independently selected from:
H, methyl, ethyl, propyl, butyl, ($C_1$–$C_4$ alkyl)carbonyl, ($C_1$–$C_4$ alkoxy)carbonyl, $C_3$–$C_7$ cycloalkyl($C_0$–$C_4$ alkyl), $C_3$–$C_7$ cycloalkyl($C_0$–$C_4$ alkyl)carbonyl, and $C_3$–$C_7$ cycloalkyl ($C_0$–$C_4$ alkoxy) carbonyl;

$R^3$ is selected from: H, methyl, ethyl, propyl, and butyl;

$R^4$ is selected from: H, methyl, ethyl, propyl, butyl cyclopropyl, and cyclopropylmethyl;

$R^5$ is selected from H, $NR^2R^4$, methyl, ethyl, propyl, butyl, pentyl, and hexyl;

$R^6$ is selected from:
H, $NR^2R^4$, $OR^3$, methyl, ethyl, propyl, butyl, pentyl, hexyl, aryl($C_0$–$C_5$ alkyl), heteroaryl($C_0$–$C_5$ alkyl), $CF_3$, F, Cl, and Br, wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$R^5$ and —$R^6$, when substituents on adjacent carbon atoms, are taken together with the carbon atoms to which they are attached to form a 6 membered heterocyclic ring containing 1 or 2 nitrogen atoms or a 5–6 membered carbocyclic ring, wherein —$R^5$–$R^6$— taken together are selected from the group —CH₂—CH₂—CH₂—, —CH₂—CH₂—CH₂—CH₂—, —CH=CH—CH=CH—, —N=CH—CH=CH—, —N=CH—CH=N—, —N=CH—N=CH—, and —N=N—CH=CH—;

$R^7$ is selected from:
H, methyl, ethyl, propyl, butyl, $C_3$–$C_6$ alkenyl, $C_3$–$C_6$ alkynyl, aryl($C_0$–$C_4$ alkyl), and heteroaryl($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, —$NHR^2$ and $R^7$, when substituents on adjacent atoms, are taken together with the atoms to which they are attached to form a 5–6 membered heterocyclic ring containing 2 or 3 nitrogen atoms, wherein —$NHR^2$—$R^7$—taken together are selected from the group —NH—CH=N—, —NH—N=N—, —NH—N=C—, —NH—CH=CH—, —NH—CH₂—CH₂—, —NH—CH₂—CH₂—CH₂—, —NH—CH₂—CH₂—NH—, —N=CH—CH=CH—, —N=CH—CH=N—, —N=CH—N=CH—, and —N=N—CH=CH—;

$U^1$ is selected from:
—(CH₂)$_n$-,
—O(CH₂)$_m$-,
—(CH₂)$_m$-O—,
—(CH₂)$_m$-N($R^3$)—,
—(CH₂)$_t$-N($R^3$)—CH₂—,
—(CH₂)$_t$-O—CH₂—,
—CH₂—O—(CH₂)$_t$-,
—CH₂—N($R^3$)—(CH₂)$_t$-, and
—N($R^4$)—(CH₂)$_m$-;

$U^2$ is selected from:
—(CH₂)$_h$-,
—O—(CH₂)$_r$-,
—(CH₂)$_r$-O—,
—(CH₂)$_r$-N($R^3$)—,
—(CH₂)$_i$-N($R^3$)—CH₂—,
—(CH₂)$_i$-O—CH₂—,
—CH₂—O—(CH₂)$_i$-,
—CH₂—N($R^3$)—(CH₂)$_i$-, and
—N($R^4$)—(CH₂)$_r$-;

$R^8$ and $R^9$ are independently selected from: H, methyl, ethyl, propyl, butyl, $CF_3$, F, Cl, Br, and $OR^{10}$;

$R^{10}$ and $R^{11}$ are independently selected from:
H, $C_1$–$C_8$ alkyl, $C_3$–$C_6$ alkenyl, $C_3$–$C_{10}$ cycloalkyl ($C_0$–$C_4$ alkyl), aryl($C_0$–$C_4$ alkyl), and heteroaryl ($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^{10}$ and $R^{11}$ when both substituents on the same nitrogen atom as in (—$NR^{10}R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from oxo, $C_1$–$C_6$ alkyl, $C_3$–$C_7$ cycloalkyl($C_0$–$C_4$ alkyl), $C_1$–C6 alkylcarbonyl, $C_3$–$C_7$ cycloalkyl($C_0$–$C_5$ alkyl) carbonyl, $C_1$–$C_6$ alkoxycarbonyl, $C_3$–$C_7$ cycloalkyl ($C_0$–$C_5$ alkoxy)carbonyl, aryl($C_0$–$C_5$ alkyl), heteroaryl ($C_0$–$C_5$ alkyl), aryl($C_1$–$C_5$ alkoxy)carbonyl, heteroaryl ($C_1$–$C_5$ alkoxy)carbonyl, $C_1$–$C_6$ alkylsulfonyl arylsulfonyl and heteroarylsulfonyl;

W is —CH₂C(=O)N($R^{13}$)—, —CH₂CH₂C(=O)N($R^{13}$)—, or —C(=O)N($R^{13}$)—;

X is —CH($R^{14}$)—CH₂— or —CH₂—CH($R^{15}$)—;

$R^{13}$ is H or methyl;

$R^{14}$ is selected from:
H, $C_1$–$C_{10}$ alkyl, $C_2$–$C_{10}$ alkenyl, $C_2$–$C_{10}$ alkynyl, $C_3$–$C_{10}$ cycloalkyl, $C_1$–$C_6$ hydroxyalkyl, $C_1$–$C_6$ alkoxy($C_1$–$C_6$ alkyl), aryl($C_0$–$C_6$ alkoxy $C_1$–$C_6$ alkyl), $C_1$–$C_6$ alkylthio($C_1$–$C_6$ alkyl), $C_1$–$C_6$ alkylsulfonyl($C_1$–$C_6$ alkyl), aryl($C_0$–$C_6$ alkylthio $C_1$–$C_6$ alkyl), aryl($C_0$–$C_6$ alkylsulfonyl $C_1$–$C_6$ alkyl), $C_3$–$C_{10}$ cycloalkyl ($C_0$–$C_6$ alkyl), aryl($C_0$–$C_6$ alkyl), heteroaryl($C_0$–$C_6$ alkyl), $R^{17}$HNC(=O) ($C_1$–$C_4$ alkyl), $R^{10}$OC(=O) ($C_1$–$C_4$ alkyl), and $R^{17}$HN($C_1$–$C_4$ alkyl), provided that any of the above alkyl, cycloalkyl, aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

R$^{15}$ is selected from:
—NH—C(=O)—O—R$^{17}$,
—NH—C(=O)—R$^{17}$,
—NH—C(=O)—NH—R$^{17}$,
—NHSO$_2$—R$^{17}$, and
—NHSO$_2$—NHR$^{17}$;

Y is —C(=O)R$^{19}$;

R$^{17}$ is selected from:
C$_1$–C$_{10}$ alkyl, C$_3$–C$_{10}$ cycloalkyl, aryl(C$_0$–C$_6$ alkyl), heteroaryl(C$_0$–C$_6$ alkyl), arylaryl(C$_0$–C$_6$ alkyl), heteroarylaryl(C$_0$–C$_6$ alkyl), arylheteroaryl(C$_0$–C$_6$ alkyl), and heteroarylheteroaryl (C$_0$–C$_6$ alkyl), wherein said aryl or heteroaryl groups are optionally substituted with 0–3 substituents independently selected from the group consisting of: C$_1$–C$_4$ alkyl, C$_1$–C$_4$ alkoxy, aryl, F, Cl, Br, CN, NH$_2$, CF$_3$, and NO$_2$;

R$^{19}$ is selected from:
hydroxy,
C$_1$–C$_{10}$ alkoxy,
methylcarbonyloxymethoxy-,
ethylcarbonyloxymethoxy-,
t-butylcarbonyloxymethoxy-,
cyclohexylcarbonyloxymethoxy-,
1-(methylcarbonyloxy)ethoxy-,
1-(ethylcarbonyloxy)ethoxy-,
1-(t-butylcarbonyloxy)ethoxy-,
1-(cyclohexylcarbonyloxy)ethoxy-,
i-propyloxycarbonyloxymethoxy-,
t-butyloxycarbonyloxymethoxy-,
1-(i-propyloxycarbonyloxy)ethoxy-,
1-(cyclohexyloxycarbonyloxy)ethoxy-,
1-(t-butyloxycarbonyloxy)ethoxy-,
dimethylaminoethoxy-,
diethylaminoethoxy-,
(5-methyl-1,3-dioxacyclopenten-2-on-4-yl)methoxy-,
(5- (t-butyl) -1, 3-dioxacyclopenten-2-on-4-yl)methoxy-,
(1,3-dioxa-5-phenyl-cyclopenten-2-on-4-yl)methoxy-,
1-(2-(2-methoxypropyl)carbonyloxy)ethoxy-,
(R$^{10}$)(R$^{11}$)N-(C$_1$–C$_{10}$ alkoxy)-, and
—O (CH$_2$)$_k$N$^+$(R$^{21}$) (R$^{22}$) (R$^{23}$) Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{21}$ R$^{22}$ and R$^{23}$ are independently selected from:
H, methyl, ethyl, propyl, butyl, C$_3$–C$_7$ cycloalkyl (C$_0$–C$_4$ alkyl), phenyl, benzyl, wherein said phenyl group is substituted with 0–2 substituents selected from the group consisting of C$_1$–C$_4$ alkyl, C$_1$–C$_4$ alkoxy, OH, F, Cl, Br, CF$_3$, and NO$_2$;
alternatively R$^{21}$ and R$^{22}$ can be taken together to form a 5–7 membered heterocyclic aromatic or non-aromatic ring system containing 1–2 heteroatoms selected from N, O and S and R$^{23}$ is defined as above or R$^{21}$, R$^{22}$, and R$^{23}$ can be taken together to form a heterobicyclic ring system containing 1–2 heteroatoms selected from N, O and S;
h is 0–4;
i is 0–2;
k is 2–6;
m is 1–4;
n is 0–5;
q is 2–3;
r is 0–3; and
t is 1–3;
provided that h, i, m, n, q, r, and t, at each occurrence, are chosen such that the number of in-chain atoms between Y and the pyrimidine, pyrimidone, triazine or triazinone of G is in the range of 8–12.

4. A compound of claim 2 wherein:
G is selected from:

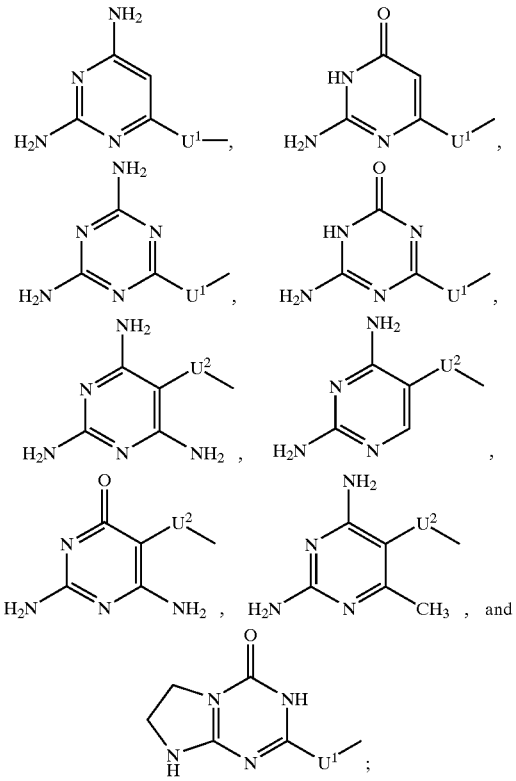

U$^1$ is selected from: —CH$_2$CH$_2$- and —CH$_2$CH$_2$CH$_2$-;
U$^2$ is selected from: —CH$_2$CH$_2$- and —CH$_2$CH$_2$CH$_2$-;
R$^8$ i selected from: H, methyl, ethyl, propyl, butyl, —OH, methoxy, ethoxy, F, Cl, Br, and CF$_3$;
R$^9$ is H,
R$^{10}$ and R$^{11}$ are independently selected from:
H, methyl, ethyl, propyl, butyl, C$_3$–C$_6$ alkenyl, C$_3$–C$_4$ cycloalkyl(C$_0$–C$_4$ alkyl), aryl(C$_0$–C$_4$ alkyl), and heteroaryl(C$_0$–C$_4$ alkyl), wherein said aryl or heteroaryl groups are subtituted with 0–2 substituents independently selected from the group consisting of C$_1$–C$_4$ alkyl, C$_1$–C$_4$ alkoxy, F, Cl, Br, CF=hd 3, and NO$_2$;
alternatively, R$^{10}$ and R$^{11}$ when both substituents on the same nitrogen atom as in (—NR$^{10}$R$^{11}$) can be taken together with the nitrogen atom to which they are attached to form a heterocycle selected from 1-aziridinyl, 1- azetidinyl, 1-piperidinyl, 1-morpholinyl, 1- pyrrolidinyl, thiamorpholinyl, thiazolidinyl, and 1- piperazinyl;
W is —CH$_2$C(=O)N(R$^{13}$)-, —CH$_2$CH$_2$C(=O)N(R$^{13}$)-, or —C(=O)N(R$^{11}$)-;
X is —CH(R$^{14}$)-CH$_2$- or —CH$_2$-CH(R$^{15}$)-;
R$^{13}$ is H, methyl, ethyl, propyl, butyl, pentyl, or hexyl;

$R^{14}$ is selected from:
  $C_2$–$C_8$ alkenyl, $C_2$–$C_8$ alkynyl, $C_3$–$C_8$ cycloalkyl, $C_1$–$C_6$ hydroxyalkyl, $C_3$–$C_8$ cycloalkyl($C_0$–$C_6$ alkyl), aryl($C_0$–$C_6$ alkyl), heteroaryl($C_0$–$C_6$ alkyl), $R^{17}$HNC(=O)($C_1$–$C_4$ alkyl), and $R^{17}$ HN($C_1$–$C_4$ alkyl), provided that any of the above alkyl, cycloalkyl, aryl or heteroaryl groups are subtituted with 0–2 substituents independently selected from the group consisting of methyl, ethyl, propyl, butyl methoxy, propoxy, butoxy, F, Cl, Br, $VF_3$, and $NO_2$;

$R^{15}$ is selected from:
  —NH-C(=O)-O-$R^{17}$,
  —$NHSO_2$-$R^{17}$ and
  —$NHSO_2$-NH$R^{17}$;

Y is —C(=O)$R^{19}$;

$R^{17}$ is selected from:
  methyl, ethyl, propyl, butyl, pentyl, hexyl, cyclopropyl, cyclobutyl, cyclopentyl, cyclohexyl, phenylmethyl, phenylethyl, phenylpropyl, phenylbutyl, heteroaryl ($C_1$–$C_3$ alkyl)-, arylaryl($C_1$–$C_3$ alkyl)-, heteroarylaryl($C_1$–$C_3$ alkyl)-, arylheteroaryl($C_1$–$C_3$ alkyl)-, heteroarylheteroaryl($C_1$–$C_3$ alkyl)-, heteroaryl, and aryl, wherein said aryl or heteroaryl groups are optionally substituted with 0–3 substituents independently selected from the group consisting of: methyl, ethyl, propyl, butyl, methoxy, ethoxym propoxy, butoxy, phenyl, F, Cl, Br, —CN, —$NH_2$, —$CF_3$, and —$NO_2$;

$R^{19}$ is selected from:
  hydroxy, methoxy, ethoxy, propoxy, butoxy,
  methylcarbonyloxymethoxy-,
  ethylcarbonyloxymethoxy-,
  t-butylcarbonyloxymethoxy-,
  cyclohexylcarbonyloxymethoxy-,
  1-(methylcarbonyloxy)ethoxy-,
  1-(ethycarbonyloxy)ethoxy-,
  1-(t-butylcarbonyloxy)ethoxy-,
  1-(cyclohexylcarbonyloxy)ethoxy-,
  i-propyloxycarbonyloxymethoxy-,
  t-butyloxycarbonyloxymethoxy-,
  1-(i-propyloxycarbonylozy)ethoxy-,
  1-(cyclohexyloxycarbonyloxy)ethoxy-,
  1-(t-butyloxycarbonyloxy)ethoxy-,
  dimethylaminoethoxy-,
  diethylaminoethoxy-,
  (5-methyl-1,3-dioacyclopenten-2-on-4yl)methoxy-,
  (5-(t-butyl)-1,3-dioxacyclopenten-2-on-4-yl)methoxy-,
  (1,3-dioxa-5-phenyl-cyclopenten-2-on-4-yl)methoxy-,
  1-(2-(2-methoxypropyl)carbonyloxy)ethoxy)-, ($R^{10}$)($R^{11}$)N-($C_1$–$C_{10}$ alkoxy)-, and
  —O($CH_2$)$_k$$N^+$($R^{21}$)($R^{22}$)($R^{23}$)$Z^-$;

$Z^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

$R^{21}$, $R^{22}$ and $R^{23}$ are independently selected from: H, methyl, ethyl, propyl and butyl;

alternatively $R^{21}$ and $R^{22}$ can be taken together to form a 5–7 membered heterocyclic ring system containing 1–2 heteroatoms selected from N, O and S and $R^{23}$ is defined as above;

h is 0–4;
i is 1–2;
k is 2–6;
m is 1–4;
n is 0–5;
q is 2–3;
r is 1–3; and
t is 1–3;
  provided that h, i, m, n, q, r, and t, at each occurrence, are chosen such that the number of in-chain atoms between Y and the pyrimidine, pyrimidine, pyrimidone, triazine or triasinone of G is in the range of 8–12.

alternatively, —NH$R^2$ and $R^7$, when substituents on adjacent atoms, are taken together with the atoms to which they are attached to form a 5–6 membered heterocyclic ring containing 2 or 3 nitrogen atoms, wherein —NH$R^2$—$R^7$—taken together are selected from the group —NH—CH=N—, —NH—N=N—, —NH—N=C—, —NH—CH=CH—, —NH—$CH_2$—$CH_2$—, —NH—$CH_2$—$CH_2$—$CH_2$—, —NH—$CH_2$—$CH_2$—NH—, —N=CH—CH=CH—, —N=CH—CH=N—, —N=CH—N=CH—, and —N=N—CH=CH—;

$U^1$ is selected from:
  —($CH_2$)$_n$-,
  —O($CH_2$)$_m$-,
  —($CH_2$)$_m$-O—,
  —($CH_2$)$_m$-N($R^3$)—,
  —($CH_2$)$_t$-N($R^3$)—$CH_2$—,
  —($CH_2$)$_t$-O—$CH_2$—,
  —$CH_2$—O—($CH_2$)$_t$-,
  —$CH_2$—N($R^3$)—($CH_2$)$_t$-, and
  —N($R^4$)—($CH_2$)$_m$-;

$U^2$ is selected from:
  —($CH_2$)$_h$-,
  —O—($CH_2$)$_r$-,
  —($CH_2$)$_r$-O—,
  —($CH_2$)$_r$-N($R^3$)—,
  —($CH_2$)$_i$-N($R^3$)—$CH_2$—,
  —($CH_2$)$_i$-O—$CH_2$—,
  —$CH_2$—O—($CH_2$)$_i$-,
  —$CH_2$—N($R^3$)—($CH_2$)$_i$-, and
  —N($R^4$)—($CH_2$)$_r$-;

$U^3$ is selected from:
  —($CH_2$)$_h$-,
  —($CH_2$)$_q$O—,
  —($CH_2$)$_q$-N($R^3$)—,
  —($CH_2$)$_q$-N($R^3$)—$CH_2$—, and
  —($CH_2$)$_q$-O—$CH_2$—;

$R^8$ and $R^9$ are independently selected from: H, methyl, ethyl, propyl, butyl, $CF_3$, F, Cl, Br, and O$R^{10}$;

$R^{10}$ and $R^{11}$ are independently selected from:
  H, $C_1$–$C_8$ alkyl, $C_3$–$C_6$ alkenyl, $C_3$–$C_{10}$ cycloalkyl ($C_0$–$C_4$ alkyl), aryl($C_0$–$C_4$ alkyl), and heteroaryl ($C_0$–$C_4$ alkyl), wherein said aryl or heteroaryl groups are substituted with 0–2 substituents independently selected from the group consisting of $C_1$–$C_4$ alkyl, $C_1$–$C_4$ alkoxy, F, Cl, Br, $CF_3$, and $NO_2$;

alternatively, $R^{10}$ and $R^{11}$ when both substituents on the same nitrogen atom as in (—N$R^{10}$$R^{11}$) can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, and 1-piperazinyl, said heterocycle being optionally substituted with 0–3 groups selected from oxo, $C_1$–$C_6$ alkyl, $C_3$–$C_7$ cycloalkyl($C_0$–$C_4$ alkyl), C$_1$–C6 alkylcarbonyl, C$_3$–C$_7$ cycloalkyl(C$_0$–C$_5$ alkyl) carbonyl, C$_1$–C$_6$ alkoxycarbonyl, C$_3$–C$_7$ cycloalkyl (C$_0$–C$_5$ alkoxy)carbonyl, aryl(C$_0$–C$_5$ alkyl), heteroaryl (C$_0$–C$_5$ alkyl), aryl(C$_1$–C$_5$ alkoxy)carbonyl, heteroaryl (C$_1$–C$_5$ alkoxy)carbonyl, C$_1$–C$_6$ alkylsulfonyl arylsulfonyl and heteroarylsulfonyl;

W is —CH$_2$C(=O)N(R$^{13}$)—, —CH$_2$CH$_2$C(=O)N (R$^{13}$)—, or —C(=O)N(R$^{13}$)—;

X is —CH(R$^{14}$)—CH$_2$— or —CH$_2$—CH(R$^{15}$)—;

R$^{13}$ is H or methyl;

R$^{14}$ is selected from:
  H, C$_1$–C$_{10}$ alkyl, C$_2$–C$_{10}$ alkenyl, C$_2$–C$_{10}$ alkynyl, C$_3$–C$_{10}$ cycloalkyl, C$_1$–C$_6$ hydroxyalkyl, C$_1$–C$_6$ alkoxy(C$_1$–C$_6$ alkyl), aryl(C$_0$–C$_6$ alkoxy C$_1$–C$_6$ alkyl), C$_1$–C$_6$ alkylthio(C$_1$–C$_6$ alkyl), C$_1$–C$_6$ alkylsulfonyl(C$_1$–C$_6$ alkyl), aryl(C$_0$–C$_6$ alkylthio C$_1$–C$_6$ alkyl), aryl(C$_0$–C$_6$ alkylsulfonyl C$_1$–C$_6$ alkyl), C$_3$–C$_{10}$ cycloalkyl (C$_0$–C$_6$ alkyl), aryl(C$_0$–C$_6$ alkyl), heteroaryl(C$_0$–C$_6$ alkyl), R$^{17}$HNC(=O) (C$_1$–C$_4$ alkyl), R$^{10}$OC(=O) (C$_1$–C$_4$ alkyl), and R$^{17}$HN(C$_1$–C$_4$ alkyl), provided that any of the above alkyl, cycloalkyl, aryl or heteroaryl groups are substituted with 0–2 substituents independently selected from the group consisting of C$_1$–C$_4$ alkyl, C$_1$–C$_4$ alkoxy, F, Cl, Br, CF$_3$, and NO$_2$;

R$^{15}$ is selected from:
  —NH—C(=O)—O—R$^{17}$,
  —NH—C(=O)—R$^{17}$,
  —NH—C(=O)—NH—R$^{17}$,
  —NHSO$_2$—R$^{17}$, and
  —NHSO$_2$—NHR$^{17}$;

Y is —C(=O)R$^{19}$;

R$^{17}$ is selected from:
  C$_1$–C$_{10}$ alkyl, C$_3$–C$_{10}$ cycloalkyl, aryl(C$_0$–C$_6$ alkyl), heteroaryl(C$_0$–C$_6$ alkyl), arylaryl(C$_0$–C$_6$ alkyl), heteroarylaryl(C$_0$–C$_6$ alkyl), arylheteroaryl(C$_0$–C$_6$ alkyl), and heteroarylheteroaryl (C$_0$–C$_6$ alkyl), wherein said aryl or heteroaryl groups are optionally substituted with 0–3 substituents independently selected from the group consisting of: C$_1$–C$_4$ alkyl, C$_1$–C$_4$ alkoxy, aryl, F, Cl, Br, CN, NH$_2$, CF$_3$, and NO$_2$;

R$^{19}$ is selected from:
  hydroxy,
  C$_1$–C$_{10}$ alkoxy,
  methylcarbonyloxymethoxy-,
  ethylcarbonyloxymethoxy-,
  t-butylcarbonyloxymethoxy-,
  cyclohexylcarbonyloxymethoxy-,
  1-(methylcarbonyloxy)ethoxy-,
  1-(ethylcarbonyloxy)ethoxy-,
  1-(t-butylcarbonyloxy)ethoxy-,
  1-(cyclohexylcarbonyloxy)ethoxy-,
  i-propyloxycarbonyloxymethoxy-,
  t-butyloxycarbonyloxymethoxy-,
  1-(i-propyloxycarbonyloxy)ethoxy-,
  1-(cyclohexyloxycarbonyloxy)ethoxy-,
  1-(t-butyloxycarbonyloxy)ethoxy-,
  dimethylaminoethoxy-,
  diethylaminoethoxy-,
  (5-methyl-1,3-dioxacyclopenten-2-on-4-yl)methoxy-,
  (5- (t-butyl) -1, 3-dioxacyclopenten-2-on-4-yl) methoxy-,
  (1,3-dioxa-5-phenyl-cyclopenten-2-on-4-yl)methoxy-,
  1-(2-(2-methoxypropyl)carbonyloxy)ethoxy-,
  (R$^{10}$)(R$^{11}$)N-(C$_1$–C$_{10}$ alkoxy)-, and
  —O (CH$_2$)$_k$N$^+$(R$^{21}$) (R$^{22}$) (R$^{23}$) Z$^-$;

Z$^-$ is a pharmaceutically acceptable anion selected from halide, bisulfate, sulfate, hydrogenphosphate, phosphate, toluenesulfonate, methanesulfonate, ethanesulfonate, acetate, trifluoroacetate, citrate, oxalate, succinate, and malonate;

R$^{21}$ R$^{22}$ and R$^{23}$ are independently selected from:
  H, methyl, ethyl, propyl, butyl, C$_3$–C$_7$ cycloalkyl (C$_0$–C$_4$ alkyl), phenyl, benzyl, wherein said phenyl group is substituted with 0–2 substituents selected from the group consisting of C$_1$–C$_4$ alkyl, C$_1$–C$_4$ alkoxy, OH, F, Cl, Br, CF$_3$, and NO$_2$;
  alternatively R$^{21}$ and R$^{22}$ can be taken together to form a 5–7 membered heterocyclic aromatic or non-aromatic ring system containing 1–2 heteroatoms selected from N, O and S and R$^{23}$ is defined as above or R$^{21}$, R$^{22}$, and R$^{23}$ can be taken together to form a heterobicyclic ring system containing 1–2 heteroatoms selected from N, O and S;

h is 0–4;

i is 0–2;

k is 2–6;

m is 1–4;

n is 0–5;

q is 2–3;

r is 0–3; and t is 1–3;

provided that h, i, m, n, q, r, and t, at each occurrence, are chosen such that the number of in-chain atoms between Y and the pyrimidine, pyrimidone, triazine or triazinone of G is in the range of 8–12.

5. A new compound of claim 1 selected from the group consisting of:
  3-[1-2-Amino-4-oxopyrimidin-6-yl)ethyl]indazol-5-ylcarbonylamino]-2(S)-(2,4,6-trimethylbenzenesulfonyl- amino)propionic acid,
  3-[1-[2-Amino-4- oxopyrimidin-6-ylmethyl]indazol-5-yl carbonylamino]-2(S)-(1-naphthalenesulfonylamino)-propionic acid,
  3-[1-[2- (2-4-Diaminopyrimidin-6-yl)ethyl]indazol-5-yl-carbonylamino]-2(S)-benzenesulfonylaminopropionic acid,
  3-[1-2-(2,3-Dihydro-5-oxo-imidazo[1,2-a]pyrimidin-7-yl)ethyl]indazol-5-ylcarbonylamino]-2(S)-(1-naphthalensulfonyl)aminopropionic acid,
  3-[1-[2-(5-Oxo-imidazo[1,2-a]pyrimidin-7-yl)ethyl]-indazol-5-ylcarbonylamino]-2(S) benzenesulfonylamino- propionic acid,
  3-[1-Methyl-3-[2-(2-amino-4-oxopyrimidin-6-yl)ethyl]-indazol-6-ylcarbonylamino]-2(S)-(isoquinoline-5-sulfonylamino)propionic acid,
and ester forms thereof, said ester being selected from the group consisting of:
  methyl,
  ethyl,
  isopropyl,
  n-butyl,
  isobutyl,
  benzyl,
  methylcarbonyloxymethyl,
  ethylcarbonyloxymethyl,
  tert-butylcarbonyloxymethyl, cyclohexylcarbonylozymethyl,
tert-butyloxycarbonyloxymethyl,
dimethylaminoethyl,
diethylaminoethyl,
morpholinoethyl,
pyrrolidinoethyl,
trimethylammonioethyl, and
2-(1-methylmorpholinium-1-yl)ethyl.

6. A pharmaceutical composition comprising a pharmaceutically acceptable carrier and a therapeutically effective amount of a compound of claim 1 or a pharmaceutically acceptable salt form thereof.

7. A pharmaceutical composition comprising a pharmaceutically acceptable carrier and a therapeutically effective amount of a compound of claim 2 or a pharmaceutically acceptable salt form thereof.

8. A pharmaceutical composition comprising a pharmaceutically acceptable carrier and a therapeutically effective amount of a compound of claim 3 or a pharmaceutically acceptable salt form thereof.

9. A pharmaceutical composition comprising a pharmaceutically accetable carrier and a therapeutically effective amount of a compound of claim 4 or a pharmaceutically acceptable salt form thereof.

10. A pharmaceutical composition comprising a pharmaceutically acceptable carrier and a therapeutically effective amount of a compound of claim 5 or a pharmaceutically acceptable salt form thereof.

11. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 1.

12. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 2.

13. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 3.

14. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 4.

15. A method for the treatment of cancer metastasis, diabetic retinopathy, neovascular glaucoma, thrombosis, restenosis, osteoporosis, or macular degeneration which comprises administering to a host in need of such treatment a therapeutically effective amount of a compound of claim 5.

* * * * *